US010392609B2

(12) United States Patent
Callewaert et al.

(10) Patent No.: US 10,392,609 B2

(45) **Date of Patent: *Aug. 27, 2019**

(54) HYDROLYSIS OF MANNOSE-1-PHOSPHO-6-MANNOSE LINKAGE TO PHOSPHO-6-MANNOSE

(71) Applicants: Oxyrane UK Limited, Manchester (GB); VIB vzw, Ghent (BE); Universiteit Gent, Ghent (BE); Vrije Universiteit Brussel, Brussels (BE)

(72) Inventors: Nico Luc Marc Callewaert, Hansbeke-Nevele (BE); Wouter Vervecken, Landskouter (BE); Petra Sophie Tiels, Gent-Zwijnaarde (BE); Han Karel Remaut, Boutersem (BE); Kathleen Camilla Telesphore Alida Maria Piens, Ghent (BE)

(73) Assignees: Oxyrane UK Limited, Manchester (GB); VIB vzw, Ghent (BE); Universiteit Gent, Ghent (BE); Vrije Universiteit Brussel, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/350,648

(22) Filed: Nov. 14, 2016

(65) Prior Publication Data

US 2017/0226493 A1 Aug. 10, 2017

Related U.S. Application Data

(63) Continuation of application No. 13/499,061, filed as application No. PCT/IB2010/000258 on Sep. 29, 2010, now Pat. No. 9,598,682.

(60) Provisional application No. 61/246,847, filed on Sep. 29, 2009.

(51) Int. Cl.

| | |
|---|---|
| ***C12P 19/14*** | (2006.01) |
| ***C12P 19/04*** | (2006.01) |
| ***C12P 21/00*** | (2006.01) |
| ***C12N 9/24*** | (2006.01) |
| ***C07K 14/00*** | (2006.01) |
| ***C12N 9/34*** | (2006.01) |
| ***C12N 9/40*** | (2006.01) |

(52) U.S. Cl.

CPC ............ *C12N 9/2488* (2013.01); *C07K 14/00* (2013.01); *C12N 9/2428* (2013.01); *C12N 9/2465* (2013.01); *C12P 19/04* (2013.01); *C12P 19/14* (2013.01); *C12P 21/00* (2013.01); *C12P 21/005* (2013.01); *C12Y 302/01* (2013.01); *C12Y 302/01003* (2013.01); *C12Y 302/01022* (2013.01); *Y02P 20/52* (2015.11)

(58) Field of Classification Search

CPC .................................................. C12N 9/2488

See application file for complete search history.

(56) References Cited

U.S. PATENT DOCUMENTS

| | | | |
|---|---|---|---|
| 4,307,717 | A | 12/1981 | Hymes et al. |
| 4,352,883 | A | 10/1982 | Lim |
| 4,353,888 | A | 10/1982 | Sefton |
| 4,407,957 | A | 10/1983 | Lim |
| 4,704,362 | A | 11/1987 | Itakura et al. |
| 4,837,148 | A | 6/1989 | Cregg |
| 4,879,231 | A | 11/1989 | Stroman et al. |
| 4,882,279 | A | 11/1989 | Cregg |
| 4,883,666 | A | 11/1989 | Sabel et al. |
| 4,929,555 | A | 5/1990 | Cregg et al. |
| 4,968,733 | A | 11/1990 | Miller et al. |
| 4,976,859 | A | 12/1990 | Wechs |
| 5,084,350 | A | 1/1992 | Chang et al. |
| 5,158,881 | A | 10/1992 | Aebischer et al. |
| 5,272,070 | A | 12/1993 | Lehrman et al. |
| 5,284,761 | A | 2/1994 | Aebischer et al. |
| 5,585,089 | A | 12/1996 | Queen et al. |
| 5,798,113 | A | 8/1998 | Dionne et al. |
| 5,800,828 | A | 9/1998 | Dionne et al. |
| 6,110,703 | A | 8/2000 | Egel-Mitani et al. |
| 6,265,185 | B1 | 7/2001 | Muller et al. |
| 6,699,658 | B1 | 3/2004 | Wittrup et al. |
| 6,803,225 | B2 | 10/2004 | Contreras et al. |
| 6,872,392 | B2 | 3/2005 | Nakamura et al. |
| 7,029,872 | B2 | 4/2006 | Gerngross |
| 7,259,007 | B2 | 8/2007 | Bobrowicz et al. |
| 7,262,287 | B2 | 8/2007 | Kang et al. |
| 7,326,681 | B2 | 2/2008 | Gerngross |
| 7,390,884 | B2 | 6/2008 | Segal et al. |
| 7,422,742 | B2 | 9/2008 | Greenfeder et al. |
| 7,422,890 | B2 | 9/2008 | Gopalakrishnakone et al. |
| 7,431,927 | B2 | 10/2008 | Couto et al. |
| 7,442,772 | B2 | 10/2008 | Goddard et al. |
| 7,449,308 | B2 | 11/2008 | Gerngross et al. |

(Continued)

FOREIGN PATENT DOCUMENTS

| | | |
|---|---|---|
| AU | 2012/206984 | 8/2012 |
| EP | 1408117 | 4/2004 |

(Continued)

OTHER PUBLICATIONS

Bones et al., "Identification of N-Glycans Displaying Mannose-6-Phosphate and their Site of Attachment on Therapeutic Enzymes for Lysosomal Storage Disorder Treatment," *Analytical Chemistry*, 83(13):5344-5352, May 23, 2011.

(Continued)

*Primary Examiner* — Rebecca E Prouty

(74) *Attorney, Agent, or Firm* — Fish & Richardson P.C.

(57) ABSTRACT

Described herein are methods and genetically engineered cells useful for uncapping a mannose-6-phosphate residue on an oligosaccharide.

39 Claims, 126 Drawing Sheets

Specification includes a Sequence Listing.

(56) References Cited

U.S. PATENT DOCUMENTS

| | | | |
|---|---|---|---|
| 7,488,591 B2 | 2/2009 | Miura et al. | |
| 7,785,856 B2 | 8/2010 | LeBowitz et al. | |
| 8,026,083 B2 | 9/2011 | Callewaert et al. | |
| 8,597,906 B2 | 12/2013 | Callewaert et al. | |
| 9,206,408 B2 | 12/2015 | Callewaert et al. | |
| 9,222,083 B2 | 12/2015 | Callewaert et al. | |
| 9,249,399 B2 | 2/2016 | Vervecken et al. | |
| 9,347,050 B2 | 5/2016 | Piens et al. | |
| 9,598,682 B2 | 3/2017 | Callewaert et al. | |
| 9,689,015 B2 | 6/2017 | Piens et al. | |
| 2002/0127219 A1 | 9/2002 | Okkels et al. | |
| 2002/0137125 A1 | 9/2002 | Zhu | |
| 2003/0147868 A1 | 8/2003 | Treco et al. | |
| 2003/0186374 A1 | 10/2003 | Hufton et al. | |
| 2004/0018588 A1 | 1/2004 | Contreras et al. | |
| 2004/0018590 A1 | 1/2004 | Gerngross et al. | |
| 2005/0014270 A1 | 1/2005 | Picataggio et al. | |
| 2005/0064539 A1 | 3/2005 | Chiba et al. | |
| 2005/0170452 A1 | 8/2005 | Wildt et al. | |
| 2005/0265988 A1 | 12/2005 | Choi et al. | |
| 2006/0014264 A1 | 1/2006 | Sauer et al. | |
| 2006/0030521 A1 | 2/2006 | Defrees et al. | |
| 2006/0040353 A1 | 2/2006 | Davidson et al. | |
| 2006/0148039 A1 | 7/2006 | Kobayashi et al. | |
| 2006/0286637 A1 | 12/2006 | Hamilton | |
| 2007/0037248 A1 | 2/2007 | Bobrowicz et al. | |
| 2008/0081035 A1 | 4/2008 | Parmely et al. | 424/94.63 |
| 2008/0171359 A1 | 7/2008 | Botes et al. | |
| 2009/0069232 A1 | 3/2009 | Callewaert et al. | |
| 2009/0186011 A1 | 7/2009 | Vellard et al. | |
| 2010/0291059 A1 | 11/2010 | Sakuraba et al. | |
| 2011/0201540 A1 | 8/2011 | Callewaert et al. | |
| 2011/0207676 A1 | 8/2011 | Callewaert et al. | |
| 2012/0135461 A1 | 5/2012 | Cook et al. | |
| 2013/0053550 A1 | 2/2013 | Geysens et al. | |
| 2013/0096281 A1 | 4/2013 | Ryckaert et al. | |
| 2013/0158239 A1 | 6/2013 | Callewaert et al. | |
| 2013/0190253 A1 | 7/2013 | Callewaert et al. | |
| 2013/0195835 A1 | 8/2013 | Callewaert et al. | |
| 2013/0243746 A1 | 9/2013 | Vervecken et al. | |
| 2013/0295603 A1 | 11/2013 | Piens et al. | |
| 2015/0031081 A1 | 1/2015 | Vervecken et al. | |
| 2015/0337273 A1 | 11/2015 | Geysens et al. | |
| 2016/0251693 A1 | 9/2016 | Piens et al. | |
| 2016/0279254 A1 | 9/2016 | Vervecken et al. | |
| 2017/0306379 A1 | 10/2017 | Piens et al. | |

FOREIGN PATENT DOCUMENTS

| | | |
|---|---|---|
| FR | 2954349 | 6/2011 |
| JP | 57 1982/05458 | 4/1982 |
| JP | 2002/369679 | 12/2002 |
| JP | 2004/313074 | 11/2004 |
| KR | 10-2004-00266663 | 3/2004 |
| KR | 2004/062304 | 7/2004 |
| WO | WO 1992/019195 | 11/1992 |
| WO | WO 1995/005452 | 2/1995 |
| WO | WO 1996/004378 | 2/1996 |
| WO | WO 1996/021038 | 7/1996 |
| WO | WO 1998/001473 | 1/1998 |
| WO | WO 1998/001535 | 1/1998 |
| WO | WO 1998/048025 | 10/1998 |
| WO | WO 1999/036569 | 7/1999 |
| WO | WO 1999/037758 | 7/1999 |
| WO | WO 2001/049830 | 7/2001 |
| WO | WO 2001/088143 | 11/2001 |
| WO | WO 2002/018570 | 3/2002 |
| WO | WO 2003/029456 | 4/2003 |
| WO | WO 2003/056914 | 7/2003 |
| WO | WO 2004/003194 | 1/2004 |
| WO | WO 2004/074458 | 9/2004 |
| WO | WO 2004/074461 | 9/2004 |
| WO | WO 2004/074498 | 9/2004 |
| WO | WO 2004/074499 | 9/2004 |
| WO | WO 2005/100584 | 10/2005 |
| WO | WO 2005/106010 | 11/2005 |
| WO | WO 2007/035930 | 3/2007 |
| WO | WO 2008/100816 | 8/2008 |
| WO | WO 2008/120107 | 10/2008 |
| WO | WO 2009/105357 | 8/2009 |
| WO | WO 2009/137721 | 11/2009 |
| WO | WO 2010/099195 | 9/2010 |
| WO | WO 2011/039634 | 4/2011 |
| WO | WO 2011/061629 | 5/2011 |
| WO | WO 2012/042386 | 4/2012 |
| WO | WO 2012/042387 | 4/2012 |
| WO | WO 2013/098651 | 7/2013 |

OTHER PUBLICATIONS

European Office Action in European Application No. EP10782375.9, dated Jun. 16, 2017, 6 pages.

Lee et al., "A biochemical and pharmacological comparison of enzyme replacement therapies for the glycolipid storage disorder Fabry disease," *Glycobiology*., 13:305-313, 2003.

Prince et al., "Lipoprotein Receptor Binding, Cellular Uptake, and Lysosomal Delivery of Fusions between the Receptorassociated Protein (RAP) and alpha-L-Iduronidase or Acid alpha-Glucosidase," J. Biol. Chem., 279:35037-35046, 2004.

Zhu et al., "Carbohydrate-remodeled acid a-glucosidase with higher affinity for the cation-independent mannose 6-phosphate receptor demonstrates improved delivery to muscles of Pompe mice," Biochem. J., 389:619-628, 2005.

"Arxula adeninivorans," Wikipedia [online] Jan. 13, 2010 [retrieved on Jan. 31, 2010]. Retrieved from the Internet: <URL: http://en.wikipedia.org/wiki/Arxula_adeninivorans>, 2 pages.

"Eukaryotes Genomes—Yarrowia Lipolytica," The European Bioinformatics Institute [online] [retrieved on Jun. 26, 2012]. Retrieved from the Internet: <URL: http://www.ebi.ac.uk/2can/genomes/eukaryotes/Yarrowia_lipolytica.html>, 1 page.

"Glycoside Hydrolase Family 38," cazy.org [online] retrieved on Dec. 1, 2016. Retrieved from the Internet: <URL: http://www.cazy.org/GH38.html>, 1 page.

"Glycoside Hydrolase Family 47," cazy.org [online] retrieved on Dec. 1, 2016. Retrieved from the Internet: <URL: http://www.cazy.org/GH47.html>, 1 page.

"Glycoside Hydrolase Family 92," cazy.org [online] retrieved on Dec. 1, 2016. Retrieved from the Internet: <URL: http://www.cazy.org/GH92.htm1>, 1 page.

Abe et al., "In vitro oligosaccharide synthesis using intact yeast cells that display glycosyltransferases at the cell surface through cell wall-anchored protein Pir.," *Glycobiology*, 13(2):87-95, print Feb. 2003, ePub Nov. 2002.

Ackerman et al., "Highly avid magnetic bead capture: an efficient selection method for de novo protein engineering utilizing yeast surface display," *Biotechnol Prog*., 25(3):774-783, May-Jun. 2009.

Aebi et al., "Cloning and characterization of the ALG3 gene of *Saccharomyces cerevisiae*," Glycobiology, vol. 6, No. 4, (1996), pp: 439-444.

Akcapinar et al., "Effect of codon optimization on the expression of Trichoderma reese endoglucanase 1 in Pichia pastoris." Biotechnol Prog., Sep.-Oct. 2011; 27(5):1257-1263. doi: 10.1002/btpr.663. Epub Jul. 2011.

Akeboshi et al., "Production of Recombinant Beta-Hexosaminidase A, a Potential Enzyme for Replacement Therapy for Tay-Sachs and Sandhoff Diseases, in the Methylotrophic Yeast Ogataea minuta", Appl. Environ. Microbiol., 73( 15):4805-4812 (2007).

Alessandrini et al., "Alterations of Glucosylceramide-b-Glucosidase Levels in the Skin of Patients with Psoriasis Vulgaris," J. Invest. Dermatol, 23(6):1030-1036, 2004.

Almeciga et al., "Production of an active recombinant human N-acetylgalactosamine-6-sulfate sulfatase enzyme in Pichia pastoris," *Molecular Genetics and Metabolism*, 111(2):S19, Abstract 11, Jan. 27, 2014.

Andrés et al., "Use of the cell wall protein Pir4 as a fusion partner for the expression of *Bacillus* sp. BP-7 xylanase A in *Saccharomyces cerevisiae," Biotechnol Bioeng*, 89(6): 690-697, Mar. 2005.

(56) References Cited

OTHER PUBLICATIONS

Aravind and Koonin, "The fukutin family—predicted enzymes modifying cell-surface molecules," Curr Biol., 9(22):R836-R837, Nov. 18, 1999.
Bagiyan et al., "The Action of α-Mannosidase from *Oerskovia* sp. on the Mannose-Rich O-Linked Sugar Chains of Glycoproteins," Eur. J. Biochem., 249(1):286-292, 1997.
Baharaeen and Vishniac, "A fixation method for visualization of yeast ultrastructure in the electron microscope ," Mycopathologia, 77(1):19-22, 1982.
Ballou, "Isolation, characterization, and properties of *Saccharomyces cerevisiae* mnn mutants with nonconditional protein glycosylation defects," Methods in Enzymology, vol. 185, (1990) pp. 440-470.
Barnay-Verdier et al., "Identification and characterization of two alpha-1,6-mannosyltransferases, Anllp and Ochlp, in the yeast yarrowia lipolytica", *Microbiology*, 150(7):2185-2195, Jul. 2004.
Barth and Gaillardin, "Physiology and genetics of the dimorphic fungus Yarrowia lipolytica," FEMS Microbiology Reviews, 19(4):219-237, Apr. 1997 [print], Jan. 2006 [online].
Bennetzen and Hall, "Codon Selection in Yeast," J. Biol. Chem., 257(6):3026-3031, 1982.
Bentley et al., "Complete genome sequence of the model actinomycete Streptomyces coelicolor A3(2)," Nature, 417:141-147, (May 2002).
Bijvoet et al., "Recombinant human acid alpha-glucosidase: high level production in mouse milk, biochemical characteristics, correction of enzyme deficiency in GSDII KO mice," Hum Mol Genet., 7(11):1815-1824, Oct. 1998.
Bobrowicz et al., "Engineering of an artificial glycosylation pathway blocked in core oligosaccharide assembly in the yeast Pichia pastoris: production of complex humanized glycoproteins with terminal galactose," *Glycobiology*, 14(9):757-766 (2004).
Boder and Wittrup, "Yeast surface display for screening combinatorial polypeptide libraries," *Nat. Biotechnol*., 15, 553-557, Jun. 1997.
Boder et al. "Directed evolution of antibody fragments with monovalent femtomolar antigen-binding affinity," *Proc Natl Acad Sci USA*., 97(20):10701-5, Sep. 2000.
Boisrame et al. "Sls1p, an endoplasmic reticulum component, is involved in the protein translocation process in the yeast Yarrowia lipolytica," J. Biol. Chem. 271(20):11668-75, 1996.
Bourbonnais et al., "Production of full-length human pre-elafin, an elastase specific inhibitor, from yeast requires the absence of a functional yapsin 1 (Yps1p) endoprotease," *Protein Expr Purif*., 20(3):485-491, Dec. 2000.
Brady, "Enzyme replacement for lysosmal diseases," *Annu. Rev. Med*., 57:283-296, 2006.
Brady, "The lipid storage diseases: new concepts and control," *Ann Intern Med*., 82(2):257-61, Feb. 1975
Bretthauer, "Genetic engineering of Pichia pastoris to humanize N-glycosylation of proteins," TRENDS in Biotechnology, 21(11): 459-462 (Nov. 2003).
Burda et al., "Ordered assembly of the asymmetrically branched lipid-linked oligosaccharide in the endoplasmic reticulum is ensured by the substrate specificity of the individual glycosyltransferases", *Glycobiology*, 9(6):617-625 (1999).
Burton and Harding, "Hydrophobic charge induction chromatography: salt independent protein adsorption and facile elution with aqueous buffers.," Chromatogr. A 814(1-2):71-81, Jul. 1998.
Callewaert et al, "Use of HDEL-tagged Trichoderma reesei mannosyl oligosaccharide 1,2-alpha-D-mannosidase for N-glycan engineering in Pichia pastoris.," FEBS Lett., 503(2-3):173-178, (Aug. 2001).
Callewaert et al., "Ultrasensitive profiling and sequencing of N-linked oligosaccharides using standard DNA-sequencing equipment," Glycobiology 11(4):275-281, Apr. 2001.
Cantarel et al., "The Carbohydrate-Active EnZymes database (CAZy): an expert resource for Glycogenomics," *Nucleic Acids Res*., 37(Database issue):D233-D238, Epub Oct. 5, 2008.
Cardone et al., "Abnormal mannose-6-phosphate receptor trafficking impairs recombinant alpha-glucosidase uptake in Pompe disease fibroblasts," Pathogenetics, 1(1):6, Dec. 1, 2008.
Carlson et al., "Function and structure of a prokaryotic formylglycine-generating enzyme " *J Biol Chem*., 283(29):20117-20125, Epub Apr. 4, 2008.
Carter et al., "Humanization of an anti-p185HER2 antibody for human cancer therapy," *Proc Natl Acad Sci USA*, 89(10): 4285-4289, (May 1992).
Chao et al., "Isolating and engineering human antibodies using yeast surface display," *Nat. Protoc*., 1(2):755-768, 2006.
Chiba et al., "Production of human compatible high mannose-type (Man5G1cNAc2) sugar chains in *Saccharomyces cerevisiae," J Biol Chem*., 273(41):26298-26304, Oct. 9, 1998.
Chiba et al., "Production in yeast of alpha-galactosidase A, a lysosomal enzyme applicable to enzyme replacement therapy for Fabry disease," *Glycobiology*, 12(12):821-828 (2002).
Cho et al., "Structure of the extracellular region of HER2 alone and in complex with the Herceptin," *Nature*, 421(6924):756-760, Feb. 2003.
Choi et al. "Use of combinatorial genetic libraries to humanize N-linked glycosylation in the yeast Pichia pastoris," Proc. Natl. Acad. Sci. USA, 100(9):5022-5027, Apr. 2003.
Choi, "Structural analysis of N-linked oligosaccharides assembled on recombinant proteins secreted from Yarrowia lipolytica Yloch1 and Yloch1 Ylmnn4 mutants," Thesis, Chungnam National University: Department of Microbiology, Republic of Korea, pp. 1-39, XP008160421, Retrieved from the Internet: URL: http://www.riss.kr/search/detail/DetailView.do?p_mat_type=75f99de66dbl8cf6&control_no=4cbf0006e9061fb5ffe0bdc3ef48d419 (2006).
Choi, et al., "Structural analysis of N-linked oligosaccharides assembled on recombinant proteins secreted from Yarrowia lipolytica Yloch1 and Yloch1 Ylmnn4 mutants.," XXIIth International Conference on Yeast Genetics and Molecular Biology, 09—Protein biosynthesis, maturation, modification and degradation, Yeast, 22:S131, Abstract 9-35, 2005.
Cipollo and Trimble, "The accumulation of Man(6)GlcNAc(2)-PP-dolichol in the *Saccharomyces cerevisiae* Deltaalg9 mutant reveals a regulatory role for the Alg3p alphal,3-Man middle-arm addition in downstream oligosaccharide-lipid and glycoprotein glycan processing," J Biol Chem., 275(6):4267-4277, (Feb. 2000).
Cobucci-Ponzano et al., "The molecular characterization of a novel GH38 alpha-mannosidase from the crenarchaeon Sulfolobus solfataricus revealed its ability in de-mannosylating glycoproteins," Biochimie., 92(12):1895-1907, (Aug. 2010).
Codon usage table: Yarrowia lipolytica CLIB122 [gbpin]: 5967 CDS's (2945919 codons), Codon Usage Database [online], [retrieved on Jul. 10, 2012]. Retrieved from the Internet:<URL: http://www.kazusa.or.jp/codon/cgi-bin/showcodon.cgi?species=284591>, 1 page.
Connock et al., "A systematic review of the clinical effectiveness and cost-effectiveness of enzyme replacement therapies for Fabry's disease and mucopolysaccharidosis type 1," Health Technol Assess., 10(20):iii-iv, ix-113, 2006.
Cregg et al., "Transformation," Molecular Biology: Pichia Protocols, Chapter 3, Humana Press, Totowa, N.J., pp. 27-39 (1998).
Database Accession No. P41546, UniProt (online), "RecName: Full Transcriptionmanal Activator HAC1"; XP002509286, Nojima et al., Nov. 1, 1995, 3 pages.
Database Geneseq, "Aspergillus oryzae alkaline protease, SEQ ID 1.", retrieved from EBI accession No. GSP:ARW11112, Database accession No. ARW11112, 1 page, Aug. 7, 2008.
Database UniProt[Online] Aug. 1, 1998 (Aug. 1, 1998), "SubName: Full= Putative secreted protein;" XP002628929 retrieved from EBI accession No. UNIPROT:069822 Database accession No. 069822, 3 pages.
Database UniProt[Online] Jul. 11, 2006 (Jul. 11, 2006), "SubName: Full= Alpha-1, 2-mannosidase, putative; Flags: Precursor;" XP002628931 retrieved from EBI accession No. UNIPROT:Q1ASW5 Database accession No. Q1ASW5, 2 pages.
Database UniProt[Online] Apr. 29, 2008 (Apr. 29, 2008), "SubName: Full= Putative uncharacterized protein;" XP002628930 retrieved from EBI accession No. UNIPROT:B1BZG6 Database accession No. B1BZG6, 2 pages.

(56) References Cited

OTHER PUBLICATIONS

Davidow et al., "Cloning and sequencing of the alkaline extracellular protease gene of Yarrowia lipolytica," *J. Bacteriol.*, 169(10):4621-4629, Oct. 1987.
Davies et al, "Nomenclature for sugar-binding subsites in glycosyl hydrolases," Biochem. J., 321:557-559 (1997).
De Pourcq et al, "Engineering Yarrowia lipolytica to produce glycoproteins homogeneously modified with the universal Man3GlcNAc2 N-glycan core," PLoS One, 7(6):e39976, 12 pages, Epub Jun. 29, 2012.
De Pourcq et al., "Engineering of glycosylation in yeast and other fungi: current state and perspectives," *Appl Microbiol Biotechnol.*, 87(5):1617-1631. Epub Jun. 29, 2010.
De Pourcq et al., "Engineering the yeast Yarrowia lipoytica for the production of therapeutic proteins homogeneously glycosylated with Man8GIcNAc2 and MansGIcNAc2 " *Microbial Cell Factories*, 11:53, 1-12, May 1, 2012.
Devos and Valencia, "Practical limits of function prediction," *Proteins.*, 41(1):98-107, Oct. 1, 2000.
Dierks et al., "Multiple sulfatase deficiency is caused by mutations in the gene encoding the human C(alpha)-formylglycine generating enzyme," *Cell*, 113(4):435-444, May 16, 2003.
Dierks et al., "Sequence determinants directing conversion of cysteine to formylglycine in eukaryotic sulfatases," *EMBO J.*, 18(8):2084-2091, Apr. 15, 1999.
Diez-Roux and Ballabio, "Sulfatases and human disease," *Annu Rev Genomics Hum Genet.*, 6:355-379 2005.
Dragosits et al., "The effect of temperature on the proteome of recombinant Pichia pastoris," *J. Proteome Res.*, 8(3):1380-1392, Mar. 2009.
Ekici et al., "Unconventional serine proteases: variations on the catalytic Ser/His/Asp triad configuration," *Protein Sci.*, 17(12):2023-2037, Epub Sep. 29, 2008.
Ettinger et al., "Intrathecal methotrexate overdose without neurotoxicity: case report and literature review," Cancer, 41(4):1270-1273, Apr. 1978.
Fickers et al. "New disruption cassettes for rapid gene disruption and marker rescue in the yeast Yarrowia lipolytica," J. Microbiol. Methods. 55(3):727-737, Dec. 2003.
Fickers et al., "Carbon and nitrogen sources modulate lipase production in the yeast Yarrowia lipolytica," J. of Applied Microbiology, vol. 96, No. 4 (2004), pp. 742-749.
Fickers, P. et al. "Hydrophobic substrate utilization by the yeast Yarrowia lipolytica and its potential applications," *FEMS Yeast Research*, Apr. 2005, vol. 5, No. 6-7, pp. 527-543.
Floudas, "Computational methods in protein structure prediction," Biotechnology and Bioengineering, 97(2): 207-213, Jun. 1, 2007.
Fournier et al., "Scarcity of ars sequences isolated in a morphogenesis mutant of the yeast Yarrowia lipolytica," *Yeast*, 7(1):25-36, Jan. 1991.
Fraldi et al., "Multistep, sequential control of the trafficking and function of the multiple sulfatase deficiency gene product, SUMF1 by PDI, ERGIC-53 and ERp44," *Hum Mol Genet.*, 17(17):2610-2621, Epub May 28, 2008.
Freire et al. "Efficient monitoring of enzymatic conjugation reaction by surface-enhanced laser desorption/ionization time of flight mass spectrometry for process optimization," Bioconjug. Chem. 17(2):559-564, 2006.
Fujii, "Antibody Affinity Maturation by Random Mutagenesis," *Antibody Engineering*, vol. 248, pp. 345-359, 2004.
Fujita and Takegawa, "Chemoenzymatic Synthesis of Neoglycoproteins Using Transglycosylation with Endo-Beta-N-acetylglucosaminidase A," Biochem. Biophys. Res. Commun., 282(3):678-682, (Apr. 2001).
Gagnon-Arsenault et al., "Activation mechanism, functional role and shedding of glycosylphosphatidylinositol-anchored Ypslp at the *Saccharomyces cerevisiae* cell surface," Mol Microbiol., 69(4):982-993, Epub Jun. 28, 2008.
Gagnon-Arsenault et al., "Fungal yapsins and cell wall: a unique family of aspartic peptidases for a distinctive cellular function," FEMS Yeast Res., 6(7):966-978, Nov. 2006.
Gao et al. "UpGene: Application of a web-based DNA codon optimization algorithm," Biotechnol. Prog., 20(2): 443-448, 2004.
García-Gómez et al., "Advantages of a proteolytic extract by Aspergillus oryzae from fish flour over a commercial proteolytic preparation," *Food Chemistry*, 112(3):604-608, Feb. 1, 2009.
Gasser et al., "Engineering of Pichia pastoris for improved production of antibody fragments," *Biotechnol. Bioeng.*, 94(2):353-361, Jun. 2006.
Gatlin et al., "Automated identification of amino acid sequence variations in proteins by HPLC/microspray tandem mass spectrometry," Anal Chem., 72(4):757-763, Feb. 15, 2000.
Gellissen, et al., "New yeast expression platforms based on methylotrophic Hansenula polymorpha and Pichia pastoris and on dimorphic Armada adeninivorans and Yarrowia lipolytica—A comparison," FEMS Yeast Res., 5(11): 1079-1096, 2005.
Genbank Acccession No. XM_502922 GI:50550898, "Yarrowia lipolytica YALI0D17028p (YALI0D17028g) mRNA, complete cds," Oct. 29, 2008, 2 pages.
Genbank Acccession No. XM_503217 GI:50551486, "Yarrowia lipolytica YALI0D24101p (YALI0D24101g) mRNA, complete cds," Oct. 29, 2008, 2 pages.
Genbank Accession No. AA034683, "mi41c04.r1 Soares mouse embryo NbME13.5 14.5 Mus musculus cDNA clone IMAGE:466086 5-, mRNA sequence," Aug. 23, 1996, 2 pages.
Genbank Accession No. AAF34579 GI:6979644, "1,2-a-D-mannosidase [Trichoderma reesei]" Feb. 16, 2000, 1 page.
Genbank Accession No. AAO78636, "putative alpha-1,2-mannosidase [Bacteroides thetaiotaomicron VPI-5482]," 1 page, Oct. 24, 2007.
Genbank Accession No. AAO78636.1 GI:29340846, putative alpha-1,2-mannosidase [Bacteroides thetaiotaomicron VPI-5482] Feb. 8, 2011, 2 pages.
Genbank Accession No. AAO79070.1 GI:29341282, "putative alpha-1,2-mannosidase [Bacteroides thetaiotaomicron VPI-5482]," Feb. 8, 2011, 2 pages.
Genbank Accession No. AAO79099.1, "putative alpha-1,2-mannosidase [Bacteroides thetaiotaomicron VPI-5482]," Feb. 8, 2011, 2 pages.
Genbank Accession No. AF212153 GI:6979643, "Hypocrea jecorina 1,2-a-D-mannosidase (MDS1) mRNA, complete cds," Feb. 16, 2000, 2 pages.
GenBank Accession No. AF441127 GI:16974782, "Yarrowia lipolytica Mnn9p (mnn9) gene, complete cds," Apr. 11, 2003, 2 pages.
GenBank Accession No. AJ563920 GI:38488499, "Yarrowia lipolytica ochl gene for alpha 1,6 mannosyltransferase," Nov. 20, 2003, 2 pages.
GenBank Accession No. AJ865333 GI:56266607, "*Trypanosoma brucei* brucei glcaseIIa gene for glucosidase II alpha subunit precursor," Oct. 25, 2005, 2 pages.
GenBank Accession No. BAA00258.1 GI:217809, "alkaline protease, partial [Aspergillus oryzae]," Dec. 20, 2002, 2 pages.
GenBank Accession No. BAA08634 GI:1171477, "alpha-mannosidase [Aspergillus saitoi]" Feb. 10, 1999, 1 page.
GenBank Accession No. BAJ83907, "sulfatase modifying factor 1 [Hemicentrotus pulcherrimus]," Nov. 10, 2011, 2 pages.
GenBank Accession No. ELW48757.1, GI: 444707484, "Sulfatase-modifying factor 1 [Tupaia chinensis]," Jan. 31, 2013, 2 pages.
GenBank Accession No. ENN77245.1, GI: 478257082, "hypothetical protein YQE_06075, partial [Dendroctonus ponderosae]," Apr. 10, 2013, 2 pages.
GenBank Accession No. NP_001069544, "sulfatase-modifying factor 1 precursor [Bos taurus]," Jan. 23, 2012, 2 pages.
GenBank Accession No. NP_215226.1, "unnamed protein product [*Mycobacterium tuberculosis* H37Rv]," Jan. 19, 2012, 2 pages.
GenBank Accession No. NP_630514 GI:21224735, "hypothetical protein SCO6428 [Streptomyces coelicolor A3(2)]," Jan. 19, 2012, 3 pages.
GenBank Accession No. NP_630514, "secreted protein [Streptomyces coelicolor A3(2)]," 2 pages, Sep. 26, 2008.

(56) References Cited

OTHER PUBLICATIONS

GenBank Accession No. NP_631591.1, "hypothetical protein SC07548 [Streptomyces coelicolor A3(2)]," Jan. 19, 2012, 2 pages.
GenBank Accession No. NP_812442 GI:29348939, "alpha-1,2-mannosidase [Bacteroides thetaiotaomicron VPI-5482]" Jan. 20, 2012, 2 pages.
Genbank Accession No. XM_499811 GI:50543289, "Yarrowia lipolytica YALI0A06589p (YALI0A06589g) mRNA, complete cds," Oct. 29, 2008, 2 pages.
GenBank Accession No. XM_500574 GI:50546093, "Yarrowia lipolytica YALI0B06600p (YALI0B06600g) mRNA, complete cds," Oct. 29, 2008, 2 pages.
Genbank Accession No. XM_500811 GI:50546682, "Yarrowia lipolytica YALI0B12716p (YALI0B12716g) mRNA, complete cds," Oct. 29, 2008, 2 pages.
GenBank Accession No. XM_503488 GI:50552026, "Yarrowia lipolytica YALI0E03190p (YALI0E03190g) mRNA, complete cds," Oct. 29, 2008, 2 pages.
GenBank Accession No. XP_001374411, GI: 126336367, "PREDICTED: sulfatase-modifying factor 1-like [Monodelphis domestica]," May 31, 2011, 1 page.
GenBank Accession No. XP_003642070.1, GI: 363738801, "PREDICTED: sulfatase-modifying factor 1-like [Gallus gallus]," Dec. 16, 2011, 1 pages.
GenBank Accession No. XP_005511340.1, GI: 543740918, "PREDICTED: sulfatase-modifying factor 1 [Columba livia]," Sep. 15, 2013, 2 pages.
GenBank Accession No. XP_503768, GI: 50552716, "YALI0E10175p [Yarrowia lipolytica CLIB122]," Oct. 29, 2008, 2 pages.
GenBank Accession No. XP_504265.1, GI: 50553708, "YALI0E22374p [Yarrowia lipolytica CLIB122]," Oct. 29, 2008, 2 pages.
GenBank Accession No. YP_003013376 YP_003013376, "alpha-1,2-mannosidase [*Paenibacillus* sp. JDR-2]" Jun. 15, 2012, 3 pages.
GenBank Accession No. YP_003120664 GI:256420011, "alpha-1,2-mannosidase [Chitinophaga pinensis DSM 2588]," Jun. 18, 2012, 2 pages.
GenBank Accession No. YP_003584502 GI:295133826, "alpha-1,2-mannosidase [Zunongwangia profunda SM-A87]," Nov. 21, 2011, 2 pages.
GenBank Accession No. Z49631 GI:1015863, "*S. cerevisiae* chromosome X reading frame ORF YJR131w," Aug. 11, 1997, 2 pages.
GenBank Accession No. ZP_01061975 GI:86143590, "putative alpha-1,2-mannosidas [Leeuwenhoeldella blandensis MED217]," Nov. 9, 2010, 1 page.
GenBank Accession No. ZP_1885202 GI:149279069, "putative alpha-1,2-mannosidase [*Pedobacter* sp. BAL39]," Nov. 9, 2010, 1 page.
GenBank Accession No. ZP_02866543 GI:169349605, "hypothetical protein CLOSPI_00343 [Clostridium spiroforme DSM 1552]," Nov. 9, 2010, 2 pages.
GenBank Accession No. ZP_03677957 GI: 224537418, "hypothetical protein BACCELL_02296 [Bacteroides cellulosilyticus DSM 14838]," Nov. 10, 2010, 1 page.
GenBank Accession No. ZP_04848482 GI:253571075, "conserved hypothetical protein [*Bacteroides* sp. 1_1_6]" Jun. 9, 2010, 2 pages.
GenBank Accession No. ZP_05522540 GI:256784109, "secreted protein [Streptomyces lividans TK24]," Dec. 9, 2010, 2 pages.
GenBank Accession No. ZP_06527366 GI:289767988, "secreted protein [Streptomyces lividans TK24]" Oct. 26, 2010, 3 pages.
GenBank Accession No. ZP_07083984 GI:300774115, "probable alpha-1,2-mannosidase [Sphingobacterium spiritivorum ATCC 33861]," Dec. 1, 2010, 1 page.
GenBank Accession: CAC87611.1, "ERp44 protein [*Homo sapiens*]," 2 pages, Oct. 7, 2008.
GenBank, "Yarrowia lipolytica CLIB122 [gbpin]: 5967 CDS's (2945919 codons)," Codon Usage Database, [online], Jun. 15 2007 [retrieved on Aug. 15, 2014]. Retrieved from the Internet: <URL: http://www.kazusa.or.jp/codon/cgi-bin/showcodon.cgi?species=284591>, 1 page.
Gentzsch and Tanner, "The PMT gene family: protein O-glycosylation in *Saccharomyces cerevisiae* is vital," Embo J, 15(21):5752-5759, (1996).
Gerngross, "Advances in the production of human therapeutic proteins in yeasts and filamentous fungi," Nature Biotech., 22(11):1409-1414, (2004).
Ghaemmaghami et al., "Global analysis of protein expression in yeast" Nature. vol. 425, No. 6959 (Oct. 2003) pp. 737-741.
Gilbert, "Glycoside Hydrolase Family 92," CAZypedia [online], Mar. 4, 2010. Retrieved from the Internet: <URL: http://www.cazypedia.org/index.php/Glycoside_Hydrolase_Family_92>, 3 pages.
Gonzalez and Jordan, "The alpha-mannosidases: Phylogeny and adaptive diversification," Mol Biol Evol., 17(2):292-300, (Feb. 2000).
Gossen and Bujard, "Studying gene function in eukaryotes by conditional gene inactivation," Ann. Rev. Genetics 36:153-173, (2002).
Grinna and Robbins, "Substrate specificities of rat liver microsomal glucosidases which process glycoproteins," J. Biol. Chem., 255(6):2255-2258, (1980).
Grove et al., "In vitro characterization of AtsB, a radical SAM formylglycine-generating enzyme that contains three [4Fe—4S] clusters," *Biochemistry*, 47(28):7523-7538, Epub Jun. 18, 2008 [author manuscript].
Grubb et al., "New strategies for enzyme replacement therapy for lysosomal storage diseases," *Rejuvenation Res*., 13(2-3):229-236, Apr.-Jun. 2010.
Guarente et al., "A GAL10-CYC1 hybrid yeast promoter identifies the GAL4 regulatory region as an upstream site," *Proc Natl Acad Sci U S A*., 79(23):7410-7414, Dec. 1982.
Hamilton and Gerngross, "Glycosylation engineering in yeast: the advent of fully humanized yeast," Curr Opin Biotechnol., 18(5):387-392, (Oct. 2007).
Hamilton et al, "Production of complex human glycoproteins in yeast," Science, 301(5637):1244-1246, Aug. 2003.
Hedstrom, "Serine protease mechanism and specificity," *Chem Rev*., 102(12):4501-4524, Dec. 2002.
Henderson and Finn, "Human tumor antigens are ready to fly," Advances in Immunology, 62:217-256 (1996).
Henrissat, "A classification of glycosyl hydrolases based on amino acid sequence similarities," *Biochem J*., 280 ( Pt 2):309-316, Dec. 1, 1991.
Hermans et al., "Human lysosomal alpha-glucosidase: functional characterization of the glycosylation sites," Biochem J., 289 ( Pt 3):681-686, (Feb. 1993).
Herscovics., "Processing glycosidases of *Saccharomyces cerevisiae,*" *Biochimica Biophysica. Acta*., 1426(2):275-285, Jan. 6, 1999.
Hinnen et al. "Transformation of yeast," *Proc Nall Acad Sci U S A*., 75(4):1929-1933, Apr. 1978.
Hosokawa et al., "EDEM1 accelerates the trimming of alpha1,2-linked mannose on the C branch of N-glycans," *Glycobiology*., 20(5):567-575, Epub Jan. 11, 2010.
Howard et al., "Identification of the Active Site Nucleophile in Jack Bean alpha-Mannosidase Using 5-Fluoro-beta-L-Gulosyl Fluoride," J. Biol. Chem., 273(4):2067-2072, 1998.
Hudson and Kortt, "High avidity scFv multimers; diabodies and triabodies," J. Immunol. Methods, 231(1-2):177-189, (1999).
Huston et al. "Engineered antibodies take center stage," Hum. Antibodies, 10(3-4):127-142, (2001).
Ichishima et al., "Molecular and enzymic properties of recombinant 1,2-alpha-mannosidase from Aspergillus saitoi overexpressed in Aspergillus oryzae cells," Biochem. J., 339: 589-597, (1999).
Inoue et al., "Molecular cloning and nucleotide sequence of the 1,2-alpha-D-mannosidase gene, msdS, from Aspergillus saitoi and expression of the gene in yeast cells," Biochim Biophys Acta. 1253(2):141-145, Dec. 6, 1995.
InterPro—Protein sequence anaylsis and classification, "Species: Sulfatase-modifying factor enzyme (IPR005532)," EMBL-EBI, [online]. Retrieved from the Internet: <URL: http://www.ebi.ac.uk/interpro/entry/IPR005532/taxonomy;jsessionid=A50B4C8B868FB85867E9D179F3959BED>, 2 pages, retrieved on Nov. 3, 2015.

(56) References Cited

OTHER PUBLICATIONS

Ito et al., "Transformation of intact yeast cells treated with alkali cations," J. Bacteriol., 153(1):163-168, (1983).
Jaafar et al., "Isolation of the MNN9 gene of Yarrowia lipolytica (Y1MNN9) and phenotype analysis of a mutant ylmnn9 Delta strain," Yeast, 20(7):633-644, May 2003.
Jacobs et al. "Engineering complex-type N-glycosylation in Pichia pastoris using Glyco Switch technology," Nat Protoc., 2009;4(1):58-70., Epub Dec. 18, 2008.
Kim et al., "Functional characterization of the Hansenula polymorpha HOC1, OCH1, and OCR1 genes as members of the yeast OCH1 mannosyltransferase family involved in protein glycosylation," J Biol Chem., 281(10):6261-6272, Epub Jan. 10, 2006.
Klis et al., "Cell wall construction in Saccharomyces cerevisiae," Yeast, 23(3):185-202, 2006.
Komeda et al., "Construction of protease-deficient Candida boidinii strains useful for recombinant protein production: cloning and disruption of proteinase A gene (PEP4) and proteinase B gene (PRBI)," Biosci Biotechnol Biochem., 66(3):628-631, Mar. 2002.
Kornfeld and Kornfeld, "Assembly of asparagine-linked oligosaccharides," Annu Rev Biochem., 55:631-664, (1985).
Kotula and Curtis, "Evaluation of foreign gene codon optimization in yeast: expression of a mouse IG kappa chain," Biotechnology (N Y)., 9(12):1386-1389, (1991).
Kuroda et al., "Production of Man5GlcNAc2-type sugar chain by the methylotrophic yeast Ogataea minuta," FEMS Yeast Res., 6:1052-1062 (2006).
Kuroda et al., "Antibody expression in protease-deficient strains of the methylotrophic yeast Ogataea minuta," FEMS Yeast Res., 7(8):1307-1316. Epub Aug. 22, 2007.
Landgrebe et al., "The human SUMF1 gene, required for post-translational sulfatase modification, defines a new gene family which is conserved from pro-to eukaryotes," Gene., 316:47-56, Oct. 16, 2003.
Laroy et al., "Glycome mapping on DNA sequencing equipment," Nature Protocols, 1: 397-405 (2006).
Le Drill et al., "Multiple-copy integration in the yeast Yarrowia lipolytica," Curr Genet., 26(1):38-44, Jul. 1994.
Lee and Park, "Enzymatic in vitro glycosylation using peptide-N-glycosidase F," Enzyme and Microbial Technology, 30(6):716-720, (2002).
Li et al., "Optimization of humanized IgGs in glycoeng neered Pichia pastoris," Nat Biotechnol., 24(2):210-215, Epub Jan. 22, 2006.
Liang et al., "The crystal structures of two cuticle-degrading proteases from nematophagous fungi and their contribution to infection against nematodes," FASEB J., 24(5):1391-1400, Epub Dec. 9, 2009.
Liao et al., "Cloning, expression, purification, and characterization of the human broad specificity lysosomal acid alpha-mannosidase," J. Biol Chem., 271(45):28348-28358, (Nov. 1996).
Lin et al., "Display of a functional hetero-oligomeric catalytic antibody on the yeast cell surface," App. Microbiol Biotechol., 62(2-3): 226-232, print Aug. 2003, Epub Mar. 2003.
Liu et al., "Disruption of the OCH1 and MNN1 genes decrease N-glycosylation on glycoprotein expressed in Kluyveromyces lactis," J Biotechnol., 143(2):95-102, Epub Jun. 24, 2009.
Lobsanov et al., "Modulation of activity by Arg407: structure of a fungal alpha-1,2-mannosidase in complex with a substrate analogue," Acta Crystallogr D Biol Crystallogr., 64(Pt 3):227-236, (2008).
Lobsanov et al., "Structure of Penicillium citrinum alpha 1,2-mannosidase reveals the basis for differences in specificity of the endoplasmic reticulum and Golgi class I enzymes," J Biol Chem., 277(7):5620-5630, Epub Nov. 19, 2001.
Luer and Hatton, "Vancomycin administration into the cerebrospinal fluid: a review ," Annals of Pharmacotherapy, 27:912-921, 1993.
Madzak et al., "Heterologous protein expression and secretion in the non-conventional yeast Yarrowia lipolytica: a review," J Biotechnol., 109(1-2):63-81, Apr. 8, 2004.
Madzak et al., "Strong hybrid promoters and integrative expression/secretion vectors for quasi-constitutive expression of heterologous proteins in the yeast Yarrowia lipolytica," J Mol Microbiol Biotechnol., 2(2):207-216, (Apr. 2000).
Maras et al., "Molecular cloning and enzymatic characterization of a Trichoderma reesei 1, 2-alpha-D-inaimosidase," J. Biotechnol, 77: 255-263 (2000).
Mariappan et al., "ERp44 mediates a thiol-independent retention of formylglycine-generating enzyme in the endoplasmic reticulum," J Biol Chem., 283(10):6375-6383, Epub Jan. 4, 2008.
Martinet et al., "Protection of mice against a lethal influenza challenge by immunization with yeast-derived recombinant influenza neuraminidase," Eur J Biochem., 247(1):332-338, (Jul. 1997).
Mast and Moremen, "Family 47 alpha-mannosidases in N-glycan processing," Methods Enzymol., 415:31-46, 2006.
Matsuoka et al., "Analysis of regions essential for the function of chromosomal replicator sequences from Yarrowia lipolytica," Mol. Gen Genet., 237(3):327-333, Mar. 1993.
Merkle et al., Cloning, expression, purification, and characterization of the murine lysosomal acid alpha-mannosidase, Biochim Biophys Acta., 1336(2):132-146, (Aug. 1997).
Mille et al., "Identification of a new family of genes involved in beta-1,2-mannosylation of glycans in Pichia pastoris and Candida albicans," J Biol Chem., 283(15):9724-9736. Epub Jan. 30, 2008.
Moreau and Morré, "Cell-free transfer of membrane lipids. Evidence for lipid processing," J Biol Chem., 266(7):4329-4333, Mar. 5, 1991.
Moreau et al., "Trafficking of lipids from the endoplasmic reticulum to the Golgi apparatus in a cell-free system from rat liver," J Biol Chem., 266(7):4322-4328, Mar. 5, 1991.
Moreland et al., "Species-specific differences in the processing of acid α-glucosidase are due to the amino acid identity at position 201," Gene, 491(1):25-30, Jan. 1, 2012.
Moreland et al., "Lysosomal acid alpha-glucosidase consists of four different peptides processed from a single chain precursor," J Biol Chem., 280(8):6780-6791, Epub Nov. 1, 2004.
Mori et al., "Signalling from endoplasmic reticulum to nucleus: transcription factor with a basic-leucine zipper motif is required for the unfolded protein-response pathway," Genes Cells, vol. 1, No. 9 (Sep. 1996), pp: 803-817.
Morya et al., "In silico characterization of alkaline proteases from different species of Aspergillus," Appl Biochem Biotechnol., 166(1):243-257, Epub Nov. 10, 2011.
Nakadai et al., "Purification and Properties of Alkaline Proteinase from Aspergillus oryzae," Agr. Biol. Chem., 37(12): 2685-2694, 1973.
NCBI Reference Sequence: NP_000909.2, "protein disulfide-isomerase precursor [Homo sapiens]," Mar. 24, 2012, 4 pages.
NCBI Reference Sequence: XP_502492.1, "YALI0D06589p [Yarrowia lipolytica CL1B122]," 2 pages, Oct. 29, 2008.
NCBI Reference Sequence: XP_502939.1, "YALI0D17424p [Yarrowia lipolytica CLIB122]," 2 pages, Oct. 29, 2008.
Nett et al., "A combinatorial genetic library approach to target heterologous glycosylation enzymes to the endoplasmic reticulum or the Golgi apparatus of Pichia pastoris," Yeast., 28(3):237-252, Epub. Jan. 6, 2011.
Newman and Ferro-Novick, "Characterization of new mutants in the early part of the yeast secretory pathway isolated by a [3H]mannose suicide selection," J. Cell Biol., 105(4):1587-1594, (1987).
Nicaud et al., "Protein expression and secretion in the yeast Yarrowia lipolytica," FEMS Yeast Res., 2(3):371-379, Aug. 2002.
Odani et al., "Cloning and analysis of the MNN4 gene required for phosphorylation of N-linked oligosaccharides in Saccharomyces cerevisiae," Glycobiology., 6(8):805-810, Dec. 1996.
Odani et al., "Mannosylphosphate transfer to cell wall mannan is regulated by the transcriptional level of the MNN4 gene in Saccharomyces cerevisiae," FEBS Letters., 420(2-3)186-190, Dec. 29, 1997.
Orlean et al., "Cloning and sequencing of the yeast gene for dolichol phosphate mannose synthase, an essential protein," J. Biol. Chem., vol. 263, (Nov. 1988), pp. 17499-17507.
Park et al, "Essential role of Y1MPO1, a novel Yarrowia lipolytica homologue of Saccharomyces cerevisiae MNN4, in man-

(56) References Cited

OTHER PUBLICATIONS nosylphosphorylation of N- and O-linked glycans," Appl Environ Microbiol., 77(4):1187-1195, Epub Dec. 23, 2010.
Paulik et al., "Cell-free transfer of the vesicular stomatitis virus G protein from an endoplasmic reticulum compartment of baby hamster kidney cells to a rat liver Golgi apparatus compartment for Man8-9 to ManS processing," *Arch Biochem Biophys.*, 367(2):265-273, Jul. 15, 1999.
Peberdy et al., "Protein secretion by fungi," Applied Micology and Biotechnology, Agriculture and Food Production, 1:73-114, 2001.
Penttilä et al., "Expression of two Trichoderma reesei endoglucanases in the yeast *Saccharomyces cerevisiae," Yeast.*, 3(3):175-185, Sep. 1987.
Perona and Craik et al., "Stuctural basis of substrate specificity in the serine proteases," *Protein Sci.*, 4(3):337-360, Mar. 1995.
Pignède et al., "Characterization of an extracellular lipase encoded by LIP2 in Yarrowia lipolytica," *J. Bacteriol.*, 182(10):2802-10, May 2000.
Platt and Lachmann, "Treating lysosomal storage disorders: Current practice and future prospects," Biochim Biophys Acta, 1793(4):737-745, 2009.
Poljak, "Production and structure of diabodies," Structure, 2(12):1121-1123, (1994).
Potgieter et al., "Production of monoclonal antibodies by glycoengineered Pichia pastoris," *J Biotechnol.*, Feb. 23, 2009;139(4):318-325, Epub Dec. 27, 2008.
Protein Data Bank, "Structure of the GH92 Family Glycosylhydrolase CCMAN5" Deposition: Sep. 29, 2010 [retrieved Jul. 17, 2012]. Retrieved from the Internet: < URL: http://www.pdb.org/pdb/explore/explore.do?structureId=2XSG>, 2 pages.
Rabuka et al., "Site-specific chemical protein conjugation using genetically encoded aldehyde tags," *Nat Protoc.*, 7(6):1052-1067, May 10, 2012.
Rakestraw and Wittrup, "Contrasting secretory processing of simultaneously expressed heterologous proteins in *Saccharomyces cerevisiae," Biotechnol. Bioeng.*, 93(5):896-905, Apr. 2006.
Rawlings and Barrett, "Evolutionary families of peptidases," *Biochem J.*, 290 ( Pt 1):205-218, Feb. 15, 1993.
Rexach et al., "Distinct biochemical requirements for the budding, targeting, and fusion of ER-derived transport vesicles," *J Cell Biol.*, 114(2):219-229, Jul. 1991.
Richard et al., "Tagging morphogenetic genes by insertional mutagenesis in the yeast Yarrowia lipolytica," J Bacteriol., 183(10):3098-3107, (May 2001).
Rodriguez et al., "Production of recombinant human N-acetylgalactosamine-6-sulfate sulfatase enzyme in Pichia pastoris," *Molecular Genetics and Metabolism*, 108(2):S79-S80, Abstract 197, Feb. 1, 2013.
Roeser et al., "A general binding mechanism for all human sulfatases by the formylglycine-generating enzyme," *Proc Natl Acad Sci U S A.* 103(1):81-86, Epub Dec. 20, 2005.
Rose, "Glycoside Hydrolase Family 38," CAZypedia [online], Feb. 2, 2010. Retrieved from the Internet: <URL: http://www.cazypedia.org/index.php/Glycoside_Hydrolase_Family_38>, 3 pages.
Ruiz-Herrera and Sentandreu, "Different effectors of dimorphism in Yarrowia lipolytica," *Arch. Microbiol.*, 178(6): 477-483, print Dec. 2002, Epub Oct. 2002.
Ryckaert et al., "Isolation of antigen-binding camelid heavy chain antibody fragments (nanobodies) from an immune library displayed on the surface of Pichia pastoris," J Biotechnol. 145(2):93-98,.
Sakuma et al., "HpSumf1 is involved in the activation of sulfatases responsible for regulation of skeletogenesis during sea urchin development," *Dev Genes Evol.*, 221(3):157-166, Epub Jun. 27, 2011.
Sardiello et al., "Sulfatases and sulfatase modifying factors: an exclusive and promiscuous relationship," Hum Mol Genet, 14(21):3203-3217, Epub Sep. 20, 2005.
Seffernick et al., "Melamine deaminase and atrazine chlorohydrolase: 98 percent identical but functionally different," J Bacteriol., 183(8):2405-2410, Apr. 2001.
Shusta et al., "Increasing the secretory capacity of *Saccharomyces cerevisiae* for production of single-chain antibody fragments," *Nat. Biotechnol.*, 16(8): 773-777, Aug. 1998.
Shusta et al., "Yeast polypeptide fusion surface display levels predict thermal stability and soluble secretion efficiency," *J. Mol. Biol.*, 292(5):949-956, Oct. 1999.
Siezen et al., "Subtilases: the superfamily of subtilisin-like serine proteases," *Protein Sci.*, 6(3):501-523, Mar. 1997.
Smith and Waterman, "Comparison of biosequences," Adv. Appl. Math., 2(4):482-489, (Dec. 1981).
Song et aI., "Characterization of Genes Involved in N-glycosylation in Yarrowia lipolytica," Yeast, 20:S147 (2003).
Song et al., "Engineering of the Yeast Yarrowia lipolytica for the Production of Glycoproteins Lacking the Outer-Chain Mannose Residues of N-Glycans," Appl Environ Microbiol., vol. 73, No. 14 (Jul. 2007), pp. 4446-4454.
Sreekrishna et al., "Invertase gene (SUC2) of *Saccharomyces cerevisiae* as a dominant marker for transformation of Pichia pastoris," *Gene*, 59(1):115-125, 1987.
Stocks, "Intrabodies: production and promise," Drug Discov. Today 9(22): 960-966, (Nov. 2004).
Swennen et al., "Folding proteome of Yarrowia lipolytica targeting with uracil permease mutants," J Proteome Res., 9(12):6169-6179, Epub Nov. 12, 2010.
Swennen et al., "Secretion of active anti-Ras single-chain Fv antibody by the yeasts Yarrowia lipolytica and Kluyveromyces lactis," *Microbiology*, 148(Pt 1):41-50, Jan. 2002.
Swiss Protein Accession No. P15291, Nov. 30, 2010, 9 pages.
Swiss Protein Accession No. P26572, Nov. 30, 2010, 4 pages.
Swiss Protein Accession No. P38069, Nov. 30, 2010, 3 pages.
Swiss Protein Accession No. Q09326, Nov. 30, 2010, 3 pages.
Swiss Protein Accession No. Q24451, Nov. 30, 2010, 12 pages.
Tajima et al., "Use of a modified alpha-N-acetylgalactosaminidase in the development of enzyme replacement therapy for Fabry disease," *Am J Hum Genet.*, 85(5):569-580 Epub Oct. 22, 2009.
Tanino et al., "Construction of a Pichia pastoris cell-surface display system using Flo1p anchor system," *Biotechnol. Prog.*, 22(4): 989-993, Jul.-Aug. 2006.
Tiels et al., "A bacterial glycosidase enables mannose-6-phosphate modification and improved cellular uptake of yeast-produced recombinant human lysosomal enzymes," Nat Biotechnol., 30(12):1225-1231, Epub Nov. 18, 2012.
Tremblay and Herscovics, "Cloning and expression of a specific human alpha 1,2-mannosidase that trims Man9GlcNAc2 to Man8GlcNAc2 isomer B during N-glycan biosynthesis," Glycobiology., 9(10):1073-1078, (Oct. 1999).
Ueda et al., "Cell surface engineering of yeast: construction of arming yeast with biocatalyst," *J. Biosci. Bioeng.*, 90(2): 125-136, 2000.
UniProtKB/Swiss-Prot: P01588, "Erythropoietin precursor (Epoetin)," Jul. 21, 1986, 7 pages.
UniProtKB/Swiss-Prot: P04062, "Glucosylceramidase precursor (Beta-glucocerebrosidase) (Acid beta-glucosidase) (D-glucosyl-N-acylsphingosine glucohydrolase) (Alglucerase) (Imiglucerase)," Nov. 1, 1986, 31 pages.
UniProtKB/Swiss-Prot: P06280.1 GI:113499, "RecName: Full=Alpha-galactosidase A; AltName: Full=Alpha-D-galactosidase A; AltName: Full=Alpha-D-galactoside galactohydrolase; AltName: Full=Melibiase; AltName: INN=Agalsidase; Flags: Precursor," Jun. 13, 2012, 26 pages.
UniProtKB/Swiss-Prot: P15291.5 GI:116241264, "RecName: Full=Beta-1,4-galactosyltransferase 1; Short=Beta-1,4-GalTase 1; Short=Beta4Gal-T1; Short=b4Gal-T1; AltName: Full=UDP-Gal:beta-GlcNAc beta-1,4-galactosyltransferase 1; AltName: Full=UDP-galactose:beta-N-acetylglucosamine beta-1,4-galactosyl transferase . . . " Jun. 13, 2012, 10 pages.
UniProtKB/Swiss-Prot: P26572.2 GI:311033399, "RecName: Full=Alpha-1,3-mannosyl-glycoprotein 2-beta-N-acetylglucosaminyltransferase; AltName: Full=N-glycosyl-oligosaccharide-glycoprotein N-acetylglucosaminyltransferase I; Short=GNT-I; Short=GlcNAc-T I," Apr. 18, 2012, 6 pages.

(56) References Cited

OTHER PUBLICATIONS

UniProtKB/Swiss-Prot: P27809.1 GI:127214, "RecName: Full=Glycolipid 2-alpha-mannosyltransferase; AltName: Full=Alpha-1,2-mannosyltransferase," Jun. 13, 2012, 8 pages.
UniProtKB/Swiss-Prot: P38069.1 GI:586137, "RecName: Full=Alpha-1,2-mannosyltransferase MNN2; AltName: Full=Calcium resistance and vanadate sensitivity protein 4; AltName: Full=Mannan synthesis protein MNN2," Jun. 13, 2012, 5 pages.
UniProtKB/Swiss-Prot: Q09326.1 GI:1169978, "RecName: Full=Alpha-1,6-mannosyl-glycoprotein 2-beta-N-acetylglucosaminyltransferase; AltName: Full=Beta-1,2-N-acetylglucosaminyltransferase II; AltName: Full=GlcNAc-T II; Short=GNT-II; AltName: Full=Mannoside acetylglucosaminyltransferase 2; AltName: Full=N-g . . . ," Jun. 13, 2012, 3 pages.
UniProtKB/Swiss-Prot: Q24451.2 GI:32130434, "RecName: Full=Alpha-mannosidase 2; AltName: Full=Golgi alpha-mannosidase II; Short=AMan II Short=Man II; AltName: Full=Mannosyl-oligosaccharide 1,3-1,6-alpha-mannosidase," Apr. 18, 2012, 13 pages.
UniProtKB/Swiss-Prot: Q9Y7X5.1 GI:74698597, "RecName: Full=Uncharacterized protein C365.14c," May 16, 2012, 2 pages.
Van den Elsen et al., "Structure of Golgi alpha-mannosidase II: a target for inhibition of growth and metastasis of cancer cells," *EMBO J.*, 20(12):3008-3017, Jun. 15, 2001.
Van Hove et al., "High-level production of recombinant human lysosomal acid alpha-glucosidase in Chinese hamster ovary cells which targets to heart muscle and corrects glycogen accumulation in fibroblasts from patients with Pompe disease," Proc Natl Acad Sci U S A., 93(1):65-70, Jan. 9, 1996.
VanAntwerp and Wittrup, "Fine affinity discrimination by yeast surface display and flow cytometry," *Biotechnol. Prog.*, 16(1): 31-7, Jan.-Feb. 2000.
Vandersall-Nairn et al., "Cloning, expression, purification, and characterization of the acid α-mannosidase from Trypanosoma cruzi," Glycobiology, 8(12):1183-1194, (1998).
Vega et al., "Partial characterization of α-mannosidase from Yarrowia lipolytica," *J Basic Microbiol.*, 28(6):371-379, 1988.
Vernis et al., "An origin of replication and a centromere are both needed to establish a replicative plasmid in the yeast Yarrowia lipolytica," *Mol. Cell Biol.*, 17(4): 1995-2004, Apr. 1997.
Verostek et al., "Glycoprotein biosynthesis in the alg3 *Saccharomyces cerevisiae* mutant. I. Role of glucose in the initial glycosylation of invertase in the endoplasmic reticulum," The Journal of Biological Chemistry, vol. 268, (Jun. 5, 1993), pp. 12095-12103.
Verostek et al., "Glycoprotein biosynthesis in the alg3 *Saccharomyces cerevisiae* mutant. II. Structure of novel Man6-10GlcNAc2 processing intermediates on secreted invertase," The Journal of Biological Chemistry, vol. 268, pp. 12104-12115, (Jun. 5, 1993).
Vervecken et al. "In Vivo Synthesis of Mammalian-Like, Hybrid-Type N-Glycans in Pichia pastoris," Appl. Environ. Microb., 70(5):2639-2646, (May 2004).
Vervecken et al., "Modification of the N-glycosylation pathway to produce homogeneous, human-like glycans using GlycoSwitch plasmids," Methods Mol Biol., 389:119-138, 2007.
Vocadlo et al., "Mechanistic insights into glycosidase chemistry," Curr. Opin. Chem. Biol., 12:539-555 (2008).
Voznyi et al., "A fluorimetric enzyme assay for the diagnosis of MPS II (Hunter disease)," *J Inherit Metab Dis.*, 24(6):675-680, Nov. 2001.
Wang and Shusta, "The use of scFv-displaying yeast in mammalian cell surface selections," *J. Immunol. Methods*, 304(1-2):30-42, Sep. 2005.
Wang et al., "A new yeast display vector permitting free scFv amino termini can augment ligand binding affinities," *Protein Eng. Des. Sel.*, 18(7): 337-343, print Jul. 2005, Epub Jun. 2005.
Wang et al., "Construction of a novel Pichia pastoris cell-surface display system based on the cell wall protein Pirl," *Curr. Microbiol.*, 56(4): 352-357, Apr. 2008.
Ward et al., "Characterization of Humanized Antibodies Secreted by Aspergillus niger," Appl. Environ. Microbiol., 70(5):2567-2576, (May 2004).
Wheeler et al. "Intrabody and Intrakine Strategies for Molecular Therapy," Mol. Ther., 8(3):355-366, (Sep. 2003).
Whisstock and Lesk, "Prediction of protein function from protein sequence and structure" *Q Rev Biophys.*, 36(3):307-340, Aug. 2003.
Witkowski et al. "Conversion of a beta-ketoacyl synthase to a malonyl decarboxylase by replacement of the active-site cysteine with glutamine" Biochemistry, 38(36):11643-11650, Sep. 7, 1999.
Wright et al., "Structure of subtilisin BPN' at 2.5 angström resolution," *Nature*, 221(5177):235-242, Jan. 18, 1969.
Wu et al., Asparagine-linked glycosylational modifications in yeast, Cell Engineering, 3:215-232, 2002.
YALI0A16819g YALI0A16819p[Yarrowia lipolytica CLIB122] Gene ID: 2906333, created on Jul. 24, 2004, 2 pages.
YALI0C10135g YALI0C10135p[Yarrowia lipolytica CLIB122] Gene ID: 7009445, created on Oct. 29, 2008, 2 pages.
YALI0D10835g YALI0D10835p[Yarrowia lipolytica CLIB122] Gene ID: 2910442, created on Jul. 24, 2004, 2 pages.
YALI0E10175g YALI0E10175p[Yarrowia lipolytica CLIB122] Gene ID: 2912589, created on Jul. 28, 2004, 2 pages.
YALI0E20823g YALI0E20823p[Yarrowia lipolytica CLIB122] Gene ID:2911836, created on Jul. 28, 2004, 2 pages.
YALI0E22374g YALI0E22374p[Yarrowia lipolytica CLIB122] Gene ID: 2912981, created on Jul. 28, 2004, 2 pages.
YALI0E24981g YALI0E24981p[Yarrowia lipolytica CLIB122 Gene ID: 2912672, created on Jul. 28, 2004, 2 pages.
YALI0E34331g YALI0E34331p[Yarrowia lipolytica CLIB122] Gene ID: 2912367, created on Jul. 28, 2004, 2 pages.
Yang et al., "Cell-surface display of the active mannanase in Yarrowia lipolytica with a novel surface-display system," Biotechnol Appl Biochem, vol. 54, No. 3 (Oct. 2009), pp. 171-176.
Yao et al., "Degradation of HSA-AX15(R13K) when expressed in Pichia pastoris can be reduced via the disruption of YPS1 gene in this yeast," J Biotechnol. 139(2):131-136. Epub Oct . 8, 2008.
Yeung and Wittrup, "Quantitative screening of yeast surface-displayed polypeptide libraries by magnetic bead capture," *Biotechnol. Prog.*, 18(2):212-220, Mar.-Apr. 2002.
Ying et al., "Soluble monomeric IgG1 Fc," *J Biol Chem.*, 287(23):19399-19408, Epub Apr. 19, 2012.
Yue et al., "Construction of a new plasmid for surface display on cells of Yarrowia lipolytica," J Microbiol Methods, vol. 72, No. 2 (Feb. 2008), pp. 116-123.
Zhu and Zhang, "SCPD: a promotor database of the yeast *Saccharomyces cerevisiae*," Bioinformatics, 15(7-8):607-611, (1999).
Zhu et al., "Glycoengineered acid alpha-glucosidase with improved efficacy at correcting the metabolic aberrations and motor function deficits in a mouse model of Pompe disease," Mol Ther., 17(6):954-963, Epub Mar. 10, 2009.
Zhu et al., "Mechanistic insights into a Ca2+-dependent family of alpha-mannosidases in a human gut symbiont," Nat. Chem. Biol., 6(2):125-132. Epub 2009 Dec. 27, 2010.
Zhu et al., "Mechanistic insights into a Ca2+-dependent family of alpha-mannosidases in a human gut symbiont," Nat. Chem. Biol., 6(2):125-132. Supplementary Information, 25 pages. Epub 2009 Dec. 27, 2010.
Zimm et al., "Cerebrospinal fluid pharmacokinetics of intraventricular and intravenous aziridinylbenzoquinone," Cancer Research, 44(4):1698-1701, Apr. 1984.
Zito et al., "Sulphatase activities are regulated by the interaction of sulphatase-modifying factor 1 with SUMF2," *EMBO Rep.*, 6(7):655-660, Jul. 2005.
International Preliminary Report on Patentability in PCT/IB2010/002589, dated May 30, 2012, 49 pages.
International Search Report and Written Opinion in PCT/IB2010/002589, dated Aug. 5, 2011.
Korean Grounds for Rejection in Korean Patent Application No. 10-2009-7022979, dated Feb. 10, 2017, 4 pages with English translation.
Korean Grounds for Rejection in Korean Patent Application No. 10-2015-7035851, dated Feb. 10, 2017, 4 pages with English translation.

(56) References Cited

OTHER PUBLICATIONS

Written Opinion of the International Preliminary Examining Authority in PCT/IB2010/002589, dated Apr. 23, 2012, 10 pages.
Written Opinion of the International Preliminary Examining Authority in PCT/IB2010/002589, dated Jan. 31, 2012, 11 pages.
Glycoside Hydrolase Family 38, accessed Jul. 30, 2017 at URL cazypedia.org/index.php/Glycoside_Hydrolase_Family_38, 1 page.
Tatsumi et al., "Cloning and Sequencing of the Alkaline Protease cDNA from Aspergillus Oryzae," Agric Biol Chem., 52(7):1887-1888, 1988.
Translation of Russian Office Action in International Application No. 2014139953, 3 pages.
Chinese Office Action in International Application No. 201410681757.1, dated Aug. 11, 2017, 5 pages (with English Translation).
Bohnsack et al., "Cation-independent mannose 6-phosphate receptor," *J Biol Chem*., 284(50):35215-35226, Dec. 11, 2009.
Gande et al., "Paralog of the formylglycine-generating enzyme—retention in the endoplasmic reticulum by canonical and noncanonical signals," FEBS J., 275(6):1118-1130, Epub Feb. 6, 2008.
glycoforum.grjp' [online] "$^{\alpha}$-Mannosidases and EDEM homolog proteins: their roles in glycoprotein ERAD," Jun. 5, 2006, Retrieved online Feb. 15, 2018, Retrieved URL: http://www.glycoforum.gr.jp/science/word/qualitycontrol/QS-A02E.html, 2 pages.
Guo et al., "Protein tolerance to random amino acid change," Proc Natl Acad Sci U S A., 101(25):9205-9210, Epub Jun. 14, 2004.
Japanese Office Action in International Application No. 2016-042290, dated Jan. 24, 2018, 19 pages (with English Translation).
Japanese Office Action in International Application No. 2017-000348, dated Jan. 17, 2018, 12 pages (with English Translation).
Korean Office Action in International Application No. 10-2013-7011113, dated Nov. 14, 2017, 13 pages (with English Translation).
Korean Office Action in International Application No. 10-2013-7011110, dated Nov. 14, 2017, 16 pages (with English Translation).
Makde et al., "Structure and Mutational Analysis of the PhoN Protein of *Salmonella typhimurium* Provide Insight into Mechanistic Details," Biochemistry., 46:2079-2090, 2007.
Song et al., "Glycan Microarray analysis of P-type lectins reveals distinct phosphomannose glycan recognition," *J Biol Chem*., 284(50):35201-35214, Dec. 11, 2009.
Zhu et al., "Conjugation of mannose 6-Phosphate-containing Oligosaccharides to acid $^{\alpha}$-Glucosidase improves the clearance of glycogen in pompe mice," J Biol Chem., 279(48):50336-50341, Nov. 26, 2004.
U.S. Appl. No. 12/062,469, filed Apr. 3, 2008, U.S. Pat. No. 8,026,083, Sep. 27, 2011, Callewaert.
U.S. Appl. No. 13/095,532, filed Apr. 27, 2011, U.S. Pat. No. 9,222,083, Dec. 29, 2015, Callewaert.
U.S. Appl. No. 13/094,606, filed Apr. 26, 2011, U.S. Pat. No. 8,597,906, Dec. 3, 2013, Callewaert.
U.S. Appl. No. 13/620,259, filed Sep. 14, 2012, 2013/0195835, Aug. 1, 2013, Callewaert.
U.S. Appl. No. 13/620,306, filed Sep. 14, 2012, U.S. Pat. No. 9,206,408, Dec. 8, 2015, Callewaert.
U.S. Appl. No. 13/574,126, filed Nov. 12, 2012, Ryckaert.
U.S. Appl. No. 13/499,061, filed Sep. 6, 2012, U.S. Pat. No. 9,598,682, Mar. 21, 2017, Callewaert.
U.S. Appl. No. 13/510,527, filed Oct. 31, 2012, 2013/0053550, Feb. 28, 2013, Geysens.
U.S. Appl. No. 14/641,002, filed Mar. 6, 2015, 2015/0337273, Nov. 26, 2015, Geysens et al.
U.S. Appl. No. 13/876,730, filed Mar. 28, 2013, U.S. Pat. No. 9,689,015, Nov. 7, 2013, Piens.
U.S. Appl. No. 15/594,256, filed May 12, 2017, Piens.
U.S. Appl. No. 13/876,769, filed Jun. 19, 2013, U.S. Pat. No. 9,347,050, May 24, 2016, Piens et al.
U.S. Appl. No. 15/087,201, filed Mar. 31, 2016, 2016/0251693, Sep. 1, 2016, Piens.
U.S. Appl. No. 14/369,324, filed Jun. 27, 2014, 2015/0031081, Jan. 29, 2015, Vervecken.
U.S. Appl. No. 13/831,368, filed Mar. 14, 2013, U.S. Pat. No. 9,249,399, Feb. 2, 2016, Vervecken.
U.S. Appl. No. 14/981,123, filed Dec. 28, 2015, 2016/0279254, Sep. 29, 2016, Vervecken.
U.S. Appl. No. 14/773,234, filed Sep. 4, 2015, Vervecken.
Wisselaar et al., "Structural and functional changes of lysosomal acid a-glucosidase during intracellular transport and maturation," J Biol Chem., 268(3):2223-2231, Jan. 25, 1993.
European Office Action in International Application No. EP 13729065.6, dated Oct. 17, 2017, 4 pages.
Alberts et al's Molecular Biology of the Cell, 4th ed., Garland Science, New York, 2002, ISGN 0-8153-3577-6, 2002, Chapter 3, pp. 129-134.
Canadian Office Action in Candia Application No. 2,775,938, dated Aug. 24, 2018, 7 pages.

ATGAGACGACCACGACTCGCCCTGCTCGCCGCGGGGCTCGCGCTCGCCGTCGCACCGGG
CACGCTGCTGCCCGTCGCCGCGGGCGCCGCCCCCGCCGACGAGGGCACCGTCACCGCCG
CCGCGGGCGACGACCTCACGCTCGAGGTCAACCCGTTCGTCGGCACCGAGAGCGAGGGC
AACGCCTACCCGGGCGCGACCGTGCCGTTCGGCATGGTCCAGCTCAGCCCGGACAACAC
GAACTCCTACGCCTCGACGTCGTACAGCACGAACGCGGGGCGCGTGTGGGGCTTCAGCC
ACCGGCACGTGAACAGCGCGGGCTGCCCCGCGGCGGGCGAGCTGCTCGTCACGCCGGAC
ACGAGCGCGACCCCGCGCACGTCGCGCTCCTTCATCGCCATCAAGGACCAGAAGAGCAC
CGAGCGCGCGTCGGCCGGGTTCTACGAGGTGACCCTCGCGAACGACGTGCACGCCGAGC
TCACCGCGACCACGCGCGTCGGCGCGCACCGCTACACGTTCCCCGCCTCGACGACGTCG
CACCTGTCGTTCAACGTGGGCCAGACCCTGCGCGACGCCGGCGCGAGCTCGGTGACGTG
GGTCGACGACCGCACGCTCGAGGGCTGGGTCGACAACGGCGGCTTCTGCGGCGGCACGC
CGGACAAGCAGCGGTACTTCTTCAGCGCGACGTTCGACCGCCCGGTCGCGTCGAGCGGC
ACGTGGGGGACCGATGCGCGCTACGTCGCGGGCTCCACGACGAGCGAGGTCGCGGGCGG
CAACAACGGCGCCGTCGCGGTGTTCGACACCACGACCGACCGCGACGTCGAGGTGAGCG
TGGGCGTGTCCTTCGTGAGCGTCGACGGCGCGCGCGCCAACCGCGAGGCCGAGGCCACC
GACGAGGGCGGGCAGGTCGCGTTCGACACCGTGCGTGAGGAGGCCCGCGACGCGTGGAA
CGCGGAGCTGGGCCGTGCCGCGATCGACGCGTCGCCCGACCAGCGCCGGATCTTCTACA
CCCAGCTCTACAAGACGCTGCTGTCCCCGACGATCGGCAGCGACGTCGACGGCCGGTAC
CGCGGCATGGACCTCGAGGTCCACCAGGCCGACGGCTGGGACTACTACCAGAACTTCTC
GCTCTGGGACACGTACCGCACGCAGGCGACGCTGCACGCCCTCCTGCTGCCCGAGCGCG
CGCAGGACATCGTGCGCTCGATGTACCAGCACCGCGTCGAGGGCGGCTGGCTGCCGCGC
TGGTCCCTCGGTGCACTGGAGACCAACATCATGGCGGGCGACCCCGTCACGCCGTGGCT
CGCGGAGAACTTCGCGCTCGGCACCGTCCCCGACGACATCGCGGACGAGCTGTGGGACT
ACCTCGTCGAGAACGCCACGACGACCCCGCCGGACGACGTCGCGTCCGTCGGGCGGCGC
AGCACCGAGTTCTACGCCGAGCACGGCCACGTGCCGTTCTACCCCGAGAACGAGGGCGG
CCTCGGCGGCCAGTTCGAGGAGTACCGCCACGGCGGCTCGGCGACGCTCGAGCTCGCGC
TCGCCGACGCGAGCCTCGGCGCTGCGGCCGAGCGCACGGGTCGCGAGGGCGGCCAGGCG
TTCCTCGACAAGGGTCGCAACTGGCGCAACCTCTGGAACCCGGACGTCGAGCTCTCGGG
TGGCTTCCAGGGCATGGTCAACGCGAAGCGCCCGACGGGCGAGTTCGTCACGCTGCCCG
AGCTGACGGACGTCACGCGCTCCGGCTTCCACGAGGGCGTGCCGTGGCAGTACCAGTGG
ATGGTGCCGCAGGACGTCACGGGCCTCCAGGAGGTCATGGGCGGCGAGGACGGCTTCGT
CGAGCGTCTCGACTACTACTTCGACCAGCCGGCGCTCGCCGCGAACCCCGGCGTCTCGC
CGAGCACGTGGGCCAAGGGCGGCAGCTCGTACTACACGACCATCCGCTACAACCCGGGC
AACGAGCCGACGATCATGAACGCGTGGCTCTACGGCTACGTGGGCCAGCCGTGGAAGAC
GAACGACGTCCTCGCCGCGAACCTCAACCGCTTCCCGGACACCCCGGGCGGCGGCGTCG
GGAACGACGACCTCGGCACGCTTGCCGCCTGGTACGTCATGGCGTCGCTCGGGTTCGAG
CCCGTCATGCCGGGCTCGGGGATCCTCGCGCTCAACGCGCCGAAGGTGCAGGCCGCGAC
GCTCACGACCGATGCCGGGGCGACGCTGCGCATCGACGCGGCGGGCGCGAACGAGAAGC
TCCCGAGCTACGTCGCCGGCCTGGAGGTCGACGGCGTCGCGCACACCGCCGCGTGGCTC
GACGTCGCGGCGCTGCAGGACGGCGGCACGCTCGACTTCGACCTGTCCGGCACGAGCGC
GGGCCTCACGTGGGGCACCGGCGCGGCCGACCGCATCCCGTCGGTCTCCGCCGTCGCCC
CGCCCGCGCCGGTCGAGGTCGAGGCGAGCGCGCGCTGCCTCGGCGGCCGGGCGTTCGTC
GCGGTCCGCGCGACCAGCACGGCCGACGCGCCGGTGGACGTGACTCTCACGACGCCGTT

FIG. 8A-1

CGGCGAGCGGACGGTCCGGCACGTGCAGCCGGGCAGGAGCGCCTACCAGTCGTTCACGA
CGCGCACGACGTCCGTCGAGGCCGGGACGGCGACCGTCACGGTCGTCGCCGCGGACGGC
ACGACGTCGACGGTCGACGCGGCGTACGAGGCGCTGGCCTGCGGC (SEQ ID NO:6)

FIG. 8A-2

MRRPRLALLAAGLALAVAPGTLLPVAAGAAPADEGTVTAAAGDDLTLEVNPFVGTESEG
NAYPGATVPFGMVQLSPDNTNSYASTSYSTNAGRVWGFSHRHVNSAGCPAAGELLVTPD
TSATPRTSRSFIAIKDQKSTERASAGFYEVTLANDVHAELTATTRVGAHRYTFPASTTS
HLSFNVGQTLRDAGASSVTWVDDRTLEGWVDNGGFCGGTPDKQRYFFSATFDRPVASSG
TWGTDARYVAGSTTSEVAGGNNGAVAVFDTTTDRDVEVSVGVSFVSVDGARANREAEAT
DEGGQVAFDTVREEARDAWNAELGRAAIDASPDQRRIFYTQLYKTLLSPTIGSDVDGRY
RGMDLEVHQADGWDYYQNFSLWDTYRTQATLHALLLPERAQDIVRSMYQHRVEGGWLPR
WSLGALETNIMAGDPVTPWLAENFALGTVPDDIADELWDYLVENATTTPPDDVASVGRR
STEFYAEHGHVPFYPENEGGLGGQFEEYRHGGSATLELALADASLGAAAERTGREGGQA
FLDKGRNWRNLWNPDVELSGGFQGMVNAKRPTGEFVTLPELTDVTRSGFHEGVPWQYQW
MVPQDVTGLQEVMGGEDGFVERLDYYFDQPALAANPGVSPSTWAKGGSSYYTTIRYNPG
NEPTIMNAWLYGYVGQPWKTNDVLAANLNRFPDTPGGGVGNDDLGTLAAWYVMASLGFE
PVMPGSGILALNAPKVQAATLTTDAGATLRIDAAGANEKLPSYVAGLEVDGVAHTAAWL
DVAALQDGGTLDFDLSGTSAGLTWGTGAADRIPSVSAVAPPAPVEVEASARCLGGRAFV
AVRATSTADAPVDVTLTTPFGERTVRHVQPGRSAYQSFTTRTTSVEAGTATVTVVAADG
TTSTVDAAYEALACG (SEQ ID NO:7)

FIG. 8B

GTGAGCCTCGCGCTCCCGCTGGCGGCGTACGCGGCGCCCGGGATCGGGGCGTCGCCCGC
GACCGCCGCCGGGACGGAGGCAGCGACGGGGTCCGATGCCGCCGCCGTCGACGGCCCGC
TGGTCGACTACGTCAACCCGTTCATCGGGACCAAGGACGACGGCAACACCTACCCGGGC
GCTGCCGTGCCGTTCGGCATGGTGCAACTCTCGCCGGACAACGGCCACAACGTCGGGTA
CGACTACGACCGCACGTCGGTGCGCGGGTTCTCGCTCGTGCACCTGTCCGGCGTCGGCT
GCGGCCTCGGCGGTCCGCTCCCGACCCTGCCGACGACGGGCGCGATCACCTCGACCGAC
TACGGCCAGTACGCGCTCGGTTTCTCGCACGACGACGAGGAGGCCTCGCCGGGGTACTA
CCGCGTGGGTCTCCAGGCGCCGGCGGGCACGATCGAGGCCGAGCTCACCGCGACCGAGC
GCACGGGCGTCCAGCGGTACACGTTCCCCGCGACGGCGCAGGCCAACGTCCTGCTCAAC
GCCGGCCAGGCGCTCAACCGGGTGACGGAGTCCGACGTGCGCGTCGTGGACGACCGCAC
GGTCGAGACGCGCATCACCGTCCGCGGCTTCTGCCAGGACACCGAGCCGCAGACGATCT
GGACCCGCACGACCTTCGACCGGCCGTTCGTCGCGCACGGCACGTGGGACGGCCAGGTC
GTCACCGCGGGCGCGGACGCCGCGTCCGGCGGCGAGGGCCGTCGCGGCGCGTACGTCAC
GTTCGACACGACCGGCGGCGACCTCGACGTCGAGGCCGTCACCGCGATGAGCTACGTGG
GCGCCGACGGCGCCGCGGCGAACCTCGCCGCGGAGGCCGGCACGTTCGACGCCGTGCAC
GACGCCGCGCGCTCGGCCTGGGAGGAGCGGCTCGGCCTCGTGCGGGTCGCGCAGGGCGA
CCCGGACGACCTGCGCACCTTCTACTCCTCGCTCTACCGCAGCTTCCTCGCGCCGAACG
TCGGCTCCGACGTCGACGGGCGCTACCGCGGCTGGGACCAGGAGGTCCACGCCGCGGAA
CCGGACTTCACCTACTACCAGAACTACTCGCTCTGGGACACGTACCGCACCCAGCAGCA
GCTCCTGTACCTGCTCGCGCCCGACGAGTCGGCCGACATGGCGCTCTCGCTCGTGCGCC
AGGGCCAGCAGGGCGGGTGGCTCCCGCGCTGGGGCTACGGCACGGTCGAGACGAACATC
ATGACCGGCGACCCGGCGACGCCGTTCCTCGTCAGCGCCTGGCGCCAGGGCCTGCTCGC
GGGCCACGAGGAGGAGGCGTACGCGGTCCTGAGGGAGAACGCCGACGGCGTCCCGCCCG
CCGACTCGCCCTTCAACGGGCGCGCGGCGAACGTCGAGTACCTGCGCGACGGGTTCGTC
CCGCACGAGCCGGCGCGCTCGGGCAAGCCCGGCGACTACGACCTCCAGCACGGCGCCTC
GGCGACCATGGAGTACGCCCTCGCCGACGCGATGCTCTCGACCATGGCGCGCGGCCTCG
GCCACGACGAGGACGCCGACCGGTACGCCGCCCGCGGCCAGAGCTACCGCAACGTGTTC
GACCCGCGCACGGGCAACTTCCGGGCGCGTAACGCGGACGGCTTCTTCGTGGGCGACGC
GGACCCCGCGCACTCCGACGGGTTCCACGAGGGCACGGCGGTGCAGTACCAGTGGCTCG
TGCCCCAGGACGTGCCGGGCCTGTTCGACCTCATGGGCGGCACCGACGCCGCGGTCGAC
CGCCTCGATGCGTTCTTCGCGTACGACGAGCTCGTCGCCGACCCCCCGCACGTCGCGAG
CGAGGTGTGGGTCAACGGCACGTACGACTACTACGGCTGGGAGACCTACAACCCGAACA
ACGAGCCCAACCTCCATGCGCCGTACGTCTACCTGTGGACCGGGCAGCCCTGGAAGACG
ACGGACGTCGTGCGCGCCGCGTCGACCCTCTTCACCGACGGCCCCGACGGCGTCACGGG
CAACGACGACCTCGGCACGATGTCCGCGTGGCACGTGCTGTCGTCGATCGGCGTGTACC
CGATCGTGCCGGGCGCCGATCTGTGGGGCCTGACGACGCCGCTCTTCGACGACGTGACG
ATCACGCTCGACCCGGAGGTCTTCGGTCGGGACTCCCTGCGCCTCACGGCGGACGGCGT
CGCGCCCGACACGCACTACACGCAGTCCGTGTCGCTCGGCGGCGAGCCGCTCGATCGCG
CCTGGGTCACGGGCGACGAGCTCACCGCGGCCGGCACGCTCGACGTGACCGTCGGCACC
GAGCCGTCCGCGTGGGCGACCGACCCCGCGGCCTCGCCGGGCGCCGTCGTGCCTGCGGA
CGGCACGGTCGAGCGCCTGTTCGTCGGCGCGACGCCGCGGCAGCCGGTCCTCGCCCCGG
GCGGGCGGACCGAGGTCGCAGTCCAGGTCGTCGCCCAGGGCGCGGGGACGTCCAGCGGG
ACGCTCGAGGTGACGTCCGACGGCGCGGTCACCGCGACGACCGACCTCGCCGAGTGGAC
CGCCGAGTCCGACGGCCTGCCGGCCACGGTCGAGGGCACGGTGACGATCGAGGCTCCCG
CCGACGCCGAGCCGGGTCTGCACACGGTGCGGCTCGTCGTGCGCGACGCCGCGGGGACC

FIG. 9A-1

GAGGCGGTCCGCGAGGTCTCGGTCGTCGTGTCCGGGGAGTCGTGGATCGCCGACGCGTT
CGACAACGTCGGCATCGGCGACGCCGGGGCGGCCAACGCGAACCTCGACGGCTCGGGCG
CCTACCTCCTGCGCGACCTGCTCGCGGACCTCGGCGCCGTCCAGGGCCTGGAGCTCACC
GTGCCGGGCACGGACCTCACCTACACGCTCGGGGCCCCGCGGGCGGGCGCGCCCGACAA
CGTCGCCGCGAGCGGCGAGGTCCTCGAGGTGCCCGAGCACCTGCGCTCGGCCCGCCACC
TCTCGGTGGTCGGGACGAGCACGCACGGCACGCACGGGGGCGGCCTCGTCCTCGGGTTC
GCCGACGGCTCGTCGCAGACCGTCGACGTGCGCCTCAGCGACTGGTGCACGGGCTCGCC
CGAGCCCGGCAACATCACGGTCGCGAAGGCCGGGGCGCGCGGCGACCGCGAGAACGTGC
AGAAGATCGGCTGCGGCCTCTACGCCACCGCGCCCGTCGCGATCCCCGAGGGCAAGGTC
CTGACGTCGGTCACGCTGCCGAGCGACGAGCGGTTCCACGTGTTCGCGATCGCGACCGA
CGCGACGGGGGACGTCCCCGCGCCGCAGGTCGAGGTCACGGCGCAGGCCCGCTGCCTCG
GCGGCAAGGCGTTCGTCGCGGTGCGCGCGCTCAACACGGGCGAGCAGCCCGCCGCGATC
GAGCTCGCGACCCCGTACGGCTCCAAGCTCTTCGGTGACGTCGCTCCCGGGGCGAACGC
GTACCAGTCGTTCGCCACCCGCGCCGCCGCCGTCGAGGCGGGCGAGGTCACGGTGACCG
TGACGACGCCCGACGGCGAGCCCCAGCAGGTCACGGCCGCGTACGACGCCGCCGCCTGC
TCC (SEQ ID NO:8)

FIG. 9A-2

VSLALPLAAYAAPGIGASPATAAGTEAATGSDAAAVDGPLVDYVNPFIGTKDDGNTYPG
AAVPFGMVQLSPDNGHNVGYDYDRTSVRGFSLVHLSGVGCGLGGPLPTLPTTGAITSTD
YGQYALGFSHDDEEASPGYYRVGLQAPAGTIEAELTATERTGVQRYTFPATAQANVLLN
AGQALNRVTESDVRVVDDRTVETRITVRGFCQDTEPQTIWTRTTFDRPFVAHGTWDGQV
VTAGADAASGGEGRRGAYVTFDTTGGDLDVEAVTAMSYVGADGAAANLAAEAGTFDAVH
DAARSAWEERLGLVRVAQGDPDDLRTFYSSLYRSFLAPNVGSDVDGRYRGWDQEVHAAE
PDFTYYQNYSLWDTYRTQQQLLYLLAPDESADMALSLVRQGQQGGWLPRWGYGTVETNI
MTGDPATPFLVSAWRQGLLAGHEEEAYAVLRENADGVPPADSPFNGRAANVEYLRDGFV
PHEPARSGKPGDYDLQHGASATMEYALADAMLSTMARGLGHDEDADRYAARGQSYRNVF
DPRTGNFRARNADGFFVGDADPAHSDGFHEGTAVQYQWLVPQDVPGLFDLMGGTDAAVD
RLDAFFAYDELVADPPHVASEVWVNGTYDYYGWETYNPNNEPNLHAPYVYLWTGQPWKT
TDVVRAASTLFTDGPDGVTGNDDLGTMSAWHVLSSIGVYPIVPGADLWGLTTPLFDDVT
ITLDPEVFGRDSLRLTADGVAPDTHYTQSVSLGGEPLDRAWVTGDELTAAGTLDVTVGT
EPSAWATDPAASPGAVVPADGTVERLFVGATPRQPVLAPGGRTEVAVQVVAQGAGTSSG
TLEVTSDGAVTATTDLAEWTAESDGLPATVEGTVTIEAPADAEPGLHTVRLVVRDAAGT
EAVREVSVVVSGESWIADAFDNVGIGDAGAANANLDGSGAYLLRDLLADLGAVQGLELT
VPGTDLTYTLGAPRAGAPDNVAASGEVLEVPEHLRSARHLSVVGTSTHGTHGGGLVLGF
ADGSSQTVDVRLSDWCTGSPEPGNITVAKAGARGDRENVQKIGCGLYATAPVAIPEGKV
LTSVTLPSDERFHVFAIATDATGDVPAPQVEVTAQARCLGGKAFVAVRALNTGEQPAAI
ELATPYGSKLFGDVAPGANAYQSFATRAAAVEAGEVTVTVTTPDGEPQQVTAAYDAAAC
S

FIG. 9B

GTGCGGCGCTCCGTCGCGGCGCTCTCTGCCACGGCGGTCCTGGCCGCCGGACTCTCGAT
CGCGCCCGCCGTCGGGCTCGCGGTCCCGGCGGTCGCGGCCGCACCCGACCTCGTTGAGG
ACCCCGTCTCCTTCGTCGACCCGTTCGTCGGGACCGGCCAGGCGACGGGCGTCGTCGGG
GAGATCAACAACTTCCCCGGGCCGTCGATGCCGTTCGGCATGATGCAGCTCTCGCCCGA
CACCCAGGTCTCCGTGGGCAACGGCGACAAGGCGTACGCGGGCTACCGCTACTCGCACC
AGGCGATCCGCGGCTTCTCCATGACGCACGCGGCCGCCGGGTGCTGGATCTTCGGCGAC
GTCCCGATCCTCCCCGTGACGGGCGACGTCGGGCAGTACCCGTGGGACCGCAAGGAGGC
GTTCAGCCACGACGCGGAGAGCGCCGAGGTCGGCCGGTACGCGGTCACGCTCCAGTCGT
CGGGGATCGATGCGGAGGTGTCGGCCGCGACCCGCTCGGGCGGACTGACGTTCGACTAC
CCCGAGGGCGGTGCCGCGTCGCAGGTGATCGTCAACGCCGCGGGCTCGCTCGCGAGCGT
GCGCAACGCGACGGTCGAGGTCGAGGACGCGCGCACGGTCACCGGCTCGGTGACGAGCG
GCGGGTTCTGCGGCAAGAACAACACGCACACGACGTACTTCGCGATCGAGCTCGACCAG
GACGCGCAGGCGTTCGGCACGTGGCAGGGCTCGACCGTCTCGCCCGGCGACCCGTCGGC
CGACGGCAACGGCGCGGGCGCGTGGCTCACCTTCGCGCCCGGCGCGACGGTGCACGCGA
AGGTCGGCATGTCCTACGTGAGCGTCGAGGGCGCGCGCGCCAACCTCGCGGCCGAGATC
CCGGGCTTCGACTTCGACGCCGTCCGGGACGCCAACCGCGCCGCCTGGTCCGACCTGCT
CGGCAAGGTCCGCGTCGCGGGGCAGGACGCCGACGACCTCACCATGTTCTACACGTCGC
TCTACCACTCGCTGCTGCACCCGAACACGTTCACCGACGTGGACGGCCGGTACGTCGGG
TTCGACGGGGAGATCCACCAGGCCCCCGAGGGGCACGAGCGGTACGCGAACTTCTCCGA
CTGGGACACGTACCGGTCGCTCGGCGCGCTCCAGGCGCTGCTGGCGCCCGACCAGGCGT
CGGACATGGCGCAGTCGCTCGTCGAGGTCGCCGACCAGTCCGGCTGGCTGCCGCGCTGG
CCCGTCGCGAACCAGCACACGGGCCAGATGACCGGTGACTCCTCGGTGCCGCTCATCGC
GAGCATGTACGCGTTCGGGGCGCGCGACTTCGACGCGGAGTCGGCGCTCGCGCACATGG
TCAAGGGTGCGACGAGCGCCGCCCCGACCGCGAACGGCTACGTGCAGCGGCGCGGGATC
GAGACGTACCTCGAGCGCGGCTACGCGCCCCAGACCGAGGAGTTCCGGGGCGACCACCG
CGTCGTCGGCGCGTCGATCACGCTCGAGTGGTCGATCGCCGACTTCGCGATCGGGCAGC
TCGCGGCCGCGCTCGGCCAGGACGACGTCGCCACCGAGTACGCCGCCCGCGGCCAGTGG
TGGCAGAACGTCCACGACCCCGTGACCCGCACGGCGGGCGCCCGGAACGACGACGGCAC
GTTCGTGCGGTCGCAGGGCGGCGGCGGGTTCGGGCAGGAGGGCTTCGACGAGGGCAACG
CCGAGCAGTACACGTGGCTCGTGCCGCAGAACGTCGCGGGGCTCACCGACGCGCTCGGC
GGGCGTGAGGCCGTCGCGGAGCGGCTCGATGCCTTCACGGTGCAGCACAACGCCGGCCC
GAACGAGCCGTACCTGTGGATCGGCAACGAGCCGAACTTCGGCGTCCCGTGGCTGTACG
ACTACGTGGGCCAGCCGTGGCGGACGAGCGAGCTCGTGGACGAGCTTACGTCCACGCTG
TTCCGGCCCGAGCCGAACGGCAAGCCCGGCAACGACGACCTCGGCGCCCAGGCCGGCTG
GTACGTGTGGGCCGCGATGGGCCTGTACCCCACCACGCCGGGCACGGACGTGCTCGCGC
TCAACGCGCCGCGCTTCGACCGCGTCGTGGTCGACCTCGGCGAGGGCGACACCCTCGAC
CTGCGCGCCCCCGGCGCCTCGACCGGCGCCCGCTACATCAGCGGCGTCACCATCGACGG
CGCAGCCTGGGACGGGACCTCCCTGCCGCGCCACGTCGCGCACGACGGCGGCGTCGTCG
AGCTCGCGATGTCGACCGCACGCGACACGACGTGGGGGACCGCAGCCGAGGACGCCCCG
CCGTCGTGGCGCGACGGCGAGTCCGCCGTGGTCGCCGCCGCGGACCCGGGCCTCGTGAC
GGTCGCCCCCGGCGGGACCGCCGACGCGTCGGTGGCCGTGCAGCTCTTCGGCGCCGACG
CCGCCGACGTGCGCGTCGCGGTCGACGCGCCCGGGGGCATCGGGGTCGGTGAGCCCGCG
CTCGTCGACGACGGCTCGGGCCACCTCACCGGGACGGTCCCCGTCCAGGTGGGTGCCGG
CGTCGCGTCCGGCTACCACGACGCGCGCCTCGTGCTCTCGGCCGGGGACGACGACGTCG
AGGTGCCCCTCACCGTCCTCGTCGCCGCGCCCGGGTCGCTCGTTGCGGCCTACGACACG

FIG. 10A-1

GTCGGCACTGCGCCCGAGGCGAACCGCGGCGTCGGGAACTTCGACGCGGCCGGCAACTC
GTTCTCGCGCGAGGCGCTCGCCGACGCGGGTCTCACGCCCGGGTCGGCGCACGACGTCG
ACGGCCTGGCGTTCACGTGGCCGTCCTCACCCGTGGGGCGCCCGGACTCGGTCACGCTC
ACCGGCGAGACCGTGCGGCTCGACGCGCCGACGAGCCGGCTCGCGTTCGTGGGCGCCGC
GACCGACGGGACCCATCGCGGGACCGCGGTCGTGACGTTCGACGACGGCAGCACCGCGA
CCACGACGATCGGCTTCGGCGACTGGGTGCTGCCGAGCGCGGACGGCTCGCCGGTCGAG
GGCAACTCGGTCGTCGCGCAGATGAACCGGCGCAACGGCGACAAGGACAGCGCGTTCGT
GTTCGCCACCGCCCCGTACACCGCGCCCGAGGACCGCCGCGTGGTCGCGGTGAGGTTCC
CCGACGTCGACGACCTGCACGTCTTTGCGATCGCGACCGAGCCGGCCGCGGACGTGCAC
CTCGTGGACGTGACGGTCTCCCTGCGCTGCCTCGCCGGGACCCCGTACGTGGCGGTGCG
CGCGGCGAACGTCTCCGCCGGGGCCGTCGACGTCGACCTCACGACGGGCGTGGGCTCGC
GGTCCTTCACGGCCGTCGCCCCCGGCGCCAACGCCTACCAGTCGTTCGCCGCCCGCGGC
GCGACCGGGAACGTCGACGTCACCGTCACGGCCACGGGGGAGGAGGGGACGCAGACGGT
CGCGCGGACCGTCGTCGTCCCGCGCTGCTCC (SEQ ID NO:10)

FIG. 10A-2

VRRSVAALSATAVLAAGLSIAPAVGLAVPAVAAAPDLVEDPVSFVDPFVGTGQATGVVG
EINNFPGPSMPFGMMQLSPDTQVSVGNGDKAYAGYRYSHQAIRGFSMTHAAAGCWIFGD
VPILPVTGDVGQYPWDRKEAFSHDAESAEVGRYAVTLQSSGIDAEVSAATRSGGLTFDY
PEGGAASQVIVNAAGSLASVRNATVEVEDARTVTGSVTSGGFCGKNNTHTTYFAIELDQ
DAQAFGTWQGSTVSPGDPSADGNGAGAWLTFAPGATVHAKVGMSYVSVEGARANLAAEI
PGFDFDAVRDANRAAWSDLLGKVRVAGQDADDLTMFYTSLYHSLLHPNTFTDVDGRYVG
FDGEIHQAPEGHERYANFSDWDTYRSLGALQALLAPDQASDMAQSLVEVADQSGWLPRW
PVANQHTGQMTGDSSVPLIASMYAFGARDFDAESALAHMVKGATSAAPTANGYVQRRGI
ETYLERGYAPQTEEFRGDHRVVGASITLEWSIADFAIGQLAAALGQDDVATEYAARGQW
WQNVHDPVTRTAGARNDDGTFVRSQGGGGFGQEGFDEGNAEQYTWLVPQNVAGLTDALG
GREAVAERLDAFTVQHNAGPNEPYLWIGNEPNFGVPWLYDYVGQPWRTSELVDELTSTL
FRPEPNGKPGNDDLGAQAGWYVWAAMGLYPTTPGTDVLALNAPRFDRVVVDLGEGDTLD
LRAPGASTGARYISGVTIDGAAWDGTSLPRHVAHDGGVVELAMSTARDTTWGTAAEDAP
PSWRDGESAVVAAADPGLVTVAPGGTADASVAVQLFGADAADVRVAVDAPGGIGVGEPA
LVDDGSGHLTGTVPVQVGAGVASGYHDARLVLSAGDDDVEVPLTVLVAAPGSLVAAYDT
VGTAPEANRGVGNFDAAGNSFSREALADAGLTPGSAHDVDGLAFTWPSSPVGRPDSVTL
TGETVRLDAPTSRLAFVGAATDGTHRGTAVVTFDDGSTATTTIGFGDWVLPSADGSPVE
GNSVVAQMNRRNGDKDSAFVFATAPYTAPEDRRVVAVRFPDVDDLHVFAIATEPAADVH
LVDVTVSLRCLAGTPYVAVRAANVSAGAVDVDLTTGVGSRSFTAVAPGANAYQSFAARG
ATGNVDVTVTATGEEGTQTVARTVVVPRCS (SEQ ID NO:11)

FIG. 10B

ATGACCAGACCACTCCCGCCCGGACGCGCGGTCGCGCGGTCCGGCAGCGGCCGCGCCCG
GCCCCTCGGCCTCGTGCTCGCCGCCGCACTCGCCGTCCCGCTCGGGGTGCCTCTCGCGG
CCCCCGCGGGAGCCCTCGCTGCCGCGCCCGCCGCGGCCGCCGAGCCCGGCGACTTCTCG
TCCTCGTTCGAGTCCGGCGACCCGGCCGCGCTGCCCACCACCGTGGCGGAGCGCGACGG
CGCGCCCTGGCAGGCGAACGTCGGCTCGTTCACGGCCGGCCTGCCCGGGAGCGTCCTCG
GGCAGCTGAAGGGCGTCACGGCGAGCGCGCAGAACCTGCCCAACGAGGGCGCGGCGAAC
CTCGCCGACGGCAGCTCGGGCACCAAGTGGCTCGCGTTCGCGTCGACCGGCTGGGTCCG
GTACGAGTTCGCCGAGCCCGTCTCGTTCGTCGCGTACACGATGACCTCCGGCGACGACG
CCGCCGGTCGCGACCCGAAGACCTGGACGGTCGAGGGGTCGAACGACGGGTCCACGTGG
GCCGCGCTCGACCGCCGGACGGACGAGGACTTCCCGAACCGCCAGCAGACGCGCACGTT
CGAGCTCGAGGCGCCCACCGCGGCGTACACGTACCTGCGCCTCAACGTCACGGCGAACT
CGGGCGACTCCATCGTCCAGCTCGCCGGGTGGGACCTCTCGGCCGACCTGAGCGCCGGC
CCGTCCGCGGCCCCCATGACGACGAAGGTCGGCACCGGGCCGCGCGTCAGCTTCACCAA
CAAGGCGGGCGTCGGGTTCTCCGGCCTGCACTCGCTCCGGTACGACGGCTCGCACCTCG
CCGACGGCGAGACGTACGCGACGAACGTGCTCTACGACGACGTGGACGTCGTCGTCGGC
GAGGACACGCGCCTGAGCTACACGATCTTCCCCGAGCTGCTCGACGATCTGCAGTACCC
GTCGACGTACGCGGCGGTGGACGTCCTGTTCACCGACGGGACCTACCTGTCCGACCTCG
GCGCGCGCGACGCGCACGAGACGGTCGCGACCGCGCAGGCGCAGGGCGAGGGCAAGATC
CTCTACGCCGACCAGTGGAACTCGGTGCGGGTCGACCTCGGCGACGTCGCCGAGGGCAA
GACCGTGGACCAGGTGCTGCTCGGGTACGACAACCCGGGCGGTCACGCCGGGACGAAGT
TCGCGGGCTGGCTCGACGACGTCGAGATCACGGCGGAGCCGGCCACGATCGACGGGTCG
AGCCTCGCCAACTACGTGGACACGCGCCGCGGCACGCTCGCGTCGGGCAGCTTCTCGCG
CGGGAACAACATCCCCGCGACGGCGACGCCGAACGGGTTCAACTTCTGGACGCCGTACA
CGAACGCCTCCTCGCAGAGCTGGCTGTACGAGTACCACAAGGCCAACAACGCCAACAAC
AAGCCCGTCCTCCAGGGCTTCGGGATCTCGCACGAGCCGAGCCCGTGGATGGGCGACCG
CAACCAGCTGACGTTCCTCCCGTCGACGGCGTCGGGGACGCCCGACGCCACGCTCTCGA
CGCGCGGCCTCGAGTTCGACCACGCGGACGAGACGGCGCGGCCGGACTACTACGGGGTC
ACGTTCACCAACGGGTCCGCGATCGAGGCGACGCCCACCGACCACGGCGCGGTGCTCCG
CTTCAGCTACCCCGGAGCCAAGGGCCACGTGCTCGTGGACAAGGTGGACGGCTCCTCCA
AGCTCACGTACGACCAGGCCACGGGCACGATCTCCGGCTGGGTCGAGAACGGCTCGGGC
CTGTCCGTGGGCCGCACGCGCATGTTCGTCGCCGGCACCTTCGACCGTAGTCCGACGGC
GGTCGGGACGGCGGCGGGCAACCGTGCGGACGCGCGCTTCGCGACGTTCGAGACGTCGT
CCGACAAGACGGTCGAGCTGCGCGTCGCGACGTCGTTCATCAGCCTCGACCAGGCGCGC
AAGAACCTCGACCTGGAGGTGACGGGCAAGACCTTCACGGAGGTCAAGGCCGCCGCCGC
GCAGGCGTGGAACGACCGCCTGGGGGTCATCGAGGTCGAGGGCGCGAGCGAGGACCAGC
TCGTCACGCTGTACTCGAACCTCTACCGCCTCAACCTGTACCCGAACTCGCAGTTCGAG
AACACGGGCACGGCGCAGGAGCCGGTGTACAGGTACGCGAGCCCGGTCTCCGCGACCAC
GGGCTCCGCGACGGACACGCAGACCAACGCGAAGATCGTCGACGGCAAGATCTACGTGA
ACAACGGGTTCTGGGACACGTACCGCACGGCCTGGCCGGCGTACTCGCTCCTCTACCCG
GAGCTCGCGGCCGAGCTGGTCGACGGGTTCGTCCAGCAGTACCGCGACGGCGGCTGGAT
CGCGCGCTGGTCCTCGCCGGGCTACGCCGACCTCATGACGGGCACGAGCTCCGACGTGG
CGTTCGCCGACGCGTACCTCAAGGGCTCGCTCCCCACGGGCACGGCGCTCGAGGCGTAC
GACGCCGCGCTGCGCAACGCGACCGTCGCGCCGCCGAGCAACGCCGTGGGCCGCAAGGG
CCTGCAGACCTCGCCGTTCCTCGGGTTCACGCCGGAGTCCACGCACGAGTCCGTGTCGT

FIG. 11A-1

GGGGCCTGGAGGGCCTGGTCAACGACTTCGGCATCGGCAACATGGCCGCCGCCCTCGCG
GAGGACCCGGCGACGCCGGAGGAGCGCCGCGAGACGCTGCGCGAGGAGTCCGCGTACTT
CCTCGAGCGGGCCACGCACTACGTCGAGCTGTTCGACCCCGAGGTCGACTTCTTCGTGC
CGCGGCACGAGGACGGCACGTGGGCCGTCGACCCCGAGACGTACGACCCGGAGGCCTGG
GGCGGCGGGTACACCGAGACGAACGGCTGGAACTTCGCGTTCCACGCCCCGCAGGACGG
CCAGGGCCTCGCCAACCTCTACGGCGGCAAGCAGGGCCTCGAGGACAAGCTCGACGAGT
TCTTCTCCACGCCGGAGAAGGGCGCCGGCAACGGCGGCATCCACGAGCAGCGCGAGGCG
CGCGACGTCCGCATGGGCCAGTGGGGCATGAGCAACCAGGTGTCGCACCACATCCCGTG
GCTCTACGACGCCGCGGGCGCGCCGTCGAAGGCGCAGGAGAAGGTCCGCGAGGTCACCC
GCCGCCTGTTCGTGGGCAGCGAGATCGGCCAGGGCTACCCGGGCGACGAGGACAACGGC
GAGATGTCGTCGTGGTGGATCTTCGCCTCGCTCGGCTTCTACCCGCTCCAGGTCGGCTC
GGACCAGTACGCGGTCGGTTCGCCGCTGTTCGACAAGGCGACCGTGCACCTGCCGGACG
GCGACCTCGTCGTCAACGCCGAGAACAACTCGGTCGACAACGTCTACGTGCAGTCCCTC
GCGGTGGACGGCGAGGCCCGCACCTCGACGTCACTCTCCCAGGCGGACCTCTCGGGCGG
CACGACTCTGGACTTCGTCATGGGTCCGGAGCCGTCGGACTGGGGCACGGGCGAGGACG
ACGCGCCGCCGTCGCTCACCGAGGGCGACGAGCCCCCGACGCCGGTGCAGGACGCGACG
ACCGCGGGCCTCGGCACCACCACCGTCGCCGACGGCGACGCCACCACGAGCGCCGCGGC
GCTCACGGACAACACGTCCGGGACGCGCACGACGTTCGCCACCACGACGCCGTCGATCA
CGTGGGCGGGCAACGGCATCCGCCCGACCGTCGGGTCGTACACGCTGACCTCCGGGGCG
AGCGGGACGGCGTCACCGTCCGCATGGACTCTCGAGGGTTCCGACGACGGCGAGACGTG
GACGACGCTCGACGAGCGGTCCGGCGAGCAGTTCCGCTGGGCCCTGCAGACGCGGCCGT
TCACGGTCGCGGAGCCGACGGCGTTCGCGCGGTACCGGGTCACGGTCACCGCGACGTCG
GGCTCCGGCGCGCTGTCGCTCGCCGAGGTCGAGCTCCTCGCCGACCCGAAGGAGTCGGG
GGCCGAGGAGCTCACCCTCTCGGCCGCGCCGGACCGTGACGGCGTCACGGGCCGCGAGG
TCTCGGGCTCGTTCGCGACCCTCACCGGGGTCGAGGGCGACGTCGCGGCGCTCGACGTG
CAGGTCGCGTTCGGCGACGGCTCCGAGCCGGTCGCCGGGACGCTGCGGGCGGGCGCGTT
CGGCGGGTACGCGGTGGACGCCGCGCACACGTGGACCGCACCCGGCGTCTACCCCGTGA
CCGTCACGGTCTCGGGCGAGGGGATCGAGACCGTCTCGGCCTCCTCGTACGTCAGCGTC
TCGCTCCTGCGCGAGGGCTCGCTGCTCGCCGCGTACGACAACGTCTGCATCGGCGACGC
CGGGACGACGGTCGGCTCGTGCGACGGCCAGGGCGTGTTCTTCGACCGGGCGCAGCTCG
CGGCGAAGGGCTTCGTCCAGGGCGAGCGCGCGACGGTGCCGGGCACGGACCTCGCGTTC
GACGTCCCGGCGGTCCCCGCCGGGCAGCCGGACAACGCCACGGGCGACGGGCAGACCAT
CGAGCTCGACGTCCCCGCGGACGCGGAGCAGCTCTCGGTGATCGGCACGGGCACGGAGA
AGAACCAGCAGGCCACCGGCACGCTGACCTTCGACGACGGCTCGACCCAGCCGATCGAC
CTGAGCTTCGGCGACTGGTCGGGCGCGGCCCGCAACCCCGTGTTCGGCAACATCCCCGT
CGCGGTGACGGACAGCCGCCTCCGCGGCGGCAGCCCGCAGACCGGCACCCCCGCCGCGT
TCTTCGCGACGGCGCCGATCACCCTCCCCGAGGGCAAGCGGCCCGTGAGCCTCACGCTC
CCGGACCAGCCGGGCGAGCTCTCGCGCGACGGCCGCATCCACGTGGTCGCGGTCGCGCA
CGACGGCACGTTCGCCGAGCACCCCGCGCTCGAGGTCACGGCCGCGGAGGGCGTGACGC
TCGCCGTCGGGCAGACCTCGGACGTGGCGCTCGCCCAGGTGGCGGGCGGCCGCGAGGGC
GCCGACCTCCGGGCGGCGGTCACGTGGGGCGACGGCTCCGACGTCGCGGCCGGCGCGGT
GACCGACGGGTCGGTCTCCGGCTCGCACGCCTACACGGCGGCCGGGACGTACACGGCGT
ACGTCGTGGTCGACGACGGCTGGACCAGCCAGGTGGTCGAGGTCCCCGTGACCGTGACC
GAGGCGGAGCCGGCCCTCGCCGTCGACGTCACGGTGAGCACACGCTGCCTCGCCGGCAA
GGCGTACGTCGCGGTCCGCGCCGAGAACGGCGAGGACGTGCCGCTCGCGATCCGGCTCG
TCACGCCGTTCGGCACCAAGGAGGTCGCGGCCGTCGCGCCGGGCGCCAACGCCTACCAG
TCGTTCGCGACGCGGGTCACGGCGGTCGAGGCCGGCACCGTCACCGTCGAGGCGACGCG

FIG. 11A-2

CGGCACCGGCGACGAGGAGGTGACGGCGTCGATCCAGGCCGACTACGCCGCCGTGACCT
GCGGC (SEQ ID NO:12)

FIG. 11A-3

MTRPLPPGRAVARSGSGRARPLGLVLAAALAVPLGVPLAAPAGALAAAPAAAAEPGDFS
SSFESGDPAALPTTVAERDGAPWQANVGSFTAGLPGSVLGQLKGVTASAQNLPNEGAAN
LADGSSGTKWLAFASTGWVRYEFAEPVSFVAYTMTSGDDAAGRDPKTWTVEGSNDGSTW
AALDRRTDEDFPNRQQTRTFELEAPTAAYTYLRLNVTANSGDSIVQLAGWDLSADLSAG
PSAAPMTTKVGTGPRVSFTNKAGVGFSGLHSLRYDGSHLADGETYATNVLYDDVDVVVG
EDTRLSYTIFPELLDDLQYPSTYAAVDVLFTDGTYLSDLGARDAHETVATAQAQGEGKI
LYADQWNSVRVDLGDVAEGKTVDQVLLGYDNPGGHAGTKFAGWLDDVEITAEPATIDGS
SLANYVDTRRGTLASGSFSRGNNIPATATPNGFNFWTPYTNASSQSWLYEYHKANNANN
KPVLQGFGISHEPSPWMGDRNQLTFLPSTASGTPDATLSTRGLEFDHADETARPDYYGV
TFTNGSAIEATPTDHGAVLRFSYPGAKGHVLVDKVDGSSKLTYDQATGTISGWVENGSG
LSVGRTRMFVAGTFDRSPTAVGTAAGNRADARFATFETSSDKTVELRVATSFISLDQAR
KNLDLEVTGKTFTEVKAAAAQAWNDRLGVIEVEGASEDQLVTLYSNLYRLNLYPNSQFE
NTGTAQEPVYRYASPVSATTGSATDTQTNAKIVDGKIYVNNGFWDTYRTAWPAYSLLYP
ELAAELVDGFVQQYRDGGWIARWSSPGYADLMTGTSSDVAFADAYLKGSLPTGTALEAY
DAALRNATVAPPSNAVGRKGLQTSPFLGFTPESTHESVSWGLEGLVNDFGIGNMAAALA
EDPATPEERRETLREESAYFLERATHYVELFDPEVDFFVPRHEDGTWAVDPETYDPEAW
GGGYTETNGWNFAFHAPQDGQGLANLYGGKQGLEDKLDEFFSTPEKGAGNGGIHEQREA
RDVRMGQWGMSNQVSHHIPWLYDAAGAPSKAQEKVREVTRRLFVGSEIGQGYPGDEDNG
EMSSWWIFASLGFYPLQVGSDQYAVGSPLFDKATVHLPDGDLVVNAENNSVDNVYVQSL
AVDGEARTSTSLSQADLSGGTTLDFVMGPEPSDWGTGEDDAPPSLTEGDEPPTPVQDAT
TAGLGTTTVADGDATTSAAALTDNTSGTRTTFATTTPSITWAGNGIRPTVGSYTLTSGA
SGTASPSAWTLEGSDDGETWTTLDERSGEQFRWALQTRPFTVAEPTAFARYRVTVTATS
GSGALSLAEVELLADPKESGAEELTLSAAPDRDGVTGREVSGSFATLTGVEGDVAALDV
QVAFGDGSEPVAGTLRAGAFGGYAVDAAHTWTAPGVYPVTVTVSGEGIETVSASSYVSV
SLLREGSLLAAYDNVCIGDAGTTVGSCDGQGVFFDRAQLAAKGFVQGERATVPGTDLAF
DVPAVPAGQPDNATGDGQTIELDVPADAEQLSVIGTGTEKNQQATGTLTFDDGSTQPID
LSFGDWSGAARNPVFGNIPVAVTDSRLRGGSPQTGTPAAFFATAPITLPEGKRPVSLTL
PDQPGELSRDGRIHVVAVAHDGTFAEHPALEVTAAEGVTLAVGQTSDVALAQVAGGREG
ADLRAAVTWGDGSDVAAGAVTDGSVSGSHAYTAAGTYTAYVVVDDGWTSQVVEVPVTVT
EAEPALAVDVTVSTRCLAGKAYVAVRAENGEDVPLAIRLVTPFGTKEVAAVAPGANAYQ
SFATRVTAVEAGTVTVEATRGTGDEEVTASIQADYAAVTCG (SEQ ID NO:13)

FIGURE 11B

GCGCTCGCCGTCGTCGGCCTCGCGCCCGCGACCGCCGCGAGCGCCGCCCCCGAGCCGCC
GTCGGCCGACTACGCGTCCCTGGTCGACGTCTTCGTCGGCACCGAGGGCGACTTCGGCA
ACGACATGCCCGCCGCGCAGGCGCCGAACGGCCTCGCGAAGGTCAACCCGCGCACGACC
CCGGGCCGCAACAACACCGGGTACGACTACGCGCAGTCGAAGATCTCGGGCTTCACGCA
CACCAACCTCGACGGGGTCGGGGGCTCCGGCGGCGGTGGTGACCTCCTCGTGGTGCCGA
CGTCCGGGTCGTACACGGCGCGCCCCGGCACGGGCACGTACGCGCACCCGTTCTCGCAC
GACGACGAGGACGCCGGACCGGGCTTCTACTCCGTCGGGCTCGGCAACGTCGCGGGCAC
GGACGGCGCGATCACCGGCGCGCCGGGCACGATCGAGGCCGAGGTCGCGGCGGCCACGC
GCTCGGGCGTGCACCGCTACGCGTTCCCCGCGGGCTCGACGCCGAGCCTCGTCGTGGAC
CTCGAGACGAACAACACGAGCCGCCGGTCGTCCTCGGTGCAGGTCGAGACGCGCGCGGA
CGGCACCGTGGAGCTGTCCGGACAGGTCACGGGCTACTTCTACAACGCGGCCTACACGC
TGTACTACACCGCGCGCACGCTCCAGCCCGCGACGGTGCAGACGTGGGGCGACGACGAC
CGGCTCGTCGACGCCACGGCCCAGGACGGCGTCGACACCGGCGCGATCCTCACGTTCGA
CCCGGCGGACGCCGGGGAGATCGGGCTCCAGGTCACCCTGTCGCCGGTGAGCGTCGAGC
AGGCGCGGATCGACCAGCAGGTCGAGCTCGGCGACCTGTCGTTCGACGCGATCCGTGAC
CGCACCCGCGCGGAGTGGAACGCGACGCTCGGGCGGGTCGCGATCGACGCCTCGACGGC
GACGGACCCGACGGGCGAGCTCCAGCGGCTCTTCTACACGCACCTCTACCGCATGTTCG
CGATGCCGATGAACGCGACGAGCACCTCGGGCACGTACCGCGGCGTCGACGGGGCGGTG
CACGCCGCGCAGGGCTTCACGTACTACGACTCGTGGGCCACGTGGGACGACTTCCGCAA
GTTCTCCGTCATCGCGTACATCGACCCGGCGCTGTACCGGGACATGGTGCAGTCGCTGG
TCTACCTGTTCGCGGACGCCGAGGCGACGGGCACCGGCGGCGGCCTCGGCGGGTTCGTG
CACTCGGTCCCGACGGTGCGCTGGGAGCGGTCGTCGGTCGTGGTCGCGGACGCGATCGC
CAAGGGCTTCGACGGGTTCGACCGCCTCGACGAGGCGTACCCGGCGCTCCAGCGGCTCG
TCGGGCAGTACAGCGCGGACGAGCTCCGGCGCGGCTACGTGGCGGGCAACCCCGGCGCG
TCCGTGCAGCGCGGCTACGACCAGTACGGCCTGTCCGTGATCGCGGACGAGCTCGGCCT
GACCGAGGAGGCCGAGACGCTGCGCGAGCAGGCGTCGTGGCCGATCGAGAAGCTCACCA
AGCCGGGCGCGTGGACCGCCGCCGACGGCACGCAGGTCGGCCTCCTCACCCCGCGCGCC
GCGGACGGGTCGTGGCAGAGCGCCGACCACGCGAAGTTCGAGGCCGCCGGCCTCTACCA
GGGCACGCTCTGGCAGTACCACTGGTACGACGCGTACGACATGGACGCGCTCGTCGAGG
CGATGGGCGGCCACGAGGCGGCGCGCCTCGGCATGCGCCACATGTTCGGTGAGCACGCG
CCGGACGACGGCAAGGCCATGCTCCACTCGAACGCCAACGAGATCGACCTCCAGGCGCC
GTACCTCTTCAACTACACGGGCGAGCCGAGCCTCACGCAGAAGTGGGCGCGCGCGATCT
ACACGAAGGAGACCTGGAACCGGTACATCGCGACCGGCTCCTCCAGCGCCGTGCCGAGC
GGCGGCGGCGAGTTCACGCCGCCCTTGAAGACGAAGGTGTACCGGCTCGACCCCCGCGG
GATGCTCCCCACGATGGACAACGACGCGGGCACGATGTCGACGATGTTCGTCGCCGCGG
CCGTCGGGCTGTTCCCGGTGACCGCGGGCTCGTCCCAGTTCCAGGTCGGGTCGCCGTTC
TTCGACTCGACGACCATCACCTACGACGACGGCAGCGCCTTCACGGTCACGGCCGACGG
CGTCTCCGAGGACGCGTTCTACGTCCAGTCCGCGACGCTCGACGGCGCGACGTTCGGCA
ACACGTGGGTCGACTACGCCACCGTGGTCGGGGGAGCCGACCTCGCGTTCCGCATGGGC
GAGCAGCCGAGCGACTGGGGCACGGACACCGCGCCCGCGTTCTCGATGAGTACCGCGAC
CGACGAGCCGGCCGAGGGACCGCGCGTCAGCGCCGAACCGACCACCGTGCAGACCGGCG
ACGGCGGCGCGCTCGACGCGACCGTGACGCTCACGCTCGACGGCGCCCGCCTCGCCGCG
CCCGCCGGCACGGACCTCGTCACGAGCGGGGCGGCGAGCGTCGTCGGGCTGCCCGACGG
CGTCACGGCGGCCGTGACGGTCGCGTCGCCGACCGCGCTGACCGTCTCCCTGACGGGGA
CGGCGTCCGCCGACGCGCGCTTCTTCGTGCACCTGCGCGACGCCGCGCTCGCCGACGGC

FIG. 12A-1

GTCGCCGCGGCGTCGCTCCAGGGACAGGGCGTCTCGGTGCGCTCGCCCCTGCGGCTGTC
CGTGGCGTCCGCCGAGCGCGACGCGCTCGCCGCGCTCGTCGACGACGCCGTGCTCGTGC
GGCACGGGAACTACTCCTCGGTGACGTTCGACCGGTTCTCCACCGCGCTGACGAAGGCG
CAGGAGGCCCTCGGTGACGAGGCCGCGACGAGCATCGCGCTGCGGTTCGCGGCCGACCG
GCTCGGTGCGGCGGCCGACGCGCTCGACCTCACGGGCGGCGGGTACCGCACGCTCGAGG
CCGAGCAGTCCGAGGCGTGGTCGGGCGGGGAGCTGAAGAACGAGGCGAACAGCTCGTCC
GGCAACCTCGGCGGCGTGCGCTCCGGGTCGTGGGTGCAGTACCGCGACATGACCTTCGA
GACCGCCGCCGGGGACACCCCGCCGCGCTTCCTCACGGTCCGGTACGACACGAGCTTCG
CCCCGACGGACACGCCGAGCACCGTGCGCGTGCACGCGGGCGACGTGAGCGGCCCTGTG
GTCGCGACCGTCGACCTGAAGGGCACGAGCGGCTGGGGCAAGTACACCGAGGTCACGGC
GGAGCTCGGCGACGTGCAGGCGCTCGTCGACGCGCAGGTCGTCACGTTCGAGCTGCTCG
CGCCGTCCGGGCGGAGCTGGGTCGGCAACTTCGACTGGTTCCGGTTCAGCGCCGAGGAC
CCGGCTGCCCCAGGTCAGCCGGGCGAGTCCCCGACGGTGACGATCGAGGCCGAGGACTG
GACCGCGAGCTCCGGTCGCGGGCTCAAGAAGGAGTCCTCGACGTGGACGAGCGGTCCGG
TGACGAACGTCGGCGGCACCGCGGACGGCGACTGGATCGCCTACGGCGAGGTCGACCTG
GGTGAGCTCCCGCTCGGCGAGCTGTCGGTCCACTACGTGCACAACTCCAACCGGTCCGG
GAACAACTCCGCGCTGTCGGTGTACCTCGACGCGTTCGACCCGGCGAACCCGGGCGAGC
CGTTCGTCACCGTGCCGCTGCCGACGACCGGGTCGAGCTGGACCGCGGACGGGACCGCG
ACCGTCGTCCTGCCCGAGACGGTGCAGGGGACGCACGAGGTGTTCGTGCGCCTGTCGAC
CGAGCCGTACGCCGACCACCCGTACGTCGCGAACCTCGACAGCCTGACGTTCGCGCCGG
GCGGCCCGACGTCGGTCGTCGTCGAGTCCGAGGCCTGGACGTCGAACTCCGGCCGCGGG
CTGAAGAACGAGAGCTCGACGTGGACGAGCGGTCCGGTGACGAACGTCGGCGGCACCGC
GGACGGCGACTGGCTCGCCTACGGCGAGATCGACCTCGGCTCCGCCGCGCTCGACCAGC
TCTCGGTCCACTACGTGCACAACTCCAACCGGTCCGGGCGGAACTCCGCGCTGTCGGTG
TACCTCGACGCGTTCGACCCGGCGAACCCGGGCGAGCCGTTCGTCACCGTCCCGCTGGC
CAACACCGGGTCGAGCTGGACGACGGACGGGACCGCCGTCGTCGACCTGCCGAGCACGG
TGCGCGGCAAGCACCAGGTGTGGGTGCGCCTGTCCACCGAGGCGTACGCCGACCACCCG
TACGTCGCCAACCTCGACAGCATGCGCTTCTTCACCGACGCGTACGACGTCGAGGTCCC
GCCGACCGACACCGCGGCGCTCGCGGCGGTGGTCGACGCGGCCGGGACGCCCGAGGCGG
AGATCGCGCGGTACGGCCGGATCGACGCGCGCGTCTTCACACGCGAGCTCGCGGCGGCA
CGGTCCGTGCTCGCCGACGCCGGCGCCACCCAGGCGCAGGCCGACGAGCGGGCGCGGCG
CCTCGGCCTGGCGACCGACCAGCTCGTGCCCGCCGAGCGCCGTCGGCTCGAGAACCTCG
TGGCGAGCGCCGAGGCCCTGACCGACGAGGGGTACAGCCCCGAGTCCTGGCAGGCCTTC
CGCACGGCTCTCGCCGCGGCGACCGGGACGCTCGACGACGCGGCGGCGTCCGACGAGGC
GCTGCACGACGCGCGGCTCGCGCTCCAGGGCGCCGTCGACGCCCTGGAGGAGCCGGCCG
ACGTCGTGCTCGTCGAGGTCGAGGTCAGCCCGCGCTGCCTCGCCGGCAAGCCCTACGTC
GCGGTCCGCGCGGTGAACGTCTCCGACGCGGCCGTCGACGTCGAGCTGGCGTCGTCACT
GGGCACGAGGTCGTTCGTCGGCGTCGCGCCGGGGGCGAGCGCGTACCAGTCGTTCGCCG
CGCGGTCCGCGACGGGCGACCTGGACGTCACCGTCACGGCGACGGGGGCGGACGGCACC
CAGACGGTCGAGCAGGTCGTCACCGTCCCGTCCTGCTCC (SEQ ID NO:14)

FIG. 12A-2

ALAVVGLAPATAASAAPEPPSADYASLVDVFVGTEGDFGNDMPAAQAPNGLAKVNPRTT
PGRNNTGYDYAQSKISGFTHTNLDGVGGSGGGGDLLVVPTSGSYTARPGTGTYAHPFSH
DDEDAGPGFYSVGLGNVAGTDGAITGAPGTIEAEVAAATRSGVHRYAFPAGSTPSLVVD
LETNNTSRRSSSVQVETRADGTVELSGQVTGYFYNAAYTLYYTARTLQPATVQTWGDDD
RLVDATAQDGVDTGAILTFDPADAGEIGLQVTLSPVSVEQARIDQQVELGDLSFDAIRD
RTRAEWNATLGRVAIDASTATDPTGELQRLFYTHLYRMFAMPMNATSTSGTYRGVDGAV
HAAQGFTYYDSWATWDDFRKFSVIAYIDPALYRDMVQSLVYLFADAEATGTGGGLGGFV
HSVPTVRWERSSVVVADAIAKGFDGFDRLDEAYPALQRLVGQYSADELRRGYVAGNPGA
SVQRGYDQYGLSVIADELGLTEEAETLREQASWPIEKLTKPGAWTAADGTQVGLLTPRA
ADGSWQSADHAKFEAAGLYQGTLWQYHWYDAYDMDALVEAMGGHEAARLGMRHMFGEHA
PDDGKAMLHSNANEIDLQAPYLFNYTGEPSLTQKWARAIYTKETWNRYIATGSSSAVPS
GGGEFTPPLKTKVYRLDPRGMLPTMDNDAGTMSTMFVAAAVGLFPVTAGSSQFQVGSPF
FDSTTITYDDGSAFTVTADGVSEDAFYVQSATLDGATFGNTWVDYATVVGGADLAFRMG
EQPSDWGTDTAPAFSMSTATDEPAEGPRVSAEPTTVQTGDGGALDATVTLTLDGARLAA
PAGTDLVTSGAASVVGLPDGVTAAVTVASPTALTVSLTGTASADARFFVHLRDAALADG
VAAASLQGQGVSVRSPLRLSVASAERDALAALVDDAVLVRHGNYSSVTFDRFSTALTKA
QEALGDEAATSIALRFAADRLGAAADALDLTGGGYRTLEAEQSEAWSGGELKNEANSSS
GNLGGVRSGSWVQYRDMTFETAAGDTPPRFLTVRYDTSFAPTDTPSTVRVHAGDVSGPV
VATVDLKGTSGWGKYTEVTAELGDVQALVDAQVVTFELLAPSGRSWVGNFDWFRFSAED
PAAPGQPGESPTVTIEAEDWTASSGRGLKKESSTWTSGPVTNVGGTADGDWIAYGEVDL
GELPLGELSVHYVHNSNRSGNNSALSVYLDAFDPANPGEPFVTVPLPTTGSSWTADGTA
TVVLPETVQGTHEVFVRLSTEPYADHPYVANLDSLTFAPGGPTSVVVESEAWTSNSGRG
LKNESSTWTSGPVTNVGGTADGDWLAYGEIDLGSAALDQLSVHYVHNSNRSGRNSALSV
YLDAFDPANPGEPFVTVPLANTGSSWTTDGTAVVDLPSTVRGKHQVWVRLSTEAYADHP
YVANLDSMRFFTDAYDVEVPPTDTAALAAVVDAAGTPEAEIARYGRIDARVFTRELAAA
RSVLADAGATQAQADERARRLGLATDQLVPAERRRLENLVASAEALTDEGYSPESWQAF
RTALAAATGTLDDAAASDEALHDARLALQGAVDALEEPADVVLVEVEVSPRCLAGKPYV
AVRAVNVSDAAVDVELASSLGTRSFVGVAPGASAYQSFAARSATGDLDVTVTATGADGT
QTVEQVVTVPSCS (SEQ ID NO:15)

FIG. 12B

APEPPSADYASLVDVFVGTEGDFGNDMPAAQAPNGLAKVNPRTTPGRNNTGYDYAQSKISGF
THTNLDGVGGSGGGGDLLVVPTSGSYTARPGTGTYAHPFSHDDEDAGPGFYSVGLGNVAGTD
GAITGAPGTIEAEVAAATRSGVHRYAFPAGSTPSLVVDLETNNTSRRSSSVQVETRADGTVE
LSGQVTGYFYNAAYTLYYTARTLQPATVQTWGDDDRLVDATAQDGVDTGAILTFDPADAGEI
GLQVTLSPVSVEQARIDQQVELGDLSFDAIRDRTRAEWNATLGRVAIDASTATDPTGELQRL
FYTHLYRMFAMPMNATSTSGTYRGVDGAVHAAQGFTYYDSWATWDDFRKFSVIAYIDPALYR
DMVQSLVYLFADAEATGTGGGLGGFVHSVPTVRWERSSVVVADAIAKGFDGFDRLDEAYPAL
QRLVGQYSADELRRGYVAGNPGASVQRGYDQYGLSVIADELGLTEEAETLREQASWPIEKLT
KPGAWTAADGTQVGLLTPRAADGSWQSADHAKFEAAGLYQGTLWQYHWYDAYDMDALVEAMG
GHEAARLGMRHMFGEHAPDDGKAMLHSNANEIDLQAPYLFNYTGEPSLTQKWARAIYTKETW
NRYIATGSSSAVPSGGGEFTPPLKTKVYRLDPRGMLPTMDNDAGTMSTMFVAAAVGLFPVTA
GSSQFQVGSPFFDSTTITYDDGSAFTVTADGVSEDAFYVQSATLDGATFGNTWVDYATVVGG
ADLAFRMGEQPSDWGTDTAPAFSMSTATDEPAEGPRVSAEPTTVQTGDGGALDATVTLTLDG
ARLAAPAGTDLVTSGAASVVGLPDGVTAAVTVASPTALTVSLTGTASADARFFVHLRDAALA
DGVAAASLQGQGVSVRSPLRLSVASAERDALAALVDDAVLVRHGNYSSVTFDRFSTALTKAQ
EALGDEAATSIALRFAADRLGAAADALDLTGGGYRTLEAEQSEAWSGGELKNEANSSSGNLG
GVRSGSWVQYRDMTFETAAGDTPPRFLTVRYDTSFAPTDTPSTVRVHAGDVSGPVVATVDLK
GTSGWGKYTEVTAELGDVQALVDAQVVTFELLAPSGRSWVGNFDWFRFSAEDPAAPGQPGES
PTVTIEAEDWTASSGRGLKKESSTWTSGPVTNVGGTADGDWIAYGEVDLGELPLGELSVHYV
HNSNRSGNNSALSVYLDAFDPANPGEPFVTVPLPTTGSSWTADGTATVVLPETVQGTHEVFV
RLSTEPYADHPYVANLDSLTFAPGGPTSVVVESEAWTSNSGRGLKNESSTWTSGPVTNVGGT
ADGDWLAYGEIDLGSAALDQLSVHYVHNSNRSGRNSALSVYLDAFDPANPGEPFVTVPLANT
GSSWTTDGTAVVDLPSTVRGKHQVWVRLSTEAYADHPYVANLDSMRFFTDAYDVEVPPTDTA
ALAAVVDAAGTPEAEIARYGRIDARVFTRELAAARSVLADAGATQAQADERARRLGLATDQL
VPAERRRLENLVASAEALTDEGYSPESWQAFRTALAAATGTLDDAAASDEALHDARLALQGA
VDALEEPADVVLVEVEVSPRCLAGKPYVAVRAVNVSDAAVDVELASSLGTRSFVGVAPGASA
YQSFAARSATGDLDVTVTATGADGTQTVEQVVTVPSCS (SEQ ID NO:50)

FIG. 12C

GCACCGGCAGATGAAGGCACCGTTACCGCAGCAGCCGGTGATGATCTGACCCTGGAAGTTAATCCGTTTGT
TGGCACCGAAAGCGAAGGTAATGCATATCCGGGTGCAACCGTTCCGTTTGGTATGGTTCAGCTGTCTCCGG
ATAATACCAATAGCTATGCCAGCACCAGCTATAGCACCAATGCAGGTCGTGTTTGGGGTTTTAGCCATCGT
CATGTTAATAGCGCAGGTTGTCCGGCAGCCGGTGAACTGCTGGTTACACCGGATACCAGCGCAACACCGCG
TACCAGCCGTAGCTTTATTGCCATCAAAGATCAGAAAAGCACCGAACGTGCAAGCGCAGGTTTTTATGAAG
TTACCCTGGCAAATGATGTTCATGCAGAACTGACCGCAACCACCCGTGTTGGTGCACATCGTTATACCTTT
CCGGCAAGCACCACCTCTCATCTGAGCTTTAATGTTGGTCAGACCCTGCGTGATGCCGGTGCAAGCAGCGT
TACCTGGGTTGATGATCGTACACTGGAAGGTTGGGTTGATAATGGTGGTTTTTGTGGTGGTACACCGGATA
AACAGCGCTATTTTTTTAGCGCAACCTTTGATCGTCCGGTTGCCAGCAGCGGTACATGGGGCACCGATGCA
CGTTATGTTGCAGGTAGCACCACCAGTGAAGTTGCCGGTGGTAATAATGGTGCAGTTGCCGTTTTTGATAC
CACCACCGATCGTGATGTTGAAGTTAGCGTTGGTGTTAGCTTTGTTAGCGTTGATGGTGCACGTGCAAATC
GTGAAGCCGAAGCAACCGATGAAGGTGGTCAGGTTGCATTTGATACCGTTCGTGAAGAAGCACGCGACGCC
TGGAATGCAGAACTGGGTCGTGCAGCAATTGATGCATCTCCGGATCAGCGTCGTATCTTTTATACCCAGCT
GTATAAAACCCTGCTGAGCCCGACCATTGGTTCTGATGTTGATGGTCGTTATCGTGGTATGGATCTGGAAG
TTCATCAGGCAGATGGCTGGGATTATTATCAGAACTTTAGCCTGTGGGATACCTATCGTACCCAGGCAACC
CTGCATGCACTGCTGCTGCCGGAACGTGCACAGGATATTGTTCGTAGCATGTATCAGCATCGTGTTGAAGG
TGGTTGGCTGCCTCGTTGGTCTCTGGGTGCACTGGAAACCAATATCATGGCAGGCGATCCGGTTACCCCGT
GGCTGGCAGAAAATTTTGCACTGGGCACCGTTCCGGATGATATTGCAGATGAACTGTGGGATTATCTGGTT
GAAAATGCAACCACCACCCCTCCGGATGATGTTGCCAGCGTTGGTCGTCGTAGCACCGAATTTTATGCCGA
ACATGGTCATGTTCCGTTTTATCCGGAAAACGAAGGTGGCCTGGGTGGTCAGTTTGAAGAATATCGTCATG
GTGGTAGCGCAACCCTGGAACTGGCACTGGCAGATGCAAGCCTGGGTGCCGCAGCAGAACGTACCGGTCGT
GAAGGTGGCCAGGCATTTCTGGATAAAGGTCGCAATTGGCGTAATCTGTGGAATCCGGATGTTGAACTGAG
CGGTGGTTTTCAGGGTATGGTTAATGCAAAACGTCCGACCGGTGAATTTGTTACCCTGCCGGAACTGACCG
ATGTTACCCGTAGCGGTTTTCATGAAGGTGTTCCGTGGCAGTATCAGTGGATGGTTCCGCAGGATGTTACC
GGTCTGCAAGAAGTTATGGGAGGCGAAGATGGTTTTGTGGAACGCCTGGATTATTATTTTGATCAGCCTGC
ACTGGCAGCAAATCCGGGTGTTAGCCCGAGCACCTGGGCAAAAGGTGGTAGCAGCTATTATACCACCATTC
GCTATAATCCGGGTAATGAACCGACCATTATGAATGCATGGCTGTATGGTTATGTTGGTCAGCCGTGGAAA
ACCAATGATGTTCTGGCAGCCAATCTGAATCGTTTTCCGGATACACCGGGTGGTGGTGTTGGTAATGATGA
TCTGGGCACCCTGGCAGCATGGTATGTTATGGCCAGCCTGGGTTTTGAACCGGTTATGCCTGGTAGCGGTA
TTCTGGCACTGAATGCACCGAAAGTTCAGGCAGCAACCCTGACCACCGATGCCGGTGCCACCCTGCGTATT
GATGCAGCCGGTGCAAATGAAAAACTGCCGAGCTATGTTGCCGGTCTGGAAGTTGATGGTGTTGCACATAC
CGCAGCATGGCTGGATGTTGCAGCACTGCAGGATGGTGGCACCCTGGATTTTGATCTGAGCGGTACAAGCG
CAGGTCTGACATGGGGTACAGGTGCAGCAGATCGTATTCCGAGCGTTAGCGCAGTTGCACCGCCTGCACCG
GTTGAAGTGGAAGCAAGCGCACGTTGTCTGGGTGGTCGTGCATTTGTTGCAGTTCGTGCAACCAGCACCGC
AGATGCACCGGTGGATGTTACACTGACCACACCGTTTGGTGAACGTACCGTTCGTCATGTTCAGCCTGGTC
GTAGCGCATATCAGAGCTTTACCACCCGTACCACCTCTGTTGAAGCAGGCACCGCAACCGTTACCGTTGTT
GCAGCAGATGGCACCACCTCAACCGTTGATGCAGCATATGAAGCACTGGCATGTGGTTAATAA (SEQ ID NO:16)

FIG. 14

GCAGGCACCGAAGCAGCAACCGGTTCTGATGCAGCAGCAGTTGATGGTCCGCTGGTTGATTATGTGAATCC
GTTTATTGGCACCAAAGATGATGGTAATACCTATCCGGGTGCAGCAGTTCCGTTTGGTATGGTTCAGCTGT
CTCCGGATAATGGTCATAATGTGGGCTATGATTATGATCGTACCAGCGTTCGTGGTTTTAGCCTGGTTCAT
CTGAGCGGTGTTGGTTGTGGTCTGGGTGGTCCGCTGCCGACACTGCCGACCACCGGTGCAATTACCAGCAC
CGATTATGGTCAGTATGCACTGGGTTTTAGCCATGATGATGAAGAAGCATCTCCGGGTTATTATCGTGTTG
GTCTGCAGGCACCTGCAGGAACCATTGAAGCAGAACTGACCGCAACCGAACGTACCGGTGTTCAGCGTTAT
ACCTTTCCGGCAACCGCACAGGCAAATGTTCTGCTGAATGCAGGTCAGGCACTGAATCGTGTTACCGAATC
TGATGTTCGTGTTGTTGATGATCGTACCGTTGAAACCCGTATTACCGTGCGTGGTTTTTGTCAGGATACCG
AACCGCAGACCATTTGGACCCGTACCACCTTTGATCGTCCGTTTGTTGCACATGGCACCTGGGATGGTCAG
GTTGTTACCGCAGGCGCAGATGCAGCAAGCGGTGGTGAAGGTCGTCGTGGTGCATATGTTACCTTTGATAC
AACCGGTGGTGATCTGGATGTTGAAGCAGTTACCGCAATGAGCTATGTTGGTGCAGATGGTGCAGCAGCAA
ATCTGGCAGCAGAAGCAGGCACCTTTGACGCAGTTCATGATGCAGCACGTAGCGCATGGGAAGAACGTCTG
GGTCTGGTTCGTGTTGCACAGGGTGATCCGGATGATCTGCGTACCTTTTATAGCAGCCTGTATCGTAGCTT
TCTGGCACCGAATGTTGGTTCTGATGTGGATGGTCGTTATCGTGGTTGGGATCAGGAAGTTCACGCAGCAG
AACCGGATTTTACCTATTATCAGAATTATAGCCTGTGGGATACCTATCGTACCCAACAGCAACTGCTGTAT
CTGCTGGCACCGGATGAAAGCGCAGATATGGCACTGAGCCTGGTTCGTCAGGGTCAGCAGGGTGGTTGGCT
GCCTCGTTGGGGTTATGGTACAGTGGAAACCAATATTATGACCGGTGATCCGGCAACCCCGTTTCTGGTTA
GCGCATGGCGTCAGGGTCTGCTGGCAGGTCATGAAGAAGCATACGCAGTCCTGCGTGAAAATGCAGAT
GGTGTTCCTCCGGCAGATAGCCCGTTTAATGGTCGTGCAGCCAATGTTGAATATCTGCGTGATGGTTTTGT
TCCGCATGAACCGGCACGTAGCGGTAAACCGGGTGATTATGATCTGCAGCATGGTGCAAGCGCAACCATGG
AATATGCACTGGCAGATGCAATGCTGAGCACCATGGCACGTGGTCTGGGTCATGATGAAGATGCAGATCGT
TATGCAGCCCGTGGTCAGAGCTATCGTAATGTTTTTGATCCGCGTACCGGTAATTTTCGTGCACGTAATGC
CGATGGTTTTTTTGTTGGTGATGCAGATCCGGCACATTCTGATGGTTTTCATGAAGGCACCGCAGTTCAGT
ATCAGTGGCTGGTTCCGCAGGATGTTCCGGGTCTGTTTGATCTGATGGGTGGCACCGATGCAGCCGTTGAT
CGTCTGGATGCATTTTTTGCCTATGATGAACTGGTTGCAGATCCTCCGCATGTTGCAAGCGAAGTTTGGGT
TAATGGCACCTATGATTATTATGGCTGGGAAACCTATAATCCGAATAATGAACCGAATCTGCATGCACCGT
ATGTTTATCTGTGGACCGGTCAGCCGTGGAAAACCACCGATGTTGTTCGTGCAGCAAGCACCCTGTTTACC
GATGGTCCGGATGGTGTTACCGGTAATGATGATCTGGGCACCATGAGCGCATGGCATGTTCTGAGCAGCAT
TGGTGTTTATCCGATTGTTCCGGGTGCCGATCTGTGGGGTCTGACCACACCGCTGTTTGATGATGTTACCA
TTACCCTGGACCCGGAAGTTTTTGGTCGTGATAGCCTGCGTCTGACCGCAGATGGTGTGGCACCGGATACC
CATTATACCCAGAGCGTTAGCCTGGGTGGTGAACCGCTGGATCGTGCATGGGTTACAGGTGATGAACTGAC
CGCTGCAGGCACCCTGGATGTTACCGTTGGCACCGAACCGAGCGCATGGGCAACCGATCCGGCAGCATCAC
CGGGTGCAGTTGTTCCGGCTGATGGCACCGTTGAACGTCTGTTTGTTGGTGCAACACCGCGTCAGCCGGTT
CTGGCACCGGGTGGTCGTACCGAAGTTGCAGTTCAGGTTGTTGCCCAGGGTGCAGGCACCTCTAGCGGCAC
CCTGGAAGTGACCTCTGATGGTGCAGTTACCGCCACCACCGATCTGGCAGAATGGACCGCAGAATCTGATG
GTCTGCCTGCCACCGTTGAAGGAACCGTTACCATTGAAGCTCCGGCAGATGCCGAACCGGGTCTGCATACC
GTTCGTCTGGTTGTTCGTGATGCAGCCGGTACAGAAGCAGTTCGCGAAGTTAGCGTTGTTGTTAGCGGTGA
AAGCTGGATTGCAGATGCCTTTGATAATGTGGGTATTGGTGATGCCGGTGCAGCAAATGCAAATCTGGATG
GTAGCGGTGCCTATCTGCTGCGTGATCTGCTGGCCGATCTGGGTGCAGTTCAGGGTCTGGAACTGACCGTT
CCGGGTACTGATCTGACCTATACCCTGGGTGCACCGCGTGCTGGTGCACCGGATAATGTTGCAGCCAGCGG
TGAAGTTCTGGAAGTTCCGGAACATCTGCGTAGCGCACGTCATCTGAGCGTTGTGGGCACCAGCACCCATG
GTACACATGGTGGTGGTCTGGTTCTGGGTTTTGCCGATGGTAGCAGCCAGACCGTTGATGTTCGTCTGAGC
GATTGGTGTACCGGTTCTCCGGAACCGGGTAATATTACCGTTGCAAAAGCCGGTGCACGTGGTGATCGTGA
AAATGTGCAGAAAATTGGCTGTGGTCTGTATGCAACCGCACCGGTGGCAATTCCGGAAGGTAAAGTTCTGA
CCAGCGTTACCCTGCCGTCTGATGAACGTTTTCATGTGTTTGCAATTGCAACCGATGCAACCGGTGATGTT
CCGGCACCGCAGGTTGAAGTTACCGCACAGGCTCGTTGTCTGGGTGGTAAAGCATTTGTTGCAGTTCGTGC
ACTGAATACCGGTGAACAGCCTGCAGCAATTGAACTGGCAACCCCGTATGGTAGCAAACTGTTTGGTGATG
TTGCTCCGGGTGCAAATGCATATCAGAGCTTTGCAACCCGTGCAGCAGCCGTTGAAGCCGGTGAAGTTACC
GTTACCGTGACCACACCGGATGGTGAACCGCAGCAGGTTACCGCAGCATATGATGCAGCGGCATGTAGCTA
ATAA (SEQ ID NO:17)

FIG. 15

GCAGGCACCGAAGCAGCAACCGGTTCTGATGCAGCAGCAGTTGATGGTCCGCTGGTTGATTATGTGAATCC
GTTTATTGGCACCAAAGATGATGGTAATACCTATCCGGGTGCAGCAGTTCCGTTTGGTATGGTTCAGCTGT
CTCCGGATAATGGTCATAATGTGGGCTATGATTATGATCGTACCAGCGTTCGTGGTTTTAGCCTGGTTCAT
CTGAGCGGTGTTGGTTGTGGTCTGGGTGGTCCGCTGCCGACACTGCCGACCACCGGTGCAATTACCAGCAC
CGATTATGGTCAGTATGCACTGGGTTTTAGCCATGATGATGAAGAAGCATCTCCGGGTTATTATCGTGTTG
GTCTGCAGGCACCTGCAGGAACCATTGAAGCAGAACTGACCGCAACCGAACGTACCGGTGTTCAGCGTTAT
ACCTTTCCGGCAACCGCACAGGCAAATGTTCTGCTGAATGCAGGTCAGGCACTGAATCGTGTTACCGAATC
TGATGTTCGTGTTGTTGATGATCGTACCGTTGAAACCCGTATTACCGTGCGTGGTTTTTGTCAGGATACCG
AACCGCAGACCATTTGGACCCGTACCACCTTTGATCGTCCGTTTGTTGCACATGGCACCTGGGATGGTCAG
GTTGTTACCGCAGGCGCAGATGCAGCAAGCGGTGGTGAAGGTCGTCGTGGTGCATATGTTACCTTTGATAC
AACCGGTGGTGATCTGGATGTTGAAGCAGTTACCGCAATGAGCTATGTTGGTGCAGATGGTGCAGCAGCAA
ATCTGGCAGCAGAAGCAGGCACCTTTGACGCAGTTCATGATGCAGCACGTAGCGCATGGGAAGAACGTCTG
GGTCTGGTTCGTGTTGCACAGGGTGATCCGGATGATCTGCGTACCTTTTATAGCAGCCTGTATCGTAGCTT
TCTGGCACCGAATGTTGGTTCTGATGTGGATGGTCGTTATCGTGGTTGGGATCAGGAAGTTCACGCAGCAG
AACCGGATTTTACCTATTATCAGAATTATAGCCTGTGGGATACCTATCGTACCCAACAGCAACTGCTGTAT
CTGCTGGCACCGGATGAAAGCGCAGATATGGCACTGAGCCTGGTTCGTCAGGGTCAGCAGGGTGGTTGGCT
GCCTCGTTGGGGTTATGGTACAGTGGAAACCAATATTATGACCGGTGATCCGGCAACCCCGTTTCTGGTTA
GCGCATGGCGTCAGGGTCTGCTGGCAGGTCATGAAGAAGAAGCATACGCAGTCCTGCGTGAAAATGCAGAT
GGTGTTCCTCCGGCAGATAGCCCGTTTAATGGTCGTGCAGCCAATGTTGAATATCTGCGTGATGGTTTTGT
TCCGCATGAACCGGCACGTAGCGGTAAACCGGGTGATTATGATCTGCAGCATGGTGCAAGCGCAACCATGG
AATATGCACTGGCAGATGCAATGCTGAGCACCATGGCACGTGGTCTGGGTCATGATGAAGATGCAGATCGT
TATGCAGCCCGTGGTCAGAGCTATCGTAATGTTTTTGATCCGCGTACCGGTAATTTTCGTGCACGTAATGC
CGATGGTTTTTTTGTTGGTGATGCAGATCCGGCACATTCTGATGGTTTTCATGAAGGCACCGCAGTTCAGT
ATCAGTGGCTGGTTCCGCAGGATGTTCCGGGTCTGTTTGATCTGATGGGTGGCACCGATGCAGCCGTTGAT
CGTCTGGATGCATTTTTTGCCTATGATGAACTGGTTGCAGATCCTCCGCATGTTGCAAGCGAAGTTTGGGT
TAATGGCACCTATGATTATTATGGCTGGGAAACCTATAATCCGAATAATGAACCGAATCTGCATGCACCGT
ATGTTTATCTGTGGACCGGTCAGCCGTGGAAAACCACCGATGTTGTTCGTGCAGCAAGCACCCTGTTTACC
GATGGTCCGGATGGTGTTACCGGTAATGATGATCTGGGCACCATGAGCGCATGGCATGTTCTGAGCAGCAT
TGGTGTTTATCCGATTGTTCCGGGTGCCGATCTGTGGGGTCTGACCACACCGCTGTTTGATGATGTTACCA
TTACCCTGGACCCGGAAGTTTTTGGTCGTGATAGCCTGCGTCTGACCGCAGATGGTGTGGCACCGGATACC
CATTATACCCAGAGCGTTAGCCTGGGTGGTGAACCGCTGGATCGTGCATGGGTTACAGGTGATGAACTGAC
CGCTGCAGGCACCCTGGATGTTACCGTTGGCACCGAACCGAGCGCATGGGCAACCGATCCGGCAGCATCAC
CGGGTGCAGTTGTTCCGGCTGATGGCACCGTTGAACGTCTGTTTGTTGGTGCAACACCGCGTCAGCCGGTT
CTGGCACCGGGTGGTCGTACCGAAGTTGCAGTTCAGGTTGTTGCCCAGGGTGCAGGCACCTCTAGCGGCAC
CCTGGAAGTGACCTCTGATGGTGCAGTTACCGCCACCACCGATCTGGCAGAATGGACCGCAGAATCTGATG
GTCTGCCTGCCACCGTTGAAGGAACCGTTACCATTGAAGCTCCGGCAGATGCCGAACCGGGTCTGCATACC
GTTCGTCTGGTTGTTCGTGATGCAGCCGGTACAGAAGCAGTTCGCGAAGTTAGCGTTGTTGTTAGCGGTGA
AAGCTGGATTGCAGATGCCTTTGATAATGTGGGTATTGGTGATGCCGGTGCAGCAAATGCAAATCTGGATG
GTAGCGGTGCCTATCTGCTGCGTGATCTGCTGGCCGATCTGGGTGCAGTTCAGGGTCTGGAACTGACCGTT
CCGGGTACTGATCTGACCTATACCCTGGGTGCACCGCGTGCTGGTGCACCGGATAATGTTGCAGCCAGCGG
TGAAGTTCTGGAAGTTCCGGAACATCTGCGTAGCGCACGTCATCTGAGCGTTGTGGGCACCAGCACCCATG
GTACACATGGTGGTGGTCTGGTTCTGGGTTTTGCCGATGGTAGCAGCCAGACCGTTGATGTTCGTCTGAGC
GATTGGTGTACCGGTTCTCCGGAACCGGGTAATATTACCGTTGCAAAAGCCGGTGCACGTGGTGATCGTGA
AAATGTGCAGAAAATTGGCTGTGGTCTGTATGCAACCGCACCGGTGGCAATTCCGGAAGGTAAAGTTCTGA
CCAGCGTTACCCTGCCGTCTGATGAACGTTTTCATGTGTTTGCAATTGCAACCGATGCAACCGGTGATGTT
CCGGCACCGCAGGTTGAAGTTACCGCACAGGCTCGTTGTCTGGGTGGTAAAGCATTTGTTGCAGTTCGTGC
ACTGAATACCGGTGAACAGCCTGCAGCAATTGAACTGGCAACCCCGTATGGTAGCAAACTGTTTGGTGATG
TTGCTCCGGGTGCAAATGCATATCAGAGCTTTGCAACCCGTGCAGCAGCCGTTGAAGCCGGTGAAGTTACC
GTTACCGTGACCACACCGGATGGTGAACCGCAGCAGGTTACCGCAGCATATGATGCAGCGGCATGTAGCTA
ATAA (SEQ ID NO:18)

FIG. 16

GCAGAACCGGGTGATTTTAGCAGCAGCTTTGAATCTGGCGATCCGGCAGCACTGCCGACCACCGTTGCAGA
ACGTGATGGTGCACCGTGGCAGGCAAATGTTGGTAGCTTTACCGCAGGTCTGCCTGGTAGCGTTCTGGGTC
AGCTGAAAGGTGTTACCGCAAGCGCACAGAATCTGCCGAATGAAGGTGCAGCAAATCTGGCAGATGGTAGC
AGCGGCACCAAATGGCTGGCATTTGCAAGCACCGGTTGGGTTCGTTATGAATTTGCAGAACCGGTTAGCTT
TGTTGCATATACCATGACCAGCGGTGATGATGCCGCAGGTCGTGATCCGAAAACCTGGACCGTTGAAGGTA
GCAATGATGGTTCTACCTGGGCAGCACTGGATCGTCGTACCGATGAAGATTTTCCGAATCGTCAGCAGACC
CGTACCTTTGAACTGGAAGCACCGACCGCAGCATATACCTATCTGCGTCTGAATGTTACCGCAAATAGCGG
TGATAGCATTGTTCAGCTGGCAGGTTGGGATCTGAGCGCAGATCTGTCTGCAGGTCCGAGCGCAGCACCGA
TGACCACCAAAGTTGGCACCGGTCCGCGTGTTAGCTTTACCAATAAAGCCGGTGTTGGTTTTAGCGGTCTG
CATAGCCTGCGTTATGATGGTAGCCATCTGGCCGATGGTGAAACCTATGCAACCAATGTGCTGTATGATGA
TGTTGATGTTGTGGTTGGTGAAGATACCCGTCTGAGCTATACCATTTTTCCGGAACTGCTGGATGATCTGC
AGTATCCGAGCACCTATGCAGCAGTTGATGTTCTGTTTACCGATGGCACCTATCTGAGCGATCTGGGTGCA
CGTGATGCACATGAAACCGTTGCAACCGCACAGGCACAGGGTGAAGGTAAAATTCTGTATGCCGATCAGTG
GAATAGCGTTCGTGTTGATCTGGGTGATGTTGCAGAAGGTAAAACCGTTGATCAGGTTCTGCTGGGTTATG
ATAATCCGGGTGGTCATGCAGGCACCAAATTTGCAGGTTGGCTGGATGATGTTGAAATTACCGCAGAACCG
GCAACCATTGATGGTAGCTCACTGGCAAATTATGTTGATACCCGTCGTGGCACCCTGGCAAGCGGTAGCTT
TAGCCGTGGTAATAATATTCCGGCAACCGCAACCCCGAATGGTTTTAATTTTTGGACCCCGTATACCAATG
CAAGCAGCCAGAGCTGGCTGTATGAATATCATAAAGCCAATAATGCGAATAATAAACCGGTTCTGCAGGGT
TTTGGTATTAGCCATGAACCGAGCCCGTGGATGGGTGATCGTAATCAGCTGACCTTTCTGCCGAGCACCGC
AAGCGGTACACCGGATGCAACCCTGAGCACCCGTGGTCTGGAATTTGATCATGCAGATGAAACCGCACGTC
CGGATTATTATGGTGTGACCTTTACCAATGGTAGCGCAATTGAAGCAACCCCGACCGATCATGGTGCAGTT
CTGCGTTTTAGCTATCCGGGTGCAAAAGGTCATGTTCTGGTGGATAAAGTTGATGGTAGCAGTAAACTGAC
CTATGATCAGGCAACCGGCACCATTAGCGGTTGGGTTGAAAATGGTAGCGGTCTGAGCGTTGGTCGTACCC
GTATGTTTGTTGCAGGCACCTTTGATCGTAGCCCGACCGCAGTTGGCACAGCAGCAGGTAATCGTGCAGAT
GCACGTTTTGCAACCTTTGAAACCAGCAGCGATAAAACCGTGGAACTGCGTGTTGCAACCAGCTTTATTAG
CCTGGATCAGGCACGTAAAAATCTGGATCTGGAAGTTACCGGTAAAACCTTTACCGAAGTTAAAGCAGCAG
CAGCACAGGCATGGAATGATCGTCTGGGTGTTATTGAAGTTGAAGGTGCAAGCGAAGATCAGCTGGTTACC
CTGTATAGCAATCTGTATCGCCTGAATCTGTATCCGAATAGCCAGTTTGAAAATACCGGCACCGCACAGGA
ACCGGTTTATCGTTACGCATCTCCGGTTAGCGCAACCACCGGTAGCGCAACCGATACCCAGACCAATGCCA
AAATTGTGGATGGCAAAATTTATGTGAATAATGGCTTTTGGGATACCTATCGTACCGCATGGCCTGCATAT
AGCCTGCTGTATCCGGAACTGGCAGCAGAACTGGTTGATGGTTTTGTTCAGCAGTATCGTGATGGTGGTTG
GATTGCACGTTGGAGCAGTCCGGGTTATGCAGATCTGATGACCGGTACAAGCTCTGATGTTGCATTTGCAG
ATGCCTATCTGAAAGGTAGCCTGCCGACCGGTACAGCACTGGAAGCATATGATGCAGCACTGCGTAATGCA
ACCGTTGCACCTCCGAGCAATGCAGTTGGTCGTAAAGGTCTGCAGACAAGCCCGTTTCTGGGTTTTACACC
GGAAAGCACCCATGAAAGCGTTAGCTGGGGTCTGGAAGGTCTGGTTAATGATTTTGGCATTGGCAATATGG
CTGCAGCACTGGCAGAAGATCCGGCAACACCGGAAGAACGTCGTGAAACCCTGCGTGAAGAAAGCGCATAT
TTTCTGGAACGTGCCACCCATTATGTTGAACTGTTTGATCCGGAAGTGGATTTTTTTGTTCCGCGTCATGA
AGATGGTACATGGGCAGTTGATCCGGAAACCTATGATCCGGAAGCATGGGGTGGTGGTTATACCGAAACCA
ATGGCTGGAATTTTGCATTTCATGCACCGCAGGATGGTCAGGGTCTGGCAAATCTGTATGGTGGTAAACAG
GGTCTGGAAGATAAACTGGATGAATTTTTTAGCACACCGGAAAAAGGTGCAGGTAATGGTGGTATTCATGA
ACAGCGTGAAGCACGTGATGTTCGTATGGGTCAGTGGGGTATGAGCAATCAGGTTAGCCATCATATTCCGT
GGCTGTATGATGCAGCCGGTGCTCCGAGCAAAGCACAGGAAAAAGTTCGCGAAGTTACCCGTCGTCTGTTT
GTTGGTAGCGAAATTGGTCAGGGTTATCCGGGTGATGAAGATAATGGTGAAATGTCCTCCTGGTGGATTTT
TGCAAGCCTGGGTTTTTATCCGCTGCAGGTTGGTAGCGATCAGTATGCAGTTGGTTCTCCGCTGTTTGATA
AAGCAACCGTTCATCTGCCGGATGGTGATCTGGTTGTTAATGCCGAAAATAATAGCGTGGATAATGTGTAT
GTTCAGAGCCTGGCAGTTGATGGTGAAGCACGTACCAGCACCAGCCTGAGCCAGGCAGATCTGAGCGGTGG
CACCACCCTGGATTTTGTTATGGGTCCGGAACCGAGCGATTGGGGCACCGGTGAAGATGATGCACCTCCGT
CACTGACCGAAGGTGATGAACCTCCGACACCGGTTCAGGATGCAACCACCGCAGGCCTGGGCACCACCACC
GTTGCCGATGGTGATGCCACCACCTCTGCAGCAGCCCTGACCGATAATACCAGCGGCACCCGTACCACCTT
TGCAACCACCACCCCGAGCATTACATGGGCAGGTAATGGCATTCGTCCGACCGTTGGTAGCTATACCCTGA
CCTCTGGTGCAAGCGGCACCGCAAGCCCGTCTGCATGGACCCTGGAAGGTTCTGATGATGGCGAAACCTGG
ACCACACTGGATGAACGTAGCGGTGAACAGTTTCGTTGGGCACTGCAGACCCGTCCGTTTACCGTTGCCGA
ACCGACCGCATTTGCACGTTATCGTGTTACCGTTACCGCAACCAGCGGTTCTGGTGCACTGAGCCTGGCAG
AAGTTGAACTGCTGGCAGATCCGAAAGAAAGCGGTGCAGAAGAACTGACCCTGTCTGCAGCACCGGATCGT

FIG. 17-I

GATGGCGTTACCGGTCGTGAAGTTAGCGGTTCTTTTGCAACCCTGACCGGTGTTGAAGGTGATGTTGCCGC
ACTGGATGTTCAGGTTGCATTTGGTGATGGTAGCGAACCGGTTGCAGGTACACTGCGTGCCGGTGCATTTG
GTGGTTATGCAGTTGATGCAGCACATACCTGGACCGCACCGGGTGTTTATCCGGTTACCGTGACCGTTAGC
GGTGAAGGTATTGAAACCGTTAGCGCAAGCAGCTATGTTAGCGTTAGCCTGCTGCGTGAAGGTTCTCTGCT
GGCAGCATATGATAATGTGTGCATTGGTGATGCAGGTACAACCGTTGGTTCTTGTGATGGTCAGGGCGTTT
TTTTTGATCGTGCACAGCTGGCAGCAAAAGGTTTTGTGCAGGGTGAACGTGCAACCGTTCCGGGTACAGAT
CTGGCATTTGATGTTCCGGCAGTTCCGGCTGGTCAGCCTGATAATGCAACCGGTGATGGTCAGACCATTGA
ACTGGATGTTCCGGCTGATGCAGAACAGCTGAGCGTTATTGGCACCGGCACCGAAAAAAATCAGCAGGCAA
CCGGTACACTGACCTTTGATGATGGTTCTACCCAGCCGATTGATCTGAGCTTTGGTGATTGGAGCGGTGCA
GCACGTAATCCGGTGTTTGGTAATATTCCGGTTGCAGTTACCGATAGCCGTCTGCGTGGTGGTTCTCCGCA
GACCGGTACACCGGCAGCATTTTTTGCCACCGCACCGATTACCCTGCCGGAAGGTAAACGTCCGGTTAGCC
TGACCCTGCCGGATCAGCCTGGTGAACTGAGCCGTGATGGTCGTATTCATGTTGTTGCAGTTGCACATGAT
GGCACCTTTGCAGAACATCCTGCACTGGAAGTGACCGCAGCAGAAGGTGTTACCCTGGCAGTTGGTCAGAC
CTCAGATGTTGCACTGGCACAGGTTGCCGGTGGTCGTGAAGGTGCAGATCTGCGTGCCGCAGTTACCTGGG
GTGATGGTTCTGATGTGGCAGCCGGTGCCGTTACCGATGGTAGCGTTAGCGGTAGCCATGCATATACCGCA
GCAGGCACCTATACCGCATATGTTGTTGTGGATGATGGTTGGACCAGCCAGGTTGTTGAAGTTCCGGTGAC
CGTTACAGAAGCCGAACCGGCACTGGCCGTTGATGTCACCGTTAGCACCCGTTGCCTGGCAGGTAAAGCAT
ATGTTGCAGTGCGTGCAGAAAATGGTGAAGATGTTCCGCTGGCAATTCGTCTGGTTACCCCGTTTGGCACC
AAAGAAGTTGCAGCAGTTGCTCCGGGAGCCAATGCATATCAGAGCTTTGCAACCCGTGTTACCGCAGTTGA
AGCAGGCACCGTTACCGTTGAAGCCACCCGTGGCACCGGTGATGAAGAAGTTACCGCCAGCATTCAGGCAG
ATTATGCAGCCGTTACCTGCGGTTAATAA (SEQ ID NO:19)

FIG. 17-2

GATATGCCTGCAGCACAGGCACCGAATGGTCTGGCAAAAGTTAATCCGCGTACCACACCGGGTCGTAATAA
TACCGGTTATGATTATGCCCAGAGCAAAATTAGCGGTTTTACCCATACCAATCTGGATGGTGTTGGTGGTA
GCGGTGGTGGTGGTGATCTGCTGGTTGTTCCGACCAGCGGTAGCTATACCGCACGTCCGGGTACAGGCACC
TATGCACATCCGTTTAGCCATGATGATGAAGATGCAGGTCCGGGTTTTTATAGCGTTGGTCTGGGTAATGT
TGCAGGCACCGATGGTGCAATTACCGGTGCTCCGGGTACAATTGAAGCAGAAGTTGCAGCAGCAACCCGTA
GCGGTGTTCATCGTTATGCATTTCCGGCAGGTAGCACCCCGAGCCTGGTTGTTGATCTGGAAACCAATAAT
ACCAGCCGTCGTAGCAGCAGCGTTCAGGTTGAAACCCGTGCAGATGGCACCGTTGAACTGAGCGGTCAGGT
TACCGGCTATTTTTATAATGCAGCCTATACCCTGTATTATACCGCACGCACCCTGCAGCCTGCAACCGTTC
AGACCTGGGGTGATGATGATCGTCTGGTTGATGCAACCGCACAGGATGGTGTTGATACCGGTGCAATTCTG
ACCTTTGATCCGGCAGATGCCGGTGAAATTGGTCTGCAGGTTACCCTGTCTCCGGTTAGCGTTGAACAGGC
ACGTATTGATCAGCAGGTTGAACTGGGTGATCTGAGCTTTGATGCAATTCGTGATCGTACCCGTGCAGAAT
GGAATGCAACCCTGGGTCGTGTTGCAATTGATGCAAGCACCGCAACCGATCCGACCGGTGAACTGCAGCGT
CTGTTTTATACCCATCTGTATCGCATGTTTGCAATGCCGATGAATGCAACCAGCACCAGCGGCACCTATCG
TGGTGTTGATGGTGCAGTTCATGCAGCACAGGGCTTTACCTATTATGATAGCTGGGCAACCTGGGATGATT
TTCGCAAATTTAGCGTGATTGCCTATATTGATCCGGCACTGTATCGTGATATGGTTCAGAGCCTGGTTTAC
CTGTTTGCAGATGCAGAAGCAACCGGTACAGGCGGTGGTCTGGGTGGTTTTGTTCATAGCGTTCCGACCGT
TCGTTGGGAACGTAGCAGCGTTGTTGTTGCAGATGCAATTGCCAAAGGCTTTGATGGTTTTGATCGTCTGG
ATGAAGCATATCCGGCACTGCAGCGCCTGGTTGGTCAGTATAGCGCAGATGAACTGCGTCGTGGTTATGTT
GCAGGTAATCCGGGTGCAAGCGTTCAGCGTGGTTATGATCAGTATGGTCTGAGCGTTATTGCCGATGAACT
GGGTCTGACCGAAGAAGCAGAAACCCTGCGCGAACAGGCAAGCTGGCCGATTGAAAAACTGACCAAACCGG
GTGCATGGACCGCAGCAGATGGTACACAGGTTGGTCTGCTGACACCGCGTGCAGCCGATGGTAGCTGGCAG
AGCGCAGATCATGCCAAATTTGAAGCAGCAGGTCTGTATCAGGGCACCCTGTGGCAGTATCATTGGTATGA
TGCCTATGATATGGATGCACTGGTTGAAGCAATGGGTGGTCATGAAGCAGCCCGTCTGGGTATGCGTCATA
TGTTTGGTGAACATGCACCGGATGATGGTAAAGCAATGCTGCATAGCAATGCCAATGAAATTGATCTGCAG
GCACCGTACCTGTTTAATTATACCGGTGAACCGAGCCTGACCCAGAAATGGGCACGTGCAATTTATACCAA
AGAAACCTGGAATCGCTATATTGCAACCGGTAGCAGCTCTGCAGTTCCGTCAGGTGGTGGTGAATTTACAC
CTCCGCTGAAAACCAAAGTTTATCGTCTGGACCCTCGTGGTATGCTGCCGACCATGGATAATGATGCAGGT
ACAATGAGCACCATGTTTGTTGCAGCAGCCGTTGGTCTGTTTCCGGTTACCGCAGGTAGCAGCCAGTTTCA
GGTTGGTAGCCCGTTTTTTGATAGCACCACCATTACCTATGATGATGGTAGCGCATTTACCGTTACCGCAG
ATGGTGTTAGCGAAGATGCCTTTTATGTTCAGAGCGCAACCCTGGATGGTGCAACCTTTGGTAATACCTGG
GTTGATTATGCAACCGTTGTTGGTGGTGCAGATCTGGCATTTCGTATGGGTGAACAGCCGAGCGATTGGGG
CACCGATACCGCACCGGCATTTAGCATGAGCACCGCCACCGATGAACCGGCAGAAGGTCCTCGCGTTAGCG
CAGAACCGACCACCGTGCAGACCGGTGATGGTGGTGCACTGGATGCAACCGTTACCCTGACACTGGATGGC
GCACGTCTGGCAGCACCGGCAGGTACAGATCTGGTTACCAGCGGTGCAGCAAGCGTTGTTGGTCTGCCGGA
TGGTGTTACCGCAGCAGTTACCGTTGCAAGCCCGACCGCACTGACCGTTAGCCTGACCGGCACCGCATCAG
CAGATGCACGTTTTTTTGTGCATCTGCGTGATGCAGCACTGGCCGATGGTGTTGCAGCCGCAAGCCTGCAG
GGTCAGGGTGTTAGCGTTCGTTCTCCGCTGCGTCTGAGCGTTGCAAGCGCAGAACGTGATGCACTGGCAGC
ACTGGTTGATGATGCCGTTCTGGTTCGTCATGGTAATTATAGCAGCGTTACCTTTGATCGTTTTAGCACCG
CTCTGACAAAAGCACAGGAAGCACTGGGCGACGAAGCAGCAACCAGCATTGCACTGCGTTTTGCAGCAGAT
CGTCTGGGTGCAGCAGCAGATGCACTGGATCTGACCGGTGGTGGTTATCGTACCCTGGAAGCAGAACAGAG
CGAAGCATGGTCTGGTGGTGAACTGAAAAATGAAGCCAATAGCAGCAGCGGTAATCTGGGTGGTGTTCGTA
GCGGTAGCTGGGTTCAGTATCGCGATATGACCTTTGAAACCGCAGCCGGTGATACACCTCCGCGTTTTCTG
ACCGTTCGTTATGATACCAGCTTTGCACCGACCGATACCCCGAGCACCGTTCGTGTTCATGCCGGTGATGT
TTCTGGTCCGGTTGTTGCAACCGTTGATCTGAAAGGCACCAGCGGTTGGGGTAAATATACCGAAGTTACCG
CAGAACTGGGTGATGTTCAGGCCCTGGTTGATGCCCAGGTTGTTACCTTTGAACTGCTGGCACCGAGCGGT
CGTAGCTGGGTTGGTAATTTTGATTGGTTTCGCTTTAGCGCAGAAGATCCGGCAGCACCGGGTCAGCCTGG
TGAAAGCCCGACCGTTACCATTGAAGCCGAAGATTGGACCGCAAGCAGCGGTCGTGGTCTGAAAAAAGAAA
GCAGCACCTGGACCAGCGGTCCGGTGACCAATGTTGGTGGTACAGCAGATGGTGATTGGATTGCCTATGGT
GAAGTTGATCTGGGTGAACTGCCGCTGGGCGAACTGAGCGTTCATTATGTGCATAATAGCAATCGCAGCGG
TAATAATAGCGCACTGAGCGTTTATCTGGATGCATTTGATCCGGCTAATCCGGGTGAACCGTTTGTTACCG
TTCCGCTGCCGACCACCGGTAGCAGTTGGACCGCAGATGGCACAGCCACCGTTGTTCTGCCGGAAACCGTG
CAGGGCACCCATGAAGTTTTTGTTCGTCTGAGCACCGAACCGTATGCAGATCATCCGTATGTTGCAAATCT
GGATAGCCTGACCTTTGCACCGGGTGGTCCGACCAGCGTTGTGGTTGAAAGCGAAGCCTGGACCAGCAATT
CTGGTCGTGGCCTGAAAAATGAATCTTCTACCTGGACCTCTGGTCCGGTTACAAATGTGGGTGGCACCGCT

FIG. 18-1

GATGGCGATTGGCTGGCATATGGCGAAATTGATCTGGGCAGCGCAGCACTGGATCAGCTGTCTGTGCATTA
TGTTCATAATTCTAATCGCTCTGGTCGTAATTCTGCACTGTCTGTGTATCTGGATGCCTTTGATCCGGCAA
ATCCGGGTGAACCGTTTGTGACAGTGCCGCTGGCAAATACCGGTAGCTCTTGGACCACCGATGGTACTGCA
GTTGTGGATCTGCCGTCTACCGTTCGTGGTAAACATCAGGTTTGGGTTCGTCTGTCTACCGAAGCATATGC
CGATCATCCGTATGTGGCCAATCTGGATTCTATGCGCTTTTTTACCGATGCATATGATGTTGAAGTTCCTC
CGACCGATACAGCAGCACTGGCAGCCGTTGTTGATGCAGCAGGTACACCGGAAGCAGAAATTGCACGTTAT
GGTCGTATTGATGCCCGTGTTTTTACCCGTGAACTGGCAGCAGCACGTAGCGTTCTGGCCGATGCCGGTGC
AACACAGGCACAGGCAGATGAACGTGCTCGTCGTCTGGGTCTGGCAACCGATCAGCTGGTTCCGGCAGAAC
GTCGTCGTCTGGAAAATCTGGTTGCCAGCGCAGAAGCACTGACCGACGAAGGTTATTCTCCGGAAAGCTGG
CAGGCATTTCGTACCGCACTGGCTGCTGCAACCGGCACCCTGGATGATGCAGCAGCATCTGATGAAGCACT
GCATGATGCACGTCTGGCGCTGCAGGGTGCAGTTGATGCACTGGAAGAACCGGCAGATGTTGTTCTGGTTG
AAGTTGAAGTTTCTCCGCGTTGTCTGGCAGGTAAACCGTATGTTGCCGTTCGTGCAGTTAATGTTTCTGAT
GCAGCCGTTGATGTTGAACTGGCAAGCTCTCTGGGCACCCGTAGCTTTGTTGGTGTGGCACCGGGTGCGAG
CGCATATCAGAGCTTTGCAGCCCGTAGCGCAACCGGTGATCTGGATGTTACCGTGACCGCAACCGGTGCAG
ATGGTACTCAGACCGTTGAACAGGTTGTGACCGTTCCGAGCTGTAGCTAATAA (SEQ ID NO:20)

FIG. 18-2

ATGAAGCTTTCCACCATCCTCTTCACAGCCTGCGCTACCCTGGCCCTGGACAACGGCCTGGCCCGAACCCC
CACCATGGGCTGGCTGCACTGGGAGCGATTCATGTGTAACCTGGACTGTCAGGAAGAGCCCGACTCTTGTA
TCTCTGAGAAGCTGTTCATGGAAATGGCCGAGCTGATGGTGTCTGAGGGCTGGAAGGACGCCGGCTACGAG
TACCTGTGTATCGACGACTGTTGGATGGCCCCCCAGCGAGACTCTGAGGGCCGACTCCAGGCCGACCCCCA
GCGATTCCCCCACGGCATCCGACAGCTCGCCAACTACGTGCACTCTAAGGGCCTGAAGCTGGGCATCTACG
CCGACGTGGGCAACAAGACCTGTGCCGGCTTCCCCGGCTCTTTCGGCTACTACGACATCGACGCCCAGACC
TTCGCCGACTGGGGCGTGGACCTGCTGAAGTTCGACGGCTGTTACTGTGACTCTCTCGAGAACCTGGCCGA
CGGCTACAAGCACATGTCTCTGGCCCTGAACCGAACCGGCCGATCTATCGTGTACTCTTGTGAGTGGCCCC
TGTACATGTGGCCCTTCCAGAAGCCCAACTACACCGAGATCCGACAGTACTGTAACCACTGGCGAAACTTC
GCCGACATCGACGACTCGTGGAAGTCTATCAAGTCTATTCTGGACTGGACCTCTTTCAACCAGGAGCGAAT
CGTCGACGTCGCCGGACCCGGCGGATGGAACGACCCCGACATGCTGGTGATCGGCAACTTCGGCCTGTCTT
GGAACCAGCAGGTGACCCAGATGGCCCTGTGGGCTATCATGGCTGCCCCCCTGTTCATGTCTAACGACCTG
CGACACATCTCTCCCCAGGCCAAGGCCCTGCTCCAGGACAAGGACGTGATCGCCATCAACCAGGACCCCCT
GGGCAAGCAGGGCTACCAGCTCCGACAGGGCGACAACTTCGAGGTGTGGGAGCGACCCCTGTCTGGCCTGG
CCTGGGCCGTGGCCATGATCAACCGACAGGAGATCGGCGGACCCCGATCTTACACCATCGCCGTGGCCTCC
CTGGGAAAGGGCGTGGCCTGTAACCCCGCCTGTTTCATCACCCAGCTCCTGCCCGTGAAGCGAAAGCTGGG
ATTCTACGAGTGGACCTCTCGACTGCGATCTCACATCAACCCCACCGGCACCGTGCTGCTCCAGCTCGAGA
ACACCATGCAGATGTCTCTGAAGGACCTGCTGACGCGTGAACAAAAACTCATCTCAGAAGAGGATCTGAAT
AGCGCCGTCGACCATCATCATCATCATCAT (SEQ ID NO:22)

FIG. 26A

MKLSTILFTACATLALDNGLARTPTMGWLHWERFMCNLDCQEEPDSCISEKLFMEMAELMVSEGWKDAGYE
YLCIDDCWMAPQRDSEGRLQADPQRFPHGIRQLANYVHSKGLKLGIYADVGNKTCAGFPGSFGYYDIDAQT
FADWGVDLLKFDGCYCDSLENLADGYKHMSLALNRTGRSIVYSCEWPLYMWPFQKPNYTEIRQYCNHWRNF
ADIDDSWKSIKSILDWTSFNQERIVDVAGPGGWNDPDMLVIGNFGLSWNQQVTQMALWAIMAAPLFMSNDL
RHISPQAKALLQDKDVIAINQDPLGKQGYQLRQGDNFEVWERPLSGLAWAVAMINRQEIGGPRSYTIAVAS
LGKGVACNPACFITQLLPVKRKLGFYEWTSRLRSHINPTGTVLLQLENTMQMSLKDLLTREQKLISEEDLN
SAVDHHHHHH (SEQ ID NO:23)

FIG. 26B

ATGAAGCTTTCCACCATCCTCTTCACAGCCTGCGCTACCCTGGCTGCCGCCCAGCAGGGAGCCT
CTCGACCCGGACCCCGAGATGCCCAGGCTCACCCCGGACGACCTCGAGCTGTGCCCACCCAGTGTG
ACGTGCCCCCCAACTCTCGATTCGACTGTGCCCCCGACAAGGCCATCACCCAGGAGCAGTGCGAGG
CCCGAGGCTGTTGTTACATCCCCGCTAAGCAGGGCCTGCAGGGCGCTCAGATGGGCCAGCCCTGGT
GTTTCTTCCCCCCCTCTTACCCCTCCTACAAGCTGGAGAACCTGTCCTCTTCGGAGATGGGCTACAC
CGCCACCCTGACCCGAACCACCCCCACCTTTTTCCCCAAGGACATCCTGACCCTGCGACTGGACGTG
ATGATGGAGACCGAGAACCGACTGCACTTCACCATCAAGGACCCCGCCAACCGACGATACGAGGT
GCCCCTGGAGACCCCCCACGTGCACTCTCGAGCCCCTTCCCCCCTGTACTCTGTGGAGTTCTCTGAG
GAGCCCTTCGGCGTGATCGTGCGACGACAGCTGGACGGCCGAGTGCTGCTGAACACCACCGTGGCC
CCCCTGTTCTTCGCCGACCAGTTCCTGCAGCTGTCTACCTCTCTGCCCTCTCAGTACATCACCGGCCT
GGCCGAGCACCTGTCCCCCCTGATGCTGTCCACCTCTTGGACTCGAATCACCCTGTGGAACCGAGA
CCTGGCCCCCACCCCCGGTGCCAACCTGTACGGCTCTCACCCCTTCTACCTGGCCCTGGAGGACGGC
GGCTCTGCCCACGGCGTGTTTCTGCTGAACTCTAACGCCATGGACGTGGTGCTGCAGCCCTCTCCCG
CCCTGTCTTGGCGATCTACCGGCGGCATCCTGGACGTGTACATCTTCCTGGGCCCTGAGCCCAAGTC
TGTGGTCCAGCAGTACCTGGACGTGGTCGGATACCCCTTCATGCCCCCCTACTGGGGCCTGGGCTTC
CACCTGTGTCGATGGGGCTACTCTTCTACCGCCATCACCCGACAGGTGGTGGAGAACATGACCCGA
GCCCACTTCCCCCTGGACGTGCAATGGAACGACCTGGACTACATGGACTCTCGACGAGACTTCACC
TTCAACAAGGACGGCTTCCGAGACTTCCCCGCCATGGTCCAGGAGCTGCACCAGGGAGGACGACG
ATACATGATGATCGTGGACCCCGCCATCTCTTCTTCCGGACCCGCCGGATCTTACCGACCCTACGAC
GAGGGCCTGCGACGAGGCGTGTTCATCACCAACGAGACCGGCCAGCCCCTGATCGGCAAGGTGTG
GCCCGGCTCTACCGCCTTCCCCGACTTCACCAACCCCACCGCCCTGGCTTGGTGGGAGGACATGGT
GGCCGAGTTCCACGACCAGGTGCCCTTCGACGGCATGTGGATCGACATGAACGAGCCCTCTAACTT
CATCCGAGGCTCTGAGGACGGCTGTCCCAACAACGAGCTGGAGAACCCCCCCTACGTGCCCGGCGT
GGTGGGCGGAACCCTGCAGGCCGCCACCATCTGTGCCTCTTCGCACCAGTTTCTGTCTACCCACTAC
AACCTGCACAACCTGTACGGACTGACCGAGGCCATTGCCTCTCACCGAGCCCTGGTGAAGGCCCGA
GGCACCCGACCCTTCGTGATCTCTCGATCTACCTTCGCCGGCCACGGCCGATACGCCGGACACTGG
ACCGGCGATGTGTGGTCCTCTTGGGAGCAGCTGGCCTCTTCTGTGCCCGAGATCCTGCAGTTCAACC
TGCTGGGCGTGCCCCTGGTGGGCGCCGACGTGTGTGGCTTCCTGGGCAACACCTCTGAGGAGCTGT
GTGTTCGATGGACCCAGCTCGGCGCCTTCTACCCTTTCATGCGAAACCACAACTCCCTGCTGTCTCT
GCCCCAGGAGCCCTACTCGTTCTCTGAGCCCGCTCAGCAGGCCATGCGAAAGGCTCTGACCCTGCG
ATACGCCCTGCTGCCCCACCTGTACACCCTGTTCCACCAGGCCCACGTGGCTGGAGAGACCGTGGC
CCGACCCCTGTTCCTGGAGTTCCCTAAGGACTCTTCTACCTGGACCGTGGACCATCAGCTGCTGTGG
GGCGAGGCCCTCCTGATCACCCCCGTGCTGCAGGCCGGCAAGGCTGAGGTGACCGGCTACTTCCCT
CTGGGCACCTGGTACGACCTGCAGACCGTGCCTGTGGAGGCCCTGGGATCTCTGCCCCCTCCTCCCG
CCGCTCCCCGAGAGCCCGCCATCCACTCTGAGGGCCAGTGGGTGACCCTGCCCGCTCCCCTGGACA
CCATCAACGTGCACCTGCGAGCCGGCTACATCATCCCTCTGCAGGGACCCGGCCTGACCACCACCG
AGTCTCGACAGCAGCCCATGGCCCTGGCCGTGGCTCTGACCAAGGGCGGAGAGGCCCGAGGCGAG
CTGTTCTGGGACGATGGCGAGTCTCTGGAGGTGCTGGAGCGAGGCGCCTACACCCAGGTGATCTTT
CTGGCCCGAAACAACACCATCGTGAACGAGCTGGTGCGAGTGACCTCTGAGGGCGCTGGTCTGCAG
CTCCAGAAGGTGACCGTCCTGGGCGTGGCCACCGCTCCCCAGCAGGTCCTGTCTAACGGCGTGCCC
GTGTCTAACTTCACCTACTCTCCCGACACCAAGGTGCTGGACATCTGTGTGTCTCTGCTGATGGGCG
AGCAGTTCCTGGTGTCTTGGTGTTAAC (SEQ ID NO:24)

FIG. 27A

MKLSTILFTACATLAAAQQGASRPGPRDAQAHPGRPRAVPTQCDVPPNSRFDCAPDK
AITQEQCEARGCCYIPAKQGLQGAQMGQPWCFFPPSYPSYKLENLSSSEMGYTATLTRT
TPTFFPKDILTLRLDVMMETENRLHFTIKDPANRRYEVPLETPHVHSRAPSPLYSVEFSE
EPFGVIVRRQLDGRVLLNTTVAPLFFADQFLQLSTSLPSQYITGLAEHLSPLMLSTSWTR
ITLWNRDLAPTPGANLYGSHPFYLALEDGGSAHGVFLLNSNAMDVVLQPSPALSWRST
GGILDVYIFLGPEPKSVVQQYLDVVGYPFMPPYWGLGFHLCRWGYSSTAITRQVVENM
TRAHFPLDVQWNDLDYMDSRRDFTFNKDGFRDFPAMVQELHQGGRRYMMIVDPAISS
SGPAGSYRPYDEGLRRGVFITNETGQPLIGKVWPGSTAFPDFTNPTALAWWEDMVAEF
HDQVPFDGMWIDMNEPSNFIRGSEDGCPNNELENPPYVPGVVGGTLQAATICASSHQF
LSTHYNLHNLYGLTEAIASHRALVKARGTRPFVISRSTFAGHGRYAGHWTGDVWSSWE
QLASSVPEILQFNLLGVPLVGADVCGFLGNTSEELCVRWTQLGAFYPFMRNHNSLLSLP
QEPYSFSEPAQQAMRKALTLRYALLPHLYTLFHQAHVAGETVARPLFLEFPKDSSTWT
VDHQLLWGEALLITPVLQAGKAEVTGYFPLGTWYDLQTVPVEALGSLPPPPAAPREPAI
HSEGQWVTLPAPLDTINVHLRAGYIIPLQGPGLTTTESRQQPMALAVALTKGGEARGEL
FWDDGESLEVLERGAYTQVIFLARNNTIVNELVRVTSEGAGLQLQKVTVLGVATAPQQ
VLSNGVPVSNFTYSPDTKVLDICVSLLMGEQFLVSWC* (SEQ ID NO:25)

Numbering for equivalent residues in SEC ID NO:50 is given in parenthesis

```
                                                                                                   Section 1
                              (1) 1        10        20        30        40        50        60        70           84
                 CcMan5 full  (1) ------------------------------------------------------------------------------------

     NP_630514 Streptomyces   (1) ------------------------------------------------------------------------------------
     ZP_02866543 Clostridium  (1) ------------------------------------------------------------------------------------
        NP_812442 Bacteroides (1) ------------------------------------------------------------------------------------
 YP_003584502 Zunongwangia    (1) ------------------------------------------------------------------------------------
 YP_003120664 Chitinophaga    (1) ------------------------------------------------------------------------------------
      AAK22560 Caulobacter    (1) ------------------------------------------------------------------------------------
      ACL94075 Caulobacter    (1) ------------------------------------------------------------------------------------
     ACT03290 Paenibacillus   (1) MFKKLFAVAMTVMCLTGILVPVGSNAAFAAAAEGITTRNVAINAAATASGQCNANESASNAVDGKTDTKWCDNTSAQKKWLKLD
     ACU59240 Chitinophaga    (1) ------------------------------------------------------------------------------------
      ACU05553 Pedobacter     (1) ------------------------------------------------------------------------------------
                                                                                                   Section 2
                             (85) 85  90        100       110       120       130       140       150             168
                 CcMan5 full  (1) ------------------------------------------------------------------------------------

     NP_630514 Streptomyces   (1) -------------------------------------------MPDRSKRPPIRSSSPRAALRATVAAVLAGALGLAALTGGGT
     ZP_02866543 Clostridium  (1) ------------------------------------------------------------------MNKKINRLLKGALAFTVA
        NP_812442 Bacteroides (1) ------------------------------------------------------------------------------------
 YP_003584502 Zunongwangia    (1) -------------------------------------------------------------------------MTLIMKRMIAA
 YP_003120664 Chitinophaga    (1) ----------------------------------------------------------------------------MKKSLIYL
      AAK22560 Caulobacter    (1) ----------------------------------------------------------------------MNPGKGPVLRFRVQ
      ACL94075 Caulobacter    (1) ----------------------------------------------------------------------MNPGKGPVLRFRVQ
     ACT03290 Paenibacillus  (85) LGKEYLVNEWVLQNAAINESGNSPFWNTKNFRLQKSDDGETWTDVDIVTNNAQTIVDRFVTPFTTRYLRLYIDKAAYDSNIARI
     ACU59240 Chitinophaga    (1) --------------------------------------------------------------------------MKRNRYLIST
      ACU05553 Pedobacter     (1) --------------------------------------------------------------------------MKNSIKLMLL
```

FIG. 31-1

```
                                                                                                     Section 13
                              (1009) 1009       1020       1030       1040       1050       1060       1070       1080      1092
                 CcMan5 full  (763) APAFSMSTATDEPAEGPR-------VSAEPTTVQTGDGGALDATVTLTLDG-ARLAAPAGTDLVTSGAASVVGLPDGVTAAVTV

     NP_630514 Streptomyces   (807) EPAYSLNTDSGDGDDEHAPGRGTTVVSARPETVRTAADGTVDASVELRLSGRASFAARKGTSLTRTGAASVTGLPDGVTADLRV
     ZP_02866543 Clostridium  (787) TAKSSSDNADTSTYDDDEIAYSSAMFEESKANDGSFDQKITITLKTKEFAGEIGEDLVATGKINITNIPEGLEASAIKTEANKV
      NP_812442 Bacteroides   (654) ------------------------------------------------------------------------------------
 YP_003584502 Zunongwangia   (687) AWVSSIRQYL--------------------------------------------------------------------------
 YP_003120664 Chitinophaga   (672) KWIADITRQ---------------------------------------------------------------------------
      AAK22560 Caulobacter   (740) VLTVRADQPSLVDGKTSTGWRAASGQSVTFSLKAPACIAAYSVSVGPDQADPSHWTLQAYDGRAWVSVDQQSNVVFDHRHATRT
      ACL94075 Caulobacter   (740) VLTVRADQPSLVDGKTSTGWRAASGQSVTFSLKAPACIAAYSVSVGPDQADPSHWTLQAYDGRAWVSVDQQSNVVFDHRHATRT
    ACT03290 Paenibacillus   (895) SAAPPTVDYNADMDNDFNHEQLIPEKSTWKYDDKGKEAGEGWTQVDFDDSSWSSGKAMLGYDSYGKPATTVSYGPNANNKYVTT
    ACU59240 Chitinophaga    (737) QAAPPSSLNYSPAGK---------------------------------------------------------------------
      ACU05553 Pedobacter    (729) ------------------------------------------------------------------------------------
                                                                                                     Section 14
                              (1093) 1093    1100       1110       1120       1130       1140       1150       1160      1176
                 CcMan5 full  (839) ASPTALTVSLTGTASADARFFVHLRDAALADGVAAASLQGQGVSVRSPLRLSVASAERDALAALVDDAVLVRHGNYSSVTFDRF

     NP_630514 Streptomyces   (891) TGKRTASLRLTGTTRTDARFGITFRDRAFPHGIPASTVTGTGVSVTDPLIVSAAAVHRGSLAALVDEASLVREGNYSDGSYGIF
     ZP_02866543 Clostridium  (871) EVSLNGKAKNHTLNDSISNLTIEITDGATNEPIKDSIRKTKDNVKVMFIDNQLTYSQSEFKESESDDGAILETSTITLTGDTTF
      NP_812442 Bacteroides   (654) ------------------------------------------------------------------------------------
 YP_003584502 Zunongwangia   (697) ------------------------------------------------------------------------------------
 YP_003120664 Chitinophaga   (681) ------------------------------------------------------------------------------------
      AAK22560 Caulobacter   (824) FPLAPGRYARLRWVLDGGSEASVSEVELIAGASCAAPTSGAPLL----------------------------------------
      ACL94075 Caulobacter   (824) FPLAPGRYARLRWVLDGGSEASVSEVELIAGASCAAPTSGAPLL----------------------------------------
    ACT03290 Paenibacillus   (979) YFRKTFDAKDLDGILELDGSLIRDDGAIVYLNGHEIFRTNMPTGAVNYSTFANATVGDERDKNGFIIDPSYLVEGKNVLTAEVH
    ACU59240 Chitinophaga    (752) ------------------------------------------------------------------------------------
      ACU05553 Pedobacter    (729) ------------------------------------------------------------------------------------
```

FIG. 31-7

```
                                                                                                          Section 15
                         (1177) 1177         1190      1200      1210      1220      1230      1240      1250      1260
               CcMan5 full (923) STALTKAQEALGDEAATSIALRFAADRLGAAADALDLTGGGYRTLEAEQSEAWSGGELKN------------------------

    NP_630514 Streptomyces (975) RTALERARTVLADSASPTGTLMAAHDALRSAVDALTLDEGGYAVLQAEDPDRMEGPSLVK------------------------
    ZP_02866543 Clostridium (955) AGEVNEDFVATGKVQINNVPEGLTVKMIKIDDHTAVLSFEGKAVNNDADAEIELAFTDSAFNGALASEIGQSSRGGMTALLLDF
    NP_812442 Bacteroides (654) ------------------------------------------------------------------------------------
YP_003584502 Zunongwangia (697) ------------------------------------------------------------------------------------
YP_003120664 Chitinophaga (681) ------------------------------------------------------------------------------------
      AAK22560 Caulobacter (868) ------------------------------------------------------------------------------------
      ACL94075 Caulobacter (868) ------------------------------------------------------------------------------------
 ACT03290 Paenibacillus (1063) QVNATSSDIAFEFSLEAVRKLNIPAAPTHPVVDDKANTIGWTPVEGINNASDYEFSTDGGKSWKQAKANPQTVGPLNYAPGIVQ
     ACU59240 Chitinophaga (752) ------------------------------------------------------------------------------------
      ACU05553 Pedobacter (729) ------------------------------------------------------------------------------------
                                                                                                          Section 16
                         (1261) 1261     1270      1280      1290      1300      1310      1320      1330          1344
               CcMan5 full (983) -----------------------------------EANSSSGNLGGVRSGSWVQYRDMTFETAAGDTPPRFLTVRYDTSFAPTD

   NP_630514 Streptomyces (1035) -----------------------------------EAYYSDGDLGGVTEGAWEQYTDLDFG----GVAPRSVSVRYANSQAAAA
   ZP_02866543 Clostridium (1039) DYDHTSKLKRTMAEATYINASAYTQSSYQAVLDAVAKGQELLDNKNATSKEIDLAIGDIIDAQEQLDIPRDGFSVLQAESSDVT
    NP_812442 Bacteroides (654) ------------------------------------------------------------------------------------
YP_003584502 Zunongwangia (697) ------------------------------------------------------------------------------------
YP_003120664 Chitinophaga (681) ------------------------------------------------------------------------------------
      AAK22560 Caulobacter (868) ------------------------------------------------------------------------------------
      ACL94075 Caulobacter (868) ------------------------------------------------------------------------------------
 ACT03290 Paenibacillus (1147) VRVMANAAANRAAGEALLSTEAYTSDVKWDVYDLDADIHQDGNMVVDVTGTLKGDYTDSAVVVFQLMDGKEHAWVSSAVPVQTG
     ACU59240 Chitinophaga (752) ------------------------------------------------------------------------------------
      ACU05553 Pedobacter (729) ------------------------------------------------------------------------------------
```

FIG. 31-8

```
                                                                                   Section 17
                         (1345) 1345 1350      1360      1370      1380      1390      1400      1410            1428
                CcMan5 full (1032) TPS-----------------------------------TVRVHAGDVSGPVVATVDLKGTSGWGKYTEVTAELGDVQALVDAQV

     NP_630514 Streptomyces (1080) EPS-----------------------------------SVDIHAGDADGPVVATVSLPGTGGWQYYTTVRAAVSDPQALLKASS
     ZP_02866543 Clostridium (1123) SGGSLRVEGSVLHGTYDGAWIRYDALDFNGLSPKYLELRYDNASNRCASDSHLEVRLDGVDGTLIGDIQLPATGTAWGSYETLQ
      NP_812442 Bacteroides  (654) ------------------------------------------------------------------------------------
  YP_003584502 Zunongwangia  (697) ------------------------------------------------------------------------------------
  YP_003120664 Chitinophaga  (681) ------------------------------------------------------------------------------------
      AAK22560 Caulobacter  (868) ------------------------------------------------------------------------------------
      ACL94075 Caulobacter  (868) ------------------------------------------------------------------------------------
    ACT03290 Paenibacillus (1231) SFD-----------------------------------ISQIYNVDASKYKVNVYLVNEFNGDIYESPLWLADPIVQQSEPGSL
     ACU59240 Chitinophaga  (752) ------------------------------------------------------------------------------------
      ACU05553 Pedobacter  (729) ------------------------------------------------------------------------------------
                                                                                   Section 18
                         (1429) 1429       1440      1450      1460      1470      1480      1490      1500        1512
                CcMan5 full (1081) VTFELLAPSGRSWVGNFDWFRFSAEDPAAPGQPGESPTVTIEAEDWTASSGRGLKKESSTWTSGPVTNVGGTADGDWIAYGEVD

     NP_630514 Streptomyces (1129) ATFVFHAPSGRQWVSNFDWYQFSPEAAPSSSPITTLATLTTANTTSTGDGSLPLKVSGGVFEN--------VTNGAWAEWRDTD
     ZP_02866543 Clostridium (1207) FEISNPELLDGKHDVYFVFKGTTEDSKPYVAKVDYLQFKETADIDSVKLEAEKSDENSGNGLKNESINLGGTYDGAWIKYNNVN
      NP_812442 Bacteroides  (654) ------------------------------------------------------------------------------------
  YP_003584502 Zunongwangia  (697) ------------------------------------------------------------------------------------
  YP_003120664 Chitinophaga  (681) ------------------------------------------------------------------------------------
      AAK22560 Caulobacter  (868) ------------------------------------------------------------------------------------
      ACL94075 Caulobacter  (868) ------------------------------------------------------------------------------------
    ACT03290 Paenibacillus (1280) PDPEGPPVTEEPLPEPIPLPDPKPDEPEEPEVPETGMKIQFEDRAEWTSAAHPNGGGGLSTEAGNGGTVVAHTFGGAWLAYNVD
     ACU59240 Chitinophaga  (752) ------------------------------------------------------------------------------------
      ACU05553 Pedobacter  (729) ------------------------------------------------------------------------------------
```

FIG. 31-9

```
                                                                                      Section 19
                          (1513) 1513   1520      1530      1540      1550      1560      1570      1580          1596
                  CcMan5 full (1165) LGELPLGELSVHYVHNSNRSGNNSALSVYLDAFDPANPGEPFVTVPLPTTGSSWTADGTATVVLPETVQG--THEVFVRLSTEP

     NP_630514 Streptomyces (1205) LGDGADTVTVSYDKPRSR-----AASDSHIELRPGAKDGPTAVTVPLDYTGSGWGTVASTSVRLDPDVFEGTQDVYAVFVSSTQ
     ZP_02866543 Clostridium (1291) FNNLEADTINVHYSTRVDACALDARIEIRKDNKDGELLGTIMLPLTGGWSDYQTVSTKLDTSVTGVQDICFVLRGTNDGG----
       NP_812442 Bacteroides (654) ------------------------------------------------------------------------------------
  YP_003584502 Zunongwangia (697) ------------------------------------------------------------------------------------
   YP_003120664 Chitinophaga (681) ------------------------------------------------------------------------------------
        AAK22560 Caulobacter (868) ------------------------------------------------------------------------------------
        ACL94075 Caulobacter (868) ------------------------------------------------------------------------------------
     ACT03290 Paenibacillus (1364) FGTTGYNNVTVQYDAPTDKVPAGSKLEFRLGSVSGELVGTVNMEDKNAGWGSYITTKANLTRTLTGQQKLYVVMVAGTPNNLPY
      ACU59240 Chitinophaga (752) ------------------------------------------------------------------------------------
        ACU05553 Pedobacter (729) ------------------------------------------------------------------------------------
                                                                                      Section 20
                          (1597) 1597         1610      1620      1630      1640      1650      1660      1670      1680
                  CcMan5 full (1247) YADHPYVANLDSLTFAPGGPTSVVVESEAWTSNSGRGLKNESSTWT--SGPVTNVGGTADGDWLAYGEIDLGSAALDQLSVHYV

     NP_630514 Streptomyces (1284) TDAQPYVANVHSLTLTRQADAPVVFDATAFEGSSGGGLKSEPATWSG-AGSATSLGGTYDGAWLDYGDVDFGDSPKNTVTLTYV
     ZP_02866543 Clostridium (1371) ---RP---YVANIDYMEFVNSGVNHIEAENKDDWSGAELKVENSTDNTGKSLTNIGGARNDAWLRYNGVEFNGKTEMTVRYSHN
       NP_812442 Bacteroides (654) ------------------------------------------------------------------------------------
  YP_003584502 Zunongwangia (697) ------------------------------------------------------------------------------------
   YP_003120664 Chitinophaga (681) ------------------------------------------------------------------------------------
        AAK22560 Caulobacter (868) ------------------------------------------------------------------------------------
        ACL94075 Caulobacter (868) ------------------------------------------------------------------------------------
     ACT03290 Paenibacillus (1448) IGNFDWFKFDYEKIRSDYAKLELESYDEWTTDVNTGNNNTPLKTEAGKGGVGQQVANTFNGAWLAYKRMDFGSEGVDKFSIEYA
      ACU59240 Chitinophaga (752) ------------------------------------------------------------------------------------
        ACU05553 Pedobacter (729) ------------------------------------------------------------------------------------
```

FIG. 31-10

```
                                                                                                  Section 21
                             (1681) 1681      1690      1700      1710      1720      1730      1740      1750          1764
                    CcMan5 full (1329) HNSNRSGRNSALSVY-------------------------------------------------LDAFDPANPGEPFVTVPLAN

      NP_630514 Streptomyces (1367) NNSARCGTGSAVQLY-------------------------------------------------LDSFDPDAPGTPYATVPLPV
      ZP_02866543 Clostridium (1449) PGTAGTNSRIDVYLDNMDGNPIGTINLPTTNGWANYTVIREVFDQEITGSHDVYLKLHTDGSGWVANFDWFEFGEPIADVDKSQ
        NP_812442 Bacteroides (654) ------------------------------------------------------------------------------------
   YP_003584502 Zunongwangia (697) ------------------------------------------------------------------------------------
   YP_003120664 Chitinophaga (681) ------------------------------------------------------------------------------------
        AAK22560 Caulobacter (868) ------------------------------------------------------------------------------------
        ACL94075 Caulobacter (868) ------------------------------------------------------------------------------------
     ACT03290 Paenibacillus (1532) GNSTNTFNNSAVEVR-------------------------------------------------LGSPTGTLVGTVATPPTAAA
       ACU59240 Chitinophaga (752) ------------------------------------------------------------------------------------
         ACU05553 Pedobacter (729) ------------------------------------------------------------------------------------
                                                                                                  Section 22
                             (1765) 1765 1770      1780      1790      1800      1810      1820      1830          1848
                    CcMan5 full (1364) TGSSWTTDGTAVVDLPSTVRGKHQVWVRLSTEAYADHPYVANLDSMRFFTDAYDVEVPPTDTAALAAVVDAAGTPEAEIARYGR

      NP_630514 Streptomyces (1402) TGSSWSSGGTTSLTLPEAITGTHAVHLRLTTNADSSHPYVANLGQVAFDRVEAPAQT---DLSALRKAIEQYEGLSEDADRYGT
      ZP_02866543 Clostridium (1533) LQAKYDENVALLQEYDKYHYVGFNIFKDRLLTGSAVIDNQNATANDVRIAIKDIDNALAALQYKIAFDLNDYVVQLENINEADY
        NP_812442 Bacteroides (654) ------------------------------------------------------------------------------------
   YP_003584502 Zunongwangia (697) ------------------------------------------------------------------------------------
   YP_003120664 Chitinophaga (681) ------------------------------------------------------------------------------------
        AAK22560 Caulobacter (868) ------------------------------------------------------------------------------------
        ACL94075 Caulobacter (868) ------------------------------------------------------------------------------------
     ACT03290 Paenibacillus (1567) WGTYATVSGSLTQKLTGLQDVYLVFTGSAANGETGKKYIGNFDNASFSLSVQEPEEPEQPQQPEQEQITVQFESKTEWNTALNT
       ACU59240 Chitinophaga (752) ------------------------------------------------------------------------------------
         ACU05553 Pedobacter (729) ------------------------------------------------------------------------------------
```

FIG. 31-11

```
                                                                                       Section 23
                        (1849) 1849       1860      1870      1880      1890      1900      1910      1920       1932
                 CcMan5 full (1448) IDARVFTRELAAARSVLADAGATQAQADERARRLGLATDQLVPAERRRLENLVASAEALTDEGYSPESWQAFRTALAAATGTLD

    NP_630514 Streptomyces (1483) IDFGVFRRELTAARDLLGTEDATQLEADLRTRSLTLAANQLVPLPRLRLESLVATASALADERYTDASWKAFTTALTAAKTALA
   ZP_02866543 Clostridium (1617) TKDSYANLMQAIEVAKAIPTDSEYEVFKNAYDGLVDAHSKLTALNRTALEEIIKQAEAIDLDLYKEEGKAEFKAALENAKTVYE
      NP_812442 Bacteroides (654) ------------------------------------------------------------------------------------
YP_003584502 Zunongwangia (697) ------------------------------------------------------------------------------------
YP_003120664 Chitinophaga (681) ------------------------------------------------------------------------------------
      AAK22560 Caulobacter (868) ------------------------------------------------------------------------------------
      ACL94075 Caulobacter (868) ------------------------------------------------------------------------------------
   ACT03290 Paenibacillus (1651) FNNQAMKIENNNGGQTVGNTYTGAWLGFKDVDFGSEKGKNQVSIVYDAPTNRVPADVKAEIRLGSPTGTLVGTVAIPNTGSTWG
     ACU59240 Chitinophaga (752) ------------------------------------------------------------------------------------
       ACU05553 Pedobacter (729) ------------------------------------------------------------------------------------
                                                                                       Section 24
                        (1933) 1933   1940      1950      1960      1970      1980      1990      2000           2016
                 CcMan5 full (1532) DAAASDEALHDARLALQGAVDALEEPADVVLVEVEVSPRCLAGKPYVAVRAVNVSDAAVDVELASSLG--------------TR

    NP_630514 Streptomyces (1567) DETATDRTLTERYAALDRARSSLTTKRRTVPAAPGAVSAAPSGTSVQVTWSAPEDDGGSPVTGYEITLSGGRQVEIADPDSRST
   ZP_02866543 Clostridium (1701) TVSLTQAQVDEAVANLDQAIKALKPIETDSVNKVALKIAVDLANAITDEDLANVVPAVVDEFIAARDEANAVYNDVSATQEEVD
      NP_812442 Bacteroides (654) ------------------------------------------------------------------------------------
YP_003584502 Zunongwangia (697) ------------------------------------------------------------------------------------
YP_003120664 Chitinophaga (681) ------------------------------------------------------------------------------------
      AAK22560 Caulobacter (868) ------------------------------------------------------------------------------------
      ACL94075 Caulobacter (868) ------------------------------------------------------------------------------------
   ACT03290 Paenibacillus (1735) QYNTATADLNTTIKGKQDLYIVMTGSTTSSLLYVGNYDSLTFGYKPVRSDYAKLELESYDEWTTAVNPLNSNTPLKTEAGKGGA
     ACU59240 Chitinophaga (752) ------------------------------------------------------------------------------------
       ACU05553 Pedobacter (729) ------------------------------------------------------------------------------------
```

FIG. 31-12

```
                                                                                                      Section 25
                               (2017) 2017        2030        2040        2050        2060        2070        2080        2090       2100
                      CcMan5 full (1602) SFVGVAPGASAYQSFAARSATGDLDVTVTATGADGTQTVEQVVTVPSCS-----------------------------------

          NP_630514 Streptomyces (1651) VFTRLKDGTSYTARVRAVNALGDSPWSARTQPAVTGDNRPQTPTVTGVVTDGERVRVNWRPAGDGGFPVVGYTVALDDGTTAHV
         ZP_02866543 Clostridium (1785) NAFDRLASVMQKLEFFKGDKKALKAFIDKVTGLDSSKYTQTTWTAFDKELTEAIAVYNDENAMQEEVNTAYSELVTAFLNLRLI
            NP_812442 Bacteroides  (654) ------------------------------------------------------------------------------------
       YP_003584502 Zunongwangia  (697) ------------------------------------------------------------------------------------
        YP_003120664 Chitinophaga  (681) ------------------------------------------------------------------------------------
            AAK22560 Caulobacter  (868) ------------------------------------------------------------------------------------
            ACL94075 Caulobacter  (868) ------------------------------------------------------------------------------------
         ACT03290 Paenibacillus (1819) GKQVANTFNGAWLAYKRMDFGTEGVNTFAVEYAGNTTNCFTNSAVEIRLGSPTGTLVGKISTPPKAGNWTTYDTVSGTLTQKLT
           ACU59240 Chitinophaga  (752) ------------------------------------------------------------------------------------
             ACU05553 Pedobacter  (729) ------------------------------------------------------------------------------------
                                                                                                      Section 26
                               (2101) 2101      2110       2120       2130       2140       2150       2160       2170       2184
                      CcMan5 full (1651) ------------------------------------------------------------------------------------

          NP_630514 Streptomyces (1735) PGTTSTAVLTAAGGAKAHTATVTAVTRAGSSDGSGATVSTAPATSTTSATSATSTGDPAEYEPSPFPGDTLDATYASDAWPETG
         ZP_02866543 Clostridium (1869) PDKSLLEDLINQANGLNGANYTKATFDGLTKALDEAKAVYENPDATQKEVDNAKDVLAKAIAGLQTVTTDNTVSTPVNNGDTTA
            NP_812442 Bacteroides  (654) ------------------------------------------------------------------------------------
       YP_003584502 Zunongwangia  (697) ------------------------------------------------------------------------------------
        YP_003120664 Chitinophaga  (681) ------------------------------------------------------------------------------------
            AAK22560 Caulobacter  (868) ------------------------------------------------------------------------------------
            ACL94075 Caulobacter  (868) ------------------------------------------------------------------------------------
         ACT03290 Paenibacillus (1903) GIQDVYLVLTGSAGNGETGKKYIGNFDNAAFSLKV-------------------------------------------------
           ACU59240 Chitinophaga  (752) ------------------------------------------------------------------------------------
             ACU05553 Pedobacter  (729) ------------------------------------------------------------------------------------
```

FIG. 31-13

```
                                                                                                    Section 27
                           (2185) 2185  2190         2200        2210        2220        2230        2240        2250        2268
                  CcMan5 full (1651) ------------------------------------------------------------------------------------

      NP_630514 Streptomyces (1819) DGSDWFTHLLSGFDDLGPATLGANSEVPAGTPLGAENDRITVSVNNAATQQQVDRAEVDASNSATVTMADGLGSRLGPLYGEAL
      ZP_02866543 Clostridium (1953) SVKTGDESLAGMFATIALLSIAGYTILKRKEN----------------------------------------------------
         NP_812442 Bacteroides  (654) ------------------------------------------------------------------------------------
   YP_003584502 Zunongwangia  (697) ------------------------------------------------------------------------------------
   YP_003120664 Chitinophaga  (681) ------------------------------------------------------------------------------------
          AAK22560 Caulobacter  (868) ------------------------------------------------------------------------------------
          ACL94075 Caulobacter  (868) ------------------------------------------------------------------------------------
       ACT03290 Paenibacillus (1938) ------------------------------------------------------------------------------------
         ACU59240 Chitinophaga  (752) ------------------------------------------------------------------------------------
          ACU05553 Pedobacter  (729) ------------------------------------------------------------------------------------
                                                                                                    Section 28
                           (2269) 2269        2280        2290        2300        2310        2320        2330        2340        2352
                  CcMan5 full (1651) ------------------------------------------------------------------------------------

      NP_630514 Streptomyces (1903) KEGRLPKTSALFSRVNENLDTHDAAKNHYQYLRPYVRLGFAGDGGAVYESQDSSYSGLAGQGSYPSGHTYGGYEAGTILATLLP
      ZP_02866543 Clostridium (1985) ------------------------------------------------------------------------------------
         NP_812442 Bacteroides  (654) ------------------------------------------------------------------------------------
   YP_003584502 Zunongwangia  (697) ------------------------------------------------------------------------------------
   YP_003120664 Chitinophaga  (681) ------------------------------------------------------------------------------------
          AAK22560 Caulobacter  (868) ------------------------------------------------------------------------------------
          ACL94075 Caulobacter  (868) ------------------------------------------------------------------------------------
       ACT03290 Paenibacillus (1938) ------------------------------------------------------------------------------------
         ACU59240 Chitinophaga  (752) ------------------------------------------------------------------------------------
          ACU05553 Pedobacter  (729) ------------------------------------------------------------------------------------
```

FIG. 31-14

```
                                                                                              Section 29
                           (2353) 2353    2360      2370      2380      2390      2400      2410      2420      2436
                 CcMan5 full (1651) ------------------------------------------------------------------------------------

  NP_630514 Streptomyces (1987) DLAPSILARTSEYGDNRIVLGFHYPLDVMGGRITAQATVAHRWADPEFAKLLGQAHTEIENVLLARCEEEGYGDTLTACAGDPY
  ZP_02866543 Clostridium (1985) ------------------------------------------------------------------------------------
      NP_812442 Bacteroides  (654) ------------------------------------------------------------------------------------
YP_003584502 Zunongwangia  (697) ------------------------------------------------------------------------------------
 YP_003120664 Chitinophaga  (681) ------------------------------------------------------------------------------------
      AAK22560 Caulobacter  (868) ------------------------------------------------------------------------------------
      ACL94075 Caulobacter  (868) ------------------------------------------------------------------------------------
    ACT03290 Paenibacillus (1938) ------------------------------------------------------------------------------------
     ACU59240 Chitinophaga  (752) ------------------------------------------------------------------------------------
      ACU05553 Pedobacter  (729) ------------------------------------------------------------------------------------
                                                                                              Section 30
                           (2437) 2437         2450      2460      2470      2480      2490      2500      2510      2520
                 CcMan5 full (1651) ------------------------------------------------------------------------------------

  NP_630514 Streptomyces (2071) AGLSTAQQVDRYTQRLTYGFSRTGEAGQALDAPSDAAALLITAFPDLTAEQRAQVLEQTATDSGYPLDLTGSGGPGWQRINLAA
  ZP_02866543 Clostridium (1985) ------------------------------------------------------------------------------------
      NP_812442 Bacteroides  (654) ------------------------------------------------------------------------------------
YP_003584502 Zunongwangia  (697) ------------------------------------------------------------------------------------
 YP_003120664 Chitinophaga  (681) ------------------------------------------------------------------------------------
      AAK22560 Caulobacter  (868) ------------------------------------------------------------------------------------
      ACL94075 Caulobacter  (868) ------------------------------------------------------------------------------------
    ACT03290 Paenibacillus (1938) ------------------------------------------------------------------------------------
     ACU59240 Chitinophaga  (752) ------------------------------------------------------------------------------------
      ACU05553 Pedobacter  (729) ------------------------------------------------------------------------------------
```

FIG. 31-15

```
                                                                                                 Section 31
                            (2521) 2521     2530      2540      2550      2560      2570      2580      2590         2604
                   CcMan5 full (1651) ------------------------------------------------------------------------------------

    NP_630514 Streptomyces (2155) AMAADVVVNADGSVTVTNFPDPTAASAAEAVAITVGGVALDGFDPDVSTYVVDWPRNGGRIPAVGAVTAASGARVKVTSGSSTV
    ZP_02866543 Clostridium (1985) ------------------------------------------------------------------------------------
       NP_812442 Bacteroides  (654) ------------------------------------------------------------------------------------
YP_003584502 Zunongwangia  (697) ------------------------------------------------------------------------------------
 YP_003120664 Chitinophaga  (681) ------------------------------------------------------------------------------------
       AAK22560 Caulobacter  (868) ------------------------------------------------------------------------------------
       ACL94075 Caulobacter  (868) ------------------------------------------------------------------------------------
    ACT03290 Paenibacillus (1938) ------------------------------------------------------------------------------------
     ACU59240 Chitinophaga  (752) ------------------------------------------------------------------------------------
      ACU05553 Pedobacter  (729) ------------------------------------------------------------------------------------
                                                                                                 Section 32
                            (2605) 2605 2610      2620      2630      2640      2650      2660      2670      2680
                   CcMan5 full (1651) ----------------------------------------------------------------------------

    NP_630514 Streptomyces (2239) SSSQRGFSTRTLTVTSADGEFTRTYTVGFRPVEQHPHRPGALRDTGGGGTAGGSAGGGDVGGGLWSPAREWELTVN
    ZP_02866543 Clostridium (1985) ----------------------------------------------------------------------------
       NP_812442 Bacteroides  (654) ----------------------------------------------------------------------------
YP_003584502 Zunongwangia  (697) ----------------------------------------------------------------------------
 YP_003120664 Chitinophaga  (681) ----------------------------------------------------------------------------
       AAK22560 Caulobacter  (868) ----------------------------------------------------------------------------
       ACL94075 Caulobacter  (868) ----------------------------------------------------------------------------
    ACT03290 Paenibacillus (1938) ----------------------------------------------------------------------------
     ACU59240 Chitinophaga  (752) ----------------------------------------------------------------------------
      ACU05553 Pedobacter  (729) ----------------------------------------------------------------------------
```

FIG. 31-16

```
                                                                                    Section 1
                               (1) 1       10        20        30        40        50        60        70         82
                 CcMan5 full   (1) ----------------------------------------------------------------------------------

   NP_630514 Streptomyces      (1) ----------------------------------------------------------------------------------
   ZP_05522540 Streptomyces    (1) ----------------------------------------------------------------------------------
   ZP_06527366 Streptomyces    (1) ----------------------------------------------------------------------------------
   YP_003013376 Paenibacillus  (1) MFKKLFAVAMTVMCLTGILVPVGSNAAFAAAAEGITTRNVAINAAATASGQCNANESASNAVDGKTDTKWCDNTSAQKKWLK
   NP_812442 Bacteroides       (1) ----------------------------------------------------------------------------------
   ZP_04848482 Bacteroides     (1) ----------------------------------------------------------------------------------
   ZP_03677957 Bacteroides     (1) ----------------------------------------------------------------------------------
   YP_003584502 Zunongwangia   (1) ----------------------------------------------------------------------------------
   ZP_01061975 Leeuwenhoekiella (1) ----------------------------------------------------------------------------------
   ZP_07083984 Sphingobacterium (1) ----------------------------------------------------------------------------------
   YP_003120664 Chitinophaga   (1) ----------------------------------------------------------------------------------
   ZP_01885202 Pedobacter      (1) ----------------------------------------------------------------------------------
   ZP_02866543 Clostridium     (1) ----------------------------------------------------------------------------------
   XP_367221 Magnaporthe       (1) ----------------------------------------------------------------------------------
   ZP_07042437 Bacteroides     (1) ----------------------------------------------------------------------------------
   ZP_05759807 Bacteroides     (1) ----------------------------------------------------------------------------------
   ZP_05287524 Bacteroides     (1) ----------------------------------------------------------------------------------
   ZP_06076108 Bacteroides     (1) ----------------------------------------------------------------------------------
   YP_001302992 Parabacteroides (1) ----------------------------------------------------------------------------------
```

FIG. 32-1

```
                                                                                                Section 2
                                (83) 83     90        100       110       120       130       140       150           164
CcMan5 full                     (1)  ----------------------------------------------------------------------------------

NP_630514 Streptomyces          (1)  ----------------------------------------------MPDRSKRPPIRSSSPRAALRATVAAVLAGALGLAAL
ZP_05522540 Streptomyces        (1)  -------------------------------------------MLVMPDRSKRPPIRSSSPRAALRATVAAVLAGALGLAAL
ZP_06527366 Streptomyces        (1)  -----------------------------------------------------------------------MLAGALGLAAL
YP_003013376 Paenibacillus      (83) LDLGKEYLVNEWVLQNAAINESGNSPFWNTKNFRLQKSDDGETWTDVDIVTNNAQTIVDRFVTPFTTRYLRLYIDKAAYDSN
NP_812442 Bacteroides           (1)  ----------------------------------------------------------------------------------
ZP_04848482 Bacteroides         (1)  -------------------------------------------------------------------------------MKN
ZP_03677957 Bacteroides         (1)  ----------------------------------------------------------------------------------
YP_003584502 Zunongwangia       (1)  ---------------------------------------------------------------------------MTLIMKR
ZP_01061975 Leeuwenhoekiella    (1)  -------------------------------------------------------------------------------MKN
ZP_07083984 Sphingobacterium    (1)  --------------------------------------------------------------------MQVLTDLLLVSMKN
YP_003120664 Chitinophaga       (1)  ----------------------------------------------------------------------------------
ZP_01885202 Pedobacter          (1)  ---------------------------------------------------------------------------MFFMLKM
ZP_02866543 Clostridium         (1)  --------------------------------------------------------------------MNKKINRLLKGALA
XP_367221 Magnaporthe           (1)  ----------------------------------------------------------------------------------
ZP_07042437 Bacteroides         (1)  ----------------------------------------------------------------------------------
ZP_05759807 Bacteroides         (1)  ----------------------------------------------------------------------------------
ZP_05287524 Bacteroides         (1)  ---------------------------------------------------------------------------------M
ZP_06076108 Bacteroides         (1)  ----------------------------------------------------------------------------------
YP_001302992 Parabacteroides    (1)  ---------------------------------------------------------------------------------M
```

FGG. 32-2

```
                                                                                                   Section 14
                               (1067) 1067         1080      1090      1100      1110      1120      1130             1148
                  CcMan5 full   (795) ALDATVTLTLDG-ARLAAPAGTDLVTSGAASVVGLPDGVTAAVTVASPTALTVSLTGTASADARFFVHLRDAALADGVAAAS

       NP_630514 Streptomyces   (846) TVDASVELRLSGRASFAARKGTSLTRTGAASVTGLPDGVTADLRVTGKRTASLRLTGTTRTDARFGITFRDRAFPHGIPAST
     ZP_05522540 Streptomyces   (849) TVDASVELRLSGRASFAARKGTSLTRTGAASVTGLPDGVTADLRVTGKRTASLRLTGTTRTDARFGITFRDRAFPHGIPAST
     ZP_06527366 Streptomyces   (821) TVDASVELRLSGRASFAARKGTSLTRTGAASVTGLPDGVTADLRVTGKRTASLRLTGTTRTDARFGITFRDRAFPHGIPAST
  YP_003013376 Paenibacillus   (934) EGWTQVDFDDSSWSSGKAMLGYDSYGKPATTVSYGPNANNKYVTTYFRKTFDAKDLDGILELDGSLIRDDGAIVYLNGHEIF
        NP_812442 Bacteroides   (654) ----------------------------------------------------------------------------------
      ZP_04848482 Bacteroides   (672) ----------------------------------------------------------------------------------
      ZP_03677957 Bacteroides   (676) ----------------------------------------------------------------------------------
   YP_003584502 Zunongwangia   (697) ----------------------------------------------------------------------------------
ZP_01061975 Leeuwenhoekiella   (683) ----------------------------------------------------------------------------------
ZP_07083984 Sphingobacterium   (698) ----------------------------------------------------------------------------------
  YP_003120664 Chitinophaga    (681) ----------------------------------------------------------------------------------
       ZP_01885202 Pedobacter   (695) ----------------------------------------------------------------------------------
      ZP_02866543 Clostridium   (826) ITITLKTKEFAGEIGEDLVATGKINITNIPEGLEASAIKTEANKVEVSLNGKAKNHTLNDSISNLTIEITDGATNEPIKDSI
      XP_367221 Magnaporthe     (802) PVAVTVPIVVVAAFAICVTFFFIRRRAAAAQKALSSGSGTPESGIETLTPTSQPVDTSKTNVQVEIVGAPPLDSTQGANIA
      ZP_07042437 Bacteroides   (754) ----------------------------------------------------------------------------------
      ZP_05759807 Bacteroides   (754) ----------------------------------------------------------------------------------
      ZP_05287524 Bacteroides   (759) ----------------------------------------------------------------------------------
      ZP_06076108 Bacteroides   (747) ----------------------------------------------------------------------------------
YP_001302992 Parabacteroides   (759) ----------------------------------------------------------------------------------
```

FIG. 32-14

```
                                                                                                              Section 15
                                    (1149) 1149       1160      1170      1180      1190      1200      1210      1220      1230
                       CcMan5 full   (876) LQGQGVSVRSPLRLSVASAERDALAALVDDAVLVRHGNYSSVTFDRFSTALTKAQEALGDEAATSIALRFAADRLGAAADAL

            NP_630514 Streptomyces   (928) VTGTGVSVTDPLIVSAAAVHRGSLAALVDEASLVREGNYSDGSYGIFRTALERARTVLADSASPTGTLMAAHDALRSAVDAL
           ZP_05522540 Streptomyces  (931) VTGTGVSVTDPLIVSAAAVHRGSLAALVDEASLVREGNYSDGSYGIFRTALERARTVLADSASPTGTLMAAHDALRSAVDAL
           ZP_06527366 Streptomyces  (903) VTGTGVSVTDPLIVSAAAVHRGSLAALVDEASLVREGNYSDGSYGIFRTALERARTVLADSASPTGTLMAAHDALRSAVDAL
        YP_003013376 Paenibacillus (1016) RTNMPTGAVNYSTFANATVGDERDKNGFIIDPSYLVEGKNVLTAEVHQVNATSSDIAFEFSLEAVRKLNIPAAPTHPVVDDK
             NP_812442 Bacteroides  (654) ----------------------------------------------------------------------------------
           ZP_04848482 Bacteroides  (672) ----------------------------------------------------------------------------------
           ZP_03677957 Bacteroides  (676) ----------------------------------------------------------------------------------
        YP_003584502 Zunongwangia  (697) ----------------------------------------------------------------------------------
     ZP_01061975 Leeuwenhoekiella  (683) ----------------------------------------------------------------------------------
    ZP_07083984 Sphingobacterium  (698) ----------------------------------------------------------------------------------
        YP_003120664 Chitinophaga  (681) ----------------------------------------------------------------------------------
           ZP_01885202 Pedobacter  (695) ----------------------------------------------------------------------------------
          ZP_02866543 Clostridium  (908) RKTKDNVKVMFIDNQLTYSQSEFKESESDDGAILETSTITLTGDTTFAGEVNEDFVATGKVQINNVPEGLTVKMIKIDDHTA
          XP_367221 Magnaporthe  (884) QLPPPVANR-------------------------------------------------------------------------
          ZP_07042437 Bacteroides  (754) ----------------------------------------------------------------------------------
          ZP_05759807 Bacteroides  (754) ----------------------------------------------------------------------------------
          ZP_05287524 Bacteroides  (759) ----------------------------------------------------------------------------------
          ZP_06076108 Bacteroides  (747) ----------------------------------------------------------------------------------
    YP_001302992 Parabacteroides  (759) ----------------------------------------------------------------------------------
```

FIG. 32-15

```
                                                                                    Section 16
                                (1231) 1231     1240      1250      1260      1270      1280      1290      1300       1312
CcMan5 full                      (958) DLTGGGYRTLEAEQSEAWSGGELKN---------------------------------------------------------

NP_630514 Streptomyces          (1010) TLDEGGYAVLQAEDPDRMEGPSLVK---------------------------------------------------------
ZP_05522540 Streptomyces        (1013) TLDEGGYAVLQAEDPDRMEGPSLVK---------------------------------------------------------
ZP_06527366 Streptomyces         (985) TLDEGGYAVLQAEDPDRMEGPSLVK---------------------------------------------------------
YP_003013376 Paenibacillus      (1098) ANTIGWTPVEGINNASDYEFSTDGGKSWKQAKANPQTVGPLNYAPGIVQVRVMANAAANRAAGEALLSTEAYTSDVKWDVYD
NP_812442 Bacteroides            (654) ----------------------------------------------------------------------------------
ZP_04848482 Bacteroides          (672) ----------------------------------------------------------------------------------
ZP_03677957 Bacteroides          (676) ----------------------------------------------------------------------------------
YP_003584502 Zunongwangia        (697) ----------------------------------------------------------------------------------
ZP_01061975 Leeuwenhoekiella     (683) ----------------------------------------------------------------------------------
ZP_07083984 Sphingobacterium     (698) ----------------------------------------------------------------------------------
YP_003120664 Chitinophaga        (681) ----------------------------------------------------------------------------------
ZP_01885202 Pedobacter           (695) ----------------------------------------------------------------------------------
ZP_02866543 Clostridium          (990) VLSFEGKAVNNDADAEIELAFTDSAFNGALASEIGQSSRGGMTALLLDFDYDHTSKLKRTMAEATYINASAYTQSSYQAVLD
XP_367221 Magnaporthe            (893) ----------------------------------------------------------------------------------
ZP_07042437 Bacteroides          (754) ----------------------------------------------------------------------------------
ZP_05759807 Bacteroides          (754) ----------------------------------------------------------------------------------
ZP_05287524 Bacteroides          (759) ----------------------------------------------------------------------------------
ZP_06076108 Bacteroides          (747) ----------------------------------------------------------------------------------
YP_001302992 Parabacteroides     (759) ----------------------------------------------------------------------------------
```

FIG. 32-16

```
                                                                                                    Section 17
                                  (1313) 1313      1320      1330      1340      1350      1360      1370      1380      1394
                     CcMan5 full   (983) ---EANSSSGNLGGVRSGSWVQYRDMTFETAAGDTPPRFLTVRYDTSFAPTD------------------------------

         NP_630514 Streptomyces   (1035) ---EAYYSDGDLGGVTEGAWEQYTDLDFGGVA----PRSVSVRYANSQAAAA------------------------------
       ZP_05522540 Streptomyces   (1038) ---EAYYSDGDLGGVTEGAWEQYTDLDFGGVP----PRSVSVRYANSQAAAA------------------------------
       ZP_06527366 Streptomyces   (1010) ---EAYYSDGDLGGVTEGAWEQYTDLDFGGVP----PRSVSVRYANSQAAAA------------------------------
    YP_003013376 Paenibacillus   (1180) LDADIHQDGNMVVDVTGTLKGDYTDSAVVVFQLMDGKEHAWVSSAVPVQTGS------------------------------
           NP_812442 Bacteroides   (654) ----------------------------------------------------------------------------------
         ZP_04848482 Bacteroides   (672) ----------------------------------------------------------------------------------
         ZP_03677957 Bacteroides   (676) ----------------------------------------------------------------------------------
      YP_003584502 Zunongwangia   (697) ----------------------------------------------------------------------------------
   ZP_01061975 Leeuwenhoekiella   (683) ----------------------------------------------------------------------------------
  ZP_07083984 Sphingobacterium   (698) ----------------------------------------------------------------------------------
      YP_003120664 Chitinophaga   (681) ----------------------------------------------------------------------------------
          ZP_01885202 Pedobacter   (695) ----------------------------------------------------------------------------------
         ZP_02866543 Clostridium  (1072) AVAKGQELLDNKNATSKEIDLAIGDIIDAQEQLDIPRDGFSVLQAESSDVTSGGSLRVEGSVLHGTYDGAWIRYDALDFNGL
          XP_367221 Magnaporthe   (893) ----------------------------------------------------------------------------------
         ZP_07042437 Bacteroides   (754) ----------------------------------------------------------------------------------
         ZP_05759807 Bacteroides   (754) ----------------------------------------------------------------------------------
         ZP_05287524 Bacteroides   (759) ----------------------------------------------------------------------------------
         ZP_06076108 Bacteroides   (747) ----------------------------------------------------------------------------------
  YP_001302992 Parabacteroides   (759) ----------------------------------------------------------------------------------
```

FIG. 32-17

```
                                                                                              Section 18
                               (1395) 1395 1400      1410      1420      1430      1440      1450      1460            1476
               CcMan5 full     (1032) ----TPSTVRVHAGDVSGPVVATVDLKGTSGWGKYTEVTAELGDVQALVDAQVVTFELLAPSGRSWVGNFDWFRFSAEDPAA

  NP_630514 Streptomyces       (1080) ----EPSSVDIHAGDADGPVVATVSLPGTGGWQYYTTVRAAVSDPQALLKASSATFVFHAPSGRQWVSNFDWYQFSPEAAPS
  ZP_05522540 Streptomyces     (1083) ----EPSSVDIHAGDADGPVVATVSLPGTGGWQYYTTVRAAVSDPQALLKASSATFVFHAPSGRQWVSNFDWYQFSPEAAPS
  ZP_06527366 Streptomyces     (1055) ----EPSSVDIHAGDADGPVVATVSLPGTGGWQYYTTVRAAVSDPQALLKASSATFVFHAPSGRQWVSNFDWYQFSPEAAPS
  YP_003013376 Paenibacillus   (1232) ----FDISQIYNVDASKYKVNVYLVNEFNGDIYESPLWLADPIVQQSEPGSLPDPEGPPVTEEPLPEPIPLPDPKPDEPEEP
  NP_812442 Bacteroides        (654) ----------------------------------------------------------------------------------
  ZP_04848482 Bacteroides      (672) ----------------------------------------------------------------------------------
  ZP_03677957 Bacteroides      (676) ----------------------------------------------------------------------------------
  YP_003584502 Zunongwangia    (697) ----------------------------------------------------------------------------------
  ZP_01061975 Leeuwenhoekiella (683) ----------------------------------------------------------------------------------
  ZP_07083984 Sphingobacterium (698) ----------------------------------------------------------------------------------
  YP_003120664 Chitinophaga    (681) ----------------------------------------------------------------------------------
  ZP_01885202 Pedobacter       (695) ----------------------------------------------------------------------------------
  ZP_02866543 Clostridium     (1154) SPKYLELRYDNASNRCASDSHLEVRLDGVDGTLIGDIQLPATGTAWGSYETLQFEISNFELLDGKHDVYFVFKGTTEDSKPY
  XP_367221 Magnaporthe        (893) ----------------------------------------------------------------------------------
  ZP_07042437 Bacteroides      (754) ----------------------------------------------------------------------------------
  ZP_05759807 Bacteroides      (754) ----------------------------------------------------------------------------------
  ZP_05287524 Bacteroides      (759) ----------------------------------------------------------------------------------
  ZP_06076108 Bacteroides      (747) ----------------------------------------------------------------------------------
  YP_001302992 Parabacteroides (759) ----------------------------------------------------------------------------------
```

FIG. 32-18

Section 19

| | | |
|---|---|---|
| | (1477) | 1477 1490 1500 1510 1520 1530 1540 1558 |
| CcMan5 full | (1110) | PGQPGESPTVTIEAEDWTASSGRGLKKESSTWTSGPVTNVGGTADGDWIAYGEVDLGELPLGELSVHYVHNSNRSGNNSALS |
| NP_630514 Streptomyces | (1158) | SSPITTLATLTTANTTSTGDGSLPLKVSGGVFEN--------VTNGAWAEWRDTDLGDGADTVTVSYDKPRSR-----AASD |
| ZP_05522540 Streptomyces | (1161) | SSPITTLATLTTANTTSTGDGALPLKVSGGVFEN--------VTNGAWAEWRDTDLGDGADTVTVSYDKPRSR-----AASD |
| ZP_06527366 Streptomyces | (1133) | SSPITTLATLTTANTTSTGDGALPLKVSGGVFEN--------VTNGAWAEWRDTDLGDGADTVTVSYDKPRSR-----AASD |
| YP_003013376 Paenibacillus | (1310) | EVPETGMKIQFEDRAEWTSAAHPNGGGGLSTEAGNGGTVVAHTFGGAWLAYNVDFGTTGYNNVTVQYDAPTDKVPAGSKLEF |
| NP_812442 Bacteroides | (654) | ---------------------------------------------------------------------------------- |
| ZP_04848482 Bacteroides | (672) | ---------------------------------------------------------------------------------- |
| ZP_03677957 Bacteroides | (676) | ---------------------------------------------------------------------------------- |
| YP_003584502 Zunongwangia | (697) | ---------------------------------------------------------------------------------- |
| ZP_01061975 Leeuwenhoekiella | (683) | ---------------------------------------------------------------------------------- |
| ZP_07083984 Sphingobacterium | (698) | ---------------------------------------------------------------------------------- |
| YP_003120664 Chitinophaga | (681) | ---------------------------------------------------------------------------------- |
| ZP_01885202 Pedobacter | (695) | ---------------------------------------------------------------------------------- |
| ZP_02866543 Clostridium | (1236) | VAKVDYLQFKETADIDSVKLEAEKSDENSGNGLKNESINLGGTYDGAWIKYNNVNFNNLEADTINVRYSTRVDACALDARIE |
| XP_367221 Magnaporthe | (893) | ---------------------------------------------------------------------------------- |
| ZP_07042437 Bacteroides | (754) | ---------------------------------------------------------------------------------- |
| ZP_05759807 Bacteroides | (754) | ---------------------------------------------------------------------------------- |
| ZP_05287524 Bacteroides | (759) | ---------------------------------------------------------------------------------- |
| ZP_06076108 Bacteroides | (747) | ---------------------------------------------------------------------------------- |
| YP_001302992 Parabacteroides | (759) | ---------------------------------------------------------------------------------- |

FIG. 32-19

```
                                                                                                              Section 20
                                       (1559) 1559      1570       1580      1590      1600      1610      1620      1630    1640
                         CcMan5 full (1192) VYLDAFDPANPGEPFVTVPLPTTGSSWTADGTATVVLPETVQG--THEVFVRLSTEPYADHPYVANLDSLTFAPGGPTSVVV

       NP_630514 Streptomyces (1227) SHIELRPGAKDGPTAVTVPLDYTGSGWGTVASTSVRLDPDVFEGTQDVYAVFVSSTQTDAQPYVANVHSLTLTRQADAPVVF
      ZP_05522540 Streptomyces (1230) SHIELRPGAKDGPTAVTVPLDYTGSGWGTVASTSVRLDPDVFEGTQDVYAVFVSSTQTDAQPYVANVHSLTLTRQADAPVVF
      ZP_06527366 Streptomyces (1202) SHIELRPGAKDGPTAVTVPLDYTGSGWGTVASTSVRLDPDVFEGTQDVYAVFVSSTQTDAQPYVANVHSLTLTRQADAPVVF
   YP_003013376 Paenibacillus (1392) RLGSVSGELVGTVNMEDKNAGWGSYITTKANLTRTLTGQQKLYVVMVAGTPNNLPYIGNFDWFKFDYEKIRSDYAKLELESY
        NP_812442 Bacteroides  (654) ----------------------------------------------------------------------------------
       ZP_04848482 Bacteroides  (672) ----------------------------------------------------------------------------------
       ZP_03677957 Bacteroides  (676) ----------------------------------------------------------------------------------
     YP_003584502 Zunongwangia  (697) ----------------------------------------------------------------------------------
  ZP_01061975 Leeuwenhoekiella  (683) ----------------------------------------------------------------------------------
ZP_07083984 Sphingobacterium  (698) ----------------------------------------------------------------------------------
     YP_003120664 Chitinophaga  (681) ----------------------------------------------------------------------------------
         ZP_01885202 Pedobacter  (695) ----------------------------------------------------------------------------------
       ZP_02866543 Clostridium (1318) IRKDNKDGELLGTIMLPLTGGWSDYQTVSTKLDTSVTGVQDICFVLRGTNDGGRPYVANLDYMEFVNSGVNHIEAENKDDWS
         XP_367221 Magnaporthe  (893) ----------------------------------------------------------------------------------
       ZP_07042437 Bacteroides  (754) ----------------------------------------------------------------------------------
       ZP_05759807 Bacteroides  (754) ----------------------------------------------------------------------------------
       ZP_05287524 Bacteroides  (759) ----------------------------------------------------------------------------------
       ZP_06076108 Bacteroides  (747) ----------------------------------------------------------------------------------
 YP_001302992 Parabacteroides  (759) ----------------------------------------------------------------------------------
```

FIG. 32-20

```
                                                                                              Section 21
                              (1641) 1641     1650      1660      1670      1680      1690      1700      1710      1722
                      CcManS full (1272) ESEAWTSNSGRGLKNESSTWT-SGPVTNVGG----------------------------------------TADGDWLAYGE

          NP_630514 Streptomyces (1309) DATAFEGSSGGGLKSEPATWSGAGSATSLGG----------------------------------------TYDGAWLDYGD
        ZP_05522540 Streptomyces (1312) DATAFEGSSGGGLKSEPATWSGAGSATSLGG----------------------------------------TYDGAWLDYGD
        ZP_06527366 Streptomyces (1284) DATAFEGSSGGGLKSEPATWSGAGSATSLGG----------------------------------------TYDGAWLDYGD
      YP_003013376 Paenibacillus (1474) DEWTTDVNTGNNNTPLKTEAGKGGVGQQVAN----------------------------------------TFNGAWLAYKR
           NP_812442 Bacteroides  (654) ----------------------------------------------------------------------------------
         ZP_04848482 Bacteroides  (672) ----------------------------------------------------------------------------------
         ZP_03677957 Bacteroides  (676) ----------------------------------------------------------------------------------
       YP_003584502 Zunongwangia  (697) ----------------------------------------------------------------------------------
   ZP_01061975 Leeuwenhoekiella  (683) ----------------------------------------------------------------------------------
  ZP_07083984 Sphingobacterium  (698) ----------------------------------------------------------------------------------
       YP_003120664 Chitinophaga  (681) ----------------------------------------------------------------------------------
          ZP_01885202 Pedobacter  (695) ----------------------------------------------------------------------------------
        ZP_02866543 Clostridium (1400) GAELKVENSTDNTGKSLTNIGGARNDAWLRYNGVEFNGKTEMTVRYSHNPGTAGTNSRIDVYLDNMDGNPIGTINLPTTNGW
         XP_367221 Magnaporthe  (893) ----------------------------------------------------------------------------------
         ZP_07042437 Bacteroides  (754) ----------------------------------------------------------------------------------
         ZP_05759807 Bacteroides  (754) ----------------------------------------------------------------------------------
         ZP_05287524 Bacteroides  (759) ----------------------------------------------------------------------------------
         ZP_06076108 Bacteroides  (747) ----------------------------------------------------------------------------------
   YP_001302992 Parabacteroides  (759) ----------------------------------------------------------------------------------
```

FIG. 32-21

Section 22

| | | |
|---|---|---|
| | (1723) | 1723 1730 1740 1750 1760 1770 1780 1790 1804 |
| CcMan5 full | (1313) | IDLGSAALDQLSVHYVHNSNRSGRNSALSVYLDAFDPANPGEPFVTVPLANTGSSWTTDGTAVVDLPSTVRGKHQVWVRLST |
| NP_630514 Streptomyces | (1351) | VDFGDSPKNTVTLTYVNNSARCGTGSAVQLYLDSFDPDAPGTPYATVPLPVTGSSWSSGGTTSLTLPEAITGTHAVHLRLTT |
| ZP_05522540 Streptomyces | (1354) | VDFGDSPKNTVTLTYVNNSARCGTGSAVQLYLDSFDPDAPGTPYATVPLPVTGSSWSSGGTTSLTLPEAITGTHAVHLRLTT |
| ZP_06527366 Streptomyces | (1326) | VDFGDSPKNTVTLTYVNNSARCGTGSAVQLYLDSFDPDAPGTPYATVPLPVTGSSWSSGGTTSLTLPEAITGTHAVHLRLTT |
| YP_003013376 Paenibacillus | (1516) | MDFGSEGVDKFSIEYAGNSTNTFNNSAVEVRLGSPTGTLVGTVATPPTAAAWGTYATVSGSLTQKLTGLQDVYLVFTGSAAN |
| NP_812442 Bacteroides | (654) | ---------------------------------------------------------------------------------- |
| ZP_04848482 Bacteroides | (672) | ---------------------------------------------------------------------------------- |
| ZP_03677957 Bacteroides | (676) | ---------------------------------------------------------------------------------- |
| YP_003584502 Zunongwangia | (697) | ---------------------------------------------------------------------------------- |
| ZP_01061975 Leeuwenhoekiella | (683) | ---------------------------------------------------------------------------------- |
| ZP_07083984 Sphingobacterium | (698) | ---------------------------------------------------------------------------------- |
| YP_003120664 Chitinophaga | (681) | ---------------------------------------------------------------------------------- |
| ZP_01885202 Pedobacter | (695) | ---------------------------------------------------------------------------------- |
| ZP_02866543 Clostridium | (1482) | ANYTVIREVFDQEITGSHDVYLKLHTDGSGWVANFDWFEFGEPIADVDKSQLQAKYDENVALLQEYDKYHYVGFNIFKDRLL |
| XP_367221 Magnaporthe | (893) | ---------------------------------------------------------------------------------- |
| ZP_07042437 Bacteroides | (754) | ---------------------------------------------------------------------------------- |
| ZP_05759807 Bacteroides | (754) | ---------------------------------------------------------------------------------- |
| ZP_05287524 Bacteroides | (759) | ---------------------------------------------------------------------------------- |
| ZP_06076108 Bacteroides | (747) | ---------------------------------------------------------------------------------- |
| YP_001302992 Parabacteroides | (759) | ---------------------------------------------------------------------------------- |

FIG. 32-22

```
                                                                                                         Section 23
                                   (1805) 1805  1810      1820      1830      1840      1850      1860      1870          1886
                        CcMan5 full (1395) EAYADHPYVANLDSMRFFTDAYDVEVPPTDTAALAAVVDAAGTPEAEIARYGRIDARVFTRELAAARSVLADAGATQAQADE

       NP_630514 Streptomyces (1433) NADSSHPYVANLGQVAFDRVEAPAQT---DLSALRKAIEQYEGLSEDADRYGTIDFGVFRRELTAARDLLGTEDATQLEADL
      ZP_05522540 Streptomyces (1436) DADSSHPYVANLGQVTFDRVEAPAQT---DLSALRKAIEQYEGLSEDADRYGTIDFGVFRRELTAARDLLGTEDATQLEADL
      ZP_06527366 Streptomyces (1408) DADSSHPYVANLGQVTFDRVEAPAQT---DLSALRKAIEQYEGLSEDADRYGTIDFGVFRRELTAARDLLGTEDATQLEADL
    YP_003013376 Paenibacillus (1598) GETGKKYIGNFDNASFSLSVQEPEEPEQPQQPEQEQITVQFESKTEWNTALNTFNNQAMKIENNNGGQTVGNTYTGAWLGFK
         NP_812442 Bacteroides (654) ----------------------------------------------------------------------------------
       ZP_04848482 Bacteroides (672) ----------------------------------------------------------------------------------
       ZP_03677957 Bacteroides (676) ----------------------------------------------------------------------------------
    YP_003584502 Zunongwangia (697) ----------------------------------------------------------------------------------
   ZP_01061975 Leeuwenhoekiella (683) ----------------------------------------------------------------------------------
 ZP_07083984 Sphingobacterium (698) ----------------------------------------------------------------------------------
    YP_003120664 Chitinophaga (681) ----------------------------------------------------------------------------------
       ZP_01885202 Pedobacter (695) ----------------------------------------------------------------------------------
      ZP_02866543 Clostridium (1564) TGSAVIDNQNATANDVRIAIKDIDNALAALQYKIAFDLNDYVVQLENINEADYTKDSYANLMQAIEVAKAIPTDSEYEVFKN
      XP_367221 Magnaporthe (893) ----------------------------------------------------------------------------------
       ZP_07042437 Bacteroides (754) ----------------------------------------------------------------------------------
       ZP_05759807 Bacteroides (754) ----------------------------------------------------------------------------------
       ZP_05287524 Bacteroides (759) ----------------------------------------------------------------------------------
       ZP_06076108 Bacteroides (747) ----------------------------------------------------------------------------------
 YP_001302992 Parabacteroides (759) ----------------------------------------------------------------------------------
```

FIG. 32-23

Section 24

| | | |
|---|---|---|
| | (1887) | 1887 1900 1910 1920 1930 1940 1950 1968 |
| CcMan5 full | (1477) | RARRLGLATDQLVPAERRRLENLVASAEALTDEGYSPESWQAFRTALAAATGTLDDAAASDEALHDARLALQGAVDALEEPA |
| NP_630514 Streptomyces | (1512) | RTRSLTLAANQLVPLPRLRLESLVATASALADERYTDASWKAFTTALTAAKTALADETATDRTLTERYAALDRARSSLTTKR |
| ZP_05522540 Streptomyces | (1515) | RTRSLTLAANQLVPLPRLRLESLVATASALADERYTDASWKAFTTALTAAKTAVADETATDRTLTERYAALDRARSSLTTKR |
| ZP_06527366 Streptomyces | (1487) | RTRSLTLAANQLVPLPRLRLESLVATASALADERYTDASWKAFTTALTAAKTAVADETATDRTLTERYAALDRARSSLTTKR |
| YP_003013376 Paenibacillus | (1680) | DVDFGSEKGKNQVSIVYDAPTNRVPADVKAEIRLGSPTGTLVGTVAIPNTGSTWGQYNTATADLNTTIKGKQDLYIVMTGST |
| NP_812442 Bacteroides | (654) | ---------------------------------------------------------------------------------- |
| ZP_04848482 Bacteroides | (672) | ---------------------------------------------------------------------------------- |
| ZP_03677957 Bacteroides | (676) | ---------------------------------------------------------------------------------- |
| YP_003584502 Zunongwangia | (697) | ---------------------------------------------------------------------------------- |
| ZP_01061975 Leeuwenhoekiella | (683) | ---------------------------------------------------------------------------------- |
| ZP_07083984 Sphingobacterium | (698) | ---------------------------------------------------------------------------------- |
| YP_003120664 Chitinophaga | (681) | ---------------------------------------------------------------------------------- |
| ZP_01885202 Pedobacter | (695) | ---------------------------------------------------------------------------------- |
| ZP_02866543 Clostridium | (1646) | AYDGLVDAHSKLTALNRTALEEIIKQAEAIDLDLYKEEGKAEFKAALENAKTVYETVSLTQAQVDEAVANLDQAIKALKPIE |
| XP_367221 Magnaporthe | (893) | ---------------------------------------------------------------------------------- |
| ZP_07042437 Bacteroides | (754) | ---------------------------------------------------------------------------------- |
| ZP_05759807 Bacteroides | (754) | ---------------------------------------------------------------------------------- |
| ZP_05287524 Bacteroides | (759) | ---------------------------------------------------------------------------------- |
| ZP_06076108 Bacteroides | (747) | ---------------------------------------------------------------------------------- |
| YP_001302992 Parabacteroides | (759) | ---------------------------------------------------------------------------------- |

FIG. 32-24

```
                                                                                            Section 25
                                (1969) 1969       1980      1990      2000      2010      2020      2030      2040      2050
                    CcMan5 full (1559) DVVLVEVEVSPRCLAGKPYVAVRAVNVSDAAVDVELASSLG----------TRS----PVGVAPGASAYQSFAARSATGDLD

        NP_630514 Streptomyces (1594) RTVPAAPGAVSAAPSGTSVQVTWSAPEDDGGSPVTGYEITLSGGRQVEIADPDSRSTVFTRLKDGTSYTARVRAVNALGDSP
      ZP_05522540 Streptomyces (1597) RTVPAAPGAVSAAPSGTSVQVTWSAPEDDGGSPVTGYEITLSGGRQVEIADPDSRSTVFTRLKDGTSYTARVRAVNALGDSP
      ZP_06527366 Streptomyces (1569) RTVPAAPGAVSAAPSGTSVQVTWSAPEDDGGSPVTGYEITLSGGRQVEIADPDSRSTVFTRLKDGTSYTARVRAVNALGDSP
    YP_003013376 Paenibacillus (1762) TSSLLYVGNYDSLTFGYKPVRSDYAKLELESYDEWTTAVNPLNSNTPLKTEAGKGGAGKQVANTFNGAWLAYKRMDFGTEGV
           NP_812442 Bacteroides (654) ----------------------------------------------------------------------------------
         ZP_04848482 Bacteroides (672) ----------------------------------------------------------------------------------
         ZP_03677957 Bacteroides (676) ----------------------------------------------------------------------------------
       YP_003584502 Zunongwangia (697) ----------------------------------------------------------------------------------
   ZP_01061975 Leeuwenhoekiella (683) ----------------------------------------------------------------------------------
  ZP_07083984 Sphingobacterium (698) ----------------------------------------------------------------------------------
      YP_003120664 Chitinophaga (681) ----------------------------------------------------------------------------------
          ZP_01885202 Pedobacter (695) ----------------------------------------------------------------------------------
       ZP_02866543 Clostridium (1728) TDSVNKVALKIAVDLANAITDEDLANVVPAVVDEFIAARDEANAVYNDVSATQEEVDNAFDRLASVMQKLEFFKGDKKALKA
         XP_367221 Magnaporthe (893) ----------------------------------------------------------------------------------
         ZP_07042437 Bacteroides (754) ----------------------------------------------------------------------------------
         ZP_05759807 Bacteroides (754) ----------------------------------------------------------------------------------
         ZP_05287524 Bacteroides (759) ----------------------------------------------------------------------------------
         ZP_06076108 Bacteroides (747) ----------------------------------------------------------------------------------
   YP_001302992 Parabacteroides (759) ----------------------------------------------------------------------------------
```

FIG. 32-25

```
                                                                                           Section 26
                                  (2051) 2051     2060      2070      2080      2090      2100      2110      2120        2132
                      CcMan5 full (1627) VTVTATGADGTQTVEQVVTVPSCS----------------------------------------------------------

     NP_630514 Streptomyces (1676) WSARTQPAVTGDNRPQTPTVTGVVTDGERVRVNWRPAGDGGFPVVGYTVALDDGTTAHVPGTTSTAVLTAAGGAKAHTATVT
    ZP_05522540 Streptomyces (1679) WSARTQPAVTGDNRPQAPTVTGVVTDGERVRVNWRPAGDGGFPVVGYTVALDDGTTAHVPGTTSTAVLTAAGGAKAHTATVT
    ZP_06527366 Streptomyces (1651) WSARTQPAVTGDNRPQAPTVTGVVTDGERVRVNWRPAGDGGFPVVGYTVALDDGTTAHVPGTTSTAVLTAAGGAKAHTATVT
  YP_003013376 Paenibacillus (1844) NTFAVEYAGNTTNCFTNSAVEIRLGSPTGTLVGKISTPPKAGNWTTYDIVSGTLTQKLTCIQDVYLVLTGSAGNGETGKKYI
       NP_812442 Bacteroides (654) ----------------------------------------------------------------------------------
     ZP_04848482 Bacteroides (672) ----------------------------------------------------------------------------------
     ZP_03677957 Bacteroides (676) ----------------------------------------------------------------------------------
   YP_003584502 Zunongwangia (697) ----------------------------------------------------------------------------------
ZP_01061975 Leeuwenhoekiella (683) ----------------------------------------------------------------------------------
ZP_07083984 Sphingobacterium (698) ----------------------------------------------------------------------------------
   YP_003120664 Chitinophaga (681) ----------------------------------------------------------------------------------
      ZP_01885202 Pedobacter (695) ----------------------------------------------------------------------------------
    ZP_02866543 Clostridium (1810) FIDKVTGLDSSKYTQTTWTAFDKELTEAIAVYNDENAMQEEVNTAYSELVTAFLNLRLIPDKSLLEDLINQANGLNGANYTK
      XP_367221 Magnaporthe (893) ----------------------------------------------------------------------------------
     ZP_07042437 Bacteroides (754) ----------------------------------------------------------------------------------
     ZP_05759807 Bacteroides (754) ----------------------------------------------------------------------------------
     ZP_05287524 Bacteroides (759) ----------------------------------------------------------------------------------
     ZP_06076108 Bacteroides (747) ----------------------------------------------------------------------------------
YP_001302992 Parabacteroides (759) ----------------------------------------------------------------------------------
```

FIG. 32-26

```
                                                                                            Section 27
                                 (2133) 2133   2140      2150      2160      2170      2180      2190      2200          2214
                       CcMan5 full (1651) ----------------------------------------------------------------------------------

      NP_630514 Streptomyces (1758) AVTRAGSSDGSGATVSTAPATSTTSATSATSTGDPAEYEPSPFPGDTLDATYASDAWPETGDGSDWFTHLLSGFDDLGPATL
    ZP_05522540 Streptomyces (1761) AVTRAGSSDGSGATVSTAPATSTTSATSAG---DPAEYEPSPFPGDTLDATYASDAWPETGDGSDWFTHLLSGFDDLGPATL
    ZP_06527366 Streptomyces (1733) AVTRAGSSDGSGATVSTAPATSTTSATSAG---DPAEYEPSPFPGDTLDATYASDAWPETGDGSDWFTHLLSGFDDLGPATL
 YP_003013376 Paenibacillus (1926) GNFDNAAFSLKV----------------------------------------------------------------------
      NP_812442 Bacteroides  (654) ----------------------------------------------------------------------------------
     ZP_04848482 Bacteroides  (672) ----------------------------------------------------------------------------------
     ZP_03677957 Bacteroides  (676) ----------------------------------------------------------------------------------
  YP_003584502 Zunongwangia  (697) ----------------------------------------------------------------------------------
ZP_01061975 Leeuwenhoekiella (683) ----------------------------------------------------------------------------------
ZP_07083984 Sphingobacterium (698) ----------------------------------------------------------------------------------
   YP_003120664 Chitinophaga (681) ----------------------------------------------------------------------------------
      ZP_01885202 Pedobacter (695) ----------------------------------------------------------------------------------
    ZP_02866543 Clostridium (1892) ATFDGLTKALDEAKAVYENPDATQKEVDNAKDVLAKAIAGLQTVTTDNTVSTPVNNGDTTASVKTGDESLAGMFATIALLSI
     XP_367221 Magnaporthe  (893) ----------------------------------------------------------------------------------
     ZP_07042437 Bacteroides (754) ----------------------------------------------------------------------------------
     ZP_05759807 Bacteroides (754) ----------------------------------------------------------------------------------
     ZP_05287524 Bacteroides (759) ----------------------------------------------------------------------------------
     ZP_06076108 Bacteroides (747) ----------------------------------------------------------------------------------
YP_001302992 Parabacteroides (759) ----------------------------------------------------------------------------------
```

FIG. 32-27

```
                                           Section 28
                       (2215) 2215 2220      2230      2240      2250      2260      2270      2280      2296
CcMan5 full            (1651) ----------------------------------------------------------------------------------
NP_630514 Streptomyces (1840) GANSEVPAGTPLGAENDRITVSVNNAATQQQVDRAEVDASNSATVTMADGLGSRLGPLYGEALKEGRLPKTSALFSRVNENL
ZP_05522540 Streptomyces (1840) GANSEVPAGTPLGAENDRITVRVNNAATQQQVDRAEVDASNSATVTMADGLGSRLGPLYGEALKEGRLPKTSALFSRVNENL
ZP_06527366 Streptomyces (1812) GANSEVPAGTPLGAENDRITVRVNNAATQQQVDRAEVDASNSATVTMADGLGSRLGPLYGEALKEGRLPKTSALFSRVNENL
YP_003013376 Paenibacillus (1938) ----------------------------------------------------------------------------------
NP_812442 Bacteroides (654) ----------------------------------------------------------------------------------
ZP_04848482 Bacteroides (672) ----------------------------------------------------------------------------------
ZP_03677957 Bacteroides (676) ----------------------------------------------------------------------------------
YP_003584502 Zunongwangia (697) ----------------------------------------------------------------------------------
ZP_01061975 Leeuwenhoekiella (683) ----------------------------------------------------------------------------------
ZP_07083984 Sphingobacterium (698) ----------------------------------------------------------------------------------
YP_003120664 Chitinophaga (681) ----------------------------------------------------------------------------------
ZP_01885202 Pedobacter (695) ----------------------------------------------------------------------------------
ZP_02866543 Clostridium (1974) AGYTILKRKEN-----------------------------------------------------------------------
XP_367221 Magnaporthe (893) ----------------------------------------------------------------------------------
ZP_07042437 Bacteroides (754) ----------------------------------------------------------------------------------
ZP_05759807 Bacteroides (754) ----------------------------------------------------------------------------------
ZP_05287524 Bacteroides (759) ----------------------------------------------------------------------------------
ZP_06076108 Bacteroides (747) ----------------------------------------------------------------------------------
YP_001302992 Parabacteroides (759) ----------------------------------------------------------------------------------
```

FIG. 32-28

```
                                                                                  Section 29
                              (2297) 2297         2310      2320      2330      2340      2350      2360             2378
                       CcMan5 full (1651) ----------------------------------------------------------------------------------

   NP_630514 Streptomyces (1922) DTHDAAKNHYQYLRPYVRLGFAGDGGAVYESQDSSYSGLAGQGSYPSGHTYGGYEAGTILATLLPDLAPSILARTSEYGDNR
 ZP_05522540 Streptomyces (1922) DTHDAAKNHYQYLRPYVRLGFAGDGGAVYESQDSSYSGLAGQGSYPSGHTYGGYEAGTILATLLPDLAPSILARTSEYGDNR
 ZP_06527366 Streptomyces (1894) DTHDAAKNHYQYLRPYVRLGFAGDGGAVYESQDSSYSGLAGQGSYPSGHTYGGYEAGTILATLLPDLAPSILARTSEYGDNR
YP_003013376 Paenibacillus (1938) ----------------------------------------------------------------------------------
      NP_812442 Bacteroides (654) ----------------------------------------------------------------------------------
    ZP_04848482 Bacteroides (672) ----------------------------------------------------------------------------------
    ZP_03677957 Bacteroides (676) ----------------------------------------------------------------------------------
  YP_003584502 Zunongwangia (697) ----------------------------------------------------------------------------------
ZP_01061975 Leeuwenhoekiella (683) ----------------------------------------------------------------------------------
ZP_07083984 Sphingobacterium (698) ----------------------------------------------------------------------------------
  YP_003120664 Chitinophaga (681) ----------------------------------------------------------------------------------
     ZP_01885202 Pedobacter (695) ----------------------------------------------------------------------------------
   ZP_02866543 Clostridium (1985) ----------------------------------------------------------------------------------
    XP_367221 Magnaporthe (893) ----------------------------------------------------------------------------------
    ZP_07042437 Bacteroides (754) ----------------------------------------------------------------------------------
    ZP_05759807 Bacteroides (754) ----------------------------------------------------------------------------------
    ZP_05287524 Bacteroides (759) ----------------------------------------------------------------------------------
    ZP_06076108 Bacteroides (747) ----------------------------------------------------------------------------------
YP_001302992 Parabacteroides (759) ----------------------------------------------------------------------------------
```

FIG. 32-29

```
                                                                                                     Section 30
                                   (2379) 2379       2390      2400      2410      2420      2430      2440      2450      2460
                          CcMan5 full (1651) ----------------------------------------------------------------------------------
          NP_630514 Streptomyces (2004) IVLGFHYPLDVMGGRITAQATVAHRWADPEFAKLLGQAHTEIENVLLARCEEEGYGDTLTACAGDPYAGLSTAQQVDRYTQR
        ZP_05522540 Streptomyces (2004) IVLGFHYPLDVMGGRITAQATVAHRWADPEFAKLLGQAHTEIENVLLARCEEEGYGDTLTACAGDPYAGLSTAQQVDRYTQR
        ZP_06527366 Streptomyces (1976) IVLGFHYPLDVMGGRITAQATVAHRWADPEFAKLLGQAHTEIENVLLARCEEEGYGDTLTACAGDPYAGLSTAQQVDRYTQR
     YP_003013376 Paenibacillus (1938) ----------------------------------------------------------------------------------
            NP_812442 Bacteroides  (654) ----------------------------------------------------------------------------------
          ZP_04848482 Bacteroides  (672) ----------------------------------------------------------------------------------
          ZP_03677957 Bacteroides  (676) ----------------------------------------------------------------------------------
        YP_003584502 Zunongwangia  (697) ----------------------------------------------------------------------------------
     ZP_01061975 Leeuwenhoekiella  (683) ----------------------------------------------------------------------------------
    ZP_07083984 Sphingobacterium  (698) ----------------------------------------------------------------------------------
         YP_003120664 Chitinophaga  (681) ----------------------------------------------------------------------------------
           ZP_01885202 Pedobacter  (695) ----------------------------------------------------------------------------------
          ZP_02866543 Clostridium (1985) ----------------------------------------------------------------------------------
           XP_367221 Magnaporthe  (893) ----------------------------------------------------------------------------------
          ZP_07042437 Bacteroides  (754) ----------------------------------------------------------------------------------
          ZP_05759807 Bacteroides  (754) ----------------------------------------------------------------------------------
          ZP_05287524 Bacteroides  (759) ----------------------------------------------------------------------------------
          ZP_06076108 Bacteroides  (747) ----------------------------------------------------------------------------------
  YP_001302992 Parabacteroides  (759) ----------------------------------------------------------------------------------
```

FIG. 32-30

```
                                                                                            Section 31
                                    (2461) 2461     2470      2480      2490      2500      2510      2520      2530        2542
                    CcMan5 full (1651) ----------------------------------------------------------------------------------
                  
         NP_630514 Streptomyces (2086) LTYGFSRTGEAGQALDAPSDAAALLITAFPDLTAEQRAQVLEQTATDSGYPLDLTGSGGPGWQRINLAAAMAADVVVNADGS
       ZP_05522540 Streptomyces (2086) LTYGFSRTGEAGQALDAPSDAAALLITAFPDLTAEQRTQVLEQTATDSGYPLDLTGSGGPGWQRINLAAAMAADVVVNADGS
       ZP_06527366 Streptomyces (2058) LTYGFSRTGEAGQALDAPSDAAALLITAFPDLTAEQRTQVLEQTATDSGYPLDLTGSGGPGWQRINLAAAMAADVVVNADGS
     YP_003013376 Paenibacillus (1938) ----------------------------------------------------------------------------------
            NP_812442 Bacteroides (654) ----------------------------------------------------------------------------------
          ZP_04848482 Bacteroides (672) ----------------------------------------------------------------------------------
          ZP_03677957 Bacteroides (676) ----------------------------------------------------------------------------------
       YP_003584502 Zunongwangia (697) ----------------------------------------------------------------------------------
   ZP_01061975 Leeuwenhoekiella (683) ----------------------------------------------------------------------------------
 ZP_07083984 Sphingobacterium (698) ----------------------------------------------------------------------------------
      YP_003120664 Chitinophaga (681) ----------------------------------------------------------------------------------
          ZP_01885202 Pedobacter (695) ----------------------------------------------------------------------------------
      ZP_02866543 Clostridium (1985) ----------------------------------------------------------------------------------
          XP_367221 Magnaporthe (893) ----------------------------------------------------------------------------------
          ZP_07042437 Bacteroides (754) ----------------------------------------------------------------------------------
          ZP_05759807 Bacteroides (754) ----------------------------------------------------------------------------------
          ZP_05287524 Bacteroides (759) ----------------------------------------------------------------------------------
          ZP_06076108 Bacteroides (747) ----------------------------------------------------------------------------------
   YP_001302992 Parabacteroides (759) ----------------------------------------------------------------------------------
```

FIG. 32-31

```
                                                                                          Section 32
                                 (2543) 2543      2550      2560      2570      2580      2590      2600      2610          2624
                          CcMan5 full (1651) ----------------------------------------------------------------------------------

        NP_630514 Streptomyces (2168) VTVTNFPDPTAASAAEAVAITVGGVALDGFDPDVSTYVVDWPRNGGRIPAVGAVTAASGARVKVTSGSSTVSSSQRGFSTRT
       ZP_05522540 Streptomyces (2168) VTVTNFPDATAASAAEAVAITVGGVALDGFDPDVSTYVVDWPRNGGRIPAVGAVTAASGARVKVTSGSSTVSSSQRGFSTRT
       ZP_06527366 Streptomyces (2140) VTVTNFPDATAASAAEAVAITVGGVALDGFDPDVSTYVVDWPRNGGRIPAVGAVTAASGARVKVTSGSSTVSSSQRGFSTRT
     YP_003013376 Paenibacillus (1938) ----------------------------------------------------------------------------------
          NP_812442 Bacteroides  (654) ----------------------------------------------------------------------------------
         ZP_04848482 Bacteroides  (672) ----------------------------------------------------------------------------------
         ZP_03677957 Bacteroides  (676) ----------------------------------------------------------------------------------
     YP_003584502 Zunongwangia  (697) ----------------------------------------------------------------------------------
   ZP_01061975 Leeuwenhoekiella  (683) ----------------------------------------------------------------------------------
  ZP_07083984 Sphingobacterium  (698) ----------------------------------------------------------------------------------
      YP_003120664 Chitinophaga  (681) ----------------------------------------------------------------------------------
         ZP_01885202 Pedobacter  (695) ----------------------------------------------------------------------------------
        ZP_02866543 Clostridium (1985) ----------------------------------------------------------------------------------
         XP_367221 Magnaporthe  (893) ----------------------------------------------------------------------------------
         ZP_07042437 Bacteroides  (754) ----------------------------------------------------------------------------------
         ZP_05759807 Bacteroides  (754) ----------------------------------------------------------------------------------
         ZP_05287524 Bacteroides  (759) ----------------------------------------------------------------------------------
         ZP_06076108 Bacteroides  (747) ----------------------------------------------------------------------------------
  YP_001302992 Parabacteroides  (759) ----------------------------------------------------------------------------------
```

FIG. 32-32

Section 33

```
                                     (2625) 2625 2630      2640      2650      2660      2670                2689
                        CcMan5 full (1651) -----------------------------------------------------------------
  NP_630514 Streptomyces (2250) LTVTSADGEFTRTYTVGFRPVEQHPHRPGALRDTGGGGTAGGSAGGGDVGGGLWSPAREWELTVN
 ZP_05522540 Streptomyces (2250) LTVTSADGEFTRTYTVGFRPVEQHPHRPGALRDTGGGGTAGGSGGGGDVGGGLWSPAREWEQTVN
 ZP_06527366 Streptomyces (2222) LTVTSADGEFTRTYTVGFRPVEQHPHRPGALRDTGGGGTAGGSGGGGDVGGGLWSPAREWEQTVN
YP_003013376 Paenibacillus (1938) -----------------------------------------------------------------
     NP_812442 Bacteroides  (654) -----------------------------------------------------------------
   ZP_04848482 Bacteroides  (672) -----------------------------------------------------------------
   ZP_03677957 Bacteroides  (676) -----------------------------------------------------------------
  YP_003584502 Zunongwangia  (697) -----------------------------------------------------------------
 ZP_01061975 Leeuwenhoekiella  (683) -----------------------------------------------------------------
ZP_07083984 Sphingobacterium  (698) -----------------------------------------------------------------
  YP_003120664 Chitinophaga  (681) -----------------------------------------------------------------
     ZP_01885202 Pedobacter  (695) -----------------------------------------------------------------
    ZP_02866543 Clostridium (1985) -----------------------------------------------------------------
     XP_367221 Magnaporthe  (893) -----------------------------------------------------------------
   ZP_07042437 Bacteroides  (754) -----------------------------------------------------------------
   ZP_05759807 Bacteroides  (754) -----------------------------------------------------------------
   ZP_05287524 Bacteroides  (759) -----------------------------------------------------------------
   ZP_06076108 Bacteroides  (747) -----------------------------------------------------------------
YP_001302992 Parabacteroides  (759) -----------------------------------------------------------------
```

FIG. 32-33

| | | | | | | | | | | | | |
|---|---|---|---|---|---|---|---|---|---|---|---|---|
| ATOM | 5859 | N | GLY | B | 21 | 8.798 | 41.888 | 151.532 | 1.00 | 6.14 | B | N |
| ATOM | 5860 | CA | GLY | B | 21 | 7.349 | 41.901 | 151.577 | 1.00 | 6.87 | B | C |
| ATOM | 5861 | C | GLY | B | 21 | 6.718 | 40.662 | 150.976 | 1.00 | 7.36 | B | C |
| ATOM | 5862 | O | GLY | B | 21 | 7.111 | 39.526 | 151.272 | 1.00 | 7.83 | B | O |
| ATOM | 5863 | N | ASP | B | 22 | 5.749 | 40.896 | 150.115 | 1.00 | 6.97 | B | N |
| ATOM | 5864 | CA | ASP | B | 22 | 5.019 | 39.846 | 149.439 | 1.00 | 6.61 | B | C |
| ATOM | 5865 | CB | ASP | B | 22 | 3.516 | 40.156 | 149.545 | 1.00 | 6.75 | B | C |
| ATOM | 5866 | CG | ASP | B | 22 | 2.645 | 38.964 | 149.165 | 1.00 | 8.00 | B | C |
| ATOM | 5867 | OD1 | ASP | B | 22 | 3.121 | 37.817 | 149.252 | 1.00 | 8.66 | B | O |
| ATOM | 5868 | OD2 | ASP | B | 22 | 1.479 | 39.168 | 148.781 | 1.00 | 10.69 | B | O |
| ATOM | 5869 | C | ASP | B | 22 | 5.471 | 39.814 | 147.976 | 1.00 | 6.58 | B | C |
| ATOM | 5870 | O | ASP | B | 22 | 4.647 | 39.889 | 147.070 | 1.00 | 6.88 | B | O |
| ATOM | 5871 | N | PHE | B | 23 | 6.785 | 39.719 | 147.753 | 1.00 | 5.72 | B | N |
| ATOM | 5872 | CA | PHE | B | 23 | 7.350 | 39.730 | 146.400 | 1.00 | 5.51 | B | C |
| ATOM | 5873 | CB | PHE | B | 23 | 8.139 | 41.020 | 146.136 | 1.00 | 5.56 | B | C |
| ATOM | 5874 | CG | PHE | B | 23 | 7.315 | 42.266 | 146.256 | 1.00 | 6.28 | B | C |
| ATOM | 5875 | CD1 | PHE | B | 23 | 7.127 | 42.875 | 147.497 | 1.00 | 7.33 | B | C |
| ATOM | 5876 | CE1 | PHE | B | 23 | 6.344 | 44.032 | 147.621 | 1.00 | 6.32 | B | C |
| ATOM | 5877 | CZ | PHE | B | 23 | 5.755 | 44.584 | 146.490 | 1.00 | 7.38 | B | C |
| ATOM | 5878 | CE2 | PHE | B | 23 | 5.941 | 43.979 | 145.235 | 1.00 | 7.39 | B | C |
| ATOM | 5879 | CD2 | PHE | B | 23 | 6.713 | 42.824 | 145.132 | 1.00 | 7.45 | B | C |
| ATOM | 5880 | C | PHE | B | 23 | 8.243 | 38.517 | 146.175 | 1.00 | 5.47 | B | C |
| ATOM | 5881 | O | PHE | B | 23 | 9.345 | 38.640 | 145.612 | 1.00 | 5.14 | B | O |
| ATOM | 5882 | N | GLY | B | 24 | 7.750 | 37.349 | 146.600 | 1.00 | 4.56 | B | N |
| ATOM | 5883 | CA | GLY | B | 24 | 8.458 | 36.090 | 146.362 | 1.00 | 4.07 | B | C |
| ATOM | 5884 | C | GLY | B | 24 | 8.397 | 35.090 | 147.499 | 1.00 | 3.76 | B | C |
| ATOM | 5885 | O | GLY | B | 24 | 8.310 | 33.871 | 147.263 | 1.00 | 4.04 | B | O |
| ATOM | 5886 | N | ASN | B | 25 | 8.467 | 35.594 | 148.734 | 1.00 | 2.92 | B | N |
| ATOM | 5887 | CA | ASN | B | 25 | 8.571 | 34.746 | 149.915 | 1.00 | 2.81 | B | C |
| ATOM | 5888 | CB | ASN | B | 25 | 7.253 | 34.007 | 150.179 | 1.00 | 3.39 | B | C |
| ATOM | 5889 | CG | ASN | B | 25 | 6.227 | 34.911 | 150.842 | 1.00 | 3.67 | B | C |
| ATOM | 5890 | OD1 | ASN | B | 25 | 6.478 | 35.461 | 151.917 | 1.00 | 6.16 | B | O |
| ATOM | 5891 | ND2 | ASN | B | 25 | 5.090 | 35.098 | 150.199 | 1.00 | 5.91 | B | N |
| ATOM | 5892 | C | ASN | B | 25 | 9.804 | 33.822 | 149.943 | 1.00 | 2.73 | B | C |
| ATOM | 5893 | O | ASN | B | 25 | 9.747 | 32.691 | 150.423 | 1.00 | 2.49 | B | O |
| ATOM | 5894 | N | ASP | B | 26 | 10.924 | 34.343 | 149.450 | 1.00 | 3.00 | B | N |
| ATOM | 5895 | CA | ASP | B | 26 | 12.206 | 33.663 | 149.535 | 1.00 | 3.13 | B | C |
| ATOM | 5896 | CB | ASP | B | 26 | 12.975 | 33.829 | 148.235 | 1.00 | 3.67 | B | C |
| ATOM | 5897 | CG | ASP | B | 26 | 12.481 | 32.904 | 147.140 | 1.00 | 4.56 | B | C |
| ATOM | 5898 | OD1 | ASP | B | 26 | 12.308 | 31.693 | 147.408 | 1.00 | 6.75 | B | O |
| ATOM | 5899 | OD2 | ASP | B | 26 | 12.281 | 33.385 | 146.007 | 1.00 | 5.43 | B | O |
| ATOM | 5900 | C | ASP | B | 26 | 13.041 | 34.166 | 150.702 | 1.00 | 3.37 | B | C |
| ATOM | 5901 | O | ASP | B | 26 | 12.747 | 35.212 | 151.278 | 1.00 | 3.44 | B | O |
| ATOM | 6036 | N | GLY | B | 46 | 7.869 | 42.799 | 161.557 | 1.00 | 5.19 | B | N |
| ATOM | 6037 | CA | GLY | B | 46 | 7.346 | 42.212 | 160.323 | 1.00 | 4.86 | B | C |
| ATOM | 6038 | C | GLY | B | 46 | 8.311 | 41.184 | 159.770 | 1.00 | 5.18 | B | C |
| ATOM | 6039 | O | GLY | B | 46 | 9.481 | 41.143 | 160.175 | 1.00 | 5.13 | B | O |
| ATOM | 6040 | N | ARG | B | 47 | 7.818 | 40.352 | 158.848 | 1.00 | 5.25 | B | N |
| ATOM | 6041 | CA | ARG | B | 47 | 8.581 | 39.247 | 158.248 | 1.00 | 4.58 | B | C |
| ATOM | 6042 | CB | ARG | B | 47 | 8.650 | 38.046 | 159.210 | 1.00 | 4.70 | B | C |
| ATOM | 6043 | CG | ARG | B | 47 | 7.282 | 37.403 | 159.599 | 1.00 | 5.20 | B | C |
| ATOM | 6044 | CD | ARG | B | 47 | 7.495 | 36.267 | 160.596 | 1.00 | 6.03 | B | C |
| ATOM | 6045 | NE | ARG | B | 47 | 6.339 | 35.388 | 160.817 | 1.00 | 5.27 | B | N |
| ATOM | 6046 | CZ | ARG | B | 47 | 5.957 | 34.374 | 160.030 | 1.00 | 7.87 | B | C |
| ATOM | 6047 | NH1 | ARG | B | 47 | 6.586 | 34.104 | 158.889 | 1.00 | 6.65 | B | N |
| ATOM | 6048 | NH2 | ARG | B | 47 | 4.910 | 33.627 | 160.378 | 1.00 | 6.18 | B | N |
| ATOM | 6049 | C | ARG | B | 47 | 7.861 | 38.854 | 156.975 | 1.00 | 4.46 | B | C |
| ATOM | 6050 | O | ARG | B | 47 | 6.656 | 39.124 | 156.837 | 1.00 | 3.68 | B | O |
| ATOM | 6051 | N | ASN | B | 48 | 8.584 | 38.257 | 156.029 | 1.00 | 4.25 | B | N |
| ATOM | 6052 | CA | ASN | B | 48 | 7.898 | 37.485 | 154.983 | 1.00 | 4.09 | B | C |
| ATOM | 6053 | CB | ASN | B | 48 | 8.627 | 37.525 | 153.605 | 1.00 | 3.81 | B | C |
| ATOM | 6054 | CG | ASN | B | 48 | 9.824 | 36.572 | 153.502 | 1.00 | 3.63 | B | C |
| ATOM | 6055 | OD1 | ASN | B | 48 | 10.191 | 35.864 | 154.455 | 1.00 | 4.51 | B | O |
| ATOM | 6056 | ND2 | ASN | B | 48 | 10.441 | 36.556 | 152.325 | 1.00 | 2.00 | B | N |
| ATOM | 6057 | C | ASN | B | 48 | 7.626 | 36.082 | 155.535 | 1.00 | 4.15 | B | C |
| ATOM | 6058 | O | ASN | B | 48 | 7.928 | 35.813 | 156.710 | 1.00 | 4.08 | B | O |

FIG. 33-1

| | | | | | | | | | | | | |
|---|---|---|---|---|---|---|---|---|---|---|---|---|
| ATOM | 6059 | N | ASN | B | 49 | 7.049 | 35.200 | 154.730 | 1.00 | 3.96 | B | N |
| ATOM | 6060 | CA | ASN | B | 49 | 6.685 | 33.858 | 155.217 | 1.00 | 4.78 | B | C |
| ATOM | 6061 | CB | ASN | B | 49 | 5.892 | 33.072 | 154.155 | 1.00 | 4.58 | B | C |
| ATOM | 6062 | CG | ASN | B | 49 | 4.528 | 33.683 | 153.864 | 1.00 | 6.22 | B | C |
| ATOM | 6063 | OD1 | ASN | B | 49 | 3.827 | 33.270 | 152.922 | 1.00 | 8.25 | B | O |
| ATOM | 6064 | ND2 | ASN | B | 49 | 4.151 | 34.685 | 154.655 | 1.00 | 4.90 | B | N |
| ATOM | 6065 | C | ASN | B | 49 | 7.840 | 33.013 | 155.763 | 1.00 | 4.50 | B | C |
| ATOM | 6066 | O | ASN | B | 49 | 7.632 | 32.168 | 156.622 | 1.00 | 5.46 | B | O |
| ATOM | 6067 | N | THR | B | 50 | 9.054 | 33.243 | 155.273 | 1.00 | 5.02 | B | N |
| ATOM | 6068 | CA | THR | B | 50 | 10.246 | 32.518 | 155.744 | 1.00 | 4.39 | B | C |
| ATOM | 6069 | CB | THR | B | 50 | 11.413 | 32.651 | 154.748 | 1.00 | 4.34 | B | C |
| ATOM | 6070 | OG1 | THR | B | 50 | 11.882 | 34.011 | 154.742 | 1.00 | 3.44 | B | O |
| ATOM | 6071 | CG2 | THR | B | 50 | 10.950 | 32.254 | 153.325 | 1.00 | 4.57 | B | C |
| ATOM | 6072 | C | THR | B | 50 | 10.745 | 33.031 | 157.096 | 1.00 | 4.84 | B | C |
| ATOM | 6073 | O | THR | B | 50 | 11.450 | 32.306 | 157.804 | 1.00 | 4.54 | B | O |
| ATOM | 6074 | N | GLY | B | 51 | 10.432 | 34.293 | 157.416 | 1.00 | 4.48 | B | N |
| ATOM | 6075 | CA | GLY | B | 51 | 10.802 | 34.910 | 158.707 | 1.00 | 4.48 | B | C |
| ATOM | 6076 | C | GLY | B | 51 | 11.560 | 36.232 | 158.553 | 1.00 | 5.18 | B | C |
| ATOM | 6077 | O | GLY | B | 51 | 11.862 | 36.918 | 159.542 | 1.00 | 5.14 | B | O |
| ATOM | 6200 | N | LEU | B | 67 | 10.876 | 26.584 | 154.563 | 1.00 | 4.27 | B | N |
| ATOM | 6201 | CA | LEU | B | 67 | 10.335 | 26.228 | 153.272 | 1.00 | 4.24 | B | C |
| ATOM | 6202 | CB | LEU | B | 67 | 8.858 | 25.822 | 153.413 | 1.00 | 3.74 | B | C |
| ATOM | 6203 | CG | LEU | B | 67 | 8.558 | 24.462 | 154.063 | 1.00 | 2.90 | B | C |
| ATOM | 6204 | CD1 | LEU | B | 67 | 7.076 | 24.167 | 154.019 | 1.00 | 2.92 | B | C |
| ATOM | 6205 | CD2 | LEU | B | 67 | 9.361 | 23.328 | 153.400 | 1.00 | 2.00 | B | C |
| ATOM | 6206 | C | LEU | B | 67 | 10.436 | 27.457 | 152.371 | 1.00 | 4.38 | B | C |
| ATOM | 6207 | O | LEU | B | 67 | 9.926 | 28.517 | 152.720 | 1.00 | 4.30 | B | O |
| ATOM | 6208 | N | ASP | B | 68 | 11.070 | 27.282 | 151.216 | 1.00 | 4.40 | B | N |
| ATOM | 6209 | CA | ASP | B | 68 | 11.312 | 28.351 | 150.252 | 1.00 | 4.81 | B | C |
| ATOM | 6210 | CB | ASP | B | 68 | 12.398 | 27.937 | 149.254 | 1.00 | 4.70 | B | C |
| ATOM | 6211 | CG | ASP | B | 68 | 13.677 | 27.502 | 149.932 | 1.00 | 5.37 | B | C |
| ATOM | 6212 | OD1 | ASP | B | 68 | 13.702 | 26.364 | 150.444 | 1.00 | 4.55 | B | O |
| ATOM | 6213 | OD2 | ASP | B | 68 | 14.636 | 28.300 | 149.964 | 1.00 | 5.37 | B | O |
| ATOM | 6214 | C | ASP | B | 68 | 10.079 | 28.727 | 149.459 | 1.00 | 4.93 | B | C |
| ATOM | 6215 | O | ASP | B | 68 | 9.469 | 27.878 | 148.818 | 1.00 | 5.94 | B | O |
| ATOM | 6216 | N | GLY | B | 69 | 9.723 | 30.005 | 149.507 | 1.00 | 5.17 | B | N |
| ATOM | 6217 | CA | GLY | B | 69 | 8.769 | 30.598 | 148.558 | 1.00 | 4.56 | B | C |
| ATOM | 6218 | C | GLY | B | 69 | 7.327 | 30.161 | 148.689 | 1.00 | 4.60 | B | C |
| ATOM | 6219 | O | GLY | B | 69 | 6.573 | 30.236 | 147.713 | 1.00 | 4.30 | B | O |
| ATOM | 6220 | N | VAL | B | 70 | 6.932 | 29.725 | 149.887 | 1.00 | 3.48 | B | N |
| ATOM | 6221 | CA | VAL | B | 70 | 5.589 | 29.149 | 150.102 | 1.00 | 3.51 | B | C |
| ATOM | 6222 | CB | VAL | B | 70 | 5.627 | 27.927 | 151.063 | 1.00 | 3.54 | B | C |
| ATOM | 6223 | CG1 | VAL | B | 70 | 6.419 | 26.772 | 150.442 | 1.00 | 3.34 | B | C |
| ATOM | 6224 | CG2 | VAL | B | 70 | 6.209 | 28.314 | 152.422 | 1.00 | 2.91 | B | C |
| ATOM | 6225 | C | VAL | B | 70 | 4.609 | 30.183 | 150.644 | 1.00 | 3.44 | B | C |
| ATOM | 6226 | O | VAL | B | 70 | 5.033 | 31.257 | 151.119 | 1.00 | 3.41 | B | O |
| ATOM | 6227 | N | GLY | B | 71 | 3.317 | 29.856 | 150.590 | 1.00 | 3.21 | B | N |
| ATOM | 6228 | CA | GLY | B | 71 | 2.243 | 30.766 | 151.033 | 1.00 | 4.39 | B | C |
| ATOM | 6229 | C | GLY | B | 71 | 1.896 | 30.610 | 152.517 | 1.00 | 5.23 | B | C |
| ATOM | 6230 | O | GLY | B | 71 | 2.732 | 30.168 | 153.313 | 1.00 | 5.01 | B | O |
| ATOM | 6231 | N | GLY | B | 72 | 0.653 | 30.950 | 152.869 | 1.00 | 5.67 | B | N |
| ATOM | 6232 | CA | GLY | B | 72 | 0.165 | 30.889 | 154.256 | 1.00 | 5.93 | B | C |
| ATOM | 6233 | C | GLY | B | 72 | 0.949 | 31.862 | 155.107 | 1.00 | 6.07 | B | C |
| ATOM | 6234 | O | GLY | B | 72 | 1.165 | 33.016 | 154.692 | 1.00 | 6.64 | B | O |
| ATOM | 6235 | N | SER | B | 73 | 1.390 | 31.404 | 156.282 | 1.00 | 5.79 | B | N |
| ATOM | 6236 | CA | SER | B | 73 | 2.360 | 32.159 | 157.086 | 1.00 | 5.71 | B | C |
| ATOM | 6237 | CB | SER | B | 73 | 1.884 | 32.320 | 158.534 | 1.00 | 5.72 | B | C |
| ATOM | 6238 | OG | SER | B | 73 | 1.572 | 31.062 | 159.111 | 1.00 | 5.04 | B | O |
| ATOM | 6239 | C | SER | B | 73 | 3.751 | 31.512 | 157.055 | 1.00 | 5.79 | B | C |
| ATOM | 6240 | O | SER | B | 73 | 4.621 | 31.864 | 157.855 | 1.00 | 5.53 | B | O |
| ATOM | 6241 | N | GLY | B | 74 | 3.943 | 30.560 | 156.136 | 1.00 | 5.50 | B | N |
| ATOM | 6242 | CA | GLY | B | 74 | 5.232 | 29.886 | 155.962 | 1.00 | 4.98 | B | C |
| ATOM | 6243 | C | GLY | B | 74 | 5.389 | 28.660 | 156.834 | 1.00 | 4.36 | B | C |
| ATOM | 6244 | O | GLY | B | 74 | 4.702 | 28.512 | 157.834 | 1.00 | 4.36 | B | O |
| ATOM | 6245 | N | GLY | B | 75 | 6.284 | 27.765 | 156.443 | 1.00 | 4.59 | B | N |
| ATOM | 6246 | CA | GLY | B | 75 | 6.527 | 26.565 | 157.216 | 1.00 | 4.40 | B | C |

FIG. 33-2

| | | | | | | | | | | | | |
|---|---|---|---|---|---|---|---|---|---|---|---|---|
| ATOM | 6247 | C | GLY | B | 75 | 7.889 | 26.594 | 157.880 | 1.00 | 4.18 | B | C |
| ATOM | 6248 | O | GLY | B | 75 | 8.717 | 27.435 | 157.575 | 1.00 | 4.41 | B | O |
| ATOM | 6249 | N | GLY | B | 76 | 8.116 | 25.653 | 158.788 | 1.00 | 4.82 | B | N |
| ATOM | 6250 | CA | GLY | B | 76 | 9.371 | 25.580 | 159.508 | 1.00 | 4.57 | B | C |
| ATOM | 6251 | C | GLY | B | 76 | 9.475 | 26.759 | 160.434 | 1.00 | 4.29 | B | C |
| ATOM | 6252 | O | GLY | B | 76 | 8.504 | 27.108 | 161.114 | 1.00 | 4.51 | B | O |
| ATOM | 6253 | N | GLY | B | 77 | 10.647 | 27.390 | 160.433 | 1.00 | 3.80 | B | N |
| ATOM | 6254 | CA | GLY | B | 77 | 10.953 | 28.443 | 161.386 | 1.00 | 3.39 | B | C |
| ATOM | 6255 | C | GLY | B | 77 | 11.241 | 27.958 | 162.792 | 1.00 | 3.21 | B | C |
| ATOM | 6256 | O | GLY | B | 77 | 11.099 | 28.729 | 163.743 | 1.00 | 3.66 | B | O |
| ATOM | 7082 | N | TYR | B | 194 | 3.643 | 22.233 | 162.238 | 1.00 | 3.12 | B | N |
| ATOM | 7083 | CA | TYR | B | 194 | 2.613 | 21.951 | 161.250 | 1.00 | 3.30 | B | C |
| ATOM | 7084 | CB | TYR | B | 194 | 1.229 | 21.842 | 161.911 | 1.00 | 3.34 | B | C |
| ATOM | 7085 | CG | TYR | B | 194 | 0.110 | 21.512 | 160.940 | 1.00 | 3.71 | B | C |
| ATOM | 7086 | CD1 | TYR | B | 194 | -0.461 | 22.504 | 160.135 | 1.00 | 4.84 | B | C |
| ATOM | 7087 | CE1 | TYR | B | 194 | -1.490 | 22.204 | 159.240 | 1.00 | 6.19 | B | C |
| ATOM | 7088 | CZ | TYR | B | 194 | -1.954 | 20.908 | 159.146 | 1.00 | 4.77 | B | C |
| ATOM | 7089 | OH | TYR | B | 194 | -2.964 | 20.602 | 158.255 | 1.00 | 6.66 | B | O |
| ATOM | 7090 | CE2 | TYR | B | 194 | -1.400 | 19.908 | 159.936 | 1.00 | 5.56 | B | C |
| ATOM | 7091 | CD2 | TYR | B | 194 | -0.370 | 20.213 | 160.817 | 1.00 | 2.00 | B | C |
| ATOM | 7092 | C | TYR | B | 194 | 2.618 | 23.039 | 160.183 | 1.00 | 3.39 | B | C |
| ATOM | 7093 | O | TYR | B | 194 | 2.833 | 24.217 | 160.484 | 1.00 | 2.89 | B | O |
| ATOM | 7094 | N | PHE | B | 195 | 2.402 | 22.634 | 158.934 | 1.00 | 3.57 | B | N |
| ATOM | 7095 | CA | PHE | B | 195 | 2.176 | 23.583 | 157.852 | 1.00 | 4.28 | B | C |
| ATOM | 7096 | CB | PHE | B | 195 | 3.495 | 24.128 | 157.273 | 1.00 | 3.41 | B | C |
| ATOM | 7097 | CG | PHE | B | 195 | 3.307 | 25.061 | 156.101 | 1.00 | 2.84 | B | C |
| ATOM | 7098 | CD1 | PHE | B | 195 | 2.857 | 26.368 | 156.296 | 1.00 | 2.00 | B | C |
| ATOM | 7099 | CE1 | PHE | B | 195 | 2.688 | 27.240 | 155.214 | 1.00 | 2.78 | B | C |
| ATOM | 7100 | CZ | PHE | B | 195 | 2.970 | 26.810 | 153.920 | 1.00 | 2.01 | B | C |
| ATOM | 7101 | CE2 | PHE | B | 195 | 3.431 | 25.487 | 153.713 | 1.00 | 3.28 | B | C |
| ATOM | 7102 | CD2 | PHE | B | 195 | 3.588 | 24.636 | 154.801 | 1.00 | 2.14 | B | C |
| ATOM | 7103 | C | PHE | B | 195 | 1.340 | 22.977 | 156.739 | 1.00 | 4.75 | B | C |
| ATOM | 7104 | O | PHE | B | 195 | 1.700 | 21.949 | 156.158 | 1.00 | 4.94 | B | O |
| ATOM | 7105 | N | TYR | B | 196 | 0.234 | 23.655 | 156.460 | 1.00 | 6.22 | B | N |
| ATOM | 7106 | CA | TYR | B | 196 | -0.598 | 23.421 | 155.296 | 1.00 | 7.19 | B | C |
| ATOM | 7107 | CB | TYR | B | 196 | 0.228 | 23.437 | 153.995 | 1.00 | 7.83 | B | C |
| ATOM | 7108 | CG | TYR | B | 196 | -0.616 | 23.795 | 152.800 | 1.00 | 10.54 | B | C |
| ATOM | 7109 | CD1 | TYR | B | 196 | -1.022 | 25.116 | 152.596 | 1.00 | 12.24 | B | C |
| ATOM | 7110 | CE1 | TYR | B | 196 | -1.824 | 25.468 | 151.513 | 1.00 | 15.08 | B | C |
| ATOM | 7111 | CZ | TYR | B | 196 | -2.227 | 24.487 | 150.619 | 1.00 | 16.10 | B | C |
| ATOM | 7112 | OH | TYR | B | 196 | -3.015 | 24.861 | 149.550 | 1.00 | 19.44 | B | O |
| ATOM | 7113 | CE2 | TYR | B | 196 | -1.840 | 23.147 | 150.800 | 1.00 | 15.05 | B | C |
| ATOM | 7114 | CD2 | TYR | B | 196 | -1.038 | 22.812 | 151.890 | 1.00 | 11.35 | B | C |
| ATOM | 7115 | C | TYR | B | 196 | -1.432 | 22.161 | 155.434 | 1.00 | 7.32 | B | C |
| ATOM | 7116 | O | TYR | B | 196 | -2.592 | 22.244 | 155.848 | 1.00 | 8.08 | B | O |
| ATOM | 7117 | N | ASN | B | 197 | -0.848 | 21.010 | 155.111 | 1.00 | 6.91 | B | N |
| ATOM | 7118 | CA | ASN | B | 197 | -1.557 | 19.737 | 155.149 | 1.00 | 7.00 | B | C |
| ATOM | 7119 | CB | ASN | B | 197 | -1.448 | 19.010 | 153.804 | 1.00 | 6.93 | B | C |
| ATOM | 7120 | CG | ASN | B | 197 | -2.381 | 19.573 | 152.756 | 1.00 | 8.25 | B | C |
| ATOM | 7121 | OD1 | ASN | B | 197 | -3.492 | 19.991 | 153.063 | 1.00 | 6.81 | B | O |
| ATOM | 7122 | ND2 | ASN | B | 197 | -1.932 | 19.577 | 151.499 | 1.00 | 9.68 | B | N |
| ATOM | 7123 | C | ASN | B | 197 | -1.097 | 18.779 | 156.242 | 1.00 | 6.55 | B | C |
| ATOM | 7124 | O | ASN | B | 197 | -1.841 | 17.875 | 156.589 | 1.00 | 6.69 | B | O |
| ATOM | 7125 | N | ALA | B | 198 | 0.104 | 18.977 | 156.793 | 1.00 | 5.68 | B | N |
| ATOM | 7126 | CA | ALA | B | 198 | 0.738 | 17.907 | 157.606 | 1.00 | 5.17 | B | C |
| ATOM | 7127 | CB | ALA | B | 198 | 1.519 | 16.952 | 156.715 | 1.00 | 3.99 | B | C |
| ATOM | 7128 | C | ALA | B | 198 | 1.644 | 18.391 | 158.727 | 1.00 | 4.90 | B | C |
| ATOM | 7129 | O | ALA | B | 198 | 2.316 | 19.416 | 158.594 | 1.00 | 5.24 | B | O |
| ATOM | 8311 | N | ALA | B | 352 | 5.634 | 20.319 | 147.023 | 1.00 | 5.44 | B | N |
| ATOM | 8312 | CA | ALA | B | 352 | 4.594 | 21.317 | 146.769 | 1.00 | 6.09 | B | C |
| ATOM | 8313 | CB | ALA | B | 352 | 5.135 | 22.730 | 146.962 | 1.00 | 5.99 | B | C |
| ATOM | 8314 | C | ALA | B | 352 | 4.223 | 21.089 | 145.329 | 1.00 | 6.35 | B | C |
| ATOM | 8315 | O | ALA | B | 352 | 4.288 | 21.990 | 144.503 | 1.00 | 6.13 | B | O |
| ATOM | 8316 | N | THR | B | 353 | 3.821 | 19.855 | 145.044 | 1.00 | 7.15 | B | N |
| ATOM | 8317 | CA | THR | B | 353 | 3.818 | 19.352 | 143.690 | 1.00 | 7.57 | B | C |
| ATOM | 8318 | CB | THR | B | 353 | 3.887 | 17.837 | 143.696 | 1.00 | 7.65 | B | C |

FIG. 33-3

| | | | | | | | | | | | | |
|---|---|---|---|---|---|---|---|---|---|---|---|---|
| ATOM | 8319 | OG1 | THR | B | 353 | 4.943 | 17.447 | 144.580 | 1.00 | 8.17 | B | O |
| ATOM | 8320 | CG2 | THR | B | 353 | 4.184 | 17.295 | 142.296 | 1.00 | 6.93 | B | C |
| ATOM | 8321 | C | THR | B | 353 | 2.656 | 19.914 | 142.859 | 1.00 | 8.28 | B | C |
| ATOM | 8322 | O | THR | B | 353 | 2.750 | 19.992 | 141.631 | 1.00 | 8.21 | B | O |
| ATOM | 8323 | N | TRP | B | 354 | 1.581 | 20.325 | 143.531 | 1.00 | 8.91 | B | N |
| ATOM | 8324 | CA | TRP | B | 354 | 0.511 | 21.060 | 142.861 | 1.00 | 10.28 | B | C |
| ATOM | 8325 | CB | TRP | B | 354 | -0.559 | 21.535 | 143.859 | 1.00 | 10.88 | B | C |
| ATOM | 8326 | CG | TRP | B | 354 | -1.795 | 22.053 | 143.189 | 1.00 | 13.77 | B | C |
| ATOM | 8327 | CD1 | TRP | B | 354 | -2.904 | 21.331 | 142.861 | 1.00 | 15.75 | B | C |
| ATOM | 8328 | NE1 | TRP | B | 354 | -3.829 | 22.131 | 142.242 | 1.00 | 18.84 | B | N |
| ATOM | 8329 | CE2 | TRP | B | 354 | -3.338 | 23.407 | 142.172 | 1.00 | 19.33 | B | C |
| ATOM | 8330 | CD2 | TRP | B | 354 | -2.050 | 23.396 | 142.759 | 1.00 | 17.76 | B | C |
| ATOM | 8331 | CE3 | TRP | B | 354 | -1.317 | 24.588 | 142.806 | 1.00 | 19.35 | B | C |
| ATOM | 8332 | CZ3 | TRP | B | 354 | -1.887 | 25.751 | 142.273 | 1.00 | 22.00 | B | C |
| ATOM | 8333 | CH2 | TRP | B | 354 | -3.175 | 25.730 | 141.696 | 1.00 | 22.73 | B | C |
| ATOM | 8334 | CZ2 | TRP | B | 354 | -3.914 | 24.569 | 141.634 | 1.00 | 22.09 | B | C |
| ATOM | 8335 | C | TRP | B | 354 | 1.082 | 22.248 | 142.090 | 1.00 | 9.94 | B | C |
| ATOM | 8336 | O | TRP | B | 354 | 0.679 | 22.498 | 140.957 | 1.00 | 10.17 | B | O |
| ATOM | 8337 | N | ASP | B | 355 | 2.027 | 22.961 | 142.708 | 1.00 | 9.68 | B | N |
| ATOM | 8338 | CA | ASP | B | 355 | 2.607 | 24.171 | 142.126 | 1.00 | 9.25 | B | C |
| ATOM | 8339 | CB | ASP | B | 355 | 3.020 | 25.161 | 143.224 | 1.00 | 9.39 | B | C |
| ATOM | 8340 | CG | ASP | B | 355 | 1.920 | 25.410 | 144.250 | 1.00 | 11.18 | B | C |
| ATOM | 8341 | OD1 | ASP | B | 355 | 2.026 | 24.884 | 145.380 | 1.00 | 12.17 | B | O |
| ATOM | 8342 | OD2 | ASP | B | 355 | 0.957 | 26.138 | 143.927 | 1.00 | 14.96 | B | O |
| ATOM | 8343 | C | ASP | B | 355 | 3.832 | 23.883 | 141.261 | 1.00 | 8.63 | B | C |
| ATOM | 8344 | O | ASP | B | 355 | 4.010 | 24.505 | 140.198 | 1.00 | 8.49 | B | O |
| ATOM | 8345 | N | ASP | B | 356 | 4.679 | 22.961 | 141.721 | 1.00 | 7.73 | B | N |
| ATOM | 8346 | CA | ASP | B | 356 | 6.027 | 22.821 | 141.162 | 1.00 | 7.97 | B | C |
| ATOM | 8347 | CB | ASP | B | 356 | 7.084 | 22.835 | 142.282 | 1.00 | 8.30 | B | C |
| ATOM | 8348 | CG | ASP | B | 356 | 7.193 | 21.517 | 143.028 | 1.00 | 10.67 | B | C |
| ATOM | 8349 | OD1 | ASP | B | 356 | 6.378 | 20.590 | 142.800 | 1.00 | 12.81 | B | O |
| ATOM | 8350 | OD2 | ASP | B | 356 | 8.130 | 21.405 | 143.856 | 1.00 | 13.11 | B | O |
| ATOM | 8351 | C | ASP | B | 356 | 6.290 | 21.648 | 140.225 | 1.00 | 6.85 | B | C |
| ATOM | 8352 | O | ASP | B | 356 | 7.432 | 21.434 | 139.843 | 1.00 | 6.23 | B | O |
| ATOM | 8702 | N | THR | B | 403 | 6.656 | 20.211 | 154.931 | 1.00 | 2.24 | B | N |
| ATOM | 8703 | CA | THR | B | 403 | 6.223 | 19.841 | 153.605 | 1.00 | 2.00 | B | C |
| ATOM | 8704 | CB | THR | B | 403 | 6.095 | 18.282 | 153.520 | 1.00 | 2.05 | B | C |
| ATOM | 8705 | OG1 | THR | B | 403 | 5.760 | 17.892 | 152.198 | 1.00 | 3.15 | B | O |
| ATOM | 8706 | CG2 | THR | B | 403 | 5.030 | 17.770 | 154.453 | 1.00 | 2.00 | B | C |
| ATOM | 8707 | C | THR | B | 403 | 4.913 | 20.578 | 153.289 | 1.00 | 2.00 | B | C |
| ATOM | 8708 | O | THR | B | 403 | 4.316 | 21.193 | 154.178 | 1.00 | 2.00 | B | O |
| ATOM | 8709 | N | VAL | B | 404 | 4.491 | 20.536 | 152.026 | 1.00 | 2.00 | B | N |
| ATOM | 8710 | CA | VAL | B | 404 | 3.295 | 21.247 | 151.582 | 1.00 | 2.02 | B | C |
| ATOM | 8711 | CB | VAL | B | 404 | 3.633 | 22.358 | 150.571 | 1.00 | 2.00 | B | C |
| ATOM | 8712 | CG1 | VAL | B | 404 | 2.406 | 23.239 | 150.320 | 1.00 | 2.00 | B | C |
| ATOM | 8713 | CG2 | VAL | B | 404 | 4.800 | 23.187 | 151.064 | 1.00 | 2.00 | B | C |
| ATOM | 8714 | C | VAL | B | 404 | 2.175 | 20.345 | 151.023 | 1.00 | 2.65 | B | C |
| ATOM | 8715 | O | VAL | B | 404 | 1.183 | 20.118 | 151.702 | 1.00 | 2.92 | B | O |
| ATOM | 8716 | N | ARG | B | 405 | 2.332 | 19.834 | 149.803 | 1.00 | 3.29 | B | N |
| ATOM | 8717 | CA | ARG | B | 405 | 1.236 | 19.105 | 149.134 | 1.00 | 3.66 | B | C |
| ATOM | 8718 | CB | ARG | B | 405 | 0.170 | 20.101 | 148.633 | 1.00 | 3.90 | B | C |
| ATOM | 8719 | CG | ARG | B | 405 | 0.641 | 20.982 | 147.480 | 1.00 | 3.00 | B | C |
| ATOM | 8720 | CD | ARG | B | 405 | -0.271 | 22.201 | 147.301 | 1.00 | 2.02 | B | C |
| ATOM | 8721 | NE | ARG | B | 405 | -1.643 | 21.828 | 146.974 | 1.00 | 3.88 | B | N |
| ATOM | 8722 | CZ | ARG | B | 405 | -2.594 | 22.700 | 146.644 | 1.00 | 5.53 | B | C |
| ATOM | 8723 | NH1 | ARG | B | 405 | -2.324 | 24.001 | 146.580 | 1.00 | 5.29 | B | N |
| ATOM | 8724 | NH2 | ARG | B | 405 | -3.812 | 22.271 | 146.379 | 1.00 | 6.56 | B | N |
| ATOM | 8725 | C | ARG | B | 405 | 1.717 | 18.221 | 147.981 | 1.00 | 3.69 | B | C |
| ATOM | 8726 | O | ARG | B | 405 | 2.837 | 18.353 | 147.494 | 1.00 | 3.54 | B | O |
| ATOM | 8727 | N | TRP | B | 406 | 0.861 | 17.315 | 147.540 | 1.00 | 4.26 | B | N |
| ATOM | 8728 | CA | TRP | B | 406 | 1.343 | 16.193 | 146.726 | 1.00 | 4.40 | B | C |
| ATOM | 8729 | CB | TRP | B | 406 | 1.380 | 14.920 | 147.575 | 1.00 | 4.23 | B | C |
| ATOM | 8730 | CG | TRP | B | 406 | 2.088 | 15.094 | 148.872 | 1.00 | 4.31 | B | C |
| ATOM | 8731 | CD1 | TRP | B | 406 | 3.417 | 14.922 | 149.110 | 1.00 | 4.94 | B | C |
| ATOM | 8732 | NE1 | TRP | B | 406 | 3.696 | 15.167 | 150.429 | 1.00 | 5.82 | B | N |
| ATOM | 8733 | CE2 | TRP | B | 406 | 2.537 | 15.516 | 151.067 | 1.00 | 4.54 | B | C |

FIG. 33-4

| | | | | | | | | | | | | |
|---|---|---|---|---|---|---|---|---|---|---|---|---|
| ATOM | 8734 | CD2 | TRP | B | 406 | 1.500 | 15.472 | 150.112 | 1.00 | 4.03 | B | C |
| ATOM | 8735 | CE3 | TRP | B | 406 | 0.192 | 15.805 | 150.507 | 1.00 | 2.57 | B | C |
| ATOM | 8736 | CZ3 | TRP | B | 406 | -0.024 | 16.148 | 151.840 | 1.00 | 4.33 | B | C |
| ATOM | 8737 | CH2 | TRP | B | 406 | 1.032 | 16.167 | 152.764 | 1.00 | 4.13 | B | C |
| ATOM | 8738 | CZ2 | TRP | B | 406 | 2.316 | 15.859 | 152.397 | 1.00 | 3.80 | B | C |
| ATOM | 8739 | C | TRP | B | 406 | 0.565 | 15.933 | 145.433 | 1.00 | 4.65 | B | C |
| ATOM | 9696 | N | GLY | B | 533 | -15.847 | 27.725 | 140.342 | 1.00 | 9.53 | B | N |
| ATOM | 9697 | CA | GLY | B | 533 | -15.211 | 26.855 | 141.335 | 1.00 | 9.25 | B | C |
| ATOM | 9698 | C | GLY | B | 533 | -13.705 | 26.691 | 141.187 | 1.00 | 8.71 | B | C |
| ATOM | 9699 | O | GLY | B | 533 | -13.098 | 25.875 | 141.883 | 1.00 | 8.16 | B | O |
| ATOM | 9700 | N | LEU | B | 534 | -13.099 | 27.477 | 140.293 | 1.00 | 8.58 | B | N |
| ATOM | 9701 | CA | LEU | B | 534 | -11.653 | 27.388 | 140.006 | 1.00 | 8.07 | B | C |
| ATOM | 9702 | CB | LEU | B | 534 | -11.286 | 28.145 | 138.734 | 1.00 | 7.63 | B | C |
| ATOM | 9703 | CG | LEU | B | 534 | -11.866 | 27.619 | 137.420 | 1.00 | 6.93 | B | C |
| ATOM | 9704 | CD1 | LEU | B | 534 | -11.597 | 28.602 | 136.307 | 1.00 | 3.89 | B | C |
| ATOM | 9705 | CD2 | LEU | B | 534 | -11.303 | 26.245 | 137.079 | 1.00 | 7.25 | B | C |
| ATOM | 9706 | C | LEU | B | 534 | -10.747 | 27.869 | 141.134 | 1.00 | 8.88 | B | C |
| ATOM | 9707 | O | LEU | B | 534 | -11.033 | 28.870 | 141.822 | 1.00 | 7.62 | B | O |
| ATOM | 9708 | N | TYR | B | 535 | -9.637 | 27.152 | 141.288 | 1.00 | 9.49 | B | N |
| ATOM | 9709 | CA | TYR | B | 535 | -8.638 | 27.486 | 142.280 | 1.00 | 10.81 | B | C |
| ATOM | 9710 | CB | TYR | B | 535 | -8.010 | 26.197 | 142.861 | 1.00 | 11.89 | B | C |
| ATOM | 9711 | CG | TYR | B | 535 | -8.753 | 25.749 | 144.106 | 1.00 | 16.97 | B | C |
| ATOM | 9712 | CD1 | TYR | B | 535 | -8.130 | 25.772 | 145.361 | 1.00 | 20.37 | B | C |
| ATOM | 9713 | CE1 | TYR | B | 535 | -8.832 | 25.389 | 146.520 | 1.00 | 23.75 | B | C |
| ATOM | 9714 | CZ | TYR | B | 535 | -10.184 | 25.009 | 146.424 | 1.00 | 23.62 | B | C |
| ATOM | 9715 | OH | TYR | B | 535 | -10.865 | 24.649 | 147.562 | 1.00 | 24.62 | B | O |
| ATOM | 9716 | CE2 | TYR | B | 535 | -10.827 | 24.987 | 145.193 | 1.00 | 22.59 | B | C |
| ATOM | 9717 | CD2 | TYR | B | 535 | -10.111 | 25.365 | 144.038 | 1.00 | 20.68 | B | C |
| ATOM | 9718 | C | TYR | B | 535 | -7.604 | 28.447 | 141.703 | 1.00 | 10.16 | B | C |
| ATOM | 9719 | O | TYR | B | 535 | -6.865 | 28.094 | 140.801 | 1.00 | 10.24 | B | O |
| ATOM | 9720 | N | GLN | B | 536 | -7.600 | 29.677 | 142.211 | 1.00 | 9.98 | B | N |
| ATOM | 9721 | CA | GLN | B | 536 | -6.568 | 30.681 | 141.905 | 1.00 | 10.33 | B | C |
| ATOM | 9722 | CB | GLN | B | 536 | -5.234 | 30.334 | 142.598 | 1.00 | 10.30 | B | C |
| ATOM | 9723 | CG | GLN | B | 536 | -5.313 | 30.141 | 144.128 | 1.00 | 13.24 | B | C |
| ATOM | 9724 | CD | GLN | B | 536 | -3.939 | 29.900 | 144.772 | 1.00 | 16.30 | B | C |
| ATOM | 9725 | OE1 | GLN | B | 536 | -2.909 | 29.886 | 144.095 | 1.00 | 17.97 | B | O |
| ATOM | 9726 | NE2 | GLN | B | 536 | -3.929 | 29.725 | 146.091 | 1.00 | 18.13 | B | N |
| ATOM | 9727 | C | GLN | B | 536 | -6.337 | 30.936 | 140.402 | 1.00 | 10.03 | B | C |
| ATOM | 9728 | O | GLN | B | 536 | -5.217 | 31.217 | 139.967 | 1.00 | 10.11 | B | O |
| ATOM | 9729 | N | GLY | B | 537 | -7.397 | 30.850 | 139.608 | 1.00 | 10.06 | B | N |
| ATOM | 9730 | CA | GLY | B | 537 | -7.264 | 31.159 | 138.187 | 1.00 | 8.79 | B | C |
| ATOM | 9731 | C | GLY | B | 537 | -8.584 | 31.268 | 137.454 | 1.00 | 8.30 | B | C |
| ATOM | 9732 | O | GLY | B | 537 | -9.659 | 31.075 | 138.037 | 1.00 | 7.71 | B | O |
| ATOM | 10119 | N | ASN | B | 586 | 1.158 | 35.774 | 134.842 | 1.00 | 4.61 | B | N |
| ATOM | 10120 | CA | ASN | B | 586 | 2.561 | 35.487 | 135.130 | 1.00 | 4.87 | B | C |
| ATOM | 10121 | CB | ASN | B | 586 | 3.446 | 36.671 | 134.695 | 1.00 | 4.94 | B | C |
| ATOM | 10122 | CG | ASN | B | 586 | 3.354 | 36.964 | 133.194 | 1.00 | 4.99 | B | C |
| ATOM | 10123 | OD1 | ASN | B | 586 | 2.930 | 38.041 | 132.796 | 1.00 | 8.76 | B | O |
| ATOM | 10124 | ND2 | ASN | B | 586 | 3.754 | 36.017 | 132.371 | 1.00 | 4.46 | B | N |
| ATOM | 10125 | C | ASN | B | 586 | 2.791 | 35.182 | 136.618 | 1.00 | 5.09 | B | C |
| ATOM | 10126 | O | ASN | B | 586 | 3.852 | 34.691 | 136.997 | 1.00 | 3.71 | B | O |
| ATOM | 10127 | N | ALA | B | 587 | 1.777 | 35.465 | 137.446 | 1.00 | 5.34 | B | N |
| ATOM | 10128 | CA | ALA | B | 587 | 1.917 | 35.442 | 138.923 | 1.00 | 6.16 | B | C |
| ATOM | 10129 | CB | ALA | B | 587 | 1.006 | 36.491 | 139.546 | 1.00 | 5.10 | B | C |
| ATOM | 10130 | C | ALA | B | 587 | 1.688 | 34.108 | 139.635 | 1.00 | 6.83 | B | C |
| ATOM | 10131 | O | ALA | B | 587 | 2.084 | 33.957 | 140.784 | 1.00 | 6.45 | B | O |
| ATOM | 10132 | N | ASN | B | 588 | 0.997 | 33.179 | 138.977 | 1.00 | 8.41 | B | N |
| ATOM | 10133 | CA | ASN | B | 588 | 0.684 | 31.857 | 139.540 | 1.00 | 9.70 | B | C |
| ATOM | 10134 | CB | ASN | B | 588 | -0.790 | 31.765 | 139.954 | 1.00 | 10.13 | B | C |
| ATOM | 10135 | CG | ASN | B | 588 | -1.026 | 30.752 | 141.077 | 1.00 | 12.26 | B | C |
| ATOM | 10136 | OD1 | ASN | B | 588 | -0.090 | 30.198 | 141.622 | 1.00 | 15.20 | B | O |
| ATOM | 10137 | ND2 | ASN | B | 588 | -2.286 | 30.513 | 141.418 | 1.00 | 15.01 | B | N |
| ATOM | 10138 | C | ASN | B | 588 | 1.027 | 30.786 | 138.509 | 1.00 | 10.25 | B | C |
| ATOM | 10139 | O | ASN | B | 588 | 1.296 | 31.109 | 137.356 | 1.00 | 10.70 | B | O |
| ATOM | 10140 | N | GLU | B | 589 | 1.014 | 29.523 | 138.913 | 1.00 | 10.86 | B | N |
| ATOM | 10141 | CA | GLU | B | 589 | 1.574 | 28.445 | 138.079 | 1.00 | 11.52 | B | C |

FIG. 33-5

| | | | | | | | | | | | | |
|---|---|---|---|---|---|---|---|---|---|---|---|---|
| ATOM | 10142 | CB | GLU | B | 589 | 2.198 | 27.370 | 138.976 | 1.00 | 11.45 | B | C |
| ATOM | 10143 | CG | GLU | B | 589 | 3.501 | 27.805 | 139.630 | 1.00 | 9.96 | B | C |
| ATOM | 10144 | CD | GLU | B | 589 | 3.311 | 28.386 | 141.028 | 1.00 | 10.68 | B | C |
| ATOM | 10145 | OE1 | GLU | B | 589 | 2.146 | 28.629 | 141.434 | 1.00 | 10.43 | B | O |
| ATOM | 10146 | OE2 | GLU | B | 589 | 4.335 | 28.606 | 141.722 | 1.00 | 8.00 | B | O |
| ATOM | 10147 | C | GLU | B | 589 | 0.608 | 27.804 | 137.071 | 1.00 | 11.76 | B | C |
| ATOM | 10148 | O | GLU | B | 589 | 1.027 | 27.008 | 136.207 | 1.00 | 11.79 | B | O |
| ATOM | 10149 | N | ILE | B | 590 | -0.670 | 28.170 | 137.171 | 1.00 | 11.86 | B | N |
| ATOM | 10150 | CA | ILE | B | 590 | -1.724 | 27.523 | 136.394 | 1.00 | 11.76 | B | C |
| ATOM | 10151 | CB | ILE | B | 590 | -3.097 | 28.106 | 136.760 | 1.00 | 11.88 | B | C |
| ATOM | 10152 | CG1 | ILE | B | 590 | -3.531 | 27.471 | 138.085 | 1.00 | 12.53 | B | C |
| ATOM | 10153 | CD1 | ILE | B | 590 | -4.228 | 28.396 | 138.985 | 1.00 | 13.66 | B | C |
| ATOM | 10154 | CG2 | ILE | B | 590 | -4.143 | 27.847 | 135.665 | 1.00 | 12.30 | B | C |
| ATOM | 10155 | C | ILE | B | 590 | -1.461 | 27.444 | 134.877 | 1.00 | 11.77 | B | C |
| ATOM | 10156 | O | ILE | B | 590 | -1.563 | 26.362 | 134.286 | 1.00 | 11.66 | B | O |
| ATOM | 10444 | CA | ILE | B | 624 | -2.166 | 38.601 | 140.777 | 1.00 | 6.95 | B | C |
| ATOM | 10445 | CB | ILE | B | 624 | -2.394 | 39.529 | 142.009 | 1.00 | 7.43 | B | C |
| ATOM | 10446 | CG1 | ILE | B | 624 | -3.881 | 39.873 | 142.189 | 1.00 | 6.21 | B | C |
| ATOM | 10447 | CD1 | ILE | B | 624 | -4.256 | 40.384 | 143.612 | 1.00 | 6.93 | B | C |
| ATOM | 10448 | CG2 | ILE | B | 624 | -1.589 | 40.820 | 141.848 | 1.00 | 5.38 | B | C |
| ATOM | 10449 | C | ILE | B | 624 | -2.529 | 37.158 | 141.097 | 1.00 | 8.00 | B | C |
| ATOM | 10450 | O | ILE | B | 624 | -3.395 | 36.597 | 140.423 | 1.00 | 7.71 | B | O |
| ATOM | 10451 | N | ALA | B | 625 | -1.876 | 36.566 | 142.107 | 1.00 | 8.28 | B | N |
| ATOM | 10452 | CA | ALA | B | 625 | -2.036 | 35.146 | 142.429 | 1.00 | 9.17 | B | C |
| ATOM | 10453 | CB | ALA | B | 625 | -0.672 | 34.532 | 142.890 | 1.00 | 8.73 | B | C |
| ATOM | 10454 | C | ALA | B | 625 | -3.121 | 34.848 | 143.476 | 1.00 | 9.67 | B | C |
| ATOM | 10455 | O | ALA | B | 625 | -3.305 | 33.688 | 143.871 | 1.00 | 9.55 | B | O |
| ATOM | 10456 | N | THR | B | 626 | -3.813 | 35.889 | 143.941 | 1.00 | 10.19 | B | N |
| ATOM | 10457 | CA | THR | B | 626 | -4.883 | 35.743 | 144.940 | 1.00 | 9.61 | B | C |
| ATOM | 10458 | CB | THR | B | 626 | -4.311 | 35.718 | 146.381 | 1.00 | 10.06 | B | C |
| ATOM | 10459 | OG1 | THR | B | 626 | -5.328 | 35.322 | 147.300 | 1.00 | 9.01 | B | O |
| ATOM | 10460 | CG2 | THR | B | 626 | -3.722 | 37.088 | 146.791 | 1.00 | 10.40 | B | C |
| ATOM | 10461 | C | THR | B | 626 | -5.890 | 36.882 | 144.760 | 1.00 | 9.89 | B | C |
| ATOM | 10462 | O | THR | B | 626 | -5.682 | 37.753 | 143.914 | 1.00 | 9.41 | B | O |
| ATOM | 10463 | N | GLY | B | 627 | -6.954 | 36.880 | 145.563 | 1.00 | 10.02 | B | N |
| ATOM | 10464 | CA | GLY | B | 627 | -8.057 | 37.828 | 145.428 | 1.00 | 11.00 | B | C |
| ATOM | 10465 | C | GLY | B | 627 | -7.684 | 39.294 | 145.557 | 1.00 | 12.06 | B | C |
| ATOM | 10466 | O | GLY | B | 627 | -8.185 | 40.135 | 144.815 | 1.00 | 12.64 | B | O |
| ATOM | 10467 | N | SER | B | 628 | -6.793 | 39.604 | 146.489 | 1.00 | 13.03 | B | N |
| ATOM | 10468 | CA | SER | B | 628 | -6.410 | 40.988 | 146.753 | 1.00 | 14.00 | B | C |
| ATOM | 10469 | CB | SER | B | 628 | -7.482 | 41.650 | 147.614 | 1.00 | 14.26 | B | C |
| ATOM | 10470 | OG | SER | B | 628 | -7.266 | 43.039 | 147.649 | 1.00 | 15.26 | B | O |
| ATOM | 10471 | C | SER | B | 628 | -5.047 | 41.111 | 147.452 | 1.00 | 14.28 | B | C |
| ATOM | 10472 | O | SER | B | 628 | -4.640 | 40.217 | 148.191 | 1.00 | 14.61 | B | O |
| ATOM | 10473 | N | SER | B | 629 | -4.362 | 42.229 | 147.219 | 1.00 | 14.43 | B | N |
| ATOM | 10474 | CA | SER | B | 629 | -3.055 | 42.511 | 147.827 | 1.00 | 14.96 | B | C |
| ATOM | 10475 | CB | SER | B | 629 | -1.950 | 42.366 | 146.779 | 1.00 | 14.81 | B | C |
| ATOM | 10476 | OG | SER | B | 629 | -0.708 | 42.826 | 147.280 | 1.00 | 15.07 | B | O |
| ATOM | 10477 | C | SER | B | 629 | -2.997 | 43.923 | 148.390 | 1.00 | 15.25 | B | C |
| ATOM | 10478 | O | SER | B | 629 | -3.433 | 44.866 | 147.747 | 1.00 | 15.02 | B | O |
| ATOM | 10680 | N | PRO | B | 657 | 4.050 | 41.388 | 143.073 | 1.00 | 6.53 | B | N |
| ATOM | 10681 | CA | PRO | B | 657 | 3.402 | 41.236 | 144.385 | 1.00 | 6.71 | B | C |
| ATOM | 10682 | CB | PRO | B | 657 | 2.633 | 42.551 | 144.560 | 1.00 | 6.75 | B | C |
| ATOM | 10683 | CG | PRO | B | 657 | 2.497 | 43.125 | 143.179 | 1.00 | 6.81 | B | C |
| ATOM | 10684 | CD | PRO | B | 657 | 3.695 | 42.650 | 142.401 | 1.00 | 6.65 | B | C |
| ATOM | 10685 | C | PRO | B | 657 | 2.446 | 40.037 | 144.343 | 1.00 | 7.09 | B | C |
| ATOM | 10686 | O | PRO | B | 657 | 1.785 | 39.823 | 143.317 | 1.00 | 7.31 | B | O |
| ATOM | 10687 | N | THR | B | 658 | 2.382 | 39.270 | 145.438 | 1.00 | 6.82 | B | N |
| ATOM | 10688 | CA | THR | B | 658 | 1.659 | 37.972 | 145.528 | 1.00 | 7.41 | B | C |
| ATOM | 10689 | CB | THR | B | 658 | 0.160 | 38.025 | 145.092 | 1.00 | 7.22 | B | C |
| ATOM | 10690 | OG1 | THR | B | 658 | 0.091 | 38.108 | 143.663 | 1.00 | 8.46 | B | O |
| ATOM | 10691 | CG2 | THR | B | 658 | -0.562 | 39.183 | 145.720 | 1.00 | 7.56 | B | C |
| ATOM | 10692 | C | THR | B | 658 | 2.281 | 36.761 | 144.802 | 1.00 | 6.95 | B | C |
| ATOM | 10693 | O | THR | B | 658 | 1.850 | 35.614 | 145.012 | 1.00 | 7.00 | B | O |
| ATOM | 10694 | N | MET | B | 659 | 3.266 | 37.002 | 143.944 | 1.00 | 6.43 | B | N |
| ATOM | 10695 | CA | MET | B | 659 | 3.892 | 35.925 | 143.184 | 1.00 | 5.95 | B | C |

FIG. 33-6

| | | | | | | | | | | | | |
|---|---|---|---|---|---|---|---|---|---|---|---|---|
| ATOM | 10696 | CB | MET | B | 659 | 4.588 | 36.511 | 141.944 | 1.00 | 5.41 | B | C |
| ATOM | 10697 | CG | MET | B | 659 | 5.187 | 35.490 | 140.977 | 1.00 | 5.34 | B | C |
| ATOM | 10698 | SD | MET | B | 659 | 5.754 | 36.339 | 139.483 | 1.00 | 5.63 | B | S |
| ATOM | 10699 | CE | MET | B | 659 | 6.973 | 35.196 | 138.813 | 1.00 | 4.33 | B | C |
| ATOM | 10700 | C | MET | B | 659 | 4.865 | 35.073 | 144.034 | 1.00 | 5.78 | B | C |
| ATOM | 10701 | O | MET | B | 659 | 6.092 | 35.284 | 144.006 | 1.00 | 6.02 | B | O |
| ATOM | 10702 | N | ASP | B | 660 | 4.327 | 34.118 | 144.791 | 1.00 | 4.92 | B | N |
| ATOM | 10703 | CA | ASP | B | 660 | 5.190 | 33.199 | 145.543 | 1.00 | 4.96 | B | C |
| ATOM | 10704 | CB | ASP | B | 660 | 4.357 | 32.285 | 146.424 | 1.00 | 5.01 | B | C |
| ATOM | 10705 | CG | ASP | B | 660 | 3.584 | 33.032 | 147.473 | 1.00 | 6.04 | B | C |
| ATOM | 10706 | OD1 | ASP | B | 660 | 4.035 | 34.111 | 147.913 | 1.00 | 7.34 | B | O |
| ATOM | 10707 | OD2 | ASP | B | 660 | 2.522 | 32.524 | 147.864 | 1.00 | 7.88 | B | O |
| ATOM | 10708 | C | ASP | B | 660 | 6.037 | 32.337 | 144.596 | 1.00 | 4.93 | B | C |
| ATOM | 10709 | O | ASP | B | 660 | 5.508 | 31.791 | 143.621 | 1.00 | 4.69 | B | O |
| ATOM | 10710 | N | ASN | B | 661 | 7.340 | 32.240 | 144.873 | 1.00 | 4.84 | B | N |
| ATOM | 10711 | CA | ASN | B | 661 | 8.255 | 31.368 | 144.118 | 1.00 | 5.08 | B | C |
| ATOM | 10712 | CB | ASN | B | 661 | 9.694 | 31.455 | 144.681 | 1.00 | 5.10 | B | C |
| ATOM | 10713 | CG | ASN | B | 661 | 10.780 | 31.140 | 143.629 | 1.00 | 6.08 | B | C |
| ATOM | 10714 | OD1 | ASN | B | 661 | 10.526 | 30.495 | 142.608 | 1.00 | 5.96 | B | O |
| ATOM | 10715 | ND2 | ASN | B | 661 | 11.992 | 31.636 | 143.872 | 1.00 | 6.67 | B | N |
| ATOM | 10716 | C | ASN | B | 661 | 7.761 | 29.903 | 144.132 | 1.00 | 5.04 | B | C |
| ATOM | 10717 | O | ASN | B | 661 | 7.831 | 29.211 | 143.113 | 1.00 | 4.57 | B | O |
| ATOM | 10718 | N | ASP | B | 662 | 7.240 | 29.473 | 145.287 | 1.00 | 4.48 | B | N |
| ATOM | 10719 | CA | ASP | B | 662 | 6.702 | 28.114 | 145.513 | 1.00 | 4.85 | B | C |
| ATOM | 10720 | CB | ASP | B | 662 | 5.483 | 27.819 | 144.630 | 1.00 | 5.02 | B | C |
| ATOM | 10721 | CG | ASP | B | 662 | 4.285 | 28.656 | 144.989 | 1.00 | 5.82 | B | C |
| ATOM | 10722 | OD1 | ASP | B | 662 | 3.900 | 28.697 | 146.173 | 1.00 | 7.25 | B | O |
| ATOM | 10723 | OD2 | ASP | B | 662 | 3.725 | 29.259 | 144.068 | 1.00 | 5.44 | B | O |
| ATOM | 10724 | C | ASP | B | 662 | 7.733 | 27.009 | 145.308 | 1.00 | 4.49 | B | C |
| ATOM | 10725 | O | ASP | B | 662 | 7.726 | 26.335 | 144.268 | 1.00 | 4.33 | B | O |
| ATOM | 10726 | N | ALA | B | 663 | 8.587 | 26.804 | 146.304 | 1.00 | 4.58 | B | N |
| ATOM | 10727 | CA | ALA | B | 663 | 9.647 | 25.783 | 146.215 | 1.00 | 5.19 | B | C |
| ATOM | 10728 | CB | ALA | B | 663 | 9.032 | 24.354 | 146.294 | 1.00 | 4.88 | B | C |
| ATOM | 10729 | C | ALA | B | 663 | 10.523 | 25.941 | 144.958 | 1.00 | 5.61 | B | C |
| ATOM | 10730 | O | ALA | B | 663 | 10.951 | 24.953 | 144.355 | 1.00 | 6.58 | B | O |
| ATOM | 10731 | N | GLY | B | 664 | 10.798 | 27.191 | 144.580 | 1.00 | 6.10 | B | N |
| ATOM | 10732 | CA | GLY | B | 664 | 11.674 | 27.503 | 143.453 | 1.00 | 5.63 | B | C |
| ATOM | 10733 | C | GLY | B | 664 | 11.067 | 27.352 | 142.068 | 1.00 | 5.88 | B | C |
| ATOM | 10734 | O | GLY | B | 664 | 11.783 | 27.416 | 141.077 | 1.00 | 6.30 | B | O |
| ATOM | 12383 | CA | CA | C | 6 | 1.503 | 30.134 | 143.317 | 1.00 | 32.32 | C | CA |
| ATOM | 11905 | O | HOH | C | 7 | 2.949 | 31.974 | 142.705 | 1.00 | 3.45 | C | O |
| ATOM | 12345 | O | HOH | C | 8 | 1.937 | 29.983 | 147.278 | 1.00 | 20.75 | C | O |
| ATOM | 12381 | O | HOH | C | 9 | 0.607 | 31.785 | 144.943 | 1.00 | 23.64 | C | O |
| ATOM | 12380 | O | HOH | C | 10 | 0.075 | 28.500 | 144.774 | 1.00 | 23.09 | C | O |
| ATOM | 12403 | O3 | GOL | E | 1 | 2.366 | 27.082 | 149.806 | 1.00 | 23.71 | E | O |
| ATOM | 12404 | C3 | GOL | E | 1 | 0.966 | 27.273 | 149.833 | 1.00 | 24.21 | E | C |
| ATOM | 12405 | C2 | GOL | E | 1 | 0.495 | 27.587 | 148.416 | 1.00 | 22.96 | E | C |
| ATOM | 12406 | O2 | GOL | E | 1 | -0.173 | 28.816 | 148.396 | 1.00 | 22.95 | E | O |
| ATOM | 12407 | C1 | GOL | E | 1 | -0.470 | 26.521 | 147.940 | 1.00 | 23.83 | E | C |
| ATOM | 12408 | O1 | GOL | E | 1 | 0.108 | 25.826 | 146.867 | 1.00 | 22.02 | E | O |
| END | | | | | | | | | | | | |

FIG. 33-7

```
CRYST1   82.202   91.158  224.523  90.00  90.00  90.00 P 2 2 21
SCALE1      0.012165  0.000000  0.000000        0.00000
SCALE2     -0.000000  0.010970  0.000000        0.00000
SCALE3      0.000000 -0.000000  0.004454        0.00000
ATOM      2  CA  ALA A   7      74.405  12.350  86.541  1.00 19.71      A    C
ATOM      7  CA  ASP A   8      72.571  11.287  83.330  1.00 16.72      A    C
ATOM     15  CA  TYR A   9      68.912  11.738  84.261  1.00 12.13      A    C
ATOM     27  CA  ALA A  10      68.003  12.081  80.575  1.00  8.97      A    C
ATOM     32  CA  SER A  11      68.548   8.297  80.172  1.00  8.34      A    C
ATOM     38  CA  LEU A  12      65.749   7.661  82.703  1.00  6.43      A    C
ATOM     46  CA  VAL A  13      63.113   9.628  80.736  1.00  5.75      A    C
ATOM     53  CA  ASP A  14      60.886   7.538  78.450  1.00  6.27      A    C
ATOM     61  CA  VAL A  15      59.534  10.004  75.843  1.00  4.66      A    C
ATOM     68  CA  PHE A  16      57.177   7.311  74.498  1.00  3.87      A    C
ATOM     79  CA  VAL A  17      55.121   7.160  77.667  1.00  3.47      A    C
ATOM     86  CA  GLY A  18      51.656   8.454  76.810  1.00  3.67      A    C
ATOM     90  CA  THR A  19      52.191   8.387  72.991  1.00  3.13      A    C
ATOM     97  CA  GLU A  20      49.720   5.556  72.200  1.00  4.27      A    C
ATOM    106  CA  GLY A  21      46.188   6.265  70.980  1.00  5.40      A    C
ATOM    110  CA  ASP A  22      43.990   8.104  73.483  1.00  5.27      A    C
ATOM    118  CA  PHE A  23      46.225   7.338  76.520  1.00  4.39      A    C
ATOM    129  CA  GLY A  24      47.673  10.774  77.312  1.00  3.08      A    C
ATOM    133  CA  ASN A  25      48.095  12.630  73.991  1.00  2.47      A    C
ATOM    141  CA  ASP A  26      51.797  13.270  74.588  1.00  3.20      A    C
ATOM    149  CA  MET A  27      54.547  13.334  71.981  1.00  3.36      A    C
ATOM    157  CA  PRO A  28      57.941  11.662  71.502  1.00  3.20      A    C
ATOM    164  CA  ALA A  29      59.066  14.935  69.784  1.00  3.06      A    C
ATOM    169  CA  ALA A  30      62.625  16.198  70.105  1.00  3.69      A    C
ATOM    174  CA  GLN A  31      62.423  19.283  72.321  1.00  5.14      A    C
ATOM    183  CA  ALA A  32      64.432  21.430  74.735  1.00  4.55      A    C
ATOM    188  CA  PRO A  33      63.094  22.317  78.204  1.00  4.64      A    C
ATOM    195  CA  ASN A  34      60.021  24.568  77.625  1.00  4.19      A    C
ATOM    203  CA  GLY A  35      60.994  24.689  73.959  1.00  3.44      A    C
ATOM    207  CA  LEU A  36      59.041  26.309  71.169  1.00  3.34      A    C
ATOM    215  CA  ALA A  37      60.477  23.938  68.541  1.00  3.52      A    C
ATOM    220  CA  LYS A  38      58.932  20.498  68.910  1.00  3.01      A    C
ATOM    229  CA  VAL A  39      60.209  18.174  66.213  1.00  2.00      A    C
ATOM    236  CA  ASN A  40      57.543  15.463  66.213  1.00  2.24      A    C
ATOM    244  CA  PRO A  41      57.420  12.468  63.910  1.00  3.24      A    C
ATOM    251  CA  ARG A  42      53.989  12.144  62.244  1.00  4.43      A    C
ATOM    262  CA  THR A  43      52.366   8.720  62.032  1.00  5.82      A    C
ATOM    269  CA  THR A  44      49.941   7.692  59.271  1.00  7.54      A    C
ATOM    276  CA  PRO A  45      47.070   6.985  58.732  1.00  7.64      A    C
ATOM    283  CA  GLY A  46      46.363   7.283  62.482  1.00  5.22      A    C
ATOM    287  CA  ARG A  47      47.876   9.677  65.005  1.00  4.33      A    C
ATOM    298  CA  ASN A  48      47.297  10.971  68.487  1.00  2.87      A    C
ATOM    306  CA  ASN A  49      46.469  14.686  68.971  1.00  3.59      A    C
ATOM    314  CA  THR A  50      50.174  15.553  68.695  1.00  2.96      A    C
ATOM    321  CA  GLY A  51      50.582  13.739  65.384  1.00  2.16      A    C
ATOM    325  CA  TYR A  52      52.147  10.463  66.622  1.00  2.75      A    C
ATOM    337  CA  ASP A  53      50.289   7.308  67.663  1.00  3.03      A    C
ATOM    345  CA  TYR A  54      52.612   4.563  69.034  1.00  3.42      A    C
ATOM    357  CA  ALA A  55      50.295   1.835  67.698  1.00  3.80      A    C
ATOM    362  CA  GLN A  56      50.932   2.905  64.064  1.00  4.22      A    C
ATOM    371  CA  SER A  57      53.533   1.527  61.658  1.00  6.71      A    C
ATOM    377  CA  LYS A  58      54.051   4.328  59.145  1.00  6.64      A    C
ATOM    386  CA  ILE A  59      55.576   7.777  59.431  1.00  5.57      A    C
ATOM    394  CA  SER A  60      55.344  10.584  56.904  1.00  4.00      A    C
ATOM    400  CA  GLY A  61      57.749  13.214  58.346  1.00  3.12      A    C
ATOM    404  CA  PHE A  62      58.483  15.778  61.088  1.00  4.01      A    C
ATOM    415  CA  THR A  63      56.355  18.741  62.206  1.00  3.06      A    C
ATOM    422  CA  HIS A  64      57.952  21.581  64.185  1.00  2.46      A    C
ATOM    432  CA  THR A  65      55.187  23.059  66.366  1.00  2.07      A    C
ATOM    439  CA  ASN A  66      52.932  21.418  68.894  1.00  2.86      A    C
ATOM    447  CA  LEU A  67      51.019  21.341  72.178  1.00  3.42      A    C
ATOM    455  CA  ASP A  68      51.501  18.692  74.851  1.00  2.88      A    C
```

FIG. 34-1

| | | | | | | | | | | | | |
|---|---|---|---|---|---|---|---|---|---|---|---|---|
| ATOM | 463 | CA | GLY | A | 69 | 48.598 | 16.584 | 76.017 | 1.00 | 3.16 | A | C |
| ATOM | 467 | CA | VAL | A | 70 | 45.743 | 18.719 | 74.687 | 1.00 | 2.95 | A | C |
| ATOM | 474 | CA | GLY | A | 71 | 42.319 | 17.506 | 73.447 | 1.00 | 4.24 | A | C |
| ATOM | 478 | CA | GLY | A | 72 | 40.310 | 18.076 | 70.238 | 1.00 | 5.07 | A | C |
| ATOM | 482 | CA | SER | A | 73 | 42.497 | 16.981 | 67.319 | 1.00 | 5.30 | A | C |
| ATOM | 488 | CA | GLY | A | 74 | 45.570 | 18.647 | 68.860 | 1.00 | 4.44 | A | C |
| ATOM | 492 | CA | GLY | A | 75 | 47.211 | 22.012 | 68.196 | 1.00 | 4.03 | A | C |
| ATOM | 496 | CA | GLY | A | 76 | 50.230 | 23.149 | 66.192 | 1.00 | 3.47 | A | C |
| ATOM | 500 | CA | GLY | A | 77 | 51.645 | 20.417 | 63.910 | 1.00 | 2.77 | A | C |
| ATOM | 504 | CA | ASP | A | 78 | 53.003 | 23.083 | 61.502 | 1.00 | 3.19 | A | C |
| ATOM | 512 | CA | LEU | A | 79 | 55.816 | 22.729 | 58.975 | 1.00 | 3.46 | A | C |
| ATOM | 520 | CA | LEU | A | 80 | 55.960 | 19.099 | 57.867 | 1.00 | 3.19 | A | C |
| ATOM | 528 | CA | VAL | A | 81 | 59.330 | 17.935 | 56.541 | 1.00 | 2.38 | A | C |
| ATOM | 535 | CA | VAL | A | 82 | 59.151 | 14.633 | 54.633 | 1.00 | 2.66 | A | C |
| ATOM | 542 | CA | PRO | A | 83 | 62.241 | 12.791 | 53.307 | 1.00 | 3.10 | A | C |
| ATOM | 549 | CA | THR | A | 84 | 61.709 | 10.950 | 50.007 | 1.00 | 3.64 | A | C |
| ATOM | 556 | CA | SER | A | 85 | 63.546 | 9.484 | 47.006 | 1.00 | 3.93 | A | C |
| ATOM | 562 | CA | GLY | A | 86 | 60.474 | 10.171 | 44.894 | 1.00 | 4.58 | A | C |
| ATOM | 566 | CA | SER | A | 87 | 59.775 | 13.000 | 42.432 | 1.00 | 6.80 | A | C |
| ATOM | 572 | CA | TYR | A | 88 | 56.783 | 15.353 | 42.023 | 1.00 | 6.34 | A | C |
| ATOM | 584 | CA | THR | A | 89 | 55.158 | 17.278 | 39.133 | 1.00 | 6.35 | A | C |
| ATOM | 591 | CA | ALA | A | 90 | 52.313 | 18.731 | 41.257 | 1.00 | 5.37 | A | C |
| ATOM | 596 | CA | ARG | A | 91 | 51.505 | 19.377 | 44.932 | 1.00 | 5.13 | A | C |
| ATOM | 607 | CA | PRO | A | 92 | 52.147 | 16.058 | 46.755 | 1.00 | 5.88 | A | C |
| ATOM | 614 | CA | GLY | A | 93 | 49.327 | 13.739 | 47.757 | 1.00 | 6.88 | A | C |
| ATOM | 618 | CA | THR | A | 94 | 49.802 | 13.201 | 51.509 | 1.00 | 7.19 | A | C |
| ATOM | 625 | CA | GLY | A | 95 | 49.477 | 9.410 | 51.104 | 1.00 | 6.49 | A | C |
| ATOM | 629 | CA | THR | A | 96 | 52.770 | 9.459 | 49.173 | 1.00 | 4.50 | A | C |
| ATOM | 636 | CA | TYR | A | 97 | 54.650 | 10.619 | 52.300 | 1.00 | 3.46 | A | C |
| ATOM | 648 | CA | ALA | A | 98 | 54.035 | 7.311 | 54.100 | 1.00 | 3.39 | A | C |
| ATOM | 653 | CA | HIS | A | 99 | 57.136 | 5.240 | 55.089 | 1.00 | 4.47 | A | C |
| ATOM | 663 | CA | PRO | A | 100 | 57.203 | 1.916 | 56.975 | 1.00 | 5.44 | A | C |
| ATOM | 670 | CA | PHE | A | 101 | 58.803 | 2.128 | 60.401 | 1.00 | 5.59 | A | C |
| ATOM | 681 | CA | SER | A | 102 | 59.416 | -0.191 | 63.342 | 1.00 | 7.19 | A | C |
| ATOM | 687 | CA | HIS | A | 103 | 59.895 | 0.563 | 67.048 | 1.00 | 6.56 | A | C |
| ATOM | 697 | CA | ASP | A | 104 | 62.859 | -1.852 | 66.789 | 1.00 | 10.20 | A | C |
| ATOM | 705 | CA | ASP | A | 105 | 64.517 | 0.789 | 64.587 | 1.00 | 10.01 | A | C |
| ATOM | 713 | CA | GLU | A | 106 | 63.589 | 3.886 | 66.611 | 1.00 | 9.26 | A | C |
| ATOM | 722 | CA | ASP | A | 107 | 65.354 | 5.697 | 69.473 | 1.00 | 9.20 | A | C |
| ATOM | 730 | CA | ALA | A | 108 | 64.518 | 8.899 | 71.371 | 1.00 | 5.45 | A | C |
| ATOM | 735 | CA | GLY | A | 109 | 65.127 | 10.798 | 74.597 | 1.00 | 4.60 | A | C |
| ATOM | 739 | CA | PRO | A | 110 | 65.502 | 14.365 | 75.895 | 1.00 | 3.95 | A | C |
| ATOM | 746 | CA | GLY | A | 111 | 66.404 | 16.609 | 72.933 | 1.00 | 4.26 | A | C |
| ATOM | 750 | CA | PHE | A | 112 | 66.407 | 13.997 | 70.163 | 1.00 | 4.28 | A | C |
| ATOM | 761 | CA | TYR | A | 113 | 64.446 | 11.529 | 68.079 | 1.00 | 5.36 | A | C |
| ATOM | 773 | CA | SER | A | 114 | 65.729 | 8.957 | 65.540 | 1.00 | 5.75 | A | C |
| ATOM | 779 | CA | VAL | A | 115 | 64.016 | 6.387 | 63.260 | 1.00 | 4.53 | A | C |
| ATOM | 786 | CA | GLY | A | 116 | 64.781 | 4.199 | 60.259 | 1.00 | 5.51 | A | C |
| ATOM | 790 | CA | LEU | A | 117 | 62.194 | 4.893 | 57.576 | 1.00 | 5.77 | A | C |
| ATOM | 798 | CA | GLY | A | 118 | 61.496 | 2.539 | 54.687 | 1.00 | 6.00 | A | C |
| ATOM | 802 | CA | ASN | A | 119 | 62.614 | 4.169 | 51.445 | 1.00 | 5.77 | A | C |
| ATOM | 810 | CA | VAL | A | 120 | 59.965 | 5.458 | 49.014 | 1.00 | 5.26 | A | C |
| ATOM | 817 | CA | ALA | A | 121 | 60.384 | 6.350 | 45.306 | 1.00 | 6.56 | A | C |
| ATOM | 822 | CA | GLY | A | 122 | 58.455 | 6.925 | 42.071 | 1.00 | 6.12 | A | C |
| ATOM | 826 | CA | THR | A | 123 | 56.572 | 9.913 | 40.635 | 1.00 | 7.50 | A | C |
| ATOM | 833 | CA | ASP | A | 124 | 53.544 | 11.573 | 42.245 | 1.00 | 7.71 | A | C |
| ATOM | 841 | CA | GLY | A | 125 | 50.654 | 9.176 | 43.087 | 1.00 | 7.97 | A | C |
| ATOM | 845 | CA | ALA | A | 126 | 52.803 | 6.284 | 41.903 | 1.00 | 8.07 | A | C |
| ATOM | 850 | CA | ILE | A | 127 | 55.283 | 6.769 | 44.795 | 1.00 | 8.60 | A | C |
| ATOM | 858 | CA | THR | A | 128 | 55.591 | 3.528 | 46.766 | 1.00 | 9.40 | A | C |
| ATOM | 865 | CA | GLY | A | 129 | 58.010 | 1.444 | 48.876 | 1.00 | 9.09 | A | C |
| ATOM | 869 | CA | ALA | A | 130 | 61.528 | 1.221 | 47.442 | 1.00 | 8.74 | A | C |
| ATOM | 874 | CA | PRO | A | 131 | 64.650 | -0.773 | 48.532 | 1.00 | 9.45 | A | C |
| ATOM | 881 | CA | GLY | A | 132 | 66.719 | 0.579 | 51.405 | 1.00 | 9.13 | A | C |
| ATOM | 885 | CA | THR | A | 133 | 66.380 | 2.820 | 54.435 | 1.00 | 8.85 | A | C |
| ATOM | 892 | CA | ILE | A | 134 | 66.150 | 6.548 | 55.020 | 1.00 | 7.14 | A | C |

FIG. 34-2

| | | | | | | | | | | | | | |
|---|---|---|---|---|---|---|---|---|---|---|---|---|---|
| ATOM | 900 | CA | GLU | A | 135 | 67.868 | 6.967 | 58.400 | 1.00 | 7.03 | A | C |
| ATOM | 909 | CA | ALA | A | 136 | 66.326 | 10.008 | 60.046 | 1.00 | 5.25 | A | C |
| ATOM | 914 | CA | GLU | A | 137 | 67.736 | 11.833 | 63.043 | 1.00 | 3.46 | A | C |
| ATOM | 923 | CA | VAL | A | 138 | 66.270 | 15.029 | 64.552 | 1.00 | 2.00 | A | C |
| ATOM | 930 | CA | ALA | A | 139 | 67.283 | 17.116 | 67.586 | 1.00 | 2.00 | A | C |
| ATOM | 935 | CA | ALA | A | 140 | 66.021 | 20.401 | 69.089 | 1.00 | 3.29 | A | C |
| ATOM | 940 | CA | ALA | A | 141 | 67.192 | 23.587 | 70.725 | 1.00 | 5.41 | A | C |
| ATOM | 945 | CA | THR | A | 142 | 64.774 | 26.112 | 72.324 | 1.00 | 3.98 | A | C |
| ATOM | 952 | CA | ARG | A | 143 | 63.747 | 27.685 | 69.007 | 1.00 | 3.05 | A | C |
| ATOM | 963 | CA | SER | A | 144 | 65.230 | 25.253 | 66.475 | 1.00 | 3.15 | A | C |
| ATOM | 969 | CA | GLY | A | 145 | 64.814 | 21.822 | 64.969 | 1.00 | 3.61 | A | C |
| ATOM | 973 | CA | VAL | A | 146 | 67.745 | 20.138 | 63.259 | 1.00 | 3.66 | A | C |
| ATOM | 980 | CA | HIS | A | 147 | 67.601 | 17.212 | 60.859 | 1.00 | 4.27 | A | C |
| ATOM | 990 | CA | ARG | A | 148 | 70.193 | 14.697 | 59.628 | 1.00 | 5.28 | A | C |
| ATOM | 1001 | CA | TYR | A | 149 | 69.133 | 12.182 | 56.930 | 1.00 | 5.88 | A | C |
| ATOM | 1013 | CA | ALA | A | 150 | 70.978 | 9.286 | 55.295 | 1.00 | 6.54 | A | C |
| ATOM | 1018 | CA | PHE | A | 151 | 69.444 | 8.138 | 51.980 | 1.00 | 6.34 | A | C |
| ATOM | 1029 | CA | PRO | A | 152 | 70.329 | 4.881 | 50.196 | 1.00 | 8.11 | A | C |
| ATOM | 1036 | CA | ALA | A | 153 | 73.284 | 5.138 | 47.799 | 1.00 | 9.27 | A | C |
| ATOM | 1041 | CA | GLY | A | 154 | 72.114 | 6.052 | 44.300 | 1.00 | 9.43 | A | C |
| ATOM | 1045 | CA | SER | A | 155 | 69.016 | 7.860 | 45.553 | 1.00 | 8.94 | A | C |
| ATOM | 1051 | CA | THR | A | 156 | 68.111 | 11.379 | 44.480 | 1.00 | 5.81 | A | C |
| ATOM | 1058 | CA | PRO | A | 157 | 67.363 | 12.771 | 47.997 | 1.00 | 5.54 | A | C |
| ATOM | 1065 | CA | SER | A | 158 | 64.501 | 15.181 | 48.463 | 1.00 | 5.58 | A | C |
| ATOM | 1071 | CA | LEU | A | 159 | 62.757 | 16.902 | 51.348 | 1.00 | 4.75 | A | C |
| ATOM | 1079 | CA | VAL | A | 160 | 59.189 | 18.092 | 50.985 | 1.00 | 3.15 | A | C |
| ATOM | 1086 | CA | VAL | A | 161 | 58.408 | 21.099 | 53.170 | 1.00 | 2.91 | A | C |
| ATOM | 1093 | CA | ASP | A | 162 | 54.597 | 21.001 | 53.529 | 1.00 | 2.92 | A | C |
| ATOM | 1101 | CA | LEU | A | 163 | 53.165 | 24.242 | 54.913 | 1.00 | 4.33 | A | C |
| ATOM | 1109 | CA | GLU | A | 164 | 49.518 | 23.198 | 54.922 | 1.00 | 4.22 | A | C |
| ATOM | 1118 | CA | THR | A | 165 | 49.840 | 20.473 | 57.636 | 1.00 | 3.08 | A | C |
| ATOM | 1125 | CA | ASN | A | 166 | 48.201 | 21.399 | 60.948 | 1.00 | 3.13 | A | C |
| ATOM | 1133 | CA | ASN | A | 167 | 46.701 | 19.356 | 63.804 | 1.00 | 3.44 | A | C |
| ATOM | 1141 | CA | THR | A | 168 | 43.479 | 21.366 | 63.648 | 1.00 | 4.11 | A | C |
| ATOM | 1148 | CA | SER | A | 169 | 43.334 | 24.170 | 61.080 | 1.00 | 2.77 | A | C |
| ATOM | 1154 | CA | ARG | A | 170 | 45.644 | 25.892 | 58.648 | 1.00 | 3.20 | A | C |
| ATOM | 1165 | CA | ARG | A | 171 | 44.592 | 29.537 | 58.189 | 1.00 | 2.85 | A | C |
| ATOM | 1176 | CA | SER | A | 172 | 47.387 | 30.959 | 56.027 | 1.00 | 2.36 | A | C |
| ATOM | 1182 | CA | SER | A | 173 | 50.992 | 30.215 | 55.065 | 1.00 | 3.42 | A | C |
| ATOM | 1188 | CA | SER | A | 174 | 53.845 | 31.585 | 52.935 | 1.00 | 4.21 | A | C |
| ATOM | 1194 | CA | VAL | A | 175 | 57.213 | 30.528 | 51.618 | 1.00 | 4.87 | A | C |
| ATOM | 1201 | CA | GLN | A | 176 | 60.036 | 32.533 | 50.050 | 1.00 | 7.10 | A | C |
| ATOM | 1210 | CA | VAL | A | 177 | 63.000 | 30.700 | 48.499 | 1.00 | 8.23 | A | C |
| ATOM | 1217 | CA | GLU | A | 178 | 66.645 | 31.960 | 48.440 | 1.00 | 10.90 | A | C |
| ATOM | 1226 | CA | THR | A | 179 | 69.583 | 30.187 | 46.804 | 1.00 | 9.85 | A | C |
| ATOM | 1233 | CA | ARG | A | 180 | 72.927 | 31.368 | 48.203 | 1.00 | 10.39 | A | C |
| ATOM | 1244 | CA | ALA | A | 181 | 76.419 | 31.485 | 46.632 | 1.00 | 11.40 | A | C |
| ATOM | 1249 | CA | ASP | A | 182 | 77.367 | 28.014 | 47.948 | 1.00 | 11.35 | A | C |
| ATOM | 1257 | CA | GLY | A | 183 | 74.201 | 26.531 | 46.431 | 1.00 | 9.02 | A | C |
| ATOM | 1261 | CA | THR | A | 184 | 72.333 | 25.942 | 49.723 | 1.00 | 6.71 | A | C |
| ATOM | 1268 | CA | VAL | A | 185 | 68.670 | 26.993 | 50.031 | 1.00 | 5.35 | A | C |
| ATOM | 1275 | CA | GLU | A | 186 | 66.959 | 29.077 | 52.696 | 1.00 | 5.35 | A | C |
| ATOM | 1284 | CA | LEU | A | 187 | 63.146 | 29.005 | 52.987 | 1.00 | 3.46 | A | C |
| ATOM | 1292 | CA | SER | A | 188 | 61.169 | 31.481 | 55.086 | 1.00 | 2.87 | A | C |
| ATOM | 1298 | CA | GLY | A | 189 | 57.690 | 32.795 | 55.787 | 1.00 | 2.92 | A | C |
| ATOM | 1302 | CA | GLN | A | 190 | 54.805 | 32.417 | 58.222 | 1.00 | 2.71 | A | C |
| ATOM | 1311 | CA | VAL | A | 191 | 52.276 | 29.832 | 59.268 | 1.00 | 2.84 | A | C |
| ATOM | 1318 | CA | THR | A | 192 | 48.954 | 30.792 | 60.850 | 1.00 | 3.69 | A | C |
| ATOM | 1325 | CA | GLY | A | 193 | 46.998 | 28.051 | 62.583 | 1.00 | 3.21 | A | C |
| ATOM | 1329 | CA | TYR | A | 194 | 44.116 | 27.757 | 64.995 | 1.00 | 3.16 | A | C |
| ATOM | 1341 | CA | PHE | A | 195 | 43.413 | 25.739 | 68.120 | 1.00 | 3.26 | A | C |
| ATOM | 1352 | CA | TYR | A | 196 | 40.408 | 25.930 | 70.460 | 1.00 | 3.84 | A | C |
| ATOM | 1364 | CA | ASN | A | 197 | 39.874 | 29.693 | 71.045 | 1.00 | 4.26 | A | C |
| ATOM | 1372 | CA | ALA | A | 198 | 42.510 | 31.491 | 69.033 | 1.00 | 3.45 | A | C |
| ATOM | 1377 | CA | ALA | A | 199 | 44.567 | 31.753 | 65.914 | 1.00 | 3.47 | A | C |
| ATOM | 1382 | CA | TYR | A | 200 | 48.369 | 32.096 | 66.243 | 1.00 | 2.36 | A | C |

FIG. 34-3

| | | | | | | | | | | | | |
|---|---|---|---|---|---|---|---|---|---|---|---|---|
| ATOM | 1394 | CA | THR | A | 201 | 51.191 | 33.045 | 63.858 | 1.00 | 2.69 | A | C |
| ATOM | 1401 | CA | LEU | A | 202 | 54.816 | 31.843 | 63.819 | 1.00 | 2.11 | A | C |
| ATOM | 1409 | CA | TYR | A | 203 | 57.621 | 32.892 | 61.467 | 1.00 | 2.45 | A | C |
| ATOM | 1421 | CA | TYR | A | 204 | 60.210 | 30.396 | 60.264 | 1.00 | 2.82 | A | C |
| ATOM | 1433 | CA | THR | A | 205 | 63.573 | 30.086 | 58.500 | 1.00 | 2.58 | A | C |
| ATOM | 1440 | CA | ALA | A | 206 | 64.904 | 26.723 | 57.213 | 1.00 | 4.47 | A | C |
| ATOM | 1445 | CA | ARG | A | 207 | 68.253 | 26.305 | 55.508 | 1.00 | 5.09 | A | C |
| ATOM | 1456 | CA | THR | A | 208 | 69.773 | 23.209 | 53.912 | 1.00 | 4.88 | A | C |
| ATOM | 1463 | CA | LEU | A | 209 | 73.404 | 22.419 | 54.654 | 1.00 | 5.26 | A | C |
| ATOM | 1471 | CA | GLN | A | 210 | 73.983 | 20.900 | 51.175 | 1.00 | 6.01 | A | C |
| ATOM | 1480 | CA | PRO | A | 211 | 73.274 | 22.391 | 47.732 | 1.00 | 6.91 | A | C |
| ATOM | 1487 | CA | ALA | A | 212 | 69.689 | 21.962 | 46.560 | 1.00 | 7.18 | A | C |
| ATOM | 1492 | CA | THR | A | 213 | 67.307 | 23.100 | 43.847 | 1.00 | 5.83 | A | C |
| ATOM | 1499 | CA | VAL | A | 214 | 63.724 | 23.957 | 44.710 | 1.00 | 5.43 | A | C |
| ATOM | 1506 | CA | GLN | A | 215 | 60.145 | 24.166 | 43.470 | 1.00 | 5.10 | A | C |
| ATOM | 1515 | CA | THR | A | 216 | 57.130 | 25.576 | 45.286 | 1.00 | 4.16 | A | C |
| ATOM | 1522 | CA | TRP | A | 217 | 53.372 | 25.146 | 45.243 | 1.00 | 3.72 | A | C |
| ATOM | 1536 | CA | GLY | A | 218 | 50.356 | 27.288 | 46.105 | 1.00 | 3.16 | A | C |
| ATOM | 1540 | CA | ASP | A | 219 | 46.606 | 26.736 | 46.322 | 1.00 | 3.69 | A | C |
| ATOM | 1548 | CA | ASP | A | 220 | 46.180 | 25.735 | 42.659 | 1.00 | 3.99 | A | C |
| ATOM | 1556 | CA | ASP | A | 221 | 48.330 | 22.647 | 43.374 | 1.00 | 5.99 | A | C |
| ATOM | 1564 | CA | ARG | A | 222 | 50.800 | 23.609 | 40.598 | 1.00 | 6.95 | A | C |
| ATOM | 1575 | CA | LEU | A | 223 | 54.426 | 22.727 | 41.314 | 1.00 | 6.51 | A | C |
| ATOM | 1583 | CA | VAL | A | 224 | 56.418 | 25.552 | 39.779 | 1.00 | 7.29 | A | C |
| ATOM | 1590 | CA | ASP | A | 225 | 59.828 | 27.203 | 39.638 | 1.00 | 8.47 | A | C |
| ATOM | 1598 | CA | ALA | A | 226 | 58.537 | 30.421 | 41.281 | 1.00 | 8.13 | A | C |
| ATOM | 1603 | CA | THR | A | 227 | 60.445 | 31.382 | 44.417 | 1.00 | 7.82 | A | C |
| ATOM | 1610 | CA | ALA | A | 228 | 57.480 | 32.859 | 46.386 | 1.00 | 7.30 | A | C |
| ATOM | 1615 | CA | GLN | A | 229 | 54.054 | 31.642 | 47.513 | 1.00 | 5.21 | A | C |
| ATOM | 1624 | CA | ASP | A | 230 | 51.457 | 33.169 | 49.802 | 1.00 | 5.36 | A | C |
| ATOM | 1632 | CA | GLY | A | 231 | 48.063 | 31.590 | 50.521 | 1.00 | 3.52 | A | C |
| ATOM | 1636 | CA | VAL | A | 232 | 46.718 | 28.704 | 52.595 | 1.00 | 2.62 | A | C |
| ATOM | 1643 | CA | ASP | A | 233 | 48.105 | 25.470 | 51.111 | 1.00 | 3.49 | A | C |
| ATOM | 1651 | CA | THR | A | 234 | 51.701 | 26.281 | 50.149 | 1.00 | 3.46 | A | C |
| ATOM | 1658 | CA | GLY | A | 235 | 54.937 | 24.312 | 50.148 | 1.00 | 3.13 | A | C |
| ATOM | 1662 | CA | ALA | A | 236 | 58.416 | 23.735 | 48.763 | 1.00 | 3.15 | A | C |
| ATOM | 1667 | CA | ILE | A | 237 | 60.286 | 20.673 | 47.495 | 1.00 | 3.80 | A | C |
| ATOM | 1675 | CA | LEU | A | 238 | 64.059 | 20.549 | 47.934 | 1.00 | 4.57 | A | C |
| ATOM | 1683 | CA | THR | A | 239 | 66.059 | 18.244 | 45.649 | 1.00 | 6.16 | A | C |
| ATOM | 1690 | CA | PHE | A | 240 | 69.681 | 17.295 | 46.371 | 1.00 | 8.00 | A | C |
| ATOM | 1701 | CA | ASP | A | 241 | 72.537 | 15.737 | 44.401 | 1.00 | 10.79 | A | C |
| ATOM | 1709 | CA | PRO | A | 242 | 72.834 | 11.907 | 44.637 | 1.00 | 10.26 | A | C |
| ATOM | 1716 | CA | ALA | A | 243 | 76.443 | 12.489 | 45.768 | 1.00 | 9.54 | A | C |
| ATOM | 1721 | CA | ASP | A | 244 | 75.082 | 13.939 | 49.047 | 1.00 | 9.68 | A | C |
| ATOM | 1729 | CA | ALA | A | 245 | 72.792 | 10.984 | 49.778 | 1.00 | 9.01 | A | C |
| ATOM | 1734 | CA | GLY | A | 246 | 75.008 | 9.953 | 52.749 | 1.00 | 8.32 | A | C |
| ATOM | 1738 | CA | GLU | A | 247 | 74.244 | 13.241 | 54.603 | 1.00 | 8.02 | A | C |
| ATOM | 1747 | CA | ILE | A | 248 | 71.325 | 15.626 | 54.100 | 1.00 | 6.42 | A | C |
| ATOM | 1755 | CA | GLY | A | 249 | 71.023 | 18.320 | 56.806 | 1.00 | 5.33 | A | C |
| ATOM | 1759 | CA | LEU | A | 250 | 68.338 | 20.892 | 57.577 | 1.00 | 3.68 | A | C |
| ATOM | 1767 | CA | GLN | A | 251 | 67.982 | 23.542 | 60.272 | 1.00 | 3.91 | A | C |
| ATOM | 1776 | CA | VAL | A | 252 | 64.613 | 25.109 | 61.086 | 1.00 | 4.45 | A | C |
| ATOM | 1783 | CA | THR | A | 253 | 64.148 | 28.007 | 63.522 | 1.00 | 4.13 | A | C |
| ATOM | 1790 | CA | LEU | A | 254 | 60.850 | 29.555 | 64.744 | 1.00 | 3.15 | A | C |
| ATOM | 1798 | CA | SER | A | 255 | 60.066 | 33.075 | 65.957 | 1.00 | 3.13 | A | C |
| ATOM | 1804 | CA | PRO | A | 256 | 56.835 | 34.755 | 67.030 | 1.00 | 2.32 | A | C |
| ATOM | 1811 | CA | VAL | A | 257 | 58.462 | 38.034 | 65.945 | 1.00 | 2.47 | A | C |
| ATOM | 1818 | CA | SER | A | 258 | 59.667 | 37.831 | 62.318 | 1.00 | 3.37 | A | C |
| ATOM | 1824 | CA | VAL | A | 259 | 61.516 | 35.892 | 59.699 | 1.00 | 3.32 | A | C |
| ATOM | 1831 | CA | GLU | A | 260 | 64.595 | 38.024 | 60.217 | 1.00 | 4.54 | A | C |
| ATOM | 1840 | CA | GLN | A | 261 | 64.385 | 37.533 | 63.976 | 1.00 | 2.88 | A | C |
| ATOM | 1849 | CA | ALA | A | 262 | 64.235 | 33.748 | 63.289 | 1.00 | 3.15 | A | C |
| ATOM | 1854 | CA | ARG | A | 263 | 67.445 | 34.085 | 61.196 | 1.00 | 4.21 | A | C |
| ATOM | 1865 | CA | ILE | A | 264 | 69.210 | 35.928 | 64.012 | 1.00 | 4.33 | A | C |
| ATOM | 1873 | CA | ASP | A | 265 | 67.932 | 33.358 | 66.544 | 1.00 | 4.14 | A | C |
| ATOM | 1881 | CA | GLN | A | 266 | 69.289 | 30.623 | 64.311 | 1.00 | 6.08 | A | C |

FIG. 34-4

| | | | | | | | | | | | | |
|---|---|---|---|---|---|---|---|---|---|---|---|---|
| ATOM | 1890 | CA | GLN | A | 267 | 72.772 | 32.164 | 64.108 | 1.00 | 9.62 | A | C |
| ATOM | 1899 | CA | VAL | A | 268 | 72.748 | 32.711 | 67.907 | 1.00 | 8.96 | A | C |
| ATOM | 1906 | CA | GLU | A | 269 | 71.365 | 29.282 | 68.815 | 1.00 | 8.04 | A | C |
| ATOM | 1915 | CA | LEU | A | 270 | 73.089 | 27.042 | 66.271 | 1.00 | 8.55 | A | C |
| ATOM | 1923 | CA | GLY | A | 271 | 76.001 | 29.052 | 64.802 | 1.00 | 10.23 | A | C |
| ATOM | 1927 | CA | ASP | A | 272 | 78.321 | 26.600 | 63.009 | 1.00 | 10.69 | A | C |
| ATOM | 1935 | CA | LEU | A | 273 | 77.764 | 23.840 | 65.566 | 1.00 | 8.02 | A | C |
| ATOM | 1943 | CA | SER | A | 274 | 77.383 | 20.316 | 64.224 | 1.00 | 5.99 | A | C |
| ATOM | 1949 | CA | PHE | A | 275 | 74.219 | 18.210 | 64.582 | 1.00 | 4.80 | A | C |
| ATOM | 1960 | CA | ASP | A | 276 | 75.912 | 16.069 | 67.289 | 1.00 | 5.78 | A | C |
| ATOM | 1968 | CA | ALA | A | 277 | 76.925 | 19.139 | 69.337 | 1.00 | 5.08 | A | C |
| ATOM | 1973 | CA | ILE | A | 278 | 73.442 | 20.669 | 69.150 | 1.00 | 5.84 | A | C |
| ATOM | 1981 | CA | ARG | A | 279 | 71.924 | 17.315 | 70.206 | 1.00 | 6.83 | A | C |
| ATOM | 1992 | CA | ASP | A | 280 | 74.549 | 16.902 | 72.944 | 1.00 | 7.77 | A | C |
| ATOM | 2000 | CA | ARG | A | 281 | 74.023 | 20.429 | 74.293 | 1.00 | 7.74 | A | C |
| ATOM | 2011 | CA | THR | A | 282 | 70.270 | 19.953 | 74.599 | 1.00 | 6.38 | A | C |
| ATOM | 2018 | CA | ARG | A | 283 | 70.839 | 16.638 | 76.431 | 1.00 | 5.81 | A | C |
| ATOM | 2029 | CA | ALA | A | 284 | 73.047 | 18.504 | 78.940 | 1.00 | 5.99 | A | C |
| ATOM | 2034 | CA | GLU | A | 285 | 70.461 | 21.247 | 79.310 | 1.00 | 6.57 | A | C |
| ATOM | 2043 | CA | TRP | A | 286 | 67.904 | 18.490 | 80.139 | 1.00 | 5.67 | A | C |
| ATOM | 2057 | CA | ASN | A | 287 | 70.291 | 16.909 | 82.648 | 1.00 | 8.00 | A | C |
| ATOM | 2065 | CA | ALA | A | 288 | 70.657 | 20.275 | 84.422 | 1.00 | 8.86 | A | C |
| ATOM | 2070 | CA | THR | A | 289 | 66.862 | 20.740 | 84.464 | 1.00 | 7.09 | A | C |
| ATOM | 2077 | CA | LEU | A | 290 | 66.138 | 17.180 | 85.630 | 1.00 | 6.19 | A | C |
| ATOM | 2085 | CA | GLY | A | 291 | 69.085 | 17.378 | 88.069 | 1.00 | 6.65 | A | C |
| ATOM | 2089 | CA | ARG | A | 292 | 67.121 | 19.931 | 90.104 | 1.00 | 6.77 | A | C |
| ATOM | 2100 | CA | VAL | A | 293 | 65.530 | 16.844 | 91.707 | 1.00 | 8.09 | A | C |
| ATOM | 2107 | CA | ALA | A | 294 | 67.845 | 14.070 | 92.912 | 1.00 | 10.40 | A | C |
| ATOM | 2112 | CA | ILE | A | 295 | 66.318 | 10.811 | 94.046 | 1.00 | 13.23 | A | C |
| ATOM | 2120 | CA | ASP | A | 296 | 67.534 | 7.879 | 96.121 | 1.00 | 14.69 | A | C |
| ATOM | 2128 | CA | ALA | A | 297 | 65.001 | 5.043 | 95.685 | 1.00 | 12.88 | A | C |
| ATOM | 2133 | CA | SER | A | 298 | 65.612 | 1.701 | 97.466 | 1.00 | 11.58 | A | C |
| ATOM | 2139 | CA | THR | A | 299 | 64.657 | -1.726 | 96.152 | 1.00 | 9.13 | A | C |
| ATOM | 2146 | CA | ALA | A | 300 | 61.955 | -1.728 | 98.846 | 1.00 | 7.00 | A | C |
| ATOM | 2151 | CA | THR | A | 301 | 59.955 | 1.150 | 97.314 | 1.00 | 6.08 | A | C |
| ATOM | 2158 | CA | ASP | A | 302 | 61.022 | 0.632 | 93.655 | 1.00 | 6.93 | A | C |
| ATOM | 2166 | CA | PRO | A | 303 | 62.048 | -3.016 | 93.116 | 1.00 | 7.98 | A | C |
| ATOM | 2173 | CA | THR | A | 304 | 62.107 | -2.745 | 89.277 | 1.00 | 8.90 | A | C |
| ATOM | 2180 | CA | GLY | A | 305 | 63.438 | 0.816 | 88.893 | 1.00 | 8.26 | A | C |
| ATOM | 2184 | CA | GLU | A | 306 | 60.285 | 1.808 | 86.935 | 1.00 | 8.98 | A | C |
| ATOM | 2193 | CA | LEU | A | 307 | 59.007 | 4.206 | 89.571 | 1.00 | 6.57 | A | C |
| ATOM | 2201 | CA | GLN | A | 308 | 62.236 | 6.260 | 89.308 | 1.00 | 7.75 | A | C |
| ATOM | 2210 | CA | ARG | A | 309 | 61.928 | 6.228 | 85.486 | 1.00 | 7.83 | A | C |
| ATOM | 2221 | CA | LEU | A | 310 | 58.276 | 7.252 | 85.828 | 1.00 | 6.95 | A | C |
| ATOM | 2229 | CA | PHE | A | 311 | 59.288 | 10.140 | 88.071 | 1.00 | 5.21 | A | C |
| ATOM | 2240 | CA | TYR | A | 312 | 61.933 | 11.475 | 85.641 | 1.00 | 4.28 | A | C |
| ATOM | 2252 | CA | THR | A | 313 | 59.676 | 10.962 | 82.611 | 1.00 | 3.87 | A | C |
| ATOM | 2259 | CA | HIS | A | 314 | 56.982 | 13.080 | 84.288 | 1.00 | 4.29 | A | C |
| ATOM | 2269 | CA | LEU | A | 315 | 59.509 | 15.636 | 85.519 | 1.00 | 3.00 | A | C |
| ATOM | 2277 | CA | TYR | A | 316 | 60.512 | 15.912 | 81.827 | 1.00 | 2.15 | A | C |
| ATOM | 2289 | CA | ARG | A | 317 | 56.827 | 16.467 | 80.909 | 1.00 | 3.71 | A | C |
| ATOM | 2300 | CA | MET | A | 318 | 56.497 | 19.172 | 83.611 | 1.00 | 6.35 | A | C |
| ATOM | 2308 | CA | PHE | A | 319 | 58.967 | 21.419 | 81.712 | 1.00 | 7.83 | A | C |
| ATOM | 2319 | CA | ALA | A | 320 | 57.045 | 21.807 | 78.404 | 1.00 | 7.53 | A | C |
| ATOM | 2324 | CA | MET | A | 321 | 54.323 | 24.487 | 78.650 | 1.00 | 6.18 | A | C |
| ATOM | 2332 | CA | PRO | A | 322 | 54.063 | 27.434 | 78.638 | 1.00 | 5.02 | A | C |
| ATOM | 2339 | CA | MET | A | 323 | 56.762 | 27.568 | 75.935 | 1.00 | 4.44 | A | C |
| ATOM | 2347 | CA | ASN | A | 324 | 59.593 | 30.069 | 75.619 | 1.00 | 3.49 | A | C |
| ATOM | 2355 | CA | ALA | A | 325 | 57.989 | 32.716 | 73.341 | 1.00 | 2.49 | A | C |
| ATOM | 2360 | CA | THR | A | 326 | 61.012 | 35.098 | 73.515 | 1.00 | 2.79 | A | C |
| ATOM | 2367 | CA | SER | A | 327 | 63.597 | 35.861 | 70.819 | 1.00 | 3.68 | A | C |
| ATOM | 2373 | CA | THR | A | 328 | 67.381 | 35.744 | 71.383 | 1.00 | 4.17 | A | C |
| ATOM | 2380 | CA | SER | A | 329 | 67.191 | 39.550 | 71.284 | 1.00 | 4.95 | A | C |
| ATOM | 2386 | CA | GLY | A | 330 | 64.860 | 39.602 | 74.327 | 1.00 | 4.52 | A | C |
| ATOM | 2390 | CA | THR | A | 331 | 61.681 | 40.533 | 72.420 | 1.00 | 2.64 | A | C |
| ATOM | 2397 | CA | TYR | A | 332 | 58.212 | 38.956 | 72.097 | 1.00 | 2.99 | A | C |

FIG. 34-5

| | | | | | | | | | | | | |
|---|---|---|---|---|---|---|---|---|---|---|---|---|
| ATOM | 2409 | CA | ARG | A | 333 | 55.039 | 39.623 | 70.103 | 1.00 | 4.36 | A | C |
| ATOM | 2420 | CA | GLY | A | 334 | 52.050 | 40.974 | 71.967 | 1.00 | 4.85 | A | C |
| ATOM | 2424 | CA | VAL | A | 335 | 48.352 | 40.362 | 71.328 | 1.00 | 5.79 | A | C |
| ATOM | 2431 | CA | ASP | A | 336 | 48.362 | 43.923 | 69.904 | 1.00 | 8.91 | A | C |
| ATOM | 2439 | CA | GLY | A | 337 | 50.391 | 42.488 | 67.010 | 1.00 | 8.05 | A | C |
| ATOM | 2443 | CA | ALA | A | 338 | 53.464 | 44.524 | 67.878 | 1.00 | 7.17 | A | C |
| ATOM | 2448 | CA | VAL | A | 339 | 56.967 | 43.729 | 69.093 | 1.00 | 6.49 | A | C |
| ATOM | 2455 | CA | HIS | A | 340 | 57.792 | 44.405 | 72.780 | 1.00 | 8.62 | A | C |
| ATOM | 2465 | CA | ALA | A | 341 | 60.735 | 44.008 | 75.137 | 1.00 | 9.13 | A | C |
| ATOM | 2470 | CA | ALA | A | 342 | 60.679 | 41.217 | 77.711 | 1.00 | 11.07 | A | C |
| ATOM | 2475 | CA | GLN | A | 343 | 62.952 | 43.339 | 79.907 | 1.00 | 14.61 | A | C |
| ATOM | 2484 | CA | GLY | A | 344 | 64.997 | 41.352 | 82.439 | 1.00 | 14.36 | A | C |
| ATOM | 2488 | CA | PHE | A | 345 | 62.907 | 38.172 | 82.163 | 1.00 | 11.18 | A | C |
| ATOM | 2499 | CA | THR | A | 346 | 61.913 | 35.493 | 79.671 | 1.00 | 8.35 | A | C |
| ATOM | 2506 | CA | TYR | A | 347 | 58.429 | 35.786 | 78.204 | 1.00 | 5.52 | A | C |
| ATOM | 2518 | CA | TYR | A | 348 | 56.503 | 32.511 | 78.127 | 1.00 | 4.55 | A | C |
| ATOM | 2530 | CA | ASP | A | 349 | 53.244 | 31.880 | 76.254 | 1.00 | 3.32 | A | C |
| ATOM | 2538 | CA | SER | A | 350 | 50.780 | 29.020 | 75.499 | 1.00 | 3.95 | A | C |
| ATOM | 2544 | CA | TRP | A | 351 | 48.175 | 28.588 | 78.184 | 1.00 | 3.88 | A | C |
| ATOM | 2558 | CA | ALA | A | 352 | 45.515 | 26.000 | 79.064 | 1.00 | 3.39 | A | C |
| ATOM | 2563 | CA | THR | A | 353 | 44.865 | 27.385 | 82.495 | 1.00 | 3.82 | A | C |
| ATOM | 2570 | CA | TRP | A | 354 | 41.278 | 26.050 | 82.947 | 1.00 | 4.26 | A | C |
| ATOM | 2584 | CA | ASP | A | 355 | 42.871 | 22.556 | 82.994 | 1.00 | 4.99 | A | C |
| ATOM | 2592 | CA | ASP | A | 356 | 46.325 | 23.205 | 84.330 | 1.00 | 5.97 | A | C |
| ATOM | 2600 | CA | PHE | A | 357 | 46.209 | 25.899 | 87.012 | 1.00 | 5.02 | A | C |
| ATOM | 2611 | CA | ARG | A | 358 | 47.423 | 23.675 | 89.886 | 1.00 | 4.11 | A | C |
| ATOM | 2622 | CA | LYS | A | 359 | 50.623 | 22.752 | 87.999 | 1.00 | 2.82 | A | C |
| ATOM | 2631 | CA | PHE | A | 360 | 52.171 | 26.201 | 88.467 | 1.00 | 2.32 | A | C |
| ATOM | 2642 | CA | SER | A | 361 | 52.008 | 25.888 | 92.261 | 1.00 | 2.68 | A | C |
| ATOM | 2648 | CA | VAL | A | 362 | 54.293 | 22.814 | 91.937 | 1.00 | 3.61 | A | C |
| ATOM | 2655 | CA | ILE | A | 363 | 56.639 | 24.444 | 89.399 | 1.00 | 3.43 | A | C |
| ATOM | 2663 | CA | ALA | A | 364 | 57.066 | 27.142 | 92.096 | 1.00 | 3.80 | A | C |
| ATOM | 2668 | CA | TYR | A | 365 | 58.855 | 24.692 | 94.414 | 1.00 | 4.70 | A | C |
| ATOM | 2680 | CA | ILE | A | 366 | 60.869 | 22.863 | 91.729 | 1.00 | 6.01 | A | C |
| ATOM | 2688 | CA | ASP | A | 367 | 62.106 | 25.826 | 89.627 | 1.00 | 5.57 | A | C |
| ATOM | 2696 | CA | PRO | A | 368 | 61.194 | 29.124 | 91.362 | 1.00 | 3.96 | A | C |
| ATOM | 2703 | CA | ALA | A | 369 | 62.922 | 31.367 | 88.734 | 1.00 | 3.74 | A | C |
| ATOM | 2708 | CA | LEU | A | 370 | 61.088 | 29.740 | 85.833 | 1.00 | 3.88 | A | C |
| ATOM | 2716 | CA | TYR | A | 371 | 57.804 | 30.009 | 87.729 | 1.00 | 4.80 | A | C |
| ATOM | 2728 | CA | ARG | A | 372 | 58.430 | 33.689 | 88.384 | 1.00 | 5.45 | A | C |
| ATOM | 2739 | CA | ASP | A | 373 | 59.035 | 34.310 | 84.651 | 1.00 | 6.19 | A | C |
| ATOM | 2747 | CA | MET | A | 374 | 55.843 | 32.441 | 83.776 | 1.00 | 3.88 | A | C |
| ATOM | 2755 | CA | VAL | A | 375 | 53.730 | 34.523 | 86.171 | 1.00 | 2.79 | A | C |
| ATOM | 2762 | CA | GLN | A | 376 | 55.358 | 37.744 | 84.962 | 1.00 | 3.18 | A | C |
| ATOM | 2771 | CA | SER | A | 377 | 54.574 | 36.606 | 81.413 | 1.00 | 3.14 | A | C |
| ATOM | 2777 | CA | LEU | A | 378 | 50.953 | 35.908 | 82.336 | 1.00 | 3.14 | A | C |
| ATOM | 2785 | CA | VAL | A | 379 | 50.799 | 39.454 | 83.766 | 1.00 | 3.57 | A | C |
| ATOM | 2792 | CA | TYR | A | 380 | 52.193 | 40.950 | 80.508 | 1.00 | 4.06 | A | C |
| ATOM | 2804 | CA | LEU | A | 381 | 49.694 | 38.961 | 78.456 | 1.00 | 4.18 | A | C |
| ATOM | 2812 | CA | PHE | A | 382 | 46.697 | 40.475 | 80.286 | 1.00 | 4.57 | A | C |
| ATOM | 2823 | CA | ALA | A | 383 | 48.397 | 43.881 | 80.475 | 1.00 | 6.03 | A | C |
| ATOM | 2828 | CA | ASP | A | 384 | 48.684 | 43.708 | 76.664 | 1.00 | 7.44 | A | C |
| ATOM | 2836 | CA | ALA | A | 385 | 44.974 | 42.882 | 76.223 | 1.00 | 9.01 | A | C |
| ATOM | 2841 | CA | GLU | A | 386 | 44.199 | 45.935 | 78.362 | 1.00 | 10.91 | A | C |
| ATOM | 2850 | CA | ALA | A | 387 | 46.670 | 48.106 | 76.365 | 1.00 | 12.41 | A | C |
| ATOM | 2855 | CA | THR | A | 388 | 44.776 | 47.471 | 73.087 | 1.00 | 13.68 | A | C |
| ATOM | 2862 | CA | GLY | A | 389 | 41.944 | 49.514 | 74.624 | 1.00 | 14.39 | A | C |
| ATOM | 2866 | CA | THR | A | 390 | 39.452 | 47.191 | 72.889 | 1.00 | 15.63 | A | C |
| ATOM | 2873 | CA | GLY | A | 391 | 38.019 | 45.522 | 76.019 | 1.00 | 14.99 | A | C |
| ATOM | 2877 | CA | GLY | A | 392 | 37.896 | 42.282 | 73.993 | 1.00 | 13.79 | A | C |
| ATOM | 2881 | CA | GLY | A | 393 | 38.759 | 38.874 | 75.470 | 1.00 | 11.07 | A | C |
| ATOM | 2885 | CA | LEU | A | 394 | 42.017 | 37.084 | 74.740 | 1.00 | 7.81 | A | C |
| ATOM | 2893 | CA | GLY | A | 395 | 40.142 | 34.863 | 72.238 | 1.00 | 7.24 | A | C |
| ATOM | 2897 | CA | GLY | A | 396 | 39.767 | 37.812 | 69.847 | 1.00 | 7.80 | A | C |
| ATOM | 2901 | CA | PHE | A | 397 | 43.479 | 38.330 | 69.213 | 1.00 | 7.11 | A | C |
| ATOM | 2912 | CA | VAL | A | 398 | 46.038 | 36.458 | 67.145 | 1.00 | 5.79 | A | C |

FIG. 34-6

| | | | | | | | | | | | | |
|---|---|---|---|---|---|---|---|---|---|---|---|---|
| ATOM | 2919 | CA | HIS | A | 399 | 48.445 | 34.799 | 69.624 | 1.00 | 3.71 | A | C |
| ATOM | 2929 | CA | SER | A | 400 | 52.295 | 34.534 | 69.502 | 1.00 | 3.42 | A | C |
| ATOM | 2935 | CA | VAL | A | 401 | 52.383 | 30.703 | 69.819 | 1.00 | 2.51 | A | C |
| ATOM | 2942 | CA | PRO | A | 402 | 49.744 | 27.945 | 69.645 | 1.00 | 3.03 | A | C |
| ATOM | 2949 | CA | THR | A | 403 | 47.621 | 28.327 | 72.753 | 1.00 | 2.63 | A | C |
| ATOM | 2956 | CA | VAL | A | 404 | 44.423 | 27.083 | 74.389 | 1.00 | 2.59 | A | C |
| ATOM | 2963 | CA | ARG | A | 405 | 42.502 | 28.941 | 77.121 | 1.00 | 2.87 | A | C |
| ATOM | 2974 | CA | TRP | A | 406 | 43.027 | 31.341 | 80.033 | 1.00 | 3.31 | A | C |
| ATOM | 2988 | CA | GLU | A | 407 | 40.430 | 30.754 | 82.763 | 1.00 | 4.40 | A | C |
| ATOM | 2997 | CA | ARG | A | 408 | 41.810 | 30.579 | 86.344 | 1.00 | 3.53 | A | C |
| ATOM | 3008 | CA | SER | A | 409 | 44.708 | 32.938 | 85.445 | 1.00 | 3.56 | A | C |
| ATOM | 3014 | CA | SER | A | 410 | 43.670 | 35.101 | 88.462 | 1.00 | 4.17 | A | C |
| ATOM | 3020 | CA | VAL | A | 411 | 44.366 | 32.099 | 90.707 | 1.00 | 3.23 | A | C |
| ATOM | 3027 | CA | VAL | A | 412 | 47.816 | 31.532 | 89.197 | 1.00 | 2.11 | A | C |
| ATOM | 3034 | CA | VAL | A | 413 | 48.819 | 35.209 | 89.648 | 1.00 | 2.29 | A | C |
| ATOM | 3041 | CA | ALA | A | 414 | 47.478 | 35.051 | 93.214 | 1.00 | 2.19 | A | C |
| ATOM | 3046 | CA | ASP | A | 415 | 49.593 | 31.906 | 93.728 | 1.00 | 3.52 | A | C |
| ATOM | 3054 | CA | ALA | A | 416 | 52.816 | 33.913 | 93.216 | 1.00 | 3.54 | A | C |
| ATOM | 3059 | CA | ILE | A | 417 | 51.560 | 36.792 | 95.351 | 1.00 | 4.96 | A | C |
| ATOM | 3067 | CA | ALA | A | 418 | 50.526 | 34.493 | 98.238 | 1.00 | 7.10 | A | C |
| ATOM | 3072 | CA | LYS | A | 419 | 53.976 | 32.864 | 97.904 | 1.00 | 7.37 | A | C |
| ATOM | 3081 | CA | GLY | A | 420 | 55.694 | 36.259 | 98.483 | 1.00 | 8.91 | A | C |
| ATOM | 3085 | CA | PHE | A | 421 | 56.789 | 37.036 | 94.914 | 1.00 | 9.86 | A | C |
| ATOM | 3096 | CA | ASP | A | 422 | 56.741 | 40.741 | 94.170 | 1.00 | 13.61 | A | C |
| ATOM | 3104 | CA | GLY | A | 423 | 57.809 | 43.423 | 91.676 | 1.00 | 13.34 | A | C |
| ATOM | 3108 | CA | PHE | A | 424 | 55.491 | 42.086 | 88.966 | 1.00 | 11.76 | A | C |
| ATOM | 3119 | CA | ASP | A | 425 | 55.749 | 44.833 | 86.387 | 1.00 | 12.47 | A | C |
| ATOM | 3127 | CA | ARG | A | 426 | 52.408 | 45.949 | 84.848 | 1.00 | 10.18 | A | C |
| ATOM | 3138 | CA | LEU | A | 427 | 50.173 | 44.147 | 87.370 | 1.00 | 9.19 | A | C |
| ATOM | 3146 | CA | ASP | A | 428 | 48.058 | 47.323 | 87.662 | 1.00 | 10.66 | A | C |
| ATOM | 3154 | CA | GLU | A | 429 | 47.378 | 47.038 | 83.880 | 1.00 | 10.07 | A | C |
| ATOM | 3163 | CA | ALA | A | 430 | 46.738 | 43.286 | 83.995 | 1.00 | 8.16 | A | C |
| ATOM | 3168 | CA | TYR | A | 431 | 44.091 | 43.690 | 86.747 | 1.00 | 8.25 | A | C |
| ATOM | 3180 | CA | PRO | A | 432 | 41.138 | 45.159 | 84.775 | 1.00 | 8.05 | A | C |
| ATOM | 3187 | CA | ALA | A | 433 | 41.670 | 42.554 | 82.030 | 1.00 | 7.78 | A | C |
| ATOM | 3192 | CA | LEU | A | 434 | 41.696 | 39.872 | 84.724 | 1.00 | 7.30 | A | C |
| ATOM | 3200 | CA | GLN | A | 435 | 38.424 | 41.359 | 86.060 | 1.00 | 9.52 | A | C |
| ATOM | 3209 | CA | ARG | A | 436 | 36.760 | 41.034 | 82.610 | 1.00 | 8.83 | A | C |
| ATOM | 3220 | CA | LEU | A | 437 | 38.067 | 37.458 | 82.349 | 1.00 | 8.34 | A | C |
| ATOM | 3228 | CA | VAL | A | 438 | 36.448 | 36.553 | 85.664 | 1.00 | 9.83 | A | C |
| ATOM | 3235 | CA | GLY | A | 439 | 33.227 | 38.399 | 84.746 | 1.00 | 9.87 | A | C |
| ATOM | 3239 | CA | GLN | A | 440 | 30.557 | 39.769 | 87.076 | 1.00 | 11.48 | A | C |
| ATOM | 3248 | CA | TYR | A | 441 | 27.387 | 38.162 | 88.403 | 1.00 | 9.32 | A | C |
| ATOM | 3260 | CA | SER | A | 442 | 24.326 | 39.771 | 86.747 | 1.00 | 9.01 | A | C |
| ATOM | 3266 | CA | ALA | A | 443 | 21.930 | 41.944 | 88.804 | 1.00 | 10.00 | A | C |
| ATOM | 3271 | CA | ASP | A | 444 | 19.645 | 38.962 | 89.504 | 1.00 | 11.36 | A | C |
| ATOM | 3279 | CA | GLU | A | 445 | 22.683 | 36.814 | 90.345 | 1.00 | 10.65 | A | C |
| ATOM | 3288 | CA | LEU | A | 446 | 24.057 | 39.420 | 92.752 | 1.00 | 12.13 | A | C |
| ATOM | 3296 | CA | ARG | A | 447 | 20.688 | 39.484 | 94.519 | 1.00 | 14.84 | A | C |
| ATOM | 3307 | CA | ARG | A | 448 | 20.411 | 35.689 | 94.956 | 1.00 | 13.37 | A | C |
| ATOM | 3318 | CA | GLY | A | 449 | 24.148 | 34.933 | 95.289 | 1.00 | 11.12 | A | C |
| ATOM | 3322 | CA | TYR | A | 450 | 24.570 | 32.356 | 92.478 | 1.00 | 11.01 | A | C |
| ATOM | 3334 | CA | VAL | A | 451 | 24.024 | 31.514 | 88.794 | 1.00 | 10.44 | A | C |
| ATOM | 3341 | CA | ALA | A | 452 | 20.597 | 29.813 | 88.469 | 1.00 | 11.06 | A | C |
| ATOM | 3346 | CA | GLY | A | 453 | 20.832 | 26.118 | 87.493 | 1.00 | 10.92 | A | C |
| ATOM | 3350 | CA | ASN | A | 454 | 24.597 | 26.415 | 86.920 | 1.00 | 9.68 | A | C |
| ATOM | 3358 | CA | PRO | A | 455 | 26.517 | 25.184 | 90.002 | 1.00 | 9.01 | A | C |
| ATOM | 3365 | CA | GLY | A | 456 | 29.710 | 24.813 | 87.923 | 1.00 | 7.30 | A | C |
| ATOM | 3369 | CA | ALA | A | 457 | 29.902 | 28.429 | 86.804 | 1.00 | 5.98 | A | C |
| ATOM | 3374 | CA | SER | A | 458 | 29.216 | 29.530 | 90.428 | 1.00 | 5.00 | A | C |
| ATOM | 3380 | CA | VAL | A | 459 | 32.021 | 27.538 | 92.097 | 1.00 | 3.77 | A | C |
| ATOM | 3387 | CA | GLN | A | 460 | 34.377 | 28.579 | 89.287 | 1.00 | 3.69 | A | C |
| ATOM | 3396 | CA | ARG | A | 461 | 33.738 | 32.298 | 89.725 | 1.00 | 3.05 | A | C |
| ATOM | 3407 | CA | GLY | A | 462 | 34.143 | 31.742 | 93.464 | 1.00 | 2.45 | A | C |
| ATOM | 3411 | CA | TYR | A | 463 | 37.707 | 30.519 | 92.994 | 1.00 | 3.51 | A | C |
| ATOM | 3423 | CA | ASP | A | 464 | 38.419 | 33.243 | 90.372 | 1.00 | 3.80 | A | C |

FIG. 34-7

| | | | | | | | | | | | | | |
|---|---|---|---|---|---|---|---|---|---|---|---|---|---|
| ATOM | 3431 | CA | GLN | A | 465 | 37.202 | 35.909 | 92.790 | 1.00 | 4.82 | A | C |
| ATOM | 3440 | CA | TYR | A | 466 | 39.300 | 34.526 | 95.621 | 1.00 | 5.23 | A | C |
| ATOM | 3452 | CA | GLY | A | 467 | 42.325 | 34.871 | 93.265 | 1.00 | 5.67 | A | C |
| ATOM | 3456 | CA | LEU | A | 468 | 41.385 | 38.365 | 92.150 | 1.00 | 6.17 | A | C |
| ATOM | 3464 | CA | SER | A | 469 | 40.991 | 39.304 | 95.828 | 1.00 | 5.97 | A | C |
| ATOM | 3470 | CA | VAL | A | 470 | 44.682 | 38.455 | 96.482 | 1.00 | 6.48 | A | C |
| ATOM | 3477 | CA | ILE | A | 471 | 45.705 | 40.579 | 93.461 | 1.00 | 6.17 | A | C |
| ATOM | 3485 | CA | ALA | A | 472 | 43.411 | 43.420 | 94.600 | 1.00 | 8.07 | A | C |
| ATOM | 3490 | CA | ASP | A | 473 | 45.060 | 43.606 | 98.080 | 1.00 | 10.08 | A | C |
| ATOM | 3498 | CA | GLU | A | 474 | 48.496 | 43.569 | 96.443 | 1.00 | 10.69 | A | C |
| ATOM | 3507 | CA | LEU | A | 475 | 47.508 | 46.603 | 94.342 | 1.00 | 11.15 | A | C |
| ATOM | 3515 | CA | GLY | A | 476 | 46.177 | 48.346 | 97.453 | 1.00 | 13.34 | A | C |
| ATOM | 3519 | CA | LEU | A | 477 | 42.538 | 48.006 | 96.344 | 1.00 | 15.39 | A | C |
| ATOM | 3527 | CA | THR | A | 478 | 41.434 | 47.034 | 99.867 | 1.00 | 17.62 | A | C |
| ATOM | 3534 | CA | GLU | A | 479 | 37.723 | 47.742 | 99.394 | 1.00 | 18.74 | A | C |
| ATOM | 3543 | CA | GLU | A | 480 | 37.595 | 45.763 | 96.110 | 1.00 | 16.33 | A | C |
| ATOM | 3552 | CA | ALA | A | 481 | 39.372 | 42.864 | 97.813 | 1.00 | 13.75 | A | C |
| ATOM | 3557 | CA | GLU | A | 482 | 36.715 | 42.720 | 100.595 | 1.00 | 14.63 | A | C |
| ATOM | 3566 | CA | THR | A | 483 | 33.842 | 42.673 | 98.101 | 1.00 | 12.95 | A | C |
| ATOM | 3573 | CA | LEU | A | 484 | 35.614 | 39.932 | 96.121 | 1.00 | 11.73 | A | C |
| ATOM | 3581 | CA | ARG | A | 485 | 36.127 | 37.758 | 99.233 | 1.00 | 11.05 | A | C |
| ATOM | 3592 | CA | GLU | A | 486 | 32.458 | 38.265 | 100.146 | 1.00 | 10.61 | A | C |
| ATOM | 3601 | CA | GLN | A | 487 | 31.331 | 37.147 | 96.664 | 1.00 | 8.60 | A | C |
| ATOM | 3610 | CA | ALA | A | 488 | 33.786 | 34.225 | 96.759 | 1.00 | 6.52 | A | C |
| ATOM | 3615 | CA | SER | A | 489 | 32.029 | 32.893 | 99.875 | 1.00 | 7.12 | A | C |
| ATOM | 3621 | CA | TRP | A | 490 | 28.661 | 32.726 | 98.010 | 1.00 | 7.33 | A | C |
| ATOM | 3635 | CA | PRO | A | 491 | 28.980 | 29.421 | 96.072 | 1.00 | 6.73 | A | C |
| ATOM | 3642 | CA | ILE | A | 492 | 29.748 | 27.439 | 99.257 | 1.00 | 8.58 | A | C |
| ATOM | 3650 | CA | GLU | A | 493 | 27.034 | 29.091 | 101.368 | 1.00 | 11.10 | A | C |
| ATOM | 3659 | CA | LYS | A | 494 | 24.283 | 29.217 | 98.744 | 1.00 | 10.38 | A | C |
| ATOM | 3668 | CA | LEU | A | 495 | 24.772 | 25.992 | 96.727 | 1.00 | 8.08 | A | C |
| ATOM | 3676 | CA | THR | A | 496 | 25.642 | 23.390 | 99.397 | 1.00 | 9.94 | A | C |
| ATOM | 3683 | CA | LYS | A | 497 | 22.269 | 21.696 | 99.874 | 1.00 | 10.32 | A | C |
| ATOM | 3692 | CA | PRO | A | 498 | 21.844 | 20.282 | 103.387 | 1.00 | 9.82 | A | C |
| ATOM | 3699 | CA | GLY | A | 499 | 21.074 | 16.559 | 103.567 | 1.00 | 10.14 | A | C |
| ATOM | 3703 | CA | ALA | A | 500 | 21.838 | 16.042 | 99.846 | 1.00 | 10.82 | A | C |
| ATOM | 3708 | CA | TRP | A | 501 | 23.386 | 12.728 | 100.863 | 1.00 | 11.71 | A | C |
| ATOM | 3722 | CA | THR | A | 502 | 22.581 | 10.696 | 104.006 | 1.00 | 12.62 | A | C |
| ATOM | 3729 | CA | ALA | A | 503 | 25.365 | 8.647 | 105.597 | 1.00 | 13.78 | A | C |
| ATOM | 3734 | CA | ALA | A | 504 | 24.951 | 4.994 | 106.737 | 1.00 | 15.02 | A | C |
| ATOM | 3739 | CA | ASP | A | 505 | 24.357 | 6.130 | 110.325 | 1.00 | 14.83 | A | C |
| ATOM | 3747 | CA | GLY | A | 506 | 21.856 | 8.861 | 109.305 | 1.00 | 12.52 | A | C |
| ATOM | 3751 | CA | THR | A | 507 | 24.298 | 11.810 | 109.343 | 1.00 | 10.12 | A | C |
| ATOM | 3758 | CA | GLN | A | 508 | 23.119 | 14.588 | 106.989 | 1.00 | 8.56 | A | C |
| ATOM | 3767 | CA | VAL | A | 509 | 25.765 | 15.604 | 104.451 | 1.00 | 6.31 | A | C |
| ATOM | 3774 | CA | GLY | A | 510 | 25.468 | 18.758 | 102.362 | 1.00 | 5.03 | A | C |
| ATOM | 3778 | CA | LEU | A | 511 | 26.594 | 18.750 | 98.722 | 1.00 | 4.48 | A | C |
| ATOM | 3786 | CA | LEU | A | 512 | 26.884 | 21.120 | 95.793 | 1.00 | 5.45 | A | C |
| ATOM | 3794 | CA | THR | A | 513 | 23.470 | 21.012 | 94.071 | 1.00 | 7.09 | A | C |
| ATOM | 3801 | CA | PRO | A | 514 | 21.941 | 23.109 | 91.250 | 1.00 | 7.88 | A | C |
| ATOM | 3808 | CA | ARG | A | 515 | 19.517 | 25.737 | 92.573 | 1.00 | 9.63 | A | C |
| ATOM | 3819 | CA | ALA | A | 516 | 16.670 | 27.438 | 90.743 | 1.00 | 11.40 | A | C |
| ATOM | 3824 | CA | ALA | A | 517 | 16.201 | 31.213 | 90.509 | 1.00 | 13.83 | A | C |
| ATOM | 3829 | CA | ASP | A | 518 | 13.518 | 31.125 | 93.261 | 1.00 | 16.58 | A | C |
| ATOM | 3837 | CA | GLY | A | 519 | 15.865 | 29.277 | 95.648 | 1.00 | 16.47 | A | C |
| ATOM | 3841 | CA | SER | A | 520 | 14.202 | 25.852 | 95.069 | 1.00 | 15.99 | A | C |
| ATOM | 3847 | CA | TRP | A | 521 | 16.785 | 23.089 | 94.870 | 1.00 | 13.14 | A | C |
| ATOM | 3861 | CA | GLN | A | 522 | 16.878 | 21.329 | 91.494 | 1.00 | 12.01 | A | C |
| ATOM | 3870 | CA | SER | A | 523 | 16.780 | 17.550 | 91.127 | 1.00 | 12.74 | A | C |
| ATOM | 3876 | CA | ALA | A | 524 | 20.170 | 15.972 | 90.267 | 1.00 | 11.18 | A | C |
| ATOM | 3881 | CA | ASP | A | 525 | 22.087 | 12.671 | 90.488 | 1.00 | 8.84 | A | C |
| ATOM | 3889 | CA | HIS | A | 526 | 25.271 | 13.887 | 92.225 | 1.00 | 6.57 | A | C |
| ATOM | 3899 | CA | ALA | A | 527 | 27.293 | 11.003 | 90.717 | 1.00 | 6.14 | A | C |
| ATOM | 3904 | CA | LYS | A | 528 | 26.151 | 11.481 | 87.106 | 1.00 | 7.50 | A | C |
| ATOM | 3913 | CA | PHE | A | 529 | 28.818 | 12.767 | 84.690 | 1.00 | 7.13 | A | C |
| ATOM | 3924 | CA | GLU | A | 530 | 27.867 | 16.202 | 83.304 | 1.00 | 7.91 | A | C |

FIG. 34-8

| | | | | | | | | | | | | | |
|---|---|---|---|---|---|---|---|---|---|---|---|---|---|
| ATOM | 3933 | CA | ALA | A | 531 | 24.533 | 16.513 | 85.106 | 1.00 | 8.44 | A | C |
| ATOM | 3938 | CA | ALA | A | 532 | 23.397 | 20.032 | 86.170 | 1.00 | 7.77 | A | C |
| ATOM | 3943 | CA | GLY | A | 533 | 25.194 | 21.889 | 83.332 | 1.00 | 6.76 | A | C |
| ATOM | 3947 | CA | LEU | A | 534 | 28.619 | 20.734 | 84.578 | 1.00 | 5.97 | A | C |
| ATOM | 3955 | CA | TYR | A | 535 | 31.682 | 20.411 | 82.372 | 1.00 | 8.46 | A | C |
| ATOM | 3967 | CA | GLN | A | 536 | 33.627 | 17.123 | 82.410 | 1.00 | 6.34 | A | C |
| ATOM | 3976 | CA | GLY | A | 537 | 32.521 | 16.050 | 85.901 | 1.00 | 4.04 | A | C |
| ATOM | 3980 | CA | THR | A | 538 | 29.936 | 15.281 | 88.564 | 1.00 | 3.50 | A | C |
| ATOM | 3987 | CA | LEU | A | 539 | 28.500 | 17.232 | 91.498 | 1.00 | 3.71 | A | C |
| ATOM | 3995 | CA | TRP | A | 540 | 30.500 | 15.072 | 93.986 | 1.00 | 3.80 | A | C |
| ATOM | 4009 | CA | GLN | A | 541 | 33.680 | 16.012 | 92.073 | 1.00 | 3.42 | A | C |
| ATOM | 4018 | CA | TYR | A | 542 | 32.808 | 19.714 | 91.708 | 1.00 | 4.03 | A | C |
| ATOM | 4030 | CA | HIS | A | 543 | 31.606 | 19.795 | 95.352 | 1.00 | 4.44 | A | C |
| ATOM | 4040 | CA | TRP | A | 544 | 35.221 | 20.315 | 96.537 | 1.00 | 4.40 | A | C |
| ATOM | 4054 | CA | TYR | A | 545 | 36.045 | 23.019 | 93.950 | 1.00 | 4.18 | A | C |
| ATOM | 4066 | CA | ASP | A | 546 | 36.276 | 26.024 | 96.237 | 1.00 | 5.25 | A | C |
| ATOM | 4074 | CA | ALA | A | 547 | 39.546 | 24.793 | 97.671 | 1.00 | 5.51 | A | C |
| ATOM | 4079 | CA | TYR | A | 548 | 40.358 | 28.217 | 99.183 | 1.00 | 6.10 | A | C |
| ATOM | 4091 | CA | ASP | A | 549 | 37.753 | 27.586 | 101.917 | 1.00 | 6.22 | A | C |
| ATOM | 4099 | CA | MET | A | 550 | 37.554 | 24.017 | 103.177 | 1.00 | 6.61 | A | C |
| ATOM | 4107 | CA | ASP | A | 551 | 36.549 | 25.382 | 106.586 | 1.00 | 8.26 | A | C |
| ATOM | 4115 | CA | ALA | A | 552 | 33.422 | 27.067 | 105.225 | 1.00 | 7.80 | A | C |
| ATOM | 4120 | CA | LEU | A | 553 | 32.800 | 24.021 | 103.028 | 1.00 | 7.77 | A | C |
| ATOM | 4128 | CA | VAL | A | 554 | 32.983 | 21.675 | 106.066 | 1.00 | 8.48 | A | C |
| ATOM | 4135 | CA | GLU | A | 555 | 30.421 | 23.906 | 107.886 | 1.00 | 10.05 | A | C |
| ATOM | 4144 | CA | ALA | A | 556 | 28.101 | 24.172 | 104.869 | 1.00 | 8.14 | A | C |
| ATOM | 4149 | CA | MET | A | 557 | 28.262 | 20.355 | 104.586 | 1.00 | 7.75 | A | C |
| ATOM | 4157 | CA | GLY | A | 558 | 26.833 | 20.080 | 108.112 | 1.00 | 7.77 | A | C |
| ATOM | 4161 | CA | GLY | A | 559 | 29.995 | 19.989 | 110.230 | 1.00 | 8.36 | A | C |
| ATOM | 4165 | CA | HIS | A | 560 | 33.086 | 17.891 | 110.775 | 1.00 | 10.24 | A | C |
| ATOM | 4175 | CA | GLU | A | 561 | 31.496 | 14.448 | 111.036 | 1.00 | 10.61 | A | C |
| ATOM | 4184 | CA | ALA | A | 562 | 29.420 | 15.118 | 107.900 | 1.00 | 9.17 | A | C |
| ATOM | 4189 | CA | ALA | A | 563 | 32.594 | 16.099 | 105.943 | 1.00 | 7.47 | A | C |
| ATOM | 4194 | CA | ARG | A | 564 | 34.534 | 13.129 | 107.304 | 1.00 | 6.15 | A | C |
| ATOM | 4205 | CA | LEU | A | 565 | 31.813 | 10.683 | 106.236 | 1.00 | 5.27 | A | C |
| ATOM | 4213 | CA | GLY | A | 566 | 31.408 | 12.469 | 102.857 | 1.00 | 4.45 | A | C |
| ATOM | 4217 | CA | MET | A | 567 | 35.136 | 12.086 | 102.137 | 1.00 | 5.05 | A | C |
| ATOM | 4225 | CA | ARG | A | 568 | 35.000 | 8.412 | 103.020 | 1.00 | 6.55 | A | C |
| ATOM | 4236 | CA | HIS | A | 569 | 31.985 | 7.943 | 100.689 | 1.00 | 7.31 | A | C |
| ATOM | 4246 | CA | MET | A | 570 | 33.786 | 9.924 | 97.906 | 1.00 | 7.92 | A | C |
| ATOM | 4254 | CA | PHE | A | 571 | 36.388 | 7.150 | 97.840 | 1.00 | 7.04 | A | C |
| ATOM | 4265 | CA | GLY | A | 572 | 34.058 | 4.168 | 98.426 | 1.00 | 8.17 | A | C |
| ATOM | 4269 | CA | GLU | A | 573 | 35.790 | 3.316 | 101.736 | 1.00 | 10.14 | A | C |
| ATOM | 4278 | CA | HIS | A | 574 | 32.693 | 1.377 | 102.888 | 1.00 | 11.27 | A | C |
| ATOM | 4288 | CA | ALA | A | 575 | 32.914 | -0.845 | 99.770 | 1.00 | 11.91 | A | C |
| ATOM | 4293 | CA | PRO | A | 576 | 36.615 | -1.198 | 98.736 | 1.00 | 13.14 | A | C |
| ATOM | 4300 | CA | ASP | A | 577 | 35.923 | -3.909 | 96.131 | 1.00 | 13.69 | A | C |
| ATOM | 4308 | CA | ASP | A | 578 | 32.994 | -2.108 | 94.404 | 1.00 | 12.41 | A | C |
| ATOM | 4316 | CA | GLY | A | 579 | 34.247 | -0.097 | 91.423 | 1.00 | 11.12 | A | C |
| ATOM | 4320 | CA | LYS | A | 580 | 30.905 | 1.748 | 91.259 | 1.00 | 11.21 | A | C |
| ATOM | 4329 | CA | ALA | A | 581 | 31.370 | 3.276 | 94.757 | 1.00 | 8.19 | A | C |
| ATOM | 4334 | CA | MET | A | 582 | 34.358 | 5.303 | 93.506 | 1.00 | 5.86 | A | C |
| ATOM | 4342 | CA | LEU | A | 583 | 33.022 | 8.889 | 93.198 | 1.00 | 4.23 | A | C |
| ATOM | 4350 | CA | HIS | A | 584 | 36.434 | 10.466 | 92.671 | 1.00 | 3.37 | A | C |
| ATOM | 4360 | CA | SER | A | 585 | 37.816 | 10.665 | 89.125 | 1.00 | 3.12 | A | C |
| ATOM | 4366 | CA | ASN | A | 586 | 41.508 | 10.091 | 88.359 | 1.00 | 3.90 | A | C |
| ATOM | 4374 | CA | ALA | A | 587 | 41.103 | 10.824 | 84.638 | 1.00 | 5.72 | A | C |
| ATOM | 4379 | CA | ASN | A | 588 | 40.425 | 14.577 | 84.853 | 1.00 | 7.03 | A | C |
| ATOM | 4387 | CA | GLU | A | 589 | 41.649 | 17.614 | 86.824 | 1.00 | 7.17 | A | C |
| ATOM | 4396 | CA | ILE | A | 590 | 38.295 | 18.647 | 88.338 | 1.00 | 7.24 | A | C |
| ATOM | 4404 | CA | ASP | A | 591 | 38.863 | 16.848 | 91.650 | 1.00 | 7.24 | A | C |
| ATOM | 4412 | CA | LEU | A | 592 | 42.668 | 16.421 | 91.471 | 1.00 | 6.70 | A | C |
| ATOM | 4420 | CA | GLN | A | 593 | 42.981 | 17.626 | 95.053 | 1.00 | 4.59 | A | C |
| ATOM | 4429 | CA | ALA | A | 594 | 40.356 | 15.206 | 96.428 | 1.00 | 4.71 | A | C |
| ATOM | 4434 | CA | PRO | A | 595 | 42.784 | 12.503 | 97.633 | 1.00 | 5.03 | A | C |
| ATOM | 4441 | CA | TYR | A | 596 | 44.506 | 15.069 | 99.845 | 1.00 | 6.02 | A | C |

FIG. 34-9

| | | | | | | | | | | | | |
|---|---|---|---|---|---|---|---|---|---|---|---|---|
| ATOM | 4453 | CA | LEU | A | 597 | 41.304 | 16.226 | 101.591 | 1.00 | 4.94 | A | C |
| ATOM | 4461 | CA | PHE | A | 598 | 41.417 | 13.474 | 104.213 | 1.00 | 5.47 | A | C |
| ATOM | 4472 | CA | ASN | A | 599 | 44.037 | 15.684 | 105.929 | 1.00 | 6.53 | A | C |
| ATOM | 4480 | CA | TYR | A | 600 | 41.176 | 18.148 | 106.491 | 1.00 | 7.92 | A | C |
| ATOM | 4492 | CA | THR | A | 601 | 38.801 | 15.556 | 107.938 | 1.00 | 9.25 | A | C |
| ATOM | 4499 | CA | GLY | A | 602 | 41.334 | 14.393 | 110.555 | 1.00 | 9.27 | A | C |
| ATOM | 4503 | CA | GLU | A | 603 | 42.259 | 11.247 | 108.634 | 1.00 | 8.63 | A | C |
| ATOM | 4512 | CA | PRO | A | 604 | 45.684 | 11.982 | 107.132 | 1.00 | 7.11 | A | C |
| ATOM | 4519 | CA | SER | A | 605 | 46.475 | 8.224 | 106.915 | 1.00 | 5.46 | A | C |
| ATOM | 4525 | CA | LEU | A | 606 | 43.781 | 7.928 | 104.201 | 1.00 | 4.96 | A | C |
| ATOM | 4533 | CA | THR | A | 607 | 45.390 | 10.729 | 102.175 | 1.00 | 4.57 | A | C |
| ATOM | 4540 | CA | GLN | A | 608 | 48.682 | 8.824 | 102.399 | 1.00 | 5.02 | A | C |
| ATOM | 4549 | CA | LYS | A | 609 | 47.008 | 5.602 | 101.265 | 1.00 | 5.44 | A | C |
| ATOM | 4558 | CA | TRP | A | 610 | 45.214 | 7.208 | 98.331 | 1.00 | 5.42 | A | C |
| ATOM | 4572 | CA | ALA | A | 611 | 48.211 | 9.266 | 97.205 | 1.00 | 6.31 | A | C |
| ATOM | 4577 | CA | ARG | A | 612 | 50.436 | 6.184 | 97.099 | 1.00 | 5.71 | A | C |
| ATOM | 4588 | CA | ALA | A | 613 | 47.643 | 4.074 | 95.492 | 1.00 | 4.20 | A | C |
| ATOM | 4593 | CA | ILE | A | 614 | 46.445 | 6.379 | 92.691 | 1.00 | 4.67 | A | C |
| ATOM | 4601 | CA | TYR | A | 615 | 49.973 | 7.212 | 91.557 | 1.00 | 4.85 | A | C |
| ATOM | 4613 | CA | THR | A | 616 | 51.897 | 3.953 | 92.071 | 1.00 | 4.62 | A | C |
| ATOM | 4620 | CA | LYS | A | 617 | 49.365 | 1.088 | 92.368 | 1.00 | 6.36 | A | C |
| ATOM | 4629 | CA | GLU | A | 618 | 46.132 | -0.236 | 90.829 | 1.00 | 7.91 | A | C |
| ATOM | 4638 | CA | THR | A | 619 | 42.939 | 1.583 | 91.795 | 1.00 | 6.88 | A | C |
| ATOM | 4645 | CA | TRP | A | 620 | 39.227 | 1.357 | 91.008 | 1.00 | 7.46 | A | C |
| ATOM | 4659 | CA | ASN | A | 621 | 38.296 | 3.692 | 88.170 | 1.00 | 6.73 | A | C |
| ATOM | 4667 | CA | ARG | A | 622 | 34.663 | 4.574 | 87.576 | 1.00 | 4.87 | A | C |
| ATOM | 4678 | CA | TYR | A | 623 | 35.087 | 7.709 | 85.473 | 1.00 | 5.03 | A | C |
| ATOM | 4690 | CA | ILE | A | 624 | 36.716 | 8.661 | 82.149 | 1.00 | 5.64 | A | C |
| ATOM | 4698 | CA | ALA | A | 625 | 37.316 | 12.291 | 81.127 | 1.00 | 6.35 | A | C |
| ATOM | 4703 | CA | THR | A | 626 | 34.590 | 12.516 | 78.472 | 1.00 | 6.19 | A | C |
| ATOM | 4710 | CA | GLY | A | 627 | 31.208 | 10.937 | 77.589 | 1.00 | 5.93 | A | C |
| ATOM | 4714 | CA | SER | A | 628 | 32.592 | 7.840 | 75.913 | 1.00 | 7.00 | A | C |
| ATOM | 4720 | CA | SER | A | 629 | 35.720 | 6.302 | 74.355 | 1.00 | 9.77 | A | C |
| ATOM | 4726 | CA | SER | A | 630 | 36.292 | 3.632 | 71.688 | 1.00 | 11.33 | A | C |
| ATOM | 4732 | CA | ALA | A | 631 | 39.492 | 2.767 | 73.559 | 1.00 | 10.90 | A | C |
| ATOM | 4737 | CA | VAL | A | 632 | 37.659 | 1.102 | 76.492 | 1.00 | 8.53 | A | C |
| ATOM | 4744 | CA | PRO | A | 633 | 34.094 | -0.107 | 77.097 | 1.00 | 7.28 | A | C |
| ATOM | 4751 | CA | SER | A | 634 | 32.472 | 3.099 | 78.345 | 1.00 | 5.04 | A | C |
| ATOM | 4757 | CA | GLY | A | 635 | 29.414 | 5.345 | 78.326 | 1.00 | 4.96 | A | C |
| ATOM | 4761 | CA | GLY | A | 636 | 27.832 | 8.244 | 80.176 | 1.00 | 6.17 | A | C |
| ATOM | 4765 | CA | GLY | A | 637 | 31.304 | 9.416 | 81.298 | 1.00 | 5.99 | A | C |
| ATOM | 4769 | CA | GLU | A | 638 | 32.099 | 6.071 | 82.923 | 1.00 | 5.01 | A | C |
| ATOM | 4778 | CA | PHE | A | 639 | 34.109 | 2.868 | 82.500 | 1.00 | 4.24 | A | C |
| ATOM | 4789 | CA | THR | A | 640 | 31.342 | 0.261 | 81.956 | 1.00 | 5.80 | A | C |
| ATOM | 4796 | CA | PRO | A | 641 | 32.109 | -1.741 | 83.969 | 1.00 | 6.76 | A | C |
| ATOM | 4803 | CA | PRO | A | 642 | 34.393 | 0.103 | 86.417 | 1.00 | 8.12 | A | C |
| ATOM | 4810 | CA | LEU | A | 643 | 38.016 | -0.971 | 85.969 | 1.00 | 9.82 | A | C |
| ATOM | 4818 | CA | LYS | A | 644 | 40.825 | -1.805 | 88.435 | 1.00 | 11.06 | A | C |
| ATOM | 4827 | CA | THR | A | 645 | 43.998 | -0.565 | 86.793 | 1.00 | 8.37 | A | C |
| ATOM | 4834 | CA | LYS | A | 646 | 47.067 | 1.637 | 87.273 | 1.00 | 7.54 | A | C |
| ATOM | 4843 | CA | VAL | A | 647 | 46.307 | 5.272 | 86.488 | 1.00 | 5.75 | A | C |
| ATOM | 4850 | CA | TYR | A | 648 | 49.922 | 5.925 | 85.527 | 1.00 | 5.56 | A | C |
| ATOM | 4862 | CA | ARG | A | 649 | 51.964 | 3.328 | 83.533 | 1.00 | 7.76 | A | C |
| ATOM | 4873 | CA | LEU | A | 650 | 55.512 | 3.322 | 82.177 | 1.00 | 6.76 | A | C |
| ATOM | 4881 | CA | ASP | A | 651 | 54.026 | 2.407 | 78.809 | 1.00 | 6.42 | A | C |
| ATOM | 4889 | CA | PRO | A | 652 | 53.043 | 4.126 | 75.570 | 1.00 | 5.92 | A | C |
| ATOM | 4896 | CA | ARG | A | 653 | 49.549 | 3.680 | 77.020 | 1.00 | 4.60 | A | C |
| ATOM | 4907 | CA | GLY | A | 654 | 50.724 | 6.058 | 79.774 | 1.00 | 4.89 | A | C |
| ATOM | 4911 | CA | MET | A | 655 | 47.517 | 7.356 | 81.356 | 1.00 | 4.93 | A | C |
| ATOM | 4919 | CA | LEU | A | 656 | 43.963 | 6.075 | 81.567 | 1.00 | 3.04 | A | C |
| ATOM | 4927 | CA | PRO | A | 657 | 42.105 | 6.134 | 78.251 | 1.00 | 3.10 | A | C |
| ATOM | 4934 | CA | THR | A | 658 | 40.754 | 9.734 | 77.676 | 1.00 | 3.53 | A | C |
| ATOM | 4941 | CA | MET | A | 659 | 43.088 | 11.046 | 80.398 | 1.00 | 3.65 | A | C |
| ATOM | 4949 | CA | ASP | A | 660 | 44.895 | 13.859 | 78.555 | 1.00 | 3.95 | A | C |
| ATOM | 4957 | CA | ASN | A | 661 | 48.031 | 15.161 | 80.276 | 1.00 | 3.15 | A | C |
| ATOM | 4965 | CA | ASP | A | 662 | 46.843 | 18.761 | 79.522 | 1.00 | 2.87 | A | C |

FIG. 34-10

| | | | | | | | | | | | | |
|---|---|---|---|---|---|---|---|---|---|---|---|---|
| ATOM | 4973 | CA | ALA | A | 663 | 50.075 | 20.739 | 79.098 | 1.00 | 3.12 | A | C |
| ATOM | 4978 | CA | GLY | A | 664 | 51.894 | 18.459 | 81.548 | 1.00 | 2.70 | A | C |
| ATOM | 4982 | CA | THR | A | 665 | 49.328 | 18.721 | 84.376 | 1.00 | 2.81 | A | C |
| ATOM | 4989 | CA | MET | A | 666 | 48.910 | 14.993 | 85.026 | 1.00 | 2.55 | A | C |
| ATOM | 4997 | CA | SER | A | 667 | 52.753 | 14.620 | 84.897 | 1.00 | 2.87 | A | C |
| ATOM | 5003 | CA | THR | A | 668 | 53.193 | 17.564 | 87.294 | 1.00 | 3.50 | A | C |
| ATOM | 5010 | CA | MET | A | 669 | 50.719 | 16.032 | 89.771 | 1.00 | 2.90 | A | C |
| ATOM | 5018 | CA | PHE | A | 670 | 52.751 | 12.810 | 89.639 | 1.00 | 2.90 | A | C |
| ATOM | 5029 | CA | VAL | A | 671 | 55.921 | 14.716 | 90.519 | 1.00 | 3.29 | A | C |
| ATOM | 5036 | CA | ALA | A | 672 | 54.049 | 16.446 | 93.385 | 1.00 | 3.04 | A | C |
| ATOM | 5041 | CA | ALA | A | 673 | 52.740 | 13.126 | 94.733 | 1.00 | 3.21 | A | C |
| ATOM | 5046 | CA | ALA | A | 674 | 56.289 | 11.665 | 94.548 | 1.00 | 4.16 | A | C |
| ATOM | 5051 | CA | VAL | A | 675 | 57.770 | 14.572 | 96.510 | 1.00 | 3.68 | A | C |
| ATOM | 5058 | CA | GLY | A | 676 | 54.729 | 14.329 | 98.773 | 1.00 | 3.81 | A | C |
| ATOM | 5062 | CA | LEU | A | 677 | 53.628 | 17.976 | 98.689 | 1.00 | 3.63 | A | C |
| ATOM | 5070 | CA | PHE | A | 678 | 50.401 | 18.865 | 96.910 | 1.00 | 4.98 | A | C |
| ATOM | 5081 | CA | PRO | A | 679 | 48.736 | 22.236 | 96.308 | 1.00 | 4.89 | A | C |
| ATOM | 5088 | CA | VAL | A | 680 | 45.131 | 21.802 | 97.449 | 1.00 | 3.54 | A | C |
| ATOM | 5095 | CA | THR | A | 681 | 44.815 | 25.594 | 97.517 | 1.00 | 3.01 | A | C |
| ATOM | 5102 | CA | ALA | A | 682 | 46.410 | 27.062 | 94.421 | 1.00 | 2.78 | A | C |
| ATOM | 5107 | CA | GLY | A | 683 | 46.558 | 30.790 | 95.067 | 1.00 | 4.10 | A | C |
| ATOM | 5111 | CA | SER | A | 684 | 47.895 | 30.234 | 98.585 | 1.00 | 5.30 | A | C |
| ATOM | 5117 | CA | SER | A | 685 | 51.390 | 29.528 | 99.913 | 1.00 | 6.30 | A | C |
| ATOM | 5123 | CA | GLN | A | 686 | 50.476 | 26.083 | 101.310 | 1.00 | 5.66 | A | C |
| ATOM | 5132 | CA | PHE | A | 687 | 51.101 | 22.447 | 100.320 | 1.00 | 5.37 | A | C |
| ATOM | 5143 | CA | GLN | A | 688 | 49.438 | 19.356 | 101.748 | 1.00 | 4.94 | A | C |
| ATOM | 5152 | CA | VAL | A | 689 | 51.517 | 16.390 | 102.936 | 1.00 | 5.79 | A | C |
| ATOM | 5159 | CA | GLY | A | 690 | 50.928 | 13.088 | 101.117 | 1.00 | 6.69 | A | C |
| ATOM | 5163 | CA | SER | A | 691 | 52.974 | 9.889 | 100.906 | 1.00 | 7.27 | A | C |
| ATOM | 5169 | CA | PRO | A | 692 | 56.528 | 10.626 | 99.669 | 1.00 | 6.85 | A | C |
| ATOM | 5176 | CA | PHE | A | 693 | 57.581 | 7.765 | 97.347 | 1.00 | 6.34 | A | C |
| ATOM | 5187 | CA | PHE | A | 694 | 61.346 | 7.747 | 97.796 | 1.00 | 6.87 | A | C |
| ATOM | 5198 | CA | ASP | A | 695 | 63.891 | 7.202 | 100.575 | 1.00 | 7.56 | A | C |
| ATOM | 5206 | CA | SER | A | 696 | 65.365 | 10.632 | 99.830 | 1.00 | 6.91 | A | C |
| ATOM | 5212 | CA | THR | A | 697 | 64.278 | 13.400 | 97.424 | 1.00 | 7.09 | A | C |
| ATOM | 5219 | CA | THR | A | 698 | 66.465 | 16.572 | 97.123 | 1.00 | 7.46 | A | C |
| ATOM | 5226 | CA | ILE | A | 699 | 65.459 | 19.752 | 95.308 | 1.00 | 6.95 | A | C |
| ATOM | 5234 | CA | THR | A | 700 | 68.553 | 21.914 | 94.670 | 1.00 | 8.40 | A | C |
| ATOM | 5241 | CA | TYR | A | 701 | 67.913 | 25.630 | 94.091 | 1.00 | 9.41 | A | C |
| ATOM | 5253 | CA | ASP | A | 702 | 69.971 | 28.028 | 91.946 | 1.00 | 11.48 | A | C |
| ATOM | 5261 | CA | ASP | A | 703 | 72.068 | 29.199 | 94.915 | 1.00 | 13.97 | A | C |
| ATOM | 5269 | CA | GLY | A | 704 | 73.018 | 25.617 | 95.847 | 1.00 | 13.70 | A | C |
| ATOM | 5273 | CA | SER | A | 705 | 70.765 | 25.419 | 98.907 | 1.00 | 12.46 | A | C |
| ATOM | 5279 | CA | ALA | A | 706 | 68.419 | 22.383 | 98.854 | 1.00 | 10.18 | A | C |
| ATOM | 5284 | CA | PHE | A | 707 | 65.052 | 21.131 | 100.137 | 1.00 | 7.55 | A | C |
| ATOM | 5295 | CA | THR | A | 708 | 65.351 | 17.581 | 101.387 | 1.00 | 7.30 | A | C |
| ATOM | 5302 | CA | VAL | A | 709 | 62.397 | 15.352 | 102.091 | 1.00 | 7.65 | A | C |
| ATOM | 5309 | CA | THR | A | 710 | 63.206 | 11.874 | 103.424 | 1.00 | 8.06 | A | C |
| ATOM | 5316 | CA | ALA | A | 711 | 60.926 | 8.889 | 103.973 | 1.00 | 8.76 | A | C |
| ATOM | 5321 | CA | ASP | A | 712 | 62.785 | 6.541 | 106.270 | 1.00 | 10.03 | A | C |
| ATOM | 5329 | CA | GLY | A | 713 | 61.790 | 2.931 | 105.687 | 1.00 | 7.18 | A | C |
| ATOM | 5333 | CA | VAL | A | 714 | 59.420 | 3.754 | 102.770 | 1.00 | 5.21 | A | C |
| ATOM | 5340 | CA | SER | A | 715 | 58.461 | 0.754 | 100.621 | 1.00 | 5.75 | A | C |
| ATOM | 5346 | CA | GLU | A | 716 | 55.621 | -0.434 | 98.399 | 1.00 | 7.40 | A | C |
| ATOM | 5355 | CA | ASP | A | 717 | 53.911 | -1.492 | 101.619 | 1.00 | 7.77 | A | C |
| ATOM | 5363 | CA | ALA | A | 718 | 55.257 | 1.143 | 103.999 | 1.00 | 5.28 | A | C |
| ATOM | 5368 | CA | PHE | A | 719 | 53.472 | 4.224 | 102.665 | 1.00 | 3.86 | A | C |
| ATOM | 5379 | CA | TYR | A | 720 | 51.935 | 5.573 | 105.926 | 1.00 | 5.07 | A | C |
| ATOM | 5391 | CA | VAL | A | 721 | 53.647 | 8.305 | 107.943 | 1.00 | 6.16 | A | C |
| ATOM | 5398 | CA | GLN | A | 722 | 54.378 | 7.196 | 111.544 | 1.00 | 8.68 | A | C |
| ATOM | 5407 | CA | SER | A | 723 | 56.107 | 10.362 | 112.750 | 1.00 | 9.44 | A | C |
| ATOM | 5413 | CA | ALA | A | 724 | 57.936 | 13.385 | 111.311 | 1.00 | 8.65 | A | C |
| ATOM | 5418 | CA | THR | A | 725 | 60.561 | 16.054 | 112.006 | 1.00 | 8.30 | A | C |
| ATOM | 5425 | CA | LEU | A | 726 | 61.170 | 19.486 | 110.467 | 1.00 | 8.74 | A | C |
| ATOM | 5433 | CA | ASP | A | 727 | 64.804 | 20.662 | 110.723 | 1.00 | 9.93 | A | C |
| ATOM | 5441 | CA | GLY | A | 728 | 65.330 | 18.182 | 113.597 | 1.00 | 11.60 | A | C |

FIG. 34-11

| | | | | | | | | | | | | |
|---|---|---|---|---|---|---|---|---|---|---|---|---|
| ATOM | 5445 | CA | ALA | A | 729 | 62.241 | 19.122 | 115.635 | 1.00 | 11.25 | A | C |
| ATOM | 5450 | CA | THR | A | 730 | 58.993 | 17.157 | 116.102 | 1.00 | 10.67 | A | C |
| ATOM | 5457 | CA | PHE | A | 731 | 56.579 | 18.068 | 113.320 | 1.00 | 9.05 | A | C |
| ATOM | 5468 | CA | GLY | A | 732 | 52.846 | 17.319 | 113.474 | 1.00 | 8.76 | A | C |
| ATOM | 5472 | CA | ASN | A | 733 | 51.196 | 19.402 | 110.742 | 1.00 | 8.99 | A | C |
| ATOM | 5480 | CA | THR | A | 734 | 49.869 | 17.843 | 107.528 | 1.00 | 9.35 | A | C |
| ATOM | 5487 | CA | TRP | A | 735 | 50.725 | 20.969 | 105.477 | 1.00 | 8.91 | A | C |
| ATOM | 5501 | CA | VAL | A | 736 | 53.901 | 22.986 | 104.955 | 1.00 | 8.70 | A | C |
| ATOM | 5508 | CA | ASP | A | 737 | 54.483 | 26.555 | 103.781 | 1.00 | 8.20 | A | C |
| ATOM | 5516 | CA | TYR | A | 738 | 56.186 | 27.338 | 100.476 | 1.00 | 6.61 | A | C |
| ATOM | 5528 | CA | ALA | A | 739 | 58.753 | 29.427 | 102.391 | 1.00 | 6.41 | A | C |
| ATOM | 5533 | CA | THR | A | 740 | 59.787 | 26.356 | 104.396 | 1.00 | 7.06 | A | C |
| ATOM | 5540 | CA | VAL | A | 741 | 60.397 | 24.354 | 101.242 | 1.00 | 6.62 | A | C |
| ATOM | 5547 | CA | VAL | A | 742 | 62.422 | 26.857 | 99.172 | 1.00 | 7.73 | A | C |
| ATOM | 5554 | CA | GLY | A | 743 | 64.172 | 27.894 | 102.414 | 1.00 | 9.90 | A | C |
| ATOM | 5558 | CA | GLY | A | 744 | 65.997 | 24.543 | 102.207 | 1.00 | 9.66 | A | C |
| ATOM | 5562 | CA | ALA | A | 745 | 64.348 | 22.686 | 105.078 | 1.00 | 9.46 | A | C |
| ATOM | 5567 | CA | ASP | A | 746 | 64.950 | 19.052 | 106.107 | 1.00 | 9.46 | A | C |
| ATOM | 5575 | CA | LEU | A | 747 | 61.574 | 17.315 | 106.252 | 1.00 | 7.98 | A | C |
| ATOM | 5583 | CA | ALA | A | 748 | 62.092 | 13.775 | 107.535 | 1.00 | 8.59 | A | C |
| ATOM | 5588 | CA | PHE | A | 749 | 59.312 | 11.203 | 107.659 | 1.00 | 9.99 | A | C |
| ATOM | 5599 | CA | ARG | A | 750 | 59.298 | 7.807 | 109.398 | 1.00 | 11.09 | A | C |
| ATOM | 5610 | CA | MET | A | 751 | 57.231 | 5.392 | 107.265 | 1.00 | 8.36 | A | C |
| ATOM | 5618 | CA | GLY | A | 752 | 55.426 | 2.175 | 108.214 | 1.00 | 8.95 | A | C |
| ATOM | 5622 | CA | GLU | A | 753 | 53.025 | -0.439 | 106.937 | 1.00 | 10.36 | A | C |
| ATOM | 5631 | CA | GLN | A | 754 | 50.077 | 0.533 | 109.170 | 1.00 | 10.20 | A | C |
| ATOM | 5640 | CA | PRO | A | 755 | 48.009 | 3.743 | 109.500 | 1.00 | 9.59 | A | C |
| ATOM | 5647 | CA | SER | A | 756 | 49.021 | 5.965 | 112.430 | 1.00 | 10.96 | A | C |
| ATOM | 5653 | CA | ASP | A | 757 | 47.455 | 8.970 | 114.180 | 1.00 | 12.99 | A | C |
| ATOM | 5661 | CA | TRP | A | 758 | 50.369 | 11.238 | 113.073 | 1.00 | 11.54 | A | C |
| ATOM | 5675 | CA | GLY | A | 759 | 49.073 | 14.673 | 112.067 | 1.00 | 12.17 | A | C |
| ATOM | 5679 | CA | THR | A | 760 | 45.608 | 14.275 | 113.614 | 1.00 | 12.83 | A | C |
| ATOM | 5686 | CA | ASP | A | 761 | 46.374 | 17.270 | 115.851 | 1.00 | 13.13 | A | C |
| ATOM | 5694 | CA | THR | A | 762 | 47.486 | 19.473 | 112.939 | 1.00 | 10.45 | A | C |
| ATOM | 5701 | CA | ALA | A | 763 | 47.395 | 23.279 | 113.167 | 1.00 | 9.30 | A | C |
| ATOM | 5706 | CA | PRO | A | 764 | 44.545 | 24.274 | 110.760 | 1.00 | 8.86 | A | C |
| ATOM | 5713 | CA | ALA | A | 765 | 45.404 | 24.788 | 107.092 | 1.00 | 8.11 | A | C |
| ATOM | 5718 | CA | PHE | A | 766 | 44.495 | 27.881 | 105.084 | 1.00 | 9.09 | A | C |
| ATOM | 5729 | CA | SER | A | 767 | 40.845 | 28.777 | 104.561 | 1.00 | 9.56 | A | C |
| ATOM | 5735 | CA | MET | A | 768 | 39.792 | 32.266 | 103.433 | 1.00 | 11.12 | A | C |
| ATOM | 5743 | CA | SER | A | 769 | 37.000 | 32.501 | 106.061 | 1.00 | 14.28 | A | C |
| ATOM | 5749 | CA | THR | A | 770 | 39.217 | 31.636 | 109.046 | 1.00 | 17.50 | A | C |
| ATOM | 5756 | CA | ALA | A | 771 | 42.527 | 33.224 | 107.955 | 1.00 | 19.68 | A | C |
| ATOM | 5761 | CA | ASP | B | 8 | 33.160 | 32.500 | 141.172 | 1.00 | 18.72 | B | C |
| ATOM | 5769 | CA | TYR | B | 9 | 29.570 | 31.506 | 140.304 | 1.00 | 14.20 | B | C |
| ATOM | 5781 | CA | ALA | B | 10 | 28.422 | 31.895 | 143.925 | 1.00 | 10.68 | B | C |
| ATOM | 5786 | CA | SER | B | 11 | 29.320 | 35.614 | 143.693 | 1.00 | 10.07 | B | C |
| ATOM | 5792 | CA | LEU | B | 12 | 26.696 | 36.062 | 140.938 | 1.00 | 8.36 | B | C |
| ATOM | 5800 | CA | VAL | B | 13 | 23.923 | 34.801 | 143.242 | 1.00 | 6.94 | B | C |
| ATOM | 5807 | CA | ASP | B | 14 | 21.880 | 37.475 | 145.012 | 1.00 | 6.81 | B | C |
| ATOM | 5815 | CA | VAL | B | 15 | 20.179 | 35.726 | 147.955 | 1.00 | 4.17 | B | C |
| ATOM | 5822 | CA | PHE | B | 16 | 18.230 | 38.889 | 148.802 | 1.00 | 3.40 | B | C |
| ATOM | 5833 | CA | VAL | B | 17 | 16.289 | 38.686 | 145.547 | 1.00 | 3.53 | B | C |
| ATOM | 5840 | CA | GLY | B | 18 | 12.666 | 38.026 | 146.520 | 1.00 | 4.03 | B | C |
| ATOM | 5844 | CA | THR | B | 19 | 13.196 | 38.689 | 150.262 | 1.00 | 5.26 | B | C |
| ATOM | 5851 | CA | GLU | B | 20 | 10.979 | 41.797 | 150.516 | 1.00 | 5.53 | B | C |
| ATOM | 5860 | CA | GLY | B | 21 | 7.349 | 41.901 | 151.577 | 1.00 | 6.87 | B | C |
| ATOM | 5864 | CA | ASP | B | 22 | 5.019 | 39.846 | 149.439 | 1.00 | 6.61 | B | C |
| ATOM | 5872 | CA | PHE | B | 23 | 7.350 | 39.730 | 146.400 | 1.00 | 5.51 | B | C |
| ATOM | 5883 | CA | GLY | B | 24 | 8.458 | 36.090 | 146.362 | 1.00 | 4.07 | B | C |
| ATOM | 5887 | CA | ASN | B | 25 | 8.571 | 34.746 | 149.915 | 1.00 | 2.81 | B | C |
| ATOM | 5895 | CA | ASP | B | 26 | 12.206 | 33.663 | 149.535 | 1.00 | 3.13 | B | C |
| ATOM | 5903 | CA | MET | B | 27 | 14.936 | 33.714 | 152.197 | 1.00 | 4.16 | B | C |
| ATOM | 5911 | CA | PRO | B | 28 | 18.521 | 35.051 | 152.473 | 1.00 | 3.52 | B | C |
| ATOM | 5918 | CA | ALA | B | 29 | 19.101 | 32.077 | 154.801 | 1.00 | 2.82 | B | C |
| ATOM | 5923 | CA | ALA | B | 30 | 22.436 | 30.302 | 154.790 | 1.00 | 2.98 | B | C |

FIG. 34-12

| | | | | | | | | | | | | |
|---|---|---|---|---|---|---|---|---|---|---|---|---|
| ATOM | 5928 | CA | GLN | B | 31 | 21.896 | 26.852 | 153.161 | 1.00 | 4.61 | B | C |
| ATOM | 5937 | CA | ALA | B | 32 | 23.671 | 24.106 | 151.121 | 1.00 | 5.14 | B | C |
| ATOM | 5942 | CA | PRO | B | 33 | 22.280 | 22.821 | 147.805 | 1.00 | 6.54 | B | C |
| ATOM | 5949 | CA | ASN | B | 34 | 18.900 | 21.202 | 148.694 | 1.00 | 5.61 | B | C |
| ATOM | 5957 | CA | GLY | B | 35 | 19.876 | 21.616 | 152.349 | 1.00 | 4.62 | B | C |
| ATOM | 5961 | CA | LEU | B | 36 | 17.780 | 20.633 | 155.336 | 1.00 | 5.14 | B | C |
| ATOM | 5969 | CA | ALA | B | 37 | 19.361 | 23.299 | 157.533 | 1.00 | 3.87 | B | C |
| ATOM | 5974 | CA | LYS | B | 38 | 18.219 | 26.746 | 156.507 | 1.00 | 3.49 | B | C |
| ATOM | 5983 | CA | VAL | B | 39 | 19.767 | 29.259 | 158.889 | 1.00 | 3.32 | B | C |
| ATOM | 5990 | CA | ASN | B | 40 | 17.444 | 32.228 | 158.346 | 1.00 | 3.22 | B | C |
| ATOM | 5998 | CA | PRO | B | 41 | 17.676 | 35.552 | 160.107 | 1.00 | 3.73 | B | C |
| ATOM | 6005 | CA | ARG | B | 42 | 14.314 | 36.534 | 161.600 | 1.00 | 3.05 | B | C |
| ATOM | 6016 | CA | THR | B | 43 | 13.161 | 40.161 | 161.230 | 1.00 | 2.90 | B | C |
| ATOM | 6023 | CA | THR | B | 44 | 10.738 | 41.938 | 163.588 | 1.00 | 5.21 | B | C |
| ATOM | 6030 | CA | PRO | B | 45 | 8.030 | 43.161 | 163.977 | 1.00 | 6.45 | B | C |
| ATOM | 6037 | CA | GLY | B | 46 | 7.346 | 42.212 | 160.323 | 1.00 | 4.86 | B | C |
| ATOM | 6041 | CA | ARG | B | 47 | 8.581 | 39.247 | 158.248 | 1.00 | 4.58 | B | C |
| ATOM | 6052 | CA | ASN | B | 48 | 7.898 | 37.485 | 154.983 | 1.00 | 4.09 | B | C |
| ATOM | 6060 | CA | ASN | B | 49 | 6.685 | 33.858 | 155.217 | 1.00 | 4.78 | B | C |
| ATOM | 6068 | CA | THR | B | 50 | 10.246 | 32.518 | 155.744 | 1.00 | 4.39 | B | C |
| ATOM | 6075 | CA | GLY | B | 51 | 10.802 | 34.910 | 158.707 | 1.00 | 4.48 | B | C |
| ATOM | 6079 | CA | TYR | B | 52 | 12.692 | 37.754 | 157.012 | 1.00 | 5.15 | B | C |
| ATOM | 6091 | CA | ASP | B | 53 | 11.399 | 40.842 | 155.301 | 1.00 | 5.15 | B | C |
| ATOM | 6099 | CA | TYR | B | 54 | 14.064 | 43.028 | 153.656 | 1.00 | 5.43 | B | C |
| ATOM | 6111 | CA | ALA | B | 55 | 11.984 | 46.169 | 154.374 | 1.00 | 5.97 | B | C |
| ATOM | 6116 | CA | GLN | B | 56 | 12.446 | 45.769 | 158.155 | 1.00 | 6.73 | B | C |
| ATOM | 6125 | CA | SER | B | 57 | 15.268 | 47.086 | 160.349 | 1.00 | 7.18 | B | C |
| ATOM | 6131 | CA | LYS | B | 58 | 15.306 | 44.770 | 163.351 | 1.00 | 4.81 | B | C |
| ATOM | 6140 | CA | ILE | B | 59 | 16.408 | 41.138 | 163.680 | 1.00 | 4.41 | B | C |
| ATOM | 6148 | CA | SER | B | 60 | 15.847 | 38.827 | 166.673 | 1.00 | 4.63 | B | C |
| ATOM | 6154 | CA | GLY | B | 61 | 17.915 | 35.758 | 165.791 | 1.00 | 3.36 | B | C |
| ATOM | 6158 | CA | PHE | B | 62 | 18.275 | 32.810 | 163.426 | 1.00 | 3.48 | B | C |
| ATOM | 6169 | CA | THR | B | 63 | 15.870 | 29.935 | 162.748 | 1.00 | 3.46 | B | C |
| ATOM | 6176 | CA | HIS | B | 64 | 17.063 | 26.576 | 161.377 | 1.00 | 3.52 | B | C |
| ATOM | 6186 | CA | THR | B | 65 | 14.187 | 25.010 | 159.402 | 1.00 | 4.13 | B | C |
| ATOM | 6193 | CA | ASN | B | 66 | 12.141 | 26.467 | 156.576 | 1.00 | 4.29 | B | C |
| ATOM | 6201 | CA | LEU | B | 67 | 10.335 | 26.228 | 153.272 | 1.00 | 4.24 | B | C |
| ATOM | 6209 | CA | ASP | B | 68 | 11.312 | 28.351 | 150.252 | 1.00 | 4.81 | B | C |
| ATOM | 6217 | CA | GLY | B | 69 | 8.769 | 30.598 | 148.558 | 1.00 | 4.56 | B | C |
| ATOM | 6221 | CA | VAL | B | 70 | 5.589 | 29.149 | 150.102 | 1.00 | 3.51 | B | C |
| ATOM | 6228 | CA | GLY | B | 71 | 2.243 | 30.766 | 151.033 | 1.00 | 4.39 | B | C |
| ATOM | 6232 | CA | GLY | B | 72 | 0.165 | 30.889 | 154.256 | 1.00 | 5.93 | B | C |
| ATOM | 6236 | CA | SER | B | 73 | 2.360 | 32.159 | 157.086 | 1.00 | 5.71 | B | C |
| ATOM | 6242 | CA | GLY | B | 74 | 5.232 | 29.886 | 155.962 | 1.00 | 4.98 | B | C |
| ATOM | 6246 | CA | GLY | B | 75 | 6.527 | 26.565 | 157.216 | 1.00 | 4.40 | B | C |
| ATOM | 6250 | CA | GLY | B | 76 | 9.371 | 25.580 | 159.508 | 1.00 | 4.57 | B | C |
| ATOM | 6254 | CA | GLY | B | 77 | 10.953 | 28.443 | 161.386 | 1.00 | 3.39 | B | C |
| ATOM | 6258 | CA | ASP | B | 78 | 11.986 | 26.048 | 164.188 | 1.00 | 3.33 | B | C |
| ATOM | 6266 | CA | LEU | B | 79 | 14.888 | 26.547 | 166.612 | 1.00 | 5.32 | B | C |
| ATOM | 6274 | CA | LEU | B | 80 | 15.348 | 30.284 | 167.110 | 1.00 | 5.08 | B | C |
| ATOM | 6282 | CA | VAL | B | 81 | 18.851 | 31.213 | 168.309 | 1.00 | 4.86 | B | C |
| ATOM | 6289 | CA | VAL | B | 82 | 19.084 | 34.745 | 169.745 | 1.00 | 5.18 | B | C |
| ATOM | 6296 | CA | PRO | B | 83 | 22.375 | 36.414 | 170.798 | 1.00 | 5.18 | B | C |
| ATOM | 6303 | CA | THR | B | 84 | 22.055 | 38.823 | 173.750 | 1.00 | 4.92 | B | C |
| ATOM | 6310 | CA | SER | B | 85 | 24.059 | 40.445 | 176.538 | 1.00 | 3.51 | B | C |
| ATOM | 6316 | CA | GLY | B | 86 | 20.865 | 40.604 | 178.572 | 1.00 | 3.93 | B | C |
| ATOM | 6320 | CA | SER | B | 87 | 19.752 | 38.579 | 181.582 | 1.00 | 5.35 | B | C |
| ATOM | 6326 | CA | TYR | B | 88 | 16.498 | 36.652 | 182.221 | 1.00 | 5.05 | B | C |
| ATOM | 6338 | CA | THR | B | 89 | 14.650 | 35.335 | 185.336 | 1.00 | 5.80 | B | C |
| ATOM | 6345 | CA | ALA | B | 90 | 11.608 | 33.987 | 183.442 | 1.00 | 4.94 | B | C |
| ATOM | 6350 | CA | ARG | B | 91 | 10.687 | 32.820 | 179.933 | 1.00 | 5.95 | B | C |
| ATOM | 6361 | CA | PRO | B | 92 | 11.913 | 35.587 | 177.603 | 1.00 | 5.93 | B | C |
| ATOM | 6368 | CA | GLY | B | 93 | 9.414 | 38.047 | 176.166 | 1.00 | 5.97 | B | C |
| ATOM | 6372 | CA | THR | B | 94 | 9.767 | 37.813 | 172.371 | 1.00 | 6.48 | B | C |
| ATOM | 6379 | CA | GLY | B | 95 | 10.124 | 41.588 | 172.055 | 1.00 | 4.67 | B | C |
| ATOM | 6383 | CA | THR | B | 96 | 13.359 | 41.564 | 174.059 | 1.00 | 4.62 | B | C |

FIG. 34-13

| | | | | | | | | | | | | |
|---|---|---|---|---|---|---|---|---|---|---|---|---|
| ATOM | 6390 | CA | TYR | B | 97 | 15.098 | 39.627 | 171.228 | 1.00 | 4.32 | B | C |
| ATOM | 6402 | CA | ALA | B | 98 | 15.015 | 42.620 | 168.846 | 1.00 | 4.26 | B | C |
| ATOM | 6407 | CA | HIS | B | 99 | 18.311 | 44.130 | 167.648 | 1.00 | 4.45 | B | C |
| ATOM | 6417 | CA | PRO | B | 100 | 18.684 | 47.027 | 165.199 | 1.00 | 4.56 | B | C |
| ATOM | 6424 | CA | PHE | B | 101 | 20.304 | 46.145 | 161.878 | 1.00 | 5.62 | B | C |
| ATOM | 6435 | CA | SER | B | 102 | 21.236 | 47.834 | 158.588 | 1.00 | 6.73 | B | C |
| ATOM | 6441 | CA | HIS | B | 103 | 21.603 | 46.324 | 155.111 | 1.00 | 7.29 | B | C |
| ATOM | 6451 | CA | ASP | B | 104 | 24.879 | 48.336 | 155.037 | 1.00 | 9.91 | B | C |
| ATOM | 6459 | CA | ASP | B | 105 | 26.290 | 45.946 | 157.703 | 1.00 | 10.20 | B | C |
| ATOM | 6467 | CA | GLU | B | 106 | 24.917 | 42.703 | 156.229 | 1.00 | 9.23 | B | C |
| ATOM | 6476 | CA | ASP | B | 107 | 26.499 | 40.286 | 153.765 | 1.00 | 9.46 | B | C |
| ATOM | 6484 | CA | ALA | B | 108 | 25.242 | 36.970 | 152.370 | 1.00 | 6.84 | B | C |
| ATOM | 6489 | CA | GLY | B | 109 | 25.559 | 34.488 | 149.524 | 1.00 | 4.80 | B | C |
| ATOM | 6493 | CA | PRO | B | 110 | 25.491 | 30.714 | 148.861 | 1.00 | 4.09 | B | C |
| ATOM | 6500 | CA | GLY | B | 111 | 26.276 | 29.034 | 152.198 | 1.00 | 4.03 | B | C |
| ATOM | 6504 | CA | PHE | B | 112 | 26.451 | 32.010 | 154.507 | 1.00 | 4.63 | B | C |
| ATOM | 6515 | CA | TYR | B | 113 | 24.841 | 35.051 | 156.062 | 1.00 | 4.43 | B | C |
| ATOM | 6527 | CA | SER | B | 114 | 26.381 | 37.783 | 158.200 | 1.00 | 5.09 | B | C |
| ATOM | 6533 | CA | VAL | B | 115 | 24.962 | 40.865 | 159.954 | 1.00 | 4.89 | B | C |
| ATOM | 6540 | CA | GLY | B | 116 | 25.874 | 43.467 | 162.573 | 1.00 | 6.35 | B | C |
| ATOM | 6544 | CA | LEU | B | 117 | 23.215 | 43.427 | 165.294 | 1.00 | 6.43 | B | C |
| ATOM | 6552 | CA | GLY | B | 118 | 22.939 | 46.299 | 167.802 | 1.00 | 6.20 | B | C |
| ATOM | 6556 | CA | ASN | B | 119 | 23.960 | 44.928 | 171.238 | 1.00 | 5.86 | B | C |
| ATOM | 6564 | CA | VAL | B | 120 | 21.162 | 44.472 | 173.803 | 1.00 | 4.83 | B | C |
| ATOM | 6571 | CA | ALA | B | 121 | 21.260 | 44.132 | 177.613 | 1.00 | 4.23 | B | C |
| ATOM | 6576 | CA | GLY | B | 122 | 19.365 | 44.559 | 180.892 | 1.00 | 4.26 | B | C |
| ATOM | 6580 | CA | THR | B | 123 | 16.919 | 42.174 | 182.582 | 1.00 | 5.43 | B | C |
| ATOM | 6587 | CA | ASP | B | 124 | 13.711 | 40.546 | 181.298 | 1.00 | 5.91 | B | C |
| ATOM | 6595 | CA | GLY | B | 125 | 11.132 | 43.006 | 179.823 | 1.00 | 6.02 | B | C |
| ATOM | 6599 | CA | ALA | B | 126 | 13.463 | 45.973 | 180.415 | 1.00 | 5.90 | B | C |
| ATOM | 6604 | CA | ILE | B | 127 | 16.092 | 44.620 | 177.976 | 1.00 | 5.52 | B | C |
| ATOM | 6612 | CA | THR | B | 128 | 17.063 | 47.192 | 175.369 | 1.00 | 4.75 | B | C |
| ATOM | 6619 | CA | GLY | B | 129 | 19.991 | 48.703 | 173.407 | 1.00 | 4.79 | B | C |
| ATOM | 6623 | CA | ALA | B | 130 | 23.437 | 48.378 | 175.037 | 1.00 | 5.28 | B | C |
| ATOM | 6628 | CA | PRO | B | 131 | 26.932 | 49.536 | 173.894 | 1.00 | 5.84 | B | C |
| ATOM | 6635 | CA | GLY | B | 132 | 28.389 | 48.225 | 170.633 | 1.00 | 5.70 | B | C |
| ATOM | 6639 | CA | THR | B | 133 | 27.548 | 45.592 | 168.062 | 1.00 | 6.06 | B | C |
| ATOM | 6646 | CA | ILE | B | 134 | 27.013 | 41.848 | 168.174 | 1.00 | 7.11 | B | C |
| ATOM | 6654 | CA | GLU | B | 135 | 28.833 | 40.654 | 165.045 | 1.00 | 8.84 | B | C |
| ATOM | 6663 | CA | ALA | B | 136 | 26.820 | 37.651 | 163.802 | 1.00 | 6.10 | B | C |
| ATOM | 6668 | CA | GLU | B | 137 | 27.966 | 35.088 | 161.226 | 1.00 | 4.63 | B | C |
| ATOM | 6677 | CA | VAL | B | 138 | 26.200 | 31.897 | 160.196 | 1.00 | 3.25 | B | C |
| ATOM | 6684 | CA | ALA | B | 139 | 26.905 | 29.212 | 157.622 | 1.00 | 3.25 | B | C |
| ATOM | 6689 | CA | ALA | B | 140 | 25.244 | 25.933 | 156.657 | 1.00 | 4.37 | B | C |
| ATOM | 6694 | CA | ALA | B | 141 | 26.177 | 22.444 | 155.558 | 1.00 | 5.98 | B | C |
| ATOM | 6699 | CA | THR | B | 142 | 23.483 | 19.964 | 154.381 | 1.00 | 4.34 | B | C |
| ATOM | 6706 | CA | ARG | B | 143 | 22.140 | 19.123 | 157.865 | 1.00 | 4.38 | B | C |
| ATOM | 6717 | CA | SER | B | 144 | 23.954 | 21.728 | 159.957 | 1.00 | 4.49 | B | C |
| ATOM | 6723 | CA | GLY | B | 145 | 23.839 | 25.419 | 160.895 | 1.00 | 5.05 | B | C |
| ATOM | 6727 | CA | VAL | B | 146 | 26.994 | 26.868 | 162.414 | 1.00 | 4.62 | B | C |
| ATOM | 6734 | CA | HIS | B | 147 | 27.242 | 30.186 | 164.272 | 1.00 | 4.38 | B | C |
| ATOM | 6744 | CA | ARG | B | 148 | 30.103 | 32.540 | 165.208 | 1.00 | 4.25 | B | C |
| ATOM | 6755 | CA | TYR | B | 149 | 29.335 | 35.704 | 167.264 | 1.00 | 4.46 | B | C |
| ATOM | 6767 | CA | ALA | B | 150 | 31.522 | 38.561 | 168.553 | 1.00 | 5.60 | B | C |
| ATOM | 6772 | CA | PHE | B | 151 | 30.094 | 40.472 | 171.553 | 1.00 | 6.42 | B | C |
| ATOM | 6783 | CA | PRO | B | 152 | 31.380 | 43.820 | 172.738 | 1.00 | 8.35 | B | C |
| ATOM | 6790 | CA | ALA | B | 153 | 34.133 | 43.586 | 175.369 | 1.00 | 8.99 | B | C |
| ATOM | 6795 | CA | GLY | B | 154 | 32.667 | 43.385 | 178.865 | 1.00 | 8.42 | B | C |
| ATOM | 6799 | CA | SER | B | 155 | 29.390 | 41.759 | 177.743 | 1.00 | 8.54 | B | C |
| ATOM | 6805 | CA | THR | B | 156 | 28.171 | 38.643 | 179.484 | 1.00 | 7.06 | B | C |
| ATOM | 6812 | CA | PRO | B | 157 | 27.319 | 36.804 | 176.247 | 1.00 | 7.08 | B | C |
| ATOM | 6819 | CA | SER | B | 158 | 24.232 | 34.650 | 176.044 | 1.00 | 6.71 | B | C |
| ATOM | 6825 | CA | LEU | B | 159 | 22.370 | 32.582 | 173.502 | 1.00 | 4.87 | B | C |
| ATOM | 6833 | CA | VAL | B | 160 | 18.646 | 31.941 | 173.847 | 1.00 | 3.09 | B | C |
| ATOM | 6840 | CA | VAL | B | 161 | 17.419 | 28.777 | 172.147 | 1.00 | 3.34 | B | C |
| ATOM | 6847 | CA | ASP | B | 162 | 13.682 | 29.337 | 171.720 | 1.00 | 4.07 | B | C |

FIG. 34-14

| | | | | | | | | | | | | |
|---|---|---|---|---|---|---|---|---|---|---|---|---|
| ATOM | 6855 | CA | LEU | B | 163 | 11.876 | 26.065 | 170.870 | 1.00 | 3.79 | B | C |
| ATOM | 6863 | CA | GLU | B | 164 | 8.402 | 27.636 | 170.688 | 1.00 | 4.18 | B | C |
| ATOM | 6872 | CA | THR | B | 165 | 9.046 | 29.648 | 167.474 | 1.00 | 2.64 | B | C |
| ATOM | 6879 | CA | ASN | B | 166 | 7.417 | 28.351 | 164.312 | 1.00 | 2.42 | B | C |
| ATOM | 6887 | CA | ASN | B | 167 | 6.159 | 30.090 | 161.193 | 1.00 | 2.44 | B | C |
| ATOM | 6895 | CA | THR | B | 168 | 2.700 | 28.469 | 161.520 | 1.00 | 2.77 | B | C |
| ATOM | 6902 | CA | SER | B | 169 | 2.191 | 26.088 | 164.470 | 1.00 | 3.44 | B | C |
| ATOM | 6908 | CA | ARG | B | 170 | 4.367 | 24.663 | 167.209 | 1.00 | 3.61 | B | C |
| ATOM | 6919 | CA | ARG | B | 171 | 2.777 | 21.329 | 168.092 | 1.00 | 4.09 | B | C |
| ATOM | 6930 | CA | SER | B | 172 | 5.367 | 20.136 | 170.618 | 1.00 | 3.92 | B | C |
| ATOM | 6936 | CA | SER | B | 173 | 9.026 | 20.436 | 171.605 | 1.00 | 4.52 | B | C |
| ATOM | 6942 | CA | SER | B | 174 | 11.644 | 19.095 | 174.010 | 1.00 | 5.26 | B | C |
| ATOM | 6948 | CA | VAL | B | 175 | 15.144 | 19.964 | 175.194 | 1.00 | 7.61 | B | C |
| ATOM | 6955 | CA | GLN | B | 176 | 17.707 | 17.942 | 177.116 | 1.00 | 9.87 | B | C |
| ATOM | 6964 | CA | VAL | B | 177 | 20.827 | 19.575 | 178.479 | 1.00 | 10.75 | B | C |
| ATOM | 6971 | CA | GLU | B | 178 | 24.266 | 17.972 | 178.853 | 1.00 | 11.75 | B | C |
| ATOM | 6980 | CA | THR | B | 179 | 27.408 | 19.621 | 180.271 | 1.00 | 10.76 | B | C |
| ATOM | 6987 | CA | ARG | B | 180 | 30.637 | 17.869 | 179.161 | 1.00 | 11.07 | B | C |
| ATOM | 6998 | CA | ALA | B | 181 | 34.052 | 17.533 | 180.867 | 1.00 | 12.22 | B | C |
| ATOM | 7003 | CA | ASP | B | 182 | 35.476 | 20.584 | 179.033 | 1.00 | 11.74 | B | C |
| ATOM | 7011 | CA | GLY | B | 183 | 32.508 | 22.707 | 180.228 | 1.00 | 9.15 | B | C |
| ATOM | 7015 | CA | THR | B | 184 | 30.755 | 22.961 | 176.837 | 1.00 | 5.80 | B | C |
| ATOM | 7022 | CA | VAL | B | 185 | 27.013 | 22.306 | 176.541 | 1.00 | 5.32 | B | C |
| ATOM | 7029 | CA | GLU | B | 186 | 24.991 | 20.053 | 174.245 | 1.00 | 6.37 | B | C |
| ATOM | 7038 | CA | LEU | B | 187 | 21.225 | 20.551 | 173.801 | 1.00 | 5.44 | B | C |
| ATOM | 7046 | CA | SER | B | 188 | 19.138 | 17.900 | 172.108 | 1.00 | 4.09 | B | C |
| ATOM | 7052 | CA | GLY | B | 189 | 15.468 | 17.073 | 171.486 | 1.00 | 3.12 | B | C |
| ATOM | 7056 | CA | GLN | B | 190 | 12.682 | 17.282 | 168.938 | 1.00 | 2.37 | B | C |
| ATOM | 7065 | CA | VAL | B | 191 | 10.502 | 19.973 | 167.357 | 1.00 | 2.26 | B | C |
| ATOM | 7072 | CA | THR | B | 192 | 7.128 | 19.112 | 165.863 | 1.00 | 2.53 | B | C |
| ATOM | 7079 | CA | GLY | B | 193 | 5.491 | 21.715 | 163.683 | 1.00 | 2.57 | B | C |
| ATOM | 7083 | CA | TYR | B | 194 | 2.613 | 21.951 | 161.250 | 1.00 | 3.30 | B | C |
| ATOM | 7095 | CA | PHE | B | 195 | 2.176 | 23.583 | 157.852 | 1.00 | 4.28 | B | C |
| ATOM | 7106 | CA | TYR | B | 196 | -0.598 | 23.421 | 155.296 | 1.00 | 7.19 | B | C |
| ATOM | 7118 | CA | ASN | B | 197 | -1.557 | 19.737 | 155.149 | 1.00 | 7.00 | B | C |
| ATOM | 7126 | CA | ALA | B | 198 | 0.738 | 17.907 | 157.606 | 1.00 | 5.17 | B | C |
| ATOM | 7131 | CA | ALA | B | 199 | 2.648 | 17.834 | 160.876 | 1.00 | 4.90 | B | C |
| ATOM | 7136 | CA | TYR | B | 200 | 6.409 | 17.069 | 160.789 | 1.00 | 4.22 | B | C |
| ATOM | 7148 | CA | THR | B | 201 | 9.101 | 16.185 | 163.362 | 1.00 | 5.31 | B | C |
| ATOM | 7155 | CA | LEU | B | 202 | 12.799 | 16.977 | 163.328 | 1.00 | 3.48 | B | C |
| ATOM | 7163 | CA | TYR | B | 203 | 15.415 | 15.973 | 165.896 | 1.00 | 3.48 | B | C |
| ATOM | 7175 | CA | TYR | B | 204 | 18.277 | 18.294 | 166.724 | 1.00 | 4.54 | B | C |
| ATOM | 7187 | CA | THR | B | 205 | 21.584 | 18.490 | 168.504 | 1.00 | 5.64 | B | C |
| ATOM | 7194 | CA | ALA | B | 206 | 23.308 | 21.765 | 169.341 | 1.00 | 5.72 | B | C |
| ATOM | 7199 | CA | ARG | B | 207 | 26.654 | 22.253 | 170.998 | 1.00 | 5.49 | B | C |
| ATOM | 7210 | CA | THR | B | 208 | 28.601 | 25.232 | 172.226 | 1.00 | 4.80 | B | C |
| ATOM | 7217 | CA | LEU | B | 209 | 32.264 | 25.598 | 171.305 | 1.00 | 4.71 | B | C |
| ATOM | 7225 | CA | GLN | B | 210 | 33.041 | 27.516 | 174.554 | 1.00 | 6.35 | B | C |
| ATOM | 7234 | CA | PRO | B | 211 | 32.110 | 26.663 | 178.148 | 1.00 | 7.67 | B | C |
| ATOM | 7241 | CA | ALA | B | 212 | 28.543 | 27.611 | 179.143 | 1.00 | 7.25 | B | C |
| ATOM | 7246 | CA | THR | B | 213 | 26.099 | 27.434 | 182.004 | 1.00 | 7.17 | B | C |
| ATOM | 7253 | CA | VAL | B | 214 | 22.470 | 26.720 | 181.121 | 1.00 | 6.69 | B | C |
| ATOM | 7260 | CA | GLN | B | 215 | 18.911 | 27.268 | 182.283 | 1.00 | 6.38 | B | C |
| ATOM | 7269 | CA | THR | B | 216 | 15.794 | 25.836 | 180.631 | 1.00 | 4.98 | B | C |
| ATOM | 7276 | CA | TRP | B | 217 | 12.111 | 26.702 | 180.466 | 1.00 | 3.64 | B | C |
| ATOM | 7290 | CA | GLY | B | 218 | 8.884 | 24.866 | 180.016 | 1.00 | 5.63 | B | C |
| ATOM | 7294 | CA | ASP | B | 219 | 5.244 | 25.649 | 179.622 | 1.00 | 8.12 | B | C |
| ATOM | 7302 | CA | ASP | B | 220 | 4.977 | 27.146 | 183.127 | 1.00 | 12.50 | B | C |
| ATOM | 7310 | CA | ASP | B | 221 | 7.168 | 30.093 | 181.953 | 1.00 | 12.91 | B | C |
| ATOM | 7318 | CA | ARG | B | 222 | 9.634 | 29.500 | 184.787 | 1.00 | 11.75 | B | C |
| ATOM | 7329 | CA | LEU | B | 223 | 13.374 | 29.633 | 184.047 | 1.00 | 9.26 | B | C |
| ATOM | 7337 | CA | VAL | B | 224 | 15.093 | 26.886 | 186.002 | 1.00 | 9.70 | B | C |
| ATOM | 7344 | CA | ASP | B | 225 | 18.254 | 24.870 | 186.542 | 1.00 | 9.71 | B | C |
| ATOM | 7352 | CA | ALA | B | 226 | 16.446 | 21.645 | 185.479 | 1.00 | 8.94 | B | C |
| ATOM | 7357 | CA | THR | B | 227 | 18.172 | 19.922 | 182.585 | 1.00 | 8.94 | B | C |
| ATOM | 7364 | CA | ALA | B | 228 | 15.027 | 18.498 | 180.872 | 1.00 | 8.41 | B | C |

FIG. 34-15

| | | | | | | | | | | | | |
|---|---|---|---|---|---|---|---|---|---|---|---|---|
| ATOM | 7369 | CA | GLN | B | 229 | 11.887 | 19.991 | 179.343 | 1.00 | 7.11 | B | C |
| ATOM | 7378 | CA | ASP | B | 230 | 9.154 | 18.361 | 177.262 | 1.00 | 7.62 | B | C |
| ATOM | 7386 | CA | GLY | B | 231 | 5.982 | 20.180 | 176.272 | 1.00 | 5.49 | B | C |
| ATOM | 7390 | CA | VAL | B | 232 | 5.019 | 22.814 | 173.687 | 1.00 | 3.91 | B | C |
| ATOM | 7397 | CA | ASP | B | 233 | 6.717 | 26.124 | 174.666 | 1.00 | 3.59 | B | C |
| ATOM | 7405 | CA | THR | B | 234 | 10.207 | 25.219 | 175.870 | 1.00 | 3.22 | B | C |
| ATOM | 7412 | CA | GLY | B | 235 | 13.760 | 26.456 | 175.485 | 1.00 | 2.52 | B | C |
| ATOM | 7416 | CA | ALA | B | 236 | 17.165 | 27.054 | 176.932 | 1.00 | 2.01 | B | C |
| ATOM | 7421 | CA | ILE | B | 237 | 19.409 | 30.014 | 177.730 | 1.00 | 2.62 | B | C |
| ATOM | 7429 | CA | LEU | B | 238 | 23.188 | 29.544 | 177.393 | 1.00 | 3.80 | B | C |
| ATOM | 7437 | CA | THR | B | 239 | 25.439 | 31.941 | 179.352 | 1.00 | 5.81 | B | C |
| ATOM | 7444 | CA | PHE | B | 240 | 29.137 | 32.391 | 178.663 | 1.00 | 7.71 | B | C |
| ATOM | 7455 | CA | ASP | B | 241 | 32.053 | 34.026 | 180.461 | 1.00 | 10.49 | B | C |
| ATOM | 7463 | CA | PRO | B | 242 | 32.976 | 37.585 | 179.419 | 1.00 | 10.21 | B | C |
| ATOM | 7470 | CA | ALA | B | 243 | 36.482 | 36.270 | 178.652 | 1.00 | 10.56 | B | C |
| ATOM | 7475 | CA | ASP | B | 244 | 34.898 | 34.545 | 175.608 | 1.00 | 10.22 | B | C |
| ATOM | 7483 | CA | ALA | B | 245 | 32.993 | 37.584 | 174.265 | 1.00 | 9.19 | B | C |
| ATOM | 7488 | CA | GLY | B | 246 | 35.260 | 37.861 | 171.199 | 1.00 | 9.07 | B | C |
| ATOM | 7492 | CA | GLU | B | 247 | 34.117 | 34.471 | 169.883 | 1.00 | 8.40 | B | C |
| ATOM | 7501 | CA | ILE | B | 248 | 30.976 | 32.504 | 170.743 | 1.00 | 6.26 | B | C |
| ATOM | 7509 | CA | GLY | B | 249 | 30.419 | 29.317 | 168.700 | 1.00 | 5.26 | B | C |
| ATOM | 7513 | CA | LEU | B | 250 | 27.365 | 27.148 | 168.128 | 1.00 | 4.75 | B | C |
| ATOM | 7521 | CA | GLN | B | 251 | 26.729 | 24.080 | 165.940 | 1.00 | 4.54 | B | C |
| ATOM | 7530 | CA | VAL | B | 252 | 23.221 | 22.815 | 165.229 | 1.00 | 4.09 | B | C |
| ATOM | 7537 | CA | THR | B | 253 | 22.517 | 19.573 | 163.382 | 1.00 | 3.14 | B | C |
| ATOM | 7544 | CA | LEU | B | 254 | 19.085 | 18.325 | 162.254 | 1.00 | 3.66 | B | C |
| ATOM | 7552 | CA | SER | B | 255 | 17.710 | 14.818 | 161.568 | 1.00 | 3.72 | B | C |
| ATOM | 7558 | CA | PRO | B | 256 | 14.350 | 13.322 | 160.581 | 1.00 | 3.90 | B | C |
| ATOM | 7565 | CA | VAL | B | 257 | 15.675 | 10.122 | 162.247 | 1.00 | 4.49 | B | C |
| ATOM | 7572 | CA | SER | B | 258 | 16.553 | 10.685 | 165.919 | 1.00 | 5.09 | B | C |
| ATOM | 7578 | CA | VAL | B | 259 | 18.811 | 12.681 | 168.270 | 1.00 | 6.85 | B | C |
| ATOM | 7585 | CA | GLU | B | 260 | 21.309 | 9.841 | 168.225 | 1.00 | 8.56 | B | C |
| ATOM | 7594 | CA | GLN | B | 261 | 21.425 | 10.162 | 164.416 | 1.00 | 7.14 | B | C |
| ATOM | 7603 | CA | ALA | B | 262 | 21.764 | 13.965 | 164.573 | 1.00 | 6.00 | B | C |
| ATOM | 7608 | CA | ARG | B | 263 | 24.840 | 13.567 | 166.780 | 1.00 | 6.59 | B | C |
| ATOM | 7619 | CA | ILE | B | 264 | 26.315 | 11.008 | 164.363 | 1.00 | 7.36 | B | C |
| ATOM | 7627 | CA | ASP | B | 265 | 25.571 | 13.292 | 161.370 | 1.00 | 6.50 | B | C |
| ATOM | 7635 | CA | GLN | B | 266 | 27.201 | 16.188 | 163.205 | 1.00 | 7.37 | B | C |
| ATOM | 7644 | CA | GLN | B | 267 | 30.403 | 14.178 | 163.786 | 1.00 | 11.20 | B | C |
| ATOM | 7653 | CA | VAL | B | 268 | 30.481 | 13.075 | 160.124 | 1.00 | 10.88 | B | C |
| ATOM | 7660 | CA | GLU | B | 269 | 29.430 | 16.369 | 158.505 | 1.00 | 11.16 | B | C |
| ATOM | 7669 | CA | LEU | B | 270 | 31.314 | 18.882 | 160.704 | 1.00 | 10.96 | B | C |
| ATOM | 7677 | CA | GLY | B | 271 | 33.869 | 16.943 | 162.740 | 1.00 | 11.80 | B | C |
| ATOM | 7681 | CA | ASP | B | 272 | 36.639 | 19.186 | 164.002 | 1.00 | 11.87 | B | C |
| ATOM | 7689 | CA | LEU | B | 273 | 36.374 | 21.606 | 161.059 | 1.00 | 9.30 | B | C |
| ATOM | 7697 | CA | SER | B | 274 | 36.585 | 25.316 | 161.684 | 1.00 | 8.10 | B | C |
| ATOM | 7703 | CA | PHE | B | 275 | 33.692 | 27.729 | 161.001 | 1.00 | 7.57 | B | C |
| ATOM | 7714 | CA | ASP | B | 276 | 35.633 | 29.179 | 158.049 | 1.00 | 9.11 | B | C |
| ATOM | 7722 | CA | ALA | B | 277 | 36.288 | 25.679 | 156.588 | 1.00 | 8.17 | B | C |
| ATOM | 7727 | CA | ILE | B | 278 | 32.607 | 24.690 | 156.805 | 1.00 | 6.31 | B | C |
| ATOM | 7735 | CA | ARG | B | 279 | 31.510 | 27.935 | 155.180 | 1.00 | 7.50 | B | C |
| ATOM | 7746 | CA | ASP | B | 280 | 34.193 | 27.585 | 152.447 | 1.00 | 8.14 | B | C |
| ATOM | 7754 | CA | ARG | B | 281 | 33.248 | 23.952 | 151.718 | 1.00 | 7.53 | B | C |
| ATOM | 7765 | CA | THR | B | 282 | 29.590 | 24.914 | 151.207 | 1.00 | 7.03 | B | C |
| ATOM | 7772 | CA | ARG | B | 283 | 30.749 | 27.741 | 148.908 | 1.00 | 8.06 | B | C |
| ATOM | 7783 | CA | ALA | B | 284 | 32.685 | 25.192 | 146.809 | 1.00 | 7.18 | B | C |
| ATOM | 7788 | CA | GLU | B | 285 | 29.647 | 22.838 | 146.826 | 1.00 | 8.04 | B | C |
| ATOM | 7797 | CA | TRP | B | 286 | 27.513 | 25.684 | 145.409 | 1.00 | 6.44 | B | C |
| ATOM | 7811 | CA | ASN | B | 287 | 30.194 | 26.541 | 142.822 | 1.00 | 7.77 | B | C |
| ATOM | 7819 | CA | ALA | B | 288 | 30.163 | 22.844 | 141.765 | 1.00 | 8.01 | B | C |
| ATOM | 7824 | CA | THR | B | 289 | 26.340 | 22.924 | 141.481 | 1.00 | 7.57 | B | C |
| ATOM | 7831 | CA | LEU | B | 290 | 25.928 | 26.258 | 139.687 | 1.00 | 6.68 | B | C |
| ATOM | 7839 | CA | GLY | B | 291 | 28.902 | 25.412 | 137.486 | 1.00 | 8.30 | B | C |
| ATOM | 7843 | CA | ARG | B | 292 | 26.832 | 22.721 | 135.807 | 1.00 | 8.97 | B | C |
| ATOM | 7854 | CA | VAL | B | 293 | 25.594 | 25.636 | 133.725 | 1.00 | 10.54 | B | C |
| ATOM | 7861 | CA | ALA | B | 294 | 28.121 | 27.918 | 132.046 | 1.00 | 12.46 | B | C |

FIG. 34-16

| | | | | | | | | | | | | |
|---|---|---|---|---|---|---|---|---|---|---|---|---|
| ATOM | 7866 | CA | ILE | B | 295 | 26.911 | 31.025 | 130.202 | 1.00 | 15.01 | B | C |
| ATOM | 7874 | CA | ASP | B | 296 | 28.503 | 33.444 | 127.742 | 1.00 | 16.68 | B | C |
| ATOM | 7882 | CA | ALA | B | 297 | 26.492 | 36.686 | 127.506 | 1.00 | 16.02 | B | C |
| ATOM | 7887 | CA | SER | B | 298 | 27.400 | 39.653 | 125.271 | 1.00 | 15.25 | B | C |
| ATOM | 7893 | CA | THR | B | 299 | 26.635 | 43.276 | 126.121 | 1.00 | 14.42 | B | C |
| ATOM | 7900 | CA | ALA | B | 300 | 24.046 | 43.110 | 123.326 | 1.00 | 11.48 | B | C |
| ATOM | 7905 | CA | THR | B | 301 | 21.783 | 40.582 | 125.103 | 1.00 | 9.84 | B | C |
| ATOM | 7912 | CA | ASP | B | 302 | 22.704 | 41.528 | 128.706 | 1.00 | 9.77 | B | C |
| ATOM | 7920 | CA | PRO | B | 303 | 23.868 | 45.197 | 128.715 | 1.00 | 10.54 | B | C |
| ATOM | 7927 | CA | THR | B | 304 | 23.489 | 45.589 | 132.512 | 1.00 | 11.07 | B | C |
| ATOM | 7934 | CA | GLY | B | 305 | 24.761 | 42.154 | 133.524 | 1.00 | 11.11 | B | C |
| ATOM | 7938 | CA | GLU | B | 306 | 21.483 | 41.714 | 135.432 | 1.00 | 10.64 | B | C |
| ATOM | 7947 | CA | LEU | B | 307 | 20.268 | 38.736 | 133.293 | 1.00 | 10.30 | B | C |
| ATOM | 7955 | CA | GLN | B | 308 | 23.365 | 36.685 | 134.127 | 1.00 | 10.19 | B | C |
| ATOM | 7964 | CA | ARG | B | 309 | 22.914 | 37.468 | 137.835 | 1.00 | 8.46 | B | C |
| ATOM | 7975 | CA | LEU | B | 310 | 19.207 | 36.600 | 137.644 | 1.00 | 6.90 | B | C |
| ATOM | 7983 | CA | PHE | B | 311 | 20.109 | 33.341 | 135.894 | 1.00 | 5.42 | B | C |
| ATOM | 7994 | CA | TYR | B | 312 | 22.509 | 32.208 | 138.679 | 1.00 | 4.65 | B | C |
| ATOM | 8006 | CA | THR | B | 313 | 20.288 | 33.567 | 141.446 | 1.00 | 3.72 | B | C |
| ATOM | 8013 | CA | HIS | B | 314 | 17.411 | 31.465 | 140.078 | 1.00 | 3.77 | B | C |
| ATOM | 8023 | CA | LEU | B | 315 | 19.597 | 28.424 | 139.419 | 1.00 | 4.98 | B | C |
| ATOM | 8031 | CA | TYR | B | 316 | 20.467 | 28.753 | 143.144 | 1.00 | 4.55 | B | C |
| ATOM | 8043 | CA | ARG | B | 317 | 16.731 | 28.839 | 144.007 | 1.00 | 5.20 | B | C |
| ATOM | 8054 | CA | MET | B | 318 | 16.085 | 25.817 | 141.789 | 1.00 | 7.54 | B | C |
| ATOM | 8062 | CA | PHE | B | 319 | 18.175 | 23.558 | 144.063 | 1.00 | 8.02 | B | C |
| ATOM | 8073 | CA | ALA | B | 320 | 16.316 | 24.249 | 147.345 | 1.00 | 7.25 | B | C |
| ATOM | 8078 | CA | MET | B | 321 | 13.403 | 21.781 | 147.467 | 1.00 | 5.88 | B | C |
| ATOM | 8086 | CA | PRO | B | 322 | 12.863 | 18.952 | 147.903 | 1.00 | 4.25 | B | C |
| ATOM | 8093 | CA | MET | B | 323 | 15.380 | 18.850 | 150.760 | 1.00 | 3.69 | B | C |
| ATOM | 8101 | CA | ASN | B | 324 | 17.944 | 16.177 | 151.447 | 1.00 | 3.38 | B | C |
| ATOM | 8109 | CA | ALA | B | 325 | 16.107 | 14.123 | 154.077 | 1.00 | 3.72 | B | C |
| ATOM | 8114 | CA | THR | B | 326 | 18.714 | 11.357 | 154.443 | 1.00 | 3.39 | B | C |
| ATOM | 8121 | CA | SER | B | 327 | 21.071 | 10.805 | 157.383 | 1.00 | 4.75 | B | C |
| ATOM | 8127 | CA | THR | B | 328 | 24.861 | 10.478 | 156.953 | 1.00 | 5.56 | B | C |
| ATOM | 8134 | CA | SER | B | 329 | 24.175 | 6.783 | 157.673 | 1.00 | 5.03 | B | C |
| ATOM | 8140 | CA | GLY | B | 330 | 21.990 | 6.586 | 154.509 | 1.00 | 5.56 | B | C |
| ATOM | 8144 | CA | THR | B | 331 | 18.681 | 6.308 | 156.385 | 1.00 | 4.67 | B | C |
| ATOM | 8151 | CA | TYR | B | 332 | 15.380 | 8.194 | 156.221 | 1.00 | 4.08 | B | C |
| ATOM | 8163 | CA | ARG | B | 333 | 12.110 | 8.234 | 158.156 | 1.00 | 5.90 | B | C |
| ATOM | 8174 | CA | GLY | B | 334 | 8.940 | 7.045 | 156.393 | 1.00 | 7.33 | B | C |
| ATOM | 8178 | CA | VAL | B | 335 | 5.362 | 8.276 | 156.776 | 1.00 | 9.86 | B | C |
| ATOM | 8185 | CA | ASP | B | 336 | 4.715 | 4.745 | 158.108 | 1.00 | 11.83 | B | C |
| ATOM | 8193 | CA | GLY | B | 337 | 6.472 | 5.889 | 161.292 | 1.00 | 12.67 | B | C |
| ATOM | 8197 | CA | ALA | B | 338 | 9.546 | 3.712 | 160.784 | 1.00 | 10.29 | B | C |
| ATOM | 8202 | CA | VAL | B | 339 | 13.181 | 4.400 | 159.827 | 1.00 | 8.36 | B | C |
| ATOM | 8209 | CA | HIS | B | 340 | 14.277 | 2.783 | 156.523 | 1.00 | 8.22 | B | C |
| ATOM | 8219 | CA | ALA | B | 341 | 17.345 | 2.468 | 154.295 | 1.00 | 9.30 | B | C |
| ATOM | 8224 | CA | ALA | B | 342 | 17.738 | 4.699 | 151.232 | 1.00 | 10.96 | B | C |
| ATOM | 8229 | CA | GLN | B | 343 | 19.736 | 1.973 | 149.549 | 1.00 | 14.92 | B | C |
| ATOM | 8238 | CA | GLY | B | 344 | 22.061 | 3.243 | 146.798 | 1.00 | 14.18 | B | C |
| ATOM | 8242 | CA | PHE | B | 345 | 20.330 | 6.658 | 146.470 | 1.00 | 9.94 | B | C |
| ATOM | 8253 | CA | THR | B | 346 | 19.663 | 9.851 | 148.454 | 1.00 | 5.70 | B | C |
| ATOM | 8260 | CA | TYR | B | 347 | 16.132 | 10.341 | 149.769 | 1.00 | 3.08 | B | C |
| ATOM | 8272 | CA | TYR | B | 348 | 14.568 | 13.786 | 149.336 | 1.00 | 2.49 | B | C |
| ATOM | 8284 | CA | ASP | B | 349 | 11.394 | 15.091 | 150.938 | 1.00 | 2.40 | B | C |
| ATOM | 8292 | CA | SER | B | 350 | 9.337 | 18.340 | 151.066 | 1.00 | 3.13 | B | C |
| ATOM | 8298 | CA | TRP | B | 351 | 6.904 | 18.658 | 148.223 | 1.00 | 3.44 | B | C |
| ATOM | 8312 | CA | ALA | B | 352 | 4.594 | 21.317 | 146.769 | 1.00 | 6.09 | B | C |
| ATOM | 8317 | CA | THR | B | 353 | 3.818 | 19.352 | 143.690 | 1.00 | 7.57 | B | C |
| ATOM | 8324 | CA | TRP | B | 354 | 0.511 | 21.060 | 142.861 | 1.00 | 10.28 | B | C |
| ATOM | 8338 | CA | ASP | B | 355 | 2.607 | 24.171 | 142.126 | 1.00 | 9.25 | B | C |
| ATOM | 8346 | CA | ASP | B | 356 | 6.027 | 22.821 | 141.162 | 1.00 | 7.97 | B | C |
| ATOM | 8354 | CA | PHE | B | 357 | 5.476 | 19.675 | 139.069 | 1.00 | 5.45 | B | C |
| ATOM | 8365 | CA | ARG | B | 358 | 7.086 | 21.219 | 135.922 | 1.00 | 4.54 | B | C |
| ATOM | 8376 | CA | LYS | B | 359 | 10.204 | 22.174 | 137.907 | 1.00 | 3.86 | B | C |
| ATOM | 8385 | CA | PHE | B | 360 | 11.251 | 18.513 | 137.948 | 1.00 | 3.85 | B | C |

FIG. 34-17

| | | | | | | | | | | | | |
|---|---|---|---|---|---|---|---|---|---|---|---|---|
| ATOM | 8396 | CA | SER | B | 361 | 11.230 | 18.254 | 134.132 | 1.00 | 4.19 | B | C |
| ATOM | 8402 | CA | VAL | B | 362 | 13.848 | 21.051 | 134.057 | 1.00 | 4.66 | B | C |
| ATOM | 8409 | CA | ILE | B | 363 | 15.981 | 19.656 | 136.859 | 1.00 | 3.60 | B | C |
| ATOM | 8417 | CA | ALA | B | 364 | 15.986 | 16.487 | 134.724 | 1.00 | 4.12 | B | C |
| ATOM | 8422 | CA | TYR | B | 365 | 18.152 | 18.190 | 132.040 | 1.00 | 5.46 | B | C |
| ATOM | 8434 | CA | ILE | B | 366 | 20.412 | 20.182 | 134.397 | 1.00 | 6.51 | B | C |
| ATOM | 8442 | CA | ASP | B | 367 | 21.232 | 17.592 | 137.055 | 1.00 | 6.76 | B | C |
| ATOM | 8450 | CA | PRO | B | 368 | 19.936 | 14.178 | 135.858 | 1.00 | 6.15 | B | C |
| ATOM | 8457 | CA | ALA | B | 369 | 21.272 | 12.238 | 138.895 | 1.00 | 5.16 | B | C |
| ATOM | 8462 | CA | LEU | B | 370 | 19.595 | 14.581 | 141.391 | 1.00 | 5.66 | B | C |
| ATOM | 8470 | CA | TYR | B | 371 | 16.368 | 14.351 | 139.411 | 1.00 | 5.00 | B | C |
| ATOM | 8482 | CA | ARG | B | 372 | 16.537 | 10.538 | 139.507 | 1.00 | 6.13 | B | C |
| ATOM | 8493 | CA | ASP | B | 373 | 16.991 | 10.482 | 143.321 | 1.00 | 4.65 | B | C |
| ATOM | 8501 | CA | MET | B | 374 | 14.069 | 12.884 | 143.690 | 1.00 | 3.74 | B | C |
| ATOM | 8509 | CA | VAL | B | 375 | 11.706 | 10.681 | 141.648 | 1.00 | 3.94 | B | C |
| ATOM | 8516 | CA | GLN | B | 376 | 12.853 | 7.548 | 143.481 | 1.00 | 3.66 | B | C |
| ATOM | 8525 | CA | SER | B | 377 | 12.139 | 9.421 | 146.732 | 1.00 | 3.93 | B | C |
| ATOM | 8531 | CA | LEU | B | 378 | 8.564 | 10.288 | 145.559 | 1.00 | 4.51 | B | C |
| ATOM | 8539 | CA | VAL | B | 379 | 8.064 | 6.634 | 144.704 | 1.00 | 3.56 | B | C |
| ATOM | 8546 | CA | TYR | B | 380 | 9.204 | 5.663 | 148.259 | 1.00 | 4.32 | B | C |
| ATOM | 8558 | CA | LEU | B | 381 | 6.959 | 8.247 | 149.897 | 1.00 | 3.49 | B | C |
| ATOM | 8566 | CA | PHE | B | 382 | 3.838 | 6.774 | 148.265 | 1.00 | 3.82 | B | C |
| ATOM | 8577 | CA | ALA | B | 383 | 5.141 | 3.221 | 148.777 | 1.00 | 4.94 | B | C |
| ATOM | 8582 | CA | ASP | B | 384 | 5.471 | 3.995 | 152.503 | 1.00 | 6.79 | B | C |
| ATOM | 8590 | CA | ALA | B | 385 | 1.923 | 5.413 | 152.611 | 1.00 | 9.08 | B | C |
| ATOM | 8595 | CA | GLU | B | 386 | 0.765 | 2.141 | 150.976 | 1.00 | 10.89 | B | C |
| ATOM | 8604 | CA | ALA | B | 387 | 2.810 | 0.119 | 153.498 | 1.00 | 13.19 | B | C |
| ATOM | 8609 | CA | THR | B | 388 | 0.740 | 1.552 | 156.445 | 1.00 | 15.38 | B | C |
| ATOM | 8616 | CA | GLY | B | 389 | -2.271 | -0.495 | 155.224 | 1.00 | 15.84 | B | C |
| ATOM | 8620 | CA | THR | B | 390 | -4.587 | 2.321 | 156.337 | 1.00 | 14.91 | B | C |
| ATOM | 8627 | CA | GLY | B | 391 | -5.415 | 3.542 | 152.829 | 1.00 | 12.96 | B | C |
| ATOM | 8631 | CA | GLY | B | 392 | -5.069 | 7.090 | 154.245 | 1.00 | 10.55 | B | C |
| ATOM | 8635 | CA | GLY | B | 393 | -3.986 | 10.168 | 152.254 | 1.00 | 8.29 | B | C |
| ATOM | 8639 | CA | LEU | B | 394 | -0.516 | 11.679 | 152.818 | 1.00 | 6.39 | B | C |
| ATOM | 8647 | CA | GLY | B | 395 | -1.926 | 14.514 | 154.938 | 1.00 | 6.61 | B | C |
| ATOM | 8651 | CA | GLY | B | 396 | -2.978 | 12.076 | 157.705 | 1.00 | 7.77 | B | C |
| ATOM | 8655 | CA | PHE | B | 397 | 0.603 | 11.030 | 158.585 | 1.00 | 7.05 | B | C |
| ATOM | 8666 | CA | VAL | B | 398 | 3.457 | 12.825 | 160.317 | 1.00 | 6.28 | B | C |
| ATOM | 8673 | CA | HIS | B | 399 | 6.082 | 13.832 | 157.779 | 1.00 | 4.37 | B | C |
| ATOM | 8683 | CA | SER | B | 400 | 9.868 | 13.714 | 158.080 | 1.00 | 4.62 | B | C |
| ATOM | 8689 | CA | VAL | B | 401 | 10.519 | 17.328 | 157.074 | 1.00 | 3.81 | B | C |
| ATOM | 8696 | CA | PRO | B | 402 | 8.279 | 20.398 | 156.732 | 1.00 | 2.81 | B | C |
| ATOM | 8703 | CA | THR | B | 403 | 6.223 | 19.841 | 153.605 | 1.00 | 2.00 | B | C |
| ATOM | 8710 | CA | VAL | B | 404 | 3.295 | 21.247 | 151.582 | 1.00 | 2.02 | B | C |
| ATOM | 8717 | CA | ARG | B | 405 | 1.236 | 19.105 | 149.134 | 1.00 | 3.66 | B | C |
| ATOM | 8728 | CA | TRP | B | 406 | 1.343 | 16.193 | 146.726 | 1.00 | 4.40 | B | C |
| ATOM | 8742 | CA | GLU | B | 407 | -1.154 | 16.632 | 143.859 | 1.00 | 4.95 | B | C |
| ATOM | 8751 | CA | ARG | B | 408 | 0.354 | 16.056 | 140.358 | 1.00 | 4.63 | B | C |
| ATOM | 8762 | CA | SER | B | 409 | 2.805 | 13.445 | 141.798 | 1.00 | 4.41 | B | C |
| ATOM | 8768 | CA | SER | B | 410 | 1.577 | 10.955 | 139.158 | 1.00 | 5.65 | B | C |
| ATOM | 8774 | CA | VAL | B | 411 | 2.871 | 13.412 | 136.534 | 1.00 | 4.55 | B | C |
| ATOM | 8781 | CA | VAL | B | 412 | 6.352 | 13.733 | 138.090 | 1.00 | 3.62 | B | C |
| ATOM | 8788 | CA | VAL | B | 413 | 6.857 | 9.945 | 138.202 | 1.00 | 3.87 | B | C |
| ATOM | 8795 | CA | ALA | B | 414 | 5.438 | 9.658 | 134.653 | 1.00 | 5.13 | B | C |
| ATOM | 8800 | CA | ASP | B | 415 | 7.928 | 12.368 | 133.664 | 1.00 | 4.82 | B | C |
| ATOM | 8808 | CA | ALA | B | 416 | 10.908 | 10.154 | 134.619 | 1.00 | 4.44 | B | C |
| ATOM | 8813 | CA | ILE | B | 417 | 9.427 | 7.020 | 132.987 | 1.00 | 5.16 | B | C |
| ATOM | 8821 | CA | ALA | B | 418 | 8.712 | 8.909 | 129.732 | 1.00 | 6.23 | B | C |
| ATOM | 8826 | CA | LYS | B | 419 | 12.303 | 10.194 | 129.851 | 1.00 | 8.29 | B | C |
| ATOM | 8835 | CA | GLY | B | 420 | 13.794 | 6.686 | 129.922 | 1.00 | 10.82 | B | C |
| ATOM | 8839 | CA | PHE | B | 421 | 14.569 | 6.285 | 133.624 | 1.00 | 11.95 | B | C |
| ATOM | 8850 | CA | ASP | B | 422 | 13.949 | 2.885 | 135.136 | 1.00 | 14.48 | B | C |
| ATOM | 8858 | CA | GLY | B | 423 | 14.815 | 0.654 | 138.084 | 1.00 | 14.15 | B | C |
| ATOM | 8862 | CA | PHE | B | 424 | 12.489 | 2.574 | 140.366 | 1.00 | 12.52 | B | C |
| ATOM | 8873 | CA | ASP | B | 425 | 12.381 | 0.289 | 143.387 | 1.00 | 12.13 | B | C |
| ATOM | 8881 | CA | ARG | B | 426 | 8.874 | -0.058 | 144.898 | 1.00 | 9.62 | B | C |

FIG. 34-18

| | | | | | | | | | | | | |
|---|---|---|---|---|---|---|---|---|---|---|---|---|
| ATOM | 8892 | CA | LEU | B | 427 | 6.950 | 1.477 | 141.964 | 1.00 | 9.74 | B | C |
| ATOM | 8900 | CA | ASP | B | 428 | 4.503 | -1.436 | 142.300 | 1.00 | 11.74 | B | C |
| ATOM | 8908 | CA | GLU | B | 429 | 3.837 | -0.485 | 145.942 | 1.00 | 10.85 | B | C |
| ATOM | 8917 | CA | ALA | B | 430 | 3.557 | 3.228 | 145.139 | 1.00 | 9.56 | B | C |
| ATOM | 8922 | CA | TYR | B | 431 | 0.970 | 2.649 | 142.393 | 1.00 | 9.69 | B | C |
| ATOM | 8934 | CA | PRO | B | 432 | -2.178 | 2.019 | 144.553 | 1.00 | 8.88 | B | C |
| ATOM | 8941 | CA | ALA | B | 433 | -1.368 | 5.086 | 146.736 | 1.00 | 7.60 | B | C |
| ATOM | 8946 | CA | LEU | B | 434 | -0.914 | 7.129 | 143.566 | 1.00 | 7.98 | B | C |
| ATOM | 8954 | CA | GLN | B | 435 | -4.332 | 5.893 | 142.378 | 1.00 | 9.79 | B | C |
| ATOM | 8963 | CA | ARG | B | 436 | -5.876 | 6.985 | 145.714 | 1.00 | 8.63 | B | C |
| ATOM | 8974 | CA | LEU | B | 437 | -4.175 | 10.398 | 145.345 | 1.00 | 8.82 | B | C |
| ATOM | 8982 | CA | VAL | B | 438 | -5.651 | 10.832 | 141.863 | 1.00 | 10.72 | B | C |
| ATOM | 8989 | CA | GLY | B | 439 | -9.074 | 9.520 | 142.973 | 1.00 | 11.53 | B | C |
| ATOM | 8993 | CA | GLN | B | 440 | -11.952 | 7.945 | 141.034 | 1.00 | 13.71 | B | C |
| ATOM | 9002 | CA | TYR | B | 441 | -14.865 | 9.454 | 139.124 | 1.00 | 12.01 | B | C |
| ATOM | 9014 | CA | SER | B | 442 | -18.189 | 8.549 | 140.760 | 1.00 | 12.74 | B | C |
| ATOM | 9020 | CA | ALA | B | 443 | -20.666 | 6.339 | 138.839 | 1.00 | 12.68 | B | C |
| ATOM | 9025 | CA | ASP | B | 444 | -22.553 | 9.434 | 137.687 | 1.00 | 12.69 | B | C |
| ATOM | 9033 | CA | GLU | B | 445 | -19.307 | 11.199 | 136.788 | 1.00 | 10.37 | B | C |
| ATOM | 9042 | CA | LEU | B | 446 | -18.282 | 8.164 | 134.766 | 1.00 | 10.75 | B | C |
| ATOM | 9050 | CA | ARG | B | 447 | -21.517 | 8.211 | 132.730 | 1.00 | 12.18 | B | C |
| ATOM | 9061 | CA | ARG | B | 448 | -21.331 | 11.954 | 131.904 | 1.00 | 11.28 | B | C |
| ATOM | 9072 | CA | GLY | B | 449 | -17.521 | 12.199 | 131.769 | 1.00 | 9.56 | B | C |
| ATOM | 9076 | CA | TYR | B | 450 | -16.840 | 15.171 | 134.104 | 1.00 | 8.69 | B | C |
| ATOM | 9088 | CA | VAL | B | 451 | -17.362 | 16.664 | 137.586 | 1.00 | 8.42 | B | C |
| ATOM | 9095 | CA | ALA | B | 452 | -20.609 | 18.655 | 137.398 | 1.00 | 9.63 | B | C |
| ATOM | 9100 | CA | GLY | B | 453 | -19.943 | 22.350 | 137.910 | 1.00 | 9.76 | B | C |
| ATOM | 9104 | CA | ASN | B | 454 | -16.242 | 21.775 | 138.624 | 1.00 | 8.50 | B | C |
| ATOM | 9112 | CA | PRO | B | 455 | -14.156 | 22.194 | 135.439 | 1.00 | 8.32 | B | C |
| ATOM | 9119 | CA | GLY | B | 456 | -11.107 | 22.756 | 137.692 | 1.00 | 8.02 | B | C |
| ATOM | 9123 | CA | ALA | B | 457 | -11.159 | 19.292 | 139.280 | 1.00 | 6.90 | B | C |
| ATOM | 9128 | CA | SER | B | 458 | -11.963 | 17.688 | 135.889 | 1.00 | 6.05 | B | C |
| ATOM | 9134 | CA | VAL | B | 459 | -8.939 | 18.989 | 133.896 | 1.00 | 5.70 | B | C |
| ATOM | 9141 | CA | GLN | B | 460 | -6.681 | 18.365 | 136.882 | 1.00 | 5.79 | B | C |
| ATOM | 9150 | CA | ARG | B | 461 | -7.804 | 14.732 | 137.121 | 1.00 | 6.42 | B | C |
| ATOM | 9161 | CA | GLY | B | 462 | -7.221 | 14.406 | 133.370 | 1.00 | 5.35 | B | C |
| ATOM | 9165 | CA | TYR | B | 463 | -3.539 | 15.278 | 133.771 | 1.00 | 5.04 | B | C |
| ATOM | 9177 | CA | ASP | B | 464 | -3.270 | 13.035 | 136.851 | 1.00 | 5.57 | B | C |
| ATOM | 9185 | CA | GLN | B | 465 | -4.804 | 10.198 | 134.841 | 1.00 | 5.78 | B | C |
| ATOM | 9194 | CA | TYR | B | 466 | -2.483 | 10.769 | 131.919 | 1.00 | 6.49 | B | C |
| ATOM | 9206 | CA | GLY | B | 467 | 0.439 | 10.511 | 134.378 | 1.00 | 5.94 | B | C |
| ATOM | 9210 | CA | LEU | B | 468 | -1.027 | 7.423 | 136.006 | 1.00 | 7.08 | B | C |
| ATOM | 9218 | CA | SER | B | 469 | -1.447 | 5.806 | 132.563 | 1.00 | 7.35 | B | C |
| ATOM | 9224 | CA | VAL | B | 470 | 2.324 | 6.119 | 131.916 | 1.00 | 7.31 | B | C |
| ATOM | 9231 | CA | ILE | B | 471 | 3.054 | 4.452 | 135.299 | 1.00 | 7.55 | B | C |
| ATOM | 9239 | CA | ALA | B | 472 | 0.432 | 1.758 | 134.635 | 1.00 | 8.69 | B | C |
| ATOM | 9244 | CA | ASP | B | 473 | 2.077 | 0.765 | 131.318 | 1.00 | 10.11 | B | C |
| ATOM | 9252 | CA | GLU | B | 474 | 5.524 | 0.684 | 132.942 | 1.00 | 11.08 | B | C |
| ATOM | 9261 | CA | LEU | B | 475 | 4.081 | -1.770 | 135.471 | 1.00 | 10.77 | B | C |
| ATOM | 9269 | CA | GLY | B | 476 | 2.557 | -3.863 | 132.643 | 1.00 | 12.28 | B | C |
| ATOM | 9273 | CA | LEU | B | 477 | -1.005 | -2.946 | 133.703 | 1.00 | 14.48 | B | C |
| ATOM | 9281 | CA | THR | B | 478 | -1.957 | -2.607 | 130.034 | 1.00 | 17.13 | B | C |
| ATOM | 9288 | CA | GLU | B | 479 | -5.736 | -2.506 | 130.474 | 1.00 | 18.35 | B | C |
| ATOM | 9297 | CA | GLU | B | 480 | -5.722 | 0.045 | 133.355 | 1.00 | 15.71 | B | C |
| ATOM | 9306 | CA | ALA | B | 481 | -3.447 | 2.289 | 131.256 | 1.00 | 13.30 | B | C |
| ATOM | 9311 | CA | GLU | B | 482 | -5.993 | 2.198 | 128.387 | 1.00 | 13.38 | B | C |
| ATOM | 9320 | CA | THR | B | 483 | -8.838 | 3.007 | 130.776 | 1.00 | 11.91 | B | C |
| ATOM | 9327 | CA | LEU | B | 484 | -6.802 | 5.857 | 132.279 | 1.00 | 9.11 | B | C |
| ATOM | 9335 | CA | ARG | B | 485 | -6.030 | 7.235 | 128.765 | 1.00 | 8.25 | B | C |
| ATOM | 9346 | CA | GLU | B | 486 | -9.735 | 7.030 | 127.831 | 1.00 | 8.59 | B | C |
| ATOM | 9355 | CA | GLN | B | 487 | -10.721 | 8.982 | 130.961 | 1.00 | 7.84 | B | C |
| ATOM | 9364 | CA | ALA | B | 488 | -7.917 | 11.568 | 130.491 | 1.00 | 6.89 | B | C |
| ATOM | 9369 | CA | SER | B | 489 | -9.413 | 12.554 | 127.143 | 1.00 | 6.88 | B | C |
| ATOM | 9375 | CA | TRP | B | 490 | -12.765 | 13.388 | 128.798 | 1.00 | 7.07 | B | C |
| ATOM | 9389 | CA | PRO | B | 491 | -12.065 | 16.904 | 130.180 | 1.00 | 7.75 | B | C |
| ATOM | 9396 | CA | ILE | B | 492 | -11.008 | 18.232 | 126.748 | 1.00 | 10.03 | B | C |

FIG. 34-19

| | | | | | | | | | | | | | |
|---|---|---|---|---|---|---|---|---|---|---|---|---|---|
| ATOM | 9404 | CA | GLU | B | 493 | -13.896 | 16.510 | 124.905 | 1.00 | 12.06 | | B | C |
| ATOM | 9413 | CA | LYS | B | 494 | -16.671 | 17.061 | 127.427 | 1.00 | 10.91 | | B | C |
| ATOM | 9422 | CA | LEU | B | 495 | -15.887 | 20.513 | 128.833 | 1.00 | 9.26 | | B | C |
| ATOM | 9430 | CA | THR | B | 496 | -14.827 | 22.544 | 125.800 | 1.00 | 9.84 | | B | C |
| ATOM | 9437 | CA | LYS | B | 497 | -17.972 | 24.524 | 124.878 | 1.00 | 10.36 | | B | C |
| ATOM | 9446 | CA | PRO | B | 498 | -18.062 | 25.503 | 121.171 | 1.00 | 10.16 | | B | C |
| ATOM | 9453 | CA | GLY | B | 499 | -18.441 | 29.251 | 120.587 | 1.00 | 11.73 | | B | C |
| ATOM | 9457 | CA | ALA | B | 500 | -17.533 | 30.238 | 124.169 | 1.00 | 12.89 | | B | C |
| ATOM | 9462 | CA | TRP | B | 501 | -15.579 | 33.120 | 122.622 | 1.00 | 13.32 | | B | C |
| ATOM | 9476 | CA | THR | B | 502 | -16.087 | 34.739 | 119.196 | 1.00 | 14.82 | | B | C |
| ATOM | 9483 | CA | ALA | B | 503 | -13.072 | 36.086 | 117.234 | 1.00 | 17.18 | | B | C |
| ATOM | 9488 | CA | ALA | B | 504 | -12.857 | 39.344 | 115.232 | 1.00 | 19.86 | | B | C |
| ATOM | 9493 | CA | ASP | B | 505 | -13.256 | 36.963 | 112.234 | 1.00 | 21.28 | | B | C |
| ATOM | 9501 | CA | GLY | B | 506 | -16.585 | 35.755 | 113.609 | 1.00 | 20.03 | | B | C |
| ATOM | 9505 | CA | THR | B | 507 | -14.731 | 32.439 | 114.087 | 1.00 | 18.03 | | B | C |
| ATOM | 9512 | CA | GLN | B | 508 | -16.251 | 30.532 | 117.010 | 1.00 | 15.34 | | B | C |
| ATOM | 9521 | CA | VAL | B | 509 | -13.708 | 29.336 | 119.570 | 1.00 | 11.34 | | B | C |
| ATOM | 9528 | CA | GLY | B | 510 | -14.366 | 26.537 | 122.049 | 1.00 | 9.07 | | B | C |
| ATOM | 9532 | CA | LEU | B | 511 | -13.197 | 27.026 | 125.631 | 1.00 | 7.86 | | B | C |
| ATOM | 9540 | CA | LEU | B | 512 | -13.219 | 25.124 | 128.921 | 1.00 | 7.01 | | B | C |
| ATOM | 9548 | CA | THR | B | 513 | -16.601 | 25.890 | 130.550 | 1.00 | 8.85 | | B | C |
| ATOM | 9555 | CA | PRO | B | 514 | -18.393 | 24.554 | 133.677 | 1.00 | 10.28 | | B | C |
| ATOM | 9562 | CA | ARG | B | 515 | -21.081 | 22.039 | 132.717 | 1.00 | 12.26 | | B | C |
| ATOM | 9573 | CA | ALA | B | 516 | -24.111 | 20.973 | 134.766 | 1.00 | 13.16 | | B | C |
| ATOM | 9578 | CA | ALA | B | 517 | -24.951 | 17.342 | 135.665 | 1.00 | 14.35 | | B | C |
| ATOM | 9583 | CA | ASP | B | 518 | -27.642 | 17.167 | 132.923 | 1.00 | 16.53 | | B | C |
| ATOM | 9591 | CA | GLY | B | 519 | -25.191 | 18.281 | 130.210 | 1.00 | 16.33 | | B | C |
| ATOM | 9595 | CA | SER | B | 520 | -26.240 | 21.945 | 129.971 | 1.00 | 15.96 | | B | C |
| ATOM | 9601 | CA | TRP | B | 521 | -23.559 | 24.648 | 130.008 | 1.00 | 15.21 | | B | C |
| ATOM | 9615 | CA | GLN | B | 522 | -23.432 | 26.929 | 133.060 | 1.00 | 15.39 | | B | C |
| ATOM | 9624 | CA | SER | B | 523 | -22.733 | 30.599 | 132.427 | 1.00 | 15.49 | | B | C |
| ATOM | 9630 | CA | ALA | B | 524 | -19.406 | 32.190 | 133.361 | 1.00 | 13.08 | | B | C |
| ATOM | 9635 | CA | ASP | B | 525 | -16.958 | 34.949 | 132.667 | 1.00 | 10.42 | | B | C |
| ATOM | 9643 | CA | HIS | B | 526 | -13.996 | 33.026 | 131.216 | 1.00 | 9.11 | | B | C |
| ATOM | 9653 | CA | ALA | B | 527 | -11.679 | 35.887 | 132.307 | 1.00 | 9.10 | | B | C |
| ATOM | 9658 | CA | LYS | B | 528 | -12.918 | 36.154 | 135.899 | 1.00 | 10.32 | | B | C |
| ATOM | 9667 | CA | PHE | B | 529 | -10.563 | 35.052 | 138.686 | 1.00 | 8.73 | | B | C |
| ATOM | 9678 | CA | GLU | B | 530 | -11.981 | 32.026 | 140.571 | 1.00 | 8.70 | | B | C |
| ATOM | 9687 | CA | ALA | B | 531 | -15.175 | 31.800 | 138.513 | 1.00 | 9.23 | | B | C |
| ATOM | 9692 | CA | ALA | B | 532 | -16.810 | 28.339 | 138.183 | 1.00 | 10.00 | | B | C |
| ATOM | 9697 | CA | GLY | B | 533 | -15.211 | 26.855 | 141.335 | 1.00 | 9.25 | | B | C |
| ATOM | 9701 | CA | LEU | B | 534 | -11.653 | 27.388 | 140.006 | 1.00 | 8.07 | | B | C |
| ATOM | 9709 | CA | TYR | B | 535 | -8.638 | 27.486 | 142.280 | 1.00 | 10.81 | | B | C |
| ATOM | 9721 | CA | GLN | B | 536 | -6.568 | 30.681 | 141.905 | 1.00 | 10.33 | | B | C |
| ATOM | 9730 | CA | GLY | B | 537 | -7.264 | 31.159 | 138.187 | 1.00 | 8.79 | | B | C |
| ATOM | 9734 | CA | THR | B | 538 | -9.626 | 31.771 | 135.278 | 1.00 | 7.44 | | B | C |
| ATOM | 9741 | CA | LEU | B | 539 | -11.154 | 29.505 | 132.643 | 1.00 | 8.31 | | B | C |
| ATOM | 9749 | CA | TRP | B | 540 | -8.976 | 31.006 | 129.900 | 1.00 | 6.79 | | B | C |
| ATOM | 9763 | CA | GLN | B | 541 | -6.001 | 30.062 | 132.087 | 1.00 | 5.72 | | B | C |
| ATOM | 9772 | CA | TYR | B | 542 | -7.247 | 26.567 | 133.014 | 1.00 | 6.07 | | B | C |
| ATOM | 9784 | CA | HIS | B | 543 | -8.336 | 25.987 | 129.378 | 1.00 | 6.44 | | B | C |
| ATOM | 9794 | CA | TRP | B | 544 | -4.804 | 24.912 | 128.489 | 1.00 | 5.93 | | B | C |
| ATOM | 9808 | CA | TYR | B | 545 | -4.279 | 22.715 | 131.546 | 1.00 | 4.79 | | B | C |
| ATOM | 9820 | CA | ASP | B | 546 | -4.407 | 19.324 | 129.817 | 1.00 | 4.56 | | B | C |
| ATOM | 9828 | CA | ALA | B | 547 | -0.984 | 19.835 | 128.277 | 1.00 | 5.44 | | B | C |
| ATOM | 9833 | CA | TYR | B | 548 | -0.609 | 16.142 | 127.393 | 1.00 | 6.08 | | B | C |
| ATOM | 9845 | CA | ASP | B | 549 | -3.092 | 16.487 | 124.510 | 1.00 | 5.83 | | B | C |
| ATOM | 9853 | CA | MET | B | 550 | -2.830 | 19.820 | 122.688 | 1.00 | 7.27 | | B | C |
| ATOM | 9861 | CA | ASP | B | 551 | -3.867 | 18.042 | 119.495 | 1.00 | 9.92 | | B | C |
| ATOM | 9869 | CA | ALA | B | 552 | -7.181 | 17.034 | 121.101 | 1.00 | 9.29 | | B | C |
| ATOM | 9874 | CA | LEU | B | 553 | -7.610 | 20.544 | 122.602 | 1.00 | 8.74 | | B | C |
| ATOM | 9882 | CA | VAL | B | 554 | -6.969 | 22.270 | 119.281 | 1.00 | 9.28 | | B | C |
| ATOM | 9889 | CA | GLU | B | 555 | -9.660 | 20.056 | 117.696 | 1.00 | 10.79 | | B | C |
| ATOM | 9898 | CA | ALA | B | 556 | -12.151 | 20.721 | 120.539 | 1.00 | 8.98 | | B | C |
| ATOM | 9903 | CA | MET | B | 557 | -11.629 | 24.480 | 120.201 | 1.00 | 9.27 | | B | C |
| ATOM | 9911 | CA | GLY | B | 558 | -12.831 | 24.096 | 116.592 | 1.00 | 11.18 | | B | C |

FIG. 34-20

| | | | | | | | | | | | | |
|---|---|---|---|---|---|---|---|---|---|---|---|---|
| ATOM | 9915 | CA | GLY | B | 559 | -9.648 | 23.449 | 114.651 | 1.00 | 12.57 | B | C |
| ATOM | 9919 | CA | HIS | B | 560 | -6.240 | 24.925 | 113.907 | 1.00 | 13.76 | B | C |
| ATOM | 9929 | CA | GLU | B | 561 | -7.665 | 28.397 | 113.047 | 1.00 | 13.40 | B | C |
| ATOM | 9938 | CA | ALA | B | 562 | -9.852 | 28.561 | 116.156 | 1.00 | 11.93 | B | C |
| ATOM | 9943 | CA | ALA | B | 563 | -6.829 | 27.744 | 118.342 | 1.00 | 11.17 | B | C |
| ATOM | 9948 | CA | ARG | B | 564 | -4.548 | 30.202 | 116.523 | 1.00 | 10.14 | B | C |
| ATOM | 9959 | CA | LEU | B | 565 | -6.933 | 33.107 | 117.193 | 1.00 | 9.78 | B | C |
| ATOM | 9967 | CA | GLY | B | 566 | -7.517 | 31.781 | 120.725 | 1.00 | 8.93 | B | C |
| ATOM | 9971 | CA | MET | B | 567 | -3.792 | 31.948 | 121.520 | 1.00 | 9.45 | B | C |
| ATOM | 9979 | CA | ARG | B | 568 | -3.398 | 35.497 | 120.126 | 1.00 | 9.92 | B | C |
| ATOM | 9990 | CA | HIS | B | 569 | -6.452 | 36.629 | 122.170 | 1.00 | 9.91 | B | C |
| ATOM | 10000 | CA | MET | B | 570 | -4.961 | 34.969 | 125.270 | 1.00 | 10.22 | B | C |
| ATOM | 10008 | CA | PHE | B | 571 | -1.992 | 37.376 | 124.985 | 1.00 | 9.43 | B | C |
| ATOM | 10019 | CA | GLY | B | 572 | -3.956 | 40.469 | 123.877 | 1.00 | 11.08 | B | C |
| ATOM | 10023 | CA | GLU | B | 573 | -2.195 | 40.540 | 120.475 | 1.00 | 13.30 | B | C |
| ATOM | 10032 | CA | HIS | B | 574 | -5.029 | 42.598 | 118.931 | 1.00 | 14.86 | B | C |
| ATOM | 10042 | CA | ALA | B | 575 | -4.622 | 45.304 | 121.645 | 1.00 | 15.90 | B | C |
| ATOM | 10047 | CA | PRO | B | 576 | -0.972 | 45.390 | 122.696 | 1.00 | 17.21 | B | C |
| ATOM | 10054 | CA | ASP | B | 577 | -1.328 | 48.595 | 124.695 | 1.00 | 18.80 | B | C |
| ATOM | 10062 | CA | ASP | B | 578 | -4.343 | 47.440 | 126.680 | 1.00 | 16.37 | B | C |
| ATOM | 10070 | CA | GLY | B | 579 | -3.447 | 45.773 | 129.999 | 1.00 | 14.31 | B | C |
| ATOM | 10074 | CA | LYS | B | 580 | -6.893 | 44.273 | 130.536 | 1.00 | 14.35 | B | C |
| ATOM | 10083 | CA | ALA | B | 581 | -6.401 | 42.289 | 127.289 | 1.00 | 11.55 | B | C |
| ATOM | 10088 | CA | MET | B | 582 | -3.732 | 40.150 | 128.992 | 1.00 | 9.08 | B | C |
| ATOM | 10096 | CA | LEU | B | 583 | -5.611 | 36.913 | 129.818 | 1.00 | 6.75 | B | C |
| ATOM | 10104 | CA | HIS | B | 584 | -2.406 | 35.066 | 130.755 | 1.00 | 5.26 | B | C |
| ATOM | 10114 | CA | SER | B | 585 | -1.183 | 35.314 | 134.331 | 1.00 | 5.08 | B | C |
| ATOM | 10120 | CA | ASN | B | 586 | 2.561 | 35.487 | 135.130 | 1.00 | 4.87 | B | C |
| ATOM | 10128 | CA | ALA | B | 587 | 1.917 | 35.442 | 138.923 | 1.00 | 6.16 | B | C |
| ATOM | 10133 | CA | ASN | B | 588 | 0.684 | 31.857 | 139.540 | 1.00 | 9.70 | B | C |
| ATOM | 10141 | CA | GLU | B | 589 | 1.574 | 28.445 | 138.079 | 1.00 | 11.52 | B | C |
| ATOM | 10150 | CA | ILE | B | 590 | -1.724 | 27.523 | 136.394 | 1.00 | 11.76 | B | C |
| ATOM | 10158 | CA | ASP | B | 591 | -0.787 | 28.589 | 132.835 | 1.00 | 11.65 | B | C |
| ATOM | 10166 | CA | LEU | B | 592 | 3.036 | 28.784 | 133.060 | 1.00 | 10.00 | B | C |
| ATOM | 10174 | CA | GLN | B | 593 | 3.220 | 26.855 | 129.797 | 1.00 | 7.99 | B | C |
| ATOM | 10183 | CA | ALA | B | 594 | 0.955 | 29.258 | 127.891 | 1.00 | 7.42 | B | C |
| ATOM | 10188 | CA | PRO | B | 595 | 3.697 | 31.434 | 126.264 | 1.00 | 6.47 | B | C |
| ATOM | 10195 | CA | TYR | B | 596 | 5.040 | 28.300 | 124.524 | 1.00 | 5.99 | B | C |
| ATOM | 10207 | CA | LEU | B | 597 | 1.684 | 27.269 | 123.043 | 1.00 | 5.41 | B | C |
| ATOM | 10215 | CA | PHE | B | 598 | 2.175 | 29.492 | 119.962 | 1.00 | 6.82 | B | C |
| ATOM | 10226 | CA | ASN | B | 599 | 4.570 | 26.728 | 118.788 | 1.00 | 7.99 | B | C |
| ATOM | 10234 | CA | TYR | B | 600 | 1.469 | 24.494 | 118.559 | 1.00 | 8.95 | B | C |
| ATOM | 10246 | CA | THR | B | 601 | -0.592 | 27.029 | 116.565 | 1.00 | 9.34 | B | C |
| ATOM | 10253 | CA | GLY | B | 602 | 2.026 | 27.493 | 113.815 | 1.00 | 9.48 | B | C |
| ATOM | 10257 | CA | GLU | B | 603 | 3.299 | 30.812 | 115.139 | 1.00 | 9.51 | B | C |
| ATOM | 10266 | CA | PRO | B | 604 | 6.593 | 29.991 | 116.946 | 1.00 | 8.50 | B | C |
| ATOM | 10273 | CA | SER | B | 605 | 7.845 | 33.578 | 116.478 | 1.00 | 7.57 | B | C |
| ATOM | 10279 | CA | LEU | B | 606 | 5.226 | 34.638 | 119.060 | 1.00 | 7.18 | B | C |
| ATOM | 10287 | CA | THR | B | 607 | 6.464 | 32.030 | 121.578 | 1.00 | 5.66 | B | C |
| ATOM | 10294 | CA | GLN | B | 608 | 9.959 | 33.487 | 121.141 | 1.00 | 5.96 | B | C |
| ATOM | 10303 | CA | LYS | B | 609 | 8.701 | 37.059 | 121.593 | 1.00 | 6.51 | B | C |
| ATOM | 10312 | CA | TRP | B | 610 | 6.714 | 36.241 | 124.769 | 1.00 | 7.00 | B | C |
| ATOM | 10326 | CA | ALA | B | 611 | 9.360 | 33.957 | 126.314 | 1.00 | 7.18 | B | C |
| ATOM | 10331 | CA | ARG | B | 612 | 11.852 | 36.768 | 125.860 | 1.00 | 7.07 | B | C |
| ATOM | 10342 | CA | ALA | B | 613 | 9.502 | 39.547 | 127.021 | 1.00 | 7.16 | B | C |
| ATOM | 10347 | CA | ILE | B | 614 | 8.036 | 37.923 | 130.160 | 1.00 | 7.15 | B | C |
| ATOM | 10355 | CA | TYR | B | 615 | 11.442 | 37.037 | 131.623 | 1.00 | 8.13 | B | C |
| ATOM | 10367 | CA | THR | B | 616 | 13.573 | 39.966 | 130.409 | 1.00 | 8.81 | B | C |
| ATOM | 10374 | CA | LYS | B | 617 | 11.308 | 42.977 | 129.716 | 1.00 | 9.89 | B | C |
| ATOM | 10383 | CA | GLU | B | 618 | 8.250 | 44.801 | 130.976 | 1.00 | 10.62 | B | C |
| ATOM | 10392 | CA | THR | B | 619 | 4.925 | 43.183 | 130.129 | 1.00 | 10.85 | B | C |
| ATOM | 10399 | CA | TRP | B | 620 | 1.277 | 43.848 | 130.780 | 1.00 | 10.87 | B | C |
| ATOM | 10413 | CA | ASN | B | 621 | 0.104 | 42.242 | 133.955 | 1.00 | 8.54 | B | C |
| ATOM | 10421 | CA | ARG | B | 622 | -3.614 | 41.858 | 134.675 | 1.00 | 6.42 | B | C |
| ATOM | 10432 | CA | TYR | B | 623 | -3.638 | 39.092 | 137.312 | 1.00 | 6.84 | B | C |
| ATOM | 10444 | CA | ILE | B | 624 | -2.166 | 38.601 | 140.777 | 1.00 | 6.95 | B | C |

FIG. 34-21

| | | | | | | | | | | | | |
|---|---|---|---|---|---|---|---|---|---|---|---|---|
| ATOM | 10452 | CA | ALA | B | 625 | -2.036 | 35.146 | 142.429 | 1.00 | 9.17 | B | C |
| ATOM | 10457 | CA | THR | B | 626 | -4.883 | 35.743 | 144.940 | 1.00 | 9.61 | B | C |
| ATOM | 10464 | CA | GLY | B | 627 | -8.057 | 37.828 | 145.428 | 1.00 | 11.00 | B | C |
| ATOM | 10468 | CA | SER | B | 628 | -6.410 | 40.988 | 146.753 | 1.00 | 14.00 | B | C |
| ATOM | 10474 | CA | SER | B | 629 | -3.055 | 42.511 | 147.827 | 1.00 | 14.96 | B | C |
| ATOM | 10480 | CA | SER | B | 630 | -2.186 | 45.392 | 150.152 | 1.00 | 15.87 | B | C |
| ATOM | 10486 | CA | ALA | B | 631 | 1.099 | 45.793 | 148.230 | 1.00 | 15.15 | B | C |
| ATOM | 10491 | CA | VAL | B | 632 | -0.451 | 46.993 | 144.954 | 1.00 | 12.68 | B | C |
| ATOM | 10498 | CA | PRO | B | 633 | -3.837 | 48.543 | 144.078 | 1.00 | 11.90 | B | C |
| ATOM | 10505 | CA | SER | B | 634 | -5.790 | 45.403 | 143.232 | 1.00 | 10.24 | B | C |
| ATOM | 10511 | CA | GLY | B | 635 | -9.047 | 43.424 | 143.655 | 1.00 | 10.87 | B | C |
| ATOM | 10515 | CA | GLY | B | 636 | -10.965 | 40.434 | 142.243 | 1.00 | 11.37 | B | C |
| ATOM | 10519 | CA | GLY | B | 637 | -7.618 | 38.717 | 141.514 | 1.00 | 10.74 | B | C |
| ATOM | 10523 | CA | GLU | B | 638 | -6.354 | 41.552 | 139.331 | 1.00 | 10.06 | B | C |
| ATOM | 10532 | CA | PHE | B | 639 | -4.034 | 44.542 | 139.288 | 1.00 | 10.96 | B | C |
| ATOM | 10543 | CA | THR | B | 640 | -6.497 | 47.479 | 139.174 | 1.00 | 13.37 | B | C |
| ATOM | 10550 | CA | PRO | B | 641 | -5.496 | 48.960 | 136.843 | 1.00 | 14.12 | B | C |
| ATOM | 10557 | CA | PRO | B | 642 | -3.275 | 46.456 | 134.964 | 1.00 | 13.72 | B | C |
| ATOM | 10564 | CA | LEU | B | 643 | 0.396 | 47.404 | 135.238 | 1.00 | 14.65 | B | C |
| ATOM | 10572 | CA | LYS | B | 644 | 3.137 | 47.317 | 132.691 | 1.00 | 13.96 | B | C |
| ATOM | 10581 | CA | THR | B | 645 | 6.095 | 45.936 | 134.647 | 1.00 | 11.78 | B | C |
| ATOM | 10588 | CA | LYS | B | 646 | 8.969 | 43.450 | 134.688 | 1.00 | 11.14 | B | C |
| ATOM | 10597 | CA | VAL | B | 647 | 7.800 | 40.166 | 136.218 | 1.00 | 8.36 | B | C |
| ATOM | 10604 | CA | TYR | B | 648 | 11.303 | 39.198 | 137.406 | 1.00 | 7.74 | B | C |
| ATOM | 10616 | CA | ARG | B | 649 | 13.591 | 41.824 | 139.020 | 1.00 | 9.04 | B | C |
| ATOM | 10627 | CA | LEU | B | 650 | 17.093 | 41.707 | 140.433 | 1.00 | 7.53 | B | C |
| ATOM | 10635 | CA | ASP | B | 651 | 15.807 | 43.347 | 143.621 | 1.00 | 5.17 | B | C |
| ATOM | 10643 | CA | PRO | B | 652 | 14.545 | 42.350 | 147.055 | 1.00 | 5.40 | B | C |
| ATOM | 10650 | CA | ARG | B | 653 | 11.139 | 42.853 | 145.381 | 1.00 | 6.53 | B | C |
| ATOM | 10661 | CA | GLY | B | 654 | 12.108 | 40.059 | 142.996 | 1.00 | 6.41 | B | C |
| ATOM | 10665 | CA | MET | B | 655 | 8.705 | 38.795 | 141.823 | 1.00 | 6.72 | B | C |
| ATOM | 10673 | CA | LEU | B | 656 | 5.334 | 40.460 | 141.196 | 1.00 | 6.70 | B | C |
| ATOM | 10681 | CA | PRO | B | 657 | 3.402 | 41.236 | 144.385 | 1.00 | 6.71 | B | C |
| ATOM | 10688 | CA | THR | B | 658 | 1.659 | 37.972 | 145.528 | 1.00 | 7.41 | B | C |
| ATOM | 10695 | CA | MET | B | 659 | 3.892 | 35.925 | 143.184 | 1.00 | 5.95 | B | C |
| ATOM | 10703 | CA | ASP | B | 660 | 5.190 | 33.199 | 145.543 | 1.00 | 4.96 | B | C |
| ATOM | 10711 | CA | ASN | B | 661 | 8.255 | 31.368 | 144.118 | 1.00 | 5.08 | B | C |
| ATOM | 10719 | CA | ASP | B | 662 | 6.702 | 28.114 | 145.513 | 1.00 | 4.85 | B | C |
| ATOM | 10727 | CA | ALA | B | 663 | 9.647 | 25.783 | 146.215 | 1.00 | 5.19 | B | C |
| ATOM | 10732 | CA | GLY | B | 664 | 11.674 | 27.503 | 143.453 | 1.00 | 5.63 | B | C |
| ATOM | 10736 | CA | THR | B | 665 | 9.108 | 26.987 | 140.680 | 1.00 | 6.11 | B | C |
| ATOM | 10743 | CA | MET | B | 666 | 9.161 | 30.568 | 139.404 | 1.00 | 7.32 | B | C |
| ATOM | 10751 | CA | SER | B | 667 | 12.973 | 30.544 | 139.595 | 1.00 | 7.14 | B | C |
| ATOM | 10757 | CA | THR | B | 668 | 13.107 | 27.187 | 137.738 | 1.00 | 8.41 | B | C |
| ATOM | 10764 | CA | MET | B | 669 | 10.894 | 28.674 | 134.975 | 1.00 | 8.61 | B | C |
| ATOM | 10772 | CA | PHE | B | 670 | 13.293 | 31.613 | 134.474 | 1.00 | 5.87 | B | C |
| ATOM | 10783 | CA | VAL | B | 671 | 16.232 | 29.234 | 134.165 | 1.00 | 5.19 | B | C |
| ATOM | 10790 | CA | ALA | B | 672 | 14.275 | 27.232 | 131.532 | 1.00 | 5.77 | B | C |
| ATOM | 10795 | CA | ALA | B | 673 | 13.327 | 30.366 | 129.576 | 1.00 | 6.53 | B | C |
| ATOM | 10800 | CA | ALA | B | 674 | 17.004 | 31.392 | 129.591 | 1.00 | 6.52 | B | C |
| ATOM | 10805 | CA | VAL | B | 675 | 18.093 | 27.945 | 128.278 | 1.00 | 6.08 | B | C |
| ATOM | 10812 | CA | GLY | B | 676 | 15.236 | 28.143 | 125.757 | 1.00 | 5.59 | B | C |
| ATOM | 10816 | CA | LEU | B | 677 | 13.801 | 24.680 | 126.537 | 1.00 | 4.36 | B | C |
| ATOM | 10824 | CA | PHE | B | 678 | 10.456 | 24.513 | 128.310 | 1.00 | 4.27 | B | C |
| ATOM | 10835 | CA | PRO | B | 679 | 8.476 | 21.441 | 129.468 | 1.00 | 4.23 | B | C |
| ATOM | 10842 | CA | VAL | B | 680 | 4.935 | 22.169 | 128.193 | 1.00 | 4.71 | B | C |
| ATOM | 10849 | CA | THR | B | 681 | 4.133 | 18.524 | 128.725 | 1.00 | 4.02 | B | C |
| ATOM | 10856 | CA | ALA | B | 682 | 5.534 | 17.401 | 132.028 | 1.00 | 2.99 | B | C |
| ATOM | 10861 | CA | GLY | B | 683 | 5.162 | 13.611 | 132.013 | 1.00 | 4.05 | B | C |
| ATOM | 10865 | CA | SER | B | 684 | 6.552 | 13.443 | 128.463 | 1.00 | 5.13 | B | C |
| ATOM | 10871 | CA | SER | B | 685 | 10.143 | 13.369 | 127.150 | 1.00 | 6.66 | B | C |
| ATOM | 10877 | CA | GLN | B | 686 | 9.863 | 16.641 | 125.200 | 1.00 | 6.38 | B | C |
| ATOM | 10886 | CA | PHE | B | 687 | 10.738 | 20.344 | 125.639 | 1.00 | 5.59 | B | C |
| ATOM | 10897 | CA | GLN | B | 688 | 9.427 | 23.232 | 123.520 | 1.00 | 6.03 | B | C |
| ATOM | 10906 | CA | VAL | B | 689 | 11.793 | 25.796 | 122.043 | 1.00 | 6.55 | B | C |
| ATOM | 10913 | CA | GLY | B | 690 | 11.579 | 29.419 | 123.274 | 1.00 | 7.04 | B | C |

FIG. 34-22

| | | | | | | | | | | | | |
|---|---|---|---|---|---|---|---|---|---|---|---|---|
| ATOM | 10917 | CA | SER | B | 691 | 14.106 | 32.286 | 122.899 | 1.00 | 7.79 | B | C |
| ATOM | 10923 | CA | PRO | B | 692 | 17.484 | 31.426 | 124.521 | 1.00 | 7.84 | B | C |
| ATOM | 10930 | CA | PHE | B | 693 | 18.864 | 34.550 | 126.227 | 1.00 | 7.82 | B | C |
| ATOM | 10941 | CA | PHE | B | 694 | 22.594 | 34.064 | 125.890 | 1.00 | 7.33 | B | C |
| ATOM | 10952 | CA | ASP | B | 695 | 25.205 | 33.655 | 123.125 | 1.00 | 9.43 | B | C |
| ATOM | 10960 | CA | SER | B | 696 | 26.210 | 30.332 | 124.574 | 1.00 | 9.32 | B | C |
| ATOM | 10966 | CA | THR | B | 697 | 24.781 | 28.206 | 127.383 | 1.00 | 8.98 | B | C |
| ATOM | 10973 | CA | THR | B | 698 | 26.586 | 24.967 | 128.241 | 1.00 | 8.91 | B | C |
| ATOM | 10980 | CA | ILE | B | 699 | 25.297 | 22.278 | 130.616 | 1.00 | 9.45 | B | C |
| ATOM | 10988 | CA | THR | B | 700 | 28.086 | 19.908 | 131.647 | 1.00 | 10.12 | B | C |
| ATOM | 10995 | CA | TYR | B | 701 | 27.061 | 16.493 | 132.887 | 1.00 | 9.88 | B | C |
| ATOM | 11007 | CA | ASP | B | 702 | 28.712 | 14.246 | 135.442 | 1.00 | 11.45 | B | C |
| ATOM | 11015 | CA | ASP | B | 703 | 30.657 | 12.267 | 132.819 | 1.00 | 13.40 | B | C |
| ATOM | 11023 | CA | GLY | B | 704 | 32.161 | 15.461 | 131.345 | 1.00 | 11.98 | B | C |
| ATOM | 11027 | CA | SER | B | 705 | 29.921 | 15.485 | 128.268 | 1.00 | 10.92 | B | C |
| ATOM | 11033 | CA | ALA | B | 706 | 27.904 | 18.613 | 127.584 | 1.00 | 10.52 | B | C |
| ATOM | 11038 | CA | PHE | B | 707 | 24.798 | 20.036 | 125.938 | 1.00 | 9.26 | B | C |
| ATOM | 11049 | CA | THR | B | 708 | 25.464 | 23.375 | 124.241 | 1.00 | 8.88 | B | C |
| ATOM | 11056 | CA | VAL | B | 709 | 22.737 | 25.748 | 123.064 | 1.00 | 9.09 | B | C |
| ATOM | 11063 | CA | THR | B | 710 | 24.043 | 28.747 | 121.128 | 1.00 | 11.17 | B | C |
| ATOM | 11070 | CA | ALA | B | 711 | 22.134 | 31.834 | 120.050 | 1.00 | 12.24 | B | C |
| ATOM | 11075 | CA | ASP | B | 712 | 24.141 | 33.564 | 117.322 | 1.00 | 14.25 | B | C |
| ATOM | 11083 | CA | GLY | B | 713 | 23.722 | 37.334 | 117.271 | 1.00 | 12.57 | B | C |
| ATOM | 11087 | CA | VAL | B | 714 | 21.303 | 37.259 | 120.194 | 1.00 | 12.10 | B | C |
| ATOM | 11094 | CA | SER | B | 715 | 20.477 | 40.687 | 121.622 | 1.00 | 11.79 | B | C |
| ATOM | 11100 | CA | GLU | B | 716 | 17.633 | 42.447 | 123.438 | 1.00 | 13.43 | B | C |
| ATOM | 11109 | CA | ASP | B | 717 | 16.112 | 43.108 | 119.987 | 1.00 | 12.74 | B | C |
| ATOM | 11117 | CA | ALA | B | 718 | 17.337 | 39.953 | 118.227 | 1.00 | 11.10 | B | C |
| ATOM | 11122 | CA | PHE | B | 719 | 15.169 | 37.456 | 120.135 | 1.00 | 10.51 | B | C |
| ATOM | 11133 | CA | TYR | B | 720 | 13.602 | 35.772 | 117.045 | 1.00 | 10.60 | B | C |
| ATOM | 11145 | CA | VAL | B | 721 | 14.971 | 32.509 | 115.687 | 1.00 | 9.51 | B | C |
| ATOM | 11152 | CA | GLN | B | 722 | 15.866 | 32.757 | 111.949 | 1.00 | 9.69 | B | C |
| ATOM | 11161 | CA | SER | B | 723 | 17.260 | 29.236 | 111.377 | 1.00 | 10.67 | B | C |
| ATOM | 11167 | CA | ALA | B | 724 | 18.749 | 26.372 | 113.367 | 1.00 | 10.44 | B | C |
| ATOM | 11172 | CA | THR | B | 725 | 21.057 | 23.385 | 113.295 | 1.00 | 10.19 | B | C |
| ATOM | 11179 | CA | LEU | B | 726 | 21.285 | 20.299 | 115.497 | 1.00 | 9.79 | B | C |
| ATOM | 11187 | CA | ASP | B | 727 | 24.740 | 18.682 | 115.470 | 1.00 | 10.78 | B | C |
| ATOM | 11195 | CA | GLY | B | 728 | 25.486 | 20.479 | 112.168 | 1.00 | 9.59 | B | C |
| ATOM | 11199 | CA | ALA | B | 729 | 22.291 | 19.355 | 110.407 | 1.00 | 9.37 | B | C |
| ATOM | 11204 | CA | THR | B | 730 | 19.314 | 21.561 | 109.427 | 1.00 | 9.54 | B | C |
| ATOM | 11211 | CA | PHE | B | 731 | 16.911 | 21.620 | 112.380 | 1.00 | 9.46 | B | C |
| ATOM | 11222 | CA | GLY | B | 732 | 13.291 | 22.799 | 111.894 | 1.00 | 10.01 | B | C |
| ATOM | 11226 | CA | ASN | B | 733 | 11.327 | 21.345 | 114.825 | 1.00 | 10.28 | B | C |
| ATOM | 11234 | CA | THR | B | 734 | 9.967 | 23.567 | 117.612 | 1.00 | 10.95 | B | C |
| ATOM | 11241 | CA | TRP | B | 735 | 10.620 | 20.889 | 120.262 | 1.00 | 9.83 | B | C |
| ATOM | 11255 | CA | VAL | B | 736 | 13.510 | 18.634 | 121.295 | 1.00 | 9.57 | B | C |
| ATOM | 11262 | CA | ASP | B | 737 | 13.581 | 15.277 | 123.044 | 1.00 | 9.41 | B | C |
| ATOM | 11270 | CA | TYR | B | 738 | 15.214 | 14.889 | 126.458 | 1.00 | 7.09 | B | C |
| ATOM | 11282 | CA | ALA | B | 739 | 17.644 | 12.232 | 125.051 | 1.00 | 6.73 | B | C |
| ATOM | 11287 | CA | THR | B | 740 | 19.020 | 14.795 | 122.576 | 1.00 | 6.66 | B | C |
| ATOM | 11294 | CA | VAL | B | 741 | 19.805 | 17.297 | 125.352 | 1.00 | 6.54 | B | C |
| ATOM | 11301 | CA | VAL | B | 742 | 21.387 | 14.908 | 127.847 | 1.00 | 6.53 | B | C |
| ATOM | 11308 | CA | GLY | B | 743 | 23.160 | 13.136 | 124.956 | 1.00 | 8.60 | B | C |
| ATOM | 11312 | CA | GLY | B | 744 | 25.256 | 16.293 | 124.535 | 1.00 | 8.96 | B | C |
| ATOM | 11316 | CA | ALA | B | 745 | 23.948 | 17.869 | 121.301 | 1.00 | 8.77 | B | C |
| ATOM | 11321 | CA | ASP | B | 746 | 24.948 | 21.245 | 119.824 | 1.00 | 9.99 | B | C |
| ATOM | 11329 | CA | LEU | B | 747 | 21.727 | 23.156 | 119.256 | 1.00 | 9.20 | B | C |
| ATOM | 11337 | CA | ALA | B | 748 | 22.723 | 26.298 | 117.347 | 1.00 | 9.57 | B | C |
| ATOM | 11342 | CA | PHE | B | 749 | 20.245 | 29.087 | 116.636 | 1.00 | 9.42 | B | C |
| ATOM | 11353 | CA | ARG | B | 750 | 20.864 | 32.051 | 114.353 | 1.00 | 10.76 | B | C |
| ATOM | 11364 | CA | MET | B | 751 | 18.965 | 35.015 | 115.906 | 1.00 | 10.21 | B | C |
| ATOM | 11372 | CA | GLY | B | 752 | 17.572 | 38.240 | 114.387 | 1.00 | 12.06 | B | C |
| ATOM | 11376 | CA | GLU | B | 753 | 15.318 | 41.247 | 114.999 | 1.00 | 14.15 | B | C |
| ATOM | 11385 | CA | GLN | B | 754 | 12.309 | 40.094 | 112.922 | 1.00 | 15.06 | B | C |
| ATOM | 11394 | CA | PRO | B | 755 | 9.930 | 37.094 | 113.128 | 1.00 | 14.14 | B | C |
| ATOM | 11401 | CA | SER | B | 756 | 10.685 | 34.248 | 110.709 | 1.00 | 14.80 | B | C |

FIG. 34-23

```
ATOM  11407  CA  ASP B 757       8.804  31.176 109.465  1.00 14.96       B    C
ATOM  11415  CA  TRP B 758      11.407  28.912 111.150  1.00 13.21       B    C
ATOM  11429  CA  GLY B 759       9.689  25.918 112.773  1.00 13.37       B    C
ATOM  11433  CA  THR B 760       6.357  26.434 111.014  1.00 13.94       B    C
ATOM  11440  CA  ASP B 761       6.914  23.033 109.382  1.00 13.96       B    C
ATOM  11448  CA  THR B 762       7.829  21.295 112.640  1.00 10.47       B    C
ATOM  11455  CA  ALA B 763       7.173  17.563 113.052  1.00  9.77       B    C
ATOM  11460  CA  PRO B 764       4.213  17.436 115.464  1.00  9.45       B    C
ATOM  11467  CA  ALA B 765       4.950  17.568 119.216  1.00  7.60       B    C
ATOM  11472  CA  PHE B 766       3.648  14.939 121.659  1.00  7.84       B    C
ATOM  11483  CA  SER B 767      -0.100  14.561 122.179  1.00  8.05       B    C
ATOM  11489  CA  MET B 768      -1.670  11.546 123.865  1.00 10.37       B    C
ATOM  11497  CA  SER B 769      -4.411  11.138 121.212  1.00 13.56       B    C
ATOM  11503  CA  THR B 770      -1.982  11.233 118.242  1.00 17.85       B    C
ATOM  11510  CA  ALA B 771       0.792   9.094 119.762  1.00 20.44       B    C
ATOM  12382 CA     CA C   1      41.425  16.915  81.268  1.00 30.05       C   CA
ATOM  12383 CA     CA C   6       1.503  30.134 143.317  1.00 32.32       C   CA
END
```

FIG. 34-24

HYDROLYSIS OF MANNOSE-1-PHOSPHO-6-MANNOSE LINKAGE TO PHOSPHO-6-MANNOSE

CROSS-REFERENCE TO RELATED APPLICATIONS

This application is a continuation, and claims priority, of co-pending U.S. application Ser. No. 13/499,061, having a 371 completion date of Sep. 6, 2012, which is a U.S. National Stage application, and claims priority of International Application No. PCT/IB2010/002589, filed Sep. 29, 2010, which claims priority of U.S. Provisional Application Ser. No. 61/246,847, filed Sep. 29, 2009. The contents of all of the prior applications are incorporated herein by reference in their entirety.

TECHNICAL FIELD

The invention relates to methods of hydrolyzing mannose-1-phospho-6-mannose linkages on glycoproteins, and more particularly, to using a mannosidase to hydrolyze mannose-1-phospho-6-mannose linkages to uncap the phospho-6-mannose residues on the glycoprotein.

BACKGROUND

High performance expression systems are required to produce most biopharmaceuticals (e.g., recombinant proteins) currently under development. The biological activity of many of these biopharmaceuticals is dependent on their post-translational modification (e.g., phosphorylation or glycosylation). A yeast-based expression system combines the case of genetic manipulation and fermentation of a microbial organism with the capability to secrete and to modify proteins. However, recombinant glycoproteins produced in yeast cells exhibit mainly heterogeneous high-mannose and hyper-munnose glycan structures, which can be detrimental to protein function, downstream processing, and subsequent therapeutic use, particularly where glycosylation plays a biologically significant role.

U.S. application Ser. No. 12/062,469 is incorporated by reference in its entirety.

SUMMARY

The present invention is based, at least in part, on the discovery of a mannosidase that is capable of hydrolyzing mannose-1-phospho-6-mannose linkages on glycoproteins. As such, the mannosidase can be used to obtain glycoproteins containing uncapped terminal mannose-6-phosphate residues. In vitro and in vivo methods of obtaining such glycoproteins are described herein. Genetically engineered cells can be used in the methods to produce target molecules having uncapped terminal mannose-6-phosphate residues.

In one aspect, this document features a method for uncapping a mannose-6-phosphate residue on an oligosaccharide. The method includes providing the oligosaccharide having a mannose-1-phospho-6-mannose linkage; and contacting the oligosaccharide with a mannosidase capable of hydrolyzing the mannose-1-phospho-6-mannose linkage to phospho-6-mannose. The contacting step can be performed using a purified mannosidase, a recombinant mannosidase, a cell lysate containing the recombinant mannosidase, or a fungal cell containing the recombinant mannosidase. The mannosidase can include a targeting sequence. The oligosaccharide can be attached to a protein (e.g., a human protein expressed in a fungal organism).

In another aspect, this document features a method of producing a target protein having terminal phospho-6-mannose residues. The method includes providing a fungal cell genetically engineered to include a nucleic acid encoding a mannosidase, the mannosidase capable of hydrolyzing a mannose-1-phospho-6-mannose linkage to phospho-6-mannose; and introducing into the cell a nucleic acid encoding a target protein, wherein the cell produces the target protein comprising the terminal phospho-6-mannose residues.

This document also features a method of producing a target protein having terminal phospho-6-mannose residues in a fungal organism. The method includes providing a fungal cell genetically engineered to include a nucleic acid encoding a mannosidase capable of hydrolyzing a mannose-1-phospho-6-mannose linkage to phospho-6-mannose, wherein the fungal cell further includes a nucleic acid encoding a target protein; and isolating the target protein having the terminal phospho-6-mannose residues. The fungal cell further can include a nucleic acid encoding a polypeptide capable of promoting mannosyl phosphorylation and/or can be genetically engineered to be deficient in OCH1 activity.

This document also features an isolated fungal cell genetically engineered to produce glycoproteins comprising terminal phospho-6-mannose residues. The fungal cell includes a nucleic acid, encoding a mannosidase, wherein expression of the mannosidase in the fungal cell produces glycoproteins comprising the terminal phospho-6-mannose residues. The fungal cell further can include a nucleic acid encoding a target glycoprotein protein.

In another aspect, this document features a substantially pure culture of *Yarrowia lipolytica, Pichia pastoris, Hansenula polymorpha, Arxula adeninovorans, Pichia methanolica, Oogataea minuta*, or *Aspergillus niger* cells, a substantial number of which are genetically engineered to produce glycoproteins comprising a terminal phospho-6-mannose residue, the cells comprising a nucleic acid encoding a mannosidase capable of hydrolyzing a mannose-1-phospho-6-mannose linkage to phospho-6-mannose.

In any of the embodiments described herein, the fungal organism can be *Yarrowia lipolytica* or *Arxula adeninivorans*. The fungal organism can be a methylotrophic yeast such as *Pichia pastoris, Pichia methanolica, Oogataea minuta*, or *Hansenula polymorpha*. The fungal organism can be a filamentous fungus (e.g., a filamentous fungus selected from the group consisting of *Aspergillus caseiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowl, Aspergillus tamari, Aspergillus terreus, Aspergillus ustus*, and *Aspergillus versicolor*).

In any of embodiments described herein, the protein can be a pathogen protein, a lysosomal protein, a growth factor, a cytokine, a chemokine, an antibody or antigen-binding fragment thereof, or a fusion protein. The lysosomal protein can be a lysosomal enzyme (e.g., a lososomal enzyme associated with a lysosomal storage disorder (LSD) such as acid alpha glucosidase or alpha galactosidase). The LSD can be Fabry's disease, mucopolysaccharidoisis I, Farber disease, Gaucher disease, GM1-gagliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartyglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia. For example, the LSD can be Pompe disease or Fabry's disease.

In any of the embodiments described herein, for the mannosidase, the three dimensional protein coordinates of the atoms in the amino acid side chains located in the minimal catalytic center fall within 1.5 Å deviation of the coordinates of the equivalent atoms in FIG. 33.

In any of the embodiments described herein, the mannosidase can include an amino acid sequence having at least 90% identity (e.g., at least 95% or 98% identity) to the amino acid sequence set forth in residues 1 to 774 of SEQ ID NO:50 or to the amino acid sequence set forth in SEQ ID NO:50.

In any of the embodiments described herein, the mannosidase can include an amino acid sequence having (i) a GVGXXGXGG motif, where X is Gly, Ala, Ser, Thr, or Cys; (ii) a VRXE motif, where X is any amino acid other than Pro; (iii) an $X_1YQGX_2$ motif, where $X_1$ is Leu, Ile, Val, Ala, Phe, Tyr or Met, and $X_2$ is Thr, Ser, or Asn; or (iv) a GDXGN motif, where X can be any amino acid other than Pro.

In any of the embodiments described herein, the mannosidase can be a *C. cellulans, Streptomyces coelicolor*, or *Streptomyces lividans* mannosidase.

In any of the embodiments described herein, the fungal cell further can include a nucleic acid encoding a polypeptide capable of promoting mannosyl phosphorylation (e.g., a MNN4 polypeptide such as *Yarrowia lipolytica, S. cerevisiae, Ogataea minuta, Pichia pastoris*, or *C. albicans* polypeptide) and/or can be genetically engineered to be deficient in OCH1 activity. For example, the polypeptide capable of promoting mannosyl phosphorylation can be a *P. pastoris* PNO1 polypeptide.

In any of the embodiments described herein, the mannosidase can include a secretion signal and/or a targeting signal to target the mannosidase to an intracellular compartment. The target protein and the mannosidase can be co-secreted.

This document also features an isolated glycoprotein that includes terminal phospho-6-mannose residues, wherein the protein is produced by the methods described herein.

In yet another aspect, this document features a composition that includes a glycoprotein, wherein at least 47% of the N-glycans on the glycoprotein have terminal phospho-6-manitose residues. For example, at least 50%, 75%, 80%, 85%, or 90% of the N-glycans on the glycoprotein can have terminal phospho-6-mannose residues.

This document also features an isolated nucleic acid that includes a nucleotide sequence set forth in SEQ ID NO:6, SEQ ID NO:8, SEQ ID NO:10, SEQ ID NO: 12, or SEQ ID NO:14, or a nucleotide sequence that is at least 90% identical, to SEQ ID NO:6, SEQ ID NO:8, SEQ ID NO:10, SEQ ID NO:12, SEQ ID NO:14, or SEQ ID NO:20. This document also features a vector that includes a promoter operably linked to such a nucleic acid, wherein the nucleic acid encodes a raannssidase. The nucleic acid further can include a secretion signal or targeting sequence to target the mannosidase to an intracellular compartment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 8A is the nucleotide sequence (SEQ ID NO:6) encoding CcMan1 (i.e., mannosidase candidate 1 from *C. Cellulans*) (on contig1003), which was identified in the MS/MS de novo sequencing. FIG. 8B is the amino acid sequence (SEQ ID NO:7) of CcMan1, including the signal sequence (in bold). The predicted molecular weight of the CcMan 1 polypeptide without the signal sequence is 92.6 kDa.

FIG. 9A is the nucleotide sequence (SEQ ID NO:8) encoding CcMan2 (on contig 774) and FIG. 9B is the amino acid sequence of CcMan2 (SEQ ID NO:9) with signal sequence (in bold). The predicted molecular weight of the CcMan2 polypeptide without the signal sequence is 121.6 kDa.

FIG. 10A is the nucleotide sequence (SEQ ID NO:10) encoding CcMan3 (on contig 774) and FIG. 10B is the amino acid sequence of CcMan3 (SEQ ID NO:11) with signal sequence (in bold). The predicted molecular weight of the CcMan3 polypeptide without the signal sequence is 116 kDa.

Figure 11A-3:
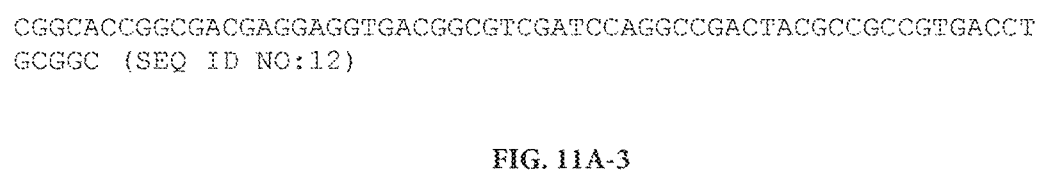

FIG. 11A is the nucleotide sequence (SEQ ID NO:12) encoding CcMan4 (on contig 1237) and FIG. 11B is the amino acid sequence of CcMan4 (SEQ ID NO:13) with signal sequence (on bold). The predicted molecular weight of the CcMan4 polypeptide without the signal sequence is 184 kDa.

FIG. 12A is the nucleotide sequence (SEQ ID NO:14) encoding CcMan5 (on contig 896). FIG. 12B is the amino acid sequence of CcMan5 with signal sequence (in bold) (SEQ ID NO:15) and FIG. 12C is the amino acid sequence of CcMan5 without signal sequence (SEQ ID NO:50). The predicted molecular weight of the CcMan5 polypeptide without the signal sequence is 173 kDa.

FIG. 14 is the nucleotide sequence of CcMan1 that has been codon optimised for expression in *E. coli* (SEQ ID NO:16).

FIG. 15 is the nucleotide sequence of CcMan2 that has been codon optimized for expression *E. coli* (SEQ ID NO:17).

FIG. 16 is the nucleotide sequence of CcMan3 that has been codon optimized for expression in *E. coli* (SEQ ID NO:18).

FIG. 17 is the nucleotide sequence of CcMan4 that has been codon optimized for expression in *E. coli* (SEQ ID NO: 19).

FIG. 18 is the nucleotide sequence of CcMan5 that has been codon optimized for expression in *E. coli* (SEQ ID NO:20).

FIG. 2 is a schematic alignment of CcMan4 (1759 AA) and CeMan5 (1650 AA) with Bt3990 (744 AA) and Bt2199 (739 AA) mannosidases described in Zhu et al., *Nat. Chem. Biol.,* 6(2):125-32. Epub 2009 Dec. 27 (2010).

FIG. 26A is the *Y. lipolytica* codon optimized nucleotide sequence encoding α-GalactosidaseA with lip2 pre sequence in bold and the Myc His tag underlined (SEQ ID NO:22). FIG. 26B is the amino acid sequence of α-GalactosidaseA with lip2 pre sequence in bold and the Myc His tag underlined (SEQ ID NO:23).

FIG. 27A is the codon optimized nucleotide sequence of human alpha glucosidase (GAA) with lip2 pre sequence in bold (SEQ ID NO:24). FIG. 27B is the amino acid sequence of human GAA with lip2 pre sequence in bold (SEQ ID NO:25), where the * represents the stop codon.

FIG. 33 contains the structural coordinates of the residues surrounding the active site of $CcMan5_{1-774}$.

FIG. 34 contains the protein C alpha atoms and the catalytic Ca2+ atoms of the two $CeMan5_{1-774}$ molecules in the asymmetric unit in PDB entry 2xsg and describes the overall fold of the protein.

DETAILED DESCRIPTION

Figure 1:
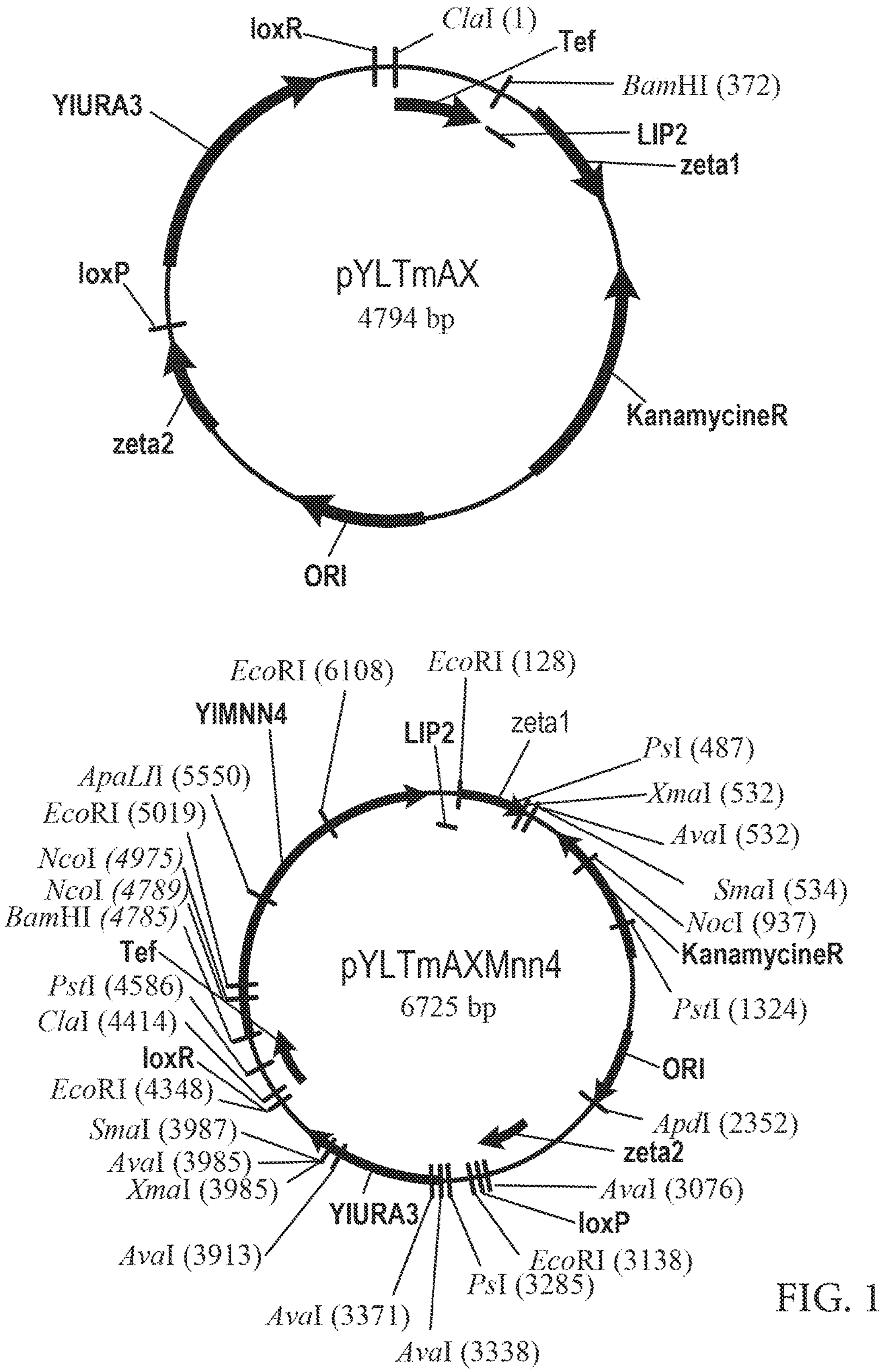
FIG. 1 is a schematic of the pYLTmAX and pYLTmAX-Mnn4 constructs.

In general, this document provides methods and materials for hydrolyzing mannose-1-phospho-6-mannose linkages on glycoproteins to produce target molecules (e.g., target proteins) having uncapped phospho-6-mannose (M6P) residues. The methods and materials described herein are particularly useful for producing agents or treating patients with lysosomal storage disorders (LSDs), a diverse group of hereditary metabolic disorders characterized by the accumulation of storage products in the lysosomes due to impaired activity of catabolic enzymes involved in their degradation. The build-up of storage products leads to cell dysfunction and progressive clinical manifestations. Deficiencies in catabolic enzymes can be corrected by enzyme replacement therapy (ERT), provided that the administered enzyme can be targeted to the lysosomes of the diseased cells. Lysosomal enzymes typically are glycoproteins that are synthesized in the endoplasmic reticulum (ER), transported via the secretory pathway to the Golgi, and then recruited to the lysosomes. One way in which lysosomal enzymes are delivered to the lysosome is via a cation-dependent (CD) mannose 6-phosphate receptor (MPR), M6P terminal glycans are recognized in the trans-Golgi network (TGN) by two MPRs that mediate the sorting of lysosomal enzymes from the secretory pathway and deliver the enzyme to the lysosome. Using the methods and materials described herein, a microbial based production process can be used to obtain therapeutic proteins with uncapped M6P glycans, which can be delivered to lysosomes by exploiting the same M6P dependent pathway. Thus, the methods and materials described herein are useful for preparing glycoproteins for the treatment of metabolic disorders such as LSDs.

Mannosidases

This document provides isolated nucleic acids encoding mannosidase polypeptides capable of hydrolyzing terminal mannose-1-phospho-6-mannose linkages on oligosaccharides, as well as isolated mannosidases capable of hydrolyzing terminal mannose-1-phospho-6-mannose linkages on oligosaccharides. The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

"Polypeptide" and "protein" are used interchangeably herein and mean any peptide-linked chain of amino acids, regardless of length or post-translational modification. Typically, a polypeptide described herein (e.g., a mannosidase or a target protein having uncapped M6P residues) is isolated when it constitutes at least 60%, by weight, of the total protein. In a preparation, e.g., 60% of the total protein in a sample. In some embodiments, a polypeptide described herein consists of at least 75%, at least 90%, or at least 99%, by weight, of the total protein in a preparation.

An "isolated nucleic acid" refers to a nucleic acid that is separated from other nucleic acid molecules that are present in a naturally-occurring genome, including nucleic acids that normally flank one or both sides of the nucleic acid in a naturally-occurring genome (e.g., a yeast genome). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuelease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The term "exogenous" as used herein with reference to nucleic acid and a particular host cell refers to any nucleic acid that does not occur in (and cannot be obtained from)

that particular cell as found in nature. Thus, a non-naturally-occuring nucleic acid is considered to be exogenous to a host cell once introduced into the host cell. It is important to note that non-naturally-occurring nucleic acids can contain nucleic acid subsequences or fragments of nucleic acid sequences that are found in nature provided that the nucleic acid as a whole does not exist in nature. For example, a nucleic acid molecule combining a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular cell. For example, an entire chromosome isolated from a cell of yeast x is an exogenous nucleic acid with respect to a cell of yeast y once that chromosome is introduced into a cell of yeast.

A nucleic acid encoding a mannosidase can have at least 70% sequence identity (e.g., at least 80%, 85%, 90%, 95%, 97%, 98%, 99%, or 100% sequence identity) to a nucleotide sequence set forth in SEQ ID NO:6, SEQ ID NO:8, SEQ ID NO:10, SEQ ID NO:12, or SEQ ID NO:14. In some embodiments, nucleic acids described herein can encode mannosidase polypeptides that have at least 70% (e.g., at least 75, 80, 85, 90, 95, 99, or 100 percent) identity to an amino acid sequence set forth in SEQ ID NOs: 7, 9, 11, 13, 15, 50. For example, a nucleic acid can encode a mannosidase having at least 90% (e.g., at least 95 or 98%) identity to the amino acid sequence set forth in SEQ ID NO:15 or SEQ ID NO:50, or a portion thereof. For example, a nucleic acid can encode a mannosidase having at least 90% identity to amino acid residues 1 to 774 of SEQ ID NO:50. The percent identity between a particular amino acid sequence and the amino acid sequence set forth in SEQ ID NO:7, SEQ ID NO:9, SEQ ID NO:11, SEQ ID NO:13, SEQ ID NO:15, or SEQ ID NO:50 is determined as follows. First, the amino acid sequences are aligned using the BLAST 2 Sequences (B12seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: –i is set to a file containing the first amino acid sequence to be compared (e.g., C:\seq1.txt); –j is set to a file containing the second amino acid sequence to be compared (e.g., C:\seq2.txt); –p is set to blastp; –o is set to any desired file name (e.g., C:\output.txt); and all other options are left at their default setting. For example, the following command can be used to generate an output file containing a comparison between two amino acid sequences: C:\B12seq–i c:\seq1.txt–j c:\seq2.txt–p blastp–o c:\output.txt. If the two compared sequences share homology, then the designated output file will present those regions of homology as aligned sequences. If the two compared sequences do not share homology, then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length mannosidase polypeptide amino acid sequence followed by multiplying the resulting value by 100. For example, an amino acid sequence that has 700 matches when aligned with the sequence set forth in SEQ ID NO:7 is 77.8 percent identical to the sequence set forth in SEQ ID NO:7 (i.e., 700÷900*100=77.8).

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given mannosidase polypeptide can be modified such that optimal expression in a particular species (e.g., bacteria or fungus) is obtained, using appropriate codon bias tables for that species. For example, the nucleic acids set forth in SEQ ID NO:6, SEQ ID NO:8, SEQ ID NO:10, SEQ ID NO:12, or SEQ ID NO:14 can be codon optimized for *E. coli* expression as set forth in FIGS. 14-18 (see SEQ ID NOs:16-20).

Hybridization also can be used to assess homology between two nucleic acid sequences. A nucleic acid sequence described herein, or a fragment or variant thereof, can be used as a hybridization probe according to standard hybridization techniques. The hybridization of a probe of interest (e.g., a probe containing a portion of a CcMan5 nucleotide sequence) to DNA or RNA from a test source is an indication of the presence of DNA or RNA (e.g., a CcMan5 nucleotide sequence) corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

Mannosidase polypeptides capable of hydrolyzing terminal mannose-1-phospho-6-mannose linkages on oligosaccharides also can be identified based on the three dimensional structure described herein for a portion of mannosidase from *C. cellulans* (residues 1 to 774 of SEQ ID NO:50, also referred to as $CcMan5_{1-774}$). The three dimensional structure can be determined by, for example, X-ray diffraction off a crystal of $CcMan5_{1-774}$. Structural coordinates of $CcMan5_{1-774}$ (e.g., the coordinates of $CcMan5_{1-774}$ deposited with the Protein Data Bank (world wide web at PDB.org under PDB ID No. 2xs), the coordinates set forth in FIG. 33 for the catalytic center of CcMan5, or the coordinates set forth in FIG. 34 for the protein C alpha atoms and the catalytic Ca2+ atoms of the two $CcMan5_{1-774}$ molecules in the asymmetric unit in PDB entry 2xsg) are useful for a number of applications, including, but not limited to, the characterization of a three dimensional structure of a mannosidase capable of hydrolyzing terminal mannose-1-phospho-6-mannose linkages on oligosaccharides, as well as the visualization, identification and characterization of regions of the mannosidase that are involved in acceptance of mannose-6-phosphate-alpha, 1-mannose (hereafter referred to as Man-P-Man) as a substrate, and conferring its ability to hydrolyse Man-P-Man to produce a terminal phospho-6-mannose. “Structural coordinates” are the Cartesian coordinates corresponding to an atom’s spatial relationship to other atoms in a molecule or molecular complex. Structural coordinates can be obtained using x-ray crystallography techniques or NMR techniques, or can be derived using molecular replacement analysis or homology modeling. Various software programs allow for the graphical representation of a set of structural coordinates to obtain a three dimensional representation of a molecule or molecular complex. The structural coordinates of the structures described herein can be modified from the original set provided in FIG. 33 or FIG. 34 by mathematical manipulation, such as by inversion or integer additions or substractions. As such, it is recognized that the structural coordinates of the present invention are relative, and are in no way specifically limited by the actual x, y, z coordinates of FIG. 33 or FIG. 34.

As set forth in Example 8, the structure of $CcMan5_{1-774}$ consists of two domains, an N-terminal β-sandwich domain (residues 8 to 271 of SEQ ID NO:50) and a C-terminal (αα)6 barrel domain (residues 291 to 771 of SEQ ID NO:50), connected via an α-helical linker (residues 272 to 290 of SEQ ID NO:50). The interface between both domains gives shape to a shallow cavity that harbors a conserved catalytic $Ca^{2+}$ ion and gives shape to the −1 substrate binding site (nomenclature as described by Davies et al., *Biochem. J.* 321:557-9 (1997)) and the catalytic center. Residues 22, 25, 71, 72, 195, 196, 354, 405, 535, 536, 588, 589, 626, 658, 660, and 662 of SEQ ID NO: 50 form the substrate binding site.

The three dimensional structure of $CcMan5_{1-774}$ can be characterized in part, or all, using the structural coordinates of PDB ID No. 2xs, or an extract of which that is presented in FIG. 33, comprising the residues surrounding the active site of $CcMan5_{1-774}$, or an extract of which that is presented in FIG. 34, comprising the protein C alpha atoms and the catalytic Ca2+ atoms of the two $CcMan5_{1-774}$ molecules in the asymmetric unit in PDB entry 2xsg, and describing the overall fold of the protein. For example, the three-dimensional structure of $CcMan5_{1-774}$ can be characterized by the structural coordinates of amino acid residues 7 to 771 according to PDB ID No. 2xs, ±a root mean square deviation from the conserved backbone atoms of said amino acids of not more than 2 Å. In some embodiments, the three dimensional structure of $CeMan5_{1-774}$ comprises the complete structural coordinates of the amino acids according to PDB ID No. 2xs, ±a root mean square deviation from the conserved backbone atoms of said amino acids of not more than 2 Å (e.g., not more than 1.5 Å, 1.0 Å or 0.5 Å). As used herein, “root mean square deviation” is the square root of the arithmetic mean of the squares of the deviations from the mean, and is a way of expressing deviation or variation from the structural coordinates described herein. The present disclosure includes all embodiments comprising conservative substitutions of the noted amino acid residues resulting in same structural coordinates within the stated root mean square deviation.

The structural coordinates provided herein can be used to characterise a three dimensional structure of a mannosidase polypeptide. From such a structure, substrate binding sites, for example, can be computationally visualized, identified and characterised based on the surface structure of the molecule, surface charge, steric arrangement, the presence of reactive amino acids, regions of hydrophobicity or hydrophilicity, etc.

In order to use the structural coordinates generated for a structure described herein as set forth in FIG. 33, FIG. 34, or PDB ID No. 2xs, the relevant coordinates can be displayed as, or converted to, a three dimensional shape or graphical representation. Software programs are commercially available that are capable of generating three dimensional graphical representation of moleculars or portions thereof from a set of structural coordinates. Examples of commercially available software programs include, without limitation, the following: GRID (Oxford University, Oxford, UK); MCSS (Molecular Simulations, San Diego, Calif.); AUTODOCK (Scripps Research Institute, La Jolla, Calif.); DOCK (University of California, San Francisco, Calif.); Flo99 (Thistlesoft, Morris Township, N.J.); Ludi (Molecular Simulations, San Diego, Calif.; QUANTA (Molecular Simulations, San Diego, Calif.); Insight (Molecular Simulations, San Diego, Calif.); SYBYL (TRIPOS, Inc., St. Louis, Mo.); and LEAPFROG (TRIPOS, Inc., St. Louis, Mo.).

The structural coordinates described herein can be used with standard homology modeling techniques in order to determine the unknown three-dimensional, structure of a molecular or molecular complex. Homology modeling involves constructing a model of an unknown structure using structural coordinates of one or more related protein molecules, molecular complexes or parts thereof. Homology modeling can be conducted by fitting common or homologous portions of the protein whose three dimensional structure is to be solved to the three dimensional structure of homologous structural elements in the known molecule, specifically using the relevant (i.e., homologous) structural coordinates provided by FIGS. 33 and 34 herein. Homology may be determined using amino acid sequence identity, homologous secondary structure elements, and/or homologous tertiary folds. Homology modeling can include rebuilding part or all of a three dimensional structure with replacement of amino acids (or other components) by those of the related structure to be solved. Accordingly, a three dimensional structure for the unknown molecule may be generated using the three dimensional structure of $CcMan5_{1-774}$ described herein, and refined using a number of techniques well known in the art.

Based on the three dimensional structure described herein, substitutions can be made in some of the atoms or side groups of $CcMan5_{1-774}$ or other mannosidases in order to improve or modify its selectivity. For example, CcMan5 contains a non-acidic residue at positions 536 and 588, which may allow the mannosidase to tolerate the phosphate linkage to the anomeric oxygen in Man-P-Man substrates. As such, corresponding residues in other mannosidases can be changed to non-acidic residues to increase the ability of the mannosidase to accept Man-P-Man substrates.

Other mannosidase polypeptide candidates suitable for use herein can be identified by analysis of nucleotide and polypeptide sequence alignments. For example, performing a query on a database of nucleotide or polypeptide sequences can identify homologs and/or orthologs of mannosidase polypeptides. Sequence analysis can involve BLAST, Reciprocal BLAST, or PSI-BLAST analysis of nonredundant databases using known mannosidase amino acid sequences. Those polypeptides in the database that have greater than 40% sequence identity can be identified as candidates for further evaluation for suitability as a mannosidase polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains suspected of being present in mannosidases capable of hydrolyzing terminal mannose-1-phospho-6-mannose linkages, e.g., one or more (e.g., 1, 2, 3, 4 or more) conserved domains or functional regions (e.g., substrate binding cavity). Such domains can include a glycine-rich motif GVGXXGXGG, where X is Gly, Ser, Thr, Val, Ala, Cys or Gln (or other amino acid with a small side chain). This motif is found at residues 69-77 of SEQ ID NO:50. This region makes a loop that provides essential hydrogen bonds to the −1 mannose and phosphate-binding subsite in the active site of the enzyme.

Another example of a conserved motif includes a VRXE motif, where Arg(R) makes a hydrogben bond to the −1 ring and possibly the +1 ring, Glu (E) is in a salt bridge to this R residue, probably shaping this motif; and X is Trp or any of the 20 amino acids except Pro. This motif is found at residues 404-407 of SEQ ID NO:50.

A suitable motif also can be an $X_1$YQGX$_2$ motif, where $X_1$ can be Leu, Ile, Val Ala, Phe, Tyr or Met, and $X_2$ can be Thr, Ser or Asn. This motif is found at residues 534-538 of SEQ ID NO:50. The Gln (Q) in this motif is important as an E is present in mannosidases that do not have the ability to hydrolyze terminal mannose-1-phospho-6-mannose linkages on oligosaccharides. The Tyr(Y) in this motif also is thought to be important for the +1 site formation.

Figure 30:
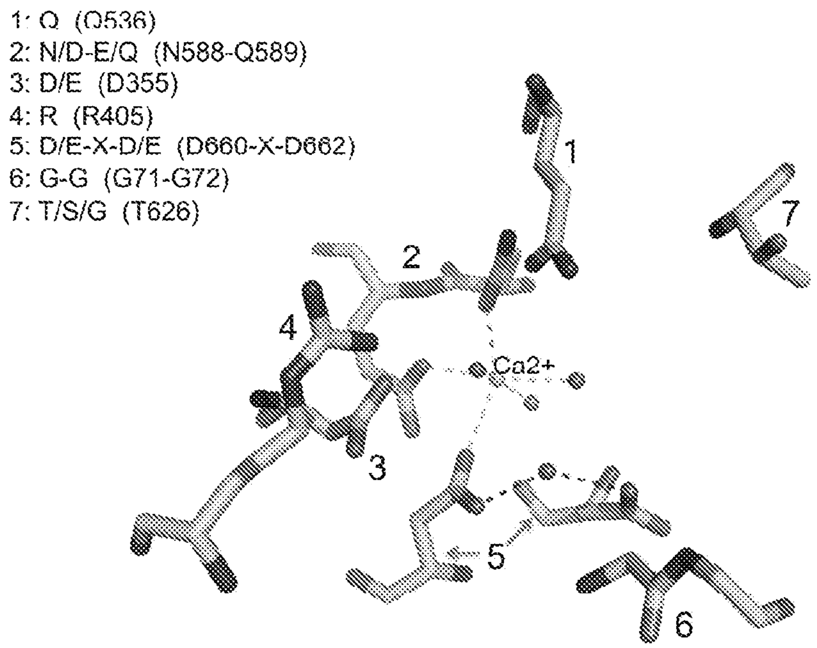
FIG. 30 is a depiction of the minimal catalytic center of CcMan5. The numbering of equivalent residues in SEQ ID NO:50 is given in parenthesis, 1: Q (Q536); 2: N/D-E/Q (N588-Q589); 3: D/E (D355); 4: R (R405); 5: D/E-X-D/E (D660-X-D662): 6: G-G (G71-G72); and 7: T/S/G (T626).

In addition, a region defined by residues 22, 25, 71, 72, 195, 196, 354, 405, 535, 536, 588, 589, 626, 658, 660, and 662 of SEQ ID NO:50 forms the substrate binding cavity of CcMan5. As a minimal requirement, G71, G72, D355, R405, Q536, N588, Q589, T626, D660, D662 form the catalytic center, where N588, Q589 and D660 are involved in coordinating the catalytic Ca2+ ion, D662 and D660 are involved in activating the nucleophilic water, Q536 stabilizes the anomeric oxygen during the transition state and G71, G71, D355, R405 and T626 are involved in substrate binding at the −1 site. See FIG. 30 for a representation of this minimal catalytic center. As such, a mannosidase can be selected as a candidate mannosidase capable of hydrolyzing terminal mannose-1-pbospho-6-mannose linkages when the three dimensional protein coordinates of the atoms in the amino acid side chains located in the minimal, catalytic center (e.g., as set forth in FIG. 30) fall within 1.5 Å deviation of the coordinates of the equivalent atoms in FIG. 33.

Figure 24:
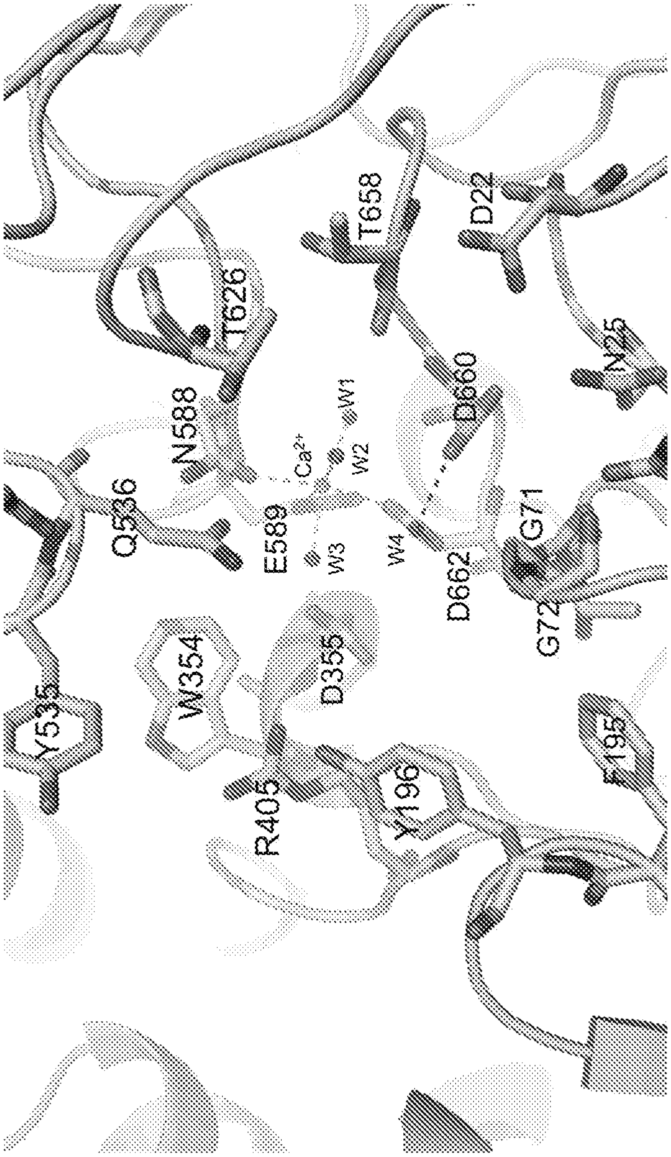
FIG. 24 is a ribbon representation of the $CcMan5_{1-774}$ protein backbone with side chains lining the substrate binding site shown in stick representation. Carbon, oxygen and nitrogen atoms are colored light gray, gray, and dark gray, respectively The $Ca^{2+}$ ion and waters W1, W2, W3 and W4 in the catalytic center are shown as spheres.

A conserved motif also can be a GDXGN motif in the N-terminal domain of the protein, where X can be any amino acid except P. This motif is found at residues 21-25 of SEQ ID NO:50 and forms part of the substrate binding pocket of the enzyme as shown in FIG. 24. In particular, the side chains of the D and N line the substrate binding cavity and may shape an alternative subpocket to bind the +1 mannose.

As set forth in Example 14, performing a query on a database of polypeptide sequences identified homologs of CcMan5 in the following organisms: *Streptomyces coelicolor* (GenBank Accession No. NP_630514), *Streptomyces lividans* (GenBank Accession No. ZP_05522540); *Streptomyces lividans* (GenBank Accession No. ZP_06527366); *Clostridium spiroforme* (GenBank Accession No. ZP_02866543) *Bacteriodes thetaiotaomicron* (GenBank Accession No. NP_812442), *Zunongwangia profunda* (GenBank Accession No. YP_003584502); *Chitinophaga pinensis* (GenBank Accession No. YP_003120664); *Paenibacillus* sp (GenBank Accession No. YP_003013376); *Bacteroides* sp. (GenBank Accession No. ZP_04848482), *Bacteroides cellulosilyticus* (GenBank Accession No. ZP_03677957) *Leeuwenhoekiella blandensis* (GenBank Accession No. ZP_01061975); *Sphingobacterium spiritivarum* (GenBank Accession No. ZP_07083984); and *Pedobacter* sp. (GenBank Accession No. ZP_01885202). The mannosidases from *Streptomyces coelicolor* and *Streptomyces lividans* are similar (66% sequence identity to the CcMan5 GH92 domain, with 501 identities over 765 aligned rersidues by BLASTP), not only in the above motifs but also in many the loops of the three dimensional structure.

Isolated nucleic acid molecules encoding mannosidase polypeptides can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specfic nucleotide sequence modifications can be introduced into a template nucleic acid. Isolated nucleic acids also can be chemically synthesized, either as a single nucleic acid molecule (e.g., using automated DNA systhesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment or complementarity (e.g., about 15 nucleotides) such that a duplex is formed when the oligonucleotide pair is annealed. DNA polymerase is used to extend the olignoucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

Figures 2, 31:
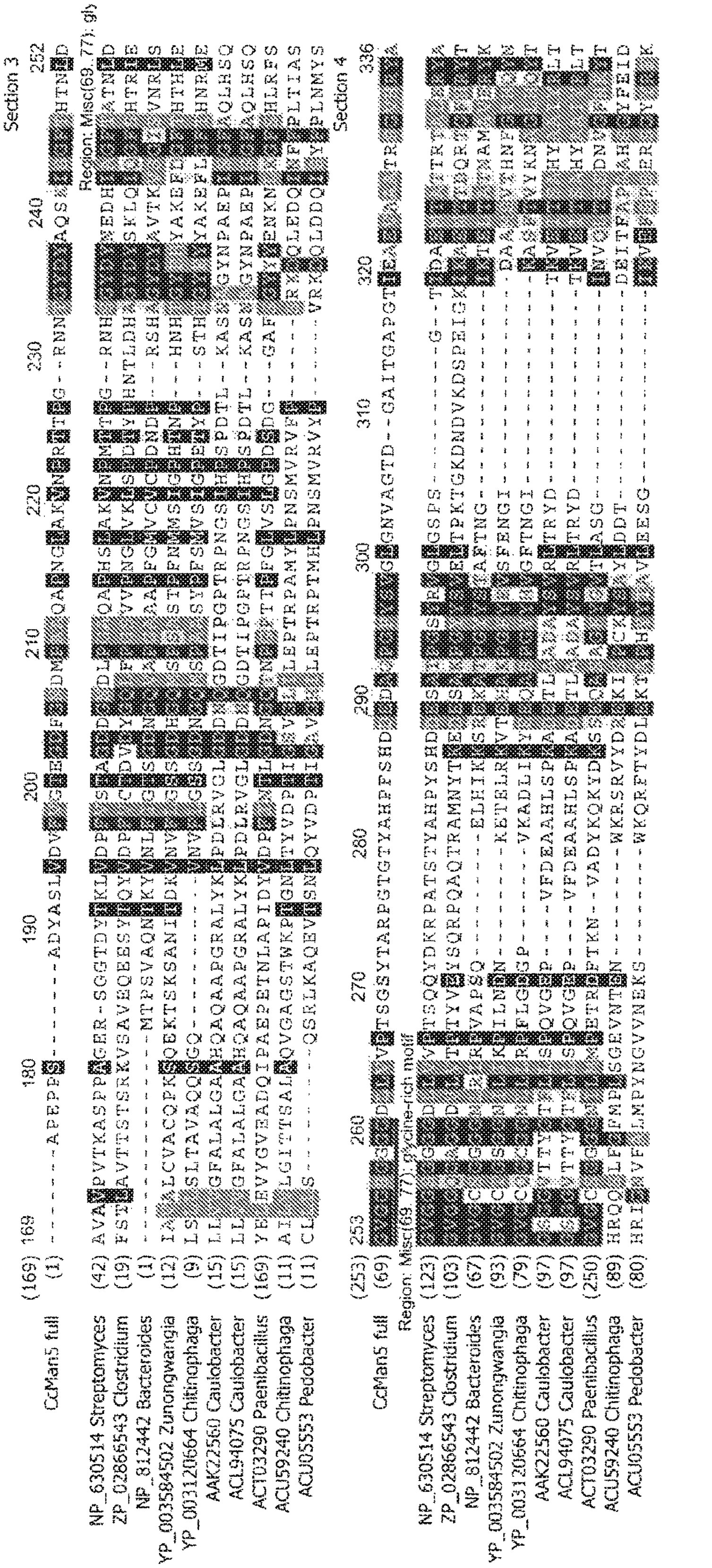
FIG. 31 is an alignment of the amino acid sequence of CcMan5 (SEQ ID NO:50, the amino acid sequence set forth in SEQ ID NO:15 without the signal peptide) and 10 of its homologs using MUSCLE (MUltiple Sequence Comparison by Log-Expectation). NP_630514 *Streptomyces,* SEQ ID NO:16; ZP_02866543 *Clostridium,* SEQ ID NO:27; NP_812442 *Bacteroides,* SEQ ID NO:28; YP_003584502 *Zunongwangia,* SEQ ID NO:29; YP_003120664 *Chitinophaga,* SEQ ID NO:30; AAK22560 *Caulobacter*, SEQ ID NO:31; ACL94075 *Caulobacter*, SEQ ID NO:32; ACT03290 *Paenibacillus*, SEQ ID NO:33; ACU59240 *Chitinophaga*, SEQ ID NO:34; ACU05553 *Pedobacter*, SEQ ID NO:35.
Figures 3, 31:
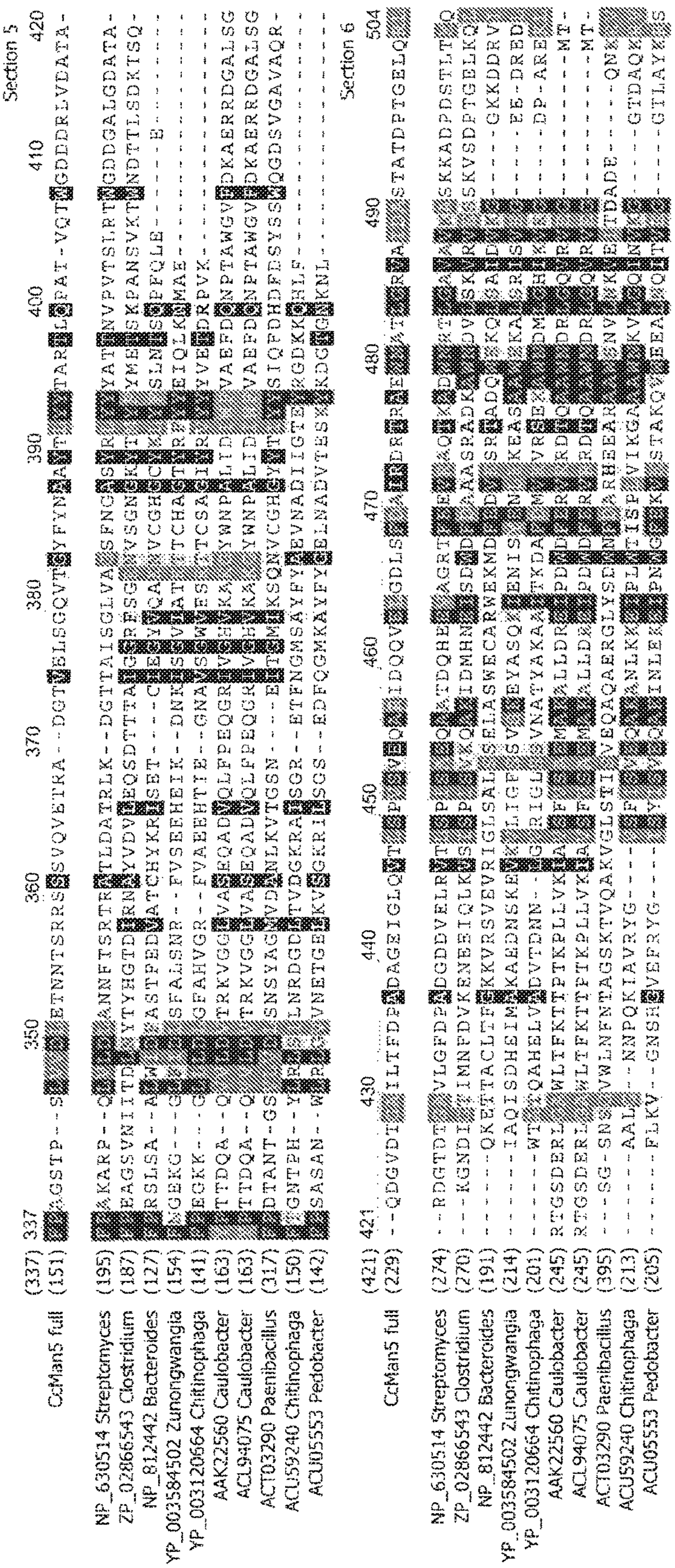
Figures 4, 31:
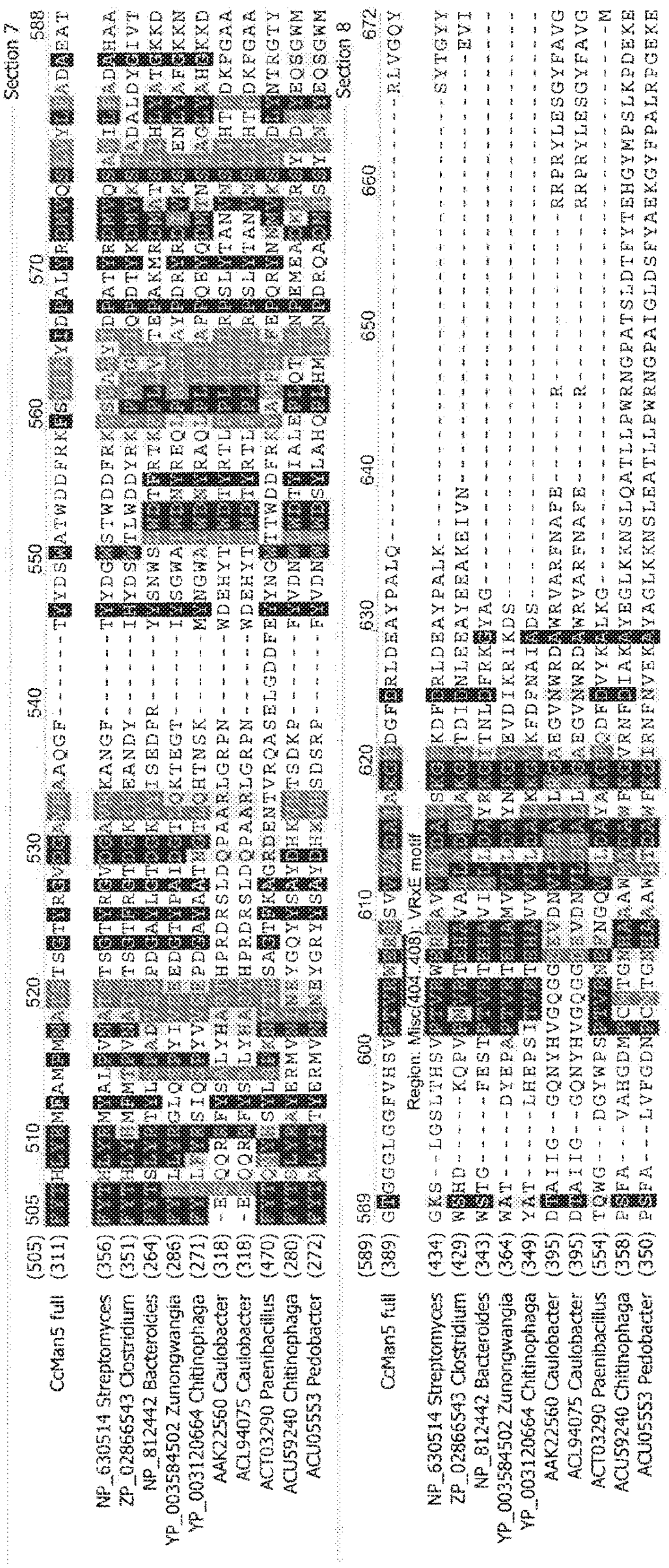
Figures 5, 31:
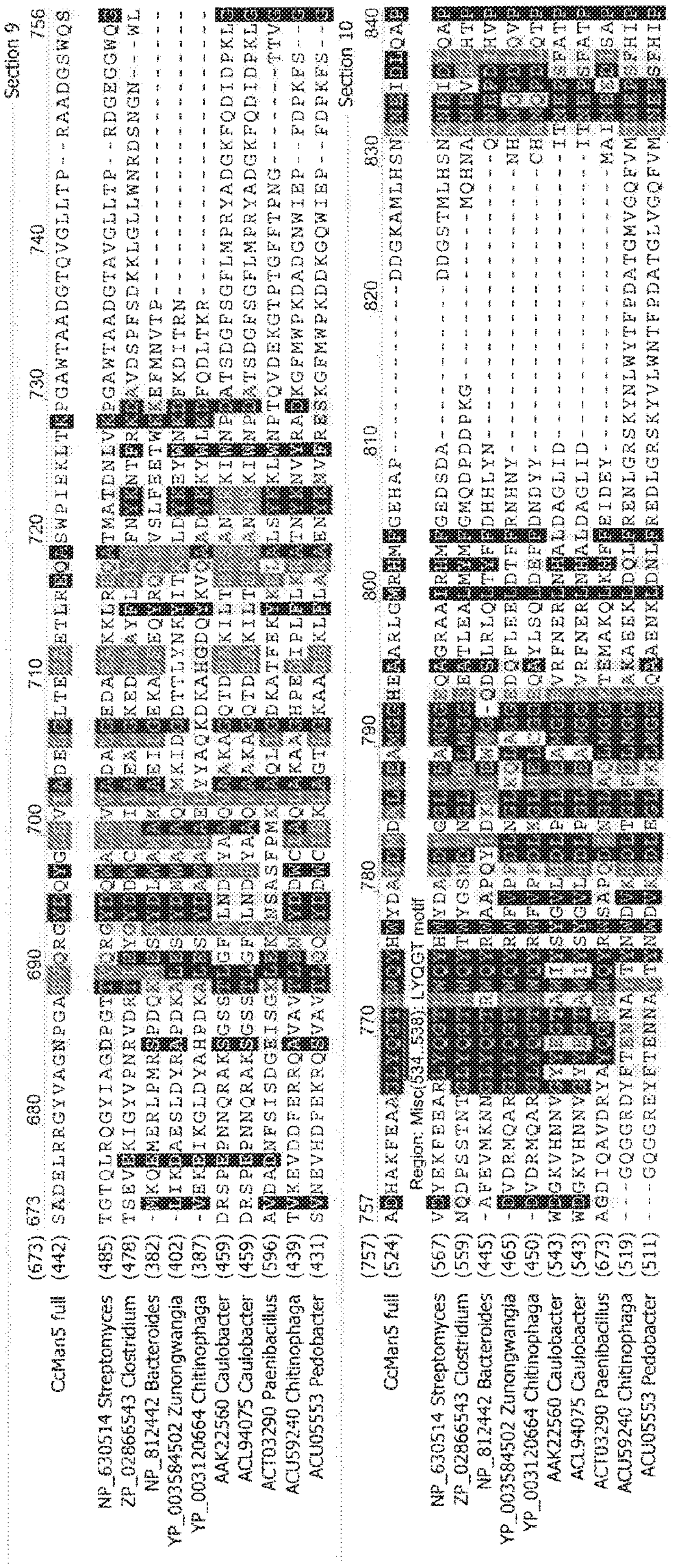
Figures 6, 31:
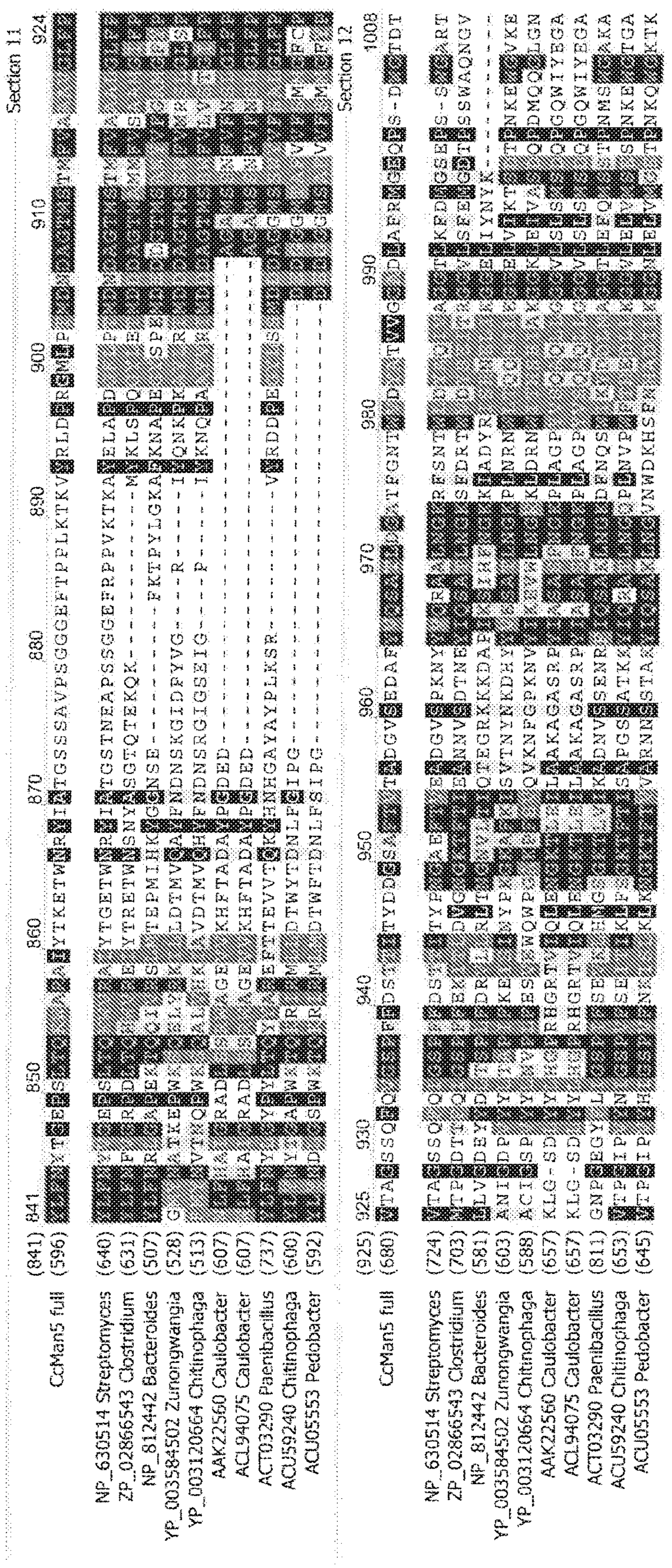
Figures 3, 32:
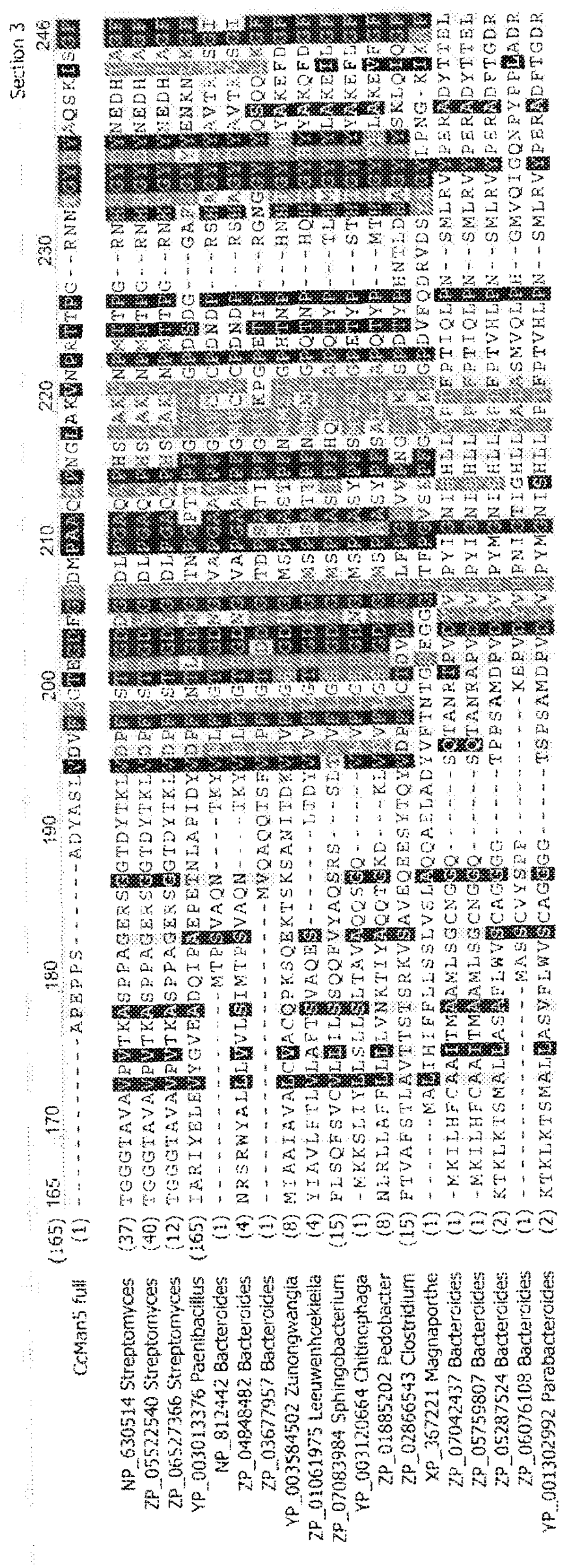
FIG. 32 is an alignment of the amino acid sequence of CcMan5 (SEQ ID NO:50) and 19 of its homologs using MUSCLE. *Streptomyces* NP_630514, SEQ ID NO:26; *Streptomyces* ZP_02866543, SEQ ID NO:36, ZP_06527366 *Streptomyces,* SEQ ID NO:37; YP_003013376 *Paenibacillus,* SEQ ID NO:38; NP_812442 *Bacteroides,* SEQ ID NO:28; ZP_04848482 *Bacteroides,* SEQ ID NO:39; ZP_03677957 *Bacteroides,* SEQ ID NO:40; YP_003584502 *Zunongwangia,* SEQ ID NO:29; ZP_01061975 *Leeuwenhoekiella,* SEQ ID NO:41; ZP_07083984 *Sphingobacterium,* SEQ ID NO:42; YP_003120664 *Chitinophaga,* SEQ ID NO:30; ZP_01885202 *Pedobacter,* SEQ ID NO:43; ZP_02866543 *Clostridium,* SEQ ID NO:27; XP_367221 *Magnaporthe,* SEQ ID NO:44; ZP_07042437 *Bacteroides,* SEQ ID NO:45; ZP_05759807 *Bacteroides,* SEQ ID NO:46; ZP_05287524 *Bacteroides,* SEQ ID NO:47; ZP_06076108 *Bacteroides,* SEQ ID NO:48; YP_001302992 *Parabacteroides,* SEQ ID NO:49.
Figures 4, 32:
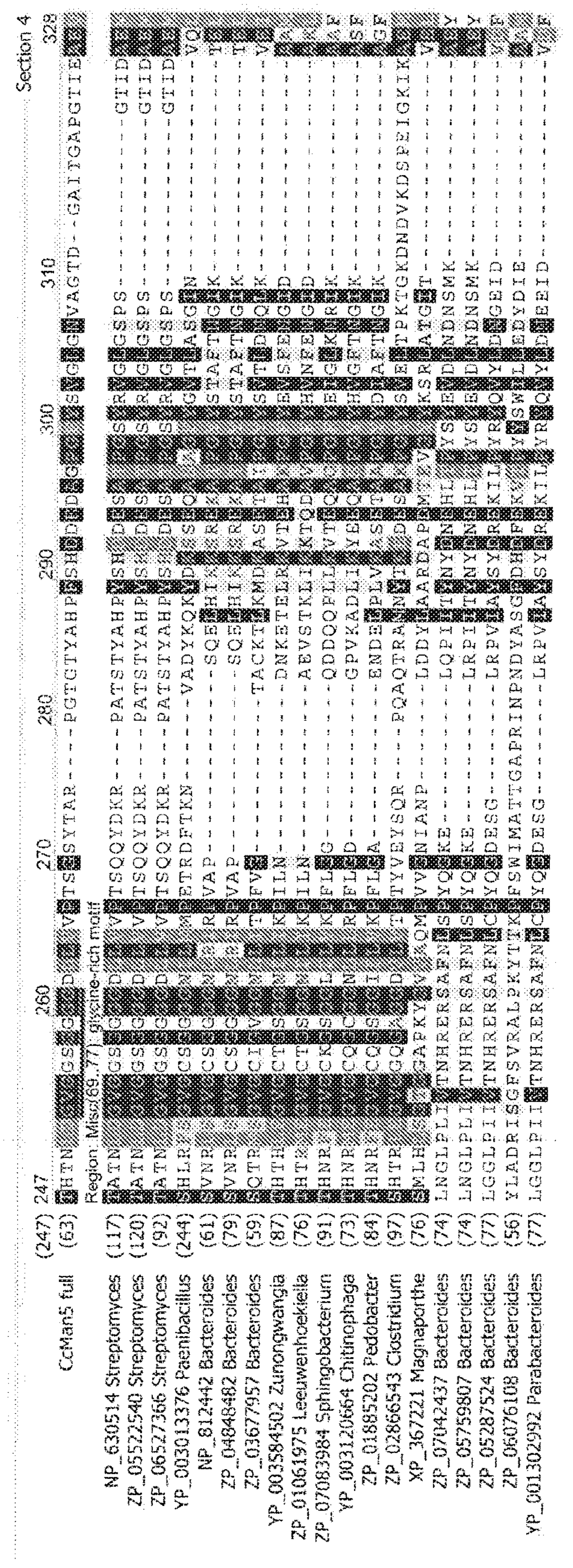
Figures 5, 32:
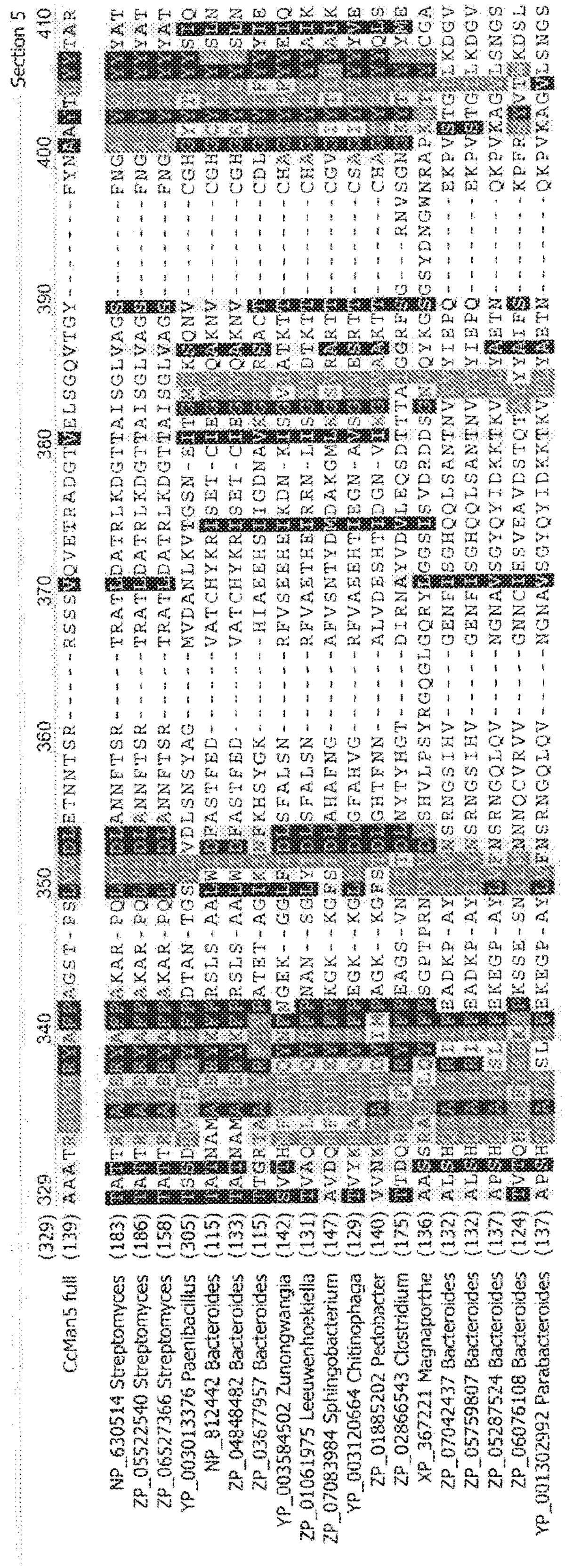
Figures 6, 32:
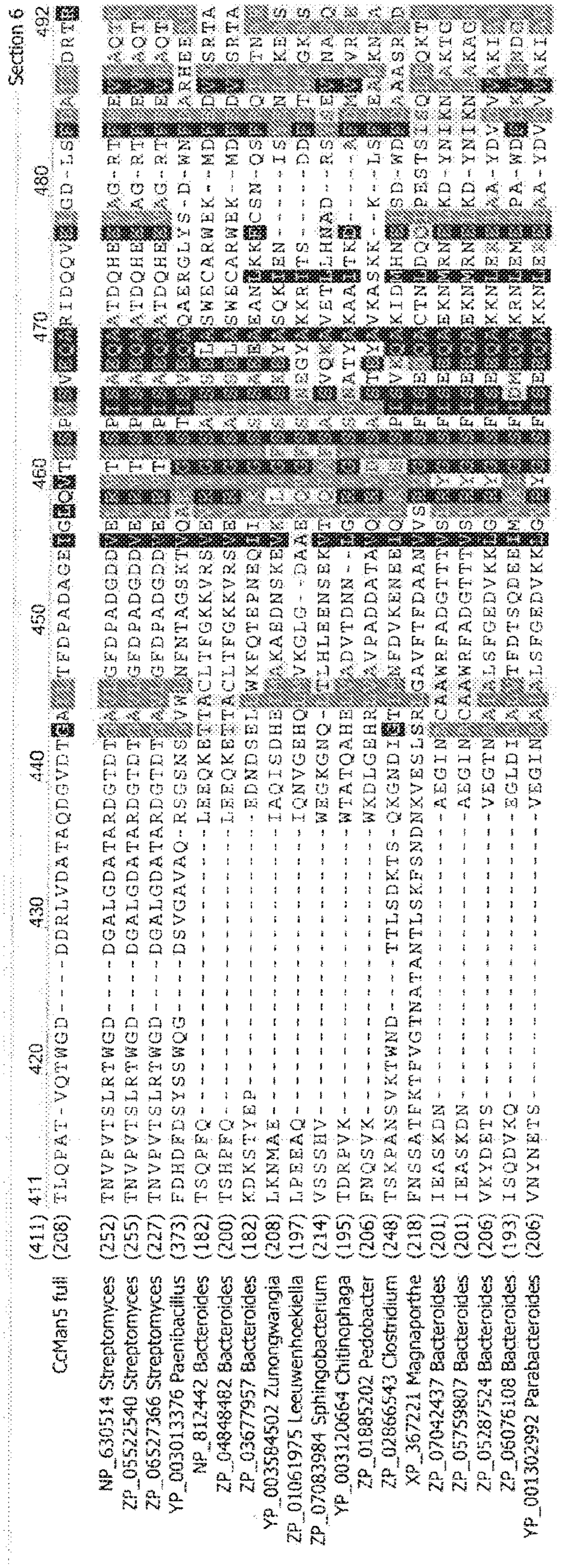
Figures 7, 32:
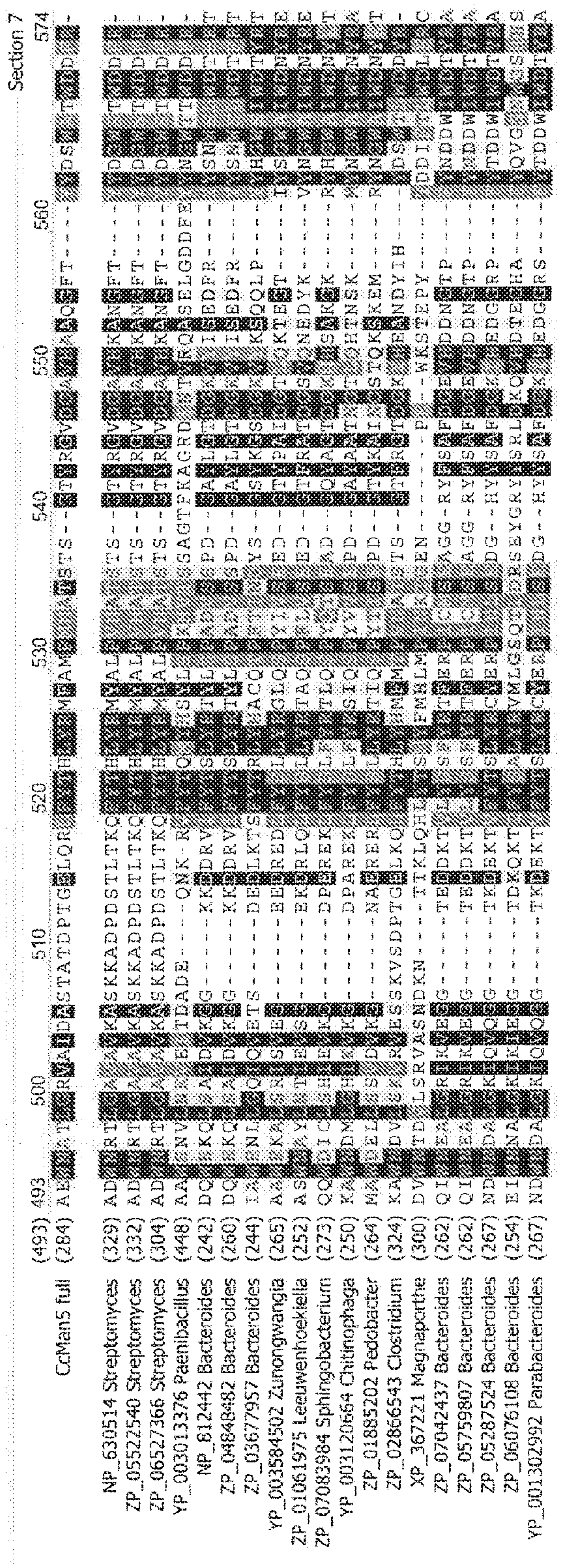
Figures 8, 32:
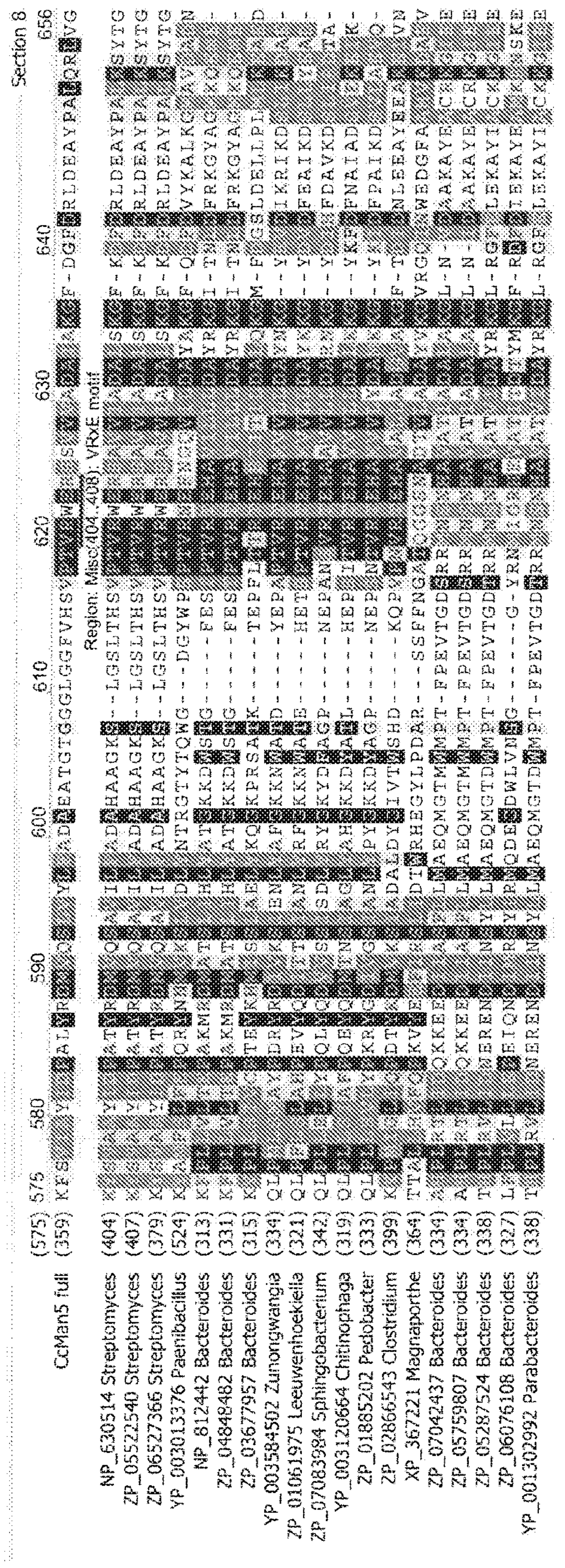
Figures 9, 32:
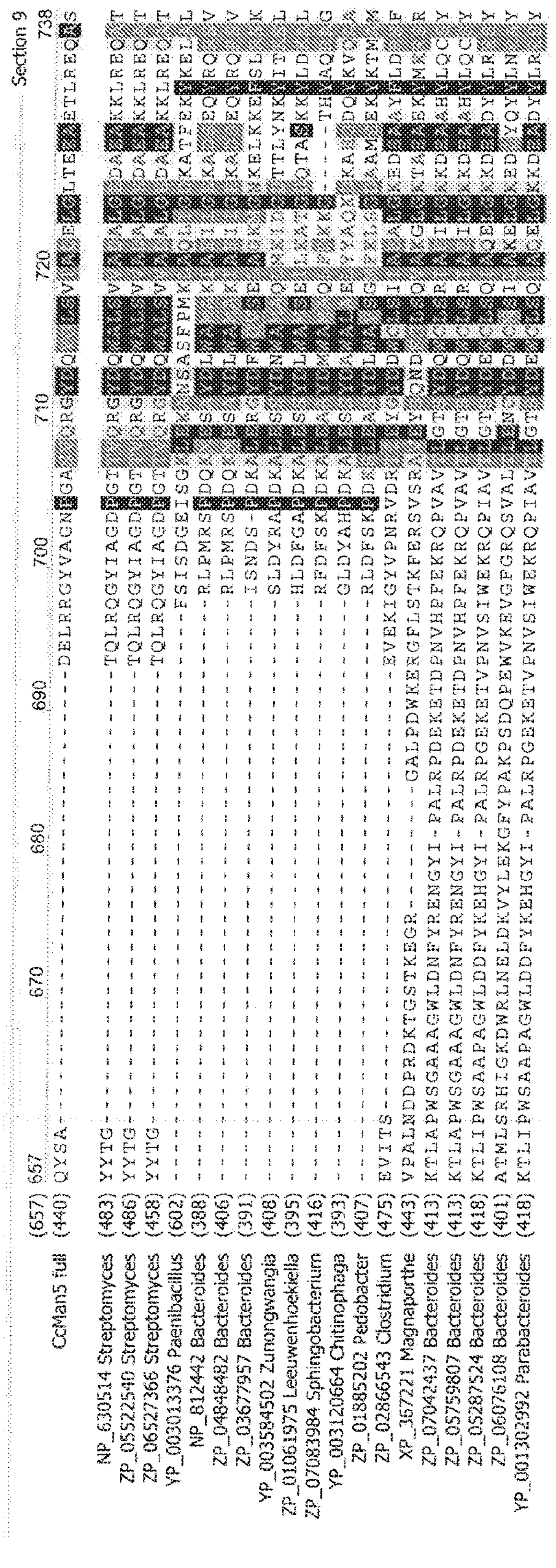
Figures 10, 32:
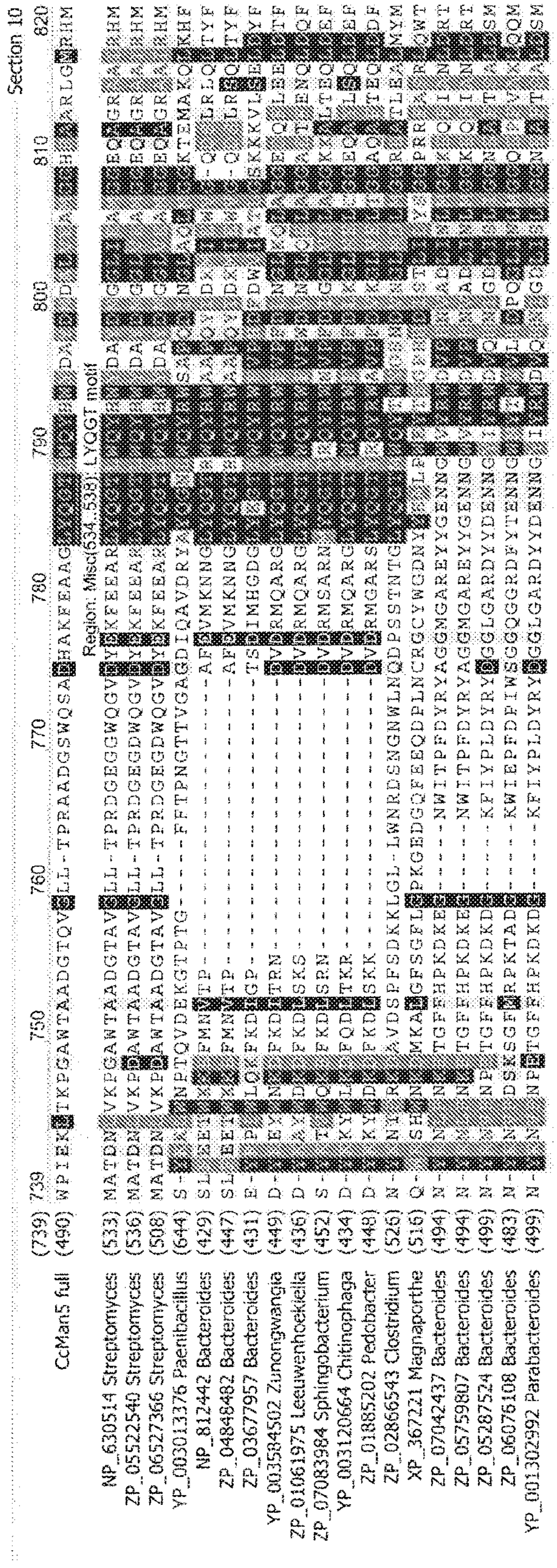
Figures 11, 32:
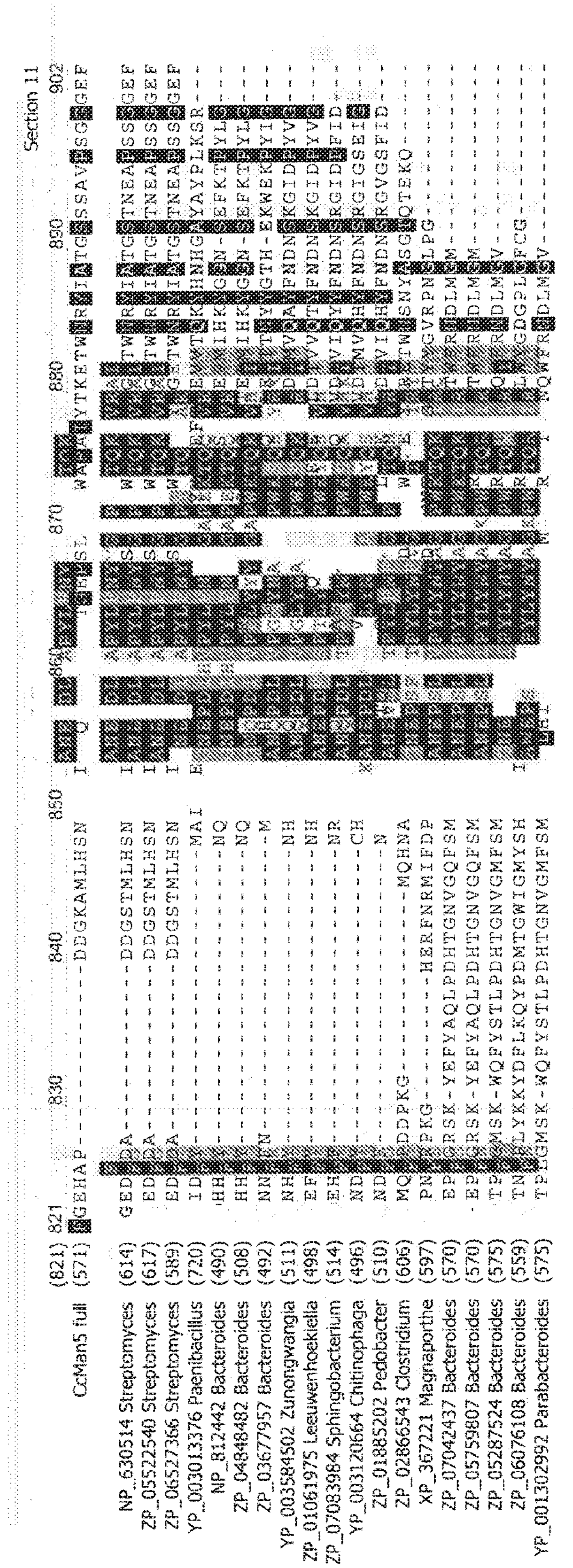
Figures 12, 32:
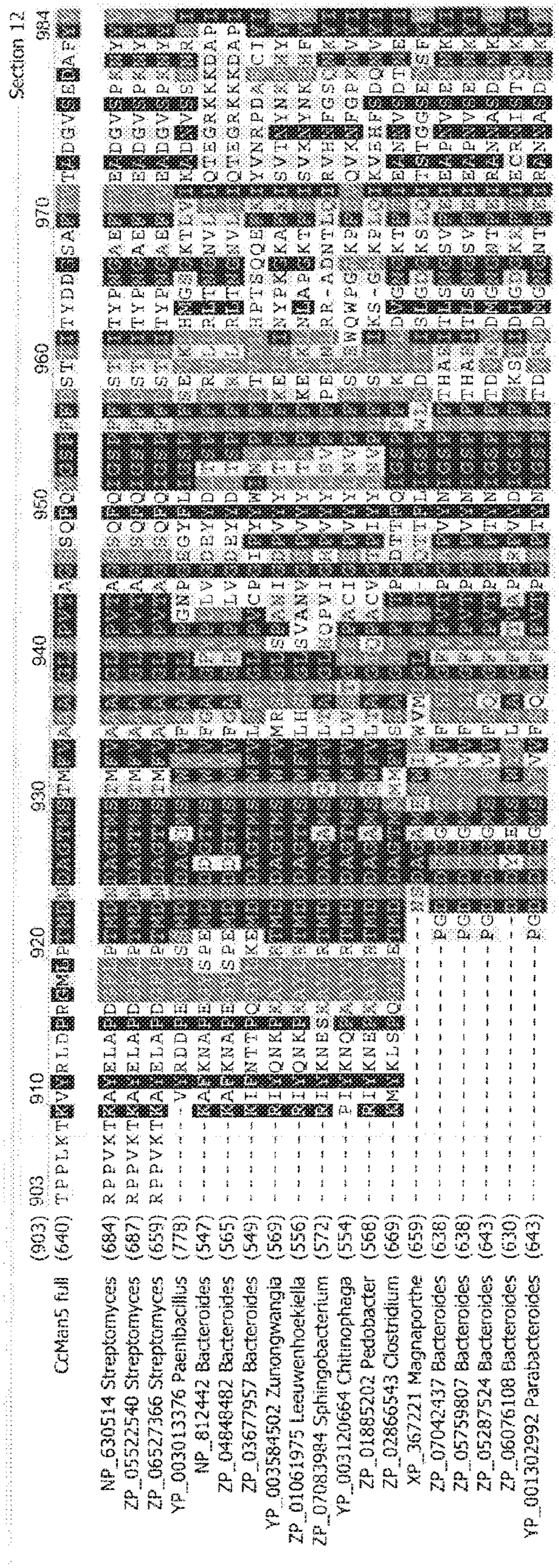
Figures 13, 32:
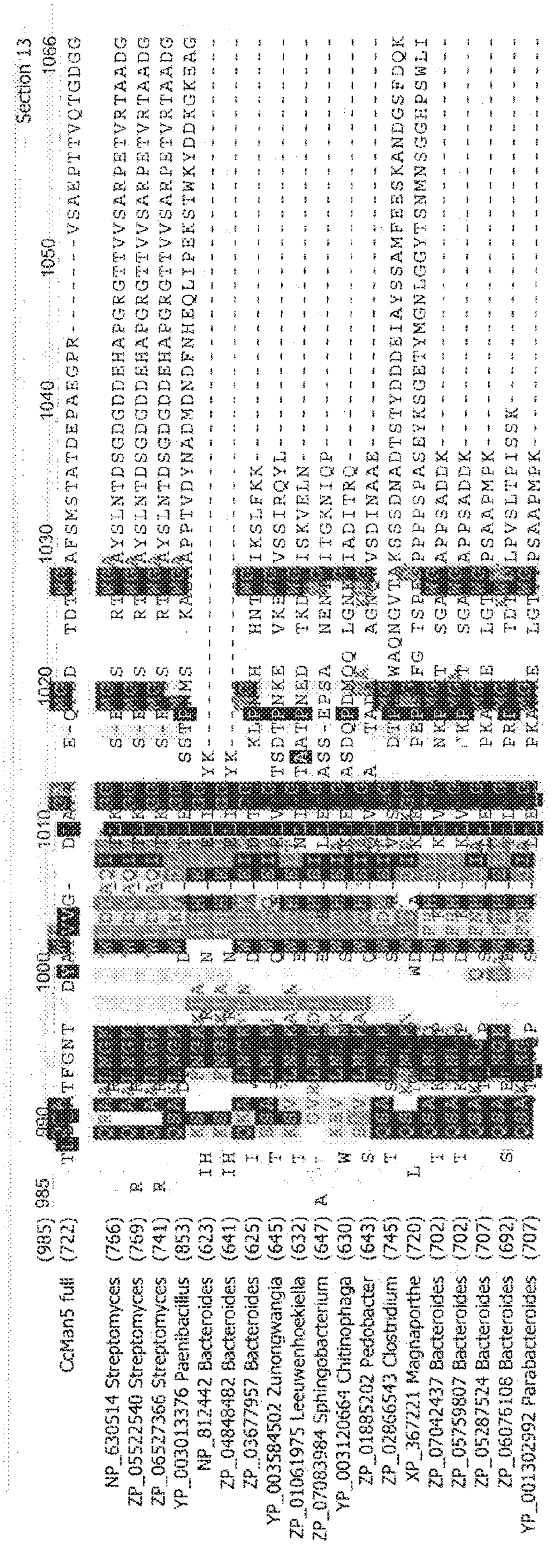

This document also provides (i) biologically active variants and (ii) biologically active fragments or biologically active variants thereof, of the mannosidases described herein. Biologically active variants of mannosidases can contain additions, deletions, or substitutions relative to the sequences set forth in SEQ ID NOs: 7, 9, 11, 13, 15, or 50. Proteins with substitutions will generally have not more than 50 (e.g., not more than one, two, three, four, five, six, seven, eight, nine, ten, 12, 15, 20, 25, 30, 35, 40, or 50) conservative amino acid substitutions. A conservative substitution is the substitution of one amino acid for another with similar characteristics. Conservative substitutions include substitutions within the following groups; valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include argninine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics. The sequence alignments set forth in FIGS. 31 and 32 provide numerous examples of amino acid substitutions that can be made.

Deletion variants can lack one, two, three, tour, five, six, seven, eight, nine, ten, 11, 12, 13, 14, 15, 16, 17, 18, 19, or 20 amino acid segments (of two or more amino acids) or non-contiguous single amino acids.

Additions (addition variants) include fusion proteins containing: (at a mannosidase set forth in SEQ ID NOs: 7, 9, 11, 13, or 15, or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences also can be proteins useful as diagnostic or detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or endoplasmic reticulum or Golgi apparatus retention signals. Heterologous sequences can be of varying length and in some cases can be a longer sequences than the full-length target proteins to which the heterologous sequences are attached.

Biologically active fragments or biologically active variants of the mannosidases have at least 40% (e.g., at least: 50%; 60%; 70%; 75%; 80%; 85%; 90%; 95%; 97%; 98%; 99%, 99.5%, or 100% or even greater) of the mannosidase activity (e.g., uncapping of M6P residues) of five wild-type, full-length, mature protein. For example, a biologically active fragment of a mannosidase can contain residues 1 to 774 of SEQ ID NO:50.

The mannosidases described herein can be used to produce molecules (e.g., target proteins) having uncapped, terminal phospho-6-mannose (M6P) residues. The methods can be performed in vitro or in vivo.

In Vitro Methods of Uncapping M6P Residues

A mannosidase described herein can be recombinantly produced and used in vitro to uncap terminal M6P residues on oligosaccharides. To recombinantly produce a mannosidase, a vector is used that contains a promoter operably linked to nucleic acid encoding a mannosidase polypeptide. As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5" end of a coding region, can also be separate from a promoter sequence and can be, e.g., within an intronic region of a gene or 3' to the coding region of the gene.

As used herein, "operably linked" means incorporated into a genetic construct (e.g., vector) so that expression control sequences effectively control expression of a coding sequence of interest.

Expression vectors can be introduced into host cells (e.g., by transformation or transection) for expression of the encoded polypeptide, which then can be purified. Expression systems that can be used for small or large scale production of mannosidase polypeptides include, without limitation, microorganisms such as bacteria (e.g., *E. coli*) transformed with recombinant bacteriophage DNA, plasmid DNA, or cosmid DNA expression sectors containing the nucleic acid molecules, and fungal (e.g., *S. cerevisiae, Yarrowia lipolytica, Arxula adeninivorans, Pichia pastoris, Hansenula polymorpha*, or *Aspergillus*) transformed with recombinant fungal expression vectors containing the nucleic acid molecules. Useful expression systems also include insect cell systems infected with recombinant virus expression vectors (e.g., baculovirus) containing the nucleic acid molecules, and plant cell systems infected with recombinant virus expression vectors (e.g., tobacco mosaic virus) or transformed with recombinant plasmid expression vectors, (e.g., Ti plasmid) containing the nucleic acid molecules. Mannosidase polypeptides also can be produced using mammalian expression systems, which include cells (e.g., immortalized cell, lines such as COS cells, Chinese hamster ovary cells, HeLa cells, human embryonic kidney 293 cells, and 3T3 L1 cells) harboring recombinant expression, constructs containing promoters derived from the genome of mammalian cells (e.g., the metallothionein promoter) or from mammalian viruses (e.g., the adenovirus late promoter and the cytomegalovirus promoter), along with the nucleic acids described herein.

Typically, recombinant mannosidase polypeptides are tagged with a heterologous amino acid sequence such FLAG, polyhistidine (e.g., hexahistidine), hemagluttanin (HA), glutathione-S-transferase (GST), or maltose-binding protein (MBP) to aid in purifying the protein. Other methods for purifying proteins include chromatographic techniques such as ion exchange, hydrophobic and reverse phase, size exclusion, affinity, hydrophobic charge-induction chromatography, and the like (see, e.g., Scopes, Protein Purification: Principles and Practice, third edition, Springer-Verlag, New York (1993); Burton and Harding, *J. Chromatogr. A* 814: 71-81 (1998)).

To produce molecules having uncapped terminal M6P residues in vitro, a target molecule containing a mannose-1-phospho-6 mannose linkage is contacted under suitable conditions with a purified mannosidase or a cell lysate containing a recombinantly produced mannosidase. The cell lysate can be from any genetically engineered cell, including a fungal cell, a plant cell, or animal cell. Non-limiting examples of animal cells include nematode, insect, plant, bird, reptile, and mammals such as a mouse, rat, rabbit, hamster, gerbil, dog, cat, goat, pig, cow, horse, whale, monkey, or human. Upon contacting the target molecule (e.g., an oligosaccharide or glycoprotein) with the purified mannosidase or cell lysate, the mannosidase hydrolyzes the mannose-1-phospho-6 mannose linkage and produces a target molecule having one or more uncapped terminal M6P residues. The methods described in Example 2 can be used to determine if the terminal M6P residues have been uncapped. Following processing by the mannosidase, the target molecule having uncapped terminal M6P residues can be isolated.

Suitable methods for obtaining cell lysates that preserve the activity or integrity of the mannosidase activity in the lysate can include the use of appropriate buffers and/or inhibitors, including nuclease, protease and phosphatase inhibitors that preserve or minimize changes in N-glycosylation activities in the cell lysate. Such inhibitors include, for example, chelators such as ethylenediamine tetraacetic acid (EDTA), ethylene glycol bis(P-aminoethyl ether) N,N,N1, N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for obtaining lysates containing enzymatic activities are described in, e.g., Ausubel et al. Current Protocols in Molecular Biology (Supplement 47), John Wiley & Sons, New York (1999); Harlow and Lane, Antibodies: A Laboratory Manual Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999).

A cell lysate can be further processed to eliminate or minimize the presence of interfering substances, as appropriate. If desired, a cell lysate can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like.

In some embodiments, a cell lysate cars be prepared to which whole cellular organelles remain intact and or functional. For example, a lysate can contain one or more of intact rough endoplasmic reticulum, intact smooth endoplasmic reticulum, or intact Golgi apparatus. Suitable methods for preparing lysates containing intact cellular organelles and testing for the functionality of the organelles are described in, e.g., Moreau et al. (1991) *J. Biol. Chem.* 266(7):4329-4333; Moreau et al. (1991) *J. Biol. Chem.* 266(7):4322-4328; Rexach et al. (1991) *J. Cell Biol.* 114 (2):219-229; and Paulik et al. (1999) *Arch. Biochem. Biophys.* 367(2):265-273.

Target molecules, as used herein, refer to any molecule containing terminal manuose-1-phospho-6 matmose linkages or any molecule, when expressed in a cell of fungal origin, that contains mannose-1-phospho-6 mannose linkages. Suitable target proteins include pathogen proteins such as tetanus toxoid or diptheria toxoid; viral surface proteins such as cytomegalovirus (CMV) glyhcoproteins B, H and gCIII, human immunodeficiency virus 1 (HIV-1) envelope glycoproteins, Rous sarcoma virus (RSV) envelope glycoproteins, herpes simplex virus (HSV) envelope glycoproteins, Epstein Barr virus (EBV) envelope glycoproteins, varicella-zoster virus (VZV) envelope glycoproteins, human papilloma virus (HPV) envelope glycoproteins, Influenza virus glycoproteins, and Hepatitis family surface antigen; lysosomal proteins (e.g., acid alpha glucosidase, alpha galatosidase, glucocerebrosidase, cerebrosidase, or galactocerebrosidase); insulin; glucagons; growth factors; cytokines; chemokines; and antibodies or fragments thereof. Growth factors include, e.g., vascular endothelial growth factor (VEGF), Insulin-like growth factor (IGF), bone morphogenic protein (BMP), Granulocyte-colony stimulating factor (G-CSF), Granulocyte-macrophage colony stimulating factor (GM-CSF), Nerve growth factor (NGF); a Neurotrophin, Platelet-derived growth factor (PDGF), Erythropoietin (EPO), Thrombopoietin (TPO), Myostatin (GDF-8), Growth Differentiation factor-9 (GDF9), basic fibroblast growth factor (bFGF or FGF2), Epidermal growth factor (EGF), Hepatocyte growth factor (HGF). Cytokines include, for example, interleukins such as IL-1 to IL-33 (e.g., IL-1, IL-2, IL-3, IL-4, IL-5, IL-6, IL-7, IL-8, IL-9, IL-10, IL-12, IL-13, or IL-15)). Chemokines include, e.g., I-309, TCA-3, MCP-1, MIP-1α, MIP-1β, RANTES, C10, MRP-2, MARC, MCP-3, MCP-2, MRP-2, CCF18, MIP-1γ, Eotaxin, MCP-5, MCP-4, NCC-1, Ckβ10, HCC-1, Leukotactin-1, LEC, NCC-4, TARC, PARC, or Eotaxin-2. Also included are tumor glycoproteins (e.g., tumor-associated antigens), for example, carcinoembryonic antigen (CEA), human mucins, HER-2/neu, and prostate-specific antigen (PSA) [Henderson and Finn, *Advances in Immunology,* 62, pp. 217-56 (1996)].

In some embodiments, the target protein can be one associated with a lysosomal storage disorder, which target proteins include, e.g., acid alpha glucosidase, alpha galactosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acetylgalactosaminidase, aspartylglucosaminidase, iduraonate-2-sulfatase, alpha-glucosaminide-N-acetyltransferase, beta-D-glucoronidase, hyaluronidase, alpha-L-mannosidase, alpha-neuraminidase, phosphotransferase, acid lipase, acid ceramidase, sphingomyelinase, thioesterase, cathepsin K, and lipoprotein lipase.

In some embodiments, the target proteins are fusion proteins in which the target protein is fused to another polypeptide sequence, or to a polymer, a carrier, an adjuvant, an immunotoxin, or a detectable (e.g., fluorescent, luminescent, or radioactive) moiety. For example, a target protein can be joined to a polymer such as polyethyleneglycol to increase the molecular weight of small proteins and/or increase circulation residence time.

In Vivo Methods of Uncapping M6P Residues

Genetically engineered cells described herein can be used to produce target molecules containing uncapped M6P residues. For example, a cell based method can include the steps of introducing into a fungal cell genetically engineered to include a nucleic acid encoding a mannosidase, a nucleic acid encoding a target molecule, wherein the cell produces the target molecule containing uncapped terminal M6P residues. In some embodiments, the nucleic acids encoding the mannosidase and target molecule contain a secretion sequence such that the mannosidase and target molecule are co-secreted.

Genetically engineered cells described herein contain a nuycleic acid encoding a mannosidase and are useful for producing one or more target molecules having uncapped terminal M6P residues. Cells suitable for in vivo production of uncapped M6P residues can be of fungal origin, including *Yarrowia lipolytica, Arxula adeninivorans,* methylotrophic yeast (such as a methylotrophic yeast of the genus *Candida, Hansenula, Oogataea, Pichia* or *Torulopsis*) or filamentous fungi of the genus *Aspergillus, Trichoderma, Neurospora, Fusarium*, or *Chrysosporium*. Exemplary fungal species include, without limitation, *Pichia anomala, Pichia bovis, Pichia canadensis, Pichia carsonii, Pichia farinose, Pichia fermentans, Pichia fluxuum, Pichia membranaefaciens, Pichia membranaefaciens, Candida valida, Candida albicans, Candida ascalaphidarum, Candida amphixae, Candida Antartica, Candida atlantica, Candida atmosphaerica, Candida blattae, Candida carpophila, Candida cerambyci-*

*darum, Candida chauliodes, Candida corydalis, Candida dosseyi, Candida dubliniensis, Candida ergatensis, Candida fructus, Candida glabrata, Candida fermentati, Candida guilliermondii, Candida haemulonii, Candida insectamens, Candida insectorum, Candida intermedia, Candida jeffresii, Candida kefyr, Candida krusei, Candida lusitaniae, Candida lyxosophila, Candida maltosa, Candida membranifaciens, Candida milleri, Candida oleophila, Candida oregonensis, Candida parapsilosis, Candida quercitrusa, Candida shehatea, Candida temnochilae, Candida tenuis, Candida tropicalis, Candida tsuchiyae, Candida sinolaborantium, Candida sojae, Candida viswanathii, Candida utilis, Oogataea minuta, Pichia membranefaciens, Pichia silvestris, Pichia membranaefaciens, Pichia chodati, Pichia membranaefaciens, Pichia membranaefaciens, Pichia minuscule, Pichia pastoris, Pichia pseudopolymorpha, Pichia quercuum, Pichia robertsii, Pichia saitol, Pichia silvestrisi, Pichia strasburgensis, Pichia terricola, Pichia vanriji, Pseudozyma Antarctica, Rhodosporidium torulides, Rhodotorula glutinis, Saccharomyces bayanus, Saccharomyces bayanus, Saccharomyces momdshuricus, Saccharomyces uvarum, Saccharomyces bayanus, Saccharomyces cerevisae, Saccharomyces bisporus, Saccharomyces chevalieri, Saccharomyces delbrueckii, Saccharomyces exiguous, Saccharomyces fermentaii, Saccharomyces fragilis, Saccharomyces marxianus, Saccharomyces mellis, Saccharomyces rosei, Saccharomyces rouxii, Saccharomyces uvarum, Saccharomyces willianus, Saccharomycodes ludwigii, Saccharomycopsis capsularis, Saccharomycopsis fibuligera, Saccharomycopsis fibuligera, Endomyces hordei, Endomycopsis fobuligera, Saturnispora saitol, Schizosaccharomyces octosporus, Schizosaccharomyces pombe, Schwanniomyces occidentalis, Torulaspora delbrueckii, Torulaspora delbrueckii, Saccharomyces dairensis, Torulaspora delbrueckii, Torulaspora fermentati, Saccharomyces fermentati, Torulaspora delbrueckii, Torulaspora rosei, Saccharomyces rosei, Torulaspora delbrueckii, Saccharomyces rosei, Torulaspora delbrueckii, Saccharomyces delbrueckii, Torulaspora delbrueckii, Saccharomyces delbrueckii, Zygosaccharomyces mongolicus, Dorulaspora globosa, Debaryomyces globosus, Torulopsis globosa, Trichosporon cutaneum, Trigonopsis variabilis, Williopsis californica, Williopsis saturnus, Zygosaccharomyces bisporus, Zygosaccharomyces bisporus, Debaryomyces disporua, Saccharomyces bisporas, Zygosaccharomyces bisporus, Saccharomyces bisporus, Zygosaccharomyces mellis, Zygosaccharomyces priorianus, Zygosaccharomyces rouxiim, Zygosaccharomyces rouxii, Zygosaccharomyces barkeri, Saccharomyces rouxii, Zygosaccharomyces rouxii, Zygosaccharomyces major, Saccharomyces rousii, Pichia anomala, Pichia bovis, Pichia Canadensis, Pichia carsonii, Pichia farinose, Pichia fermentans, Pichia fluxuum, Pichia membranaefaciens, Pichia pseudopohmorpha, Pichia quercuum, Pichia robertsii, Pseudozyma Antarctica, Rhodosporidium toruloides, Rhodosporidium toruloides, Rhodotorula glutinis, Saccharomyces bayanus, Saccharomyces bayanus, Saccharomyces bisporus, Saccharomyces cerevisiae, Saccharomyces chevalieri, Saccharomyces delbrueckii, Saccharomyces fermentati, Saccharomyces fragilis, Saccharomycodes ludwigii, Schizosaccharomyces pombe, Schwanniomyces occidentalis, Torulaspora delbrueckii, Torulaspora globosa, Trigonopsis variabilis, Williopsis californica, Williopsis saturnus, Zygosaccharomyces bisporus, Zygosaccharomyces mellis*, or *Zygosaccharomyces rouxii*. Exemplary filamentous fungi include various species of *Aspergillus* including, but not limited to, *Aspergillus caesiellus, Aspergillus candidus, Aspergillus carneus, Aspergillus clavatus, Aspergillus* deflected *Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus*, or *Aspergillus versicolor*. Such cells, prior to the genetic engineering as specified herein, can be obtained from a variety of commercial sources and research resource facilities, such as, for example, the American Type Culture Collection (Rockville, Md.). Target molecules include proteins such as any of the target proteins described herein (see above).

Genetic engineering of a cell can include, in addition to an exogenous nucleic acid encoding a mannosidase, one or more genetic modifications such, as: (i) deletion of an endogenous gene encoding an Outer CHain elongation (OCH1) protein; (ii) introduction of a recombinant nucleic acid encoding a polypeptide capable of promoting mannosyl phosphorylation (e.g, a MNN4 polypeptide from *Yarrowia lipolytica, S. cerevisiae, Ogataea minuta, Pichia pastoris*, or *C. albicans*, or PNO1 polypeptide from *P. pastoris*) to increasing phosphorylation of mannose residues; (iii) introduction or expression of an RNA molecule that interferes with the functional expression, of an OCH1 protein; (iv) introduction of a recombinant nucleic acid encoding a wild-type (e.g., endogenous or exogenous) protein having a N-glycosylation activity (i.e., expressing a protein having an N-glycosylation activity); (v) introduction of a recombinant nucleic acid encoding a target molecule described above; or (v) altering the promoter or enhancer elements of one or more endogenous genes encoding proteins having N-glycosylation activity to thus alter the expression of their encoded proteins. RNA molecules include, e.g., small-interfering RNA (siRNA), short hairpin RNA (shRNA), anti-sense RNA, or micro RNA (miRNA). Genetic engineering also includes altering an endogenous gene encoding a protein having an N-glycosylation activity to produce a protein having additions (e.g., a heterologous sequence), deletions, or substitutions (e.g., mutations such as point mutations; conservative or non-conservative mutations). Mutations can be introduced specifically (e.g., by site-directed mutagenesis or homologous recombination) or can be introduced randomly (for example, cells can be chemically mutagenized as described in, e.g., Newman and Ferro-Novick (1987) *J. Cell Biol.* 105(4):1587.

Genetic modifications described herein can result in one or more of (i) an increase in one or more activities in the genetically modified cell, (ii) a decrease in one or more activities in the genetically modified cell, or (iii) a change in the localization or intracellular distribution of one or more activities in the genetically modified cell. It is understood that an increase in the amount of a particular activity (e.g., promoting mannosyl phosphorylation) can be due to overexpressing one or more proteins capable of promoting mannosyl phosphorylation, an increase in copy number of an endogenous gene (e.g., gene duplication), or an alteration in the promoter or enhancer of an endogenous gene that stimulates an increase in expression of the protein encoded by the gene. A decrease in one or more particular activities can be due to overexpression of a mutant form (e.g., a dominant negative form), introduction or expression of one or more intefering RNA molecules that reduce the expression of one or more proteins having a particular activity, or deletion of one or more endogenous genes that encode a protein having the particular activity.

To disrupt a gene by homologous recombination, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes which either complement host cell auxotrophy or provide antibiotic resistance, including URA3, Leu2 and HIS3 genes. Other suitable selectable markers include the CAT gene, which confers chloramphenicol resistance to yeast cells, or the lacZ gene, which results in blue colonies due to the expression of β-galactosidase. Linearized DNA fragments of the gene replacement vector are then introduced into the cells using methods well known in the art (see below). Integration of the linear fragments into the genome and the disruption of the gene can be determined based on the selection marker and can be verified by, for example, Southern blot analysis. A selectable marker can be removed from the genome of the host cell by, e.g., Cre-loxP system (see below).

Alternatively, a gene replacement vector can be constructed in such a way as to include a portion of the gene to be disrupted, which portion is devoid fo any endogenous gene promoter sequence and encodes none or an inactive fragment of the coding sequence of the gene. An “inactive fragment” is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the game.

Expression vectors can be autonomous or integrative. A recombinant nucleic acid (e.g., one encoding a mannosidase) can be in introduced into the cell in the form of an expression vector such as a plasmid, phage, transposon, cosmid or virus particle. The recombinant nucleic acid can be maintained extrachromosomally or it can be integrated into the yeast cell chromosomal DNA. Expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids (see, e.g., U.S. Pat. No. 4,704,362). Expression vectors can also include an autonomous replication sequence (ARS). For example, U.S. Pat. No. 4,837,148 describes autonomous replication sequences which provide a suitable means for maintaining plasmids in *Pichia pastoris.*

Integrative vectors are disclosed, e.g., in U.S. Pat. No. 4,882,279. Integrative vectors generally include a serially arranged sequence of at least a first insertable DNA fragment, a selectable marker gene, and a second insertable DNA fragment. The first and second insertahie DNA fragments are each about 200 (e.g., about 250, about 300, about 350, about 400, about 450, about 500, or about 1000 or more) nucleotides in length and have nucleotide sequences which are homologous to portions of the genomic DNA of the species to be transformed. A nucleotide sequence containing a gene of interest (e.g., a gene encoding a protein having N-glycosylation activity) for expression is inserted in this vector between the first and second insertable DNA fragments whether before or after the marker gene. Integrative vectors can be linearized prior to yeast transformation to facilitate the integration of the nucleotide sequence of interest into the host cell genome.

An expression vector can feature a recombinant nucleic acid under the control of a yeast (e.g., *Yarrowia lipotytica, Arxula adeninivorans, P. pastoris*, or other suitable fungal species) promoter, which enables them to be expressed in fungal cells. Suitable yeast promoters include, e.g., ADC1, TP11, ADB2, hp4d, POX, and Gal10 (see, e.g., Guarente et al (1982) *Proc. Natl. Acad. Sci. USA* 79(23):7410) promoters. Additional suitable promoters are described, in, e.g., Zhu and Zhang (1999) *Bioinformatics* 15(7-8):608-611 and U.S. Pat. No. 6,265,185.

A promoter can be constitutive or inducible (conditional). A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical, inducing agent such as an alcohol tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

It is understood that other genetically engineered modifications can also be conditional. For example, a gene can be conditionally deleted using, e.g., a site-specific DNA recombinase such as the Cre-loxP system (see, e.g., Gossen et al. (2002) *Ann. Rev. Genetics* 36:153-173 and U.S. Application Publication No. 20060014264).

A recombinant nucleic acid can be introduced into a cell described herein using a variety of methods such as the spheroplast technique or the whole-cell lithium chloride yeast transformation method. Other methods useful for transformation of plasmids or linear nucleic acid vectors into cells are described in, for example, U.S. Pat. No. 4,929,555; Hinnen et al. (1978) *Proc. Nat. Acad. Sci. USA* 75:1929; Ito et al. (1983) *J. Bacteriol.* 153:163; U.S. Pat. No. 4,879,231; and Sreekrishna et al. (1987) (*Gene* 59:115, the disclosures of each of which are incorporated herein by reference in their entirety, Electroporation and PEG1000 whole cell transformation procedures may also be used, as described by Cregg and Russel, Methods in Molecular Biology: *Pichia* Protocols, Chapter 3, Humana Press, Totowa, N.J., pp. 27-39 (1998).

Transformed fungal cells can be selected for by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or POR analysis.

Prior to introducing the vectors into a target cell of interest, the vectors can be grown (e.g., amplified) in bacterial cells such as *Esherichia coli* (*E. coli*) as described above. The vector DNA can be isolated from bacterial cells by any of the methods known in the an which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

In some embodiments, the genetically engineered fungal cell lacks the OCH1 gene or gene products (e.g., mRNA or protein) thereof, and is deficient in OCH1 activity. In some embodiments, the genetically engineered cell expresses a polypeptide capable of promoting mannosyl phosphorylation (e.g., a MNN4 polypeptide from *Yarrowia lipolytica, S. cerevisiae, Ogataea minuta, Pichia pastoris*, or *C. albicans*, or a PNO1 polypeptide from *P. pastoris*). For example, the fungal cell can express a MNN4 polypeptide from *Y. lipolytica* (Genbank® Acccession Nos: XM_503217, Genolevures Ref: YAL10D24101g). In some embodiments, the genetically engineered cell is deficient in OCH1 activity and expresses a polypeptide capable of promoting mannosyl phosphorylation.

Following uncapping of the M6P residues, the target molecule can be isolate. In some embodiments, the target molecule is maintained within the yeast cell and released upon cell lysis. In some embodiments, the target molecule is secreted into the culture medium via a mechanism provided by a coding sequence (either native to the exogenous nucleic acid or engineered into the expression vector), which directs secretion of the molecule from the cell. The presence of the uncapped target molecule in the cell lysate or culture medium can be verified by a variety of standard protocols for detecting the presence of the molecule. For example, where the altered target molecule is a protein, such protocols can include, but are not limited to, immunoblotting or radioimmunoprecipitation with an antibody specific for the altered target protein (or the target protein itself), binding of a ligand specific for the altered target protein (or the target protein itself), or testing for a specific enzyme activity of the altered target protein (or the target protein itself).

In the target molecules produced using the methods described herein, at least 47% (e.g., at least 50, 55, 60, 65, 70, 75, 80, 85, or 90%) of the N-glycans on the glycoprotein have terminal phospho-6-mannose residues. The percentage of N-glycans having terminal phospho-6-mannose residues can be estimated from the peak areas in the DSA-FACE electropherograms. See Example 13.

In some embodiments, following isolation, the uncapped target molecule can be attached to a heterologous moiety, e.g., using enzymatic or chemical means. A "heterologous moiety" refers to any constituent that is joined (e.g., covalently or non-covalently) to the altered target molecule, which constituent is different from a constituent originally present on the altered target molecule. Heterologous moieties include, e.g., polymers, carriers, adjuvants, immunotoxins, or detectable (e.g., fluorescent, luminescent, or radioactive) moieties. In some embodiments, an additional N-glycan can be added to the altered target molecule.

Methods for detecting glycosylation of a target molecule include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. The derivatized N-glycans can then be concentrated. Instrumentation suitable for N-glycan analysis includes, e.g., the ABI PRISM® 377 DNA sequencer (Applied Biosystems). Data analysis can be performed using, e.g., GENESCAN® 3.1 softward (Applied Biosystmes). Optionally, isolated mannoproteins can be further treated with one or more enzymes to confirm their N-glycan status. Additional methods of N-glycan analysis include, e.g., mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) *Glycobiology* 11(4):275-281 and Friere et al. (2006) *Bioconjug. Chem.* 17(2):559-564.

Cultures of Engineered Cells

This document also provides a substantially pure culture of any of the genetically engineered cells described herein. As used herein, a "substantially pure culture" of a genetically engineered cell is a culture of that cell in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the genetically engineered cell, e.g., bacterial, fungal (including yeast), mycoplasmal, or protozoan cells. The term "about" in this context means that the relevant percentage can be 15% percent of the specified percentage above or below the specified percentage. Thus, for example, about 20% can be 17% to 23%. Such a culture of genetically engineered cells includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

The genetically engineered cells described herein can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidized bed drying or spray drying, or any other suitable drying method.

Metabolic Disorders

Molecules having uncapped terminal M6P residues can be used to treat a variety of metabolic disorders. A metabolic disorder is one that affects the production of energy within individual human (or animal) cells. Most metabolic disorders are genetic, though some can be "acquired" as a result of diet, toxins, infections, etc. Genetic metabolic disorders are also known as inborn errors of metabolism. In general, the genetic metabolic disorders are caused by genetic defects that result in missing or improperly constructed enzymes necessary for some step in the metabolic process of the cell. The largest classes of metabolic disorders are disorders of carbohydrate metabolism, disorders of amino acid metabolism, disorders of organic acid metabolism (organic acidurias), disorders of fatty acid, oxidation and mitochondrial metabolism, disorders of porphyrin metabolism, disorders of purine or pyrimidine metabolism, disorders of steroid metabolism disorders of mitochondrial function, disorders of peroxisomal, function, and lysosomal storage disorders (LSDs).

Examples of metabolic disorders that can be treated through the administration of one or more molecules having uncapped terminal M6P residues (or pharmaceutical compositions of the same) can include hereditary hemochromatosis, oculocutaneous albinism, protein C deficiency, type I hereditary angioedema, congenital sucraseisomaltrase deficiency, Crigler-Najjar type II, Laron syndrome, hereditary Mycloperoxidase, primary hypothryoidism, congenital long QT syndrome, tyroxine binding globulin deficiency, familial hypercholesterolemia, familial chylomicronermia, abeta-lipoproteinerma, low plasma lipoprotein A levels, hereditary emphysema with liver injury, congenital hypothryoidism, osteogenesis imperfecta, hereditary hypofibrinogenemia, alpha-lantichymotrypsin deficiency, nephrogenic diabetes insipidus, neurohypophyseal diabetes insipidus, adenosne deaminase deficiency, Pelizaeus Merzbacher disease, von Willebrand disease type IIA, combined factors V and VIII deficiency, spondylo-epiphyseal dysplasia tarda, chloriderernia, I cell disease, Batten disease, ataxia telangiectasias, ADPKD-autosomal dorminant polycystic kidney disease, microvillus inclusion disease, tuberous sclerosis, oculocerebro-renal syndrome of Lowe, amyotrophic lateral sclerosis, myelodysplastic syndrome, Bare lymphocyte syndrome, Tangier disease, familial intrahepatic cholestasis, X-linked adreno-leukodystrophy, Scott syndrome, Hermansky-Pudlak syndrome types 1 and 2, Zellweger syndrome, rhizomelic chondroidysplasia puncta, autosomal recessive primary hyperoxaluria, Mohr Tranebjaerg syndrome, spinal and bullar muscular atrophy, primary ciliary diskenesia (Kartagener's syndrome), giantism and acromegaly, galactorrhea, Addison's disease, adrenal virilism, Cushing's syndrome, ketoacidosis, primary or secondary aldosteronism, Miller Dieker syndrome, lissencephaly, motor neuron disease, User's syndrome, Wiskott-Aldrich syndrome, Optiz syndrome, Huntington's disease, hereditary pancreatitis, anti-phospholipid syndrome, overlap connective tissue disease, Sjögren's syndrome, stiff-man syndrome, Brugada syndrome, congenital nephritic syndrome of the Finnish type, Dublin-Johnson syndrome, X-linked hypophosphosphatemia, Pendred syndrome, persistent hyperinsulinemic hypoglycemia of infancy, hereditary spherocytosis, aceruloplasminemia, infantile neuronal ceroid lipofuscinosis, pseudoachondroplasia and multiple epiphyseal, Stargardt-like macular dystrophy, X-linked Charcot-Marie-Tooth disease, autosomal dominant retinitis pigmentosa, Wolcott-Rallison syndrome, Cushing's disease, limb-girdle muscular dystrophy, mucoploy-saccharoidosis type IV, hereditary familial amyloidosis of Finish, Anderson Disease, sarcoma, chronic myelomonocytic leukemia, cardiomyopathy, faciogenital dysplasia, Torsion disease, Huntington and spinocerebellar ataxias, hereditary hyperhomosyteinemia, polyneuropathy, lower motor neuron disease, pigmented reitinitis, seronegative polyarthritis, interstitial pulmonary fibrosis, Raynaud's phenomenon, Wegner's granulomatosis, preoteinuria, CDG-Ia, CDG-Ib, CDG-Ic, CDG-Id, CDG-Ie, CDG-If, CDG-IIa, CDG-IIb, CDG-IIc, CDG-IId, Ehlers-Danlos syndrome, multiple exostoses, Griscelli syndrome (type 1 or type 2), or X-linked non-specific mental retardation. In addition, metabolic disorders can also include lysosomal storage disorders such as, but not limited to, Fabry disease, mucopolysaccharidosis I, Farber disease, Gaucher disease, $GM_1$-gangliosidosis, Tay-Sachs disease, Sandhoff disease, $GM_2$ activator disease, Krabbe disease, metachromatic leukodystrophy, Niemann-Pick disease (types A, B, and C), Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipfuscinosis, chloesterol ester storage disease, Wolman disease, Multiple sulfatase deficiency, galactosialidosis, mucolipidosis (types II, III, and IV), cystinosis, sialic acid storage disorder, chlormicron retention disease with Marinesco-Sjögren syndrome, Hermansky-Pudlak syndrome, Chediak-Higashi syndrome, Danon disease, or Geleophysic dysplasia.

Symptoms of a metabolic disorder are numerous and diverse and can include one or more of, e.g., anemia, fatigue, bruising easily, low blood platelets, liver enlargement, spleen enlargement, skeletal weakening, lung impairment, infectious (e.g., chest infections or pneumonias), kidney impairment, progressive brain damage, seizures, extra thick meconium, coughing, wheezing, excess saliva or mucous production, shortness of breath, abdominal, pain, occluded bowel or gut, fertility problems, polyps in the nose, clubbing of the finger/toe nails and skin, pain in the hands or feet, angiokeratoma, decreased perspiration, corneal and lenticular opacities, cataracts, mitral valve prolapse and/or regurgitation, cardiomegaly, temperature intolerance, difficulty walking, difficulty swallowing, progressive vision loss, progressive hearing loss, hypotonia, microglossia, areflexia, lower back pain, sleep apnea, orthopnea, somnolence, lordosis, or scoliosis. It is understood, that due to the diverse nature of the defective or absent proteins and the resulting disease phenotypes (e.g., symptomatic presentation of a metabolic disorder), a given disorder will generally present only symptoms characteristic to that particular disorder. For example, a patient with Fabry disease can present a particular subset of the above-mentioned symptoms sueh as, but not limited to, temperature intolerance, corneal whirling, pain, skin rashes, nausea, or dirarrhea. A patient with Gaucher syndrome can present with splenomegaly, cirrhosis, convulsions, hypertonia, apnea, osteoporosis, or skin discoloration.

In addition to the administration of one or more uncapped molecules described herein, a metabolic disorder can also be treated by proper nutrition and vitamins (e.g., cofactor therapy), physical therapy, and pain medications.

Depending on the specific nature of a given metabolic disorder, a patient can present these symptoms at any age. In many cases, symptoms can present in childhood or in early adulthood. For example, symptoms of Fabry disease can present at an early age, e.g., at 10 or 11 years of age.

As used herein, a subject "at risk of developing a metabolic disorder" is a subject that has a predisposition to develop a disorder, i.e., a genetic predisposition to develop metabolic disorder as a result of a mutation in a enzyme such as acid alpha glucosidase, alpha galactosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acteylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neurominidase, phosphotransferase, acid lipase, acid ceramidase, sphinogmyelinase, thioesterase, cathepsin K, or lipoprotein lipase. Clearly, subjects "at risk of developing a metabolic disorder" are not all the subjects witnin a species of interest.

A subject "suspected of having a disorder" is one having one or more symptoms of a metabolic disorder such as any of those described herein.

Pharmaceutical Compositions and Methods of Treatment

A target molecule having uncapped M6P residues can be incorporated into a pharmaceutical composition containing a therapeutically effective amount of the molecule and one or more adjuvants, exeipients, carriers, and/or diluents. Acceptable diluents, carriers and excipients typically do not adversely affect a recipient's homeostasis (e.g., electrolyte balance). Acceptable carriers include biocompatible, inert or bioresorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., Remington's Pharmaceutical Sciences (Maack Publishing Co., Easton, Pa.). Supplementary active compounds can also be incorporated into the compositions.

Administration of a pharmaceutical composition containing molecules with uncapped M6P residues can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartifical organ, or a colony of implanted altered N-glycosylation molecule production cells). See, e.g., U.S. Pat. Nos. 4,407,957, 5,798,113, and 5,800,828. Administration of a pharmaceutical composition can be achieved using suitable delivery means such as: a pump (see, e.g., Annals of Pharmacotherapy, 27:912 (1993); Cancer, 41:1270 (1993); Cancer Research, 44; 1698 (1984); microencapsulation (see, e.g., U.S. Pat. Nos. 4,352,883; 4,353,888; and 5,084,350); continuous release polymer implants (see, e.g., Sabel, U.S. Pat. No. 4,883,666); microencapsulation (see, e.g., U.S. Pat. Nos. 5,284,761, 5,158,881, 4,976,859 and 4,968,733 and published PCT patent applications WO92/19195, WO95/05452); injection, either subcutaneously, intravenously, intra-arterially, intramuscularly, or to other suitable site; or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporatlon, and transdermal patch.

Formulations suitable for parenteral, administration, conveniently contain a sterile aqueous preparation of the altered N-glycosylation molecule, which preferably is isotonic with the blood of the recipient (e.g., physiological saline solution). Formulations can be presented in unit-dose or multi-dose form.

Formulations suitable for oral administration can be presented as discrete units such as capsules, cachets, tablets, or lozenges, each containing a predetermined amount of the altered N-glycosylation molecule; or a suspension in an aqueous liquor or a non-aqueous liquid, such as a syrup, an elixir, an emulsion, or a draught.

A molecule having uncapped M6P residues suitable for topical administration can be administered to a mammal (e.g., a human patient) as, e.g., a cream, a spray, a foam, a gel, an ointment, a salve, or a dry rub. A dry rub can be rehydrated at the site of administration. Such molecules can also be infused directly into (e.g., soaked into and dried) a bandage, gauze, or patch, which can then be applied topically. Such molecules can also be maintained in a semi-liquid, gelled, or fully-liquid state in a bandage, gauze, or patch for topical administration (see, e.g., U.S. Pat. No. 4,307,717).

Therapeutically effective amounts of a pharmaceutical composition can be administered to a subject in need thereof in a dosage regimen ascertainable by one of skill in the art. For example, a composition can be administered to the subject, e.g., systemically at a dosage from 0.01 μg/kg to 10,000 μg/kg body weight of the subject, per dose. In another example, the dosage is from 1 μg/kg to 100 μg/kg body weight of the subject, per dose. In another example, the dosage is from 1 μg/kg to 30 μg/kg body weight of the subject, per dose, e.g., from 3 μg/kg to 10 μg/kg body weight of the subject, per dose.

In order to optimize therapeutic efficacy, a molecule having uncapped M6P residues can be first administered at different dosing regimens. The unit dose and regimen depend on factors that include, e.g., the species of mammal, its immune status, the body weight of the mammal. Typically, levels of a such a molecule in a tissue can be monitored using appropriate screening assays as part of a clinical testing procedure, e.g., to determine the efficacy of a given treatment regimen.

The frequency of dosing for a molecule having uncapped M6P residues is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status. The frequency of dosing can be varied depending on whether the treatment is prophylactic or therapeutic.

Toxicity and therapeutic efficacy of such molecules or pharmaceutical compositions thereof can be determined by known pharmaceutical procedures in, for example, cell cultures or experimental animals. These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Pharmaceutical compositions that exhibit high therapeutic indices are preferred. While pharmaceutical compositions that exhibit toxic side effects can be used, care should be taken to design a deli very system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human, patients). The dosage of such pharmaceutical compositions lies generally within a range of circulating concentrations that include the ED50 with little or no toxicity. The dosage may vary within this range depending upon the dosage form employed and the route of administration utilized. For a pharmaceutical composition, used as described herein (e.g., for treating a metabolic disorder in a subject), the therapeutically effective dose can be estimated initially from cell culture assays. A dose can be formulated in animal models to achieve a circulating plasma concentration range that includes the IC50 (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

As defined herein, a "therapeutically effective amount" of a molecule having uncapped M6P residues is an amount of the molecule that is capable of producing a medically desirable result (e.g., amelioration of one or more symptoms of a metabolic disorder) in a treated subject. A therapeutically effective amount (i.e., an effective dosage) can includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

The subject can be any mammal, e.g., a human (e.g., a human patient) or a non-human, primate (e.g., chimpanzee, baboon, or monkey), a mouse, a rat, a rabbit, a guinea pig, a gerbil, a hamster, a horse, a type of livestock (e.g., cow, pig, sheep, or goat), a dog, a cat, or a whale.

A molecule or pharmaceutical composition thereof described herein can be administered to a subject as a combination therapy with another treatment, e.g., a treatment for a metabolic disorder (e.g., a lysosomal storage disorder). For example, the combination therapy can include administering to the subject (e.g., a human patient) one or more additional agents that provide a therapeutic benefit to the subject who has, or is at risk of developing, (or suspected of having) a metabolic disorder (e.g., a lysosomal storage disorder). Thus, the compound or pharmaceutical composition and the one or more additional agents can be administered at the same time. Alternatively, the molecule can be administered first and the one or more additional agents administered second, or vice versa.

It will be appreciated that in instances where a previous therapy is particularly toxic (e.g., a treatment for a metabolic disorder with significant side-effect profiles), administration of a molecule described herein can be used to offset and/or lessen the amount of the previously therapy to a level sufficient to give the same or improved therapeutic benefit, but without the toxicity.

Any of the pharmaceutical compositions described herein can be included in a container, pack, or dispenser together with instructions for administration.

The following are examples of the practice of the invention. They are not to be construed as limiting the scope of the invention in any way.

EXAMPLES

Example 1

Figure 2:
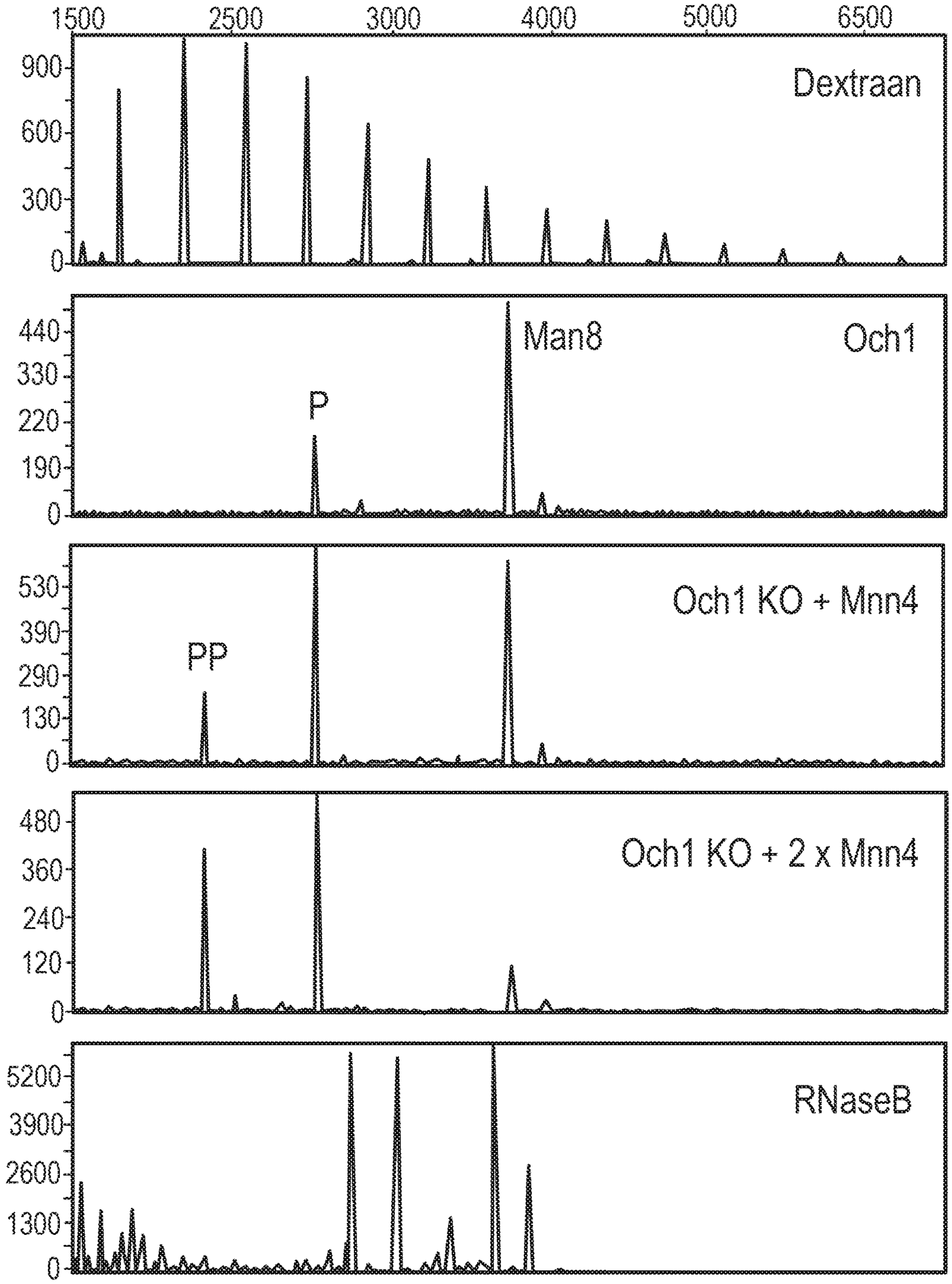
FIG. 2 is a series of electroferograms depicting sugar analysis of MTLY60Δoch1 (1 wild type copy of Mnn4), MTLY60Δoch1+Hdp4dMnn4 (1 WT+1 extra copy of Mnn4) and MTLY60Δoch1+Hp4dMnn4+TEFMnn4, P represents the monophosphorylated peak, PP represents the diphosphorylated peak, and Man8 represents the $Man_8GlcNAc_2$ peak.

Creation of a *Yarrowia lipolytica* Strain with a Higher Degree of Phosphorylated N-Glycans To upregulate the phosphorylation of glycans in *Y. lipolytica*, strain MTLY60 was transformed with 2 extra copies of the MNN4 gene, each in a separate expression vector. The MNN4 gene is involved in increasing glycan phosphorylation in yeast. FIG. 1 contains a schematic of the pYLTmAX plasmid into which the MNN4 gene was cloned to produce pYLTmAXMnn4, which contains the MNN4 open reading frame under control the TEF promoter. A strain was made that contains two extra copies of the MNN4 gene, one under control of the hp4d promoter and one under control of the TEF1 promoter. N-glycans were prepared from strain MTLY60Δoch1 (1 wild type copy of MNN4), strain MTLY60Δoch1+Hp4dMNN4 (1 WT+1 extra copy of MNN4) and strain MTLY60Δoch1+Hp4dMNN4+TEF-MNN4 (1 WT+2 extra copies of Mnn4) and assayed by DNA sequencer-assisted (DSA), fluorophore-assisted carbohydrate electrophoresis (FACE). See, Callewaert et al., *Glycobiology* 11(4):275-281 (2001). Based on the results in FIG. 2, it can be deduced that the mono phosphorylated peak is upregulated in the strain with 1 extra copy and that a peak of double phosphorylation appears. In the strain with 2 extra copies, the double phosphorylated peak was much higher and the peak of neutral $Man_8GlcNAc_2$ sugars was much lower.

Example 2

Figure 3:
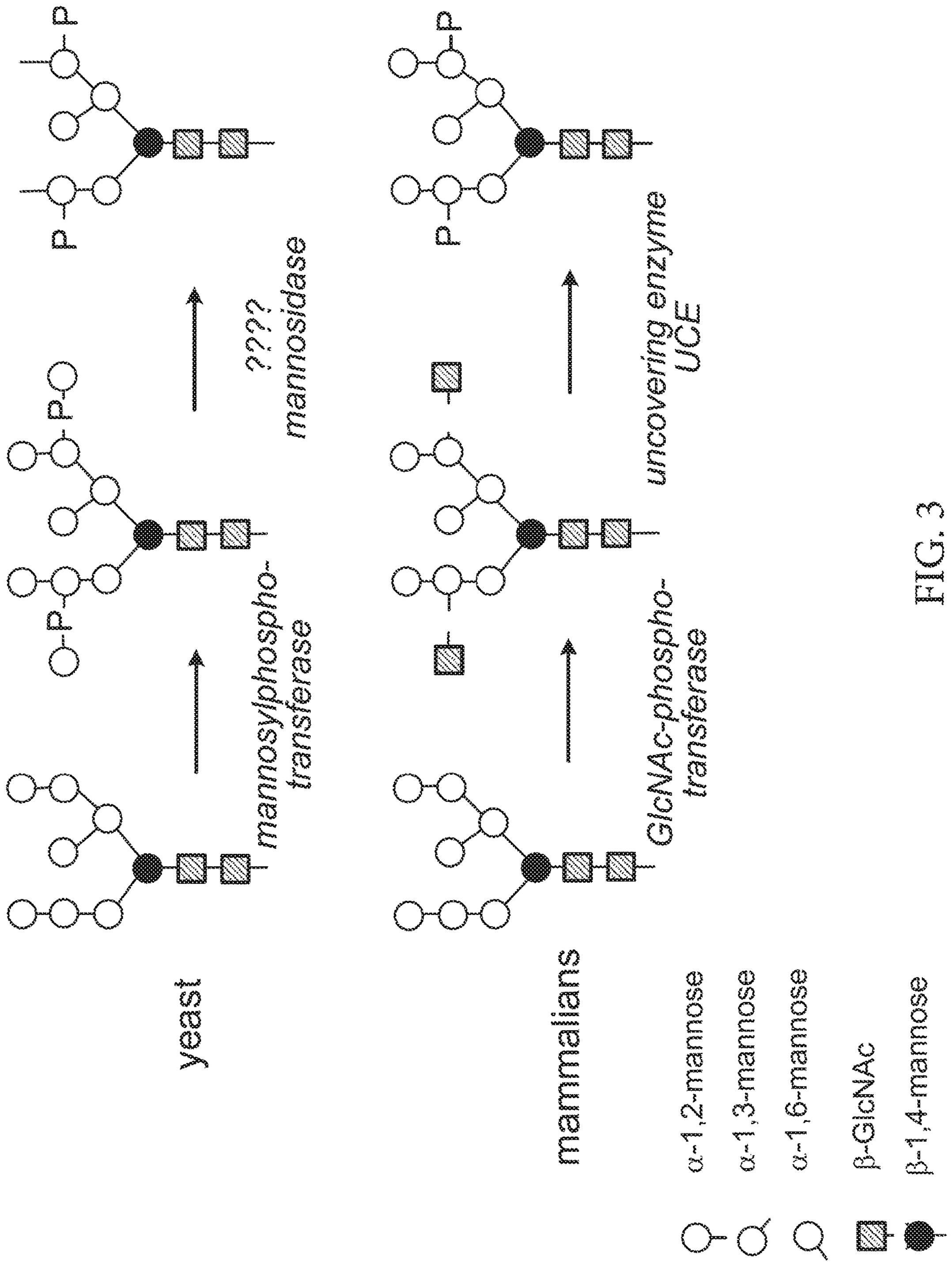
FIG. 3 is a schematic of mammalian and yeast glycan phosphorylation pathways. The mammalian glycan phosphorylation pathway involves addition of a phospho-GlcNAc catalyzed by GlcNAc-phosphotransferase to $Man_8GlcNAc_2$ glycans followed by decapping of the GlcNAc to expose the phosphate by an uncovering enzyme. In contrast, yeast glycan phosphorylation, involves addition of a phospho-mannose to $Man_8GlcNAc_2$ glycans, but no endogenous enzyme is present to uncap the mannose to expose the phosphate.

Identification of a Mannosidase Activity that can Uncap the Capping Mannose Residue Present on Phosphorylated Glycans of Fungal Origin The phosphorylation of sugars by yeast and filamentous fungi results in a mannose-phospho-mannose di-ester linkage (FIG. 3). To obtain a structure where the phosphate is in a mono-ester linkage, a mannosidase is required that is able to hydrolyze the mannose-phosphate linkage, leaving the phosphate attached to the 6 position of a mannose of the high mannose glycan structure. Chiba et al., *Glycobiology,* 12(12):821-8 (2002) indicate that a mannosidase from a *Cellulomonas* species is capable of decapping the mannose. However, Chiba et at only partially purified the mannosidase protein and could not identity the gene encoding the protein.

Figure 4:
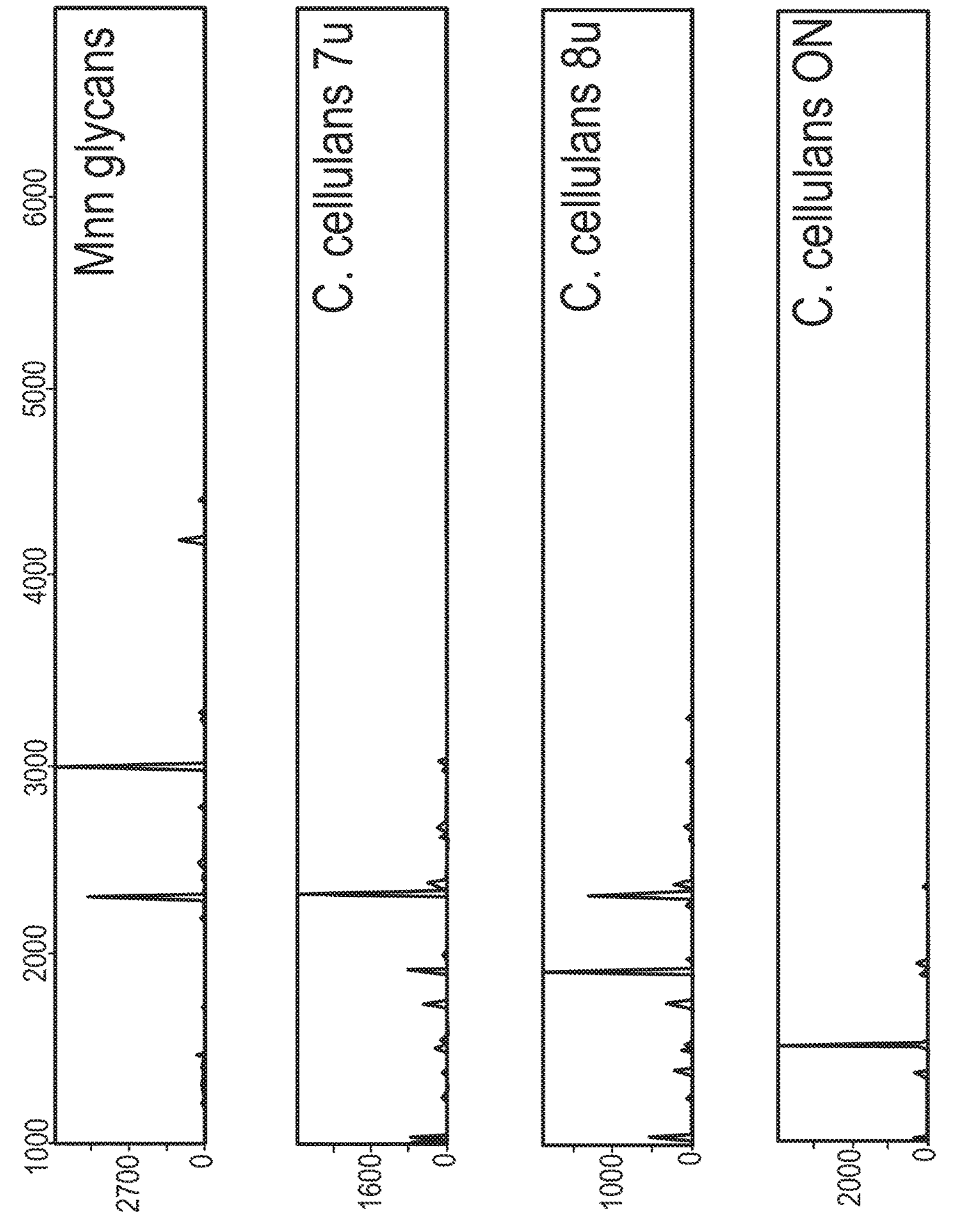
FIG. 4 is a series of electroferograms depicting N-glycans derived from strain MTLY60Δoch1+Hp4dMnn4+TEFMnn4 treated for different time frames (7 hrs, 8 hrs, or overnight (ON)) with supernatants from *C. cellulans* medium.

A *Cellulosimicrobium cellulans* (also known as *Oerskovia xanthineolytica* and *Arthrobacter luteus*) isolate was obtained from the LMG bacteria collection and tested for production of mannosidase activity. The bacteria were grown at 30° C. and in mannan containing medium to secrete the mannosidase in the medium. Bacterial supernatants (SN) were obtained from the cultures and tested for the desired mannosidase activity by incubating the SN with isolated N-glycans derived from the MNN4 overexpressing strain described in Example 1. After incubation, the glycans were assayed by DSA-FACE (FIG. 4).

Figure 5:
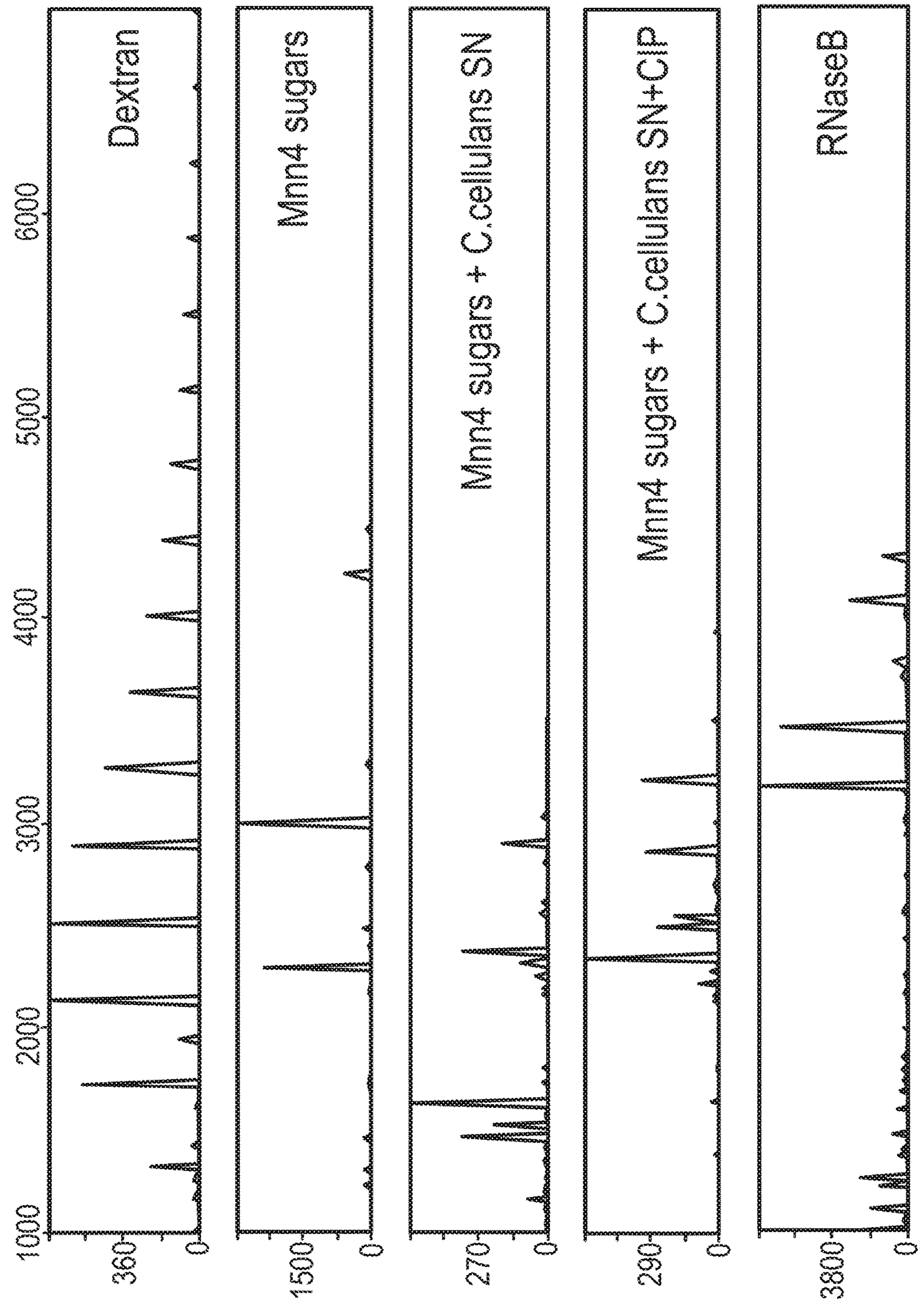
FIG. 5 is a series of electroferograms depicting N-glycans derived from an MNN4 overexpressing strain treated with *C. cellulans* supernatant (SN) with and without phosphatase (CIP) incubation.

After treatment with the SN, glycans gain an additional charge and migrate faster in the electric field and shift to the left hand side of the electroferogram. If these fast-running structures are indeed phosphomonoester-substituted high mannose glycans, they would be larger in size than the neutral products running at the same position. Treatment of such glycans with a phosphatase would result in neutral oligosaccharides that run much slower. As shown in FIG. 5, treatment with calf intestine phosphatase (CIP) resulted in the peaks displaying lower electrophoretic mobility, proving that the phosphates are terminal and that the mannose was decapped.

Example 3

Partial Purification and Further Identification of a Mannosidase

To purify the mannosidase, *C. cellulans* was grown in 1 L of medium B (Bagiyan et al., *Eur. J. Biochem.* 249(1):

286-92 (1997)) or medium A (Chiba et al., 2002, supra). See Table 1. Thereafter, the medium was precipitated with 40% and 80% ammonium sulphate and the samples were analysed by SDS-PAGE. The ammonium sulphate fractions were dialyzed against 20 mM Na-phosphate buffer pH 6.5 with 1 mM $CaCl_2$, and then tested for activity on oligosaccharides derived from a MNN4 overexpressing strain (Example 1).

TABLE 1

| Medium components | |
|---|---|
| Medium A (1 liter) | Medium B (1 liter) |
| 2 g mannan | 2 g mannan |
| 0.5 g $(NH_4)_2SO_4$ | 2 g $(NH_4)_2SO_4$ |
| 0.4 g $MgSO_4$•$7H_2O$ | 0.02 g $MgSO_4$•$7H_2O$ |
| 20 mg $FeSO_4$•$7H_2O$ | 1 mg $FeSO_4$•$7H_2O$ |
| 60 mg $CaCl_2$•$2H_2O$ | 1 g yeast extract |
| 1 g yeast extract | 4.2 g KOH |
| 7.54 g $K_2HPO_4$ | 14 g $KH_2PO_4$ |
| 2.32 g $KH_2PO_4$ | |

Both cultivation conditions resulted in the production of the uncapping activity. Only the 40% ammonium sulphate fraction derived from medium B showed activity, whereas all fractions of the medium A supernatant displayed activity.

Figure 6:
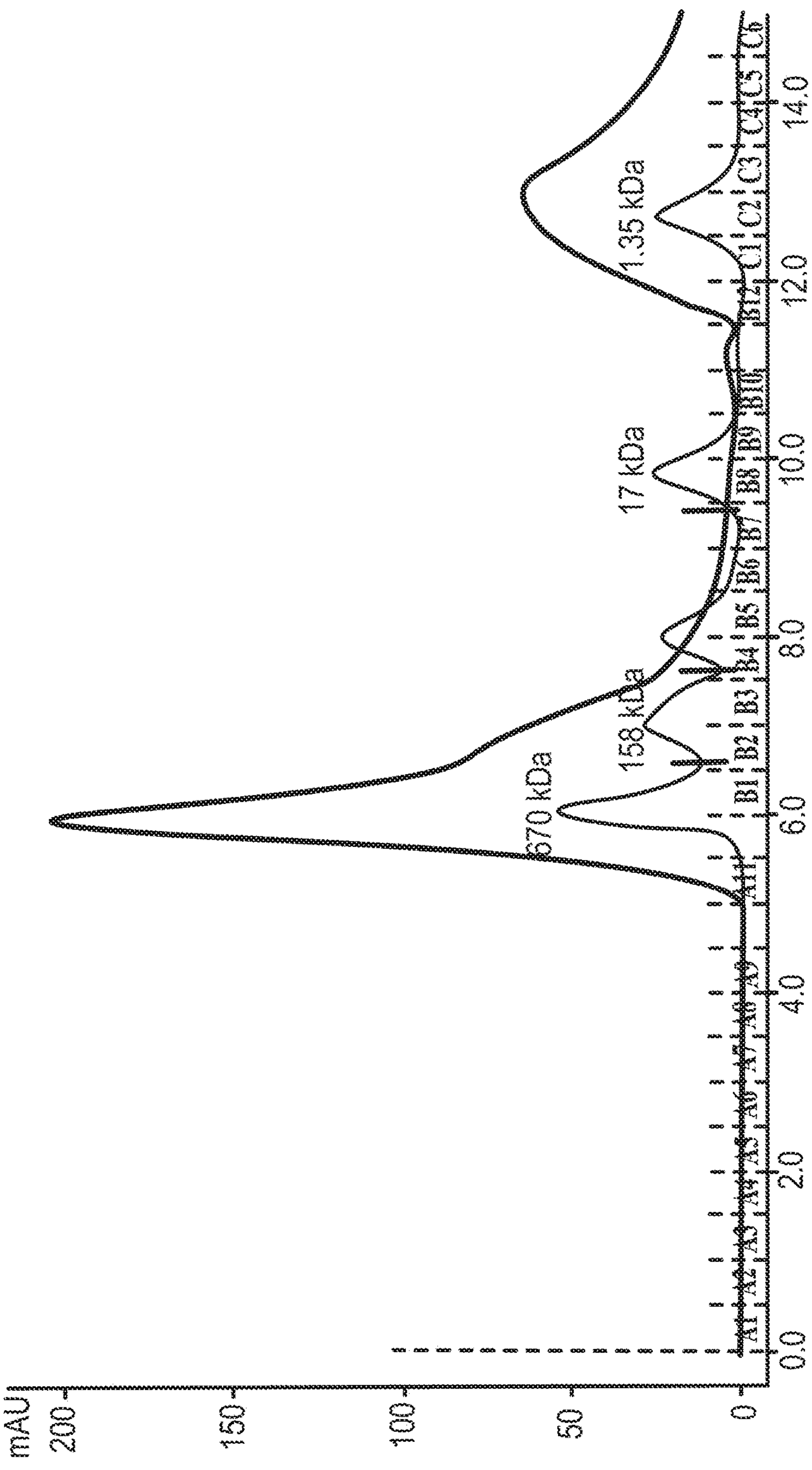
FIG. 6 is a graph of the absorbance units (mAU) of elution fractions at the indicated MW. Each elution fraction contained ~500 µl.

The 40% ammonium sulphate sample derived from the medium A cultivation was further purified over a silica-based gel filtration column (FIG. 6). This resulted in a peak with a shoulder around 670 kDa.

Figure 7:
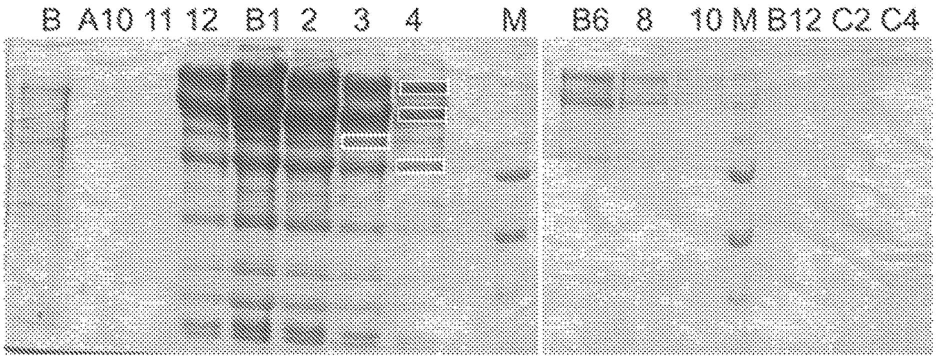
FIG. 7 is a representation of a SDS-polyacrylamide gel after electrophoresis of elution fractions from silica-based gel filtration (250 µl of each fraction was DOC/TCA precipitated). The boxed bands were cut out for peptide mass fingerprinting and de novo sequencing using tandem mass spectrometry (MS/MS).

All elution fractions were incubated with oligosaccharides derived from a MNN4 overexpressing *Yarrowia lipolytica* strain (described in Example 1) (with or without a following CIP-digest) to test for the phosphate uncapping activity. The decapping and mannosidase activity was observed in all of the samples. Samples were also analyzed on SDS-PAGE (FIG. 7), which showed not just one protein band, but several protein bands. Several bands were cutout from the gel and portions of their sequence analyzed by de novo peptide sequencing using Mass Spectrometry.

The de novo sequencing results revealed several peptide sequences, which were compared against the sequences in the non redundant database using BLAST. Peptides with homology to the following proteins were identified: a phosphodiesterase, a hypothetical protein, a putative alpha-1,2 mannosidase (identified peptides shown in Table 2) (homology to a mannosidase from *Magnetospirillum*), and an aminopeptidase Y. The phosphodiesterase was a possible candidate, but here only 2 of the 6 peptides gave a hit. The mannosidase also was a candidate with 3/5 and 5/5 hits for 2 different mannosidases.

TABLE 2

| Peptide Sequences | |
|---|---|
| Peptide Sequence | SEQ ID NO |
| SAYQSFTTR | 1 |
| VWGFSHR | 2 |
| VEGGWLPR | 3 |
| TQGNNFALLLPER | 4 |
| DVHAELTAMAR | 5 |

Example 4

Identification of Mannosidases with the Desired Sequence Based on Whole Genome Sequencing To identify the mannosidase gene coding for the desired activity, the genome of *C. cellulans* was sequenced using a Titanium 454 sequencing (Eurofins MWG Operon). Due to the high GC content, the sequencing was only partial (1.96 Mbases) and of poor quality (with only a low average contig size). The high GC content of the genome that causes loop formation during the emulsion PCR (emPCR), resulting in deletions and very short sequences.

This problem was overcome using new sequencing chemistry for the emPCR that was made available in beta testing by Roche. This gave a much improved sequence (4.7 Mbases), allowing the identification of 5 mannosidase genes belonging to glycosyl hydrolase family 92, one of which (CeMan1, SEQ ID NO:6) corresponds to the sequence from which the peptides described in Example 3 were obtained. No mannosidases from family 38 or 47 were found. The start codon of each of CcMan1-CcMan4 was predicted by MetaGeneAnnotator (see the world wide web at metagene.cb.k.u-tokyo.ae.jp/metagene/) and compared to Blast results with known genes. The start codon of CcMan5 could not be predicted since it is missing from the sequence. The signal sequence of each gene was predicted with signal P (see the world wide web at ebs.dtu.dk/services/SignalP/) by two methods (neural networks and hidden markov models).

FIGS. 8-12 contain the nucleotide and encoded amino acid sequences of the 5 mannosidase genes from *C. cellulans.*

Example 5

Figure 13:
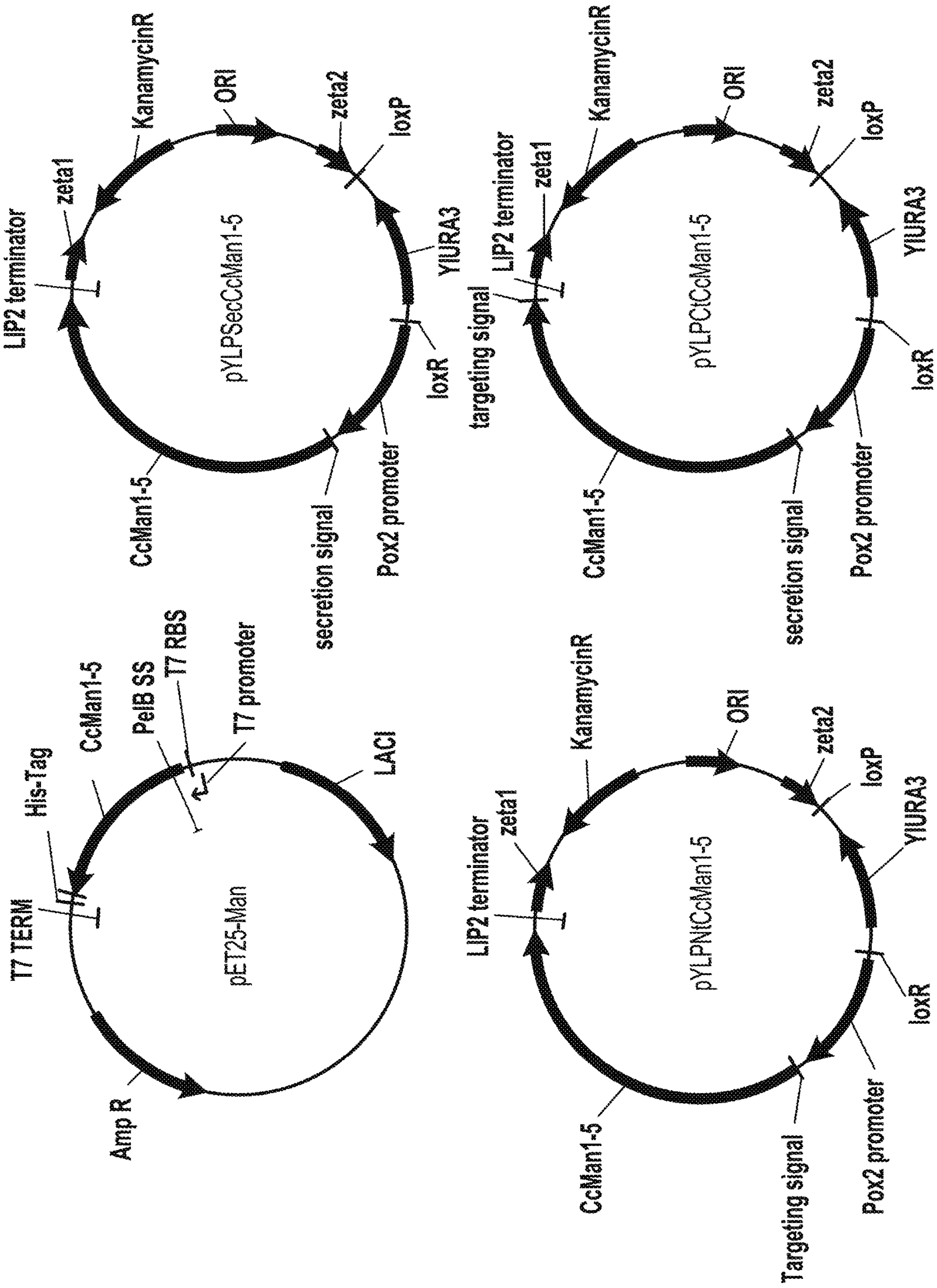
FIG. 13 contains examples of expression plasmids for the expression of CcMan-1 5 in the periplasm of *E. coli* (pET25-Man), as secreted proteins in *Yarrowia lipolytica* (pYLP-SecCcMan1-5), as proteins targeted to the secretory pathway of *Yarrowia lipolytica*, tagged to the N-terminus (pYLPNtCcMan1-5) or tagged to the C-terminus (pYLPCtCcMan1-5).

Heterologous Expression of Mannosidase for In Vitro or In Vivo Mannose Decapping In order to allow decapping of the yeast type phosphorylation by the mannosidase, it has to be expressed either heterologously in a different host or in the same fungal host from which the protein for therapeutic use is expressed. In the latter case it can be co-secreted or targeted to an intracellular compartment (e.g., Golgi apparatus or endoplasmic reticulum). This can be accomplished by cloning the gene (be it codon optimised for the target host or not) operably linked after a promoter in an expression vector. The mannosidase can be tagged with an epitope tag to allow easy detection and purification or expressed as such. It can be secreted in the periplasm of a bacterial cell or expressed intracellularly. In case of expression in the fungal host, the sequence can contain a secretion signal or a targeting signal to target the protein to an intracellular compartment or both. Table 3 contains a list of secretion and targeting signals for expression in fungal organisms. Examples of such expression vectors are presented in FIG. 13.

TABLE 3

| Secretion and targeting signals for expression in fungal organisms | | |
|---|---|---|
| | Golgi targeting signal | |
| Secretion signals | N-terminal | C-terminal |
| LIP2 prepro | MNN2 | KEX2 |
| LIP2 pre | MNN4 | |
| S.c. α mating factor | MNN6 | |

TABLE 3-continued

| Secretion and targeting signals for expression in fungal organisms | | |
|---|---|---|
| | Golgi targeting signal | |
| Secretion signals | N-terminal | C-terminal |
| XPR2 prepro | MNN1 | |
| XPR2 pre | MNN9 | |
| | OCH1 | |
| | SEC12 | |
| | KRE2 | |

The CcMan1-Man5 genes were codon optimized for expression in *E. coli*. See FIGS. 14-18 for the codon optimized sequences. Table 4 contains the length of each codon optimized nucleotide sequence and the predicted molecular weight of each polypeptide without the signal sequence.

TABLE 4

| Codon Optimized Genes | | | |
|---|---|---|---|
| | Length (bp) | SEQ ID NO | Size (kDa) of encoded product |
| CcMan1 | 2613 | 16 | 92.6 |
| CcMan2 | 3483 | 17 | 121.6 |
| CcMan3 | 3363 | 18 | 116 |
| CcMan4 | 5283 | 19 | 184 |
| CcMan5 | 4956 | 20 | 173 |

Example 6

Figure 19:
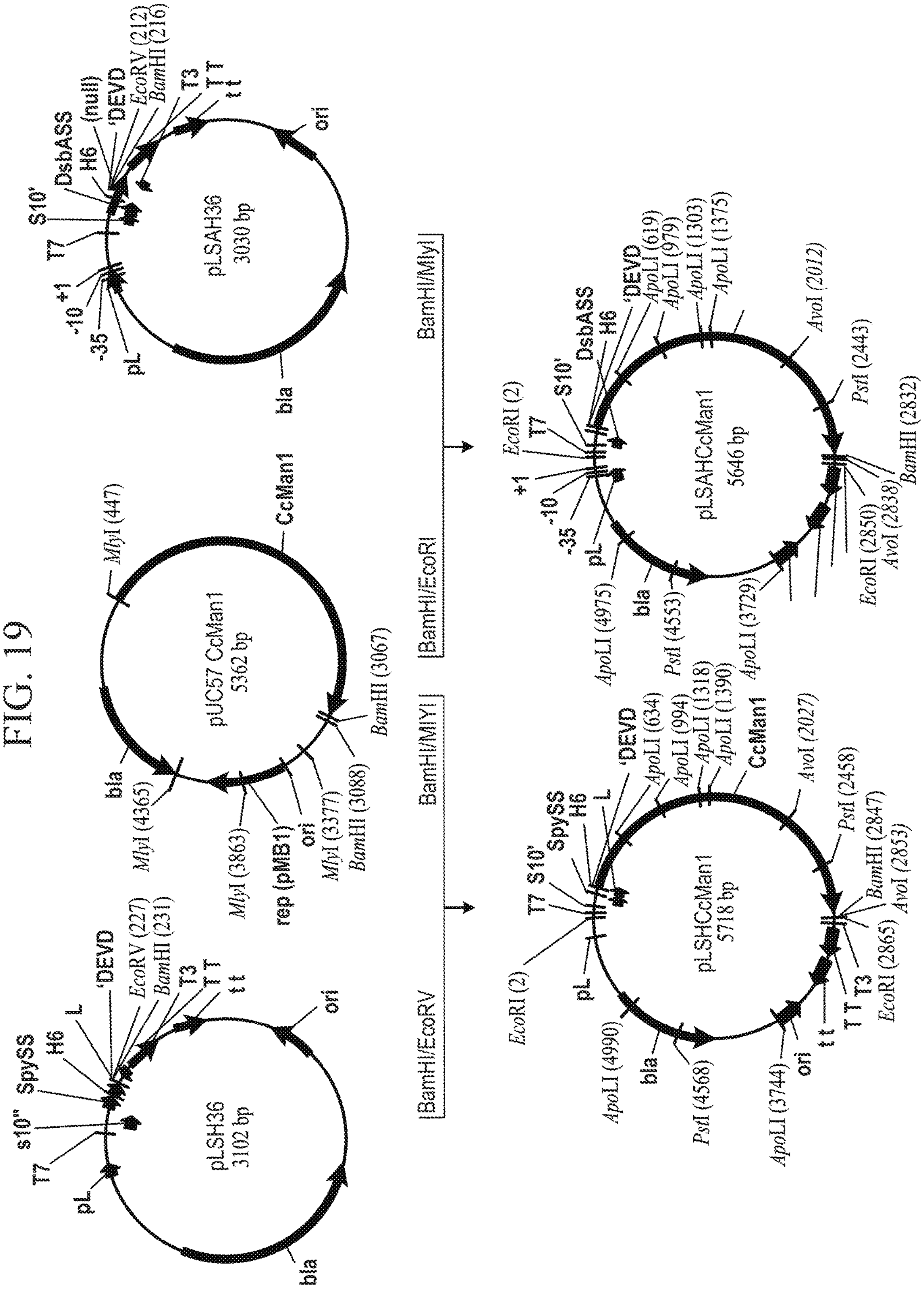
FIG. 19 is a schematic of the pLSAH64 and pLSH36 vectors and the cloning strategy for introducing the *C. cellulans* genes into the vectors.

Cloning and Activity if *C. cellulans* Glycosyl Hydrolase (GH) Family 92 Enzymes The CeMan1-CcMan5 codon optimized nucleic acids were cloned into *E. coli* vectors pLSH36, which contains a Spy signal sequence, and/or pLSAH36, which contains a DsbA signal sequence for penptasmic expression. Both pLSH36 and pLSAH36 result in the encoded polypeptide having a polyhistidine tag and a murine caspase-3 site, which can be used for the removal of the His6-tag during purification FIG. 19 contains a schematic of the pLSH36 and pLSAH36 vectors as well as the cloning strategy tor introducing the *C. cellulans* GH92 genes into the vectors. After cloning, the different mannosidases were transformed into *E. coli* BL21+plCa2 expression strain. The transformed strains were grown to an optical density (OD) of 0.5 to 1 and induced with 1 mM isopropyl β-D-1-thiogalactopyranoside (IPTG). Different cell fractions (medium, periplasm, soluble and insoluble fraction) were isolated and analyzed by SDS PAGE and Western blotting with an anti-His6 antibody. For CeMan1, CeMan2, and CeMan3, expression was detected in all fractions. For CcMan4 and CcMan5, expression was the highest in the soluble fraction, but some expression also was detected in the other fractions.

To determine the activity of the CcMan1-CcMan5 proteins, activity tests were performed using methylumbelliferyl alpha mannoside (MUM) as set forth in Chiba et al., 2002, supra. For CcMan1 and CcMan2, the medium and periplasm samples were able to hydrolyze MUM weakly, whereas CcMan3 and CcMan5 were not able to hydrolyze MUM. The soluble fraction of CcMan4 gave the highest fluorescent signal, indicating that CcMan4 is the only mannosidase with α1,2-mannosidase activity.

Figure 20:
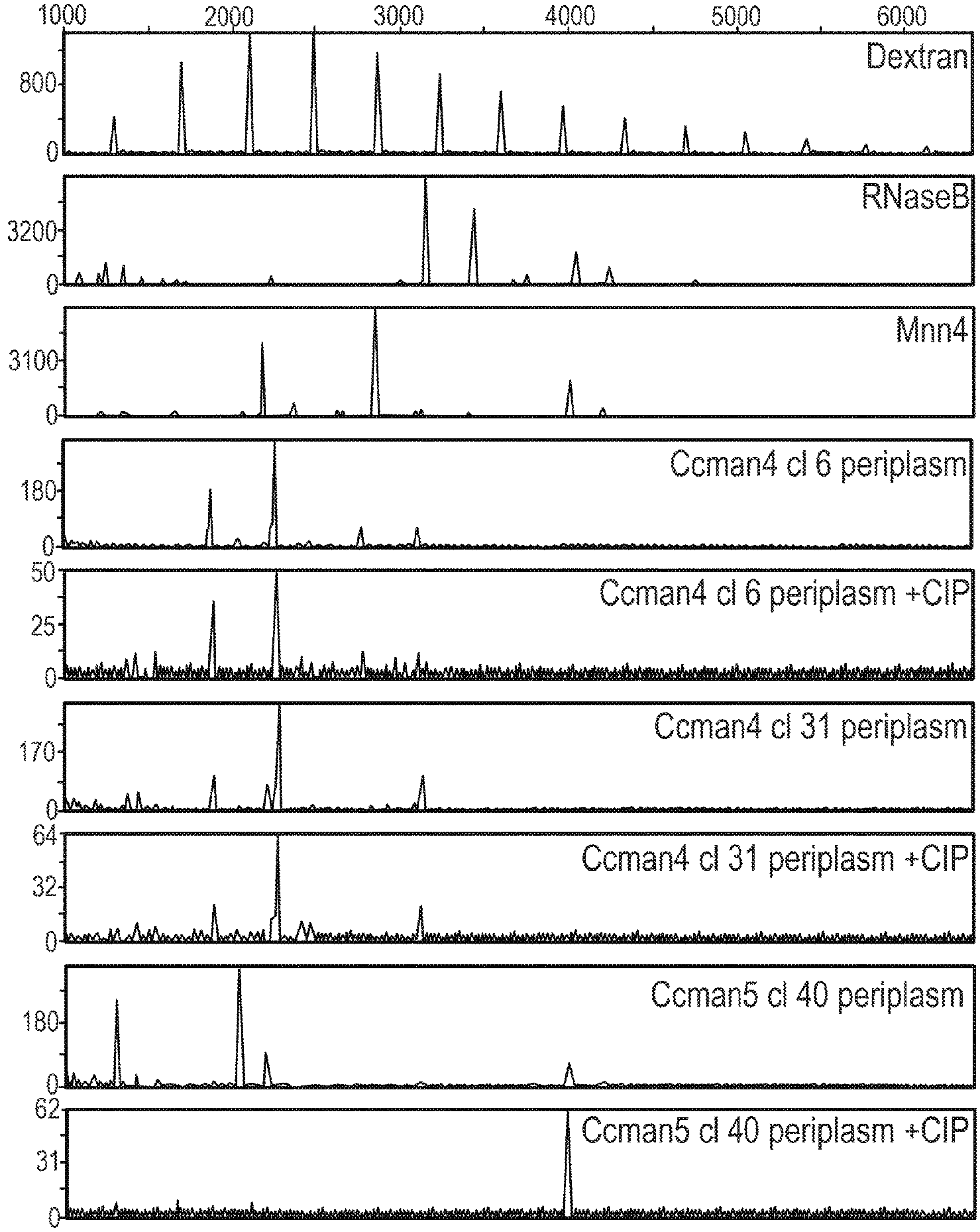
FIG. 20 is a series of electroferograms depicting analysis of the periplasmic fraction of CcMan4 and CcMan5 expressing *E. coli* cells. Analysis was performed using DNA sequencer-assisted, fluorophore-assisted carbohydrate electrophoresis (DSA-FACE). The first and second panels represent the dextran ladder and the sugars from RNaseB, respectively. The third panel is the untreated Mnn4 sugars with "P" corresponding to the mono mannophosphorylated $Man_8GlcNAc_2$ peak, "PP" corresponding to the double mannophosphorylated $Man_8GlcNAc_2$ peak, and "Man8" corresponding to the $Man_8GlcNAc_2$ peak. Panels 4 to 9 are the results obtained with Mnn4 glycans incubated with the indicated periplasm, with or without a subsequent calf intestinal phosphatase (CIP) digest.

All medium and periplasmic samples of the 5 different *C. cellulans* mannosidases also were tested on sugars derived from the MNN4 overexpressing strain of Example 1 (referred to herein as MNN4 sugars) to see if they were able to degrade the sugars and uncap the mannose of the mannose-6-phosphate. The sugars were incubated overnight and analysed by DNA sequencer-assisted, fluorophore-assisted carbohydrate electrophoresis (DSA-FACE). The sugar profiles of the medium samples could not be analysed due to fluorophoric molecules in the medium presentation resulting in irrelevant peaks in the electroferogram. The sugar profiles of the periplasm of CcMan1, CcMan2 and CcMan3 showed neither degradation nor decapping, CcMan4 showed degradation, and CeMan5 showed decapping activity (FIG. 20). A CIP-digest on the decapped sugars confirmed the decapping activity of CcMan5 as the dephosphorylated peaks moved to neutral Man8.

Figure 21:
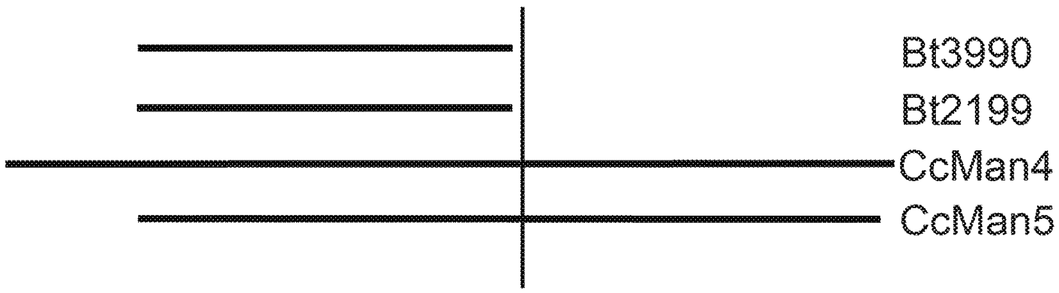

The active mannosidases CcMan4 and CcMan5 were aligned with Br3990 (744 AA) and Bt2199 (739 AA), family 92 mannosidases with known structure (see Zhu et al., *Nat. Chem. Biol.*, 6(2):125-32. Epub 2009 Dec. 27 (2010)). See FIG. 21. Since only the first part of CcMan4 and CcMan5 aligned with Bt2990 and Bt2199, and because they are large proteins, it was decided to clone the first domain of each protein separately and test the activity. CcMan4domain (1-3357 bp, i.e., nucleotides 1-3357 of SEQ ID NO:20) and CcMan5domain (1-2322 bp, i.e., nucleotides 1-2322 of SEQ ID NO:20) were cloned into the pLSAH36 *E. coli* expression vector. See, FIG. 19 for a schematic of the pLSAH36 cloning vector. The expression vectors were transformed into the *E. coli* BL21+pICa2 expression strain, which was grown to an OD of 0.5 to 1, and induced with 1 mM IPTG. Different cell fractions (medium, periplasm, soluble and insoluble fraction) were isolated and analyzed by SDS PAGE and Western blotting with an anti-His6 antibody. Expression was detected in all 4 cell fractions.

Figure 22:
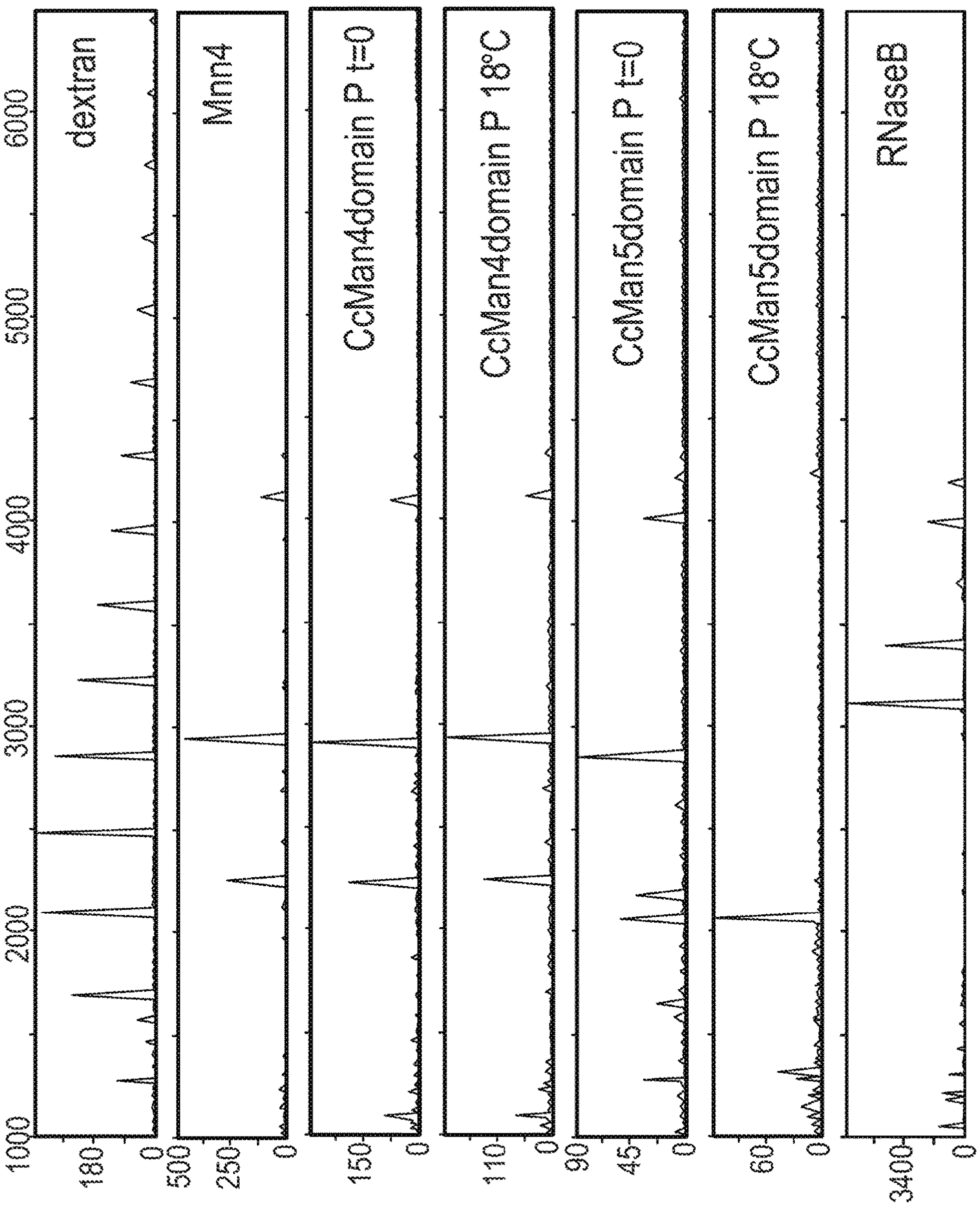
FIG. 22 is a series of electroferogram depicting the analysis of the CcMan4 and CcMan5 enzymes obtained from expressing *E. coli* cells. Analysis was performed using DSA-FACE using MNN4 overexpressing strain derived glycans (referred to as MNN4 glycans or MNN4 sugars) as a substrate. The first panel represents the dextran ladder and the second panel represents the untreated Mnn4 sugars in the third through sixth panels, the sugars were incubated with the CeMan4domain periplasmic fraction not induced, induced overnight at 18° C. with IPTG, the CcMan5 domain periplasmic fraction not induced, and induced overnight at 18° C. with IPTG respectively. The last pancel represents the sugars from RNaseB.

The activity of the domains was tested on Mnn4 sugars. Hereto, the periplasmic fraction of each of the CcMan4domain and CcMan5domain was incubated in the presence of Mnn4 sugars (FIG. 22) and analyzed by DSA-FACE. This experiment showed that the CcMan4domaln lost its mannosidase activity since no degradation could be detected (FIG. 22, panel 4). In contrast, the CeMan5 domain kept its uncapping activity (FIG. 22, panel 6).

Example 7

Production and Purification of CcMan5 and Its Family 92 Homologous Domain

The recombinant CCman5 nucleotides 1-4005 of SEQ ID NO:20 and CcMan5 domain (nucleotides 1-2322 of SEQ ID NO:20) were expressed in *E. coli* strain BL21codon+pICA2 that were transformed with the expression vectors pLSAH-CcMan5 and pLSAHCcMan5 domain. Expression was induced by IPTG under control of a λpL-promoter (see WO 98/48025 and WO 04/074488). See Example 6 and FIG. 19 for a description of pLSAH. The transformed bacteria were grown in Luria Bertani (LB) medium supplemented with ampicillin (100 μg ml) and kanamycin (50 μg/ml) overnight at 28° C. before 1/100 inoculation in a 20 liter fermenter provided with LB medium supplemented with ampicillin (100 μg/ml; and 1% glycerol. The initial stirring and airflow was 200 rpm and 1.5 l/min., respectively, and was automatically adapted to keep the $pO_2$ at 30%. The temperature was kept at 28° C. The cells were grown to an optical density of $A_{600\ am}$=1.0, transferred at 20° C. and expression was induced by addition of 1 mM IPTG overnight. Cells were then harvested and frozen at −20° C. After thawing, the cells were gently resuspended at a concentration of 3 ml/g in 50 mM $NaH_2PO_4$ pH 8.0, 300 mM NaCl, 1 mM PMSF and 10 μg/nu DNaseI. The periplasmic fraction was prepared by stirring the cell suspension for 1 h at 4° C. and was isolated by centrifugation at 18,000×g for 30 min. All steps were conducted at 4° C. The clear supernatant was applied to a 20 ml Ni-Sepharose 6 FF column (GE Healthcare), equilibrated with 20 mM $NaH_2PO_4$ pH 7.4, 300 mM NaCl, 20 mM imidazole, 0.1% CHAPS. The column was eluted with 20 mM $NaH_2PO_4$ pH 7.4, 20 mM NaCl, 400 mM imidazole, 0.1% CHAPS after an extra wash step with 50 mM of imidazole in the same buffer. The elation fraction was diluted 1/10 with 20 mM Tris pH 8.0, 0.1% CHAPS and loaded on an 14 ml Source 15Q column (GE Healthcare) to remove contaminants. After equilibration, the protein of interest was eluted by a linear gradient over 10 column volumes of NaCl from 0 to 1 M in 20 mM Tris, 0.1% CHAPS. The CcMan5 and CcMan5 domain containing fractions were further injected on a HiLoad 26/60 Superdex 200 prep grade with PBS as running solution. The obtained fractions were analyzed by SDS-PAGE and western blotting with an anti-His6 antibody. Finally, the concentration was determined using the BCA assay (Pierce). The purified yield for the full-length. CeMan5 protein was 5.7 mg, and for the CeMan5 family 92 domain, it was 110 mg from these 20 L fermentations, showing that the family 92 domain alone can be produced and purified in higher yield. The activity of the purified CeMan5 domain was tested on the Mnn4 isolated sugars as set forth in Example 6. A decapped sugar profile was obtained.

Example 8

Structure of CcMan5 Domain $CcMan5_{1-774}$ (residues 1 to 774 of SEQ ID NO:50, encoded by nucleotides 1-2322 of SEQ ID NO:20; corresponding to the mature protein after removal its natural leader sequence) was expressed in *E. coli* BL21 (DE3) periplasm as a fusion product starting with an N-terminal 6×His tag followed by a 9 amino acid linker (VGPGS-DEVD, SEQ ID NO:21) after the DsbA leader sequence. Cells were cultured in M9 medium containing 100 μg/ml of kanamycin and 100 μg/ml ampicllin at 28 C. At an $OD_{600}$ of 0.4, $CcMan5_{1-774}$ expression was induced by addition of 1 mM JPTG and the culture was further grown overnight at 18° C. Cells from the overnight culture were harvested by centrifugation, washed and incubated for 20 min at 4° C. with buffer containing 20 mM Tris/HCl pH 8.0, 20% sucrose, 5 mM EDTA, and 0.1 mg/ml lysozyme to make spheroplasts. Periplasmic proteins were isolated from spheroplasts by centrifugation at 20,000×g for 20 min. $CcMan5_{1-774}$ was purified from the periplasmic extract by metal ion affinity chromatography (HisTrap HP, GE Healthcare, loading under a buffer containing 50 mM Tris-HCl pH 8.0, 150 mM NaCl, and eluted using an imidazole gradient up to 400 mM), ion exchange chromatography (HiTrap Q FF, GE Healthcare, buffer: 20 mM Tris-HCl pH 8.0, 40 mM NaCl and a NaCl gradient up to 1 M) and hydrophobic interaction chromatography (HiTrap Phenyl HP, GE Healthcare, loading buffer: 20 mM Tris-HCl pH 8.0, 10 mM NaCl, 1 M $(NH_4)_2SO_4$ and eluted using a $(NH_4)_2SO_4$ gradient up to 0 mM).

Purified $CcMan5_{1-774}$ was concentrated to 130 mg/ml in 10 mM Tris-HCl pH 8.0, 10 mM NaCl and plate-like crystals ($0.2\times0.07\times0.01$ $mm^3$) were grown by vapor diffusion using a crystallization solution containing 0.2 M Na fluoride, 0.1 M Bis-Tris propane pH 7.5 and 20% PEG 3350. Crystals were briefly transferred into a cryoprotecting solutikon containing the crystallization solution supplemented with 10% (v/v) glycerol and flash-cooled in liquid nitrogen. Single crystal diffraction data were collected at 100 K at the PXIII beamline at the Swiss Light Source (SLS, Villigen, Swiss) and beamline BM30A at the European Synchrotron Radiation Facility (ESRF, Grenoble, France). The structure of $CcMan5_{1-774}$ was solved using a KAuC14-soaked for the calculation of experimental phases from a SAD experiment at 11.95 keV, corresponding to the Au L-III absorption edge. FIG. 33 contains the structural coordinates of the catalytic center. The CcMan5 model built from the experimental phases was refined by maximum likelihood methods against 2 Å resolution data collected on a native crystal to a final R- and freeR-factor of 19.3 and 23.9%, respectively. The final model contains 2 $CeMan5_{1-774}$ molecules per asymmetric unit (residues 8 to 771), comprising 11.513 protein atoms, 860 solvent atoms, 2 $Ca^{2+}$ ions and 1 bis-tris-propane and glycerol molecule each.

Figure 23:
FIG. 23 is a ribbon representation of $CcMan5_{1-774}$, $CcMan5_{1-774}$ consists of a N-terminal β-sandwich domain (residues 8-271; light gray, an α-helical linker (residues 272-290; black) and a (αα)6 barrel domain (residues 291-771; dark gray). The catalytic Ca2+ is shown as a sphere.

Based on sequence similarity, CcMan5 falls within family 92 of glycosyl hydrolases (GH92), which are defined as exo-acting alpha-mannosidases. The X-ray structures for two GH92 family members with α1,2-mannosidase activity are available: Bt3990 and Bt2199 (PDB access codes 2WVX and 2WVY, respectively). The overall fold seen from the $CcMan5_{1-774}$ structure solved here, and deposited as PDB entry 2xsg, corresponds well with that seen in both Bt3990 and Bt2199, with r.m.s.d (root mean standard deviation) values of 1.99 Å and 2.12 Å over 624 and 621 matched Cα atoms, respectively. $CcMan5_{1-774}$ consists of two domains, an N-terminal β-sandwich domain (residues 8 to 271) and C-terminal (αα)6 barrel domain (residues 291 to 771), connected via an α-helical linker (residues 272 to 290). The interface between both domains gives shape to a shallow cavity that harbors a conserved catalytic $Ca^{2+}$ ion and gives shape to the −1 substrate binding site (nomenclature: Davies et al., *Biochem. J.* 321:557-9 (1997)) and the catalytic center (FIGS. 23 and 24).

GH92 family glycosyl hydrolases are $Ca^{2+}$-dependent alpha-mannosidases that catalyse glycosidic bond hydrolysis through a single displacement mechanism, leading to inversion of the anomeric configuration in the released mannose (Zhu et. al., 2010, supra). In $CcMan5_{1-774}$, the catalytic $Ca^{2+}$ is octahedrally coordinated via the carbonyl oxygen of Asn 588, a carboxyl oxygen of Glu589 and Asp662 each, and three water molecules (W1, W2, W3—see FIG. 23) that lie in the equatorial coordination plane. An additional water molecule (W4) is present near the catalytic center, bound to the carboxyl groups of the conserved pair Asp 660 and Asp 662. The substrate binding cavity surrounding the catalytic $Ca^{2+}$ is lined by the residues Asn 588, Gln 589, Thr 626, Thr 658, Asp 22, Asn 25, Gly 71, Gly 72, Phe 195, Tyr 196, Arg 405, Trp 354, Tyr 535, and and Gln536 (FIG. 23).

Figure 25:
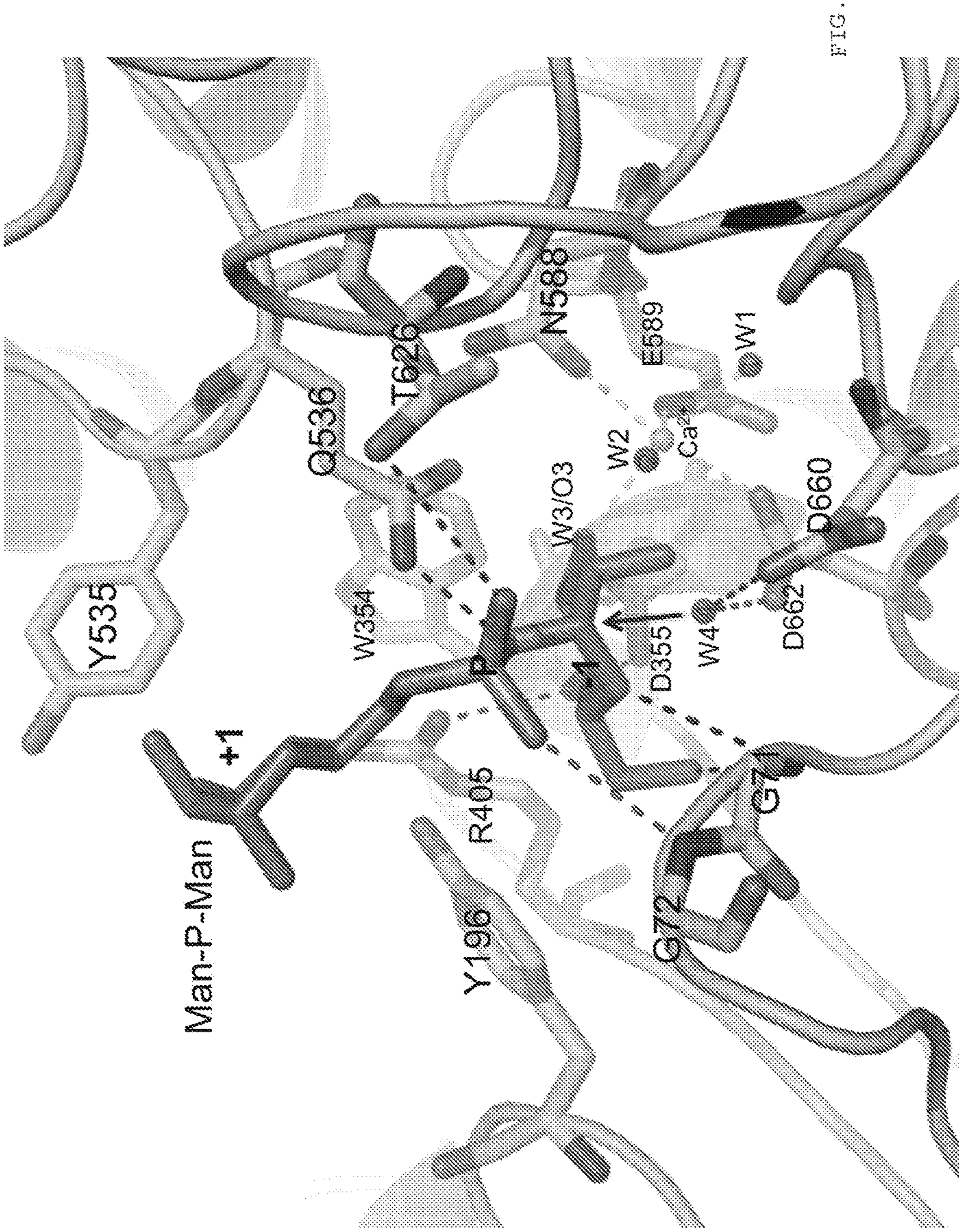
FIG. 25 iS a ribbon representation of the $CcMan5_{1-774}$ protein backbone with side chains lining the substrate binding site and the modeled position of mannose-1-phospho-6-mannose (labeled Man-P-Man) shown in stick representation. Carbon, oxygen and nitrogen atoms are coloured light gray, gray, and dark gray, respectively. The Ca2+ ion and water molecules W1, W2, W3 and W4 in the catalytic center are shown as spheres (for comparison, the positions of W2 and W3 which will be displaced by the substrate O2 and O3 hydroxyl groups are still shown). Yellow, red and black dashed lines indicate coordination bonds with Ca2+, H-bonds with the proposed nucleophilic water (W4) and H-binds with the −1 site mannose and phosphate, respectively. The −1 site mannose is modeled in its ground state chair conformation. During catalysis, its O2 hydroxyl will occupy a position nearer that seen for W2, in the equatorial coordination plane of Ca2+ ion, thereby leading to a distortion to a half-chair conformation in the mannose-1 ring and facilitating in line attack of the nucleophilic water (W4) on the C1 carbon (arrow).

CcMan5 sets itself apart from other alpha-mannosidases in the GH92 family because of its unique ability to accept mannose-alpha-1-phospho-6-mannose (Man-P-Man) as a substrate and a lack of alpha-1,2-, alpha-1,3-, alpha-1,4- or alpha-1,6-mannosidase activity. In order to obtain insight in the discriminating residues in the CcMan5 active site that give rise to this unique substrate specificity, Man-P-Man was modeled, into the $CcMan5_{1-774}$ active site of molecule B of the asymmetric unit (FIG. 25). Positioning of the −1 mannose was based on the gross binding conformation observed in Bt3990 and guided by the positions of two water molecules (W2 and W3) and a glycerol molecule present in the apo active site. In this way, the O2, O3, O4 and O6 hydroxyl groups of the −1 mannose take equivalent positions to those observed for the water molecules W2, W3 and the O1 and O3 hydroxyl groups of the glycerol molecule, respectively. Thus, the mannose −1 O2 and O3 hydroxyl group position in the equatorial plane of the actohedral $Ca^{2+}$ coordination sphere, O3 makes an additional hydrogen bond to the Asp 355 carboxyl group. The latter is further provides a H-bond to the O4 hydroxyl, which also comes within H-bonding distance of the Arg 405 guanidinium group. The O6 hydoxyl and O5 oxygen can be involved in H-bonding with the Gly 71 amide. For modeling, the −1 mannose was retained in its ground slate chair conformation. As observed for Bt3990, positioning of the O2 hydroxyl group to come in to idealized coordination with $Ca^{2+}$ will lead to a distortion of the sugar ring to a half chair conformation (see FIG. 25). This is in line with the general acceptance that a distortion of the sugar ring during catalysis is required for the nucleophilic substitution at the acetal center in α-mannosides in order to break the 1,2-diaxial interaction of the incoming nuclcophile with the O2 hydroxyl (Vocadlo et al. *Curr. Opin. Chem. Biol* 12:539-55 (2008)). The obtained model for substrate binding in the −1 site further shows that water molecule W4 lies in a good position to act as nneieophiie for in line attack on the acetal carbon. W4 is in H-bond interaction with the carboxyl groups of Asp 660 and Asp 662, which are conserved throughout GH92 enzymes and are proposed to form the base catalyst(s) for activation of the nucleophile. Therefore, the modeled substrate binding at the −1 site and the position of catalytic residues and nucleophile are consistent with the mechanistic requirements for nucleophilic substitution with inversion of the anomeric center in the released mannose. As discussed above, CcMan5 distinguishes itself by the ability to bind and hydrolyse Man-P-Man. The obtained model for Man-P-Man binding to the CcMan5 active site now provides a rationale for these observations. In known GH92 family members, the anomeric oxygen making the glycosidic bond, is in electrostatic interaction with the carboxyl group of a conserved glutamic acid residue (Glu 533 in Bt3990). The glutamic acid residue has been shown to serve as catalytic acid, stabilizing the transition intermediate by binding the anomeric oxygen and protonating the leaving group (Zhu et al., 2010, supra). In CcMan5, the equivalent residue to Bt3990 Glu 533 is mutated to glutamine, which is not able to serve as a proton donor and therefore explains the loss-of-function in CcMan5 for hydrolysis of mannobiosides. In Man-P-Man substrates, however, the phosphate bound to the anomeric oxygen constitutes a much stronger leaving group that would not require an acid catalyst to protonate the anomeric oxygen, explaining why enzymes like CcMan5 can retain catalytic activity for Man-P-Man substrates. Concomitant with substitution of the catalytic acid, the equivalent of Glu 585 in Bt3990 is replaced by Thr in CcMan5 (Thr626). In Bt3990, Glu 585 interacts with Glu533 and has been suggested to regulate the latter's $pK_a$ and/or play a role in binding the leaving group in 2-linked mannosides (Zhu et. al., 2010, supra).

It appears that mutation to non-acidic residues in the Gln 536 and Thr 626 pair alleviates part of the negative electrostatic potential in the binding site, thereby tolerating the phosphate linkage to the anomeric oxygen in Man-P-Man substrates. In CcMan5, the modeled phosphate binding site (P in FIG. 25) is shaped by Thr 626 and the amide of Gly 72, both of which appear able to donate a H-bond to the non-glycosidic oxygens in the phosphate.

Finally, based on the modeled binding of Man-p-Man in the $CcMan5_{1-774}$ active site, the reducing end mannose comes in the vicinity of two tyrosine residues, Tyr 535 and Tyr 196, suggesting the latter to residues form part of the +1 mannose binding site. Both residues lay at the edge of a shallow cleft that could be involved in further interactions with glycans at the reducing end of the glycan tree.

Example 9

Expression of αGalactosidaseA in *Y. lipolytica*

A nucleic acid encoding human α-GalactosidaseA, without pre and pro sequence, was synthesized with codon optimization for *Y. lipolytica* and addition of a Myc-His tag. The obtained sequence was cloned in frame after the pre sequence of the lip2 gene. The nucleotide sequence of the codon optimized nucleotide sequence (SEQ ID NO:22) is set forth in FIG. 26A; amino acid sequence (SEQ ID NO:23) is presented in FIG. 26B.

*Y. lipolytica* MTLY60 with 2 extra copies of MNN4 and one copy of α-GalactosidaseA was induced in a larger culture to purify over a Ni-NTA column. Thus, they were grown in YTG and induced in oleic acid medium in 2×225 ml (2 L shake flask) during 48 hours. The culture was centrifuged, followed by filtration of the medium over a 0.22 μm filter. The filtered medium was desalted on a sephadex G25 XK50/100 column (GE Healthcare) to 20 mM $NaH_2PO_4$ ph 7.4, 0.5 M NaCl, 20 mM imidazole to remove non-protein disturbing contaminants before purification on Ni-sepharose 6 FF. The desalted protein fraction was loaded on a 4.3 ml Ni-sepharose 6 FF column (GE Healthcare), equilibrated with 20 mM $NaH_2PO_4$ pH 7.4, 0.5 M NaCl, 20 mM imidazole, washed with 50 mM imidazole in the same buffer and eluted with 20 mM $NaH_2PO_4$ pH 7.4, 20 mM NaCl, 400 mM imidazole. Samples 3-10 and 36-49 after the Ni-sepharose column were analysed on SDS-PAGE and Western blotting using an anti-His6 antibody. A protein band of around 50 kDa and of 65 kDa was present on coomassie in samples 40 and 41 was revealed by Coomassie blue staining of the SDS-PAGE gel. In the western blot, only a band of 50 kDa was detected and is most likely the α-GalactosidaseA. The estimated yield of the purified α-GalactosidaseA was 100-125 μg/L culture medium.

The purified sample was used to determine the type of sugars on the recombinant α-GalactosidaseA. The sugars were removed in solution and afterwards labelled with APTS. After cleaning the sample by gel filtration, the sugars were analyzed on DSA-FACE. The expected sugars, the mono mannophosphorylated $Man_8GlcNAc_2$ peak (P) and the double mannophophorylated $Man_8GlcNAc_2$ peak (PP) were present as major peaks.

Example 10

Expression of Human Alpha Glucosidase in *Y. lipolytica*

*Y. lipolytica* strain OXYY1589 was constructed that contained three copies of the human alpha glucosidase (also known as acid alpha glucosidase (GAA) or acid maltase EC3.2.1.3) and two copies of the *Y. lipolytica* MNN4 gene. The genotype of strain OXY1589 is as follows:

MatA, leu2-958, ura3-302, xpr2-322,
gut2-744, ade2-844
POX2-Lip2pre-huGAA:URA3Ex::zeta
POX2-Lip2pre-huGAA:LeU2Ex::zeta POX2-Lip2pre-hGM-CSF:GUTEx::zeta
YIMNN4-POX2-HP4d-YLMNN4:ADE2::PT targeted All transformations were carried out according to well established protocols with modifications for the different selective markers. In all cases (unless otherwise specified), a huGAA integration fragment has been obtained by NotI restriction digestion in order to remove the kanamycin resistance gene from the expression plasmids. The resulting fragments were all separated by agarose gel electrophoresis followed by Qiagen column purification of the correct huGAA fragment. Strain OXYY1589 was constructed by first cloning human GAA (huGAA) into a *Y. lipolytica* expression vector and constructing a *Y. lipolytica* MNN4 tandem expression vector. Three stable integrative transformations then were performed in order to obtain the final huGAA production strain OXYY1589.

*Y. lipolytica* Codon Optimized huGAA Expression Vector:

The nucleotide sequence encoding the 110 kDA human GAA (huGAA) precursor was chemically synthesized and codon optimized for *Y. lipolytica* expression. In the synthetic construct, the pre- and the pro-huGAA signal peptides were eliminated such that the protein starts at amino acid 57. The synthetic ORF of huGAA (FIG. 27A) is fused in frame at the 5' end to the 3' end of the *Y. lipolytica* LIP2 signal sequence (pre), followed by the coding sequence of two Xxx-Ala cleavage sites and flanked by BamHI and AvrII restriction sites for cloning in expression vector. The construct is under the control of the inducible POX2 promoter. The complete amino acid sequence of the fusion construct is shown on FIG. 27B.

Figure 28:
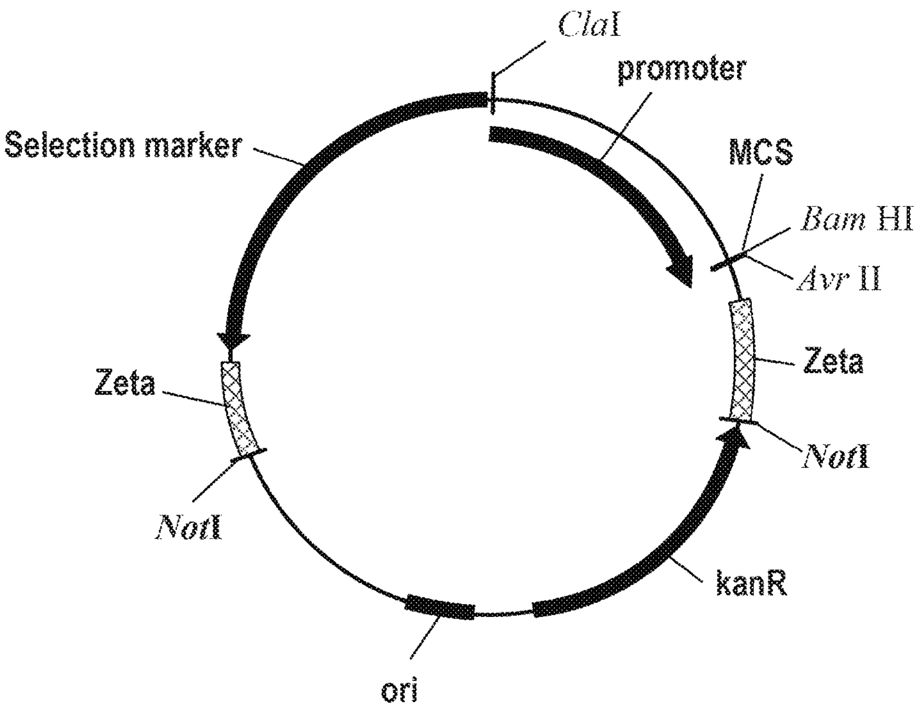
FIG. 28 is a schematic of a *Y. lipolytica* expression vector used for cloning of huGAA.

A general scheme of an expression vector is presented in FIG. 28. The bacterial moiety is derived from the plasmid pHSS6, and comprises a bacterial origin of replication (ori) and the kanamycin-resistant gene conferring resistance to kanamycin (KanR). The integration cassette comprises a) the selection marker for transformation to *Yarrowia lipolytica* (URA3; LEU2; GUT2), b) the expression cassette composed of a promoter, c) a multiple cloning site (MCS) to insert huGAA in frame with signal sequence and d) the terminator of the LIP2 gene. The integration cassette is flanked by zeta sequences for stable non-homologous integration into the *Y. lipolytica* genome. Two NotI restriction sites enable the isolation of the expression cassette before transformation. Plasmids pRAN034, pRAN036 and OXYP183 have been used to generate huGAA expression vectors pRAN058, pRAN059 and pRAN060, respectively, containing URA3, LEU2 and GUT2 transformation markers, respectively.

Tandem YIMNN4 Expression Vector:

The YIMNN4 gene was cloned under control of the inducible pPOX2 promoter and the (semi)constitutive hp4d promoter. These two expression cassettes of YIMNN4 were subloned in one vector as a tandem construct carrying flanking regions (PT) of the ADE2 gene for targeted integration into the ADE2 locus of the genome and the ADE2 gene as a selection marker.

Intermediate Strain OXYY1569:

The first transformation was a co-transformation of the expression cassette purified from pRAN058 and pRAN059 vectors using URA3 and LEU2 marker to produce intermediate recombinant strain OXYY1569, OXYY1569 carries two expression constructs of huGAA under control of the pPOX2 promoter randomly integrated in the genome of strain G014.

OXYY1569 was selected as follows. PCR screening of genomic DNA was performed in order to confirm the integration of the foreign huGAA DNA into the genome of *Y. lipolytica*. Primers were designed to amplify a fragment of 2552 bp from huGAA nucleotide sequence. Southern blot analysis of the genomic DNA also was performed in order to confirm the integration of at least 2 copies of huGAA DNA. In particular, genomic DNA from OXYY1569 clones were digested with Hind III and probed with huGAA DIG labeled specific probe.

In order to select a clone secreting high levels of huGAA, several randomly selected clones that were identified as positive in the PGR screening and Southern blot were grown in shake flasks under POX2 inducing conditions according to a standard procedure. In all cases, the culture supernatant was collected 72 h post-induction and screened in a standard Western blot and enzyme activity assay analysis. N-Glycan analysis of OXYY1569 indicated the predominant structure in OXYY1569 is $Man_8GlcNAc_2$.

Intermediate Strain OXYY1584:

Recombinant strain OXYY1569 was transformed in order to integrate two copies of the *Y. lipolytica* MNN4 gene into its genome to produce OXYY1584. The transformatinn was performed with a SacII/XmaI derived expression cassette excised from plasmid OXYP1479B. The expression cassette was designed for targeted integration into the ADE2 locus of *Y. lipolytica* genome. The recombinant strain was selected after Southern blotting and glycan analysts to evaluate the strain behavior with respect to the increased phosphorylation. Genomic DNA of several arbitrary chosen transformants was SpeI digested and probed with MNN4 specific DIG labeled probe. Correct targeted integration of MNN4 expression cassette into the ADP2 locus of *Y. lipolytica* genome should give 4207 bp and 5683 bp bands. Southern blot positive clones were grown in a standard shake flask procedure. X-glycan analysis of secreted proteins was performed in order to select the intermediate clone OXYY1584. Compared so the parent stain OXXY1569, the predominant structures after MNN4 over-expression are $Man_8GlcNAc_2$ $(PMan)_1$ and $Man_8GlcNAc_2$ $(PMan)_2$.

Production Strain OXYY1589:

To generate the final prototrophic production strain OXYY1589, a third copy of huGAA was integrated into the genome of recombinant OXYY1584 strain. The transformation was performed with NotI excised expression cassette from pRAN069. Transformants were first screened by PCR on gDNA for presence of the additional copy of huGAA. To evaluate huGAA production arbitrary selected PCR positive clones were further analyzed for expression after a standard shake flask cultivation. The clone expressing the highest level of huGAA (OXYY1589) was chosen after Western blot analysis and enzymatic activity assay. It also was reconfirmed that the conversion levels of M8 to MP2-M8 and MP-M8 N-glycans was not influenced by the presence of the additional huGAA expression cassette.

Example 11

Fed, Batch, Cultivation of Strain OXYY1589

To produce huGAA from strain OXYY1589 (Example 10), a fed batch process was established using a 10 L stirred tank, with a working volume of 6-8 liters. The process was divided is two phases:

1) Batch growth on glucose for biomass formation

2) Product formation by induction with help of a limited oleic acid feed.

Typically the batch phase was about 20 hours (h) and the production phase approximately 72 hours. At the end of the process, the culture broth was centrifuged and the supernatant was collected. The supernatant was used as starting material for the purification of the GAA (see Example 12).

The following parameters were controlled during the fermentation. Aeration was maintained at a constant value of 1.5 vvm air (volume per volume per minute). Dissolved oxygen (DO) was initially kept at 30%. The stirring was increased from 600 to 1200 rpm depending on the DO levels. Once it reached the maximum of 1200 rpm, this speed was kept constant and the DO-setpoint was set to 10%. To maintain 10% DO, oxygen was spiked into the reactor with a maximal percentage of 50%. Foam evolution was controlled by a foam probe. In case of foam detection, antifoam was added to the bioreactor. The pH was controlled by adding 14% (v/v) ammonia (base) or 10% phosphoric acid to maintain a constant value of pH 6.8. The temperature was kept constant at 28° C. throughout the whole process.

Biomass was monitored by measurement of optical density at 600 nm (OD600), The samples were diluted 2-1000 times in distilled water to obtain values in the linear range of the spectrophotometer. Product formation was detected by Western blot analysis and specific enzymatic activity tests.

Example 12

Purification of Recombinant huGAA (rhGAA)

The supernatant after cultivation (see Example 11) was clarified via depth filtration. The resulting material was then concentrated 20 times via TFF and diafiltered against 20 mM sodium phosphate pH 6 and 100 mM NaCl on a 10 kDa MWCO membrane (Millipore).

Purification of rhGAA was start by adding ammonium sulphate up to a concentration of 1 M. After centrifugation, the supernatant was loaded on a Toyopearl-Phenyl 650M (Tosoh Biosciences) packed XK16/40 column. A linear gradient from 1 to 0 M ammonium sulphate was applied for elution. Those fractions that contain rhGAA were then pooled and subjected to a buffer exchange into 10 mM BIS-TRIS pH 6. Further purification was achieved via anion exchange chromatography on a source 30Q packed Tricorn 10/50 or XK25/20 column (GE Healthcare) using a linear salt gradient from 0 to 1 M NaCl. The resulting GAA-containing fractions were then concentrated before loading onto a final Hiload 16/60 superdex 200 gel filtration column (GE Healthcare) that was pre-equilibrated with 50 mM sodium phosphate pH 6 and 200 mM NaCl. Fractions were selected on the basis of specific activity and purity on Coomassie-stained SDS-PAGE gels and then combined and concentrated to a final concentration of 5-10 mg/ml. Protein concentration was done on 15 ml Amicon Ultra centrifugal devices (millipore) with a MWCO of 10 kDa.

The reactions for the qualitative screening for rhGAA were started by adding the reaction buffer consisting of 0.35 mM 4-MUG, 0.1% BSA and 100 mM sodium acetate pH 4 in a 10:1 or 20:1 volume proportion to 10 or 5 µl of elution fraction. All reactions were done in 96-well flat-bottom microtiter plates. After an incubation period of 30 minutes to 1 hour at 37° C., an equal volume of 100 mM glycine pH11 was added to stop the reaction and the release of the fluorogenic reaction product 4-methylumbelliferone was observed under UV-light. Specific activities (units/mg protein) were determined using a colorlmetric assay with the synthetic substrate p-nitrophenyl-α-D-glucopyranoside (PNPG) that measures the enzymatic release of the yellow coloured p-nitrophenolate reaction product. The reactions were started by mixing 10 µl of enzyme solution and 90 µl of substrate reaction buffer (2 mM PNPG in 150 mM citrate-phosphate buffer pH4, 1% BSA) in reaction-wells of a microtiterplate and were subsequently incubated at 37° C. After 1 to 2 hours an equal volume of stop buffer, 10% sodium carbonate pH 12, was added to quench the reaction and bring the released, p-nitrophenol (PNP) in its ionized stale. Background-corrected absorbanees and p-nitrophenolate standards were measured at a wavelength of 405 nm and specific activities were calculated. Protein concentrations were determined with the bieinchoninic acid (BCA) method. One unit was defined as the amount of enzyme that catalyzes the con version, of 1 nmol of PNPG to 1 nmol PNP and D-glucose per min at 37° C. at a final substrate concentration of 2 mM in a citrate-phosphate buffer, pH4.0.

Example 13

Phosphate, Uncapping Activity of Heterpipgpusly Expressed CcMan5 on Glycoproteins Expressed in a *Y. lipolytica* Strain with a Higher Degree of Phosphorylated N-glycans The huGAA was expressed in *Y. lipolytica* strain OXYY1589 to yield a glycoprotein with a high degree of phosphorylated N-glycan structures (see Example 10). The huGAA was purified as described in Example 12.

Figure 29:
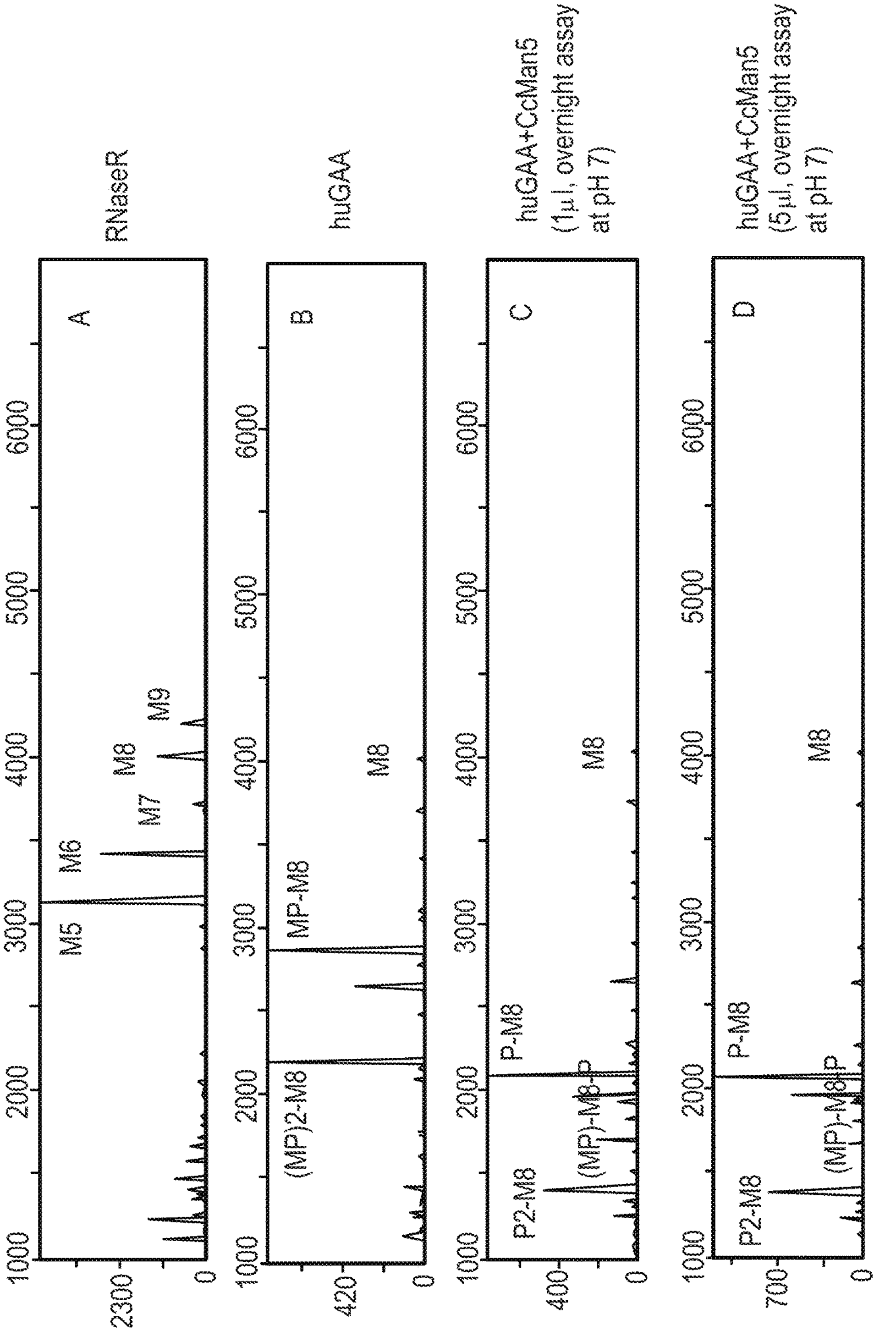
FIG. 29 is a series of electroferograms depicting analysis of treatment of huGAA with CcMan5 derived from the periplasmic fraction of *E. coli* cells. Analysis was performed using DSA-FACE.

CcMan5 (1 and 5 µl respectively at a concentration of 70 µg/ml) was added to a solution of 4 µg huGAA in 100 mM HEPES buffer pH 7.0 with 2 mM $CaCl_2$. The 20 µl reaction mixture was incubated overnight at room temperature. The N-glycans were released with PNGaseF, labelled with APTS and subsequently analysed on DSA-FACE, essentially as described in Laroy W. et al., *Nature Protocols,* 1:397-405 (2006). The N-glycan profiles before and after CcMan5 treatment are shown in FIG. 29. The N-glycan mixture released from purified huGAA is mainly composed of ManP-Man8GlcNAc$_2$ and (ManP)2-Man8GlcNAc$_2$ (FIG. 29, panel B). A peak running slightly faster than ManP-Man8GlcNac$_2$ can be assigned to ManP-Man7GlcNAc$_2$. Only very minor amounts of $Man_8GlcNAc_2$ and $Man_7GlcNAc_2$ are present. After incubation of huGAA with CcMan5 the conversion of ManP-Man8GlcNAc$_2$ and (ManP)2-Man8GlcNAc$_2$ to P-Man8GlcNAc$_2$ and P2-Man8GlcNAc$_2$ respectively is observed (FIG. 29, panel C and D). The peak in the electropherogram running between P-Man8GlcNAc$_2$ and P2-Man8GlcNAc$_2$ corresponds to the partially uncapped bi-phosphorylated (ManP) 2-Man8GlcNac$_2$ with a phosphodiester- and a phosphomonoester-linkage present ((MP)-M8-P in FIG. 29, panel C and D). This product is further hydrolyzed to the fully uncapped P2-Man8GlcNAc$_2$ when using a higher concentration of CcMan5 or a longer incubation time.

The percentage of phosphorylated N-glycans versus neutral N-glycans was estimated from measuring the peak areas in the DSA-FACE electropherograms (FIG. 29). The figures related to the area under the curve are presented for the different N-glycans present on huGAA before (Panel B) and after CcMan5 treatment (Panel D). In huGAA (Panel B), (ManP)2-Man8GlcNac$_2$ (11597), ManP-Man6GlcNAc$_2$ (1261), ManP-Man7GlcNac$_2$ (5901), ManP-Man8GlcNAc$_2$ (15576), Man6GlcNAc$_2$ (680), Man7GlcNAc$_2$ (1716), Man8GlcNAc$_2$ (1572) were present. Approximately 90% of the N-glycans on recombinant huGAA were composed of mannose-phosphate containing structures.

After overnight treatment of recombinant huGAA with CcMan5 (Panel D), P2-Man8GlcNAc$_2$ (16182), (ManP)P-Man8GlcNAc$_2$ (1997), P-Man7GlcNAc$_2$ (8254), P-Man8GlcNAc$_2$ (17893), ManP-Man6GlcNAc$_2$ (500), ManP-Man7GlcNAc$_2$ (2495), ManP-Man8GlcNAc$_2$ (1326), Man6GlcNAc$_2$(1097), Man7GlcNAc$_2$(2143), Man8GlcNAc$_2$(1599) were present. The N-glycans released from huGAA were composed of 83% uncapped phosphorylated structures, 8% is still mannose-phosphate capped and 9% neutral N-glycans are present. The percentage of uncapped phosphorylated structures can be increased when using a higher concentration of CeMan5 or a longer incubation time.

Example 14

Identification of Homologs Likely to Have Uncapping Activity

To identify other GH92 family members with similar predicted catalytic site topology and functionality, curated GH92 family members, as mined from the world wide web at cazy.org/GH92_all.html, were analyzed as were the top 500 hits obtained by Blastp search with the CcMan5 domain sequence on the Non Redundant Protein Sequences database at NCBI. Subsequently, these 392 sequences were used as the input for the multiple sequence alignment package MUSCLE (Multiple Sequence Comparison by Log-Expectation), which also ranks the sequences in order of 'phylogenetic' distance (from closest related to furthest related).

Based on the curated GH92 family members from the Cazy database, MUSCLE alignment of all GB92 protein sequences (392) and the CcMan5 domain sequence identified the following as the closest homologs of CcMan5.

*Streptomyces coelicolor* CAA18915 (GenBank Accession No. NP_630514)

*Clostridium spiroforme* (GenBank Accession No. ZP_02866543)

*Bacteroides thetaiotaomicron* AAO78636 (GenBank Accession No. NP_812442)

*Zunongwangia profunda* ADF52306 (GenBank Accession No. YP_003584502)

*Chitinophaga pinensis* ACU58463 (GenBank Accession No. YP_003120664)

Their sequences and those of the next 5 closest homologs are aligned in FIG. 31.

Based on MUSCLE alignment of the 500 best scoring blastp protein hits versus the CcMan5 domain, the following were considered the closest homologs of CcMan5

*Streptomyces coelicolor* (GenBank Accession No. NP_630514)

*Streptomyces lividans* (GenBank Accession No. ZP_05522540)

*Streptomyces lividans* (GenBank Accession No. ZP_06527366)

*Paenibacillus* sp (GenBank Accession No. YP_003013376

*Bacteroides thetaiotaomicron* (GenBank Accession No. NP_812442)

*Bacteroides* sp. (GenBank Accession No. ZP_04848482)

*Bacteroides cellulosilyticus* (GenBank Accession No. ZP_03677957)

*Zunongwangia profunda* (GenBank Accession No. YP_003584502)

*Leeuwenhoekiella blandensis* (GenBank Accession No. ZP_01061975)

*Sphingobacterium spiritivorum* (GenBank Accession No. ZP_07083984)

*Chitinophaga pinensis* (GenBank Accession No. YP_003120664)

*Pedobacter* sp. (GenBank Accession No. ZP_01885202)

*Clostridium spiroforme* (GenBassk Accession No. ZP_02866543)

Alignment of these and the 5 text-best homologs can be found in FIG. 32. All 5 best hits from the annotated GH92 database are also found in these 13 best hits from the Blast search on the entire sequence database.

The top 5 hits in FIG. 31 and the top 13 hits in FIG. 32 uniquely share the following three motifs, which were shown in the crystal structure of Example 8 to be different from the alpha-1,2-mannosidase GH92 family members of which the structure was reported in Zhu al., 2010, supra.

1) a glycine-rich motif GVGxxGxGG, with each X being G, S, T, V, A, C or Q (small side chains), numbering of crystal structure residues of CcMan5 domain: 69-77. This region makes a loop that provides essential hydrogen bonds to the −1 and phosphate-binding subsite in the active site of the enzyme.

2) a VRxE motif. The R makes a hydrogen bond to the −1 ring and possibly the +1 ring. E is in a salt bridge to this R residue, probably shaping this motif. x is W in the closes-related subfamily (top 3 homologs to CcMan5), or could be any of the 20 amino acids except P. This motif is found at residues 404-407 of SEQ ID NO:50.

3) a LYQGT motif, containing Q which is an E in the mannosidases (proton donor), and which contains Y535, which is important for the +1 site formation. In some of the sequences, the L is A or Y and could reasonably be expected to also be I, V, A, F or M, and in some of them the T is N and can be expected to also tolerate S. Two *Caulobacter* sequences have an E instead of Q and would thus be predicted not to work on phosphorylated glycans.

4) a GDXGN motif. The D and N make part of the substrate binding cavity and may shape an alternative sub-pocket to bind the +1 mannose. X can be any amino acid other than P. This motif is found at residues 21-25 of SEQ ID NO:50.

Based on the above biomformatics workflow and motif search based on the structure, it is thus possible to filter the GH92 sequences present in the non-redundant proteins sequence database (currently containing over 1220 sequences) for those rare family members that are good candidates for having the same substrate specificity to CcMan5, i.e., to be capable of uncapping Man-6-Pi-Man structures. In particular, the 3 sequences from *Streptomyces coelicolor* and *Streptomyces lividans* are similar to CcMan5, not only in the above motifs but also in many of the loops of the structure.

A search with Hidden Markov Models based on the sequence elements unique to CcMan5 and its closest homologs, reveals no further GH92 sequences which contain all of these elements, strongly indicating that no such GH92 members have obtained these elements through convergent evolution (these are the ones that would not be top-ranked in multiple-sequence alignments).

Example 15

The Presence of Phosphate Uncapping Activity in GH92 Glycosidases from *Bacteroides thetaiotaomicron*

An enzymatic analysis of 23 family GH92 α-mannosidases from *Bacteroides thetaiotaomicron* has been reported by Zhu, Y. et al, 2010, supra. Enzymes with α1,2-, α1,4-, α1,3- or α1,6-mannosidase activity are present in this group of enzymes, although some variants display very low activity. The three-dimensional structure of two α-1,2 mannosidases (Bt3990 and Bt2199) allowed to identity key amino-acid residues which seem to be a signature motif for α-1,2-mannosidase activity, i.e. His584-Glu585 and Trp99 in Bt3990. The activity on phosphorylated N-glycans (MNN4 sugars described in Example 1) of three GH92 enzymes from *B. thetaiotaomicron*, Bt3530 (Genbank nr AAO78636.1), Bt3965 (Genbank nr AAO79070.1) and Bt3994 (Genbank nr AAO79099.1) was tested. These enzymes display low α1,4-mannosidase activity and lack the His-Glu and Pro-Tip motif.

Bt3530, Bt3965 and Bt3994 were expressed in *E. coli* and purified as described in Zhu et al, 2010, supra. Samples (1 μl enzyme at a concentration of 0.1 mg/ml) were incubated with 7 μl APTS-labeled MNN4 sugars dissolved in 10 mM HEPES buffer pH 7.0 with 2 mM $CaCl_2$ in an overnight assay at room temperature. A control assay with CcMan5 was included. To confirm the presence of a terminal phosphate the reaction mixture was incubated with CIP. An N-glycan preparation containing $Man8GlcNAc_2$ (M8) and the monophosphorylated $ManP-Man8GlcNAc_2$ (MP-M8) was used as substrate. No uncapping activity for Bt3530, Bt3965 and Bt3994 was detected under the above assay conditions. No shift in electrophoretic mobility of the peaks was observed compared to the CcMan5 control reaction (appearance of fast running P-M8 peak), followed by CIP treatment (disappearance of P-M8).

In an additional experiment, 1 μl of enzyme, i.e., Bt3530 (0.1 mg/ml), Bt3965 (4.75 mg/ml) and Bt3994 (1.37 mg/ml) respectively, was incubated with MNN4 N-glycans at pH 7.0 (10 mM HEPES buffer pH 7.0 with 2 mM $CaCl_2$) and at pH 5.0 (10 mM Ammonium Acetate pH 5.0 with 2 mM $CaCl_2$) during 60 hours at room temperature. Very minor α1,2-mannosidase activity was observed with Bt3530 at pH 7.0, as a small $Man5GlcNAc_2$ (M5) peak appears in the electropherogram. At pH 5.0, on the other hand, no α1,2-mannosidase activity is present, but a fast running peak at the left hand side of the electropherogram appears. This peak has the same electrophoretic mobility as $P-Man8GlcNAc_2$ (P-M8) and the terminal phosphate is hydrolyzed after incubation with CIP. CcMan5 (used at same concentration as Bt3530) is fully uncapping $ManP-Man8GlcNAc_2$ within 20 hours incubation at room temperature and at pH 7.0; therefore the observed activity of Bt3530 is rather low. After purification, the Bt3530 sample slowly precipitates when stored at 4° C. in 20 mM TRIS buffer, pH 8.0 with 300 mM NaCl. Therefore it is possible that instability of the Bt3530 protein influences the activity under the assay conditions used. Bt3965, which was used at a 40 times higher concentration, gave a similar result as Bt3530 at pH 7.0 (Panel G and H) and pH 5.0 (Panel I and J). No activity at all was observed with Bt3994 under the same reaction conditions (Panel K till N).

From these experiments can be concluded that phosphate uncapping activity is only a minor side activity of two of the three *B. thetaiotaomicron* GH 92 enzymes tested on MNN4 sugars.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for uncapping a mannose-6-phosphate residue on an oligosaccharide, said method comprising a) providing said oligosaccharide having a mannose-1-phospho-6-mannose linkage; and b) contacting said oligosaccharide with a mannosidase capable of hydrolyzing said mannose-1-phospho-6-mannose residue to phospho-6-mannose, wherein said mannosidase is a member of glycosyl hydrolase family 92 and wherein said mannosidase does not contain a catalytic acid residue capable of protonating the anomeric oxygen, and wherein said mannosidase comprises an amino acid sequence having (i) a GVGXXGXGG motif where X is Gly, Ala, Ser, Thr, or Cys; (ii) a VRXE motif, where X is any amino acid other than Pro; (iii) an $X_1$YQG$X_2$ motif, where $X_1$ is Leu, Ile, Val, Ala, Phe, Tyr or Met, and $X_2$ is Thr, Ser, or Asn; and (iv) GDXGN, where X can be any amino acid other than Pro, and wherein said mannosidase comprises an amino acid sequence having at least 90% identity to residues 1 to 774 of SEQ ID NO:50 or an amino acid sequence having at least 95% identity to SEQ ID NO: 50.

2. The method of claim 1, wherein for said mannosidase, the three dimensional protein coordinates of the atoms in the amino acid side chains located in the minimal catalytic center fall within 1.5 Å deviation of the coordinates of the equivalent atoms in FIG. 33.

3. The method of claim 1, wherein said contacting step is performed using a purified mannosidase, a recombinant mannosidase, a cell lysate containing said recombinant mannosidase, or a fungal cell containing said recombinant mannosidase.

4. The method of claim 1, wherein said oligosaccharide is attached to a protein.

5. The method of claim 4, wherein said protein is a human protein expressed in a fungal organism.

6. The method of claim 5, wherein said fungal organism is *Yarrowia lipolytica* or *Arxula adeninivorans*.

7. The method of claim 5, wherein said fungal organism is a methylotrophic yeast.

8. The method of claim 7, wherein said methylotrophic yeast is *Pichia pastoris, Pichia methanolica, Oogataea minuta*, or *Hansenula polymorpha*.

9. The method of claim 5, wherein said fungal organism is a filamentous fungus.

10. The method of claim 9, wherein said filamentous fungus is selected from the group consisting of *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowii, Aspergillus tamari, Aspergillus terreus, Aspergillus ustus*, and *Aspergillus versicolor*.

11. The method of claim 5, said fungal organism further comprising a nucleic acid encoding a polypeptide capable of promoting mannosyl phosphorylation.

12. The method of claim 5, wherein said fungal organism is genetically engineered to be deficient in OCH1 (Outer CHain elongation) activity.

13. The method of claim 5, said fungal organism further comprising a nucleic acid encoding a polypeptide capable of promoting mannosyl phosphorylation, and wherein said fungal organism is genetically engineered to be deficient in OCH1 activity.

14. The method of claim 11, wherein said polypeptide capable of promoting mannosyl phosphorylation is a MNN4 polypeptide.

15. The method of claim 11, wherein said polypeptide capable of promoting mannosyl phosphorylation is a *P. pastoris* PNO1 polypeptide.

16. The method of claim 4, wherein said protein is a pathogen protein, a lysosomal protein, a growth factor, a cytokine, a chemokine, an antibody or antigen-binding fragment thereof, or a fusion protein.

17. The method of claim 16, wherein said lysosomal protein is a lysosomal enzyme.

18. The method of claim 17, wherein said lysosomal enzyme is associated with a lysosomal storage disorder (LSD).

19. The method of claim 18, wherein said LSD is selected from the group consisting of Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, and Geleophysic dysplasia.

20. The method of claim 18, wherein said LSD is Pompe disease or Fabry's disease.

21. The method of claim 17, wherein said lysosomal enzyme is acid alpha glucosidase or alpha galactosidase.

22. The method of claim 1, wherein said mannosidase comprises a targeting sequence to target the mannosidase to an intracellular compartment.

23. The method of claim 1, wherein the residue of said mannosidase corresponding to glutamic acid residue Glu 585 of the *Bacteroides thetaiotaomicron* alpha-1,2-mannosidase Bt3990 is a non-acidic residue.

24. The method of claim 23, wherein the residue of the mannosidase corresponding to the glutamic acid residue Glu 585 of the *Bacteroides thetaiotaomicron* alpha-1,2-mannosidase Bt3990 is a threonine or serine residue.

25. The method of claim 1, wherein said mannosidase is a *C. cellulans* mannosidase.

26. A method for uncapping a mannose-6-phosphate residue on an oligosaccharide, said method comprising a) providing said oligosaccharide having a mannose-1-phospho-6-mannose linkage; and b) contacting said oligosaccharide with a mannosidase capable of hydrolyzing said mannose-1-phospho-6-mannose residue to phospho-6-mannose, wherein said mannosidase is a member of glycosyl hydrolase family 92 and wherein said mannosidase does not contain a catalytic acid residue capable of protonating the anomeric oxygen, and wherein for said mannosidase, the three dimensional protein coordinates of the atoms in the amino acid side chains located in the minimal catalytic center fall within 1.5 Å deviation of the coordinates of the equivalent atoms in FIG. 33, and wherein said mannosidase comprises an amino acid sequence having at least 90% identity to residues 1 to 774 of SEQ ID NO:50 or an amino acid sequence having at least 95% identity to SEQ ID NO: 50.

27. The method of claim 26, wherein said contacting step is performed using a purified mannosidase, a recombinant mannosidase, a cell lysate containing said recombinant mannosidase, or a fungal cell containing said recombinant mannosidase.

28. The method of claim 26, wherein said oligosaccharide is attached to a protein.

29. The method of claim 28, wherein:

said protein is a human protein expressed in a fungal organism; or said protein is a pathogen protein, a lysosomal protein, a growth factor, a cytokine, a chemokine, an antibody or antigen-binding fragment thereof, or a fusion protein.

30. The method of claim 26, wherein said mannosidase comprises a targeting sequence to target the mannosidase to an intracellular compartment.

31. The method of claim 26, wherein:

the residue of said mannosidase corresponding to glutamic acid residue Glu 533 of the *Bacteroides thetaiotaomicron* alpha-1,2-mannosidase Bt3990 is a non-acidic residue; and/or the residue of said mannosidase corresponding to glutamic acid residue Glu 585 of the *Bacteroides thetaiotaomicron* alpha-1,2-mannosidase Bt3990 is a non-acidic residue.

32. The method of claim 26, wherein said mannosidase is a *C. cellulans* mannosidase.

33. A method for uncapping a mannose-6-phosphate residue on an oligosaccharide, said method comprising a) providing said oligosaccharide having a mannose-1-phospho-6-mannose linkage; and b) contacting said oligosaccharide with a mannosidase capable of hydrolyzing said mannose-1-phospho-6-mannose residue to phospho-6-mannose, wherein said mannosidase is a member of glycosyl hydrolase family 92 and wherein said mannosidase does not contain a catalytic acid residue capable of protonating the anomeric oxygen, and wherein said mannosidase comprises an amino acid sequence having at least the following residues forming the catalytic center: G71, G72, D355, R405, Q536, N588, Q589, T626, D660 and D662, and wherein said mannosidase comprises an amino acid sequence having at least 90% identity to residues 1 to 774 of SEQ ID NO:50 or an amino acid sequence having at least 95% identity to SEQ ID NO: 50.

34. The method of claim 33, wherein for said mannosidase, the three dimensional protein coordinates of the atoms in the amino acid side chains located in the minimal catalytic center fall within 1.5 Å deviation of the coordinates of the equivalent atoms in FIG. 33.

35. The method of claim 33, wherein said contacting step is performed using a purified mannosidase, a recombinant mannosidase, a cell lysate containing said recombinant mannosidase, or a fungal cell containing said recombinant mannosidase.

36. The method of claim 33, wherein said oligosaccharide is attached to a protein.

37. The method of claim 36, wherein:

said protein is a human protein expressed in a fungal organism; or said protein is a pathogen protein, a lysosomal protein, a growth factor, a cytokine, a chemokine, an antibody or antigen-binding fragment thereof, or a fusion protein.

38. The method of claim 33, wherein said mannosidase comprises a targeting sequence to target the mannosidase to an intracellular compartment.

39. The method of claim 33, wherein said mannosidase is a *C. cellulans* mannosidase.

* * * * *

SEQUENCE LISTING

```
<160> NUMBER OF SEQ ID NOS: 58

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Ser Ala Tyr Gln Ser Phe Thr Thr Arg
1               5


<210> SEQ ID NO 2
<211> LENGTH: 7
<212> TYPE: PRT
<213> ORGANISM: Artificial Sequence
<220> FEATURE:
<223> OTHER INFORMATION: synthetic peptide

<400> SEQUENCE: 2

Val Trp Gly Phe Ser His Arg
1               5


<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3
```

-continued

```
Val Glu Gly Gly Trp Leu Pro Arg
1               5


<210> SEQ ID NO 4
<211> LENGTH: 13
<212> TYPE: PRT
<213> ORGANISM: Artificial Sequence
<220> FEATURE:
<223> OTHER INFORMATION: synthetic peptide

<400> SEQUENCE: 4

Thr Gln Gly Asn Asn Phe Ala Leu Leu Leu Pro Glu Arg
1               5                   10


<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Asp Val His Ala Glu Leu Thr Ala Met Ala Arg
1               5                   10


<210> SEQ ID NO 6
<211> LENGTH: 2700
<212> TYPE: DNA
<213> ORGANISM: Cellulosimicrobium cellulans

<400> SEQUENCE: 6

atgagacgac cacgactcgc cctgctcgcc gcggggctcg cgctcgccgt cgcaccgggc     60

acgctgctgc ccgtcgccgc gggcgccgcc cccgccgacg agggcaccgt caccgccgcc    120

gcgggcgacg acctcacgct cgaggtcaac ccgttcgtcg gcaccgagag cgagggcaac    180

gcctacccgg gcgcgaccgt gccgttcggc atggtccagc tcagcccgga caacacgaac    240

tcctacgcct cgacgtcgta cagcacgaac gcggggcgcg tgtggggctt cagccaccgg    300

cacgtgaaca gcgcgggctg ccccgcggcg ggcgagctgc tcgtcacgcc ggacacgagc    360

gcgaccccgc gcacgtcgcg ctccttcatc gccatcaagg accagaagag caccgagcgc    420

gcgtcggccg ggttctacga ggtgaccctc gcgaacgacg tgcacgccga gctcaccgcg    480

accacgcgcg tcggcgcgca ccgctacacg ttccccgcct cgacgacgtc gcacctgtcg    540

ttcaacgtgg gccagaccct gcgcgacgcc ggcgcgagct cggtgacgtg ggtcgacgac    600

cgcacgctcg agggctgggt cgacaacggc ggcttctgcg gcggcacgcc ggacaagcag    660

cggtacttct tcagcgcgac gttcgaccgc ccggtcgcgt cgagcggcac gtgggggacc    720

gatgcgcgct acgtcgcggg ctccacgacg agcgaggtcg cgggcggcaa caacggcgcc    780

gtcgcggtgt tcgacaccac gaccgaccgc gacgtcgagg tgagcgtggg cgtgtccttc    840

gtgagcgtcg acggcgcgcg cgccaaccgc gaggccgagg ccaccgacga gggcgggcag    900

gtcgcgttcg acaccgtgcg tgaggaggcc cgcgacgcgt ggaacgcgga gctgggccgt    960

gccgcgatcg acgcgtcgcc cgaccagcgc cggatcttct acacccagct ctacaagacg   1020

ctgctgtccc cgacgatcgg cagcgacgtc gacggccggt accgcggcat ggacctcgag   1080

gtccaccagg ccgacggctg ggactactac cagaacttct cgctctggga cacgtaccgc   1140

acgcaggcga cgctgcacgc cctcctgctg cccgagcgcg cgcaggacat cgtgcgctcg   1200

atgtaccagc accgcgtcga gggcggctgg ctgccgcgct ggtccctcgg tgcactggag   1260
```

accaacatca tggcgggcga ccccgtcacg ccgtggctcg cggagaactt cgcgctcggc 1320
accgtccccg acgacatcgc ggacgagctg tgggactacc tcgtcgagaa cgccacgacg 1380
accccgccgg acgacgtcgc gtccgtcggg cggcgcagca ccgagttcta cgccgagcac 1440
ggccacgtgc cgttctaccc cgagaacgag ggcggcctcg gcggccagtt cgaggagtac 1500
cgccacggcg gctcggcgac gctcgagctc gcgctcgccg acgcgagcct cggcgctgcg 1560
gccgagcgca cgggtcgcga gggcggccag gcgttcctcg acaagggtcg caactggcgc 1620
aacctctgga acccggacgt cgagctctcg ggtggcttcc agggcatggt caacgcgaag 1680
cgcccgacgg gcgagttcgt cacgctgccc gagctgacgg acgtcacgcg ctccggcttc 1740
cacgagggcg tgccgtggca gtaccagtgg atggtgccgc aggacgtcac gggcctccag 1800
gaggtcatgg gcggcgagga cggcttcgtc gagcgtctcg actactactt cgaccagccg 1860
gcgctcgccg cgaaccccgg cgtctcgccg agcacgtggg ccaagggcgg cagctcgtac 1920
tacacgacca tccgctacaa cccgggcaac gagccgacga tcatgaacgc gtggctctac 1980
ggctacgtgg gccagccgtg gaagacgaac gacgtcctcg ccgcgaacct caaccgcttc 2040
ccggacaccc cgggcggcgg cgtcgggaac gacgacctcg gcacgcttgc cgcctggtac 2100
gtcatggcgt cgctcgggtt cgagcccgtc atgccgggct cggggatcct cgcgctcaac 2160
gcgccgaagg tgcaggccgc gacgctcacg accgatgccg gggcgacgct gcgcatcgac 2220
gcggcgggcg cgaacgagaa gctcccgagc tacgtcgccg gcctggaggt cgacggcgtc 2280
gcgcacaccg ccgcgtggct cgacgtcgcg gcgctgcagg acggcggcac gctcgacttc 2340
gacctgtccg gcacgagcgc gggcctcacg tggggcaccg gcgcggccga ccgcatcccg 2400
tcggtctccg ccgtcgcccc gcccgcgccg gtcgaggtcg aggcgagcgc gcgctgcctc 2460
ggcggccggg cgttcgtcgc ggtccgcgcg accagcacgg ccgacgcgcc ggtggacgtg 2520
actctcacga cgccgttcgg cgagcggacg gtccggcacg tgcagccggg caggagcgcc 2580
taccagtcgt tcacgacgcg cacgacgtcc gtcgaggccg ggacggcgac cgtcacggtc 2640
gtcgccgcgg acggcacgac gtcgacggtc gacgcggcgt acgaggcgct ggcctgcggc 2700

<210> SEQ ID NO 7
<211> LENGTH: 900
<212> TYPE: PRT
<213> ORGANISM: Cellulosimicrobium cellulans

<400> SEQUENCE: 7

Met Arg Arg Pro Arg Leu Ala Leu Leu Ala Ala Gly Leu Ala Leu Ala
1               5                   10                  15

Val Ala Pro Gly Thr Leu Leu Pro Val Ala Ala Gly Ala Ala Pro Ala
            20                  25                  30

Asp Glu Gly Thr Val Thr Ala Ala Ala Gly Asp Asp Leu Thr Leu Glu
        35                  40                  45

Val Asn Pro Phe Val Gly Thr Glu Ser Glu Gly Asn Ala Tyr Pro Gly
    50                  55                  60

Ala Thr Val Pro Phe Gly Met Val Gln Leu Ser Pro Asp Asn Thr Asn
65                  70                  75                  80

Ser Tyr Ala Ser Thr Ser Tyr Ser Thr Asn Ala Gly Arg Val Trp Gly
                85                  90                  95

Phe Ser His Arg His Val Asn Ser Ala Gly Cys Pro Ala Ala Gly Glu
            100                 105                 110

Leu Leu Val Thr Pro Asp Thr Ser Ala Thr Pro Arg Thr Ser Arg Ser

-continued

```
        115                 120                 125

Phe Ile Ala Ile Lys Asp Gln Lys Ser Thr Glu Arg Ala Ser Ala Gly
    130                 135                 140

Phe Tyr Glu Val Thr Leu Ala Asn Asp Val His Ala Glu Leu Thr Ala
145                 150                 155                 160

Thr Thr Arg Val Gly Ala His Arg Tyr Thr Phe Pro Ala Ser Thr Thr
                165                 170                 175

Ser His Leu Ser Phe Asn Val Gly Gln Thr Leu Arg Asp Ala Gly Ala
            180                 185                 190

Ser Ser Val Thr Trp Val Asp Asp Arg Thr Leu Glu Gly Trp Val Asp
        195                 200                 205

Asn Gly Gly Phe Cys Gly Gly Thr Pro Asp Lys Gln Arg Tyr Phe Phe
    210                 215                 220

Ser Ala Thr Phe Asp Arg Pro Val Ala Ser Ser Gly Thr Trp Gly Thr
225                 230                 235                 240

Asp Ala Arg Tyr Val Ala Gly Ser Thr Thr Ser Glu Val Ala Gly Gly
                245                 250                 255

Asn Asn Gly Ala Val Ala Val Phe Asp Thr Thr Thr Asp Arg Asp Val
            260                 265                 270

Glu Val Ser Val Gly Val Ser Phe Val Ser Val Asp Gly Ala Arg Ala
        275                 280                 285

Asn Arg Glu Ala Glu Ala Thr Asp Glu Gly Gly Gln Val Ala Phe Asp
    290                 295                 300

Thr Val Arg Glu Glu Ala Arg Asp Ala Trp Asn Ala Glu Leu Gly Arg
305                 310                 315                 320

Ala Ala Ile Asp Ala Ser Pro Asp Gln Arg Arg Ile Phe Tyr Thr Gln
                325                 330                 335

Leu Tyr Lys Thr Leu Leu Ser Pro Thr Ile Gly Ser Asp Val Asp Gly
            340                 345                 350

Arg Tyr Arg Gly Met Asp Leu Glu Val His Gln Ala Asp Gly Trp Asp
        355                 360                 365

Tyr Tyr Gln Asn Phe Ser Leu Trp Asp Thr Tyr Arg Thr Gln Ala Thr
    370                 375                 380

Leu His Ala Leu Leu Leu Pro Glu Arg Ala Gln Asp Ile Val Arg Ser
385                 390                 395                 400

Met Tyr Gln His Arg Val Glu Gly Gly Trp Leu Pro Arg Trp Ser Leu
                405                 410                 415

Gly Ala Leu Glu Thr Asn Ile Met Ala Gly Asp Pro Val Thr Pro Trp
            420                 425                 430

Leu Ala Glu Asn Phe Ala Leu Gly Thr Val Pro Asp Asp Ile Ala Asp
        435                 440                 445

Glu Leu Trp Asp Tyr Leu Val Glu Asn Ala Thr Thr Thr Pro Pro Asp
    450                 455                 460

Asp Val Ala Ser Val Gly Arg Arg Ser Thr Glu Phe Tyr Ala Glu His
465                 470                 475                 480

Gly His Val Pro Phe Tyr Pro Glu Asn Glu Gly Gly Leu Gly Gly Gln
                485                 490                 495

Phe Glu Glu Tyr Arg His Gly Gly Ser Ala Thr Leu Glu Leu Ala Leu
            500                 505                 510

Ala Asp Ala Ser Leu Gly Ala Ala Ala Glu Arg Thr Gly Arg Glu Gly
        515                 520                 525

Gly Gln Ala Phe Leu Asp Lys Gly Arg Asn Trp Arg Asn Leu Trp Asn
    530                 535                 540
```

Pro Asp Val Glu Leu Ser Gly Gly Phe Gln Gly Met Val Asn Ala Lys
545 550 555 560

Arg Pro Thr Gly Glu Phe Val Thr Leu Pro Glu Leu Thr Asp Val Thr
565 570 575

Arg Ser Gly Phe His Glu Gly Val Pro Trp Gln Tyr Gln Trp Met Val
580 585 590

Pro Gln Asp Val Thr Gly Leu Gln Glu Val Met Gly Gly Glu Asp Gly
595 600 605

Phe Val Glu Arg Leu Asp Tyr Tyr Phe Asp Gln Pro Ala Leu Ala Ala
610 615 620

Asn Pro Gly Val Ser Pro Ser Thr Trp Ala Lys Gly Gly Ser Ser Tyr
625 630 635 640

Tyr Thr Thr Ile Arg Tyr Asn Pro Gly Asn Glu Pro Thr Ile Met Asn
645 650 655

Ala Trp Leu Tyr Gly Tyr Val Gly Gln Pro Trp Lys Thr Asn Asp Val
660 665 670

Leu Ala Ala Asn Leu Asn Arg Phe Pro Asp Thr Pro Gly Gly Gly Val
675 680 685

Gly Asn Asp Asp Leu Gly Thr Leu Ala Ala Trp Tyr Val Met Ala Ser
690 695 700

Leu Gly Phe Glu Pro Val Met Pro Gly Ser Gly Ile Leu Ala Leu Asn
705 710 715 720

Ala Pro Lys Val Gln Ala Ala Thr Leu Thr Thr Asp Ala Gly Ala Thr
725 730 735

Leu Arg Ile Asp Ala Ala Gly Ala Asn Glu Lys Leu Pro Ser Tyr Val
740 745 750

Ala Gly Leu Glu Val Asp Gly Val Ala His Thr Ala Ala Trp Leu Asp
755 760 765

Val Ala Ala Leu Gln Asp Gly Gly Thr Leu Asp Phe Asp Leu Ser Gly
770 775 780

Thr Ser Ala Gly Leu Thr Trp Gly Thr Gly Ala Ala Asp Arg Ile Pro
785 790 795 800

Ser Val Ser Ala Val Ala Pro Pro Ala Pro Val Glu Val Glu Ala Ser
805 810 815

Ala Arg Cys Leu Gly Gly Arg Ala Phe Val Ala Val Arg Ala Thr Ser
820 825 830

Thr Ala Asp Ala Pro Val Asp Val Thr Leu Thr Thr Pro Phe Gly Glu
835 840 845

Arg Thr Val Arg His Val Gln Pro Gly Arg Ser Ala Tyr Gln Ser Phe
850 855 860

Thr Thr Arg Thr Thr Ser Val Glu Ala Gly Thr Ala Thr Val Thr Val
865 870 875 880

Val Ala Ala Asp Gly Thr Thr Ser Thr Val Asp Ala Ala Tyr Glu Ala
885 890 895

Leu Ala Cys Gly
900

<210> SEQ ID NO 8
<211> LENGTH: 3543
<212> TYPE: DNA
<213> ORGANISM: Cellulosimicrobium cellulans

<400> SEQUENCE: 8
gtgagcctcg cgctcccgct ggcggcgtac gcggcgcccg ggatcggggc gtcgcccgcg 60

-continued

```
accgccgccg ggacggaggc agcgacgggg tccgatgccg ccgccgtcga cggcccgctg    120
gtcgactacg tcaacccgtt catcgggacc aaggacgacg gcaacaccta cccgggcgct    180
gccgtgccgt tcggcatggt gcaactctcg ccggacaacg gccacaacgt cgggtacgac    240
tacgaccgca cgtcggtgcg cgggttctcg ctcgtgcacc tgtccggcgt cggctgcggc    300
ctcggcggtc cgctcccgac cctgccgacg acgggcgcga tcacctcgac cgactacggc    360
cagtacgcgc tcggtttctc gcacgacgac gaggaggcct cgccggggta ctaccgcgtg    420
ggtctccagg cgccggcggg cacgatcgag gccgagctca ccgcgaccga gcgcacgggc    480
gtccagcggt acacgttccc cgcgacggcg caggccaacg tcctgctcaa cgccggccag    540
gcgctcaacc gggtgacgga gtccgacgtg cgcgtcgtgg acgaccgcac ggtcgagacg    600
cgcatcaccg tccgcggctt ctgccaggac accgagccgc agacgatctg gacccgcacg    660
accttcgacc ggccgttcgt cgcgcacggc acgtgggacg gccaggtcgt caccgcgggc    720
gcggacgccg cgtccggcgg cgagggccgt cgcggcgcgt acgtcacgtt cgacacgacc    780
ggcggcgacc tcgacgtcga ggccgtcacc gcgatgagct acgtgggcgc cgacggcgcc    840
gcggcgaacc tcgccgcgga ggccggcacg ttcgacgccg tgcacgacgc cgcgcgctcg    900
gcctgggagg agcggctcgg cctcgtgcgg gtcgcgcagg gcgacccgga cgacctgcgc    960
accttctact cctcgctcta ccgcagcttc ctcgcgccga acgtcggctc cgacgtcgac   1020
gggcgctacc gcggctggga ccaggaggtc cacgccgcgg aaccggactt cacctactac   1080
cagaactact cgctctggga cacgtaccgc acccagcagc agctcctgta cctgctcgcg   1140
cccgacgagt cggccgacat ggcgctctcg ctcgtgcgcc agggccagca gggcgggtgg   1200
ctcccgcgct ggggctacgg cacggtcgag acgaacatca tgaccggcga cccggcgacg   1260
ccgttcctcg tcagcgcctg gcgccagggc ctgctcgcgg gccacgagga ggaggcgtac   1320
gcggtcctga gggagaacgc cgacggcgtc ccgcccgccg actcgccctt caacgggcgc   1380
gcggcgaacg tcgagtacct gcgcgacggg ttcgtcccgc acgagccggc gcgctcgggc   1440
aagcccggcg actacgacct ccagcacggc gcctcggcga ccatggagta cgccctcgcc   1500
gacgcgatgc tctcgaccat ggcgcgcggc ctcggccacg acgaggacgc cgaccggtac   1560
gccgcccgcg gccagagcta ccgcaacgtg ttcgacccgc gcacgggcaa cttccgggcg   1620
cgtaacgcgg acggcttctt cgtgggcgac gcggaccccg cgcactccga cgggttccac   1680
gagggcacgg cggtgcagta ccagtggctc gtgccccagg acgtgccggg cctgttcgac   1740
ctcatgggcg gcaccgacgc cgcggtcgac cgcctcgatg cgttcttcgc gtacgacgag   1800
ctcgtcgccg accccccgca cgtcgcgagc gaggtgtggg tcaacggcac gtacgactac   1860
tacggctggg agacctacaa cccgaacaac gagcccaacc tccatgcgcc gtacgtctac   1920
ctgtggaccg ggcagccctg gaagacgacg gacgtcgtgc gcgccgcgtc gaccctcttc   1980
accgacggcc ccgacggcgt cacgggcaac gacgacctcg gcacgatgtc cgcgtggcac   2040
gtgctgtcgt cgatcggcgt gtacccgatc gtgccgggcg ccgatctgtg gggcctgacg   2100
acgccgctct tcgacgacgt gacgatcacg ctcgacccgg aggtcttcgg tcgggactcc   2160
ctgcgcctca cggcggacgg cgtcgcgccc gacacgcact acacgcagtc cgtgtcgctc   2220
ggcggcgagc cgctcgatcg cgcctgggtc acgggcgacg agctcaccgc ggccggcacg   2280
ctcgacgtga ccgtcggcac cgagccgtcc gcgtgggcga ccgaccccgc ggcctcgccg   2340
ggcgccgtcg tgcctgcgga cggcacggtc gagcgcctgt tcgtcggcgc gacgccgcgg   2400
```

-continued cagccggtcc tcgccccggg cgggcggacc gaggtcgcag tccaggtcgt cgcccagggc 2460
gcggggacgt ccagcgggac gctcgaggtg acgtccgacg gcgcggtcac cgcgacgacc 2520
gacctcgccg agtggaccgc cgagtccgac ggcctgccgg ccacggtcga gggcacggtg 2580
acgatcgagg ctcccgccga cgccgagccg ggtctgcaca cggtgcggct cgtcgtgcgc 2640
gacgccgcgg ggaccgaggc ggtccgcgag gtctcggtcg tcgtgtccgg ggagtcgtgg 2700
atcgccgacg cgttcgacaa cgtcggcatc ggcgacgccg gggcggccaa cgcgaacctc 2760
gacggctcgg gcgcctacct cctgcgcgac ctgctcgcgg acctcggcgc cgtccagggc 2820
ctggagctca ccgtgccggg cacggacctc acctacacgc tcggggcccc gcgggcgggc 2880
gcgcccgaca acgtcgccgc gagcggcgag gtcctcgagg tgcccgagca cctgcgctcg 2940
gcccgccacc tctcggtggt cgggacgagc acgcacggca cgcacggggg cggcctcgtc 3000
ctcgggttcg ccgacggctc gtcgcagacc gtcgacgtgc gcctcagcga ctggtgcacg 3060
ggctcgcccg agcccggcaa catcacggtc gcgaaggccg gggcgcgcgg cgaccgcgag 3120
aacgtgcaga agatcggctg cggcctctac gccaccgcgc ccgtcgcgat ccccgagggc 3180
aaggtcctga cgtcggtcac gctgccgagc gacgagcggt tccacgtgtt cgcgatcgcg 3240
accgacgcga cgggggacgt ccccgcgccg caggtcgagg tcacggcgca ggcccgctgc 3300
ctcggcggca aggcgttcgt cgcggtgcgc gcgctcaaca cgggcgagca gcccgccgcg 3360
atcgagctcg cgaccccgta cggctccaag ctcttcggtg acgtcgctcc cggggcgaac 3420
gcgtaccagt cgttcgccac ccgcgccgcc gccgtcgagg cgggcgaggt cacggtgacc 3480
gtgacgacgc ccgacggcga gccccagcag gtcacggccg cgtacgacgc cgccgcctgc 3540
tcc 3543

<210> SEQ ID NO 9
<211> LENGTH: 1181
<212> TYPE: PRT
<213> ORGANISM: Cellulosimicrobium cellulans

<400> SEQUENCE: 9

Val Ser Leu Ala Leu Pro Leu Ala Ala Tyr Ala Ala Pro Gly Ile Gly
1 5 10 15

Ala Ser Pro Ala Thr Ala Ala Gly Thr Glu Ala Ala Thr Gly Ser Asp
20 25 30

Ala Ala Ala Val Asp Gly Pro Leu Val Asp Tyr Val Asn Pro Phe Ile
35 40 45

Gly Thr Lys Asp Asp Gly Asn Thr Tyr Pro Gly Ala Ala Val Pro Phe
50 55 60

Gly Met Val Gln Leu Ser Pro Asp Asn Gly His Asn Val Gly Tyr Asp
65 70 75 80

Tyr Asp Arg Thr Ser Val Arg Gly Phe Ser Leu Val His Leu Ser Gly
85 90 95

Val Gly Cys Gly Leu Gly Gly Pro Leu Pro Thr Leu Pro Thr Thr Gly
100 105 110

Ala Ile Thr Ser Thr Asp Tyr Gly Gln Tyr Ala Leu Gly Phe Ser His
115 120 125

Asp Asp Glu Glu Ala Ser Pro Gly Tyr Tyr Arg Val Gly Leu Gln Ala
130 135 140

Pro Ala Gly Thr Ile Glu Ala Glu Leu Thr Ala Thr Glu Arg Thr Gly
145 150 155 160

Val Gln Arg Tyr Thr Phe Pro Ala Thr Ala Gln Ala Asn Val Leu Leu

-continued

```
                165                 170                 175

Asn Ala Gly Gln Ala Leu Asn Arg Val Thr Glu Ser Asp Val Arg Val
            180                 185                 190

Val Asp Asp Arg Thr Val Glu Thr Arg Ile Thr Val Arg Gly Phe Cys
        195                 200                 205

Gln Asp Thr Glu Pro Gln Thr Ile Trp Thr Arg Thr Thr Phe Asp Arg
    210                 215                 220

Pro Phe Val Ala His Gly Thr Trp Asp Gly Gln Val Val Thr Ala Gly
225                 230                 235                 240

Ala Asp Ala Ala Ser Gly Gly Glu Gly Arg Arg Gly Ala Tyr Val Thr
                245                 250                 255

Phe Asp Thr Thr Gly Gly Asp Leu Asp Val Glu Ala Val Thr Ala Met
            260                 265                 270

Ser Tyr Val Gly Ala Asp Gly Ala Ala Ala Asn Leu Ala Ala Glu Ala
        275                 280                 285

Gly Thr Phe Asp Ala Val His Asp Ala Ala Arg Ser Ala Trp Glu Glu
    290                 295                 300

Arg Leu Gly Leu Val Arg Val Ala Gln Gly Asp Pro Asp Asp Leu Arg
305                 310                 315                 320

Thr Phe Tyr Ser Ser Leu Tyr Arg Ser Phe Leu Ala Pro Asn Val Gly
                325                 330                 335

Ser Asp Val Asp Gly Arg Tyr Arg Gly Trp Asp Gln Glu Val His Ala
            340                 345                 350

Ala Glu Pro Asp Phe Thr Tyr Tyr Gln Asn Tyr Ser Leu Trp Asp Thr
        355                 360                 365

Tyr Arg Thr Gln Gln Gln Leu Leu Tyr Leu Leu Ala Pro Asp Glu Ser
    370                 375                 380

Ala Asp Met Ala Leu Ser Leu Val Arg Gln Gly Gln Gln Gly Gly Trp
385                 390                 395                 400

Leu Pro Arg Trp Gly Tyr Gly Thr Val Glu Thr Asn Ile Met Thr Gly
                405                 410                 415

Asp Pro Ala Thr Pro Phe Leu Val Ser Ala Trp Arg Gln Gly Leu Leu
            420                 425                 430

Ala Gly His Glu Glu Glu Ala Tyr Ala Val Leu Arg Glu Asn Ala Asp
        435                 440                 445

Gly Val Pro Pro Ala Asp Ser Pro Phe Asn Gly Arg Ala Ala Asn Val
    450                 455                 460

Glu Tyr Leu Arg Asp Gly Phe Val Pro His Glu Pro Ala Arg Ser Gly
465                 470                 475                 480

Lys Pro Gly Asp Tyr Asp Leu Gln His Gly Ala Ser Ala Thr Met Glu
                485                 490                 495

Tyr Ala Leu Ala Asp Ala Met Leu Ser Thr Met Ala Arg Gly Leu Gly
            500                 505                 510

His Asp Glu Asp Ala Asp Arg Tyr Ala Ala Arg Gly Gln Ser Tyr Arg
        515                 520                 525

Asn Val Phe Asp Pro Arg Thr Gly Asn Phe Arg Ala Arg Asn Ala Asp
    530                 535                 540

Gly Phe Phe Val Gly Asp Ala Asp Pro Ala His Ser Asp Gly Phe His
545                 550                 555                 560

Glu Gly Thr Ala Val Gln Tyr Gln Trp Leu Val Pro Gln Asp Val Pro
                565                 570                 575

Gly Leu Phe Asp Leu Met Gly Gly Thr Asp Ala Ala Val Asp Arg Leu
            580                 585                 590
```

-continued

```
Asp Ala Phe Phe Ala Tyr Asp Glu Leu Val Ala Asp Pro Pro His Val
        595                 600                 605

Ala Ser Glu Val Trp Val Asn Gly Thr Tyr Asp Tyr Tyr Gly Trp Glu
    610                 615                 620

Thr Tyr Asn Pro Asn Asn Glu Pro Asn Leu His Ala Pro Tyr Val Tyr
625                 630                 635                 640

Leu Trp Thr Gly Gln Pro Trp Lys Thr Thr Asp Val Val Arg Ala Ala
                645                 650                 655

Ser Thr Leu Phe Thr Asp Gly Pro Asp Gly Val Thr Gly Asn Asp Asp
            660                 665                 670

Leu Gly Thr Met Ser Ala Trp His Val Leu Ser Ser Ile Gly Val Tyr
        675                 680                 685

Pro Ile Val Pro Gly Ala Asp Leu Trp Gly Leu Thr Thr Pro Leu Phe
    690                 695                 700

Asp Asp Val Thr Ile Thr Leu Asp Pro Glu Val Phe Gly Arg Asp Ser
705                 710                 715                 720

Leu Arg Leu Thr Ala Asp Gly Val Ala Pro Asp Thr His Tyr Thr Gln
                725                 730                 735

Ser Val Ser Leu Gly Gly Glu Pro Leu Asp Arg Ala Trp Val Thr Gly
            740                 745                 750

Asp Glu Leu Thr Ala Ala Gly Thr Leu Asp Val Thr Val Gly Thr Glu
        755                 760                 765

Pro Ser Ala Trp Ala Thr Asp Pro Ala Ala Ser Pro Gly Ala Val Val
    770                 775                 780

Pro Ala Asp Gly Thr Val Glu Arg Leu Phe Val Gly Ala Thr Pro Arg
785                 790                 795                 800

Gln Pro Val Leu Ala Pro Gly Gly Arg Thr Glu Val Ala Val Gln Val
                805                 810                 815

Val Ala Gln Gly Ala Gly Thr Ser Ser Gly Thr Leu Glu Val Thr Ser
            820                 825                 830

Asp Gly Ala Val Thr Ala Thr Thr Asp Leu Ala Glu Trp Thr Ala Glu
        835                 840                 845

Ser Asp Gly Leu Pro Ala Thr Val Glu Gly Thr Val Thr Ile Glu Ala
    850                 855                 860

Pro Ala Asp Ala Glu Pro Gly Leu His Thr Val Arg Leu Val Val Arg
865                 870                 875                 880

Asp Ala Ala Gly Thr Glu Ala Val Arg Glu Val Ser Val Val Val Ser
                885                 890                 895

Gly Glu Ser Trp Ile Ala Asp Ala Phe Asp Asn Val Gly Ile Gly Asp
            900                 905                 910

Ala Gly Ala Ala Asn Ala Asn Leu Asp Gly Ser Gly Ala Tyr Leu Leu
        915                 920                 925

Arg Asp Leu Leu Ala Asp Leu Gly Ala Val Gln Gly Leu Glu Leu Thr
    930                 935                 940

Val Pro Gly Thr Asp Leu Thr Tyr Thr Leu Gly Ala Pro Arg Ala Gly
945                 950                 955                 960

Ala Pro Asp Asn Val Ala Ala Ser Gly Glu Val Leu Glu Val Pro Glu
                965                 970                 975

His Leu Arg Ser Ala Arg His Leu Ser Val Val Gly Thr Ser Thr His
            980                 985                 990

Gly Thr His Gly Gly Gly Leu Val Leu Gly Phe Ala Asp Gly Ser Ser
        995                 1000                1005
```

-continued

```
Gln Thr Val Asp Val Arg Leu Ser Asp Trp Cys Thr Gly Ser Pro Glu
    1010                1015                1020

Pro Gly Asn Ile Thr Val Ala Lys Ala Gly Ala Arg Gly Asp Arg Glu
1025                1030                1035                1040

Asn Val Gln Lys Ile Gly Cys Gly Leu Tyr Ala Thr Ala Pro Val Ala
                1045                1050                1055

Ile Pro Glu Gly Lys Val Leu Thr Ser Val Thr Leu Pro Ser Asp Glu
            1060                1065                1070

Arg Phe His Val Phe Ala Ile Ala Thr Asp Ala Thr Gly Asp Val Pro
        1075                1080                1085

Ala Pro Gln Val Glu Val Thr Ala Gln Ala Arg Cys Leu Gly Gly Lys
    1090                1095                1100

Ala Phe Val Ala Val Arg Ala Leu Asn Thr Gly Glu Gln Pro Ala Ala
1105                1110                1115                1120

Ile Glu Leu Ala Thr Pro Tyr Gly Ser Lys Leu Phe Gly Asp Val Ala
                1125                1130                1135

Pro Gly Ala Asn Ala Tyr Gln Ser Phe Ala Thr Arg Ala Ala Ala Val
            1140                1145                1150

Glu Ala Gly Glu Val Thr Val Thr Val Thr Thr Pro Asp Gly Glu Pro
        1155                1160                1165

Gln Gln Val Thr Ala Ala Tyr Asp Ala Ala Ala Cys Ser
    1170                1175                1180
```

<210> SEQ ID NO 10
<211> LENGTH: 3453
<212> TYPE: DNA
<213> ORGANISM: Cellulosimicrobium cellulans

<400> SEQUENCE: 10

```
gtgcggcgct ccgtcgcggc gctctctgcc acggcggtcc tggccgccgg actctcgatc     60

gcgcccgccg tcgggctcgc ggtcccggcg gtcgcggccg cacccgacct cgttgaggac    120

cccgtctcct tcgtcgaccc gttcgtcggg accggccagg cgacgggcgt cgtcggggag    180

atcaacaact tccccgggcc gtcgatgccg ttcggcatga tgcagctctc gcccgacacc    240

caggtctccg tgggcaacgg cgacaaggcg tacgcgggct accgctactc gcaccaggcg    300

atccgcggct tctccatgac gcacgcggcc gccgggtgct ggatcttcgg cgacgtcccg    360

atcctccccg tgacgggcga cgtcgggcag tacccgtggg accgcaagga ggcgttcagc    420

cacgacgcgg agagcgccga ggtcggccgg tacgcggtca cgctccagtc gtcggggatc    480

gatgcggagg tgtcggccgc gacccgctcg ggcggactga cgttcgacta ccccgagggc    540

ggtgccgcgt cgcaggtgat cgtcaacgcc gcgggctcgc tcgcgagcgt gcgcaacgcg    600

acggtcgagg tcgaggacgc gcgcacggtc accggctcgg tgacgagcgg cgggttctgc    660

ggcaagaaca acacgcacac gacgtacttc gcgatcgagc tcgaccagga cgcgcaggcg    720

ttcggcacgt ggcagggctc gaccgtctcg cccggcgacc cgtcggccga cggcaacggc    780

gcgggcgcgt ggctcacctt cgcgcccggc gcgacggtgc acgcgaaggt cggcatgtcc    840

tacgtgagcg tcgagggcgc gcgcgccaac ctcgcggccg agatcccggg cttcgacttc    900

gacgccgtcc gggacgccaa ccgcgccgcc tggtccgacc tgctcggcaa ggtccgcgtc    960

gcggggcagg acgccgacga cctcaccatg ttctacacgt cgctctacca ctcgctgctg   1020

cacccgaaca cgttcaccga cgtggacggc cggtacgtcg ggttcgacgg ggagatccac   1080

caggcccccg aggggcacga gcggtacgcg aacttctccg actgggacac gtaccggtcg   1140
```

-continued

```
ctcggcgcgc tccaggcgct gctggcgccc gaccaggcgt cggacatggc gcagtcgctc   1200
gtcgaggtcg ccgaccagtc cggctggctg ccgcgctggc ccgtcgcgaa ccagcacacg   1260
ggccagatga ccggtgactc ctcggtgccg ctcatcgcga gcatgtacgc gttcggggcg   1320
cgcgacttcg acgcggagtc ggcgctcgcg cacatggtca agggtgcgac gagcgccgcc   1380
ccgaccgcga acggctacgt gcagcggcgc gggatcgaga cgtacctcga gcgcggctac   1440
gcgccccaga ccgaggagtt ccggggcgac caccgcgtcg tcggcgcgtc gatcacgctc   1500
gagtggtcga tcgccgactt cgcgatcggg cagctcgcgg ccgcgctcgg ccaggacgac   1560
gtcgccaccg agtacgccgc ccgcggccag tggtggcaga acgtccacga ccccgtgacc   1620
cgcacggcgg gcgcccggaa cgacgacggc acgttcgtgc ggtcgcaggg cggcggcggg   1680
ttcgggcagg agggcttcga cgagggcaac gccgagcagt acacgtggct cgtgccgcag   1740
aacgtcgcgg ggctcaccga cgcgctcggc gggcgtgagg ccgtcgcgga gcggctcgat   1800
gccttcacgg tgcagcacaa cgccggcccg aacgagccgt acctgtggat cggcaacgag   1860
ccgaacttcg gcgtcccgtg gctgtacgac tacgtgggcc agccgtggcg gacgagcgag   1920
ctcgtggacg agcttacgtc cacgctgttc cggcccgagc cgaacggcaa gcccggcaac   1980
gacgacctcg gcgcccaggc cggctggtac gtgtgggccg cgatgggcct gtaccccacc   2040
acgccgggca cggacgtgct cgcgctcaac gcgccgcgct tcgaccgcgt cgtggtcgac   2100
ctcggcgagg gcgacaccct cgacctgcgc gccccggcgg cctcgaccgg cgcccgctac   2160
atcagcggcg tcaccatcga cggcgcagcc tgggacggga cctccctgcc gcgccacgtc   2220
gcgcacgacg gcggcgtcgt cgagctcgcg atgtcgaccg cacgcgacac gacgtggggg   2280
accgcagccg aggacgcccc gccgtcgtgg cgcgacggcg agtccgccgt ggtcgccgcc   2340
gcggacccgg gcctcgtgac ggtcgccccc ggcgggaccg ccgacgcgtc ggtggccgtg   2400
cagctcttcg gcgccgacgc cgccgacgtg cgcgtcgcgg tcgacgcgcc cgggggcatc   2460
ggggtcggtg agcccgcgct cgtcgacgac ggctcgggcc acctcaccgg gacggtcccc   2520
gtccaggtgg gtgccggcgt cgcgtccggc taccacgacg cgcgcctcgt gctctcggcc   2580
ggggacgacg acgtcgaggt gcccctcacc gtcctcgtcg ccgcgcccgg gtcgctcgtt   2640
gcggcctacg acacggtcgg cactgcgccc gaggcgaacc gcggcgtcgg gaacttcgac   2700
gcggccggca actcgttctc gcgcgaggcg ctcgccgacg cgggtctcac gcccgggtcg   2760
gcgcacgacg tcgacggcct ggcgttcacg tggccgtcct cacccgtggg gcgcccggac   2820
tcggtcacgc tcaccggcga gaccgtgcgg ctcgacgcgc cgacgagccg gctcgcgttc   2880
gtgggcgccg cgaccgacgg gacccatcgc gggaccgcgg tcgtgacgtt cgacgacggc   2940
agcaccgcga ccacgacgat cggcttcggc gactgggtgc tgccgagcgc ggacggctcg   3000
ccggtcgagg gcaactcggt cgtcgcgcag atgaaccggc gcaacggcga caaggacagc   3060
gcgttcgtgt tcgccaccgc cccgtacacc gcgcccgagg accgccgcgt ggtcgcggtg   3120
aggttccccg acgtcgacga cctgcacgtc tttgcgatcg cgaccgagcc ggccgcggac   3180
gtgcacctcg tggacgtgac ggtctccctg cgctgcctcg ccgggacccc gtacgtggcg   3240
gtgcgcgcgg cgaacgtctc cgccggggcc gtcgacgtcg acctcacgac gggcgtgggc   3300
tcgcggtcct tcacggccgt cgccccggc gccaacgcct accagtcgtt cgccgcccgc   3360
ggcgcgaccg ggaacgtcga cgtcaccgtc acggccacgg gggaggaggg gacgcagacg   3420
gtcgcgcgga ccgtcgtcgt cccgcgctgc tcc                                3453
```

-continued

<210> SEQ ID NO 11
<211> LENGTH: 1151
<212> TYPE: PRT
<213> ORGANISM: Cellulosimicrobium cellulans

<400> SEQUENCE: 11

```
Val Arg Arg Ser Val Ala Ala Leu Ser Ala Thr Ala Val Leu Ala Ala
1               5                   10                  15

Gly Leu Ser Ile Ala Pro Ala Val Gly Leu Ala Val Pro Ala Val Ala
            20                  25                  30

Ala Ala Pro Asp Leu Val Glu Asp Pro Val Ser Phe Val Asp Pro Phe
        35                  40                  45

Val Gly Thr Gly Gln Ala Thr Gly Val Val Gly Glu Ile Asn Asn Phe
    50                  55                  60

Pro Gly Pro Ser Met Pro Phe Gly Met Met Gln Leu Ser Pro Asp Thr
65                  70                  75                  80

Gln Val Ser Val Gly Asn Gly Asp Lys Ala Tyr Ala Gly Tyr Arg Tyr
                85                  90                  95

Ser His Gln Ala Ile Arg Gly Phe Ser Met Thr His Ala Ala Ala Gly
            100                 105                 110

Cys Trp Ile Phe Gly Asp Val Pro Ile Leu Pro Val Thr Gly Asp Val
        115                 120                 125

Gly Gln Tyr Pro Trp Asp Arg Lys Glu Ala Phe Ser His Asp Ala Glu
    130                 135                 140

Ser Ala Glu Val Gly Arg Tyr Ala Val Thr Leu Gln Ser Ser Gly Ile
145                 150                 155                 160

Asp Ala Glu Val Ser Ala Ala Thr Arg Ser Gly Gly Leu Thr Phe Asp
                165                 170                 175

Tyr Pro Glu Gly Gly Ala Ala Ser Gln Val Ile Val Asn Ala Ala Gly
            180                 185                 190

Ser Leu Ala Ser Val Arg Asn Ala Thr Val Glu Val Glu Asp Ala Arg
        195                 200                 205

Thr Val Thr Gly Ser Val Thr Ser Gly Gly Phe Cys Gly Lys Asn Asn
    210                 215                 220

Thr His Thr Thr Tyr Phe Ala Ile Glu Leu Asp Gln Asp Ala Gln Ala
225                 230                 235                 240

Phe Gly Thr Trp Gln Gly Ser Thr Val Ser Pro Gly Asp Pro Ser Ala
                245                 250                 255

Asp Gly Asn Gly Ala Gly Ala Trp Leu Thr Phe Ala Pro Gly Ala Thr
            260                 265                 270

Val His Ala Lys Val Gly Met Ser Tyr Val Ser Val Glu Gly Ala Arg
        275                 280                 285

Ala Asn Leu Ala Ala Glu Ile Pro Gly Phe Asp Phe Asp Ala Val Arg
    290                 295                 300

Asp Ala Asn Arg Ala Ala Trp Ser Asp Leu Leu Gly Lys Val Arg Val
305                 310                 315                 320

Ala Gly Gln Asp Ala Asp Asp Leu Thr Met Phe Tyr Thr Ser Leu Tyr
                325                 330                 335

His Ser Leu Leu His Pro Asn Thr Phe Thr Asp Val Asp Gly Arg Tyr
            340                 345                 350

Val Gly Phe Asp Gly Glu Ile His Gln Ala Pro Glu Gly His Glu Arg
        355                 360                 365

Tyr Ala Asn Phe Ser Asp Trp Asp Thr Tyr Arg Ser Leu Gly Ala Leu
    370                 375                 380
```

-continued

```
Gln Ala Leu Leu Ala Pro Asp Gln Ala Ser Asp Met Ala Gln Ser Leu
385                 390                 395                 400

Val Glu Val Ala Asp Gln Ser Gly Trp Leu Pro Arg Trp Pro Val Ala
                405                 410                 415

Asn Gln His Thr Gly Gln Met Thr Gly Asp Ser Ser Val Pro Leu Ile
            420                 425                 430

Ala Ser Met Tyr Ala Phe Gly Ala Arg Asp Phe Asp Ala Glu Ser Ala
        435                 440                 445

Leu Ala His Met Val Lys Gly Ala Thr Ser Ala Ala Pro Thr Ala Asn
    450                 455                 460

Gly Tyr Val Gln Arg Arg Gly Ile Glu Thr Tyr Leu Glu Arg Gly Tyr
465                 470                 475                 480

Ala Pro Gln Thr Glu Glu Phe Arg Gly Asp His Arg Val Val Gly Ala
                485                 490                 495

Ser Ile Thr Leu Glu Trp Ser Ile Ala Asp Phe Ala Ile Gly Gln Leu
            500                 505                 510

Ala Ala Ala Leu Gly Gln Asp Asp Val Ala Thr Glu Tyr Ala Ala Arg
        515                 520                 525

Gly Gln Trp Trp Gln Asn Val His Asp Pro Val Thr Arg Thr Ala Gly
    530                 535                 540

Ala Arg Asn Asp Asp Gly Thr Phe Val Arg Ser Gln Gly Gly Gly Gly
545                 550                 555                 560

Phe Gly Gln Glu Gly Phe Asp Glu Gly Asn Ala Glu Gln Tyr Thr Trp
                565                 570                 575

Leu Val Pro Gln Asn Val Ala Gly Leu Thr Asp Ala Leu Gly Gly Arg
            580                 585                 590

Glu Ala Val Ala Glu Arg Leu Asp Ala Phe Thr Val Gln His Asn Ala
        595                 600                 605

Gly Pro Asn Glu Pro Tyr Leu Trp Ile Gly Asn Glu Pro Asn Phe Gly
    610                 615                 620

Val Pro Trp Leu Tyr Asp Tyr Val Gly Gln Pro Trp Arg Thr Ser Glu
625                 630                 635                 640

Leu Val Asp Glu Leu Thr Ser Thr Leu Phe Arg Pro Glu Pro Asn Gly
                645                 650                 655

Lys Pro Gly Asn Asp Asp Leu Gly Ala Gln Ala Gly Trp Tyr Val Trp
            660                 665                 670

Ala Ala Met Gly Leu Tyr Pro Thr Thr Pro Gly Thr Asp Val Leu Ala
        675                 680                 685

Leu Asn Ala Pro Arg Phe Asp Arg Val Val Val Asp Leu Gly Glu Gly
    690                 695                 700

Asp Thr Leu Asp Leu Arg Ala Pro Gly Ala Ser Thr Gly Ala Arg Tyr
705                 710                 715                 720

Ile Ser Gly Val Thr Ile Asp Gly Ala Ala Trp Asp Gly Thr Ser Leu
                725                 730                 735

Pro Arg His Val Ala His Asp Gly Gly Val Val Glu Leu Ala Met Ser
            740                 745                 750

Thr Ala Arg Asp Thr Thr Trp Gly Thr Ala Ala Glu Asp Ala Pro Pro
        755                 760                 765

Ser Trp Arg Asp Gly Glu Ser Ala Val Val Ala Ala Ala Asp Pro Gly
    770                 775                 780

Leu Val Thr Val Ala Pro Gly Gly Thr Ala Asp Ala Ser Val Ala Val
785                 790                 795                 800

Gln Leu Phe Gly Ala Asp Ala Ala Asp Val Arg Val Ala Val Asp Ala
```

-continued

```
                805                 810                 815

Pro Gly Gly Ile Gly Val Gly Glu Pro Ala Leu Val Asp Asp Gly Ser
            820                 825                 830

Gly His Leu Thr Gly Thr Val Pro Val Gln Val Gly Ala Gly Val Ala
        835                 840                 845

Ser Gly Tyr His Asp Ala Arg Leu Val Leu Ser Ala Gly Asp Asp Asp
    850                 855                 860

Val Glu Val Pro Leu Thr Val Leu Val Ala Ala Pro Gly Ser Leu Val
865                 870                 875                 880

Ala Ala Tyr Asp Thr Val Gly Thr Ala Pro Glu Ala Asn Arg Gly Val
                885                 890                 895

Gly Asn Phe Asp Ala Ala Gly Asn Ser Phe Ser Arg Glu Ala Leu Ala
            900                 905                 910

Asp Ala Gly Leu Thr Pro Gly Ser Ala His Asp Val Asp Gly Leu Ala
        915                 920                 925

Phe Thr Trp Pro Ser Ser Pro Val Gly Arg Pro Asp Ser Val Thr Leu
    930                 935                 940

Thr Gly Glu Thr Val Arg Leu Asp Ala Pro Thr Ser Arg Leu Ala Phe
945                 950                 955                 960

Val Gly Ala Ala Thr Asp Gly Thr His Arg Gly Thr Ala Val Val Thr
                965                 970                 975

Phe Asp Asp Gly Ser Thr Ala Thr Thr Thr Ile Gly Phe Gly Asp Trp
            980                 985                 990

Val Leu Pro Ser Ala Asp Gly Ser Pro Val Glu Gly Asn Ser Val Val
        995                 1000                1005

Ala Gln Met Asn Arg Arg Asn Gly Asp Lys Asp Ser Ala Phe Val Phe
    1010                1015                1020

Ala Thr Ala Pro Tyr Thr Ala Pro Glu Asp Arg Arg Val Val Ala Val
1025                1030                1035                1040

Arg Phe Pro Asp Val Asp Asp Leu His Val Phe Ala Ile Ala Thr Glu
                1045                1050                1055

Pro Ala Ala Asp Val His Leu Val Asp Val Thr Val Ser Leu Arg Cys
            1060                1065                1070

Leu Ala Gly Thr Pro Tyr Val Ala Val Arg Ala Ala Asn Val Ser Ala
        1075                1080                1085

Gly Ala Val Asp Val Asp Leu Thr Thr Gly Val Gly Ser Arg Ser Phe
    1090                1095                1100

Thr Ala Val Ala Pro Gly Ala Asn Ala Tyr Gln Ser Phe Ala Ala Arg
1105                1110                1115                1120

Gly Ala Thr Gly Asn Val Asp Val Thr Val Thr Ala Thr Gly Glu Glu
                1125                1130                1135

Gly Thr Gln Thr Val Ala Arg Thr Val Val Val Pro Arg Cys Ser
            1140                1145                1150
```

<210> SEQ ID NO 12
<211> LENGTH: 5433
<212> TYPE: DNA
<213> ORGANISM: Cellulosimicrobium cellulans

<400> SEQUENCE: 12

```
atgaccagac cactcccgcc cggacgcgcg gtcgcgcggt ccggcagcgg ccgcgcccgg      60

cccctcggcc tcgtgctcgc cgccgcactc gccgtcccgc tcggggtgcc tctcgcggcc     120

cccgcgggag ccctcgctgc cgcgcccgcc gcggccgccg agcccggcga cttctcgtcc     180
```

-continued

```
tcgttcgagt ccggcgaccc ggccgcgctg cccaccaccg tggcggagcg cgacggcgcg    240
ccctggcagg cgaacgtcgg ctcgttcacg gccggcctgc ccgggagcgt cctcgggcag    300
ctgaagggcg tcacggcgag cgcgcagaac ctgcccaacg agggcgcggc gaacctcgcc    360
gacggcagct cgggcaccaa gtggctcgcg ttcgcgtcga ccggctgggt ccggtacgag    420
ttcgccgagc ccgtctcgtt cgtcgcgtac acgatgacct ccggcgacga cgccgccggt    480
cgcgacccga agacctggac ggtcgagggg tcgaacgacg ggtccacgtg ggccgcgctc    540
gaccgccgga cggacgagga cttcccgaac cgccagcaga cgcgcacgtt cgagctcgag    600
gcgcccaccg cggcgtacac gtacctgcgc ctcaacgtca cggcgaactc gggcgactcc    660
atcgtccagc tcgccgggtg ggacctctcg gccgacctga gcgccggccc gtccgcggcc    720
cccatgacga cgaaggtcgg caccgggccg cgcgtcagct tcaccaacaa ggcgggcgtc    780
gggttctccg gcctgcactc gctccggtac gacggctcgc acctcgccga cggcgagacg    840
tacgcgacga acgtgctcta cgacgacgtg gacgtcgtcg tcggcgagga cacgcgcctg    900
agctacacga tcttccccga gctgctcgac gatctgcagt acccgtcgac gtacgcggcg    960
gtggacgtcc tgttcaccga cgggacctac ctgtccgacc tcggcgcgcg cgacgcgcac   1020
gagacggtcg cgaccgcgca ggcgcagggc gagggcaaga tcctctacgc cgaccagtgg   1080
aactcggtgc gggtcgacct cggcgacgtc gccgagggca agaccgtgga ccaggtgctg   1140
ctcgggtacg acaacccggg cggtcacgcc gggacgaagt tcgcgggctg gctcgacgac   1200
gtcgagatca cggcggagcc ggccacgatc gacgggtcga gcctcgccaa ctacgtggac   1260
acgcgccgcg gcacgctcgc gtcgggcagc ttctcgcgcg ggaacaacat ccccgcgacg   1320
gcgacgccga acgggttcaa cttctggacg ccgtacacga acgcctcctc gcagagctgg   1380
ctgtacgagt accacaaggc caacaacgcc aacaacaagc ccgtcctcca gggcttcggg   1440
atctcgcacg agccgagccc gtggatgggc gaccgcaacc agctgacgtt cctcccgtcg   1500
acggcgtcgg ggacgcccga cgccacgctc tcgacgcgcg gcctcgagtt cgaccacgcg   1560
gacgagacgg cgcggccgga ctactacggg gtcacgttca ccaacgggtc cgcgatcgag   1620
gcgacgccca ccgaccacgg cgcggtgctc cgcttcagct accccggagc caagggccac   1680
gtgctcgtgg acaaggtgga cggctcctcc aagctcacgt acgaccaggc cacgggcacg   1740
atctccggct gggtcgagaa cggctcgggc ctgtccgtgg gccgcacgcg catgttcgtc   1800
gccggcacct tcgaccgtag tccgacggcg gtcgggacgg cggcgggcaa ccgtgcggac   1860
gcgcgcttcg cgacgttcga gacgtcgtcc gacaagacgg tcgagctgcg cgtcgcgacg   1920
tcgttcatca gcctcgacca ggcgcgcaag aacctcgacc tggaggtgac gggcaagacc   1980
ttcacggagg tcaaggccgc cgccgcgcag gcgtggaacg accgcctggg ggtcatcgag   2040
gtcgagggcg cgagcgagga ccagctcgtc acgctgtact cgaacctcta ccgcctcaac   2100
ctgtacccga actcgcagtt cgagaacacg ggcacggcgc aggagccggt gtacaggtac   2160
gcgagcccgg tctccgcgac cacgggctcc gcgacggaca cgcagaccaa cgcgaagatc   2220
gtcgacggca agatctacgt gaacaacggg ttctgggaca cgtaccgcac ggcctggccg   2280
gcgtactcgc tcctctaccc ggagctcgcg gccgagctgg tcgacgggtt cgtccagcag   2340
taccgcgacg gcggctggat cgcgcgctgg tcctcgccgg gctacgccga cctcatgacg   2400
ggcacgagct ccgacgtggc gttcgccgac gcgtacctca agggctcgct ccccacgggc   2460
acggcgctcg aggcgtacga cgccgcgctg cgcaacgcga ccgtcgcgcc gccgagcaac   2520
gccgtgggcc gcaagggcct gcagacctcg ccgttcctcg ggttcacgcc ggagtccacg   2580
```

-continued

```
cacgagtccg tgtcgtgggg cctggagggc ctggtcaacg acttcggcat cggcaacatg   2640
gccgccgccc tcgcggagga cccggcgacg ccggaggagc gccgcgagac gctgcgcgag   2700
gagtccgcgt acttcctcga gcgggccacg cactacgtcg agctgttcga ccccgaggtc   2760
gacttcttcg tgccgcggca cgaggacggc acgtgggccg tcgaccccga gacgtacgac   2820
ccggaggcct ggggcggcgg gtacaccgag acgaacggct ggaacttcgc gttccacgcc   2880
ccgcaggacg gccagggcct cgccaacctc tacggcggca agcagggcct cgaggacaag   2940
ctcgacgagt tcttctccac gccggagaag ggcgccggca acggcggcat ccacgagcag   3000
cgcgaggcgc gcgacgtccg catgggccag tggggcatga gcaaccaggt gtcgcaccac   3060
atcccgtggc tctacgacgc cgcgggcgcg ccgtcgaagg cgcaggagaa ggtccgcgag   3120
gtcacccgcc gcctgttcgt gggcagcgag atcggccagg gctacccggg cgacgaggac   3180
aacggcgaga tgtcgtcgtg gtggatcttc gcctcgctcg gcttctaccc gctccaggtc   3240
ggctcggacc agtacgcggt cggttcgccg ctgttcgaca aggcgaccgt gcacctgccg   3300
gacggcgacc tcgtcgtcaa cgccgagaac aactcggtcg acaacgtcta cgtgcagtcc   3360
ctcgcggtgg acggcgaggc ccgcacctcg acgtcactct cccaggcgga cctctcgggc   3420
ggcacgactc tggacttcgt catgggtccg gagccgtcgg actggggcac gggcgaggac   3480
gacgcgccgc cgtcgctcac cgagggcgac gagcccccga cgccggtgca ggacgcgacg   3540
accgcgggcc tcggcaccac caccgtcgcc gacggcgacg ccaccacgag cgccgcggcg   3600
ctcacggaca acacgtccgg gacgcgcacg acgttcgcca ccacgacgcc gtcgatcacg   3660
tgggcgggca acggcatccg cccgaccgtc gggtcgtaca cgctgacctc cggggcgagc   3720
gggacggcgt caccgtccgc atggactctc gagggttccg acgacggcga gacgtggacg   3780
acgctcgacg agcggtccgg cgagcagttc cgctgggccc tgcagacgcg gccgttcacg   3840
gtcgcggagc cgacggcgtt cgcgcggtac cgggtcacgg tcaccgcgac gtcgggctcc   3900
ggcgcgctgt cgctcgccga ggtcgagctc ctcgccgacc cgaaggagtc gggggccgag   3960
gagctcaccc tctcggccgc gccggaccgt gacggcgtca cgggccgcga ggtctcgggc   4020
tcgttcgcga ccctcaccgg ggtcgagggc gacgtcgcgg cgctcgacgt gcaggtcgcg   4080
ttcggcgacg gctccgagcc ggtcgccggg acgctgcggg cgggcgcgtt cggcgggtac   4140
gcggtggacg ccgcgcacac gtggaccgca cccggcgtct accccgtgac cgtcacggtc   4200
tcgggcgagg ggatcgagac cgtctcggcc tcctcgtacg tcagcgtctc gctcctgcgc   4260
gagggctcgc tgctcgccgc gtacgacaac gtctgcatcg gcgacgccgg gacgacggtc   4320
ggctcgtgcg acggccaggg cgtgttcttc gaccgggcgc agctcgcggc gaagggcttc   4380
gtccagggcg agcgcgcgac ggtgccgggc acggacctcg cgttcgacgt cccggcggtc   4440
cccgccgggc agccggacaa cgccacgggc gacgggcaga ccatcgagct cgacgtcccc   4500
gcggacgcgg agcagctctc ggtgatcggc acgggcacgg agaagaacca gcaggccacc   4560
ggcacgctga ccttcgacga cggctcgacc cagccgatcg acctgagctt cggcgactgg   4620
tcgggcgcgg cccgcaaccc cgtgttcggc aacatccccg tcgcggtgac ggacagccgc   4680
ctccgcggcg gcagcccgca gaccggcacc cccgccgcgt tcttcgcgac ggcgccgatc   4740
accctccccg agggcaagcg gcccgtgagc ctcacgctcc cggaccagcc gggcgagctc   4800
tcgcgcgacg gccgcatcca cgtggtcgcg gtcgcgcacg acggcacgtt cgccgagcac   4860
cccgcgctcg aggtcacggc cgcggagggc gtgacgctcg ccgtcgggca gacctcggac   4920
```

```
gtggcgctcg cccaggtggc gggcggccgc gagggcgccg acctccgggc ggcggtcacg   4980

tggggcgacg gctccgacgt cgcggccggc gcggtgaccg acgggtcggt ctccggctcg   5040

cacgcctaca cggcggccgg gacgtacacg gcgtacgtcg tggtcgacga cggctggacc   5100

agccaggtgg tcgaggtccc cgtgaccgtg accgaggcgg agccggccct cgccgtcgac   5160

gtcacggtga gcacacgctg cctcgccggc aaggcgtacg tcgcggtccg cgccgagaac   5220

ggcgaggacg tgccgctcgc gatccggctc gtcacgccgt tcggcaccaa ggaggtcgcg   5280

gccgtcgcgc cgggcgccaa cgcctaccag tcgttcgcga cgcgggtcac ggcggtcgag   5340

gccggcaccg tcaccgtcga ggcgacgcgc ggcaccggcg acgaggaggt gacggcgtcg   5400

atccaggccg actacgccgc cgtgacctgc ggc                                5433


<210> SEQ ID NO 13
<211> LENGTH: 1811
<212> TYPE: PRT
<213> ORGANISM: Cellulosimicrobium cellulans

<400> SEQUENCE: 13

Met Thr Arg Pro Leu Pro Pro Gly Arg Ala Val Ala Arg Ser Gly Ser
1               5                   10                  15

Gly Arg Ala Arg Pro Leu Gly Leu Val Leu Ala Ala Ala Leu Ala Val
            20                  25                  30

Pro Leu Gly Val Pro Leu Ala Ala Pro Ala Gly Ala Leu Ala Ala Ala
        35                  40                  45

Pro Ala Ala Ala Ala Glu Pro Gly Asp Phe Ser Ser Ser Phe Glu Ser
    50                  55                  60

Gly Asp Pro Ala Ala Leu Pro Thr Thr Val Ala Glu Arg Asp Gly Ala
65                  70                  75                  80

Pro Trp Gln Ala Asn Val Gly Ser Phe Thr Ala Gly Leu Pro Gly Ser
                85                  90                  95

Val Leu Gly Gln Leu Lys Gly Val Thr Ala Ser Ala Gln Asn Leu Pro
            100                 105                 110

Asn Glu Gly Ala Ala Asn Leu Ala Asp Gly Ser Ser Gly Thr Lys Trp
        115                 120                 125

Leu Ala Phe Ala Ser Thr Gly Trp Val Arg Tyr Glu Phe Ala Glu Pro
    130                 135                 140

Val Ser Phe Val Ala Tyr Thr Met Thr Ser Gly Asp Asp Ala Ala Gly
145                 150                 155                 160

Arg Asp Pro Lys Thr Trp Thr Val Glu Gly Ser Asn Asp Gly Ser Thr
                165                 170                 175

Trp Ala Ala Leu Asp Arg Arg Thr Asp Glu Asp Phe Pro Asn Arg Gln
            180                 185                 190

Gln Thr Arg Thr Phe Glu Leu Glu Ala Pro Thr Ala Ala Tyr Thr Tyr
        195                 200                 205

Leu Arg Leu Asn Val Thr Ala Asn Ser Gly Asp Ser Ile Val Gln Leu
    210                 215                 220

Ala Gly Trp Asp Leu Ser Ala Asp Leu Ser Ala Gly Pro Ser Ala Ala
225                 230                 235                 240

Pro Met Thr Thr Lys Val Gly Thr Gly Pro Arg Val Ser Phe Thr Asn
                245                 250                 255

Lys Ala Gly Val Gly Phe Ser Gly Leu His Ser Leu Arg Tyr Asp Gly
            260                 265                 270

Ser His Leu Ala Asp Gly Glu Thr Tyr Ala Thr Asn Val Leu Tyr Asp
        275                 280                 285
```

-continued

```
Asp Val Asp Val Val Val Gly Glu Asp Thr Arg Leu Ser Tyr Thr Ile
    290                 295                 300

Phe Pro Glu Leu Leu Asp Asp Leu Gln Tyr Pro Ser Thr Tyr Ala Ala
305                 310                 315                 320

Val Asp Val Leu Phe Thr Asp Gly Thr Tyr Leu Ser Asp Leu Gly Ala
                325                 330                 335

Arg Asp Ala His Glu Thr Val Ala Thr Ala Gln Ala Gln Gly Glu Gly
            340                 345                 350

Lys Ile Leu Tyr Ala Asp Gln Trp Asn Ser Val Arg Val Asp Leu Gly
        355                 360                 365

Asp Val Ala Glu Gly Lys Thr Val Asp Gln Val Leu Leu Gly Tyr Asp
    370                 375                 380

Asn Pro Gly Gly His Ala Gly Thr Lys Phe Ala Gly Trp Leu Asp Asp
385                 390                 395                 400

Val Glu Ile Thr Ala Glu Pro Ala Thr Ile Asp Gly Ser Ser Leu Ala
                405                 410                 415

Asn Tyr Val Asp Thr Arg Arg Gly Thr Leu Ala Ser Gly Ser Phe Ser
            420                 425                 430

Arg Gly Asn Asn Ile Pro Ala Thr Ala Thr Pro Asn Gly Phe Asn Phe
        435                 440                 445

Trp Thr Pro Tyr Thr Asn Ala Ser Ser Gln Ser Trp Leu Tyr Glu Tyr
    450                 455                 460

His Lys Ala Asn Asn Ala Asn Asn Lys Pro Val Leu Gln Gly Phe Gly
465                 470                 475                 480

Ile Ser His Glu Pro Ser Pro Trp Met Gly Asp Arg Asn Gln Leu Thr
                485                 490                 495

Phe Leu Pro Ser Thr Ala Ser Gly Thr Pro Asp Ala Thr Leu Ser Thr
            500                 505                 510

Arg Gly Leu Glu Phe Asp His Ala Asp Glu Thr Ala Arg Pro Asp Tyr
        515                 520                 525

Tyr Gly Val Thr Phe Thr Asn Gly Ser Ala Ile Glu Ala Thr Pro Thr
    530                 535                 540

Asp His Gly Ala Val Leu Arg Phe Ser Tyr Pro Gly Ala Lys Gly His
545                 550                 555                 560

Val Leu Val Asp Lys Val Asp Gly Ser Ser Lys Leu Thr Tyr Asp Gln
                565                 570                 575

Ala Thr Gly Thr Ile Ser Gly Trp Val Glu Asn Gly Ser Gly Leu Ser
            580                 585                 590

Val Gly Arg Thr Arg Met Phe Val Ala Gly Thr Phe Asp Arg Ser Pro
        595                 600                 605

Thr Ala Val Gly Thr Ala Ala Gly Asn Arg Ala Asp Ala Arg Phe Ala
    610                 615                 620

Thr Phe Glu Thr Ser Ser Asp Lys Thr Val Glu Leu Arg Val Ala Thr
625                 630                 635                 640

Ser Phe Ile Ser Leu Asp Gln Ala Arg Lys Asn Leu Asp Leu Glu Val
                645                 650                 655

Thr Gly Lys Thr Phe Thr Glu Val Lys Ala Ala Ala Ala Gln Ala Trp
            660                 665                 670

Asn Asp Arg Leu Gly Val Ile Glu Val Glu Gly Ala Ser Glu Asp Gln
        675                 680                 685

Leu Val Thr Leu Tyr Ser Asn Leu Tyr Arg Leu Asn Leu Tyr Pro Asn
    690                 695                 700
```

-continued

```
Ser Gln Phe Glu Asn Thr Gly Thr Ala Gln Glu Pro Val Tyr Arg Tyr
705                 710                 715                 720

Ala Ser Pro Val Ser Ala Thr Thr Gly Ser Ala Thr Asp Thr Gln Thr
                725                 730                 735

Asn Ala Lys Ile Val Asp Gly Lys Ile Tyr Val Asn Asn Gly Phe Trp
            740                 745                 750

Asp Thr Tyr Arg Thr Ala Trp Pro Ala Tyr Ser Leu Leu Tyr Pro Glu
        755                 760                 765

Leu Ala Ala Glu Leu Val Asp Gly Phe Val Gln Gln Tyr Arg Asp Gly
    770                 775                 780

Gly Trp Ile Ala Arg Trp Ser Ser Pro Gly Tyr Ala Asp Leu Met Thr
785                 790                 795                 800

Gly Thr Ser Ser Asp Val Ala Phe Ala Asp Ala Tyr Leu Lys Gly Ser
                805                 810                 815

Leu Pro Thr Gly Thr Ala Leu Glu Ala Tyr Asp Ala Ala Leu Arg Asn
            820                 825                 830

Ala Thr Val Ala Pro Pro Ser Asn Ala Val Gly Arg Lys Gly Leu Gln
        835                 840                 845

Thr Ser Pro Phe Leu Gly Phe Thr Pro Glu Ser Thr His Glu Ser Val
    850                 855                 860

Ser Trp Gly Leu Glu Gly Leu Val Asn Asp Phe Gly Ile Gly Asn Met
865                 870                 875                 880

Ala Ala Ala Leu Ala Glu Asp Pro Ala Thr Pro Glu Glu Arg Arg Glu
                885                 890                 895

Thr Leu Arg Glu Glu Ser Ala Tyr Phe Leu Glu Arg Ala Thr His Tyr
            900                 905                 910

Val Glu Leu Phe Asp Pro Glu Val Asp Phe Phe Val Pro Arg His Glu
        915                 920                 925

Asp Gly Thr Trp Ala Val Asp Pro Glu Thr Tyr Asp Pro Glu Ala Trp
    930                 935                 940

Gly Gly Gly Tyr Thr Glu Thr Asn Gly Trp Asn Phe Ala Phe His Ala
945                 950                 955                 960

Pro Gln Asp Gly Gln Gly Leu Ala Asn Leu Tyr Gly Gly Lys Gln Gly
                965                 970                 975

Leu Glu Asp Lys Leu Asp Glu Phe Phe Ser Thr Pro Glu Lys Gly Ala
            980                 985                 990

Gly Asn Gly Gly Ile His Glu Gln Arg Glu Ala Arg Asp Val Arg Met
        995                 1000                1005

Gly Gln Trp Gly Met Ser Asn Gln Val Ser His His Ile Pro Trp Leu
    1010                1015                1020

Tyr Asp Ala Ala Gly Ala Pro Ser Lys Ala Gln Glu Lys Val Arg Glu
1025                1030                1035                1040

Val Thr Arg Arg Leu Phe Val Gly Ser Glu Ile Gly Gln Gly Tyr Pro
                1045                1050                1055

Gly Asp Glu Asp Asn Gly Glu Met Ser Ser Trp Trp Ile Phe Ala Ser
            1060                1065                1070

Leu Gly Phe Tyr Pro Leu Gln Val Gly Ser Asp Gln Tyr Ala Val Gly
        1075                1080                1085

Ser Pro Leu Phe Asp Lys Ala Thr Val His Leu Pro Asp Gly Asp Leu
    1090                1095                1100

Val Val Asn Ala Glu Asn Asn Ser Val Asp Asn Val Tyr Val Gln Ser
1105                1110                1115                1120

Leu Ala Val Asp Gly Glu Ala Arg Thr Ser Thr Ser Leu Ser Gln Ala
```

-continued

```
            1125                1130                1135

Asp Leu Ser Gly Gly Thr Thr Leu Asp Phe Val Met Gly Pro Glu Pro
        1140                1145                1150

Ser Asp Trp Gly Thr Gly Glu Asp Asp Ala Pro Pro Ser Leu Thr Glu
    1155                1160                1165

Gly Asp Glu Pro Pro Thr Pro Val Gln Asp Ala Thr Thr Ala Gly Leu
    1170                1175                1180

Gly Thr Thr Thr Val Ala Asp Gly Asp Ala Thr Thr Ser Ala Ala Ala
1185                1190                1195                1200

Leu Thr Asp Asn Thr Ser Gly Thr Arg Thr Thr Phe Ala Thr Thr Thr
            1205                1210                1215

Pro Ser Ile Thr Trp Ala Gly Asn Gly Ile Arg Pro Thr Val Gly Ser
        1220                1225                1230

Tyr Thr Leu Thr Ser Gly Ala Ser Gly Thr Ala Ser Pro Ser Ala Trp
    1235                1240                1245

Thr Leu Glu Gly Ser Asp Asp Gly Glu Thr Trp Thr Thr Leu Asp Glu
    1250                1255                1260

Arg Ser Gly Glu Gln Phe Arg Trp Ala Leu Gln Thr Arg Pro Phe Thr
1265                1270                1275                1280

Val Ala Glu Pro Thr Ala Phe Ala Arg Tyr Arg Val Thr Val Thr Ala
            1285                1290                1295

Thr Ser Gly Ser Gly Ala Leu Ser Leu Ala Glu Val Glu Leu Leu Ala
        1300                1305                1310

Asp Pro Lys Glu Ser Gly Ala Glu Glu Leu Thr Leu Ser Ala Ala Pro
    1315                1320                1325

Asp Arg Asp Gly Val Thr Gly Arg Glu Val Ser Gly Ser Phe Ala Thr
    1330                1335                1340

Leu Thr Gly Val Glu Gly Asp Val Ala Ala Leu Asp Val Gln Val Ala
1345                1350                1355                1360

Phe Gly Asp Gly Ser Glu Pro Val Ala Gly Thr Leu Arg Ala Gly Ala
            1365                1370                1375

Phe Gly Gly Tyr Ala Val Asp Ala Ala His Thr Trp Thr Ala Pro Gly
        1380                1385                1390

Val Tyr Pro Val Thr Val Thr Val Ser Gly Glu Gly Ile Glu Thr Val
    1395                1400                1405

Ser Ala Ser Ser Tyr Val Ser Val Ser Leu Leu Arg Glu Gly Ser Leu
    1410                1415                1420

Leu Ala Ala Tyr Asp Asn Val Cys Ile Gly Asp Ala Gly Thr Thr Val
1425                1430                1435                1440

Gly Ser Cys Asp Gly Gln Gly Val Phe Phe Asp Arg Ala Gln Leu Ala
            1445                1450                1455

Ala Lys Gly Phe Val Gln Gly Glu Arg Ala Thr Val Pro Gly Thr Asp
        1460                1465                1470

Leu Ala Phe Asp Val Pro Ala Val Pro Ala Gly Gln Pro Asp Asn Ala
    1475                1480                1485

Thr Gly Asp Gly Gln Thr Ile Glu Leu Asp Val Pro Ala Asp Ala Glu
    1490                1495                1500

Gln Leu Ser Val Ile Gly Thr Gly Thr Glu Lys Asn Gln Gln Ala Thr
1505                1510                1515                1520

Gly Thr Leu Thr Phe Asp Asp Gly Ser Thr Gln Pro Ile Asp Leu Ser
            1525                1530                1535

Phe Gly Asp Trp Ser Gly Ala Ala Arg Asn Pro Val Phe Gly Asn Ile
        1540                1545                1550
```

```
Pro Val Ala Val Thr Asp Ser Arg Leu Arg Gly Gly Ser Pro Gln Thr
        1555                1560                1565

Gly Thr Pro Ala Ala Phe Phe Ala Thr Ala Pro Ile Thr Leu Pro Glu
    1570                1575                1580

Gly Lys Arg Pro Val Ser Leu Thr Leu Pro Asp Gln Pro Gly Glu Leu
1585                1590                1595                1600

Ser Arg Asp Gly Arg Ile His Val Val Ala Val Ala His Asp Gly Thr
                1605                1610                1615

Phe Ala Glu His Pro Ala Leu Glu Val Thr Ala Ala Glu Gly Val Thr
            1620                1625                1630

Leu Ala Val Gly Gln Thr Ser Asp Val Ala Leu Ala Gln Val Ala Gly
        1635                1640                1645

Gly Arg Glu Gly Ala Asp Leu Arg Ala Ala Val Thr Trp Gly Asp Gly
    1650                1655                1660

Ser Asp Val Ala Ala Gly Ala Val Thr Asp Gly Ser Val Ser Gly Ser
1665                1670                1675                1680

His Ala Tyr Thr Ala Ala Gly Thr Tyr Thr Ala Tyr Val Val Val Asp
                1685                1690                1695

Asp Gly Trp Thr Ser Gln Val Val Glu Val Pro Val Thr Val Thr Glu
            1700                1705                1710

Ala Glu Pro Ala Leu Ala Val Asp Val Thr Val Ser Thr Arg Cys Leu
        1715                1720                1725

Ala Gly Lys Ala Tyr Val Ala Val Arg Ala Glu Asn Gly Glu Asp Val
    1730                1735                1740

Pro Leu Ala Ile Arg Leu Val Thr Pro Phe Gly Thr Lys Glu Val Ala
1745                1750                1755                1760

Ala Val Ala Pro Gly Ala Asn Ala Tyr Gln Ser Phe Ala Thr Arg Val
                1765                1770                1775

Thr Ala Val Glu Ala Gly Thr Val Thr Val Glu Ala Thr Arg Gly Thr
            1780                1785                1790

Gly Asp Glu Glu Val Thr Ala Ser Ile Gln Ala Asp Tyr Ala Ala Val
        1795                1800                1805

Thr Cys Gly
    1810


<210> SEQ ID NO 14
<211> LENGTH: 4995
<212> TYPE: DNA
<213> ORGANISM: Cellulosimicrobium cellulans

<400> SEQUENCE: 14

gcgctcgccg tcgtcggcct cgcgcccgcg accgccgcga gcgccgcccc cgagccgccg      60

tcggccgact acgcgtccct ggtcgacgtc ttcgtcggca ccgagggcga cttcggcaac     120

gacatgcccg ccgcgcaggc gccgaacggc ctcgcgaagg tcaacccgcg cacgaccccg     180

ggccgcaaca acaccgggta cgactacgcg cagtcgaaga tctcgggctt cacgcacacc     240

aacctcgacg gggtcggggg ctccggcggc ggtggtgacc tcctcgtggt gccgacgtcc     300

gggtcgtaca cggcgcgccc cggcacgggc acgtacgcgc acccgttctc gcacgacgac     360

gaggacgccg gaccgggctt ctactccgtc gggctcggca acgtcgcggg cacggacggc     420

gcgatcaccg gcgcgccggg cacgatcgag gccgaggtcg cggcggccac gcgctcgggc     480

gtgcaccgct acgcgttccc cgcgggctcg acgccgagcc tcgtcgtgga cctcgagacg     540

aacaacacga gccgccggtc gtcctcggtg caggtcgaga cgcgcgcgga cggcaccgtg     600
```

-continued

```
gagctgtccg gacaggtcac gggctacttc tacaacgcgg cctacacgct gtactacacc    660
gcgcgcacgc tccagcccgc gacggtgcag acgtggggcg acgacgaccg gctcgtcgac    720
gccacggccc aggacggcgt cgacaccggc gcgatcctca cgttcgaccc ggcggacgcc    780
ggggagatcg ggctccaggt caccctgtcg ccggtgagcg tcgagcaggc gcggatcgac    840
cagcaggtcg agctcggcga cctgtcgttc gacgcgatcc gtgaccgcac ccgcgcggag    900
tggaacgcga cgctcgggcg ggtcgcgatc gacgcctcga cggcgacgga cccgacgggc    960
gagctccagc ggctcttcta cacgcacctc taccgcatgt tcgcgatgcc gatgaacgcg   1020
acgagcacct cgggcacgta ccgcggcgtc gacggggcgg tgcacgccgc gcagggcttc   1080
acgtactacg actcgtgggc cacgtgggac gacttccgca agttctccgt catcgcgtac   1140
atcgacccgg cgctgtaccg ggacatggtg cagtcgctgg tctacctgtt cgcggacgcc   1200
gaggcgacgg gcaccggcgg cggcctcggc gggttcgtgc actcggtccc gacggtgcgc   1260
tgggagcggt cgtcggtcgt ggtcgcggac gcgatcgcca agggcttcga cgggttcgac   1320
cgcctcgacg aggcgtaccc ggcgctccag cggctcgtcg ggcagtacag cgcggacgag   1380
ctccggcgcg gctacgtggc gggcaacccc ggcgcgtccg tgcagcgcgg ctacgaccag   1440
tacggcctgt ccgtgatcgc ggacgagctc ggcctgaccg aggaggccga gacgctgcgc   1500
gagcaggcgt cgtggccgat cgagaagctc accaagccgg gcgcgtggac cgccgccgac   1560
ggcacgcagg tcggcctcct caccccgcgc gccgcggacg ggtcgtggca gagcgccgac   1620
cacgcgaagt tcgaggccgc cggcctctac cagggcacgc tctggcagta ccactggtac   1680
gacgcgtacg acatggacgc gctcgtcgag gcgatgggcg gccacgaggc ggcgcgcctc   1740
ggcatgcgcc acatgttcgg tgagcacgcg ccggacgacg gcaaggccat gctccactcg   1800
aacgccaacg agatcgacct ccaggcgccg tacctcttca actacacggg cgagccgagc   1860
ctcacgcaga agtgggcgcg cgcgatctac acgaaggaga cctggaaccg gtacatcgcg   1920
accggctcct ccagcgccgt gccgagcggc ggcggcgagt tcacgccgcc cttgaagacg   1980
aaggtgtacc ggctcgaccc ccgcgggatg ctccccacga tggacaacga cgcgggcacg   2040
atgtcgacga tgttcgtcgc cgcggccgtc gggctgttcc cggtgaccgc gggctcgtcc   2100
cagttccagg tcgggtcgcc gttcttcgac tcgacgacca tcacctacga cgacggcagc   2160
gccttcacgg tcacggccga cggcgtctcc gaggacgcgt tctacgtcca gtccgcgacg   2220
ctcgacggcg cgacgttcgg caacacgtgg gtcgactacg ccaccgtggt cgggggagcc   2280
gacctcgcgt tccgcatggg cgagcagccg agcgactggg gcacggacac cgcgcccgcg   2340
ttctcgatga gtaccgcgac cgacgagccg gccgagggac cgcgcgtcag cgccgaaccg   2400
accaccgtgc agaccggcga cggcggcgcg ctcgacgcga ccgtgacgct cacgctcgac   2460
ggcgcccgcc tcgccgcgcc cgccggcacg gacctcgtca cgagcggggc ggcgagcgtc   2520
gtcgggctgc ccgacggcgt cacggcggcc gtgacggtcg cgtcgccgac cgcgctgacc   2580
gtctccctga cggggacggc gtccgccgac gcgcgcttct tcgtgcacct gcgcgacgcc   2640
gcgctcgccg acggcgtcgc cgcggcgtcg ctccagggac agggcgtctc ggtgcgctcg   2700
cccctgcggc tgtccgtggc gtccgccgag cgcgacgcgc tcgccgcgct cgtcgacgac   2760
gccgtgctcg tgcggcacgg gaactactcc tcggtgacgt tcgaccggtt ctccaccgcg   2820
ctgacgaagg cgcaggaggc cctcggtgac gaggccgcga cgagcatcgc gctgcggttc   2880
gcggccgacc ggctcggtgc ggcggccgac gcgctcgacc tcacgggcgg cgggtaccgc   2940
```

-continued

```
acgctcgagg ccgagcagtc cgaggcgtgg tcgggcgggg agctgaagaa cgaggcgaac   3000

agctcgtccg gcaacctcgg cggcgtgcgc tccgggtcgt gggtgcagta ccgcgacatg   3060

accttcgaga ccgccgccgg ggacaccccg ccgcgcttcc tcacggtccg gtacgacacg   3120

agcttcgccc cgacggacac gccgagcacc gtgcgcgtgc acgcgggcga cgtgagcggc   3180

cctgtggtcg cgaccgtcga cctgaagggc acgagcggct ggggcaagta caccgaggtc   3240

acggcggagc tcggcgacgt gcaggcgctc gtcgacgcgc aggtcgtcac gttcgagctg   3300

ctcgcgccgt ccgggcggag ctgggtcggc aacttcgact ggttccggtt cagcgccgag   3360

gacccggctg ccccaggtca gccgggcgag tccccgacgg tgacgatcga ggccgaggac   3420

tggaccgcga gctccggtcg cgggctcaag aaggagtcct cgacgtggac gagcggtccg   3480

gtgacgaacg tcggcggcac cgcggacggc gactggatcg cctacggcga ggtcgacctg   3540

ggtgagctcc cgctcggcga gctgtcggtc cactacgtgc acaactccaa ccggtccggg   3600

aacaactccg cgctgtcggt gtacctcgac gcgttcgacc cggcgaaccc gggcgagccg   3660

ttcgtcaccg tgccgctgcc gacgaccggg tcgagctgga ccgcggacgg gaccgcgacc   3720

gtcgtcctgc ccgagacggt gcaggggacg cacgaggtgt tcgtgcgcct gtcgaccgag   3780

ccgtacgccg accacccgta cgtcgcgaac ctcgacagcc tgacgttcgc gccgggcggc   3840

ccgacgtcgg tcgtcgtcga gtccgaggcc tggacgtcga actccggccg cgggctgaag   3900

aacgagagct cgacgtggac gagcggtccg gtgacgaacg tcggcggcac cgcggacggc   3960

gactggctcg cctacggcga gatcgacctc ggctccgccg cgctcgacca gctctcggtc   4020

cactacgtgc acaactccaa ccggtccggg cggaactccg cgctgtcggt gtacctcgac   4080

gcgttcgacc cggcgaaccc gggcgagccg ttcgtcaccg tcccgctggc caacaccggg   4140

tcgagctgga cgacggacgg gaccgccgtc gtcgacctgc cgagcacggt gcgcggcaag   4200

caccaggtgt gggtgcgcct gtccaccgag gcgtacgccg accacccgta cgtcgccaac   4260

ctcgacagca tgcgcttctt caccgacgcg tacgacgtcg aggtcccgcc gaccgacacc   4320

gcggcgctcg cggcggtggt cgacgcggcc gggacgcccg aggcggagat cgcgcggtac   4380

ggccggatcg acgcgcgcgt cttcacacgc gagctcgcgg cggcacggtc cgtgctcgcc   4440

gacgccggcg ccacccaggc gcaggccgac gagcgggcgc ggcgcctcgg cctggcgacc   4500

gaccagctcg tgcccgccga gcgccgtcgg ctcgagaacc tcgtggcgag cgccgaggcc   4560

ctgaccgacg aggggtacag ccccgagtcc tggcaggcct tccgcacggc tctcgccgcg   4620

gcgaccggga cgctcgacga cgcggcggcg tccgacgagg cgctgcacga cgcgcggctc   4680

gcgctccagg gcgccgtcga cgccctggag gagccggccg acgtcgtgct cgtcgaggtc   4740

gaggtcagcc cgcgctgcct cgccggcaag ccctacgtcg cggtccgcgc ggtgaacgtc   4800

tccgacgcgg ccgtcgacgt cgagctggcg tcgtcactgg gcacgaggtc gttcgtcggc   4860

gtcgcgccgg gggcgagcgc gtaccagtcg ttcgccgcgc ggtccgcgac gggcgacctg   4920

gacgtcaccg tcacggcgac gggggcggac ggcacccaga cggtcgagca ggtcgtcacc   4980

gtcccgtcct gctcc                                                    4995
```

<210> SEQ ID NO 15
<211> LENGTH: 1665
<212> TYPE: PRT
<213> ORGANISM: Cellulosimicrobium cellulans

<400> SEQUENCE: 15

Ala Leu Ala Val Val Gly Leu Ala Pro Ala Thr Ala Ala Ser Ala Ala

-continued

```
1               5                   10                  15

Pro Glu Pro Pro Ser Ala Asp Tyr Ala Ser Leu Val Asp Val Phe Val
            20                  25                  30

Gly Thr Glu Gly Asp Phe Gly Asn Asp Met Pro Ala Ala Gln Ala Pro
        35                  40                  45

Asn Gly Leu Ala Lys Val Asn Pro Arg Thr Thr Pro Gly Arg Asn Asn
    50                  55                  60

Thr Gly Tyr Asp Tyr Ala Gln Ser Lys Ile Ser Gly Phe Thr His Thr
65                  70                  75                  80

Asn Leu Asp Gly Val Gly Gly Ser Gly Gly Gly Gly Asp Leu Leu Val
                85                  90                  95

Val Pro Thr Ser Gly Ser Tyr Thr Ala Arg Pro Gly Thr Gly Thr Tyr
            100                 105                 110

Ala His Pro Phe Ser His Asp Asp Glu Asp Ala Gly Pro Gly Phe Tyr
        115                 120                 125

Ser Val Gly Leu Gly Asn Val Ala Gly Thr Asp Gly Ala Ile Thr Gly
    130                 135                 140

Ala Pro Gly Thr Ile Glu Ala Glu Val Ala Ala Ala Thr Arg Ser Gly
145                 150                 155                 160

Val His Arg Tyr Ala Phe Pro Ala Gly Ser Thr Pro Ser Leu Val Val
                165                 170                 175

Asp Leu Glu Thr Asn Asn Thr Ser Arg Arg Ser Ser Ser Val Gln Val
            180                 185                 190

Glu Thr Arg Ala Asp Gly Thr Val Glu Leu Ser Gly Gln Val Thr Gly
        195                 200                 205

Tyr Phe Tyr Asn Ala Ala Tyr Thr Leu Tyr Tyr Thr Ala Arg Thr Leu
    210                 215                 220

Gln Pro Ala Thr Val Gln Thr Trp Gly Asp Asp Asp Arg Leu Val Asp
225                 230                 235                 240

Ala Thr Ala Gln Asp Gly Val Asp Thr Gly Ala Ile Leu Thr Phe Asp
                245                 250                 255

Pro Ala Asp Ala Gly Glu Ile Gly Leu Gln Val Thr Leu Ser Pro Val
            260                 265                 270

Ser Val Glu Gln Ala Arg Ile Asp Gln Gln Val Glu Leu Gly Asp Leu
        275                 280                 285

Ser Phe Asp Ala Ile Arg Asp Arg Thr Arg Ala Glu Trp Asn Ala Thr
    290                 295                 300

Leu Gly Arg Val Ala Ile Asp Ala Ser Thr Ala Thr Asp Pro Thr Gly
305                 310                 315                 320

Glu Leu Gln Arg Leu Phe Tyr Thr His Leu Tyr Arg Met Phe Ala Met
                325                 330                 335

Pro Met Asn Ala Thr Ser Thr Ser Gly Thr Tyr Arg Gly Val Asp Gly
            340                 345                 350

Ala Val His Ala Ala Gln Gly Phe Thr Tyr Tyr Asp Ser Trp Ala Thr
        355                 360                 365

Trp Asp Asp Phe Arg Lys Phe Ser Val Ile Ala Tyr Ile Asp Pro Ala
    370                 375                 380

Leu Tyr Arg Asp Met Val Gln Ser Leu Val Tyr Leu Phe Ala Asp Ala
385                 390                 395                 400

Glu Ala Thr Gly Thr Gly Gly Gly Leu Gly Gly Phe Val His Ser Val
                405                 410                 415

Pro Thr Val Arg Trp Glu Arg Ser Ser Val Val Val Ala Asp Ala Ile
            420                 425                 430
```

-continued

```
Ala Lys Gly Phe Asp Gly Phe Asp Arg Leu Asp Glu Ala Tyr Pro Ala
        435                 440                 445

Leu Gln Arg Leu Val Gly Gln Tyr Ser Ala Asp Glu Leu Arg Arg Gly
    450                 455                 460

Tyr Val Ala Gly Asn Pro Gly Ala Ser Val Gln Arg Gly Tyr Asp Gln
465                 470                 475                 480

Tyr Gly Leu Ser Val Ile Ala Asp Glu Leu Gly Leu Thr Glu Glu Ala
                485                 490                 495

Glu Thr Leu Arg Glu Gln Ala Ser Trp Pro Ile Glu Lys Leu Thr Lys
            500                 505                 510

Pro Gly Ala Trp Thr Ala Ala Asp Gly Thr Gln Val Gly Leu Leu Thr
        515                 520                 525

Pro Arg Ala Ala Asp Gly Ser Trp Gln Ser Ala Asp His Ala Lys Phe
    530                 535                 540

Glu Ala Ala Gly Leu Tyr Gln Gly Thr Leu Trp Gln Tyr His Trp Tyr
545                 550                 555                 560

Asp Ala Tyr Asp Met Asp Ala Leu Val Glu Ala Met Gly Gly His Glu
                565                 570                 575

Ala Ala Arg Leu Gly Met Arg His Met Phe Gly Glu His Ala Pro Asp
            580                 585                 590

Asp Gly Lys Ala Met Leu His Ser Asn Ala Asn Glu Ile Asp Leu Gln
        595                 600                 605

Ala Pro Tyr Leu Phe Asn Tyr Thr Gly Glu Pro Ser Leu Thr Gln Lys
    610                 615                 620

Trp Ala Arg Ala Ile Tyr Thr Lys Glu Thr Trp Asn Arg Tyr Ile Ala
625                 630                 635                 640

Thr Gly Ser Ser Ser Ala Val Pro Ser Gly Gly Gly Glu Phe Thr Pro
                645                 650                 655

Pro Leu Lys Thr Lys Val Tyr Arg Leu Asp Pro Arg Gly Met Leu Pro
            660                 665                 670

Thr Met Asp Asn Asp Ala Gly Thr Met Ser Thr Met Phe Val Ala Ala
        675                 680                 685

Ala Val Gly Leu Phe Pro Val Thr Ala Gly Ser Ser Gln Phe Gln Val
    690                 695                 700

Gly Ser Pro Phe Phe Asp Ser Thr Thr Ile Thr Tyr Asp Asp Gly Ser
705                 710                 715                 720

Ala Phe Thr Val Thr Ala Asp Gly Val Ser Glu Asp Ala Phe Tyr Val
                725                 730                 735

Gln Ser Ala Thr Leu Asp Gly Ala Thr Phe Gly Asn Thr Trp Val Asp
            740                 745                 750

Tyr Ala Thr Val Val Gly Gly Ala Asp Leu Ala Phe Arg Met Gly Glu
        755                 760                 765

Gln Pro Ser Asp Trp Gly Thr Asp Thr Ala Pro Ala Phe Ser Met Ser
    770                 775                 780

Thr Ala Thr Asp Glu Pro Ala Glu Gly Pro Arg Val Ser Ala Glu Pro
785                 790                 795                 800

Thr Thr Val Gln Thr Gly Asp Gly Gly Ala Leu Asp Ala Thr Val Thr
                805                 810                 815

Leu Thr Leu Asp Gly Ala Arg Leu Ala Ala Pro Ala Gly Thr Asp Leu
            820                 825                 830

Val Thr Ser Gly Ala Ala Ser Val Val Gly Leu Pro Asp Gly Val Thr
        835                 840                 845
```

-continued

```
Ala Ala Val Thr Val Ala Ser Pro Thr Ala Leu Thr Val Ser Leu Thr
    850                 855                 860

Gly Thr Ala Ser Ala Asp Ala Arg Phe Phe Val His Leu Arg Asp Ala
865                 870                 875                 880

Ala Leu Ala Asp Gly Val Ala Ala Ala Ser Leu Gln Gly Gln Gly Val
                885                 890                 895

Ser Val Arg Ser Pro Leu Arg Leu Ser Val Ala Ser Ala Glu Arg Asp
            900                 905                 910

Ala Leu Ala Ala Leu Val Asp Asp Ala Val Leu Val Arg His Gly Asn
        915                 920                 925

Tyr Ser Ser Val Thr Phe Asp Arg Phe Ser Thr Ala Leu Thr Lys Ala
    930                 935                 940

Gln Glu Ala Leu Gly Asp Glu Ala Ala Thr Ser Ile Ala Leu Arg Phe
945                 950                 955                 960

Ala Ala Asp Arg Leu Gly Ala Ala Ala Asp Ala Leu Asp Leu Thr Gly
                965                 970                 975

Gly Gly Tyr Arg Thr Leu Glu Ala Glu Gln Ser Glu Ala Trp Ser Gly
            980                 985                 990

Gly Glu Leu Lys Asn Glu Ala Asn Ser Ser Ser Gly Asn Leu Gly Gly
        995                 1000                1005

Val Arg Ser Gly Ser Trp Val Gln Tyr Arg Asp Met Thr Phe Glu Thr
    1010                1015                1020

Ala Ala Gly Asp Thr Pro Pro Arg Phe Leu Thr Val Arg Tyr Asp Thr
1025                1030                1035                1040

Ser Phe Ala Pro Thr Asp Thr Pro Ser Thr Val Arg Val His Ala Gly
                1045                1050                1055

Asp Val Ser Gly Pro Val Val Ala Thr Val Asp Leu Lys Gly Thr Ser
            1060                1065                1070

Gly Trp Gly Lys Tyr Thr Glu Val Thr Ala Glu Leu Gly Asp Val Gln
        1075                1080                1085

Ala Leu Val Asp Ala Gln Val Val Thr Phe Glu Leu Leu Ala Pro Ser
    1090                1095                1100

Gly Arg Ser Trp Val Gly Asn Phe Asp Trp Phe Arg Phe Ser Ala Glu
1105                1110                1115                1120

Asp Pro Ala Ala Pro Gly Gln Pro Gly Glu Ser Pro Thr Val Thr Ile
                1125                1130                1135

Glu Ala Glu Asp Trp Thr Ala Ser Ser Gly Arg Gly Leu Lys Lys Glu
            1140                1145                1150

Ser Ser Thr Trp Thr Ser Gly Pro Val Thr Asn Val Gly Gly Thr Ala
        1155                1160                1165

Asp Gly Asp Trp Ile Ala Tyr Gly Glu Val Asp Leu Gly Glu Leu Pro
    1170                1175                1180

Leu Gly Glu Leu Ser Val His Tyr Val His Asn Ser Asn Arg Ser Gly
1185                1190                1195                1200

Asn Asn Ser Ala Leu Ser Val Tyr Leu Asp Ala Phe Asp Pro Ala Asn
                1205                1210                1215

Pro Gly Glu Pro Phe Val Thr Val Pro Leu Pro Thr Thr Gly Ser Ser
            1220                1225                1230

Trp Thr Ala Asp Gly Thr Ala Thr Val Val Leu Pro Glu Thr Val Gln
        1235                1240                1245

Gly Thr His Glu Val Phe Val Arg Leu Ser Thr Glu Pro Tyr Ala Asp
    1250                1255                1260

His Pro Tyr Val Ala Asn Leu Asp Ser Leu Thr Phe Ala Pro Gly Gly
```

-continued

```
1265                1270                1275                1280

Pro Thr Ser Val Val Val Glu Ser Glu Ala Trp Thr Ser Asn Ser Gly
                1285                1290                1295

Arg Gly Leu Lys Asn Glu Ser Ser Thr Trp Thr Ser Gly Pro Val Thr
            1300                1305                1310

Asn Val Gly Gly Thr Ala Asp Gly Asp Trp Leu Ala Tyr Gly Glu Ile
        1315                1320                1325

Asp Leu Gly Ser Ala Ala Leu Asp Gln Leu Ser Val His Tyr Val His
    1330                1335                1340

Asn Ser Asn Arg Ser Gly Arg Asn Ser Ala Leu Ser Val Tyr Leu Asp
1345                1350                1355                1360

Ala Phe Asp Pro Ala Asn Pro Gly Glu Pro Phe Val Thr Val Pro Leu
                1365                1370                1375

Ala Asn Thr Gly Ser Ser Trp Thr Thr Asp Gly Thr Ala Val Val Asp
            1380                1385                1390

Leu Pro Ser Thr Val Arg Gly Lys His Gln Val Trp Val Arg Leu Ser
        1395                1400                1405

Thr Glu Ala Tyr Ala Asp His Pro Tyr Val Ala Asn Leu Asp Ser Met
    1410                1415                1420

Arg Phe Phe Thr Asp Ala Tyr Asp Val Glu Val Pro Pro Thr Asp Thr
1425                1430                1435                1440

Ala Ala Leu Ala Ala Val Val Asp Ala Ala Gly Thr Pro Glu Ala Glu
                1445                1450                1455

Ile Ala Arg Tyr Gly Arg Ile Asp Ala Arg Val Phe Thr Arg Glu Leu
            1460                1465                1470

Ala Ala Ala Arg Ser Val Leu Ala Asp Ala Gly Ala Thr Gln Ala Gln
        1475                1480                1485

Ala Asp Glu Arg Ala Arg Arg Leu Gly Leu Ala Thr Asp Gln Leu Val
    1490                1495                1500

Pro Ala Glu Arg Arg Arg Leu Glu Asn Leu Val Ala Ser Ala Glu Ala
1505                1510                1515                1520

Leu Thr Asp Glu Gly Tyr Ser Pro Glu Ser Trp Gln Ala Phe Arg Thr
                1525                1530                1535

Ala Leu Ala Ala Ala Thr Gly Thr Leu Asp Asp Ala Ala Ala Ser Asp
            1540                1545                1550

Glu Ala Leu His Asp Ala Arg Leu Ala Leu Gln Gly Ala Val Asp Ala
        1555                1560                1565

Leu Glu Glu Pro Ala Asp Val Val Leu Val Glu Val Glu Val Ser Pro
    1570                1575                1580

Arg Cys Leu Ala Gly Lys Pro Tyr Val Ala Val Arg Ala Val Asn Val
1585                1590                1595                1600

Ser Asp Ala Ala Val Asp Val Glu Leu Ala Ser Ser Leu Gly Thr Arg
                1605                1610                1615

Ser Phe Val Gly Val Ala Pro Gly Ala Ser Ala Tyr Gln Ser Phe Ala
            1620                1625                1630

Ala Arg Ser Ala Thr Gly Asp Leu Asp Val Thr Val Thr Ala Thr Gly
        1635                1640                1645

Ala Asp Gly Thr Gln Thr Val Glu Gln Val Val Thr Val Pro Ser Cys
    1650                1655                1660

Ser
1665
```

<210> SEQ ID NO 16

<211> LENGTH: 2619
<212> TYPE: DNA
<213> ORGANISM: Artificial Sequence
<220> FEATURE:
<223> OTHER INFORMATION: synthetic polynucleotide

<400> SEQUENCE: 16
gcaccggcag atgaaggcac cgttaccgca gcagccggtg atgatctgac cctggaagtt 60
aatccgtttg ttggcaccga aagcgaaggt aatgcatatc cgggtgcaac cgttccgttt 120
ggtatggttc agctgtctcc ggataatacc aatagctatg ccagcaccag ctatagcacc 180
aatgcaggtc gtgtttgggg ttttagccat cgtcatgtta atagcgcagg ttgtccggca 240
gccggtgaac tgctggttac accggatacc agcgcaacac cgcgtaccag ccgtagcttt 300
attgccatca aagatcagaa aagcaccgaa cgtgcaagcg caggttttta tgaagttacc 360
ctggcaaatg atgttcatgc agaactgacc gcaaccaccc gtgttggtgc acatcgttat 420
acctttccgg caagcaccac ctctcatctg agctttaatg ttggtcagac cctgcgtgat 480
gccggtgcaa gcagcgttac ctgggttgat gatcgtacac tggaaggttg ggttgataat 540
ggtggttttt gtggtggtac accggataaa cagcgctatt tttttagcgc aacctttgat 600
cgtccggttg ccagcagcgg tacatggggc accgatgcac gttatgttgc aggtagcacc 660
accagtgaag ttgccggtgg taataatggt gcagttgccg tttttgatac caccaccgat 720
cgtgatgttg aagttagcgt tggtgttagc tttgttagcg ttgatggtgc acgtgcaaat 780
cgtgaagccg aagcaaccga tgaaggtggt caggttgcat ttgataccgt tcgtgaagaa 840
gcacgcgacg cctggaatgc agaactgggt cgtgcagcaa ttgatgcatc tccggatcag 900
cgtcgtatct tttataccca gctgtataaa accctgctga gcccgaccat tggttctgat 960
gttgatggtc gttatcgtgg tatggatctg gaagttcatc aggcagatgg ctgggattat 1020
tatcagaact ttagcctgtg ggatacctat cgtacccagg caaccctgca tgcactgctg 1080
ctgccggaac gtgcacagga tattgttcgt agcatgtatc agcatcgtgt tgaaggtggt 1140
tggctgcctc gttggtctct gggtgcactg gaaaccaata tcatggcagg cgatccggtt 1200
accccgtggc tggcagaaaa ttttgcactg ggcaccgttc cggatgatat tgcagatgaa 1260
ctgtgggatt atctggttga aaatgcaacc accacccctc cggatgatgt tgccagcgtt 1320
ggtcgtcgta gcaccgaatt ttatgccgaa catggtcatg ttccgtttta tccggaaaac 1380
gaaggtggcc tgggtggtca gtttgaagaa tatcgtcatg gtggtagcgc aaccctggaa 1440
ctggcactgg cagatgcaag cctgggtgcc gcagcagaac gtaccggtcg tgaaggtggc 1500
caggcatttc tggataaagg tcgcaattgg cgtaatctgt ggaatccgga tgttgaactg 1560
agcggtggtt ttcagggtat ggttaatgca aaacgtccga ccggtgaatt tgttaccctg 1620
ccggaactga ccgatgttac ccgtagcggt tttcatgaag gtgttccgtg gcagtatcag 1680
tggatggttc cgcaggatgt taccggtctg caagaagtta tgggaggcga agatggtttt 1740
gtggaacgcc tggattatta ttttgatcag cctgcactgg cagcaaatcc gggtgttagc 1800
ccgagcacct gggcaaaagg tggtagcagc tattatacca ccattcgcta taatccgggt 1860
aatgaaccga ccattatgaa tgcatggctg tatggttatg ttggtcagcc gtggaaaacc 1920
aatgatgttc tggcagccaa tctgaatcgt tttccggata caccgggtgg tggtgttggt 1980
aatgatgatc tgggcaccct ggcagcatgg tatgttatgg ccagcctggg ttttgaaccg 2040
gttatgcctg gtagcggtat tctggcactg aatgcaccga aagttcaggc agcaaccctg 2100
accaccgatg ccggtgccac cctgcgtatt gatgcagccg gtgcaaatga aaaactgccg 2160

```
agctatgttg ccggtctgga agttgatggt gttgcacata ccgcagcatg gctggatgtt   2220

gcagcactgc aggatggtgg caccctggat tttgatctga gcggtacaag cgcaggtctg   2280

acatggggta caggtgcagc agatcgtatt ccgagcgtta gcgcagttgc accgcctgca   2340

ccggttgaag tggaagcaag cgcacgttgt ctgggtggtc gtgcatttgt tgcagttcgt   2400

gcaaccagca ccgcagatgc accggtggat gttacactga ccacaccgtt tggtgaacgt   2460

accgttcgtc atgttcagcc tggtcgtagc gcatatcaga gctttaccac ccgtaccacc   2520

tctgttgaag caggcaccgc aaccgttacc gttgttgcag cagatggcac cacctcaacc   2580

gttgatgcag catatgaagc actggcatgt ggttaataa                          2619
```

<210> SEQ ID NO 17
<211> LENGTH: 3483
<212> TYPE: DNA
<213> ORGANISM: Artificial Sequence
<220> FEATURE:
<223> OTHER INFORMATION: synthetic polynucleotide

<400> SEQUENCE: 17

```
gcaggcaccg aagcagcaac cggttctgat gcagcagcag ttgatggtcc gctggttgat     60

tatgtgaatc cgtttattgg caccaaagat gatggtaata cctatccggg tgcagcagtt    120

ccgtttggta tggttcagct gtctccggat aatggtcata atgtgggcta tgattatgat    180

cgtaccagcg ttcgtggttt tagcctggtt catctgagcg gtgttggttg tggtctgggt    240

ggtccgctgc cgacactgcc gaccaccggt gcaattacca gcaccgatta tggtcagtat    300

gcactgggtt ttagccatga tgatgaagaa gcatctccgg gttattatcg tgttggtctg    360

caggcacctg caggaaccat tgaagcagaa ctgaccgcaa ccgaacgtac cggtgttcag    420

cgttatacct ttccggcaac cgcacaggca aatgttctgc tgaatgcagg tcaggcactg    480

aatcgtgtta ccgaatctga tgttcgtgtt gttgatgatc gtaccgttga aacccgtatt    540

accgtgcgtg gtttttgtca ggataccgaa ccgcagacca tttggacccg taccaccttt    600

gatcgtccgt ttgttgcaca tggcacctgg gatggtcagg ttgttaccgc aggcgcagat    660

gcagcaagcg gtggtgaagg tcgtcgtggt gcatatgtta cctttgatac aaccggtggt    720

gatctggatg ttgaagcagt taccgcaatg agctatgttg gtgcagatgg tgcagcagca    780

aatctggcag cagaagcagg cacctttgac gcagttcatg atgcagcacg tagcgcatgg    840

gaagaacgtc tgggtctggt tcgtgttgca cagggtgatc cggatgatct gcgtaccttt    900

tatagcagcc tgtatcgtag ctttctggca ccgaatgttg gttctgatgt ggatggtcgt    960

tatcgtggtt gggatcagga agttcacgca gcagaaccgg attttaccta ttatcagaat   1020

tatagcctgt gggataccta tcgtacccaa cagcaactgc tgtatctgct ggcaccggat   1080

gaaagcgcag atatggcact gagcctggtt cgtcagggtc agcagggtgg ttggctgcct   1140

cgttggggtt atggtacagt ggaaaccaat attatgaccg gtgatccggc aaccccgttt   1200

ctggttagcg catggcgtca gggtctgctg gcaggtcatg aagaagaagc atacgcagtc   1260

ctgcgtgaaa atgcagatgg tgttcctccg gcagatagcc cgtttaatgg tcgtgcagcc   1320

aatgttgaat atctgcgtga tggttttgtt ccgcatgaac cggcacgtag cggtaaaccg   1380

ggtgattatg atctgcagca tggtgcaagc gcaaccatgg aatatgcact ggcagatgca   1440

atgctgagca ccatggcacg tggtctgggt catgatgaag atgcagatcg ttatgcagcc   1500

cgtggtcaga gctatcgtaa tgtttttgat ccgcgtaccg gtaattttcg tgcacgtaat   1560
```

-continued gccgatggtt tttttgttgg tgatgcagat ccggcacatt ctgatggttt tcatgaaggc 1620
accgcagttc agtatcagtg gctggttccg caggatgttc cgggtctgtt tgatctgatg 1680
ggtggcaccg atgcagccgt tgatcgtctg gatgcatttt ttgcctatga tgaactggtt 1740
gcagatcctc cgcatgttgc aagcgaagtt tgggttaatg gcacctatga ttattatggc 1800
tgggaaacct ataatccgaa taatgaaccg aatctgcatg caccgtatgt ttatctgtgg 1860
accggtcagc cgtggaaaac caccgatgtt gttcgtgcag caagcaccct gtttaccgat 1920
ggtccggatg gtgttaccgg taatgatgat ctgggcacca tgagcgcatg gcatgttctg 1980
agcagcattg gtgtttatcc gattgttccg ggtgccgatc tgtggggtct gaccacaccg 2040
ctgtttgatg atgttaccat taccctggac ccggaagttt ttggtcgtga tagcctgcgt 2100
ctgaccgcag atggtgtggc accggatacc cattataccc agagcgttag cctgggtggt 2160
gaaccgctgg atcgtgcatg ggttacaggt gatgaactga ccgctgcagg caccctggat 2220
gttaccgttg gcaccgaacc gagcgcatgg gcaaccgatc cggcagcatc accgggtgca 2280
gttgttccgg ctgatggcac cgttgaacgt ctgtttgttg gtgcaacacc gcgtcagccg 2340
gttctggcac cgggtggtcg taccgaagtt gcagttcagg ttgttgccca gggtgcaggc 2400
acctctagcg gcaccctgga agtgacctct gatggtgcag ttaccgccac caccgatctg 2460
gcagaatgga ccgcagaatc tgatggtctg cctgccaccg ttgaaggaac cgttaccatt 2520
gaagctccgg cagatgccga accgggtctg cataccgttc gtctggttgt tcgtgatgca 2580
gccggtacag aagcagttcg cgaagttagc gttgttgtta gcggtgaaag ctggattgca 2640
gatgcctttg ataatgtggg tattggtgat gccggtgcag caaatgcaaa tctggatggt 2700
agcggtgcct atctgctgcg tgatctgctg gccgatctgg gtgcagttca gggtctggaa 2760
ctgaccgttc cgggtactga tctgacctat accctgggtg caccgcgtgc tggtgcaccg 2820
gataatgttg cagccagcgg tgaagttctg gaagttccgg aacatctgcg tagcgcacgt 2880
catctgagcg ttgtgggcac cagcacccat ggtacacatg gtggtggtct ggttctgggt 2940
tttgccgatg gtagcagcca gaccgttgat gttcgtctga gcgattggtg taccggttct 3000
ccggaaccgg gtaatattac cgttgcaaaa gccggtgcac gtggtgatcg tgaaaatgtg 3060
cagaaaattg gctgtggtct gtatgcaacc gcaccggtgg caattccgga aggtaaagtt 3120
ctgaccagcg ttaccctgcc gtctgatgaa cgttttcatg tgtttgcaat tgcaaccgat 3180
gcaaccggtg atgttccggc accgcaggtt gaagttaccg cacaggctcg ttgtctgggt 3240
ggtaaagcat ttgttgcagt tcgtgcactg aataccggtg aacagcctgc agcaattgaa 3300
ctggcaaccc cgtatggtag caaactgttt ggtgatgttg ctccgggtgc aaatgcatat 3360
cagagctttg caacccgtgc agcagccgtt gaagccggtg aagttaccgt taccgtgacc 3420
acaccggatg gtgaaccgca gcaggttacc gcagcatatg atgcagcggc atgtagctaa 3480
taa 3483

<210> SEQ ID NO 18
<211> LENGTH: 3483
<212> TYPE: DNA
<213> ORGANISM: Artificial Sequence
<220> FEATURE:
<223> OTHER INFORMATION: synthetic polynucleotide

<400> SEQUENCE: 18
gcaggcaccg aagcagcaac cggttctgat gcagcagcag ttgatggtcc gctggttgat 60
tatgtgaatc cgtttattgg caccaaagat gatggtaata cctatccggg tgcagcagtt 120

```
ccgtttggta tggttcagct gtctccggat aatggtcata atgtgggcta tgattatgat    180
cgtaccagcg ttcgtggttt tagcctggtt catctgagcg gtgttggttg tggtctgggt    240
ggtccgctgc cgacactgcc gaccaccggt gcaattacca gcaccgatta tggtcagtat    300
gcactgggtt ttagccatga tgatgaagaa gcatctccgg gttattatcg tgttggtctg    360
caggcacctg caggaaccat tgaagcagaa ctgaccgcaa ccgaacgtac cggtgttcag    420
cgttatacct ttccggcaac cgcacaggca aatgttctgc tgaatgcagg tcaggcactg    480
aatcgtgtta ccgaatctga tgttcgtgtt gttgatgatc gtaccgttga aacccgtatt    540
accgtgcgtg gtttttgtca ggataccgaa ccgcagacca tttggacccg taccaccttt    600
gatcgtccgt ttgttgcaca tggcacctgg gatggtcagg ttgttaccgc aggcgcagat    660
gcagcaagcg gtggtgaagg tcgtcgtggt gcatatgtta cctttgatac aaccggtggt    720
gatctggatg ttgaagcagt taccgcaatg agctatgttg gtgcagatgg tgcagcagca    780
aatctggcag cagaagcagg caccttgac gcagttcatg atgcagcacg tagcgcatgg    840
gaagaacgtc tgggtctggt tcgtgttgca cagggtgatc cggatgatct gcgtaccttt    900
tatagcagcc tgtatcgtag ctttctggca ccgaatgttg gttctgatgt ggatggtcgt    960
tatcgtggtt gggatcagga agttcacgca gcagaaccgg attttaccta ttatcagaat   1020
tatagcctgt gggataccta tcgtacccaa cagcaactgc tgtatctgct ggcaccggat   1080
gaaagcgcag atatggcact gagcctggtt cgtcagggtc agcagggtgg ttggctgcct   1140
cgttggggtt atggtacagt ggaaaccaat attatgaccg gtgatccggc aaccccgttt   1200
ctggttagcg catggcgtca gggtctgctg gcaggtcatg aagaagaagc atacgcagtc   1260
ctgcgtgaaa atgcagatgg tgttcctccg gcagatagcc cgtttaatgg tcgtgcagcc   1320
aatgttgaat atctgcgtga tggttttgtt ccgcatgaac cggcacgtag cggtaaaccg   1380
ggtgattatg atctgcagca tggtgcaagc gcaaccatgg aatatgcact ggcagatgca   1440
atgctgagca ccatggcacg tggtctgggt catgatgaag atgcagatcg ttatgcagcc   1500
cgtggtcaga gctatcgtaa tgtttttgat ccgcgtaccg gtaattttcg tgcacgtaat   1560
gccgatggtt tttttgttgg tgatgcagat ccggcacatt ctgatggttt tcatgaaggc   1620
accgcagttc agtatcagtg gctggttccg caggatgttc cgggtctgtt tgatctgatg   1680
ggtggcaccg atgcagccgt tgatcgtctg gatgcatttt ttgcctatga tgaactggtt   1740
gcagatcctc cgcatgttgc aagcgaagtt tgggttaatg gcacctatga ttattatggc   1800
tgggaaacct ataatccgaa taatgaaccg aatctgcatg caccgtatgt ttatctgtgg   1860
accggtcagc cgtggaaaac caccgatgtt gttcgtgcag caagcaccct gtttaccgat   1920
ggtccggatg gtgttaccgg taatgatgat ctgggcacca tgagcgcatg gcatgttctg   1980
agcagcattg gtgtttatcc gattgttccg ggtgccgatc tgtggggtct gaccacaccg   2040
ctgtttgatg atgttaccat taccctggac ccggaagttt ttggtcgtga tagcctgcgt   2100
ctgaccgcag atggtgtggc accggatacc cattataccc agagcgttag cctgggtggt   2160
gaaccgctgg atcgtgcatg ggttacaggt gatgaactga ccgctgcagg caccctggat   2220
gttaccgttg gcaccgaacc gagcgcatgg gcaaccgatc cggcagcatc accgggtgca   2280
gttgttccgg ctgatggcac cgttgaacgt ctgtttgttg gtgcaacacc gcgtcagccg   2340
gttctggcac cgggtggtcg taccgaagtt gcagttcagg ttgttgccca gggtgcaggc   2400
acctctagcg gcaccctgga agtgacctct gatggtgcag ttaccgccac caccgatctg   2460
```

-continued gcagaatgga ccgcagaatc tgatggtctg cctgccaccg ttgaaggaac cgttaccatt 2520
gaagctccgg cagatgccga accgggtctg cataccgttc gtctggttgt tcgtgatgca 2580
gccggtacag aagcagttcg cgaagttagc gttgttgtta gcggtgaaag ctggattgca 2640
gatgcctttg ataatgtggg tattggtgat gccggtgcag caaatgcaaa tctggatggt 2700
agcggtgcct atctgctgcg tgatctgctg gccgatctgg gtgcagttca gggtctggaa 2760
ctgaccgttc cgggtactga tctgacctat accctgggtg caccgcgtgc tggtgcaccg 2820
gataatgttg cagccagcgg tgaagttctg gaagttccgg aacatctgcg tagcgcacgt 2880
catctgagcg ttgtgggcac cagcacccat ggtacacatg gtggtggtct ggttctgggt 2940
tttgccgatg gtagcagcca gaccgttgat gttcgtctga gcgattggtg taccggttct 3000
ccggaaccgg gtaatattac cgttgcaaaa gccggtgcac gtggtgatcg tgaaaatgtg 3060
cagaaaattg gctgtggtct gtatgcaacc gcaccggtgg caattccgga aggtaaagtt 3120
ctgaccagcg ttaccctgcc gtctgatgaa cgttttcatg tgtttgcaat tgcaaccgat 3180
gcaaccggtg atgttccggc accgcaggtt gaagttaccg cacaggctcg ttgtctgggt 3240
ggtaaagcat ttgttgcagt tcgtgcactg aataccggtg aacagcctgc agcaattgaa 3300
ctggcaaccc cgtatggtag caaactgttt ggtgatgttg ctccgggtgc aaatgcatat 3360
cagagctttg caacccgtgc agcagccgtt gaagccggtg aagttaccgt taccgtgacc 3420
acaccggatg gtgaaccgca gcaggttacc gcagcatatg atgcagcggc atgtagctaa 3480
taa 3483

<210> SEQ ID NO 19
<211> LENGTH: 5283
<212> TYPE: DNA
<213> ORGANISM: Artificial Sequence
<220> FEATURE:
<223> OTHER INFORMATION: synthetic polynucleotide

<400> SEQUENCE: 19
gcagaaccgg gtgattttag cagcagcttt gaatctggcg atccggcagc actgccgacc 60
accgttgcag aacgtgatgg tgcaccgtgg caggcaaatg ttggtagctt taccgcaggt 120
ctgcctggta gcgttctggg tcagctgaaa ggtgttaccg caagcgcaca gaatctgccg 180
aatgaaggtg cagcaaatct ggcagatggt agcagcggca ccaaatggct ggcatttgca 240
agcaccggtt gggttcgtta tgaatttgca gaaccggtta gctttgttgc atataccatg 300
accagcggtg atgatgccgc aggtcgtgat ccgaaaacct ggaccgttga aggtagcaat 360
gatggttcta cctgggcagc actggatcgt cgtaccgatg aagattttcc gaatcgtcag 420
cagacccgta cctttgaact ggaagcaccg accgcagcat atacctatct gcgtctgaat 480
gttaccgcaa atagcggtga tagcattgtt cagctggcag gttgggatct gagcgcagat 540
ctgtctgcag gtccgagcgc agcaccgatg accaccaaag ttggcaccgg tccgcgtgtt 600
agctttacca ataaagccgg tgttggtttt agcggtctgc atagcctgcg ttatgatggt 660
agccatctgg ccgatggtga aacctatgca accaatgtgc tgtatgatga tgttgatgtt 720
gtggttggtg aagatacccg tctgagctat accatttttc cggaactgct ggatgatctg 780
cagtatccga gcacctatgc agcagttgat gttctgttta ccgatggcac ctatctgagc 840
gatctgggtg cacgtgatgc acatgaaacc gttgcaaccg cacaggcaca gggtgaaggt 900
aaaattctgt atgccgatca gtggaatagc gttcgtgttg atctgggtga tgttgcagaa 960
ggtaaaaccg ttgatcaggt tctgctgggt tatgataatc cgggtggtca tgcaggcacc 1020

```
aaatttgcag gttggctgga tgatgttgaa attaccgcag aaccggcaac cattgatggt   1080
agctcactgg caaattatgt tgatacccgt cgtggcaccc tggcaagcgg tagctttagc   1140
cgtggtaata atattccggc aaccgcaacc ccgaatggtt ttaatttttg gaccccgtat   1200
accaatgcaa gcagccagag ctggctgtat gaatatcata aagccaataa tgcgaataat   1260
aaaccggttc tgcagggttt tggtattagc catgaaccga gcccgtggat gggtgatcgt   1320
aatcagctga cctttctgcc gagcaccgca agcggtacac cggatgcaac cctgagcacc   1380
cgtggtctgg aatttgatca tgcagatgaa accgcacgtc cggattatta tggtgtgacc   1440
tttaccaatg gtagcgcaat tgaagcaacc ccgaccgatc atggtgcagt tctgcgtttt   1500
agctatccgg gtgcaaaagg tcatgttctg gtggataaag ttgatggtag cagtaaactg   1560
acctatgatc aggcaaccgg caccattagc ggttgggttg aaaatggtag cggtctgagc   1620
gttggtcgta cccgtatgtt tgttgcaggc acctttgatc gtagcccgac cgcagttggc   1680
acagcagcag gtaatcgtgc agatgcacgt tttgcaacct ttgaaaccag cagcgataaa   1740
accgtggaac tgcgtgttgc aaccagcttt attagcctgg atcaggcacg taaaaatctg   1800
gatctggaag ttaccggtaa aacctttacc gaagttaaag cagcagcagc acaggcatgg   1860
aatgatcgtc tgggtgttat tgaagttgaa ggtgcaagcg aagatcagct ggttaccctg   1920
tatagcaatc tgtatcgcct gaatctgtat ccgaatagcc agtttgaaaa taccggcacc   1980
gcacaggaac cggtttatcg ttacgcatct ccggttagcg caaccaccgg tagcgcaacc   2040
gatacccaga ccaatgccaa aattgtggat ggcaaaattt atgtgaataa tggcttttgg   2100
gatacctatc gtaccgcatg gcctgcatat agcctgctgt atccggaact ggcagcagaa   2160
ctggttgatg gttttgttca gcagtatcgt gatggtggtt ggattgcacg ttggagcagt   2220
ccgggttatg cagatctgat gaccggtaca agctctgatg ttgcatttgc agatgcctat   2280
ctgaaaggta gcctgccgac cggtacagca ctggaagcat atgatgcagc actgcgtaat   2340
gcaaccgttg cacctccgag caatgcagtt ggtcgtaaag gtctgcagac aagcccgttt   2400
ctgggtttta caccggaaag cacccatgaa agcgttagct ggggtctgga aggtctggtt   2460
aatgattttg gcattggcaa tatggctgca gcactggcag aagatccggc aacaccggaa   2520
gaacgtcgtg aaaccctgcg tgaagaaagc gcatattttc tggaacgtgc cacccattat   2580
gttgaactgt ttgatccgga agtggatttt tttgttccgc gtcatgaaga tggtacatgg   2640
gcagttgatc cggaaaccta tgatccggaa gcatggggtg gtggttatac cgaaaccaat   2700
ggctggaatt ttgcatttca tgcaccgcag gatggtcagg gtctggcaaa tctgtatggt   2760
ggtaaacagg gtctggaaga taaactggat gaattttta gcacaccgga aaaaggtgca   2820
ggtaatggtg gtattcatga acagcgtgaa gcacgtgatg ttcgtatggg tcagtggggt   2880
atgagcaatc aggttagcca tcatattccg tggctgtatg atgcagccgg tgctccgagc   2940
aaagcacagg aaaaagttcg cgaagttacc cgtcgtctgt ttgttggtag cgaaattggt   3000
cagggttatc cgggtgatga agataatggt gaaatgtcct cctggtggat tttgcaagc   3060
ctgggttttt atccgctgca ggttggtagc gatcagtatg cagttggttc tccgctgttt   3120
gataaagcaa ccgttcatct gccggatggt gatctggttg ttaatgccga aaataatagc   3180
gtggataatg tgtatgttca gagcctggca gttgatggtg aagcacgtac cagcaccagc   3240
ctgagccagg cagatctgag cggtggcacc accctggatt ttgttatggg tccggaaccg   3300
agcgattggg gcaccggtga agatgatgca cctccgtcac tgaccgaagg tgatgaacct   3360
```

-continued

```
ccgacaccgg ttcaggatgc aaccaccgca ggcctgggca ccaccaccgt tgccgatggt   3420

gatgccacca cctctgcagc agccctgacc gataatacca gcggcacccg taccaccttt   3480

gcaaccacca ccccgagcat tacatgggca ggtaatggca ttcgtccgac cgttggtagc   3540

tataccctga cctctggtgc aagcggcacc gcaagcccgt ctgcatggac cctggaaggt   3600

tctgatgatg gcgaaacctg gaccacactg gatgaacgta gcggtgaaca gtttcgttgg   3660

gcactgcaga cccgtccgtt taccgttgcc gaaccgaccg catttgcacg ttatcgtgtt   3720

accgttaccg caaccagcgg ttctggtgca ctgagcctgg cagaagttga actgctggca   3780

gatccgaaag aaagcggtgc agaagaactg accctgtctg cagcaccgga tcgtgatggc   3840

gttaccggtc gtgaagttag cggttctttt gcaaccctga ccggtgttga aggtgatgtt   3900

gccgcactgg atgttcaggt tgcatttggt gatggtagcg aaccggttgc aggtacactg   3960

cgtgccggtg catttggtgg ttatgcagtt gatgcagcac atacctggac cgcaccgggt   4020

gtttatccgg ttaccgtgac cgttagcggt gaaggtattg aaaccgttag cgcaagcagc   4080

tatgttagcg ttagcctgct gcgtgaaggt tctctgctgg cagcatatga taatgtgtgc   4140

attggtgatg caggtacaac cgttggttct tgtgatggtc agggcgtttt ttttgatcgt   4200

gcacagctgg cagcaaaagg ttttgtgcag ggtgaacgtg caaccgttcc gggtacagat   4260

ctggcatttg atgttccggc agttccggct ggtcagcctg ataatgcaac cggtgatggt   4320

cagaccattg aactggatgt tccggctgat gcagaacagc tgagcgttat tggcaccggc   4380

accgaaaaaa atcagcaggc aaccggtaca ctgacctttg atgatggttc tacccagccg   4440

attgatctga gctttggtga ttggagcggt gcagcacgta atccggtgtt tggtaatatt   4500

ccggttgcag ttaccgatag ccgtctgcgt ggtggttctc cgcagaccgg tacaccggca   4560

gcattttttg ccaccgcacc gattaccctg ccggaaggta aacgtccggt tagcctgacc   4620

ctgccggatc agcctggtga actgagccgt gatggtcgta ttcatgttgt tgcagttgca   4680

catgatggca cctttgcaga acatcctgca ctggaagtga ccgcagcaga aggtgttacc   4740

ctggcagttg gtcagacctc agatgttgca ctggcacagg ttgccggtgg tcgtgaaggt   4800

gcagatctgc gtgccgcagt tacctggggt gatggttctg atgtggcagc cggtgccgtt   4860

accgatggta gcgttagcgg tagccatgca tataccgcag caggcaccta taccgcatat   4920

gttgttgtgg atgatggttg gaccagccag gttgttgaag ttccggtgac cgttacagaa   4980

gccgaaccgg cactggccgt tgatgtcacc gttagcaccc gttgcctggc aggtaaagca   5040

tatgttgcag tgcgtgcaga aaatggtgaa gatgttccgc tggcaattcg tctggttacc   5100

ccgtttggca ccaaagaagt tgcagcagtt gctccgggag ccaatgcata tcagagcttt   5160

gcaacccgtg ttaccgcagt tgaagcaggc accgttaccg ttgaagccac ccgtggcacc   5220

ggtgatgaag aagttaccgc cagcattcag gcagattatg cagccgttac ctgcggttaa   5280

taa                                                                 5283
```

<210> SEQ ID NO 20
<211> LENGTH: 4881
<212> TYPE: DNA
<213> ORGANISM: Artificial Sequence
<220> FEATURE:
<223> OTHER INFORMATION: synthetic polynucleotide

<400> SEQUENCE: 20

```
gatatgcctg cagcacaggc accgaatggt ctggcaaaag ttaatccgcg taccacaccg     60

ggtcgtaata ataccggtta tgattatgcc cagagcaaaa ttagcggttt tacccatacc    120
```

-continued

```
aatctggatg gtgttggtgg tagcggtggt ggtggtgatc tgctggttgt tccgaccagc    180
ggtagctata ccgcacgtcc gggtacaggc acctatgcac atccgtttag ccatgatgat    240
gaagatgcag gtccgggttt ttatagcgtt ggtctgggta atgttgcagg caccgatggt    300
gcaattaccg gtgctccggg tacaattgaa gcagaagttg cagcagcaac ccgtagcggt    360
gttcatcgtt atgcatttcc ggcaggtagc accccgagcc tggttgttga tctggaaacc    420
aataatacca gccgtcgtag cagcagcgtt caggttgaaa cccgtgcaga tggcaccgtt    480
gaactgagcg gtcaggttac cggctatttt tataatgcag cctataccct gtattatacc    540
gcacgcaccc tgcagcctgc aaccgttcag acctggggtg atgatgatcg tctggttgat    600
gcaaccgcac aggatggtgt tgataccggt gcaattctga cctttgatcc ggcagatgcc    660
ggtgaaattg gtctgcaggt taccctgtct ccggttagcg ttgaacaggc acgtattgat    720
cagcaggttg aactgggtga tctgagcttt gatgcaattc gtgatcgtac ccgtgcagaa    780
tggaatgcaa ccctgggtcg tgttgcaatt gatgcaagca ccgcaaccga tccgaccggt    840
gaactgcagc gtctgtttta tacccatctg tatcgcatgt ttgcaatgcc gatgaatgca    900
accagcacca gcggcaccta tcgtggtgtt gatggtgcag ttcatgcagc acagggcttt    960
acctattatg atagctgggc aacctgggat gattttcgca aatttagcgt gattgcctat   1020
attgatccgg cactgtatcg tgatatggtt cagagcctgg tttacctgtt tgcagatgca   1080
gaagcaaccg gtacaggcgg tggtctgggt ggttttgttc atagcgttcc gaccgttcgt   1140
tgggaacgta gcagcgttgt tgttgcagat gcaattgcca aaggctttga tggttttgat   1200
cgtctggatg aagcatatcc ggcactgcag cgcctggttg gtcagtatag cgcagatgaa   1260
ctgcgtcgtg gttatgttgc aggtaatccg ggtgcaagcg ttcagcgtgg ttatgatcag   1320
tatggtctga gcgttattgc cgatgaactg ggtctgaccg aagaagcaga aaccctgcgc   1380
gaacaggcaa gctggccgat tgaaaaactg accaaaccgg gtgcatggac cgcagcagat   1440
ggtacacagg ttggtctgct gacaccgcgt gcagccgatg gtagctggca gagcgcagat   1500
catgccaaat ttgaagcagc aggtctgtat cagggcaccc tgtggcagta tcattggtat   1560
gatgcctatg atatggatgc actggttgaa gcaatgggtg gtcatgaagc agcccgtctg   1620
ggtatgcgtc atatgtttgg tgaacatgca ccggatgatg gtaaagcaat gctgcatagc   1680
aatgccaatg aaattgatct gcaggcaccg tacctgttta attataccgg tgaaccgagc   1740
ctgacccaga aatgggcacg tgcaatttat accaaagaaa cctggaatcg ctatattgca   1800
accggtagca gctctgcagt tccgtcaggt ggtggtgaat ttacacctcc gctgaaaacc   1860
aaagtttatc gtctggaccc tcgtggtatg ctgccgacca tggataatga tgcaggtaca   1920
atgagcacca tgtttgttgc agcagccgtt ggtctgtttc cggttaccgc aggtagcagc   1980
cagtttcagg ttggtagccc gtttttttgat agcaccacca ttacctatga tgatggtagc   2040
gcatttaccg ttaccgcaga tggtgttagc gaagatgcct tttatgttca gagcgcaacc   2100
ctggatggtg caaccttttgg taatacctgg gttgattatg caaccgttgt tggtggtgca   2160
gatctggcat ttcgtatggg tgaacagccg agcgattggg gcaccgatac cgcaccggca   2220
tttagcatga gcaccgccac cgatgaaccg gcagaaggtc ctcgcgttag cgcagaaccg   2280
accaccgtgc agaccggtga tggtggtgca ctggatgcaa ccgttaccct gacactggat   2340
ggcgcacgtc tggcagcacc ggcaggtaca gatctggtta ccagcggtgc agcaagcgtt   2400
gttggtctgc cggatggtgt taccgcagca gttaccgttg caagcccgac cgcactgacc   2460
```

-continued

```
gttagcctga ccggcaccgc atcagcagat gcacgttttt ttgtgcatct gcgtgatgca   2520
gcactggccg atggtgttgc agccgcaagc ctgcagggtc agggtgttag cgttcgttct   2580
ccgctgcgtc tgagcgttgc aagcgcagaa cgtgatgcac tggcagcact ggttgatgat   2640
gccgttctgg ttcgtcatgg taattatagc agcgttacct ttgatcgttt tagcaccgct   2700
ctgacaaaag cacaggaagc actgggcgac gaagcagcaa ccagcattgc actgcgtttt   2760
gcagcagatc gtctgggtgc agcagcagat gcactggatc tgaccggtgg tggttatcgt   2820
accctggaag cagaacagag cgaagcatgg tctggtggtg aactgaaaaa tgaagccaat   2880
agcagcagcg gtaatctggg tggtgttcgt agcggtagct gggttcagta tcgcgatatg   2940
acctttgaaa ccgcagccgg tgatacacct ccgcgttttc tgaccgttcg ttatgatacc   3000
agctttgcac cgaccgatac ccccgagcacc gttcgtgttc atgccggtga tgtttctggt   3060
ccggttgttg caaccgttga tctgaaaggc accagcggtt ggggtaaata taccgaagtt   3120
accgcagaac tgggtgatgt tcaggccctg gttgatgccc aggttgttac ctttgaactg   3180
ctggcaccga gcggtcgtag ctgggttggt aattttgatt ggtttcgctt tagcgcagaa   3240
gatccggcag caccgggtca gcctggtgaa agcccgaccg ttaccattga agccgaagat   3300
tggaccgcaa gcagcggtcg tggtctgaaa aaagaaagca gcacctggac cagcggtccg   3360
gtgaccaatg ttggtggtac agcagatggt gattggattg cctatggtga agttgatctg   3420
ggtgaactgc cgctgggcga actgagcgtt cattatgtgc ataatagcaa tcgcagcggt   3480
aataatagcg cactgagcgt ttatctggat gcatttgatc cggctaatcc gggtgaaccg   3540
tttgttaccg ttccgctgcc gaccaccggt agcagttgga ccgcagatgg cacagccacc   3600
gttgttctgc cggaaaccgt gcagggcacc catgaagttt ttgttcgtct gagcaccgaa   3660
ccgtatgcag atcatccgta tgttgcaaat ctggatagcc tgacctttgc accgggtggt   3720
ccgaccagcg ttgtggttga aagcgaagcc tggaccagca attctggtcg tggcctgaaa   3780
aatgaatctt ctacctggac ctctggtccg gttacaaatg tgggtggcac cgctgatggc   3840
gattggctgg catatggcga aattgatctg ggcagcgcag cactggatca gctgtctgtg   3900
cattatgttc ataattctaa tcgctctggt cgtaattctg cactgtctgt gtatctggat   3960
gcctttgatc cggcaaatcc gggtgaaccg tttgtgacag tgccgctggc aaataccggt   4020
agctcttgga ccaccgatgg tactgcagtt gtggatctgc cgtctaccgt tcgtggtaaa   4080
catcaggttt gggttcgtct gtctaccgaa gcatatgccg atcatccgta tgtggccaat   4140
ctggattcta tgcgcttttt taccgatgca tatgatgttg aagttcctcc gaccgataca   4200
gcagcactgg cagccgttgt tgatgcagca ggtacaccgg aagcagaaat tgcacgttat   4260
ggtcgtattg atgcccgtgt ttttacccgt gaactggcag cagcacgtag cgttctggcc   4320
gatgccggtg caacacaggc acaggcagat gaacgtgctc gtcgtctggg tctggcaacc   4380
gatcagctgg ttccggcaga acgtcgtcgt ctggaaaatc tggttgccag cgcagaagca   4440
ctgaccgacg aaggttattc tccggaaagc tggcaggcat ttcgtaccgc actggctgct   4500
gcaaccggca ccctggatga tgcagcagca tctgatgaag cactgcatga tgcacgtctg   4560
gcgctgcagg gtgcagttga tgcactggaa gaaccggcag atgttgttct ggttgaagtt   4620
gaagtttctc cgcgttgtct ggcaggtaaa ccgtatgttg ccgttcgtgc agttaatgtt   4680
tctgatgcag ccgttgatgt tgaactggca agctctctgg gcacccgtag ctttgttggt   4740
gtggcaccgg gtgcgagcgc atatcagagc tttgcagccc gtagcgcaac cggtgatctg   4800
gatgttaccg tgaccgcaac cggtgcagat ggtactcaga ccgttgaaca ggttgtgacc   4860
```

gttccgagct gtagctaata a 4881

<210> SEQ ID NO 21
<211> LENGTH: 9
<212> TYPE: PRT
<213> ORGANISM: Artificial Sequence
<220> FEATURE:
<223> OTHER INFORMATION: synthetic peptide

<400> SEQUENCE: 21

Val Gly Pro Gly Ser Asp Glu Val Asp
1 5

<210> SEQ ID NO 22
<211> LENGTH: 1308
<212> TYPE: DNA
<213> ORGANISM: Artificial Sequence
<220> FEATURE:
<223> OTHER INFORMATION: synthetic polynucleotide

<400> SEQUENCE: 22
atgaagcttt ccaccatcct cttcacagcc tgcgctaccc tggccctgga caacggcctg 60
gcccgaaccc ccaccatggg ctggctgcac tgggagcgat tcatgtgtaa cctggactgt 120
caggaagagc ccgactcttg tatctctgag aagctgttca tggaaatggc cgagctgatg 180
gtgtctgagg gctggaagga cgccggctac gagtacctgt gtatcgacga ctgttggatg 240 gcccccccagc gagactctga gggccgactc caggccgacc cccagcgatt cccccacggc 300
atccgacagc tcgccaacta cgtgcactct aagggcctga agctgggcat ctacgccgac 360
gtgggcaaca agacctgtgc cggcttcccc ggctctttcg gctactacga catcgacgcc 420
cagaccttcg ccgactgggg cgtggacctg ctgaagttcg acggctgtta ctgtgactct 480
ctcgagaacc tggccgacgg ctacaagcac atgtctctgg ccctgaaccg aaccggccga 540
tctatcgtgt actcttgtga gtggcccctg tacatgtggc ccttccagaa gcccaactac 600
accgagatcc gacagtactg taaccactgg cgaaacttcg ccgacatcga cgactcgtgg 660
aagtctatca agtctattct ggactggacc tctttcaacc aggagcgaat cgtcgacgtc 720
gccggacccg gcggatggaa cgaccccgac atgctggtga tcggcaactt cggcctgtct 780
tggaaccagc aggtgaccca gatggccctg tgggctatca tggctgcccc cctgttcatg 840
tctaacgacc tgcgacacat ctctccccag gccaaggccc tgctccagga caaggacgtg 900
atcgccatca accaggaccc cctgggcaag cagggctacc agctccgaca gggcgacaac 960
ttcgaggtgt gggagcgacc cctgtctggc ctggcctggg ccgtggccat gatcaaccga 1020
caggagatcg gcggaccccg atcttacacc atcgccgtgg cctccctggg aaagggcgtg 1080
gcctgtaacc ccgcctgttt catcacccag ctcctgcccg tgaagcgaaa gctgggattc 1140
tacgagtgga cctctcgact gcgatctcac atcaacccca ccggcaccgt gctgctccag 1200
ctcgagaaca ccatgcagat gtctctgaag gacctgctga cgcgtgaaca aaaactcatc 1260
tcagaagagg atctgaatag cgccgtcgac catcatcatc atcatcat 1308

<210> SEQ ID NO 23
<211> LENGTH: 436
<212> TYPE: PRT
<213> ORGANISM: Artificial Sequence
<220> FEATURE:
<223> OTHER INFORMATION: synthetic polypeptide

<400> SEQUENCE: 23

-continued

```
Met Lys Leu Ser Thr Ile Leu Phe Thr Ala Cys Ala Thr Leu Ala Leu
1               5                   10                  15

Asp Asn Gly Leu Ala Arg Thr Pro Thr Met Gly Trp Leu His Trp Glu
            20                  25                  30

Arg Phe Met Cys Asn Leu Asp Cys Gln Glu Glu Pro Asp Ser Cys Ile
        35                  40                  45

Ser Glu Lys Leu Phe Met Glu Met Ala Glu Leu Met Val Ser Glu Gly
    50                  55                  60

Trp Lys Asp Ala Gly Tyr Glu Tyr Leu Cys Ile Asp Asp Cys Trp Met
65                  70                  75                  80

Ala Pro Gln Arg Asp Ser Glu Gly Arg Leu Gln Ala Asp Pro Gln Arg
                85                  90                  95

Phe Pro His Gly Ile Arg Gln Leu Ala Asn Tyr Val His Ser Lys Gly
            100                 105                 110

Leu Lys Leu Gly Ile Tyr Ala Asp Val Gly Asn Lys Thr Cys Ala Gly
        115                 120                 125

Phe Pro Gly Ser Phe Gly Tyr Tyr Asp Ile Asp Ala Gln Thr Phe Ala
    130                 135                 140

Asp Trp Gly Val Asp Leu Leu Lys Phe Asp Gly Cys Tyr Cys Asp Ser
145                 150                 155                 160

Leu Glu Asn Leu Ala Asp Gly Tyr Lys His Met Ser Leu Ala Leu Asn
                165                 170                 175

Arg Thr Gly Arg Ser Ile Val Tyr Ser Cys Glu Trp Pro Leu Tyr Met
            180                 185                 190

Trp Pro Phe Gln Lys Pro Asn Tyr Thr Glu Ile Arg Gln Tyr Cys Asn
        195                 200                 205

His Trp Arg Asn Phe Ala Asp Ile Asp Asp Ser Trp Lys Ser Ile Lys
    210                 215                 220

Ser Ile Leu Asp Trp Thr Ser Phe Asn Gln Glu Arg Ile Val Asp Val
225                 230                 235                 240

Ala Gly Pro Gly Gly Trp Asn Asp Pro Asp Met Leu Val Ile Gly Asn
                245                 250                 255

Phe Gly Leu Ser Trp Asn Gln Gln Val Thr Gln Met Ala Leu Trp Ala
            260                 265                 270

Ile Met Ala Ala Pro Leu Phe Met Ser Asn Asp Leu Arg His Ile Ser
        275                 280                 285

Pro Gln Ala Lys Ala Leu Leu Gln Asp Lys Asp Val Ile Ala Ile Asn
    290                 295                 300

Gln Asp Pro Leu Gly Lys Gln Gly Tyr Gln Leu Arg Gln Gly Asp Asn
305                 310                 315                 320

Phe Glu Val Trp Glu Arg Pro Leu Ser Gly Leu Ala Trp Ala Val Ala
                325                 330                 335

Met Ile Asn Arg Gln Glu Ile Gly Gly Pro Arg Ser Tyr Thr Ile Ala
            340                 345                 350

Val Ala Ser Leu Gly Lys Gly Val Ala Cys Asn Pro Ala Cys Phe Ile
        355                 360                 365

Thr Gln Leu Leu Pro Val Lys Arg Lys Leu Gly Phe Tyr Glu Trp Thr
    370                 375                 380

Ser Arg Leu Arg Ser His Ile Asn Pro Thr Gly Thr Val Leu Leu Gln
385                 390                 395                 400

Leu Glu Asn Thr Met Gln Met Ser Leu Lys Asp Leu Leu Thr Arg Glu
                405                 410                 415
```

```
Gln Lys Leu Ile Ser Glu Glu Asp Leu Asn Ser Ala Val Asp His His
            420                 425                 430

His His His His
        435


<210> SEQ ID NO 24
<211> LENGTH: 2743
<212> TYPE: DNA
<213> ORGANISM: Artificial Sequence
<220> FEATURE:
<223> OTHER INFORMATION: synthetic polynucleotide

<400> SEQUENCE: 24

atgaagcttt ccaccatcct cttcacagcc tgcgctaccc tggctgccgc ccagcaggga      60

gcctctcgac ccggaccccg agatgcccag gctcaccccg gacgacctcg agctgtgccc     120

acccagtgtg acgtgccccc caactctcga ttcgactgtg cccccgacaa ggccatcacc     180

caggagcagt gcgaggcccg aggctgttgt tacatccccg ctaagcaggg cctgcagggc     240

gctcagatgg gccagccctg gtgtttcttc ccccctcttt acccctccta caagctggag     300

aacctgtcct cttcggagat gggctacacc gccaccctga cccgaaccac ccccaccttt     360

ttccccaagg acatcctgac cctgcgactg gacgtgatga tggagaccga gaaccgactg     420

cacttcacca tcaaggaccc cgccaaccga cgatacgagg tgcccctgga gacccccccac     480

gtgcactctc gagccccttc ccccctgtac tctgtggagt tctctgagga gcccttcggc     540

gtgatcgtgc gacgacagct ggacggccga gtgctgctga acaccaccgt ggccccccctg     600

ttcttcgccg accagttcct gcagctgtct acctctctgc cctctcagta catcaccggc     660

ctggccgagc acctgtcccc cctgatgctg tccacctctt ggactcgaat caccctgtgg     720

aaccgagacc tggcccccac ccccggtgcc aacctgtacg gctctcaccc cttctacctg     780

gccctggagg acggcggctc tgcccacggc gtgtttctgc tgaactctaa cgccatggac     840

gtggtgctgc agccctctcc cgccctgtct tggcgatcta ccggcggcat cctggacgtg     900

tacatcttcc tgggccctga gcccaagtct gtggtccagc agtacctgga cgtggtcgga     960

taccccttca tgccccccta ctggggcctg ggcttccacc tgtgtcgatg gggctactct    1020

tctaccgcca tcacccgaca ggtggtggag aacatgaccc gagcccactt cccccctggac    1080

gtgcaatgga acgacctgga ctacatggac tctcgacgag acttcacctt caacaaggac    1140

ggcttccgag acttccccgc catggtccag gagctgcacc agggaggacg acgatacatg    1200

atgatcgtgg accccgccat ctcttcttcc ggacccgccg gatcttaccg accctacgac    1260

gagggcctgc gacgaggcgt gttcatcacc aacgagaccg gccagcccct gatcggcaag    1320

gtgtggcccg gctctaccgc cttccccgac ttcaccaacc ccaccgccct ggcttggtgg    1380

gaggacatgg tggccgagtt ccacgaccag gtgcccttcg acggcatgtg gatcgacatg    1440

aacgagccct ctaacttcat ccgaggctct gaggacggct gtcccaacaa cgagctggag    1500

aacccccccct acgtgcccgg cgtggtgggc ggaaccctgc aggccgccac catctgtgcc    1560

tcttcgcacc agtttctgtc tacccactac aacctgcaca acctgtacgg actgaccgag    1620

gccattgcct ctcaccgagc cctggtgaag gcccgaggca cccgaccctt cgtgatctct    1680

cgatctacct tcgccggcca cggccgatac gccggacact ggaccggcga tgtgtggtcc    1740

tcttgggagc agctggcctc ttctgtgccc gagatcctgc agttcaacct gctgggcgtg    1800

cccctggtgg gcgccgacgt gtgtggcttc ctgggcaaca cctctgagga gctgtgtgtt    1860

cgatggaccc agctcggcgc cttctaccct ttcatgcgaa accacaactc cctgctgtct    1920
```

```
ctgccccagg agccctactc gttctctgag cccgctcagc aggccatgcg aaaggctctg   1980

accctgcgat acgccctgct gccccacctg tacaccctgt tccaccaggc ccacgtggct   2040

ggagagaccg tggcccgacc cctgttcctg gagttcccta aggactcttc tacctggacc   2100

gtggaccatc agctgctgtg gggcgaggcc ctcctgatca cccccgtgct gcaggccggc   2160

aaggctgagg tgaccggcta cttccctctg ggcacctggt acgacctgca gaccgtgcct   2220

gtggaggccc tgggatctct gcccccctcct cccgccgctc cccgagagcc cgccatccac   2280

tctgagggcc agtgggtgac cctgcccgct cccctggaca ccatcaacgt gcacctgcga   2340

gccggctaca tcatccctct gcagggaccc ggcctgacca ccaccgagtc tcgacagcag   2400

cccatggccc tggccgtggc tctgaccaag ggcggagagg cccgaggcga gctgttctgg   2460

gacgatggcg agtctctgga ggtgctggag cgaggcgcct acacccaggt gatctttctg   2520

gcccgaaaca acaccatcgt gaacgagctg gtgcgagtga cctctgaggg cgctggtctg   2580

cagctccaga aggtgaccgt cctgggcgtg gccaccgctc cccagcaggt cctgtctaac   2640

ggcgtgcccg tgtctaactt cacctactct cccgacacca aggtgctgga catctgtgtg   2700

tctctgctga tgggcgagca gttcctggtg tcttggtgtt aac                    2743


<210> SEQ ID NO 25
<211> LENGTH: 913
<212> TYPE: PRT
<213> ORGANISM: Artificial Sequence
<220> FEATURE:
<223> OTHER INFORMATION: synthetic polypeptide

<400> SEQUENCE: 25

Met Lys Leu Ser Thr Ile Leu Phe Thr Ala Cys Ala Thr Leu Ala Ala
1               5                   10                  15

Ala Gln Gln Gly Ala Ser Arg Pro Gly Pro Arg Asp Ala Gln Ala His
            20                  25                  30

Pro Gly Arg Pro Arg Ala Val Pro Thr Gln Cys Asp Val Pro Pro Asn
        35                  40                  45

Ser Arg Phe Asp Cys Ala Pro Asp Lys Ala Ile Thr Gln Glu Gln Cys
    50                  55                  60

Glu Ala Arg Gly Cys Cys Tyr Ile Pro Ala Lys Gln Gly Leu Gln Gly
65                  70                  75                  80

Ala Gln Met Gly Gln Pro Trp Cys Phe Phe Pro Pro Ser Tyr Pro Ser
                85                  90                  95

Tyr Lys Leu Glu Asn Leu Ser Ser Ser Glu Met Gly Tyr Thr Ala Thr
            100                 105                 110

Leu Thr Arg Thr Thr Pro Thr Phe Phe Pro Lys Asp Ile Leu Thr Leu
        115                 120                 125

Arg Leu Asp Val Met Met Glu Thr Glu Asn Arg Leu His Phe Thr Ile
    130                 135                 140

Lys Asp Pro Ala Asn Arg Arg Tyr Glu Val Pro Leu Glu Thr Pro His
145                 150                 155                 160

Val His Ser Arg Ala Pro Ser Pro Leu Tyr Ser Val Glu Phe Ser Glu
                165                 170                 175

Glu Pro Phe Gly Val Ile Val Arg Arg Gln Leu Asp Gly Arg Val Leu
            180                 185                 190

Leu Asn Thr Thr Val Ala Pro Leu Phe Phe Ala Asp Gln Phe Leu Gln
        195                 200                 205

Leu Ser Thr Ser Leu Pro Ser Gln Tyr Ile Thr Gly Leu Ala Glu His
```

-continued

```
    210                 215                 220

Leu Ser Pro Leu Met Leu Ser Thr Ser Trp Thr Arg Ile Thr Leu Trp
225                 230                 235                 240

Asn Arg Asp Leu Ala Pro Thr Pro Gly Ala Asn Leu Tyr Gly Ser His
                245                 250                 255

Pro Phe Tyr Leu Ala Leu Glu Asp Gly Gly Ser Ala His Gly Val Phe
            260                 265                 270

Leu Leu Asn Ser Asn Ala Met Asp Val Val Leu Gln Pro Ser Pro Ala
        275                 280                 285

Leu Ser Trp Arg Ser Thr Gly Gly Ile Leu Asp Val Tyr Ile Phe Leu
    290                 295                 300

Gly Pro Glu Pro Lys Ser Val Val Gln Gln Tyr Leu Asp Val Val Gly
305                 310                 315                 320

Tyr Pro Phe Met Pro Pro Tyr Trp Gly Leu Gly Phe His Leu Cys Arg
                325                 330                 335

Trp Gly Tyr Ser Ser Thr Ala Ile Thr Arg Gln Val Val Glu Asn Met
            340                 345                 350

Thr Arg Ala His Phe Pro Leu Asp Val Gln Trp Asn Asp Leu Asp Tyr
        355                 360                 365

Met Asp Ser Arg Arg Asp Phe Thr Phe Asn Lys Asp Gly Phe Arg Asp
    370                 375                 380

Phe Pro Ala Met Val Gln Glu Leu His Gln Gly Gly Arg Arg Tyr Met
385                 390                 395                 400

Met Ile Val Asp Pro Ala Ile Ser Ser Ser Gly Pro Ala Gly Ser Tyr
                405                 410                 415

Arg Pro Tyr Asp Glu Gly Leu Arg Arg Gly Val Phe Ile Thr Asn Glu
            420                 425                 430

Thr Gly Gln Pro Leu Ile Gly Lys Val Trp Pro Gly Ser Thr Ala Phe
        435                 440                 445

Pro Asp Phe Thr Asn Pro Thr Ala Leu Ala Trp Trp Glu Asp Met Val
    450                 455                 460

Ala Glu Phe His Asp Gln Val Pro Phe Asp Gly Met Trp Ile Asp Met
465                 470                 475                 480

Asn Glu Pro Ser Asn Phe Ile Arg Gly Ser Glu Asp Gly Cys Pro Asn
                485                 490                 495

Asn Glu Leu Glu Asn Pro Pro Tyr Val Pro Gly Val Val Gly Gly Thr
            500                 505                 510

Leu Gln Ala Ala Thr Ile Cys Ala Ser Ser His Gln Phe Leu Ser Thr
        515                 520                 525

His Tyr Asn Leu His Asn Leu Tyr Gly Leu Thr Glu Ala Ile Ala Ser
    530                 535                 540

His Arg Ala Leu Val Lys Ala Arg Gly Thr Arg Pro Phe Val Ile Ser
545                 550                 555                 560

Arg Ser Thr Phe Ala Gly His Gly Arg Tyr Ala Gly His Trp Thr Gly
                565                 570                 575

Asp Val Trp Ser Ser Trp Glu Gln Leu Ala Ser Ser Val Pro Glu Ile
            580                 585                 590

Leu Gln Phe Asn Leu Leu Gly Val Pro Leu Val Gly Ala Asp Val Cys
        595                 600                 605

Gly Phe Leu Gly Asn Thr Ser Glu Glu Leu Cys Val Arg Trp Thr Gln
    610                 615                 620

Leu Gly Ala Phe Tyr Pro Phe Met Arg Asn His Asn Ser Leu Leu Ser
625                 630                 635                 640
```

```
Leu Pro Gln Glu Pro Tyr Ser Phe Ser Glu Pro Ala Gln Gln Ala Met
                645                 650                 655

Arg Lys Ala Leu Thr Leu Arg Tyr Ala Leu Leu Pro His Leu Tyr Thr
            660                 665                 670

Leu Phe His Gln Ala His Val Ala Gly Glu Thr Val Ala Arg Pro Leu
        675                 680                 685

Phe Leu Glu Phe Pro Lys Asp Ser Ser Thr Trp Thr Val Asp His Gln
    690                 695                 700

Leu Leu Trp Gly Glu Ala Leu Leu Ile Thr Pro Val Leu Gln Ala Gly
705                 710                 715                 720

Lys Ala Glu Val Thr Gly Tyr Phe Pro Leu Gly Thr Trp Tyr Asp Leu
                725                 730                 735

Gln Thr Val Pro Val Glu Ala Leu Gly Ser Leu Pro Pro Pro Pro Ala
            740                 745                 750

Ala Pro Arg Glu Pro Ala Ile His Ser Glu Gly Gln Trp Val Thr Leu
        755                 760                 765

Pro Ala Pro Leu Asp Thr Ile Asn Val His Leu Arg Ala Gly Tyr Ile
    770                 775                 780

Ile Pro Leu Gln Gly Pro Gly Leu Thr Thr Thr Glu Ser Arg Gln Gln
785                 790                 795                 800

Pro Met Ala Leu Ala Val Ala Leu Thr Lys Gly Gly Glu Ala Arg Gly
                805                 810                 815

Glu Leu Phe Trp Asp Asp Gly Glu Ser Leu Glu Val Leu Glu Arg Gly
            820                 825                 830

Ala Tyr Thr Gln Val Ile Phe Leu Ala Arg Asn Asn Thr Ile Val Asn
        835                 840                 845

Glu Leu Val Arg Val Thr Ser Glu Gly Ala Gly Leu Gln Leu Gln Lys
    850                 855                 860

Val Thr Val Leu Gly Val Ala Thr Ala Pro Gln Gln Val Leu Ser Asn
865                 870                 875                 880

Gly Val Pro Val Ser Asn Phe Thr Tyr Ser Pro Asp Thr Lys Val Leu
                885                 890                 895

Asp Ile Cys Val Ser Leu Leu Met Gly Glu Gln Phe Leu Val Ser Trp
            900                 905                 910

Cys


<210> SEQ ID NO 26
<211> LENGTH: 2314
<212> TYPE: PRT
<213> ORGANISM: Streptomyces coelicolor

<400> SEQUENCE: 26

Met Pro Asp Arg Ser Lys Arg Pro Pro Ile Arg Ser Ser Ser Pro Arg
1               5                   10                  15

Ala Ala Leu Arg Ala Thr Val Ala Ala Val Leu Ala Gly Ala Leu Gly
            20                  25                  30

Leu Ala Ala Leu Thr Gly Gly Gly Thr Ala Val Ala Val Pro Val Thr
        35                  40                  45

Lys Ala Ser Pro Pro Ala Gly Glu Arg Ser Gly Gly Thr Asp Tyr Thr
    50                  55                  60

Lys Leu Val Asp Pro Phe Val Ser Thr Ala Gly Asp Asp Gly Asn Asp
65                  70                  75                  80

Leu Pro Gly Ala Gln Ala Pro His Ser Leu Ala Lys Val Asn Pro Met
                85                  90                  95
```

```
Thr Thr Pro Gly Arg Asn His Ser Gly Tyr Asp Tyr Asn Glu Asp His
            100                 105                 110

Ile Ala Gly Phe Thr Ala Thr Asn Leu Asp Gly Val Gly Gly Ser Gly
        115                 120                 125

Gly Gly Gly Asp Leu Leu Val Val Pro Thr Ser Gln Gln Tyr Asp Lys
    130                 135                 140

Arg Pro Ala Thr Ser Thr Tyr Ala His Pro Tyr Ser His Asp Asp Glu
145                 150                 155                 160

Ser Ala Thr Pro Gly Ser Tyr Arg Val Gly Leu Gly Ser Pro Ser Gly
                165                 170                 175

Thr Ile Asp Ala Glu Met Thr Ala Thr Thr Arg Thr Ala Leu Glu Arg
            180                 185                 190

Tyr Ala Phe Pro Ala Lys Ala Arg Pro Gln Leu Val Leu Asp Leu Ala
        195                 200                 205

Asn Asn Phe Thr Ser Arg Thr Arg Ala Thr Leu Asp Ala Thr Arg Leu
    210                 215                 220

Lys Asp Gly Thr Thr Ala Ile Ser Gly Leu Val Ala Gly Ser Phe Asn
225                 230                 235                 240

Gly Ala Ser Tyr Arg Leu Tyr Tyr Tyr Ala Thr Thr Asn Val Pro Val
                245                 250                 255

Thr Ser Leu Arg Thr Trp Gly Asp Asp Gly Ala Leu Gly Asp Ala Thr
            260                 265                 270

Ala Arg Asp Gly Thr Asp Thr Gly Ala Val Leu Gly Phe Asp Pro Ala
        275                 280                 285

Asp Gly Asp Asp Val Glu Leu Arg Val Thr Leu Ser Pro Ile Ser Ala
    290                 295                 300

Glu Gln Ala Ala Thr Asp Gln His Glu Glu Val Ala Gly Arg Thr Phe
305                 310                 315                 320

Glu Glu Val Arg Ala Gln Thr Lys Ala Asp Trp Asn Arg Thr Leu Gly
                325                 330                 335

Ala Val Ala Val Lys Ala Ser Lys Lys Ala Asp Pro Asp Ser Thr Leu
            340                 345                 350

Thr Lys Gln Phe Tyr Thr His Leu Tyr Arg Met Tyr Ala Leu Pro Val
        355                 360                 365

Asn Ala Thr Ser Thr Ser Gly Thr Tyr Arg Gly Val Asp Gly Ala Val
    370                 375                 380

His Lys Ala Asn Gly Phe Thr Tyr Tyr Asp Gly Trp Ser Thr Trp Asp
385                 390                 395                 400

Asp Phe Arg Lys Tyr Ser Val Ala Ala Tyr Ile Asp Pro Ala Thr Tyr
                405                 410                 415

Arg Asp Met Val Gln Ser Ala Val Ile Leu Phe Ala Asp Ala His Ala
            420                 425                 430

Ala Gly Lys Ser Leu Gly Ser Leu Thr His Ser Val Pro Thr Val Arg
        435                 440                 445

Trp Glu Arg Ser Ala Val Val Ile Ala Asp Ala Leu Ser Lys Gly Phe
    450                 455                 460

Lys Asp Phe Asp Arg Leu Asp Glu Ala Tyr Pro Ala Leu Lys Ser Tyr
465                 470                 475                 480

Thr Gly Tyr Tyr Thr Gly Thr Gln Leu Arg Gln Gly Tyr Ile Ala Gly
                485                 490                 495

Asp Pro Gly Thr Thr Val Gln Arg Gly Tyr Asp Gln Trp Ala Leu Ser
            500                 505                 510
```

-continued

```
Val Val Ala Asp Ala Leu Gly Glu Asp Ala Glu Ala Lys Lys Leu Arg
        515                 520                 525

Glu Gln Ala Thr Met Ala Thr Asp Asn Leu Val Lys Pro Gly Ala Trp
    530                 535                 540

Thr Ala Ala Asp Gly Thr Ala Val Gly Leu Leu Thr Pro Arg Asp Gly
545                 550                 555                 560

Glu Gly Gly Trp Gln Gly Val Asp Tyr Glu Lys Phe Glu Glu Ala Arg
                565                 570                 575

Leu Tyr Gln Gly Thr Leu Trp Gln Tyr His Trp Tyr Asp Ala Tyr Asp
            580                 585                 590

Met Gly Gly Leu Ile Glu Ala Met Gly Gly Glu Gln Ala Gly Arg Ala
        595                 600                 605

Ala Ile Arg His Met Phe Gly Glu Asp Ser Asp Ala Asp Asp Gly Ser
    610                 615                 620

Thr Met Leu His Ser Asn Ala Asn Glu Ile Asp Leu Gln Ala Pro Tyr
625                 630                 635                 640

Leu Phe Asn Tyr Val Gly Glu Pro Ser Leu Thr Gln Lys Trp Val Arg
                645                 650                 655

Ala Ile Tyr Thr Gly Glu Thr Trp Asn Arg Tyr Ile Ala Thr Gly Ser
            660                 665                 670

Thr Asn Glu Ala Pro Ser Ser Gly Gly Glu Phe Arg Pro Pro Val Lys
        675                 680                 685

Thr Lys Ala Tyr Glu Leu Ala Pro Asp Gly Phe Leu Pro Thr Met Asp
    690                 695                 700

Asn Asp Ala Gly Thr Met Ser Thr Met Phe Val Ala Ala Ala Leu Gly
705                 710                 715                 720

Leu Phe Pro Val Thr Ala Gly Ser Ser Gln Phe Gln Ile Gly Ser Pro
                725                 730                 735

Phe Phe Asp Ser Thr Thr Ile Thr Tyr Pro Asn Gly Ala Glu Phe Thr
            740                 745                 750

Val Glu Ala Asp Gly Val Ser Pro Lys Asn Tyr Tyr Val Gln Arg Ala
        755                 760                 765

Ala Leu Asn Gly Lys Arg Phe Ser Asn Thr Trp Leu Asp Tyr Ala Gln
    770                 775                 780

Ile Val Ala Gly Gly Thr Leu Lys Phe Asp Met Gly Ser Glu Pro Ser
785                 790                 795                 800

Ser Trp Gly Ala Arg Thr Glu Pro Ala Tyr Ser Leu Asn Thr Asp Ser
                805                 810                 815

Gly Asp Gly Asp Asp Glu His Ala Pro Gly Arg Gly Thr Thr Val Val
            820                 825                 830

Ser Ala Arg Pro Glu Thr Val Arg Thr Ala Ala Asp Gly Thr Val Asp
        835                 840                 845

Ala Ser Val Glu Leu Arg Leu Ser Gly Arg Ala Ser Phe Ala Ala Arg
    850                 855                 860

Lys Gly Thr Ser Leu Thr Arg Thr Gly Ala Ala Ser Val Thr Gly Leu
865                 870                 875                 880

Pro Asp Gly Val Thr Ala Asp Leu Arg Val Thr Gly Lys Arg Thr Ala
                885                 890                 895

Ser Leu Arg Leu Thr Gly Thr Thr Arg Thr Asp Ala Arg Phe Gly Ile
            900                 905                 910

Thr Phe Arg Asp Arg Ala Phe Pro His Gly Ile Pro Ala Ser Thr Val
        915                 920                 925

Thr Gly Thr Gly Val Ser Val Thr Asp Pro Leu Ile Val Ser Ala Ala
```

```
    930                 935                 940

Ala Val His Arg Gly Ser Leu Ala Ala Leu Val Asp Glu Ala Ser Leu
945                 950                 955                 960

Val Arg Glu Gly Asn Tyr Ser Asp Gly Ser Tyr Gly Ile Phe Arg Thr
                965                 970                 975

Ala Leu Glu Arg Ala Arg Thr Val Leu Ala Asp Ser Ala Ser Pro Thr
            980                 985                 990

Gly Thr Leu Met Ala Ala His Asp Ala Leu Arg Ser Ala Val Asp Ala
        995                 1000                1005

Leu Thr Leu Asp Glu Gly Gly Tyr Ala Val Leu Gln Ala Glu Asp Pro
    1010                1015                1020

Asp Arg Met Glu Gly Pro Ser Leu Val Lys Glu Ala Tyr Tyr Ser Asp
1025                1030                1035                1040

Gly Asp Leu Gly Gly Val Thr Glu Gly Ala Trp Glu Gln Tyr Thr Asp
                1045                1050                1055

Leu Asp Phe Gly Gly Val Ala Pro Arg Ser Val Ser Val Arg Tyr Ala
            1060                1065                1070

Asn Ser Gln Ala Ala Ala Ala Glu Pro Ser Ser Val Asp Ile His Ala
        1075                1080                1085

Gly Asp Ala Asp Gly Pro Val Val Ala Thr Val Ser Leu Pro Gly Thr
    1090                1095                1100

Gly Gly Trp Gln Tyr Tyr Thr Thr Val Arg Ala Ala Val Ser Asp Pro
1105                1110                1115                1120

Gln Ala Leu Leu Lys Ala Ser Ser Ala Thr Phe Val Phe His Ala Pro
                1125                1130                1135

Ser Gly Arg Gln Trp Val Ser Asn Phe Asp Trp Tyr Gln Phe Ser Pro
            1140                1145                1150

Glu Ala Ala Pro Ser Ser Ser Pro Ile Thr Thr Leu Ala Thr Leu Thr
        1155                1160                1165

Thr Ala Asn Thr Thr Ser Thr Gly Asp Gly Ser Leu Pro Leu Lys Val
    1170                1175                1180

Ser Gly Gly Val Phe Glu Asn Val Thr Asn Gly Ala Trp Ala Glu Trp
1185                1190                1195                1200

Arg Asp Thr Asp Leu Gly Asp Gly Ala Asp Thr Val Thr Val Ser Tyr
                1205                1210                1215

Asp Lys Pro Arg Ser Arg Ala Ala Ser Asp Ser His Ile Glu Leu Arg
            1220                1225                1230

Pro Gly Ala Lys Asp Gly Pro Thr Ala Val Thr Val Pro Leu Asp Tyr
        1235                1240                1245

Thr Gly Ser Gly Trp Gly Thr Val Ala Ser Thr Ser Val Arg Leu Asp
    1250                1255                1260

Pro Asp Val Phe Glu Gly Thr Gln Asp Val Tyr Ala Val Phe Val Ser
1265                1270                1275                1280

Ser Thr Gln Thr Asp Ala Gln Pro Tyr Val Ala Asn Val His Ser Leu
                1285                1290                1295

Thr Leu Thr Arg Gln Ala Asp Ala Pro Val Val Phe Asp Ala Thr Ala
            1300                1305                1310

Phe Glu Gly Ser Ser Gly Gly Gly Leu Lys Ser Glu Pro Ala Thr Trp
        1315                1320                1325

Ser Gly Ala Gly Ser Ala Thr Ser Leu Gly Gly Thr Tyr Asp Gly Ala
    1330                1335                1340

Trp Leu Asp Tyr Gly Asp Val Asp Phe Gly Asp Ser Pro Lys Asn Thr
1345                1350                1355                1360
```

-continued

```
Val Thr Leu Thr Tyr Val Asn Asn Ser Ala Arg Cys Gly Thr Gly Ser
                1365                1370                1375

Ala Val Gln Leu Tyr Leu Asp Ser Phe Asp Pro Asp Ala Pro Gly Thr
            1380                1385                1390

Pro Tyr Ala Thr Val Pro Leu Pro Val Thr Gly Ser Ser Trp Ser Ser
        1395                1400                1405

Gly Gly Thr Thr Ser Leu Thr Leu Pro Glu Ala Ile Thr Gly Thr His
    1410                1415                1420

Ala Val His Leu Arg Leu Thr Thr Asn Ala Asp Ser Ser His Pro Tyr
1425                1430                1435                1440

Val Ala Asn Leu Gly Gln Val Ala Phe Asp Arg Val Glu Ala Pro Ala
                1445                1450                1455

Gln Thr Asp Leu Ser Ala Leu Arg Lys Ala Ile Glu Gln Tyr Glu Gly
            1460                1465                1470

Leu Ser Glu Asp Ala Asp Arg Tyr Gly Thr Ile Asp Phe Gly Val Phe
        1475                1480                1485

Arg Arg Glu Leu Thr Ala Ala Arg Asp Leu Leu Gly Thr Glu Asp Ala
    1490                1495                1500

Thr Gln Leu Glu Ala Asp Leu Arg Thr Arg Ser Leu Thr Leu Ala Ala
1505                1510                1515                1520

Asn Gln Leu Val Pro Leu Pro Arg Leu Arg Leu Glu Ser Leu Val Ala
                1525                1530                1535

Thr Ala Ser Ala Leu Ala Asp Glu Arg Tyr Thr Asp Ala Ser Trp Lys
            1540                1545                1550

Ala Phe Thr Thr Ala Leu Thr Ala Ala Lys Thr Ala Leu Ala Asp Glu
        1555                1560                1565

Thr Ala Thr Asp Arg Thr Leu Thr Glu Arg Tyr Ala Ala Leu Asp Arg
    1570                1575                1580

Ala Arg Ser Ser Leu Thr Thr Lys Arg Arg Thr Val Pro Ala Ala Pro
1585                1590                1595                1600

Gly Ala Val Ser Ala Ala Pro Ser Gly Thr Ser Val Gln Val Thr Trp
                1605                1610                1615

Ser Ala Pro Glu Asp Asp Gly Gly Ser Pro Val Thr Gly Tyr Glu Ile
            1620                1625                1630

Thr Leu Ser Gly Gly Arg Gln Val Glu Ile Ala Asp Pro Asp Ser Arg
        1635                1640                1645

Ser Thr Val Phe Thr Arg Leu Lys Asp Gly Thr Ser Tyr Thr Ala Arg
    1650                1655                1660

Val Arg Ala Val Asn Ala Leu Gly Asp Ser Pro Trp Ser Ala Arg Thr
1665                1670                1675                1680

Gln Pro Ala Val Thr Gly Asp Asn Arg Pro Gln Thr Pro Thr Val Thr
                1685                1690                1695

Gly Val Val Thr Asp Gly Glu Arg Val Arg Val Asn Trp Arg Pro Ala
            1700                1705                1710

Gly Asp Gly Gly Phe Pro Val Val Gly Tyr Thr Val Ala Leu Asp Asp
        1715                1720                1725

Gly Thr Thr Ala His Val Pro Gly Thr Thr Ser Thr Ala Val Leu Thr
    1730                1735                1740

Ala Ala Gly Gly Ala Lys Ala His Thr Ala Thr Val Thr Ala Val Thr
1745                1750                1755                1760

Arg Ala Gly Ser Ser Asp Gly Ser Gly Ala Thr Val Ser Thr Ala Pro
                1765                1770                1775
```

-continued

```
Ala Thr Ser Thr Thr Ser Ala Thr Ser Ala Thr Ser Thr Gly Asp Pro
            1780                1785                1790

Ala Glu Tyr Glu Pro Ser Pro Phe Pro Gly Asp Thr Leu Asp Ala Thr
        1795                1800                1805

Tyr Ala Ser Asp Ala Trp Pro Glu Thr Gly Asp Gly Ser Asp Trp Phe
    1810                1815                1820

Thr His Leu Leu Ser Gly Phe Asp Asp Leu Gly Pro Ala Thr Leu Gly
1825                1830                1835                1840

Ala Asn Ser Glu Val Pro Ala Gly Thr Pro Leu Gly Ala Glu Asn Asp
                1845                1850                1855

Arg Ile Thr Val Ser Val Asn Asn Ala Ala Thr Gln Gln Gln Val Asp
            1860                1865                1870

Arg Ala Glu Val Asp Ala Ser Asn Ser Ala Thr Val Thr Met Ala Asp
        1875                1880                1885

Gly Leu Gly Ser Arg Leu Gly Pro Leu Tyr Gly Glu Ala Leu Lys Glu
    1890                1895                1900

Gly Arg Leu Pro Lys Thr Ser Ala Leu Phe Ser Arg Val Asn Glu Asn
1905                1910                1915                1920

Leu Asp Thr His Asp Ala Ala Lys Asn His Tyr Gln Tyr Leu Arg Pro
                1925                1930                1935

Tyr Val Arg Leu Gly Phe Ala Gly Asp Gly Gly Ala Val Tyr Glu Ser
            1940                1945                1950

Gln Asp Ser Ser Tyr Ser Gly Leu Ala Gly Gln Gly Ser Tyr Pro Ser
        1955                1960                1965

Gly His Thr Tyr Gly Gly Tyr Glu Ala Gly Thr Ile Leu Ala Thr Leu
    1970                1975                1980

Leu Pro Asp Leu Ala Pro Ser Ile Leu Ala Arg Thr Ser Glu Tyr Gly
1985                1990                1995                2000

Asp Asn Arg Ile Val Leu Gly Phe His Tyr Pro Leu Asp Val Met Gly
                2005                2010                2015

Gly Arg Ile Thr Ala Gln Ala Thr Val Ala His Arg Trp Ala Asp Pro
            2020                2025                2030

Glu Phe Ala Lys Leu Leu Gly Gln Ala His Thr Glu Ile Glu Asn Val
        2035                2040                2045

Leu Leu Ala Arg Cys Glu Glu Glu Gly Tyr Gly Asp Thr Leu Thr Ala
    2050                2055                2060

Cys Ala Gly Asp Pro Tyr Ala Gly Leu Ser Thr Ala Gln Gln Val Asp
2065                2070                2075                2080

Arg Tyr Thr Gln Arg Leu Thr Tyr Gly Phe Ser Arg Thr Gly Glu Ala
                2085                2090                2095

Gly Gln Ala Leu Asp Ala Pro Ser Asp Ala Ala Ala Leu Leu Ile Thr
            2100                2105                2110

Ala Phe Pro Asp Leu Thr Ala Glu Gln Arg Ala Gln Val Leu Glu Gln
        2115                2120                2125

Thr Ala Thr Asp Ser Gly Tyr Pro Leu Asp Leu Thr Gly Ser Gly Gly
    2130                2135                2140

Pro Gly Trp Gln Arg Ile Asn Leu Ala Ala Ala Met Ala Ala Asp Val
2145                2150                2155                2160

Val Val Asn Ala Asp Gly Ser Val Thr Val Thr Asn Phe Pro Asp Pro
                2165                2170                2175

Thr Ala Ala Ser Ala Ala Glu Ala Val Ala Ile Thr Val Gly Gly Val
            2180                2185                2190

Ala Leu Asp Gly Phe Asp Pro Asp Val Ser Thr Tyr Val Val Asp Trp
```

```
        2195                2200                2205

Pro Arg Asn Gly Gly Arg Ile Pro Ala Val Gly Ala Val Thr Ala Ala
    2210                2215                2220

Ser Gly Ala Arg Val Lys Val Thr Ser Gly Ser Ser Thr Val Ser Ser
2225                2230                2235                2240

Ser Gln Arg Gly Phe Ser Thr Arg Thr Leu Thr Val Thr Ser Ala Asp
                2245                2250                2255

Gly Glu Phe Thr Arg Thr Tyr Thr Val Gly Phe Arg Pro Val Glu Gln
            2260                2265                2270

His Pro His Arg Pro Gly Ala Leu Arg Asp Thr Gly Gly Gly Gly Thr
        2275                2280                2285

Ala Gly Gly Ser Ala Gly Gly Gly Asp Val Gly Gly Gly Leu Trp Ser
    2290                2295                2300

Pro Ala Arg Glu Trp Glu Leu Thr Val Asn
2305                2310


<210> SEQ ID NO 27
<211> LENGTH: 1984
<212> TYPE: PRT
<213> ORGANISM: Clostridium spiroforme

<400> SEQUENCE: 27

Met Asn Lys Lys Ile Asn Arg Leu Leu Lys Gly Ala Leu Ala Phe Thr
1               5                   10                  15

Val Ala Phe Ser Thr Leu Ala Val Thr Thr Ser Thr Ser Arg Lys Val
            20                  25                  30

Ser Ala Val Glu Gln Glu Glu Ser Tyr Thr Gln Tyr Val Asp Pro Phe
        35                  40                  45

Val Cys Thr Asp Val Asp Tyr Gly Gln Leu Phe Pro Gly Ser Val Val
    50                  55                  60

Pro Asn Gly Leu Val Lys Leu Ser Pro Asp Thr Tyr Pro His Asn Thr
65                  70                  75                  80

Leu Asp His Ala Gly Tyr Asp Tyr Ser Lys Leu Gln Ile Gln Gly Phe
                85                  90                  95

Ser His Thr Arg Ile Glu Gly Val Gly Gly Gln Gly Ala Gly Gly Asp
            100                 105                 110

Val Leu Val Thr Pro Thr Tyr Val Glu Tyr Ser Gln Arg Pro Gln Ala
        115                 120                 125

Gln Thr Arg Ala Met Asn Tyr Thr Lys Glu Asp Glu Ser Ala Lys Pro
    130                 135                 140

Gly Tyr Tyr Ser Val Glu Leu Thr Pro Lys Thr Gly Lys Asp Asn Asp
145                 150                 155                 160

Val Lys Asp Ser Pro Glu Ile Gly Lys Ile Lys Ala Glu Met Thr Thr
                165                 170                 175

Asp Gln Arg Thr Gly Phe His Arg Tyr Thr Phe Pro Glu Ala Gly Ser
            180                 185                 190

Val Asn Ile Ile Thr Asp Leu Asn Tyr Thr Tyr His Gly Thr Asp Ile
        195                 200                 205

Arg Asn Ala Tyr Val Asp Val Leu Glu Gln Ser Asp Thr Thr Thr Ala
    210                 215                 220

Ile Gly Gly Arg Phe Ser Gly Arg Asn Val Ser Gly Asn Gly Lys Tyr
225                 230                 235                 240

Thr Met Tyr Phe Tyr Met Glu Thr Ser Lys Pro Ala Asn Ser Val Lys
                245                 250                 255
```

-continued

```
Thr Trp Asn Asp Thr Thr Leu Ser Asp Lys Thr Ser Gln Lys Gly Asn
            260                 265                 270

Asp Ile Gly Thr Ile Met Asn Phe Asp Val Lys Glu Asn Glu Glu Ile
        275                 280                 285

Gln Leu Lys Val Ser Ile Ser Pro Ile Ser Val Lys Gln Ala Lys Ile
    290                 295                 300

Asp Met His Asn Glu Ile Ser Asp Trp Asp Phe Asp Ala Ala Ala Ser
305                 310                 315                 320

Arg Ala Asp Lys Ala Trp Asn Asp Val Leu Ser Lys Val Arg Val Glu
                325                 330                 335

Ser Ser Lys Val Ser Asp Pro Thr Gly Glu Leu Lys Gln Leu Phe Tyr
            340                 345                 350

Thr His Leu Tyr His Met Phe Met Thr Pro Val Asn Ala Thr Ser Thr
        355                 360                 365

Ser Gly Thr Phe Arg Gly Thr Asp Gly Lys Ile His Glu Ala Asn Asp
    370                 375                 380

Tyr Ile His Tyr Asp Ser Trp Thr Leu Trp Asp Asp Tyr Arg Lys Tyr
385                 390                 395                 400

Pro Met Ile Gly Leu Ile Gln Pro Asp Thr Tyr Lys Asp Met Val Lys
                405                 410                 415

Ser Ile Ala Asp Ala Leu Asp Tyr Gly Ile Val Thr Trp Ser His Asp
            420                 425                 430

Lys Gln Pro Val Pro Asn Val Arg Thr Glu His Ala Val Ala Leu Leu
        435                 440                 445

Ala Asp Gly Val Ala Lys Gly Phe Thr Asp Ile Asp Asn Leu Glu Glu
    450                 455                 460

Ala Tyr Glu Glu Ala Lys Glu Ile Val Asn Glu Val Ile Thr Ser Glu
465                 470                 475                 480

Val Glu Lys Ile Gly Tyr Val Pro Asn Arg Val Asp Arg Thr Ile Glu
                485                 490                 495

Tyr Gly Tyr Asp Asp Trp Cys Leu Ser Ile Ile Ala Glu Ala Leu Gly
            500                 505                 510

Lys Glu Asp Glu Ala Ala Tyr Phe Leu Asp Arg Ser Phe Asn Tyr Lys
        515                 520                 525

Asn Thr Phe Arg Lys Asp Ala Val Asp Ser Pro Phe Ser Asp Lys Lys
    530                 535                 540

Leu Gly Leu Leu Trp Asn Arg Asp Ser Asn Gly Asn Trp Leu Asn Gln
545                 550                 555                 560

Asp Pro Ser Ser Thr Asn Thr Gly Leu Tyr Gln Gly Thr Met Trp Gln
                565                 570                 575

Tyr Thr Trp Tyr Gly Ser Asn Asp Val Asn Gly Leu Met Asp Leu Met
            580                 585                 590

Gly Gly Arg Glu Ala Thr Leu Glu Ala Leu Met Tyr Met Phe Gly Met
        595                 600                 605

Gln Asp Pro Asp Asp Pro Lys Gly Met Gln His Asn Ala Ala Asn Glu
    610                 615                 620

Val Glu Leu His Thr Pro Tyr Leu Phe Asn Phe Val Gly Arg Pro Asp
625                 630                 635                 640

Leu Thr Gln His Trp Val Arg Glu Ile Tyr Thr Arg Glu Thr Trp Asn
                645                 650                 655

Ser Asn Tyr Ala Ser Gly Thr Gln Thr Glu Lys Gln Lys Met Tyr Lys
            660                 665                 670

Leu Ser Pro Gln Gly Tyr Leu Glu Thr Met Asp Asp Asp Ala Gly Thr
```

-continued

```
        675                 680                 685

Met Ala Met Met Phe Val Ser Ala Ala Met Gly Ile Phe Pro Met Thr
    690                 695                 700

Pro Gly Asp Thr Thr Phe Gln Ile Gly Ser Pro Phe Phe Glu Lys Ile
705                 710                 715                 720

Thr Leu Asp Val Gly Asn Gly Lys Thr Phe Thr Ile Glu Ala Asn Asn
                725                 730                 735

Val Ser Asp Thr Asn Glu Tyr Ile Gln Ser Ala Thr Leu Asn Gly Lys
            740                 745                 750

Ser Phe Asp Arg Thr Trp Val Asp Tyr Ser Glu Ile Thr Arg Gly Gly
        755                 760                 765

Val Leu Ser Phe Glu Met Gly Asp Thr Pro Ser Ser Trp Ala Gln Asn
    770                 775                 780

Gly Val Thr Ala Lys Ser Ser Ser Asp Asn Ala Asp Thr Ser Thr Tyr
785                 790                 795                 800

Asp Asp Asp Glu Ile Ala Tyr Ser Ser Ala Met Phe Glu Glu Ser Lys
                805                 810                 815

Ala Asn Asp Gly Ser Phe Asp Gln Lys Ile Thr Ile Thr Leu Lys Thr
            820                 825                 830

Lys Glu Phe Ala Gly Glu Ile Gly Glu Asp Leu Val Ala Thr Gly Lys
        835                 840                 845

Ile Asn Ile Thr Asn Ile Pro Glu Gly Leu Glu Ala Ser Ala Ile Lys
    850                 855                 860

Thr Glu Ala Asn Lys Val Glu Val Ser Leu Asn Gly Lys Ala Lys Asn
865                 870                 875                 880

His Thr Leu Asn Asp Ser Ile Ser Asn Leu Thr Ile Glu Ile Thr Asp
                885                 890                 895

Gly Ala Thr Asn Glu Pro Ile Lys Asp Ser Ile Arg Lys Thr Lys Asp
            900                 905                 910

Asn Val Lys Val Met Phe Ile Asp Asn Gln Leu Thr Tyr Ser Gln Ser
        915                 920                 925

Glu Phe Lys Glu Ser Glu Ser Asp Asp Gly Ala Ile Leu Glu Thr Ser
    930                 935                 940

Thr Ile Thr Leu Thr Gly Asp Thr Thr Phe Ala Gly Glu Val Asn Glu
945                 950                 955                 960

Asp Phe Val Ala Thr Gly Lys Val Gln Ile Asn Asn Val Pro Glu Gly
                965                 970                 975

Leu Thr Val Lys Met Ile Lys Ile Asp Asp His Thr Ala Val Leu Ser
            980                 985                 990

Phe Glu Gly Lys Ala Val Asn Asn Asp Ala Asp Ala Glu Ile Glu Leu
        995                 1000                1005

Ala Phe Thr Asp Ser Ala Phe Asn Gly Ala Leu Ala Ser Glu Ile Gly
    1010                1015                1020

Gln Ser Ser Arg Gly Gly Met Thr Ala Leu Leu Leu Asp Phe Asp Tyr
1025                1030                1035                1040

Asp His Thr Ser Lys Leu Lys Arg Thr Met Ala Glu Ala Thr Tyr Ile
                1045                1050                1055

Asn Ala Ser Ala Tyr Thr Gln Ser Ser Tyr Gln Ala Val Leu Asp Ala
            1060                1065                1070

Val Ala Lys Gly Gln Glu Leu Leu Asp Asn Lys Asn Ala Thr Ser Lys
        1075                1080                1085

Glu Ile Asp Leu Ala Ile Gly Asp Ile Ile Asp Ala Gln Glu Gln Leu
    1090                1095                1100
```

-continued

```
Asp Ile Pro Arg Asp Gly Phe Ser Val Leu Gln Ala Glu Ser Ser Asp
1105                1110                1115                1120

Val Thr Ser Gly Gly Ser Leu Arg Val Glu Gly Ser Val Leu His Gly
                1125                1130                1135

Thr Tyr Asp Gly Ala Trp Ile Arg Tyr Asp Ala Leu Asp Phe Asn Gly
            1140                1145                1150

Leu Ser Pro Lys Tyr Leu Glu Leu Arg Tyr Asp Asn Ala Ser Asn Arg
        1155                1160                1165

Cys Ala Ser Asp Ser His Leu Glu Val Arg Leu Asp Gly Val Asp Gly
    1170                1175                1180

Thr Leu Ile Gly Asp Ile Gln Leu Pro Ala Thr Gly Thr Ala Trp Gly
1185                1190                1195                1200

Ser Tyr Glu Thr Leu Gln Phe Glu Ile Ser Asn Pro Glu Leu Leu Asp
                1205                1210                1215

Gly Lys His Asp Val Tyr Phe Val Phe Lys Gly Thr Thr Glu Asp Ser
            1220                1225                1230

Lys Pro Tyr Val Ala Lys Val Asp Tyr Leu Gln Phe Lys Glu Thr Ala
        1235                1240                1245

Asp Ile Asp Ser Val Lys Leu Glu Ala Glu Lys Ser Asp Glu Asn Ser
    1250                1255                1260

Gly Asn Gly Leu Lys Asn Glu Ser Ile Asn Leu Gly Gly Thr Tyr Asp
1265                1270                1275                1280

Gly Ala Trp Ile Lys Tyr Asn Asn Val Asn Phe Asn Asn Leu Glu Ala
                1285                1290                1295

Asp Thr Ile Asn Val His Tyr Ser Thr Arg Val Asp Ala Cys Ala Leu
            1300                1305                1310

Asp Ala Arg Ile Glu Ile Arg Lys Asp Asn Lys Asp Gly Glu Leu Leu
        1315                1320                1325

Gly Thr Ile Met Leu Pro Leu Thr Gly Gly Trp Ser Asp Tyr Gln Thr
    1330                1335                1340

Val Ser Thr Lys Leu Asp Thr Ser Val Thr Gly Val Gln Asp Ile Cys
1345                1350                1355                1360

Phe Val Leu Arg Gly Thr Asn Asp Gly Gly Arg Pro Tyr Val Ala Asn
                1365                1370                1375

Ile Asp Tyr Met Glu Phe Val Asn Ser Gly Val Asn His Ile Glu Ala
            1380                1385                1390

Glu Asn Lys Asp Asp Trp Ser Gly Ala Glu Leu Lys Val Glu Asn Ser
        1395                1400                1405

Thr Asp Asn Thr Gly Lys Ser Leu Thr Asn Ile Gly Gly Ala Arg Asn
    1410                1415                1420

Asp Ala Trp Leu Arg Tyr Asn Gly Val Glu Phe Asn Gly Lys Thr Glu
1425                1430                1435                1440

Met Thr Val Arg Tyr Ser His Asn Pro Gly Thr Ala Gly Thr Asn Ser
                1445                1450                1455

Arg Ile Asp Val Tyr Leu Asp Asn Met Asp Gly Asn Pro Ile Gly Thr
            1460                1465                1470

Ile Asn Leu Pro Thr Thr Asn Gly Trp Ala Asn Tyr Thr Val Ile Arg
        1475                1480                1485

Glu Val Phe Asp Gln Glu Ile Thr Gly Ser His Asp Val Tyr Leu Lys
    1490                1495                1500

Leu His Thr Asp Gly Ser Gly Trp Val Ala Asn Phe Asp Trp Phe Glu
1505                1510                1515                1520
```

-continued

```
Phe Gly Glu Pro Ile Ala Asp Val Asp Lys Ser Gln Leu Gln Ala Lys
                1525                1530                1535

Tyr Asp Glu Asn Val Ala Leu Leu Gln Glu Tyr Asp Lys Tyr His Tyr
            1540                1545                1550

Val Gly Phe Asn Ile Phe Lys Asp Arg Leu Leu Thr Gly Ser Ala Val
        1555                1560                1565

Ile Asp Asn Gln Asn Ala Thr Ala Asn Asp Val Arg Ile Ala Ile Lys
    1570                1575                1580

Asp Ile Asp Asn Ala Leu Ala Ala Leu Gln Tyr Lys Ile Ala Phe Asp
1585                1590                1595                1600

Leu Asn Asp Tyr Val Val Gln Leu Glu Asn Ile Asn Glu Ala Asp Tyr
                1605                1610                1615

Thr Lys Asp Ser Tyr Ala Asn Leu Met Gln Ala Ile Glu Val Ala Lys
            1620                1625                1630

Ala Ile Pro Thr Asp Ser Glu Tyr Glu Val Phe Lys Asn Ala Tyr Asp
        1635                1640                1645

Gly Leu Val Asp Ala His Ser Lys Leu Thr Ala Leu Asn Arg Thr Ala
    1650                1655                1660

Leu Glu Glu Ile Ile Lys Gln Ala Glu Ala Ile Asp Leu Asp Leu Tyr
1665                1670                1675                1680

Lys Glu Glu Gly Lys Ala Glu Phe Lys Ala Ala Leu Glu Asn Ala Lys
                1685                1690                1695

Thr Val Tyr Glu Thr Val Ser Leu Thr Gln Ala Gln Val Asp Glu Ala
            1700                1705                1710

Val Ala Asn Leu Asp Gln Ala Ile Lys Ala Leu Lys Pro Ile Glu Thr
        1715                1720                1725

Asp Ser Val Asn Lys Val Ala Leu Lys Ile Ala Val Asp Leu Ala Asn
    1730                1735                1740

Ala Ile Thr Asp Glu Asp Leu Ala Asn Val Val Pro Ala Val Val Asp
1745                1750                1755                1760

Glu Phe Ile Ala Ala Arg Asp Glu Ala Asn Ala Val Tyr Asn Asp Val
                1765                1770                1775

Ser Ala Thr Gln Glu Glu Val Pro Arg Thr Phe Asp Arg Leu Ala Ser
            1780                1785                1790

Val Met Gln Lys Leu Glu Phe Phe Lys Gly Asp Lys Lys Ala Leu Lys
        1795                1800                1805

Ala Phe Ile Asp Lys Val Thr Gly Leu Asp Ser Ser Lys Tyr Thr Gln
    1810                1815                1820

Thr Thr Trp Thr Ala Phe Asp Lys Glu Leu Thr Glu Ala Ile Ala Val
1825                1830                1835                1840

Tyr Asn Asp Glu Asn Ala Met Gln Glu Glu Val Asn Thr Ala Tyr Ser
                1845                1850                1855

Glu Leu Val Thr Ala Phe Leu Asn Leu Arg Leu Ile Pro Asp Lys Ser
            1860                1865                1870

Leu Leu Glu Asp Leu Ile Asn Gln Ala Asn Gly Leu Asn Gly Ala Asn
        1875                1880                1885

Tyr Thr Lys Ala Thr Phe Asp Gly Leu Thr Lys Ala Leu Asp Glu Ala
    1890                1895                1900

Lys Ala Val Tyr Glu Asn Pro Asp Ala Thr Gln Lys Glu Val Pro Arg
1905                1910                1915                1920

Thr Lys Asp Val Leu Ala Lys Ala Ile Ala Gly Leu Gln Thr Val Thr
                1925                1930                1935

Thr Asp Asn Thr Val Ser Thr Pro Val Asn Asn Gly Asp Thr Thr Ala
```

1940 1945 1950

Ser Val Lys Thr Gly Asp Glu Ser Leu Ala Gly Met Phe Ala Thr Ile
1955 1960 1965

Ala Leu Leu Ser Ile Ala Gly Tyr Thr Ile Leu Lys Arg Lys Glu Asn
1970 1975 1980

<210> SEQ ID NO 28
<211> LENGTH: 653
<212> TYPE: PRT
<213> ORGANISM: Bacteroides thetaiotaomicron

<400> SEQUENCE: 28

Met Thr Pro Ser Val Ala Gln Asn Thr Lys Tyr Val Asn Leu Phe Ile
1 5 10 15

Gly Thr Ser Gly Asp Asn Gly Gln Val Ala Pro Gly Ala Ala Ala Pro
20 25 30

Phe Gly Met Val Cys Val Cys Pro Asp Asn Asp Pro Arg Ser His Ala
35 40 45

Gly Tyr Asp Tyr Ala Val Thr Lys Val Ser Gly Ile Ser Val Asn Arg
50 55 60

Leu Ser Gly Val Gly Cys Ser Gly Gly Gly Gly Asn Leu Arg Ile Arg
65 70 75 80

Pro Val Ala Pro Ser Gln Glu Leu His Ile Lys Lys Ser Arg Glu Lys
85 90 95

Ala Thr Pro Gly Tyr Tyr Ser Thr Ala Phe Thr Asn Gly Ile Lys Thr
100 105 110

Glu Leu Thr Ala Thr Asn Ala Met Ala Val Glu Arg Tyr Lys Phe Pro
115 120 125

Arg Ser Leu Ser Ala Ala Leu Trp Ile Asp Phe Ala Ser Thr Phe Glu
130 135 140

Asp Val Ala Thr Cys His Tyr Lys Arg Ile Ser Glu Thr Cys Ile Glu
145 150 155 160

Gly Tyr Val Gln Ala Lys Asn Val Cys Gly His Gly Cys Tyr Lys Leu
165 170 175

Tyr Phe Ser Leu Asn Thr Ser Gln Pro Phe Gln Leu Glu Glu Gln Lys
180 185 190

Glu Thr Thr Ala Cys Leu Thr Phe Gly Lys Lys Val Arg Ser Val Glu
195 200 205

Val Arg Ile Gly Leu Ser Ala Leu Ser Ser Glu Leu Ala Ser Trp Glu
210 215 220

Cys Ala Arg Trp Glu Lys Met Asp Phe Glu Asp Val Lys Ser Arg Thr
225 230 235 240

Ala Asp Gln Trp Glu Lys Gln Leu Ser Ala Ile Asp Val Lys Gly Gly
245 250 255

Lys Lys Asp Asp Arg Val Ile Phe Tyr Thr Ser Leu Tyr Arg Thr Tyr
260 265 270

Leu Ser Pro Ala Asp Val Ser Ser Pro Asp Gly Ala Tyr Leu Gly Thr
275 280 285

Asp Gly Lys Val Tyr Ile Ser Glu Asp Phe Arg Tyr Tyr Ser Asn Trp
290 295 300

Ser Leu Trp Asp Thr Phe Arg Thr Lys Phe Pro Leu Leu Val Leu Thr
305 310 315 320

Glu Pro Ala Lys Met Arg Asp Met Ala Thr Ser Leu Ile His Leu Tyr
325 330 335

```
Ala Thr Gly Lys Lys Asp Trp Ser Thr Gly Phe Glu Ser Thr Pro Thr
            340                 345                 350

Val Arg Thr Glu His Ala Val Ile Leu Leu Leu Asp Ala Tyr Arg Lys
        355                 360                 365

Gly Ile Thr Asn Leu Asp Phe Arg Lys Gly Tyr Ala Gly Met Lys Gln
    370                 375                 380

Glu Met Glu Arg Leu Pro Met Arg Ser Pro Asp Gln Lys Met Glu Ser
385                 390                 395                 400

Ala Tyr Asp Leu Trp Ala Met Ala Lys Ile Ala Glu Ile Ile Gly Glu
                405                 410                 415

Lys Ala Asp Ser Glu Gln Tyr Arg Gln Arg Ser Val Ser Leu Phe Glu
            420                 425                 430

Glu Thr Trp Lys Lys Glu Phe Met Asn Val Thr Pro Ala Phe Glu Val
        435                 440                 445

Met Lys Asn Asn Gly Leu Tyr Gln Gly Thr Arg Trp Gln Tyr Arg Trp
    450                 455                 460

Ala Ala Pro Gln Tyr Ile Asp Lys Met Ile Glu Trp Val Gly Gln Asp
465                 470                 475                 480

Ser Leu Arg Leu Gln Leu Thr Tyr Phe Phe Asp His His Leu Tyr Asn
                485                 490                 495

Gln Gly Asn Glu Pro Asp Ile His Val Pro Tyr Leu Phe Asn Arg Leu
            500                 505                 510

Gly Ala Pro Glu Lys Thr Gln Gln Ile Val Arg Ser Leu Met Thr Glu
        515                 520                 525

Pro Met Ile His Lys Tyr Gly Gly Asn Ser Glu Phe Lys Thr Pro Tyr
    530                 535                 540

Leu Gly Lys Ala Phe Lys Asn Ala Pro Glu Gly Tyr Ser Pro Glu Met
545                 550                 555                 560

Asp Glu Asp Asp Gly Thr Met Ser Ala Trp Tyr Val Phe Gly Ala Met
                565                 570                 575

Gly Phe Tyr Pro Leu Leu Val Gly Asp Glu Tyr Tyr Asp Leu Thr Ser
            580                 585                 590

Pro Leu Phe Asp Arg Val Leu Leu Arg Leu Thr Asn Gly Asn Val Leu
        595                 600                 605

Thr Ile Gln Thr Glu Gly Arg Lys Lys Lys Asp Ala Pro Ile Lys Ser
    610                 615                 620

Ile His Phe Asn Gly Lys Lys Ile Ala Asp Tyr Arg Ile Ser His Asn
625                 630                 635                 640

Glu Leu Ile Lys Gly Gly Glu Leu Ile Tyr Asn Tyr Lys
                645                 650
```

<210> SEQ ID NO 29
<211> LENGTH: 696
<212> TYPE: PRT
<213> ORGANISM: Zunongwangia profunda

<400> SEQUENCE: 29

```
Met Thr Leu Ile Met Lys Arg Met Ile Ala Ala Ile Ala Val Ala Leu
1               5                   10                  15

Cys Val Ala Cys Gln Pro Lys Ser Gln Glu Lys Thr Ser Lys Ser Ala
            20                  25                  30

Asn Ile Thr Asp Lys Val Asn Val Phe Leu Gly Ser Ser Gly Asp His
        35                  40                  45

Gly Gln Met Ser Pro Ser Ala Ser Thr Pro Phe Asn Met Met Ser Ile
    50                  55                  60
```

Gly Pro His Thr Asn Pro His Asn His Thr Gly Tyr Glu His Tyr Ala
65 70 75 80

Lys Glu Phe Asp Gly Phe Thr His Thr His Leu Glu Gly Val Gly Cys
85 90 95

Thr Gly Ser Gly Gly Asn Ile Leu Ile Lys Pro Ile Leu Asn Asp Asn
100 105 110

Lys Glu Thr Glu Leu Arg Lys Val Thr Glu His Ala Lys Pro Gly Phe
115 120 125

Tyr Glu Val Ser Phe Glu Asn Gly Ile Asp Ala Ala Met Ser Val Thr
130 135 140

His Asn Phe Gly Ile His Gln Tyr Asn Phe Asn Gly Glu Lys Gly Gly
145 150 155 160

Leu Phe Ile Asp Leu Ser Phe Ala Leu Ser Asn Arg Phe Val Ser Glu
165 170 175

Glu His Glu Ile Lys Asp Asn Lys Ile Ser Gly Val Ile Ala Thr Lys
180 185 190

Thr Thr Cys His Ala Gly Thr Tyr Arg Phe Tyr Tyr Glu Ile Gln Leu
195 200 205

Lys Asn Met Ala Glu Ile Ala Gln Ile Ser Asp His Glu Ile Met Ala
210 215 220

Lys Ala Glu Asp Asn Ser Lys Glu Val Lys Val Leu Ile Gly Phe Ser
225 230 235 240

Ser Val Ser Lys Glu Tyr Ala Ser Gln Lys Ile Glu Asn Ile Ser Tyr
245 250 255

Glu Asn Leu Lys Lys Glu Ala Ser Ala Ala Trp Glu Lys Ala Leu Ser
260 265 270

Arg Ile Ser Val Glu Gly Glu Glu Asp Arg Glu Asp Leu Phe Tyr Ser
275 280 285

Leu Leu Tyr Arg Gly Leu Gln Ser Pro Tyr Ile Val Ser Glu Glu Asp
290 295 300

Gly Thr Tyr Pro Ala Ile Asp Gly Thr Leu Gln Lys Thr Glu Gly Thr
305 310 315 320

Ile Tyr Ser Gly Trp Ala Ile Trp Asp Asn Tyr Arg Glu Gln Leu Pro
325 330 335

Met Leu Ser Met Ala Tyr Pro Asp Arg Tyr Arg Asp Ile Val Lys Ser
340 345 350

Ile Glu Asn Leu Tyr Ala Phe Gly Lys Lys Asn Trp Ala Thr Asp Tyr
355 360 365

Glu Pro Ala Pro Thr Val Arg Thr Glu His Ala Met Val Val Leu Leu
370 375 380

Asp Ala Tyr Asn Lys Gly Tyr Glu Val Asp Ile Lys Arg Ile Lys Asp
385 390 395 400

Ser Leu Ile Lys Asp Ala Glu Ser Leu Asp Tyr Arg Ala Pro Asp Lys
405 410 415

Ala Leu Glu Ser Ser Tyr Asp Asn Trp Ala Met Ala Gln Leu Met Lys
420 425 430

Ile Asp Gly Asp Thr Thr Leu Tyr Asn Lys Tyr Ile Thr Lys Ser Leu
435 440 445

Asp Tyr Lys Glu Tyr Trp Asn Lys Asp Phe Lys Asp Ile Thr Arg Asn
450 455 460

Asp Val Asp Arg Met Gln Ala Arg Gly Leu Tyr Gln Gly Thr Ile Trp
465 470 475 480

```
Gln Tyr Arg Trp Phe Val Pro Phe Asp Leu Asn Gly Leu Lys Gln Leu
                485                 490                 495

Ala Gly Gly Glu Asp Gln Phe Leu Glu Glu Leu Asp Thr Phe Phe Arg
            500                 505                 510

Asn His Asn Tyr Asn His Ala Asn Gln Pro Asp Leu Gln Val Pro Gly
        515                 520                 525

Met Tyr Asn Ala Thr Lys Glu Pro Trp Lys Ser Gln Glu Leu Tyr Arg
    530                 535                 540

Lys Ile Leu Leu Asp Thr Met Val Gln Ala Tyr Phe Asn Asp Asn Ser
545                 550                 555                 560

Lys Gly Ile Asp Pro Tyr Val Gly Arg Ile Tyr Gln Asn Lys Pro Lys
                565                 570                 575

Ala Tyr Leu Arg Thr Met Asp Asp Asp Ala Gly Thr Met Ser Ser Trp
            580                 585                 590

Phe Val Met Arg Ser Leu Gly Leu Ser Pro Ala Asn Ile Gly Asp Pro
        595                 600                 605

Val Tyr Tyr Leu Thr Ala Pro Ile Phe Lys Glu Ile Ser Ile Asn Tyr
    610                 615                 620

Pro Lys Gly Lys Ala Phe Lys Ile Ser Val Thr Asn Tyr Asn Lys Asp
625                 630                 635                 640

His Tyr Tyr Val Glu Ser Ala Thr Leu Asn Gly Lys Pro Leu Asn Arg
                645                 650                 655

Asn Trp Leu Thr Gln Gln Glu Ile Leu Glu Gly Gly Glu Leu Val Ile
            660                 665                 670

Lys Thr Ser Asp Thr Pro Asn Lys Glu Trp Gly Val Lys Glu Ala Trp
        675                 680                 685

Val Ser Ser Ile Arg Gln Tyr Leu
    690                 695


<210> SEQ ID NO 30
<211> LENGTH: 680
<212> TYPE: PRT
<213> ORGANISM: Chitinophaga pinensis

<400> SEQUENCE: 30

Met Lys Lys Ser Leu Ile Tyr Leu Leu Ser Leu Leu Ser Leu Thr Ala
1               5                   10                  15

Val Ala Gln Gln Ser Gly Gln Val Asn Val Phe Leu Gly Ser Ser Gly
            20                  25                  30

Asp Asn Gly Gln Met Ser Pro Ala Ala Ser Tyr Pro Phe Ser Met Val
        35                  40                  45

Ser Ile Gly Pro Glu Thr Tyr Pro Ser Thr His Thr Gly Tyr Glu Tyr
    50                  55                  60

Tyr Ala Lys Glu Phe Leu Gly Phe Thr His Asn Arg Met Glu Gly Val
65                  70                  75                  80

Gly Cys Gln Gly Cys Gly Gly Asn Leu Leu Leu Arg Pro Phe Leu Gly
                85                  90                  95

Asp Gly Pro Val Lys Ala Asp Leu Ile Lys Tyr Glu Glu Gln Ala Ser
            100                 105                 110

Pro Gly Tyr Tyr His Val Gly Phe Thr Asn Gly Ile Lys Ala Ser Phe
        115                 120                 125

Thr Val Tyr Lys Asn Ala Gly Leu His Gln Tyr Thr Phe Pro Glu Gly
    130                 135                 140

Lys Lys Gly Leu Leu Leu Asp Leu Gly Phe Ala His Val Gly Arg Phe
145                 150                 155                 160
```

```
Val Ala Glu Glu His Thr Ile Glu Gly Asn Ala Val Ser Gly Trp Val
                165                 170                 175

Glu Ser Arg Thr Thr Cys Ser Ala Gly Ile Tyr Arg Val Tyr Tyr Tyr
            180                 185                 190

Val Glu Thr Asp Arg Pro Val Lys Trp Thr Ala Thr Gln Ala His Glu
        195                 200                 205

Leu Val Ala Asp Val Thr Asp Asn Asn Leu Gly Val Arg Ile Gly Leu
    210                 215                 220

Ser Ser Val Asn Ala Thr Tyr Ala Lys Ala Ala Ile Thr Lys Asp Ala
225                 230                 235                 240

Phe Asp Met Val Lys Val Arg Ser Glu Lys Ala Trp Asn Asp Met Leu
                245                 250                 255

Gly His Ile Lys Val Lys Gly Asp Pro Ala Arg Glu Lys Leu Phe Tyr
            260                 265                 270

Ser Leu Phe Tyr Arg Ser Ile Gln Ser Pro Tyr Val Val Ser Glu Pro
        275                 280                 285

Asp Gly Ala Tyr Ala Ala Thr Asn Gly Thr Leu Gln His Thr Asn Ser
    290                 295                 300

Lys Met Tyr Asn Gly Trp Ala Ile Trp Asp Asn Tyr Arg Ala Gln Leu
305                 310                 315                 320

Pro Leu Leu Ser Ile Ala Phe Pro Gln Glu Tyr Gln Asp Met Thr Asn
                325                 330                 335

Ser Ile Ala Gly Leu Tyr Ala His Gly Lys Lys Asp Tyr Ala Thr Leu
            340                 345                 350

His Glu Pro Ser Ile Thr Val Arg Thr Glu His Ala Val Val Val Leu
        355                 360                 365

Leu Asp Ala Leu Lys Lys Gly Tyr Lys Phe Asp Phe Asn Ala Ile Ala
    370                 375                 380

Asp Ser Val Glu Lys Glu Ile Lys Gly Leu Asp Tyr Ala His Pro Asp
385                 390                 395                 400

Lys Ala Leu Glu Ser Ser Tyr Asp Ala Trp Ala Leu Ala Glu Leu Tyr
                405                 410                 415

Tyr Ala Gln Lys Asp Lys Ala His Gly Asp Gln Tyr Lys Val Gln Ala
            420                 425                 430

Ala Asp Tyr Lys Lys Tyr Trp Leu Lys Asp Phe Gln Asp Leu Thr Lys
        435                 440                 445

Arg Asp Val Asp Arg Met Gln Ala Arg Gly Leu Tyr Gln Gly Thr Ile
    450                 455                 460

Trp Gln Tyr Arg Trp Phe Val Pro Phe Asp Leu Lys Gly Leu Met Glu
465                 470                 475                 480

Leu Cys Gly Gly Glu Gln Ala Tyr Leu Ser Gln Leu Asp Glu Phe Phe
                485                 490                 495

Asp Asn Asp Tyr Tyr Cys His Ala Asn Gln Pro Asp Leu Gln Thr Pro
            500                 505                 510

Phe Met Tyr Asn Val Thr Asn Gln Pro Trp Lys Ser Gln Ala Leu Val
        515                 520                 525

His Lys Ile Ala Val Asp Thr Met Val Gln His Tyr Phe Asn Asp Asn
    530                 535                 540

Ser Arg Gly Ile Gly Ser Glu Ile Gly Pro Ile Tyr Lys Asn Gln Pro
545                 550                 555                 560

Ala Ala Tyr Val Arg Thr Met Asp Asp Asp Ala Gly Thr Met Ser Ser
                565                 570                 575
```

-continued

```
Trp Phe Val Leu Val Ser Thr Gly Ile Phe Pro Ala Cys Ile Gly Ser
            580                 585                 590

Pro Val Tyr Tyr Leu Asn Val Pro Leu Phe Glu Ser Val Glu Trp Gln
        595                 600                 605

Trp Pro Gly Ala Lys Pro Phe Ser Val Gln Val Lys Asn Phe Gly Pro
    610                 615                 620

Lys Asn Val Tyr Ile Lys Glu Val Trp Leu Asn Gly Arg Lys Leu Asp
625                 630                 635                 640

Arg Asn Trp Ile Thr His Ser Glu Ile Ala Lys Gly Gly Lys Leu Glu
                645                 650                 655

Ile Val Ala Ser Asp Gln Pro Asp Met Gln Gln Gly Leu Gly Asn Lys
            660                 665                 670

Trp Ile Ala Asp Ile Thr Arg Gln
        675                 680


<210> SEQ ID NO 31
<211> LENGTH: 867
<212> TYPE: PRT
<213> ORGANISM: Caulobacter crescentus

<400> SEQUENCE: 31

Met Asn Pro Gly Lys Gly Pro Val Leu Arg Phe Arg Val Gln Leu Leu
1               5                   10                  15

Val Val Gly Phe Ala Leu Ala Leu Gly Ala Ala His Gln Ala Gln Ala
            20                  25                  30

Ala Pro Gly Arg Ala Leu Tyr Lys Leu Pro Asp Leu Arg Val Gly Leu
        35                  40                  45

Gly Asp Asp Asn Gln Gly Asp Thr Ile Pro Gly Pro Thr Arg Pro Asn
    50                  55                  60

Gly Ser Ile His Pro Ser Pro Asp Thr Leu Lys Ala Ser Asn Ala Gly
65                  70                  75                  80

Tyr Asn Pro Ala Glu Pro Ile Ser Gly Phe Ala Gln Leu His Ser Gln
                85                  90                  95

Gly Ser Gly Gly Val Thr Thr Tyr Gly Thr Phe Leu Leu Ser Pro Gln
            100                 105                 110

Val Gly Glu Pro Val Phe Asp Glu Ala Ala His Leu Ser Pro Lys Ala
        115                 120                 125

Asp Glu Thr Leu Ala Ala Asp Ala Tyr Ser Val Arg Leu Thr Arg Tyr
    130                 135                 140

Asp Thr Lys Val Glu Ile Thr Ser Ala His Tyr Ala Ala Ile Tyr Arg
145                 150                 155                 160

Leu Thr Tyr Pro Thr Thr Asp Gln Ala Gln Val Val Leu Asp Val Thr
                165                 170                 175

Arg Lys Val Gly Gly Leu Val Ala Ser Glu Gln Ala Asp Val Gln Leu
            180                 185                 190

Phe Pro Glu Gln Gly Arg Ile Val Gly His Val Lys Ala Lys Gly Tyr
        195                 200                 205

Trp Asn Pro Ala Leu Ile Asp Ile Trp Phe Val Ala Glu Phe Asp Gln
    210                 215                 220

Asn Pro Thr Ala Trp Gly Val Phe Asp Lys Ala Glu Arg Arg Asp Gly
225                 230                 235                 240

Ala Leu Ser Gly Arg Thr Gly Ser Asp Glu Arg Leu Gly Ala Trp Leu
                245                 250                 255

Thr Phe Lys Thr Thr Pro Thr Lys Pro Leu Leu Val Lys Ile Ala Val
            260                 265                 270
```

```
Ser Phe Val Ser Ala Glu Met Ala Lys Ala Leu Leu Asp Arg Glu Ile
        275                 280                 285

Pro Asp Trp Asp Phe Glu Arg Val Arg Arg Asp Thr Gln Ala Ala Trp
    290                 295                 300

Asn Asp Arg Leu Gly Gln Val Arg Val Glu Gly Met Thr Glu Ser Gln
305                 310                 315                 320

Gln Arg Arg Phe Tyr Ser Ala Leu Tyr His Ala Ser Thr His Pro Arg
                325                 330                 335

Asp Arg Ser Leu Asp Gln Pro Ala Ala Arg Leu Gly Arg Pro Asn Trp
            340                 345                 350

Asp Glu His Tyr Thr Leu Trp Asp Thr Tyr Arg Thr Leu Phe Pro Leu
        355                 360                 365

Ile Ser Val Leu Arg Pro Ser Leu Tyr Thr Ala Asn Val Asn Ser Leu
    370                 375                 380

Ile His Thr Phe Asp Lys Phe Gly Ala Ala Asp Thr Ala Ile Ile Gly
385                 390                 395                 400

Gly Gln Asn Tyr His Val Gly Gln Gly Gly Asp Glu Val Asp Asn Val
                405                 410                 415

Leu Gly Glu Ala Leu Leu Arg Gly Ala Glu Gly Val Asn Trp Arg Asp
            420                 425                 430

Ala Trp Arg Val Ala Arg Phe Asn Ala Phe Glu Arg Arg Arg Pro Arg
        435                 440                 445

Tyr Leu Glu Ser Gly Tyr Phe Ala Val Gly Asp Arg Ser Pro Glu Pro
    450                 455                 460

Asn Asn Gln Arg Ala Lys Ser Gly Ser Ser Thr Leu Gly Phe Ala Leu
465                 470                 475                 480

Asn Asp Phe Tyr Ala Ala Gln Val Ala Ala Lys Ala Gly Gln Thr Asp
                485                 490                 495

Glu Ala Lys Ile Leu Thr Glu Arg Ser Ala Asn Trp Arg Lys Ile Trp
            500                 505                 510

Asn Pro Asp Ala Thr Ser Asp Gly Phe Ser Gly Phe Leu Met Pro Arg
        515                 520                 525

Tyr Ala Asp Gly Lys Phe Gln Asp Ile Asp Pro Lys Leu Gly Trp Asp
    530                 535                 540

Gly Lys Val His Asn Asn Val Gly Tyr Tyr Glu Gly Thr Ala Trp Ile
545                 550                 555                 560

Tyr Ser Tyr Gly Val Leu His Asp Leu Pro Gly Leu Val Glu Ala Met
                565                 570                 575

Gly Gly Arg Val Arg Phe Asn Glu Arg Leu Asn His Ala Leu Asp Ala
            580                 585                 590

Gly Leu Ile Asp Ile Thr Asn Glu Pro Ser Phe Ala Thr Pro Trp Leu
        595                 600                 605

Phe His Ala Ile Gly Arg Ala Asp Leu Ser Ser Arg Trp Ala Gly Glu
    610                 615                 620

Val Val Lys His Phe Thr Ala Asp Ala Tyr Pro Gly Asp Glu Asp Ala
625                 630                 635                 640

Gly Ala Met Ser Ser Asn Phe Val Phe Asn Ser Leu Gly Leu Phe Pro
                645                 650                 655

Lys Leu Gly Ser Asp Leu Tyr Tyr Leu His Gly Pro Arg His Gly Arg
            660                 665                 670

Thr Val Ile Gln Leu Glu Asn Gly Lys Thr Leu Glu Ile Leu Ala Ala
        675                 680                 685
```

```
Lys Ala Gly Ala Ser Arg Pro Tyr Ile Ala Ser Ala Ser Phe Asn Gly
    690                 695                 700

Lys Pro Leu Ala Gly Pro Tyr Val Ser Gln Ala Gln Leu Leu Gly Gly
705                 710                 715                 720

Gly Val Leu Ser Leu Ser Met Ser Asp Gln Pro Gly Gln Trp Ile Tyr
                725                 730                 735

Glu Gly Ala Val Leu Thr Val Arg Ala Asp Gln Pro Ser Leu Val Asp
            740                 745                 750

Gly Lys Thr Ser Thr Gly Trp Arg Ala Ala Ser Gly Gln Ser Val Thr
        755                 760                 765

Phe Ser Leu Lys Ala Pro Ala Cys Ile Ala Ala Tyr Ser Val Ser Val
    770                 775                 780

Gly Pro Asp Gln Ala Asp Pro Ser His Trp Thr Leu Gln Ala Tyr Asp
785                 790                 795                 800

Gly Arg Ala Trp Val Ser Val Asp Gln Gln Ser Asn Val Val Phe Asp
                805                 810                 815

His Arg His Ala Thr Arg Thr Phe Pro Leu Ala Pro Gly Arg Tyr Ala
            820                 825                 830

Arg Leu Arg Trp Val Leu Asp Gly Gly Ser Glu Ala Ser Val Ser Glu
        835                 840                 845

Val Glu Leu Ile Ala Gly Ala Ser Cys Ala Ala Pro Thr Ser Gly Ala
    850                 855                 860

Pro Leu Leu
865


<210> SEQ ID NO 32
<211> LENGTH: 867
<212> TYPE: PRT
<213> ORGANISM: Caulobacter crescentus

<400> SEQUENCE: 32

Met Asn Pro Gly Lys Gly Pro Val Leu Arg Phe Arg Val Gln Leu Leu
1               5                   10                  15

Val Val Gly Phe Ala Leu Ala Leu Gly Ala Ala His Gln Ala Gln Ala
            20                  25                  30

Ala Pro Gly Arg Ala Leu Tyr Lys Leu Pro Asp Leu Arg Val Gly Leu
        35                  40                  45

Gly Asp Asp Asn Gln Gly Asp Thr Ile Pro Gly Pro Thr Arg Pro Asn
    50                  55                  60

Gly Ser Ile His Pro Ser Pro Asp Thr Leu Lys Ala Ser Asn Ala Gly
65                  70                  75                  80

Tyr Asn Pro Ala Glu Pro Ile Ser Gly Phe Ala Gln Leu His Ser Gln
                85                  90                  95

Gly Ser Gly Gly Val Thr Thr Tyr Gly Thr Phe Leu Leu Ser Pro Gln
            100                 105                 110

Val Gly Glu Pro Val Phe Asp Glu Ala Ala His Leu Ser Pro Lys Ala
        115                 120                 125

Asp Glu Thr Leu Ala Ala Asp Ala Tyr Ser Val Arg Leu Thr Arg Tyr
    130                 135                 140

Asp Thr Lys Val Glu Ile Thr Ser Ala His Tyr Ala Ala Ile Tyr Arg
145                 150                 155                 160

Leu Thr Tyr Pro Thr Thr Asp Gln Ala Gln Val Val Leu Asp Val Thr
                165                 170                 175

Arg Lys Val Gly Gly Leu Val Ala Ser Glu Gln Ala Asp Val Gln Leu
            180                 185                 190
```

```
Phe Pro Glu Gln Gly Arg Ile Val Gly His Val Lys Ala Lys Gly Tyr
        195                 200                 205

Trp Asn Pro Ala Leu Ile Asp Ile Trp Phe Val Ala Glu Phe Asp Gln
    210                 215                 220

Asn Pro Thr Ala Trp Gly Val Phe Asp Lys Ala Glu Arg Arg Asp Gly
225                 230                 235                 240

Ala Leu Ser Gly Arg Thr Gly Ser Asp Glu Arg Leu Gly Ala Trp Leu
                245                 250                 255

Thr Phe Lys Thr Thr Pro Thr Lys Pro Leu Leu Val Lys Ile Ala Val
            260                 265                 270

Ser Phe Val Ser Ala Glu Met Ala Lys Ala Leu Leu Asp Arg Glu Ile
        275                 280                 285

Pro Asp Trp Asp Phe Glu Arg Val Arg Arg Asp Thr Gln Ala Ala Trp
    290                 295                 300

Asn Asp Arg Leu Gly Gln Val Arg Val Glu Gly Met Thr Glu Ser Gln
305                 310                 315                 320

Gln Arg Arg Phe Tyr Ser Ala Leu Tyr His Ala Ser Thr His Pro Arg
                325                 330                 335

Asp Arg Ser Leu Asp Gln Pro Ala Ala Arg Leu Gly Arg Pro Asn Trp
            340                 345                 350

Asp Glu His Tyr Thr Leu Trp Asp Thr Tyr Arg Thr Leu Phe Pro Leu
        355                 360                 365

Ile Ser Val Leu Arg Pro Ser Leu Tyr Thr Ala Asn Val Asn Ser Leu
    370                 375                 380

Ile His Thr Phe Asp Lys Phe Gly Ala Ala Asp Thr Ala Ile Ile Gly
385                 390                 395                 400

Gly Gln Asn Tyr His Val Gly Gln Gly Gly Asp Glu Val Asp Asn Val
                405                 410                 415

Leu Gly Glu Ala Leu Leu Arg Gly Ala Glu Gly Val Asn Trp Arg Asp
            420                 425                 430

Ala Trp Arg Val Ala Arg Phe Asn Ala Phe Glu Arg Arg Arg Pro Arg
        435                 440                 445

Tyr Leu Glu Ser Gly Tyr Phe Ala Val Gly Asp Arg Ser Pro Glu Pro
    450                 455                 460

Asn Asn Gln Arg Ala Lys Ser Gly Ser Ser Thr Leu Gly Phe Ala Leu
465                 470                 475                 480

Asn Asp Phe Tyr Ala Ala Gln Val Ala Ala Lys Ala Gly Gln Thr Asp
                485                 490                 495

Glu Ala Lys Ile Leu Thr Glu Arg Ser Ala Asn Trp Arg Lys Ile Trp
            500                 505                 510

Asn Pro Asp Ala Thr Ser Asp Gly Phe Ser Gly Phe Leu Met Pro Arg
        515                 520                 525

Tyr Ala Asp Gly Lys Phe Gln Asp Ile Asp Pro Lys Leu Gly Trp Asp
    530                 535                 540

Gly Lys Val His Asn Asn Val Gly Tyr Tyr Glu Gly Thr Ala Trp Ile
545                 550                 555                 560

Tyr Ser Tyr Gly Val Leu His Asp Leu Pro Gly Leu Val Glu Ala Met
                565                 570                 575

Gly Gly Arg Val Arg Phe Asn Glu Arg Leu Asn His Ala Leu Asp Ala
            580                 585                 590

Gly Leu Ile Asp Ile Thr Asn Glu Pro Ser Phe Ala Thr Pro Trp Leu
        595                 600                 605
```

-continued

Phe His Ala Ile Gly Arg Ala Asp Leu Ser Ser Arg Trp Ala Gly Glu
    610                 615                 620

Val Val Lys His Phe Thr Ala Asp Ala Tyr Pro Gly Asp Glu Asp Ala
625                 630                 635                 640

Gly Ala Met Ser Ser Asn Phe Val Phe Asn Ser Leu Gly Leu Phe Pro
                645                 650                 655

Lys Leu Gly Ser Asp Leu Tyr Tyr Leu His Gly Pro Arg His Gly Arg
            660                 665                 670

Thr Val Ile Gln Leu Glu Asn Gly Lys Thr Leu Glu Ile Leu Ala Ala
        675                 680                 685

Lys Ala Gly Ala Ser Arg Pro Tyr Ile Ala Ser Ala Ser Phe Asn Gly
    690                 695                 700

Lys Pro Leu Ala Gly Pro Tyr Val Ser Gln Ala Gln Leu Leu Gly Gly
705                 710                 715                 720

Gly Val Leu Ser Leu Ser Met Ser Asp Gln Pro Gly Gln Trp Ile Tyr
                725                 730                 735

Glu Gly Ala Val Leu Thr Val Arg Ala Asp Gln Pro Ser Leu Val Asp
            740                 745                 750

Gly Lys Thr Ser Thr Gly Trp Arg Ala Ala Ser Gly Gln Ser Val Thr
        755                 760                 765

Phe Ser Leu Lys Ala Pro Ala Cys Ile Ala Ala Tyr Ser Val Ser Val
    770                 775                 780

Gly Pro Asp Gln Ala Asp Pro Ser His Trp Thr Leu Gln Ala Tyr Asp
785                 790                 795                 800

Gly Arg Ala Trp Val Ser Val Asp Gln Gln Ser Asn Val Val Phe Asp
                805                 810                 815

His Arg His Ala Thr Arg Thr Phe Pro Leu Ala Pro Gly Arg Tyr Ala
            820                 825                 830

Arg Leu Arg Trp Val Leu Asp Gly Gly Ser Glu Ala Ser Val Ser Glu
        835                 840                 845

Val Glu Leu Ile Ala Gly Ala Ser Cys Ala Ala Pro Thr Ser Gly Ala
    850                 855                 860

Pro Leu Leu
865

<210> SEQ ID NO 33
<211> LENGTH: 1937
<212> TYPE: PRT
<213> ORGANISM: Paenibacillus sp.

<400> SEQUENCE: 33

Met Phe Lys Lys Leu Phe Ala Val Ala Met Thr Val Met Cys Leu Thr
1               5                   10                  15

Gly Ile Leu Val Pro Val Gly Ser Asn Ala Ala Phe Ala Ala Ala Ala
            20                  25                  30

Glu Gly Ile Thr Thr Arg Asn Val Ala Ile Asn Ala Ala Ala Thr Ala
        35                  40                  45

Ser Gly Gln Cys Asn Ala Asn Glu Ser Ala Ser Asn Ala Val Asp Gly
    50                  55                  60

Lys Thr Asp Thr Lys Trp Cys Asp Asn Thr Ser Ala Gln Lys Lys Trp
65                  70                  75                  80

Leu Lys Leu Asp Leu Gly Lys Glu Tyr Leu Val Asn Glu Trp Val Leu
                85                  90                  95

Gln Asn Ala Ala Ile Asn Glu Ser Gly Asn Ser Pro Phe Trp Asn Thr
            100                 105                 110

```
Lys Asn Phe Arg Leu Gln Lys Ser Asp Asp Gly Glu Thr Trp Thr Asp
        115                 120                 125

Val Asp Ile Val Thr Asn Asn Ala Gln Thr Ile Val Asp Arg Phe Val
    130                 135                 140

Thr Pro Phe Thr Thr Arg Tyr Leu Arg Leu Tyr Ile Asp Lys Ala Ala
145                 150                 155                 160

Tyr Asp Ser Asn Ile Ala Arg Ile Tyr Glu Leu Glu Val Tyr Gly Val
                165                 170                 175

Glu Ala Asp Gln Ile Pro Ala Glu Pro Glu Thr Asn Leu Ala Pro Ile
            180                 185                 190

Asp Tyr Val Asp Pro Phe Ile Asn Thr Leu Gly Asp Asn Gly Gln Thr
        195                 200                 205

Asn Pro Gly Pro Thr Thr Pro Phe Gly Leu Val Ser Leu Gly Pro Asp
    210                 215                 220

Ser Asp Gly Gly Ala Phe Ser Gly Tyr Tyr Tyr Glu Asn Lys Asn Leu
225                 230                 235                 240

Lys Gly Phe Ser His Leu Arg Phe Ser Gly Val Gly Cys Ser Gly Gly
                245                 250                 255

Gly Gly Asn Ile Leu Met Met Pro Glu Thr Arg Asp Phe Thr Lys Asn
            260                 265                 270

Val Ala Asp Tyr Lys Gln Lys Tyr Asp Lys Ser Ser Glu Gln Ala Ser
        275                 280                 285

Ala Gly Phe Tyr Gly Val Thr Leu Ala Ser Gly Ile Asn Val Gln Leu
    290                 295                 300

Thr Ser Ser Asp Asn Val Gly Phe His Lys Tyr Thr Phe Pro Asp Thr
305                 310                 315                 320

Ala Asn Thr Gly Ser Val Leu Val Asp Leu Ser Asn Ser Tyr Ala Gly
                325                 330                 335

Met Val Asp Ala Asn Leu Lys Val Thr Gly Ser Asn Glu Ile Thr Gly
            340                 345                 350

Met Ile Lys Ser Gln Asn Val Cys Gly His Gly Tyr Tyr Thr Ile Tyr
        355                 360                 365

Tyr Ser Ile Gln Phe Asp His Asp Phe Asp Ser Tyr Ser Ser Trp Gln
    370                 375                 380

Gly Asp Ser Val Gly Ala Val Ala Gln Arg Ser Gly Ser Asn Ser Gly
385                 390                 395                 400

Val Trp Leu Asn Phe Asn Thr Ala Gly Ser Lys Thr Val Gln Ala Lys
                405                 410                 415

Val Gly Leu Ser Thr Ile Ser Val Glu Gln Ala Gln Ala Glu Arg Gly
            420                 425                 430

Leu Tyr Ser Asp Trp Asn Phe Asp Ala Arg His Glu Glu Ala Arg Ala
        435                 440                 445

Ala Trp Ser Asn Val Leu Asn Lys Val Glu Ile Thr Asp Ala Asp Glu
    450                 455                 460

Gln Asn Lys Arg Val Phe Tyr Thr Gln Met Tyr His Ser Tyr Leu Ser
465                 470                 475                 480

Pro Lys Asn Val Thr Ser Ser Ala Gly Thr Phe Lys Ala Gly Arg Asp
                485                 490                 495

Glu Asn Thr Val Arg Gln Ala Ser Glu Leu Gly Asp Asp Phe Glu Tyr
            500                 505                 510

Tyr Asn Gly Trp Thr Thr Trp Asp Asp Phe Arg Lys Tyr Ala Met Phe
        515                 520                 525
```

```
Ser Leu Phe Glu Pro Gln Arg Tyr Asn Asn Met Val Lys Ser Leu Val
    530                 535                 540

Asp Leu Tyr Asn Thr Arg Gly Thr Tyr Thr Gln Trp Gly Asp Gly Tyr
545                 550                 555                 560

Trp Pro Ser Pro Thr Val Arg Asn Glu Phe Asn Gly Gln Val Ile Leu
                565                 570                 575

Asp Ala Tyr Ala Lys Gly Phe Gln Asp Phe Asp Val Tyr Lys Ala Leu
            580                 585                 590

Lys Gly Met Ala Val Asp Ala Asp Asn Phe Ser Ile Ser Asp Gly Glu
        595                 600                 605

Ile Ser Gly Lys Leu Glu Lys Ala Asn Ser Ala Ser Phe Pro Met Lys
    610                 615                 620

Leu Ala Gln Leu Ile Gly Asp Lys Ala Thr Phe Glu Lys Tyr Lys Glu
625                 630                 635                 640

Leu Ala Leu Ser Tyr Lys Lys Leu Trp Asn Pro Thr Gln Val Asp Glu
                645                 650                 655

Lys Gly Thr Pro Thr Gly Phe Phe Thr Pro Asn Gly Thr Thr Val Gly
            660                 665                 670

Ala Gly Asp Ile Gln Ala Val Asp Arg Tyr Ala Tyr Gln Gly Asn Leu
        675                 680                 685

Trp Gln Tyr Arg Trp Ser Ala Pro Gln Asp Ile Asn Gly Leu Ala Gln
    690                 695                 700

Leu Met Gly Gly Lys Thr Glu Met Ala Lys Gln Leu Lys His Phe Phe
705                 710                 715                 720

Glu Ile Asp Glu Tyr Met Ala Ile Asn Glu Glu Asp Ile Ser Ala Pro
                725                 730                 735

Tyr Leu Phe Asn Tyr Leu Gly Tyr Pro Tyr Leu Thr Gln Tyr Tyr Ala
            740                 745                 750

Arg Glu Phe Thr Thr Glu Val Val Thr Gln Lys Tyr His Asn His Gly
        755                 760                 765

Ala Tyr Ala Tyr Pro Leu Lys Ser Arg Val Tyr Arg Asp Asp Pro Glu
    770                 775                 780

Gly Tyr Leu Ser Ser Met Asp Asp Asp Ala Gly Gly Met Ser Ser Trp
785                 790                 795                 800

Tyr Val Phe Ser Ala Leu Gly Leu Phe Pro Gly Asn Pro Gly Glu Gly
                805                 810                 815

Tyr Phe Leu Ile Gly Ser Pro Ile Phe Ser Glu Val Lys Leu His Met
            820                 825                 830

Gly Ser Gly Lys Thr Leu Val Ile Lys Ala Asp Asn Val Ser Ser Glu
        835                 840                 845

Asn Arg Phe Ile Gln Ser Ala Lys Leu Asn Gly Lys Asp Phe Asn Gln
    850                 855                 860

Ser Trp Ile Lys Tyr Asp Asp Leu Met Ala Gly Gly Thr Leu Glu Phe
865                 870                 875                 880

Gln Met Ser Ser Thr Pro Asn Met Ser Trp Gly Ala Lys Ala Ser Ala
                885                 890                 895

Ala Pro Pro Thr Val Asp Tyr Asn Ala Asp Met Asp Asn Asp Phe Asn
            900                 905                 910

His Glu Gln Leu Ile Pro Glu Lys Ser Thr Trp Lys Tyr Asp Asp Lys
        915                 920                 925

Gly Lys Glu Ala Gly Glu Gly Trp Thr Gln Val Asp Phe Asp Asp Ser
    930                 935                 940

Ser Trp Ser Ser Gly Lys Ala Met Leu Gly Tyr Asp Ser Tyr Gly Lys
```

```
945                 950                 955                 960

Pro Ala Thr Thr Val Ser Tyr Gly Pro Asn Ala Asn Asn Lys Tyr Val
                965                 970                 975

Thr Thr Tyr Phe Arg Lys Thr Phe Asp Ala Lys Asp Leu Asp Gly Ile
            980                 985                 990

Leu Glu Leu Asp Gly Ser Leu Ile Arg Asp Asp Gly Ala Ile Val Tyr
        995                 1000                1005

Leu Asn Gly His Glu Ile Phe Arg Thr Asn Met Pro Thr Gly Ala Val
    1010                1015                1020

Asn Tyr Ser Thr Phe Ala Asn Ala Thr Val Gly Asp Glu Arg Asp Lys
1025                1030                1035                1040

Asn Gly Phe Ile Ile Asp Pro Ser Tyr Leu Val Glu Gly Lys Asn Val
                1045                1050                1055

Leu Thr Ala Glu Val His Gln Val Asn Ala Thr Ser Ser Asp Ile Ala
            1060                1065                1070

Phe Glu Phe Ser Leu Glu Ala Val Arg Lys Leu Asn Ile Pro Ala Ala
        1075                1080                1085

Pro Thr His Pro Val Val Asp Asp Lys Ala Asn Thr Ile Gly Trp Thr
    1090                1095                1100

Pro Val Glu Gly Ile Asn Asn Ala Ser Asp Tyr Glu Phe Ser Thr Asp
1105                1110                1115                1120

Gly Gly Lys Ser Trp Lys Gln Ala Lys Ala Asn Pro Gln Thr Val Gly
                1125                1130                1135

Pro Leu Asn Tyr Ala Pro Gly Ile Val Gln Val Arg Val Met Ala Asn
            1140                1145                1150

Ala Ala Ala Asn Arg Ala Ala Gly Glu Ala Leu Leu Ser Thr Glu Ala
        1155                1160                1165

Tyr Thr Ser Asp Val Lys Trp Asp Val Tyr Asp Leu Asp Ala Asp Ile
    1170                1175                1180

His Gln Asp Gly Asn Met Val Val Asp Val Thr Gly Thr Leu Lys Gly
1185                1190                1195                1200

Asp Tyr Thr Asp Ser Ala Val Val Val Phe Gln Leu Met Asp Gly Lys
                1205                1210                1215

Glu His Ala Trp Val Ser Ser Ala Val Pro Val Gln Thr Gly Ser Phe
            1220                1225                1230

Asp Ile Ser Gln Ile Tyr Asn Val Asp Ala Ser Lys Tyr Lys Val Asn
        1235                1240                1245

Val Tyr Leu Val Asn Glu Phe Asn Gly Asp Ile Tyr Glu Ser Pro Leu
    1250                1255                1260

Trp Leu Ala Asp Pro Ile Val Gln Gln Ser Glu Pro Gly Ser Leu Pro
1265                1270                1275                1280

Asp Pro Glu Gly Pro Pro Val Thr Glu Glu Pro Leu Pro Glu Pro Ile
                1285                1290                1295

Pro Leu Pro Asp Pro Lys Pro Asp Glu Pro Glu Glu Pro Glu Val Pro
            1300                1305                1310

Glu Thr Gly Met Lys Ile Gln Phe Glu Asp Arg Ala Glu Trp Thr Ser
        1315                1320                1325

Ala Ala His Pro Asn Gly Gly Gly Gly Leu Ser Thr Glu Ala Gly Asn
    1330                1335                1340

Gly Gly Thr Val Val Ala His Thr Phe Gly Gly Ala Trp Leu Ala Tyr
1345                1350                1355                1360

Asn Val Asp Phe Gly Thr Thr Gly Tyr Asn Asn Val Thr Val Gln Tyr
                1365                1370                1375
```

-continued

```
Asp Ala Pro Thr Asp Lys Val Pro Ala Gly Ser Lys Leu Glu Phe Arg
            1380                1385                1390

Leu Gly Ser Val Ser Gly Glu Leu Val Gly Thr Val Asn Met Glu Asp
        1395                1400                1405

Lys Asn Ala Gly Trp Gly Ser Tyr Ile Thr Thr Lys Ala Asn Leu Thr
    1410                1415                1420

Arg Thr Leu Thr Gly Gln Gln Lys Leu Tyr Val Val Met Val Ala Gly
1425                1430                1435                1440

Thr Pro Asn Asn Leu Pro Tyr Ile Gly Asn Phe Asp Trp Phe Lys Phe
                1445                1450                1455

Asp Tyr Glu Lys Ile Arg Ser Asp Tyr Ala Lys Leu Glu Leu Glu Ser
            1460                1465                1470

Tyr Asp Glu Trp Thr Thr Asp Val Asn Thr Gly Asn Asn Asn Thr Pro
        1475                1480                1485

Leu Lys Thr Glu Ala Gly Lys Gly Gly Val Gly Gln Gln Val Ala Asn
    1490                1495                1500

Thr Phe Asn Gly Ala Trp Leu Ala Tyr Lys Arg Met Asp Phe Gly Ser
1505                1510                1515                1520

Glu Gly Val Asp Lys Phe Ser Ile Glu Tyr Ala Gly Asn Ser Thr Asn
                1525                1530                1535

Thr Phe Asn Asn Ser Ala Val Glu Val Arg Leu Gly Ser Pro Thr Gly
            1540                1545                1550

Thr Leu Val Gly Thr Val Ala Thr Pro Pro Thr Ala Ala Ala Trp Gly
        1555                1560                1565

Thr Tyr Ala Thr Val Ser Gly Ser Leu Thr Gln Lys Leu Thr Gly Leu
    1570                1575                1580

Gln Asp Val Tyr Leu Val Phe Thr Gly Ser Ala Ala Asn Gly Glu Thr
1585                1590                1595                1600

Gly Lys Lys Tyr Ile Gly Asn Phe Asp Asn Ala Ser Phe Ser Leu Ser
                1605                1610                1615

Val Gln Glu Pro Glu Glu Pro Glu Gln Pro Gln Gln Pro Glu Gln Glu
            1620                1625                1630

Gln Ile Thr Val Gln Phe Glu Ser Lys Thr Glu Trp Asn Thr Ala Leu
        1635                1640                1645

Asn Thr Phe Asn Asn Gln Ala Met Lys Ile Glu Asn Asn Asn Gly Gly
    1650                1655                1660

Gln Thr Val Gly Asn Thr Tyr Thr Gly Ala Trp Leu Gly Phe Lys Asp
1665                1670                1675                1680

Val Asp Phe Gly Ser Glu Lys Gly Lys Asn Gln Val Ser Ile Val Tyr
                1685                1690                1695

Asp Ala Pro Thr Asn Arg Val Pro Ala Asp Val Lys Ala Glu Ile Arg
            1700                1705                1710

Leu Gly Ser Pro Thr Gly Thr Leu Val Gly Thr Val Ala Ile Pro Asn
        1715                1720                1725

Thr Gly Ser Thr Trp Gly Gln Tyr Asn Thr Ala Thr Ala Asp Leu Asn
    1730                1735                1740

Thr Thr Ile Lys Gly Lys Gln Asp Leu Tyr Ile Val Met Thr Gly Ser
1745                1750                1755                1760

Thr Thr Ser Ser Leu Leu Tyr Val Gly Asn Tyr Asp Ser Leu Thr Phe
                1765                1770                1775

Gly Tyr Lys Pro Val Arg Ser Asp Tyr Ala Lys Leu Glu Leu Glu Ser
            1780                1785                1790
```

-continued

```
Tyr Asp Glu Trp Thr Thr Ala Val Asn Pro Leu Asn Ser Asn Thr Pro
        1795                1800                1805

Leu Lys Thr Glu Ala Gly Lys Gly Gly Ala Gly Lys Gln Val Ala Asn
    1810                1815                1820

Thr Phe Asn Gly Ala Trp Leu Ala Tyr Lys Arg Met Asp Phe Gly Thr
1825                1830                1835                1840

Glu Gly Val Asn Thr Phe Ala Val Glu Tyr Ala Gly Asn Thr Thr Asn
                1845                1850                1855

Cys Phe Thr Asn Ser Ala Val Glu Ile Arg Leu Gly Ser Pro Thr Gly
            1860                1865                1870

Thr Leu Val Gly Lys Ile Ser Thr Pro Pro Lys Ala Gly Asn Trp Thr
        1875                1880                1885

Thr Tyr Asp Thr Val Ser Gly Thr Leu Thr Gln Lys Leu Thr Gly Ile
    1890                1895                1900

Gln Asp Val Tyr Leu Val Leu Thr Gly Ser Ala Gly Asn Gly Glu Thr
1905                1910                1915                1920

Gly Lys Lys Tyr Ile Gly Asn Phe Asp Asn Ala Ala Phe Ser Leu Lys
                1925                1930                1935

Val
```

<210> SEQ ID NO 34
<211> LENGTH: 751
<212> TYPE: PRT
<213> ORGANISM: Chitinophaga pinensis

<400> SEQUENCE: 34

```
Met Lys Arg Asn Arg Tyr Leu Ile Ser Thr Ala Ile Leu Val Leu Gly
1               5                   10                  15

Ile Thr Thr Ser Ala Leu Ala Gln Val Gly Ala Gly Ser Thr Trp Lys
            20                  25                  30

Pro Thr Gly Asn Leu Thr Tyr Val Asp Pro Thr Ile Gly Ser Val Gly
        35                  40                  45

Leu Ile Leu Glu Pro Thr Arg Pro Ala Met Tyr Leu Pro Asn Ser Met
    50                  55                  60

Val Arg Val Phe Pro Ser Arg Lys Asp Gln Leu Glu Asp Gln Ile Asn
65                  70                  75                  80

Phe Phe Pro Leu Thr Ile Ala Ser His Arg Gln Gln Ser Leu Phe Gly
                85                  90                  95

Phe Met Pro Leu Ser Gly Glu Val Asn Thr Glu Asn Trp Lys Arg Ser
            100                 105                 110

Arg Val Tyr Asp Arg Glu Lys Ile Ser Pro Cys Lys Tyr Ser Ala Tyr
        115                 120                 125

Leu Asp Asp Thr Asp Glu Ile Thr Phe Ala Pro Ala Ala His Ser Gly
    130                 135                 140

Tyr Phe Glu Ile Asp Phe Thr Gly Asn Thr Pro His Tyr Leu Arg Leu
145                 150                 155                 160

Ser Ile Leu Asn Arg Asp Gly Asp Leu Thr Val Asp Gly Lys Arg Ala
                165                 170                 175

Ile Ser Gly Arg Glu Thr Phe Asn Gly Met Ser Ala Tyr Phe Tyr Ala
            180                 185                 190

Glu Val Asn Ala Asp Ile Ile Gly Thr Glu Tyr Arg Gly Asp Lys Lys
        195                 200                 205

Gln His Leu Phe Ala Ala Leu Gly Asn Asn Pro Gln Lys Ile Ala Val
    210                 215                 220
```

-continued

```
Arg Tyr Gly Val Ser Phe Ile Ser Val Glu Gln Ala Lys Ala Asn Leu
225                 230                 235                 240

Lys Lys Glu Ile Pro Leu Trp Thr Ile Ser Pro Leu Val Ile Lys Gly
                245                 250                 255

Ala Ala Ala Trp Asn Lys Val Leu Gly Gln Ile Asn Val Lys Gly Gly
            260                 265                 270

Thr Asp Ala Gln Lys Arg Val Phe Tyr Thr Ser Leu Tyr Arg Ala Tyr
        275                 280                 285

Glu Arg Met Val Asn Ile Asn Glu Tyr Gly Gln Tyr Tyr Ser Ala Tyr
    290                 295                 300

Asp His Lys Val His Thr Ser Asp Lys Pro Phe Tyr Val Asp Asn Trp
305                 310                 315                 320

Leu Trp Asp Thr Tyr Ile Ala Leu Glu Pro Leu Gln Thr Leu Leu Asn
                325                 330                 335

Pro Glu Met Glu Ala Asp Lys Ile Arg Ser Tyr Val Asp Met Tyr Glu
            340                 345                 350

Gln Ser Gly Trp Met Pro Ser Phe Ala Val Ala His Gly Asp Met Pro
        355                 360                 365

Cys Met Thr Gly Asn His Ala Ala Ala Trp Met Ala Asp Ala Trp Phe
    370                 375                 380

Lys Gly Val Arg Asn Phe Asp Ile Ala Lys Ala Tyr Glu Gly Leu Lys
385                 390                 395                 400

Lys Asn Ser Leu Gln Ala Thr Leu Leu Pro Trp Arg Asn Gly Pro Ala
                405                 410                 415

Thr Ser Leu Asp Thr Phe Tyr Thr Glu His Gly Tyr Met Pro Ser Leu
            420                 425                 430

Lys Pro Asp Glu Lys Glu Thr Val Lys Glu Val Asp Asp Phe Glu Arg
        435                 440                 445

Arg Gln Ala Val Ala Val Thr Leu Glu Asn Ser Tyr Asp Asp Trp Cys
    450                 455                 460

Ile Ala Gln Leu Ala Lys Ala Ala Gly His Pro Glu Asp Ile Pro Leu
465                 470                 475                 480

Phe Leu Lys Arg Ala Thr Asn Tyr Lys Asn Val Tyr Arg Ala Asp Lys
                485                 490                 495

Gly Phe Met Trp Pro Lys Asp Ala Asp Gly Asn Trp Ile Glu Pro Phe
            500                 505                 510

Asp Pro Lys Phe Ser Gly Gly Gln Gly Gly Arg Asp Tyr Phe Thr Glu
        515                 520                 525

Asn Asn Ala Tyr Thr Tyr Asn Trp Asp Val Lys His Asp Leu Thr Gly
    530                 535                 540

Leu Phe Asp Leu Met Gly Gly Lys Ala Lys Ala Glu Glu Lys Leu Asp
545                 550                 555                 560

Gln Leu Phe Arg Glu Asn Leu Gly Arg Ser Lys Tyr Asn Leu Trp Tyr
                565                 570                 575

Thr Phe Pro Asp Ala Thr Gly Met Val Gly Gln Phe Val Met Gly Asn
            580                 585                 590

Glu Pro Ser Phe His Ile Pro Tyr Leu Tyr Asn Tyr Thr Gly Ala Pro
        595                 600                 605

Trp Lys Thr Gln Lys Arg Ile Arg Met Leu Leu Asp Thr Trp Tyr Thr
    610                 615                 620

Asp Asn Leu Phe Gly Ile Pro Gly Asp Glu Asp Gly Gly Gly Met Thr
625                 630                 635                 640

Ala Phe Val Val Phe Ser Met Met Gly Phe Cys Pro Val Thr Pro Gly
```

```
                645                 650                 655

Ile Pro Val Tyr Asn Ile Gly Ser Pro Val Phe Ser Glu Ile Thr Ile
            660                 665                 670

Lys Leu Phe Ser Gly Lys Thr Phe Thr Ile Ser Ala Pro Gly Ser Ser
        675                 680                 685

Ala Thr Lys Lys Tyr Ile Gln Arg Ala Thr Leu Asn Gly Gln Pro Leu
    690                 695                 700

Asn Val Pro Trp Phe Thr His Glu Asp Leu Leu Lys Gly Gly Val Leu
705                 710                 715                 720

Glu Leu Val Met Ser Glu Ser Pro Asn Lys Glu Trp Gly Thr Gly Ala
                725                 730                 735

Gln Ala Ala Pro Pro Ser Ser Leu Asn Tyr Ser Pro Ala Gly Lys
            740                 745                 750


<210> SEQ ID NO 35
<211> LENGTH: 728
<212> TYPE: PRT
<213> ORGANISM: Pedobacter heparinus

<400> SEQUENCE: 35

Met Lys Asn Ser Ile Lys Leu Met Leu Leu Cys Leu Leu Leu Ser Gln
1               5                   10                  15

Ser Arg Leu Lys Ala Gln Glu Val Thr Ser Asn Leu Gln Tyr Val Asp
            20                  25                  30

Pro Thr Ile Gly Ala Val Gly His Ile Leu Glu Pro Thr Arg Pro Thr
        35                  40                  45

Met His Leu Pro Asn Ser Met Val Arg Val Tyr Pro Val Arg Lys Asp
    50                  55                  60

Gln Leu Asp Asp Gln Ile Ser Tyr Phe Pro Leu Asn Met Tyr Ser His
65                  70                  75                  80

Arg Ile Gly Asn Val Phe Ala Leu Met Pro Tyr Asn Gly Val Val Asn
                85                  90                  95

Glu Lys Ser Trp Lys Gln Arg Phe Thr Tyr Asp Leu Glu Lys Thr Ala
            100                 105                 110

Pro His Tyr Tyr Thr Ala Val Leu Glu Glu Ser Gly Ile Lys Val Glu
        115                 120                 125

Phe Ser Pro Ser Glu Arg Ser Gly Tyr Tyr Arg Phe Lys Phe Pro Ser
    130                 135                 140

Ala Ser Ala Asn Trp Leu Arg Leu Gly Val Val Asn Glu Thr Gly Glu
145                 150                 155                 160

Leu Lys Val Ser Gly Lys Arg Ile Leu Ser Gly Ser Glu Asp Phe Gln
                165                 170                 175

Gly Met Lys Ala Tyr Phe Tyr Gly Glu Leu Asn Ala Asp Val Thr Glu
            180                 185                 190

Ser Lys Tyr Lys Asp Gly Thr Gly Asn Lys Asn Leu Phe Leu Lys Val
        195                 200                 205

Gly Asn Ser His Gly Val Glu Phe Arg Tyr Gly Ile Ser Tyr Ile Ser
    210                 215                 220

Val Glu Gln Ala Lys Ile Asn Leu Glu Lys Glu Ile Pro Asn Trp Gly
225                 230                 235                 240

Phe Glu Lys Val Lys Ser Thr Ala Lys Gln Val Trp Glu Glu Ala Leu
                245                 250                 255

Asn Gln Ile Thr Val Glu Gly Gly Thr Leu Ala Tyr Lys Arg Ser Phe
            260                 265                 270
```

-continued

```
Tyr Thr Ala Leu Tyr Arg Thr Tyr Glu Arg Met Val Asn Ile Asn Glu
        275                 280                 285

Tyr Gly Arg Tyr Tyr Ser Ala Tyr Asp His Lys Val His Ser Asp Ser
    290                 295                 300

Arg Pro Phe Tyr Val Asp Asn Trp Ile Trp Asp Ser Tyr Leu Ala His
305                 310                 315                 320

Gln Pro Leu His Met Ile Leu Asn Pro Asp Arg Gln Ala Asp Met Ile
                325                 330                 335

Ser Ser Tyr Val Asn Met Tyr Glu Gln Ser Gly Trp Met Pro Ser Phe
            340                 345                 350

Ala Leu Val Phe Gly Asp Asn Pro Cys Met Thr Gly Asn His Ala Ala
        355                 360                 365

Ala Trp Ile Thr Asp Ala Trp Phe Lys Gly Ile Arg Asn Phe Asn Val
    370                 375                 380

Glu Lys Ala Tyr Ala Gly Leu Lys Lys Asn Ser Leu Glu Ala Thr Leu
385                 390                 395                 400

Leu Pro Trp Arg Asn Gly Pro Ala Ile Gly Leu Asp Ser Phe Tyr Ala
                405                 410                 415

Glu Lys Gly Tyr Phe Pro Ala Leu Arg Pro Gly Glu Lys Glu Ser Val
            420                 425                 430

Asn Glu Val His Asp Phe Glu Lys Arg Gln Ser Val Ala Val Thr Leu
        435                 440                 445

Gln Gln Ser Tyr Asp Asp Trp Cys Ile Ser Lys Leu Ala Gly Thr Leu
    450                 455                 460

Gly Lys Ala Ala Asp Ser Lys Leu Phe Leu Ala Lys Ala Glu Asn Tyr
465                 470                 475                 480

Lys Asn Val Phe Arg Glu Ser Lys Gly Phe Met Trp Pro Lys Asp Asp
                485                 490                 495

Lys Gly Gln Trp Ile Glu Pro Phe Asp Pro Lys Phe Ser Gly Gly Gln
            500                 505                 510

Gly Gly Arg Glu Tyr Phe Thr Glu Asn Asn Ala Tyr Thr Tyr Asn Trp
        515                 520                 525

Asp Val Lys His Asp Leu Glu Gly Leu Phe Lys Leu Met Gly Gly Lys
    530                 535                 540

Gln Ala Ala Glu Asn Lys Leu Asp Asn Leu Phe Arg Glu Asp Leu Gly
545                 550                 555                 560

Arg Ser Lys Tyr Val Leu Trp Asn Thr Phe Pro Asp Ala Thr Gly Leu
                565                 570                 575

Val Gly Gln Phe Val Met Gly Asn Glu Pro Ser Phe His Ile Pro Tyr
            580                 585                 590

Leu Tyr Asn Asp Leu Gly Ser Pro Trp Lys Thr Gln Lys Arg Ile Arg
        595                 600                 605

Met Leu Met Asp Thr Trp Phe Thr Asp Asn Leu Phe Ser Ile Pro Gly
    610                 615                 620

Asp Glu Asp Gly Gly Gly Met Ser Ala Phe Val Val Phe Ser Met Met
625                 630                 635                 640

Gly Phe Tyr Pro Val Thr Pro Gly Ile Pro Val Tyr His Ile Gly Ser
                645                 650                 655

Pro Val Phe Asn Lys Ile Ser Leu Lys Leu Lys Asn Gly Lys Thr Phe
            660                 665                 670

Thr Val Val Ala Arg Asn Asn Ser Ser Thr Ala Lys Tyr Ile Gln Ser
        675                 680                 685

Ala Lys Leu Asn Gly Val Asn Trp Asp Lys His Ser Phe Asn His Ala
```

690                 695                 700

Asp Ile Leu Lys Gly Gly Asn Leu Glu Leu Val Met Gly Glu Thr Pro
705                 710                 715                 720

Asn Lys Gln Trp Gly Lys Thr Lys
                725

<210> SEQ ID NO 36
<211> LENGTH: 2234
<212> TYPE: PRT
<213> ORGANISM: Streptomyces

<400> SEQUENCE: 36

Met Leu Val Met Pro Asp Arg Ser Lys Arg Pro Pro Ile Arg Ser Ser
1               5                   10                  15

Ser Pro Arg Ala Ala Leu Arg Ala Thr Val Ala Ala Val Leu Ala Gly
            20                  25                  30

Ala Leu Gly Leu Ala Ala Leu Thr Gly Gly Gly Thr Ala Val Ala Val
        35                  40                  45

Pro Val Thr Lys Ala Ser Pro Pro Ala Gly Glu Arg Ser Gly Gly Thr
    50                  55                  60

Asp Tyr Thr Lys Leu Val Asp Pro Phe Val Ser Thr Ala Gly Asp Tyr
65                  70                  75                  80

Gly Asn Asp Leu Pro Gly Ala Gln Ala Pro His Ser Leu Ala Lys Val
                85                  90                  95

Asn Pro Met Thr Thr Pro Gly Arg Asn His Ser Gly Tyr Asp Tyr Asn
            100                 105                 110

Glu Asp His Ile Ala Gly Phe Thr Ala Thr Asn Leu Asp Gly Val Gly
        115                 120                 125

Gly Ser Gly Gly Gly Gly Asp Leu Leu Val Val Pro Thr Ser Gln Gln
    130                 135                 140

Tyr Asp Lys Arg Pro Ala Thr Ser Thr Tyr Ala His Pro Tyr Ser His
145                 150                 155                 160

Asp Asp Glu Ser Ala Thr Pro Gly Ser Tyr Arg Val Gly Leu Gly Ser
                165                 170                 175

Pro Ser Gly Thr Ile Asp Ala Glu Met Thr Ala Thr Thr Arg Thr Ala
            180                 185                 190

Leu Glu Arg Tyr Ala Phe Pro Ala Lys Ala Arg Pro Gln Leu Val Leu
        195                 200                 205

Asp Leu Ala Asn Asn Phe Thr Ser Arg Thr Arg Ala Thr Leu Asp Ala
    210                 215                 220

Thr Arg Leu Lys Asp Gly Thr Thr Ala Ile Ser Gly Leu Val Ala Gly
225                 230                 235                 240

Ser Phe Asn Gly Ala Ser Tyr Arg Leu Tyr Tyr Tyr Ala Thr Thr Asn
                245                 250                 255

Val Pro Val Thr Ser Leu Arg Thr Trp Gly Asp Asp Gly Ala Leu Gly
            260                 265                 270

Asp Ala Thr Ala Arg Asp Gly Thr Asp Thr Gly Ala Val Leu Gly Phe
        275                 280                 285

Asp Pro Ala Asp Gly Asp Asp Val Glu Leu Arg Val Thr Leu Ser Pro
    290                 295                 300

Ile Ser Ala Glu Gln Ala Ala Thr Asp Gln His Glu Glu Val Ala Gly
305                 310                 315                 320

Arg Thr Phe Glu Glu Val Arg Ala Gln Thr Lys Ala Asp Trp Asn Arg
                325                 330                 335

```
Thr Leu Gly Ala Val Ala Val Lys Ala Ser Lys Lys Ala Asp Pro Asp
            340                 345                 350

Ser Thr Leu Thr Lys Gln Phe Tyr Thr His Leu Tyr Arg Met Tyr Ala
        355                 360                 365

Leu Pro Val Asn Ala Thr Ser Thr Ser Gly Thr Tyr Arg Gly Val Asp
    370                 375                 380

Gly Ala Val His Lys Ala Asn Gly Phe Thr Tyr Tyr Asp Gly Trp Ser
385                 390                 395                 400

Thr Trp Asp Asp Phe Arg Lys Tyr Ser Val Ala Ala Tyr Ile Asp Pro
                405                 410                 415

Ala Thr Tyr Arg Asp Met Val Gln Ser Ala Val Ile Leu Phe Ala Asp
            420                 425                 430

Ala His Ala Ala Gly Lys Ser Leu Gly Ser Leu Thr His Ser Val Pro
        435                 440                 445

Thr Val Arg Trp Glu Arg Ser Ala Val Val Ile Ala Asp Ala Leu Ser
    450                 455                 460

Lys Gly Phe Lys Asp Phe Asp Arg Leu Asp Glu Ala Tyr Pro Ala Leu
465                 470                 475                 480

Lys Ser Tyr Thr Gly Tyr Tyr Thr Gly Thr Gln Leu Arg Gln Gly Tyr
                485                 490                 495

Ile Ala Gly Asp Pro Gly Thr Thr Val Gln Arg Gly Tyr Asp Gln Trp
            500                 505                 510

Ala Leu Ser Val Val Ala Asp Ala Leu Gly Glu Asp Ala Glu Ala Lys
        515                 520                 525

Lys Leu Arg Glu Gln Ala Thr Met Ala Thr Asp Asn Leu Val Lys Pro
    530                 535                 540

Asp Ala Trp Thr Ala Ala Asp Gly Thr Ala Val Gly Leu Leu Thr Pro
545                 550                 555                 560

Arg Asp Gly Glu Gly Asp Trp Gln Gly Val Asp Tyr Glu Lys Phe Glu
                565                 570                 575

Glu Ala Arg Leu Tyr Gln Gly Thr Leu Trp Gln Tyr His Trp Tyr Asp
            580                 585                 590

Ala Tyr Asp Met Gly Gly Leu Val Glu Ala Met Gly Gly Glu Gln Ala
        595                 600                 605

Gly Arg Ala Ala Ile Arg His Met Phe Gly Glu Asp Ser Asp Ala Asp
    610                 615                 620

Asp Gly Ser Thr Met Leu His Ser Asn Ala Asn Glu Ile Asp Leu Gln
625                 630                 635                 640

Ala Pro Tyr Leu Phe Asn Tyr Val Gly Glu Pro Ser Leu Thr Gln Lys
                645                 650                 655

Trp Val Arg Ala Ile Tyr Thr Gly Glu Thr Trp Asn Arg Tyr Ile Ala
            660                 665                 670

Thr Gly Ser Thr Asn Glu Ala Pro Ser Ser Gly Gly Glu Phe Arg Pro
        675                 680                 685

Pro Val Lys Thr Lys Ala Tyr Glu Leu Ala Pro Asp Gly Phe Leu Pro
    690                 695                 700

Thr Met Asp Asn Asp Ala Gly Thr Met Ser Thr Met Phe Val Ala Ala
705                 710                 715                 720

Ala Leu Gly Leu Phe Pro Val Thr Ala Gly Ser Ser Gln Phe Gln Ile
                725                 730                 735

Gly Ser Pro Phe Phe Asp Ser Thr Thr Ile Thr Tyr Pro Asn Gly Ala
            740                 745                 750

Glu Phe Thr Val Glu Ala Asp Gly Val Ser Pro Lys Asn Tyr Tyr Val
```

```
        755                 760                 765

Thr Val Asp Ala Ser Val Glu Leu Arg Leu Ser Gly Arg Ala Ser Phe
    770                 775                 780

Ala Ala Arg Lys Gly Thr Ser Leu Thr Arg Thr Gly Ala Ala Ser Val
785                 790                 795                 800

Thr Gly Leu Pro Asp Gly Val Thr Ala Asp Leu Arg Val Thr Gly Lys
                805                 810                 815

Arg Thr Ala Ser Leu Arg Leu Thr Gly Thr Thr Arg Thr Asp Ala Arg
            820                 825                 830

Phe Gly Ile Thr Phe Arg Asp Arg Ala Phe Pro His Gly Ile Pro Ala
        835                 840                 845

Ser Thr Val Thr Gly Thr Gly Val Ser Val Thr Asp Pro Leu Ile Val
    850                 855                 860

Ser Ala Ala Ala Val His Arg Gly Ser Leu Ala Ala Leu Val Asp Glu
865                 870                 875                 880

Ala Ser Leu Val Arg Glu Gly Asn Tyr Ser Asp Gly Ser Tyr Gly Ile
                885                 890                 895

Phe Arg Thr Ala Leu Glu Arg Ala Arg Thr Val Leu Ala Asp Ser Ala
            900                 905                 910

Ser Pro Thr Gly Thr Leu Met Ala Ala His Asp Ala Leu Arg Ser Ala
        915                 920                 925

Val Asp Ala Leu Thr Leu Asp Glu Gly Gly Tyr Ala Val Leu Gln Ala
    930                 935                 940

Glu Asp Pro Asp Arg Met Glu Gly Pro Ser Leu Val Lys Glu Ala Tyr
945                 950                 955                 960

Tyr Ser Asp Gly Asp Leu Gly Gly Val Thr Glu Gly Ala Trp Glu Gln
                965                 970                 975

Tyr Thr Asp Leu Asp Phe Gly Gly Val Pro Pro Arg Ser Val Ser Val
            980                 985                 990

Arg Tyr Ala Asn Ser Gln Ala Ala Ala Ala Glu Pro Ser Ser Val Asp
        995                 1000                1005

Ile His Ala Gly Asp Ala Asp Gly Pro Val Val Ala Thr Val Ser Leu
    1010                1015                1020

Pro Gly Thr Gly Gly Trp Gln Tyr Tyr Thr Thr Val Arg Ala Ala Val
1025                1030                1035                1040

Ser Asp Pro Gln Ala Leu Leu Lys Ala Ser Ser Ala Thr Phe Val Phe
                1045                1050                1055

His Ala Pro Ser Gly Arg Gln Trp Val Ser Asn Phe Asp Trp Tyr Gln
            1060                1065                1070

Phe Ser Pro Glu Ala Ala Pro Ser Ser Ser Pro Ile Thr Thr Leu Ala
        1075                1080                1085

Thr Leu Thr Thr Ala Asn Thr Thr Ser Thr Gly Asp Gly Ala Leu Pro
    1090                1095                1100

Leu Lys Val Ser Gly Gly Val Phe Glu Asn Val Thr Asn Gly Ala Trp
1105                1110                1115                1120

Ala Glu Trp Arg Asp Thr Asp Leu Gly Asp Gly Ala Asp Thr Val Thr
                1125                1130                1135

Val Ser Tyr Asp Lys Pro Arg Ser Arg Ala Ala Ser Asp Ser His Ile
            1140                1145                1150

Glu Leu Arg Pro Gly Ala Lys Asp Gly Pro Thr Ala Val Thr Val Pro
        1155                1160                1165

Leu Asp Tyr Thr Gly Ser Gly Trp Gly Thr Val Ala Ser Thr Ser Val
    1170                1175                1180
```

-continued

```
Arg Leu Asp Pro Asp Val Phe Glu Gly Thr Gln Asp Val Tyr Ala Val
1185                1190                1195                1200

Phe Val Ser Ser Thr Gln Thr Asp Ala Gln Pro Tyr Val Ala Asn Val
                1205                1210                1215

His Ser Leu Thr Leu Thr Arg Gln Ala Asp Ala Pro Val Val Phe Asp
            1220                1225                1230

Ala Thr Ala Phe Glu Gly Ser Ser Gly Gly Gly Leu Lys Ser Glu Pro
        1235                1240                1245

Ala Thr Trp Ser Gly Ala Gly Ser Ala Thr Ser Leu Gly Gly Thr Tyr
    1250                1255                1260

Asp Gly Ala Trp Leu Asp Tyr Gly Asp Val Asp Phe Gly Asp Ser Pro
1265                1270                1275                1280

Lys Asn Thr Val Thr Leu Thr Tyr Val Asn Asn Ser Ala Arg Cys Gly
                1285                1290                1295

Thr Gly Ser Ala Val Gln Leu Tyr Leu Asp Ser Phe Asp Pro Asp Ala
            1300                1305                1310

Pro Gly Thr Pro Tyr Ala Thr Val Pro Leu Pro Val Thr Gly Ser Ser
        1315                1320                1325

Trp Ser Ser Gly Gly Thr Thr Ser Leu Thr Leu Pro Glu Ala Ile Thr
    1330                1335                1340

Gly Thr His Ala Val His Leu Arg Leu Thr Thr Asp Ala Asp Ser Ser
1345                1350                1355                1360

His Pro Tyr Val Ala Asn Leu Gly Gln Val Thr Phe Asp Arg Val Glu
                1365                1370                1375

Ala Pro Ala Gln Thr Asp Leu Ser Ala Leu Arg Lys Ala Ile Glu Gln
            1380                1385                1390

Tyr Glu Gly Leu Ser Glu Asp Ala Asp Arg Tyr Gly Thr Ile Asp Phe
        1395                1400                1405

Gly Val Phe Arg Arg Glu Leu Thr Ala Ala Arg Asp Leu Leu Gly Thr
    1410                1415                1420

Glu Asp Ala Thr Gln Leu Glu Ala Asp Leu Arg Thr Arg Ser Leu Thr
1425                1430                1435                1440

Leu Ala Ala Asn Gln Leu Val Pro Leu Pro Arg Leu Arg Leu Glu Ser
                1445                1450                1455

Leu Val Ala Thr Ala Ser Ala Leu Ala Asp Glu Arg Tyr Thr Asp Ala
            1460                1465                1470

Ser Trp Lys Ala Phe Thr Thr Ala Leu Thr Ala Ala Lys Thr Ala Val
        1475                1480                1485

Ala Asp Glu Thr Ala Thr Asp Arg Thr Leu Thr Glu Arg Tyr Ala Ala
    1490                1495                1500

Leu Asp Arg Ala Arg Ser Ser Leu Thr Thr Lys Arg Arg Thr Val Pro
1505                1510                1515                1520

Ala Ala Pro Gly Ala Val Ser Ala Ala Pro Ser Gly Thr Ser Val Gln
                1525                1530                1535

Val Thr Trp Ser Ala Pro Glu Asp Asp Gly Gly Ser Pro Val Thr Gly
            1540                1545                1550

Tyr Glu Ile Thr Leu Ser Gly Gly Arg Gln Val Glu Ile Ala Asp Pro
        1555                1560                1565

Asp Ser Arg Ser Thr Val Phe Thr Arg Leu Lys Asp Gly Thr Ser Tyr
    1570                1575                1580

Thr Ala Arg Val Arg Ala Val Asn Ala Leu Gly Asp Ser Pro Trp Ser
1585                1590                1595                1600
```

-continued

```
Ala Arg Thr Gln Pro Ala Val Thr Gly Asp Asn Arg Pro Gln Ala Pro
                1605                1610                1615

Thr Val Thr Gly Val Val Thr Asp Gly Glu Arg Val Arg Val Asn Trp
            1620                1625                1630

Arg Pro Ala Gly Asp Gly Gly Phe Pro Val Val Gly Tyr Thr Val Ala
        1635                1640                1645

Leu Asp Asp Gly Thr Thr Ala His Val Pro Gly Thr Thr Ser Thr Ala
    1650                1655                1660

Val Leu Thr Ala Ala Gly Gly Ala Lys Ala His Thr Ala Thr Val Thr
1665                1670                1675                1680

Ala Val Thr Arg Ala Gly Ser Ser Asp Gly Ser Gly Ala Thr Val Ser
                1685                1690                1695

Thr Ala Pro Ala Thr Ser Thr Thr Ser Ala Thr Ser Ala Gly Asp Pro
            1700                1705                1710

Ala Glu Tyr Glu Pro Ser Pro Phe Pro Gly Asp Thr Leu Asp Ala Thr
        1715                1720                1725

Tyr Ala Ser Asp Ala Trp Pro Glu Thr Gly Asp Gly Ser Asp Trp Phe
    1730                1735                1740

Thr His Leu Leu Ser Gly Phe Asp Asp Leu Gly Pro Ala Thr Leu Gly
1745                1750                1755                1760

Ala Asn Ser Glu Val Pro Ala Gly Thr Pro Leu Gly Ala Glu Asn Asp
                1765                1770                1775

Arg Ile Thr Val Arg Val Asn Asn Ala Ala Thr Gln Gln Gln Val Asp
            1780                1785                1790

Arg Ala Glu Val Asp Ala Ser Asn Ser Ala Thr Val Thr Met Ala Asp
        1795                1800                1805

Gly Leu Gly Ser Arg Leu Gly Pro Leu Tyr Gly Glu Ala Leu Lys Glu
    1810                1815                1820

Gly Arg Leu Pro Lys Thr Ser Ala Leu Phe Ser Arg Val Asn Glu Asn
1825                1830                1835                1840

Leu Asp Thr His Asp Ala Ala Lys Asn His Tyr Gln Tyr Leu Arg Pro
                1845                1850                1855

Tyr Val Arg Leu Gly Phe Ala Gly Asp Gly Gly Ala Val Tyr Glu Ser
            1860                1865                1870

Gln Asp Ser Ser Tyr Ser Gly Leu Ala Gly Gln Gly Ser Tyr Pro Ser
        1875                1880                1885

Gly His Thr Tyr Gly Gly Tyr Glu Ala Gly Thr Ile Leu Ala Thr Leu
    1890                1895                1900

Leu Pro Asp Leu Ala Pro Ser Ile Leu Ala Arg Thr Ser Glu Tyr Gly
1905                1910                1915                1920

Asp Asn Arg Ile Val Leu Gly Phe His Tyr Pro Leu Asp Val Met Gly
                1925                1930                1935

Gly Arg Ile Thr Ala Gln Ala Thr Val Ala His Arg Trp Ala Asp Pro
            1940                1945                1950

Glu Phe Ala Lys Leu Leu Gly Gln Ala His Thr Glu Ile Glu Asn Val
        1955                1960                1965

Leu Leu Ala Arg Cys Glu Glu Glu Gly Tyr Gly Asp Thr Leu Thr Ala
    1970                1975                1980

Cys Ala Gly Asp Pro Tyr Ala Gly Leu Ser Thr Ala Gln Gln Val Asp
1985                1990                1995                2000

Arg Tyr Thr Gln Arg Leu Thr Tyr Gly Phe Ser Arg Thr Gly Glu Ala
                2005                2010                2015

Gly Gln Ala Leu Asp Ala Pro Ser Asp Ala Ala Ala Leu Leu Ile Thr
```

2020 2025 2030

Ala Phe Pro Asp Leu Thr Ala Glu Gln Arg Thr Gln Val Leu Glu Gln
2035 2040 2045

Thr Ala Thr Asp Ser Gly Tyr Pro Leu Asp Leu Thr Gly Ser Gly Gly
2050 2055 2060

Pro Gly Trp Gln Arg Ile Asn Leu Ala Ala Ala Met Ala Ala Asp Val
2065 2070 2075 2080

Val Val Asn Ala Asp Gly Ser Val Thr Val Thr Asn Phe Pro Asp Ala
2085 2090 2095

Thr Ala Ala Ser Ala Ala Glu Ala Val Ala Ile Thr Val Gly Gly Val
2100 2105 2110

Ala Leu Asp Gly Phe Asp Pro Asp Val Ser Thr Tyr Val Val Asp Trp
2115 2120 2125

Pro Arg Asn Gly Gly Arg Ile Pro Ala Val Gly Ala Val Thr Ala Ala
2130 2135 2140

Ser Gly Ala Arg Val Lys Val Thr Ser Gly Ser Ser Thr Val Ser Ser
2145 2150 2155 2160

Ser Gln Arg Gly Phe Ser Thr Arg Thr Leu Thr Val Thr Ser Ala Asp
2165 2170 2175

Gly Glu Phe Thr Arg Thr Tyr Thr Val Gly Phe Arg Pro Val Glu Gln
2180 2185 2190

His Pro His Arg Pro Gly Ala Leu Arg Asp Thr Gly Gly Gly Gly Thr
2195 2200 2205

Ala Gly Gly Ser Gly Gly Gly Gly Asp Val Gly Gly Gly Leu Trp Ser
2210 2215 2220

Pro Ala Arg Glu Trp Glu Gln Thr Val Asn
2225 2230

<210> SEQ ID NO 37
<211> LENGTH: 2202
<212> TYPE: PRT
<213> ORGANISM: Streptomyces lividans

<400> SEQUENCE: 37

Met Leu Ala Gly Ala Leu Gly Leu Ala Ala Leu Thr Gly Gly Gly Thr
1 5 10 15

Ala Val Ala Val Pro Val Thr Lys Ala Ser Pro Pro Ala Gly Glu Arg
20 25 30

Ser Gly Gly Thr Asp Tyr Thr Lys Leu Val Asp Pro Phe Val Ser Thr
35 40 45

Ala Gly Asp Tyr Gly Asn Asp Leu Pro Gly Ala Gln Ala Pro His Ser
50 55 60

Leu Ala Lys Val Asn Pro Met Thr Thr Pro Gly Arg Asn His Ser Gly
65 70 75 80

Tyr Asp Tyr Asn Glu Asp His Ile Ala Gly Phe Thr Ala Thr Asn Leu
85 90 95

Asp Gly Val Gly Gly Ser Gly Gly Gly Gly Asp Leu Leu Val Val Pro
100 105 110

Thr Ser Gln Gln Tyr Asp Lys Arg Pro Ala Thr Ser Thr Tyr Ala His
115 120 125

Pro Tyr Ser His Asp Asp Glu Ser Ala Thr Pro Gly Ser Tyr Arg Val
130 135 140

Gly Leu Gly Ser Pro Ser Gly Thr Ile Asp Ala Glu Met Thr Ala Thr
145 150 155 160

-continued

```
Thr Arg Thr Ala Leu Glu Arg Tyr Ala Phe Pro Ala Lys Ala Arg Pro
                165                 170                 175

Gln Leu Val Leu Asp Leu Ala Asn Asn Phe Thr Ser Arg Thr Arg Ala
            180                 185                 190

Thr Leu Asp Ala Thr Arg Leu Lys Asp Gly Thr Thr Ala Ile Ser Gly
        195                 200                 205

Leu Val Ala Gly Ser Phe Asn Gly Ala Ser Tyr Arg Leu Tyr Tyr Tyr
    210                 215                 220

Ala Thr Thr Asn Val Pro Val Thr Ser Leu Arg Thr Trp Gly Asp Asp
225                 230                 235                 240

Gly Ala Leu Gly Asp Ala Thr Ala Arg Asp Gly Thr Asp Thr Gly Ala
                245                 250                 255

Val Leu Gly Phe Asp Pro Ala Asp Gly Asp Asp Val Glu Leu Arg Val
            260                 265                 270

Thr Leu Ser Pro Ile Ser Ala Glu Gln Ala Ala Thr Asp Gln His Glu
        275                 280                 285

Glu Val Ala Gly Arg Thr Phe Glu Glu Val Arg Ala Gln Thr Lys Ala
    290                 295                 300

Asp Trp Asn Arg Thr Leu Gly Ala Val Ala Val Lys Ala Ser Lys Lys
305                 310                 315                 320

Ala Asp Pro Asp Ser Thr Leu Thr Lys Gln Phe Tyr Thr His Leu Tyr
                325                 330                 335

Arg Met Tyr Ala Leu Pro Val Asn Ala Thr Ser Thr Ser Gly Thr Tyr
            340                 345                 350

Arg Gly Val Asp Gly Ala Val His Lys Ala Asn Gly Phe Thr Tyr Tyr
        355                 360                 365

Asp Gly Trp Ser Thr Trp Asp Asp Phe Arg Lys Tyr Ser Val Ala Ala
    370                 375                 380

Tyr Ile Asp Pro Ala Thr Tyr Arg Asp Met Val Gln Ser Ala Val Ile
385                 390                 395                 400

Leu Phe Ala Asp Ala His Ala Ala Gly Lys Ser Leu Gly Ser Leu Thr
                405                 410                 415

His Ser Val Pro Thr Val Arg Trp Glu Arg Ser Ala Val Val Ile Ala
            420                 425                 430

Asp Ala Leu Ser Lys Gly Phe Lys Asp Phe Asp Arg Leu Asp Glu Ala
        435                 440                 445

Tyr Pro Ala Leu Lys Ser Tyr Thr Gly Tyr Tyr Thr Gly Thr Gln Leu
    450                 455                 460

Arg Gln Gly Tyr Ile Ala Gly Asp Pro Gly Thr Thr Val Gln Arg Gly
465                 470                 475                 480

Tyr Asp Gln Trp Ala Leu Ser Val Val Ala Asp Ala Leu Gly Glu Asp
                485                 490                 495

Ala Glu Ala Lys Lys Leu Arg Glu Gln Ala Thr Met Ala Thr Asp Asn
            500                 505                 510

Leu Val Lys Pro Asp Ala Trp Thr Ala Ala Asp Gly Thr Ala Val Gly
        515                 520                 525

Leu Leu Thr Pro Arg Asp Gly Glu Gly Asp Trp Gln Gly Val Asp Tyr
    530                 535                 540

Glu Lys Phe Glu Glu Ala Arg Leu Tyr Gln Gly Thr Leu Trp Gln Tyr
545                 550                 555                 560

His Trp Tyr Asp Ala Tyr Asp Met Gly Gly Leu Val Glu Ala Met Gly
                565                 570                 575

Gly Glu Gln Ala Gly Arg Ala Ala Ile Arg His Met Phe Gly Glu Asp
```

-continued

```
            580                 585                 590

Ser Asp Ala Asp Asp Gly Ser Thr Met Leu His Ser Asn Ala Asn Glu
        595                 600                 605

Ile Asp Leu Gln Ala Pro Tyr Leu Phe Asn Tyr Val Gly Glu Pro Ser
    610                 615                 620

Leu Thr Gln Lys Trp Val Arg Ala Ile Tyr Thr Gly Glu Thr Trp Asn
625                 630                 635                 640

Arg Tyr Ile Ala Thr Gly Ser Thr Asn Glu Ala Pro Ser Ser Gly Gly
                645                 650                 655

Glu Phe Arg Pro Pro Val Lys Thr Lys Ala Tyr Glu Leu Ala Pro Asp
            660                 665                 670

Gly Phe Leu Pro Thr Met Asp Asn Asp Ala Gly Thr Met Ser Thr Met
        675                 680                 685

Phe Val Ala Ala Ala Leu Gly Leu Phe Pro Val Thr Ala Gly Ser Ser
    690                 695                 700

Gln Phe Gln Ile Gly Ser Pro Phe Phe Asp Ser Thr Thr Ile Thr Tyr
705                 710                 715                 720

Pro Asn Gly Ala Glu Phe Thr Val Glu Ala Asp Gly Val Ser Pro Lys
                725                 730                 735

Asn Tyr Tyr Val Thr Val Asp Ala Ser Val Glu Leu Arg Leu Ser Gly
            740                 745                 750

Arg Ala Ser Phe Ala Ala Arg Lys Gly Thr Ser Leu Thr Arg Thr Gly
        755                 760                 765

Ala Ala Ser Val Thr Gly Leu Pro Asp Gly Val Thr Ala Asp Leu Arg
    770                 775                 780

Val Thr Gly Lys Arg Thr Ala Ser Leu Arg Leu Thr Gly Thr Thr Arg
785                 790                 795                 800

Thr Asp Ala Arg Phe Gly Ile Thr Phe Arg Asp Arg Ala Phe Pro His
                805                 810                 815

Gly Ile Pro Ala Ser Thr Val Thr Gly Thr Gly Val Ser Val Thr Asp
            820                 825                 830

Pro Leu Ile Val Ser Ala Ala Ala Val His Arg Gly Ser Leu Ala Ala
        835                 840                 845

Leu Val Asp Glu Ala Ser Leu Val Arg Glu Gly Asn Tyr Ser Asp Gly
    850                 855                 860

Ser Tyr Gly Ile Phe Arg Thr Ala Leu Glu Arg Ala Arg Thr Val Leu
865                 870                 875                 880

Ala Asp Ser Ala Ser Pro Thr Gly Thr Leu Met Ala Ala His Asp Ala
                885                 890                 895

Leu Arg Ser Ala Val Asp Ala Leu Thr Leu Asp Glu Gly Gly Tyr Ala
            900                 905                 910

Val Leu Gln Ala Glu Asp Pro Asp Arg Met Glu Gly Pro Ser Leu Val
        915                 920                 925

Lys Glu Ala Tyr Tyr Ser Asp Gly Asp Leu Gly Gly Ala Trp Glu Gln
    930                 935                 940

Tyr Thr Asp Leu Asp Phe Gly Gly Val Pro Pro Arg Ser Val Ser Val
945                 950                 955                 960

Arg Tyr Ala Asn Ser Gln Ala Ala Ala Ala Glu Pro Ser Ser Val Asp
                965                 970                 975

Ile His Ala Gly Asp Ala Asp Gly Pro Val Val Ala Thr Val Ser Leu
            980                 985                 990

Pro Gly Thr Gly Gly Trp Gln Tyr Tyr Thr Thr Val Arg Ala Ala Val
        995                 1000                1005
```

-continued

```
Ser Asp Pro Gln Ala Leu Leu Lys Ala Ser Ser Ala Thr Phe Val Phe
    1010                1015                1020

His Ala Pro Ser Gly Arg Gln Trp Val Ser Asn Phe Asp Trp Tyr Gln
1025                1030                1035                1040

Phe Ser Pro Glu Ala Ala Pro Ser Ser Ser Pro Ile Thr Thr Leu Ala
                1045                1050                1055

Thr Leu Thr Thr Ala Asn Thr Thr Ser Thr Gly Asp Gly Ala Leu Pro
            1060                1065                1070

Leu Lys Val Ser Gly Gly Val Phe Glu Asn Val Thr Asn Gly Ala Trp
        1075                1080                1085

Ala Glu Trp Arg Asp Thr Asp Leu Gly Asp Gly Ala Asp Thr Val Thr
    1090                1095                1100

Val Ser Tyr Asp Lys Pro Arg Ser Arg Ala Ala Ser Asp Ser His Ile
1105                1110                1115                1120

Glu Leu Arg Pro Gly Ala Lys Asp Gly Pro Thr Ala Val Thr Val Pro
                1125                1130                1135

Leu Asp Tyr Thr Gly Ser Gly Trp Gly Thr Val Ala Ser Thr Ser Val
            1140                1145                1150

Arg Leu Asp Pro Asp Val Phe Glu Gly Thr Gln Asp Val Tyr Ala Val
        1155                1160                1165

Phe Val Ser Ser Thr Gln Thr Asp Ala Gln Pro Tyr Val Ala Asn Val
    1170                1175                1180

His Ser Leu Thr Leu Thr Arg Gln Ala Asp Ala Pro Val Val Phe Asp
1185                1190                1195                1200

Ala Thr Ala Phe Glu Gly Ser Ser Gly Gly Gly Leu Lys Ser Glu Pro
                1205                1210                1215

Ala Thr Trp Ser Gly Ala Gly Ser Ala Thr Ser Leu Gly Gly Thr Tyr
            1220                1225                1230

Asp Gly Ala Trp Leu Asp Tyr Gly Asp Val Asp Phe Gly Asp Ser Pro
        1235                1240                1245

Lys Asn Thr Val Thr Leu Thr Tyr Val Asn Asn Ser Ala Arg Cys Gly
    1250                1255                1260

Thr Gly Ser Ala Val Gln Leu Tyr Leu Asp Ser Phe Asp Pro Asp Ala
1265                1270                1275                1280

Pro Gly Thr Pro Tyr Ala Thr Val Pro Leu Pro Val Thr Gly Ser Ser
                1285                1290                1295

Trp Ser Ser Gly Gly Thr Thr Ser Leu Thr Leu Pro Glu Ala Ile Thr
            1300                1305                1310

Gly Thr His Ala Val His Leu Arg Leu Thr Thr Asp Ala Asp Ser Ser
        1315                1320                1325

His Pro Tyr Val Ala Asn Leu Gly Gln Val Thr Phe Asp Arg Val Glu
    1330                1335                1340

Ala Pro Ala Gln Thr Asp Leu Ser Ala Leu Arg Lys Ala Ile Glu Gln
1345                1350                1355                1360

Tyr Glu Gly Leu Ser Glu Asp Ala Asp Arg Tyr Gly Thr Ile Asp Phe
                1365                1370                1375

Gly Val Phe Arg Arg Glu Leu Thr Ala Ala Arg Asp Leu Leu Gly Thr
            1380                1385                1390

Glu Asp Ala Thr Gln Leu Glu Ala Asp Leu Arg Thr Arg Ser Leu Thr
        1395                1400                1405

Leu Ala Ala Asn Gln Leu Val Pro Leu Pro Arg Leu Arg Leu Glu Ser
    1410                1415                1420
```

-continued

```
Leu Val Ala Thr Ala Ser Ala Leu Ala Asp Glu Arg Tyr Thr Asp Ala
1425                1430                1435                1440

Ser Trp Lys Ala Phe Thr Thr Ala Leu Thr Ala Ala Lys Thr Ala Val
                1445                1450                1455

Ala Asp Glu Thr Ala Thr Asp Arg Thr Leu Thr Glu Arg Tyr Ala Ala
            1460                1465                1470

Leu Asp Arg Ala Arg Ser Ser Leu Thr Thr Lys Arg Arg Thr Val Pro
        1475                1480                1485

Ala Ala Pro Gly Ala Val Ser Ala Ala Pro Ser Gly Thr Ser Val Gln
    1490                1495                1500

Val Thr Trp Ser Ala Pro Glu Asp Asp Gly Gly Ser Pro Val Thr Gly
1505                1510                1515                1520

Tyr Glu Ile Thr Leu Ser Gly Gly Arg Gln Val Glu Ile Ala Asp Pro
                1525                1530                1535

Asp Ser Arg Ser Thr Val Phe Thr Arg Leu Lys Asp Gly Thr Ser Tyr
            1540                1545                1550

Thr Ala Arg Val Arg Ala Val Asn Ala Leu Gly Asp Ser Pro Trp Ser
        1555                1560                1565

Ala Arg Thr Gln Pro Ala Val Thr Gly Asp Asn Arg Pro Gln Ala Pro
    1570                1575                1580

Thr Val Thr Gly Val Val Thr Asp Gly Glu Arg Val Arg Val Asn Trp
1585                1590                1595                1600

Arg Pro Ala Gly Asp Gly Gly Phe Pro Val Val Gly Tyr Thr Val Ala
                1605                1610                1615

Leu Asp Asp Gly Thr Thr Ala His Val Pro Gly Thr Thr Ser Thr Ala
            1620                1625                1630

Val Leu Thr Ala Ala Gly Gly Ala Lys Ala His Thr Ala Thr Val Thr
        1635                1640                1645

Ala Val Thr Arg Ala Gly Ser Ser Asp Gly Ser Gly Ala Thr Val Ser
    1650                1655                1660

Thr Ala Pro Ala Thr Ser Thr Thr Ser Ala Thr Ser Ala Gly Asp Pro
1665                1670                1675                1680

Ala Glu Tyr Glu Pro Ser Pro Phe Pro Gly Asp Thr Leu Asp Ala Thr
                1685                1690                1695

Tyr Ala Ser Asp Ala Trp Pro Glu Thr Gly Asp Gly Ser Asp Trp Phe
            1700                1705                1710

Thr His Leu Leu Ser Gly Phe Asp Asp Leu Gly Pro Ala Thr Leu Gly
        1715                1720                1725

Ala Asn Ser Glu Val Pro Ala Gly Thr Pro Leu Gly Ala Glu Asn Asp
    1730                1735                1740

Arg Ile Thr Val Arg Val Asn Asn Ala Ala Thr Gln Gln Gln Val Asp
1745                1750                1755                1760

Arg Ala Glu Val Asp Ala Ser Asn Ser Ala Thr Val Thr Met Ala Asp
                1765                1770                1775

Gly Leu Gly Ser Arg Leu Gly Pro Leu Tyr Gly Glu Ala Leu Lys Glu
            1780                1785                1790

Gly Arg Leu Pro Lys Thr Ser Ala Leu Phe Ser Arg Val Asn Glu Asn
        1795                1800                1805

Leu Asp Thr His Asp Ala Ala Lys Asn His Tyr Gln Tyr Leu Arg Pro
    1810                1815                1820

Tyr Val Arg Leu Gly Phe Ala Gly Asp Gly Gly Ala Val Tyr Glu Ser
1825                1830                1835                1840

Gln Asp Ser Ser Tyr Ser Gly Leu Ala Gly Gln Gly Ser Tyr Pro Ser
```

```
                1845                1850                1855

Gly His Thr Tyr Gly Gly Tyr Glu Ala Gly Thr Ile Leu Ala Thr Leu
            1860                1865                1870

Leu Pro Asp Leu Ala Pro Ser Ile Leu Ala Arg Thr Ser Glu Tyr Gly
        1875                1880                1885

Asp Asn Arg Ile Val Leu Gly Phe His Tyr Pro Leu Asp Val Met Gly
    1890                1895                1900

Gly Arg Ile Thr Ala Gln Ala Thr Val Ala His Arg Trp Ala Asp Pro
1905                1910                1915                1920

Glu Phe Ala Lys Leu Leu Gly Gln Ala His Thr Glu Ile Glu Asn Val
                1925                1930                1935

Leu Leu Ala Arg Cys Glu Glu Glu Gly Tyr Gly Asp Thr Leu Thr Ala
            1940                1945                1950

Cys Ala Gly Asp Pro Tyr Ala Gly Leu Ser Thr Ala Gln Gln Val Asp
        1955                1960                1965

Arg Tyr Thr Gln Arg Leu Thr Tyr Gly Phe Ser Arg Thr Gly Glu Ala
    1970                1975                1980

Gly Gln Ala Leu Asp Ala Pro Ser Asp Ala Ala Ala Leu Leu Ile Thr
1985                1990                1995                2000

Ala Phe Pro Asp Leu Thr Ala Glu Gln Arg Thr Gln Val Leu Glu Gln
                2005                2010                2015

Thr Ala Thr Asp Ser Gly Tyr Pro Leu Asp Leu Thr Gly Ser Gly Gly
            2020                2025                2030

Pro Gly Trp Gln Arg Ile Asn Leu Ala Ala Ala Met Ala Ala Asp Val
        2035                2040                2045

Val Val Asn Ala Asp Gly Ser Val Thr Val Thr Asn Phe Pro Asp Ala
    2050                2055                2060

Thr Ala Ala Ser Ala Ala Glu Ala Val Ala Ile Thr Val Gly Gly Val
2065                2070                2075                2080

Ala Leu Asp Gly Phe Asp Pro Asp Val Ser Thr Tyr Val Val Asp Trp
                2085                2090                2095

Pro Arg Asn Gly Gly Arg Ile Pro Ala Val Gly Ala Val Thr Ala Ala
            2100                2105                2110

Ser Gly Ala Arg Val Lys Val Thr Ser Gly Ser Ser Thr Val Ser Ser
        2115                2120                2125

Ser Gln Arg Gly Phe Ser Thr Arg Thr Leu Thr Val Thr Ser Ala Asp
    2130                2135                2140

Gly Glu Phe Thr Arg Thr Tyr Thr Val Gly Phe Arg Pro Val Glu Gln
2145                2150                2155                2160

His Pro His Arg Pro Gly Ala Leu Arg Asp Thr Gly Gly Gly Gly Thr
                2165                2170                2175

Ala Gly Gly Ser Gly Gly Gly Gly Asp Val Gly Gly Gly Leu Trp Ser
            2180                2185                2190

Pro Ala Arg Glu Trp Glu Gln Thr Val Asn
        2195                2200
```

<210> SEQ ID NO 38
<211> LENGTH: 1856
<212> TYPE: PRT
<213> ORGANISM: Paenibacillus sp.

<400> SEQUENCE: 38

```
Met Phe Lys Lys Leu Phe Ala Val Ala Met Thr Val Met Cys Leu Thr
1               5                   10                  15
```

-continued

```
Gly Ile Leu Val Pro Val Gly Ser Asn Ala Ala Phe Ala Ala Ala Ala
            20                  25                  30

Glu Gly Ile Thr Thr Arg Asn Val Ala Ile Asn Ala Ala Ala Thr Ala
        35                  40                  45

Ser Gly Gln Cys Asn Ala Asn Glu Ser Ala Ser Asn Ala Val Asp Gly
    50                  55                  60

Lys Thr Asp Thr Lys Trp Cys Asp Asn Thr Ser Ala Gln Lys Lys Trp
65                  70                  75                  80

Leu Lys Leu Asp Leu Gly Lys Glu Tyr Leu Val Asn Glu Trp Val Leu
                85                  90                  95

Gln Asn Ala Ala Ile Asn Glu Ser Gly Asn Ser Pro Phe Trp Asn Thr
            100                 105                 110

Lys Asn Phe Arg Leu Gln Lys Ser Asp Asp Gly Glu Thr Trp Thr Asp
        115                 120                 125

Val Asp Ile Val Thr Asn Asn Ala Gln Thr Ile Val Asp Arg Phe Val
    130                 135                 140

Thr Pro Phe Thr Thr Arg Tyr Leu Arg Leu Tyr Ile Asp Lys Ala Ala
145                 150                 155                 160

Tyr Asp Ser Asn Ile Ala Arg Ile Tyr Glu Leu Glu Val Tyr Gly Val
                165                 170                 175

Glu Ala Asp Gln Ile Pro Ala Glu Pro Glu Thr Asn Leu Ala Pro Ile
            180                 185                 190

Asp Tyr Val Asp Pro Phe Ile Asn Thr Leu Gly Asp Asn Gly Gln Thr
        195                 200                 205

Asn Pro Gly Pro Thr Thr Pro Phe Gly Leu Val Ser Leu Gly Pro Asp
    210                 215                 220

Ser Asp Gly Gly Ala Phe Ser Gly Tyr Tyr Tyr Glu Asn Lys Asn Leu
225                 230                 235                 240

Lys Gly Phe Ser His Leu Arg Phe Ser Gly Val Gly Cys Ser Gly Gly
                245                 250                 255

Gly Gly Asn Ile Leu Met Met Pro Glu Thr Arg Asp Phe Thr Lys Asn
            260                 265                 270

Val Ala Asp Tyr Lys Gln Lys Tyr Asp Lys Ser Ser Glu Gln Ala Ser
        275                 280                 285

Ala Gly Phe Tyr Gly Val Thr Leu Ala Ser Gly Ile Asn Val Gln Leu
    290                 295                 300

Thr Ser Ser Asp Asn Val Gly Phe His Lys Tyr Thr Phe Pro Asp Thr
305                 310                 315                 320

Ala Asn Thr Gly Ser Val Leu Val Asp Leu Ser Asn Ser Tyr Ala Gly
                325                 330                 335

Met Val Asp Ala Asn Leu Lys Val Thr Gly Ser Asn Glu Ile Thr Gly
            340                 345                 350

Met Ile Lys Ser Gln Asn Val Cys Gly His Gly Tyr Tyr Thr Ile Tyr
        355                 360                 365

Tyr Ser Ile Gln Phe Asp His Asp Phe Asp Ser Tyr Ser Ser Trp Gln
    370                 375                 380

Gly Asp Ser Val Gly Ala Val Ala Gln Arg Ser Gly Ser Asn Ser Gly
385                 390                 395                 400

Val Trp Leu Asn Phe Asn Thr Ala Gly Ser Lys Thr Val Gln Ala Lys
                405                 410                 415

Val Gly Leu Ser Thr Ile Ser Val Glu Gln Ala Gln Ala Glu Arg Gly
            420                 425                 430

Leu Tyr Ser Asp Trp Asn Phe Asp Ala Arg His Glu Glu Ala Arg Ala
```

```
        435                 440                 445

Ala Trp Ser Asn Val Leu Asn Lys Val Glu Ile Thr Asp Ala Asp Glu
    450                 455                 460

Gln Asn Lys Arg Val Phe Tyr Thr Gln Met Tyr His Ser Tyr Leu Ser
465                 470                 475                 480

Pro Lys Asn Val Thr Ser Ser Ala Gly Thr Phe Lys Ala Gly Arg Asp
                485                 490                 495

Glu Asn Thr Val Arg Gln Ala Ser Glu Leu Gly Asp Asp Phe Glu Tyr
            500                 505                 510

Tyr Asn Gly Trp Thr Thr Trp Asp Asp Phe Arg Lys Tyr Ala Met Phe
        515                 520                 525

Ser Leu Phe Glu Pro Gln Arg Tyr Asn Asn Met Val Lys Ser Leu Val
    530                 535                 540

Asp Leu Tyr Asn Thr Arg Gly Thr Tyr Thr Gln Trp Gly Asp Gly Tyr
545                 550                 555                 560

Trp Pro Ser Pro Thr Val Arg Asn Glu Phe Asn Gly Gln Val Ile Leu
                565                 570                 575

Asp Ala Tyr Ala Lys Gly Phe Gln Asp Phe Asp Val Tyr Lys Ala Leu
            580                 585                 590

Lys Gly Met Ala Val Asp Ala Asp Asn Phe Ser Ile Ser Asp Gly Glu
        595                 600                 605

Ile Ser Gly Lys Leu Glu Lys Ala Asn Ser Ala Ser Phe Pro Met Lys
    610                 615                 620

Leu Ala Gln Leu Ile Gly Asp Lys Ala Thr Phe Glu Lys Tyr Lys Glu
625                 630                 635                 640

Leu Ala Leu Ser Tyr Lys Lys Leu Trp Asn Pro Thr Gln Val Asp Glu
                645                 650                 655

Lys Gly Thr Pro Thr Gly Phe Phe Thr Pro Asn Gly Thr Thr Val Gly
            660                 665                 670

Ala Gly Asp Ile Gln Ala Val Asp Arg Tyr Ala Tyr Gln Gly Asn Leu
        675                 680                 685

Trp Gln Tyr Arg Trp Ser Ala Pro Gln Asp Ile Asn Gly Leu Ala Gln
    690                 695                 700

Leu Met Gly Gly Lys Thr Glu Met Ala Lys Gln Leu Lys His Phe Phe
705                 710                 715                 720

Glu Ile Asp Glu Tyr Met Ala Ile Asn Glu Glu Asp Ile Ser Ala Pro
                725                 730                 735

Tyr Leu Phe Asn Tyr Leu Gly Tyr Pro Tyr Leu Thr Gln Tyr Tyr Ala
            740                 745                 750

Arg Glu Phe Thr Thr Glu Val Val Thr Gln Lys Tyr His Asn His Gly
        755                 760                 765

Ala Tyr Ala Tyr Pro Leu Lys Ser Arg Val Tyr Arg Asp Asp Pro Glu
    770                 775                 780

Gly Tyr Leu Ser Ser Met Asp Asp Asp Ala Gly Gly Met Ser Ser Trp
785                 790                 795                 800

Tyr Val Phe Ser Ala Leu Gly Leu Phe Pro Gly Asn Pro Gly Glu Gly
                805                 810                 815

Tyr Phe Leu Ile Gly Ser Pro Ile Phe Ser Glu Val Lys Leu His Met
            820                 825                 830

Gly Ser Gly Lys Thr Leu Val Ile Lys Ala Asp Asn Val Ser Ser Glu
        835                 840                 845

Asn Arg Phe Ile Glu Gly Trp Thr Gln Val Asp Phe Asp Asp Ser Ser
    850                 855                 860
```

```
Trp Ser Ser Gly Lys Ala Met Leu Gly Tyr Asp Ser Tyr Gly Lys Pro
865                 870                 875                 880

Ala Thr Thr Val Ser Tyr Gly Pro Asn Ala Asn Asn Lys Tyr Val Thr
                885                 890                 895

Thr Tyr Phe Arg Lys Thr Phe Asp Ala Lys Asp Leu Asp Gly Ile Leu
            900                 905                 910

Glu Leu Asp Gly Ser Leu Ile Arg Asp Asp Gly Ala Ile Val Tyr Leu
        915                 920                 925

Asn Gly His Glu Ile Phe Arg Thr Asn Met Pro Thr Gly Ala Val Asn
    930                 935                 940

Tyr Ser Thr Phe Ala Asn Ala Thr Val Gly Asp Glu Arg Asp Lys Asn
945                 950                 955                 960

Gly Phe Ile Ile Asp Pro Ser Tyr Leu Val Glu Gly Lys Asn Val Leu
                965                 970                 975

Thr Ala Glu Val His Gln Val Asn Ala Thr Ser Ser Asp Ile Ala Phe
            980                 985                 990

Glu Phe Ser Leu Glu Ala Val Arg Lys Leu Asn Ile Pro Ala Ala Pro
        995                 1000                1005

Thr His Pro Val Val Asp Asp Lys Ala Asn Thr Ile Gly Trp Thr Pro
    1010                1015                1020

Val Glu Gly Ile Asn Asn Ala Ser Asp Tyr Glu Phe Ser Thr Asp Gly
1025                1030                1035                1040

Gly Lys Ser Trp Lys Gln Ala Lys Ala Asn Pro Gln Thr Val Gly Pro
                1045                1050                1055

Leu Asn Tyr Ala Pro Gly Ile Val Gln Val Arg Val Met Ala Asn Ala
            1060                1065                1070

Ala Ala Asn Arg Ala Ala Gly Glu Ala Leu Leu Ser Thr Glu Ala Tyr
        1075                1080                1085

Thr Ser Asp Val Lys Trp Asp Val Tyr Asp Leu Asp Ala Asp Ile His
    1090                1095                1100

Gln Asp Gly Asn Met Val Val Asp Val Thr Gly Thr Leu Lys Gly Asp
1105                1110                1115                1120

Tyr Thr Asp Ser Ala Val Val Val Phe Gln Leu Met Asp Gly Lys Glu
                1125                1130                1135

His Ala Trp Val Ser Ser Ala Val Pro Val Gln Thr Gly Ser Phe Asp
            1140                1145                1150

Ile Ser Gln Ile Tyr Asn Val Asp Ala Ser Lys Tyr Lys Val Asn Val
        1155                1160                1165

Tyr Leu Val Asn Glu Phe Asn Gly Asp Ile Tyr Glu Ser Pro Leu Trp
    1170                1175                1180

Leu Ala Asp Pro Ile Val Gln Gln Ser Glu Pro Gly Ser Leu Pro Asp
1185                1190                1195                1200

Pro Glu Gly Pro Pro Val Thr Glu Glu Pro Leu Pro Glu Pro Ile Pro
                1205                1210                1215

Leu Pro Asp Pro Lys Pro Asp Glu Pro Glu Glu Pro Glu Val Pro Glu
            1220                1225                1230

Thr Gly Met Lys Ile Gln Phe Glu Asp Arg Ala Glu Trp Thr Ser Ala
        1235                1240                1245

Ala His Pro Asn Gly Gly Gly Gly Leu Ser Thr Glu Ala Gly Asn Gly
    1250                1255                1260

Gly Thr Val Val Ala His Thr Phe Gly Gly Ala Trp Leu Ala Tyr Asn
1265                1270                1275                1280
```

-continued

```
Val Asp Phe Gly Thr Thr Gly Tyr Asn Asn Val Thr Val Gln Tyr Asp
                1285                1290                1295

Ala Pro Thr Asp Lys Val Pro Ala Gly Ser Lys Leu Glu Phe Arg Leu
            1300                1305                1310

Gly Ser Val Ser Gly Glu Leu Val Gly Thr Val Asn Met Glu Asp Lys
        1315                1320                1325

Asn Ala Gly Trp Gly Ser Tyr Ile Thr Thr Lys Ala Asn Leu Thr Arg
    1330                1335                1340

Thr Leu Thr Gly Gln Gln Lys Leu Tyr Val Val Met Val Ala Gly Thr
1345                1350                1355                1360

Pro Asn Asn Leu Pro Tyr Ile Gly Asn Phe Asp Trp Phe Lys Phe Asp
                1365                1370                1375

Tyr Glu Lys Ile Arg Ser Asp Tyr Ala Lys Leu Glu Leu Glu Ser Tyr
            1380                1385                1390

Asp Glu Trp Thr Thr Asp Val Asn Thr Gly Asn Asn Asn Thr Pro Leu
        1395                1400                1405

Lys Thr Glu Ala Gly Lys Gly Gly Val Gly Gln Gln Val Ala Asn Thr
    1410                1415                1420

Phe Asn Gly Ala Trp Leu Ala Tyr Lys Arg Met Asp Phe Gly Ser Glu
1425                1430                1435                1440

Gly Val Asp Lys Phe Ser Ile Glu Tyr Ala Gly Asn Ser Thr Asn Thr
                1445                1450                1455

Phe Asn Asn Ser Ala Val Glu Val Arg Leu Gly Ser Pro Thr Gly Thr
            1460                1465                1470

Leu Val Gly Thr Val Ala Thr Pro Pro Thr Ala Ala Ala Trp Gly Thr
        1475                1480                1485

Tyr Ala Thr Val Ser Gly Ser Leu Thr Gln Lys Leu Thr Gly Leu Gln
    1490                1495                1500

Asp Val Tyr Leu Val Phe Thr Gly Ser Ala Ala Asn Gly Glu Thr Gly
1505                1510                1515                1520

Lys Lys Tyr Ile Gly Asn Phe Asp Asn Ala Ser Phe Ser Leu Ser Val
                1525                1530                1535

Gln Glu Pro Glu Glu Pro Glu Gln Pro Gln Gln Pro Glu Gln Glu Gln
            1540                1545                1550

Ile Thr Val Gln Phe Glu Ser Lys Thr Glu Trp Asn Thr Ala Leu Asn
        1555                1560                1565

Thr Phe Asn Asn Gln Ala Met Lys Ile Glu Asn Asn Asn Gly Gly Gln
    1570                1575                1580

Thr Val Gly Asn Thr Tyr Thr Gly Ala Trp Leu Gly Phe Lys Asp Val
1585                1590                1595                1600

Asp Phe Gly Ser Glu Lys Gly Lys Asn Gln Val Ser Ile Val Tyr Asp
                1605                1610                1615

Ala Pro Thr Asn Arg Val Pro Ala Asp Val Lys Ala Glu Ile Arg Leu
            1620                1625                1630

Gly Ser Pro Thr Gly Thr Leu Val Gly Thr Val Ala Ile Pro Asn Thr
        1635                1640                1645

Gly Ser Thr Trp Gly Gln Tyr Asn Thr Ala Thr Ala Asp Leu Asn Thr
    1650                1655                1660

Thr Ile Lys Gly Lys Gln Asp Leu Tyr Ile Val Met Thr Gly Ser Thr
1665                1670                1675                1680

Thr Ser Ser Leu Leu Tyr Val Gly Asn Tyr Asp Ser Leu Thr Phe Gly
                1685                1690                1695

Tyr Lys Pro Val Arg Ser Asp Tyr Ala Lys Leu Glu Leu Glu Ser Tyr
```

```
            1700                1705                1710

Asp Glu Trp Thr Thr Ala Val Asn Pro Leu Asn Ser Asn Thr Pro Leu
        1715                1720                1725

Lys Thr Glu Ala Gly Lys Gly Gly Ala Gly Lys Gln Val Ala Asn Thr
    1730                1735                1740

Phe Asn Gly Ala Trp Leu Ala Tyr Lys Arg Met Asp Phe Gly Thr Glu
1745                1750                1755                1760

Gly Val Asn Thr Phe Ala Val Glu Tyr Ala Gly Asn Thr Thr Asn Cys
                1765                1770                1775

Phe Thr Asn Ser Ala Val Glu Ile Arg Leu Gly Ser Pro Thr Gly Thr
            1780                1785                1790

Leu Val Gly Lys Ile Ser Thr Pro Pro Lys Ala Gly Asn Trp Thr Thr
        1795                1800                1805

Tyr Asp Thr Val Ser Gly Thr Leu Thr Gln Lys Leu Thr Gly Ile Gln
    1810                1815                1820

Asp Val Tyr Leu Val Leu Thr Gly Ser Ala Gly Asn Gly Glu Thr Gly
1825                1830                1835                1840

Lys Lys Tyr Ile Gly Asn Phe Asp Asn Ala Ala Phe Ser Leu Lys Val
                1845                1850                1855


<210> SEQ ID NO 39
<211> LENGTH: 640
<212> TYPE: PRT
<213> ORGANISM: Bacteroides sp.

<400> SEQUENCE: 39

Met Lys Asn Asn Arg Ser Arg Trp Tyr Ala Leu Leu Leu Val Val Leu
1               5                   10                  15

Ser Ile Met Thr Pro Ser Val Ala Gln Asn Thr Lys Tyr Val Asn Leu
            20                  25                  30

Phe Ile Gly Thr Ser Gly Asp Asn Gly Gln Val Ala Pro Gly Ala Ala
        35                  40                  45

Ala Pro Phe Gly Met Val Cys Val Cys Pro Asp Asn Asp Pro Arg Ser
    50                  55                  60

His Ala Gly Tyr Asp Tyr Ala Val Thr Lys Val Ser Gly Ile Ser Val
65                  70                  75                  80

Asn Arg Leu Ser Gly Val Gly Cys Ser Gly Gly Gly Gly Asn Leu Arg
                85                  90                  95

Ile Arg Pro Val Ala Pro Ser Gln Glu Leu His Ile Lys Lys Ser Arg
            100                 105                 110

Glu Lys Ala Thr Pro Gly Tyr Tyr Ser Thr Ala Phe Thr Asn Gly Ile
        115                 120                 125

Lys Thr Glu Leu Thr Ala Thr Asn Ala Met Ala Val Glu Arg Tyr Lys
    130                 135                 140

Phe Pro Arg Ser Leu Ser Ala Ala Leu Trp Ile Asp Phe Ala Ser Thr
145                 150                 155                 160

Phe Glu Asp Val Ala Thr Cys His Tyr Lys Arg Ile Ser Glu Thr Cys
                165                 170                 175

Ile Glu Gly Tyr Val Gln Ala Lys Asn Val Cys Gly His Gly Arg Tyr
            180                 185                 190

Lys Leu Tyr Phe Ser Leu Asn Thr Ser His Pro Phe Gln Leu Glu Glu
        195                 200                 205

Gln Lys Glu Thr Thr Ala Cys Leu Thr Phe Gly Lys Lys Val Arg Ser
    210                 215                 220
```

-continued

Val Glu Val Arg Ile Gly Leu Ser Ala Leu Ser Ser Glu Leu Ala Ser
225 230 235 240

Trp Glu Cys Ala Arg Trp Glu Lys Met Asp Phe Glu Asp Val Lys Ser
245 250 255

Arg Thr Ala Asp Gln Trp Glu Lys Gln Leu Ser Ala Ile Asp Val Lys
260 265 270

Gly Gly Lys Lys Asp Asp Arg Val Ile Phe Tyr Thr Ser Leu Tyr Arg
275 280 285

Thr Tyr Leu Ser Pro Ala Asp Val Ser Ser Pro Asp Gly Ala Tyr Leu
290 295 300

Gly Thr Asp Gly Lys Val Tyr Ile Ser Glu Asp Phe Arg Tyr Tyr Ser
305 310 315 320

Asn Trp Ser Leu Trp Asp Thr Phe Arg Thr Lys Phe Pro Leu Leu Val
325 330 335

Leu Thr Glu Pro Ala Lys Met Arg Asp Met Ala Thr Ser Leu Ile His
340 345 350

Leu Tyr Ala Thr Gly Lys Lys Asp Trp Ser Thr Gly Phe Glu Ser Thr
355 360 365

Pro Thr Val Arg Thr Glu His Ala Val Ile Leu Leu Leu Asp Ala Tyr
370 375 380

Arg Lys Gly Ile Thr Asn Leu Asp Phe Arg Lys Gly Tyr Ala Gly Met
385 390 395 400

Lys Gln Glu Met Glu Arg Leu Pro Met Arg Ser Pro Asp Gln Lys Met
405 410 415

Glu Ser Ala Tyr Asp Leu Trp Ala Met Ala Lys Ile Ala Glu Ile Ile
420 425 430

Gly Glu Lys Ala Asp Ser Glu Gln Tyr Arg Gln Arg Ser Val Ser Leu
435 440 445

Phe Glu Glu Thr Trp Lys Lys Glu Phe Met Asn Val Thr Pro Ala Phe
450 455 460

Glu Val Met Lys Asn Asn Gly Leu Tyr Gln Gly Thr Arg Trp Gln Tyr
465 470 475 480

Arg Trp Ala Ala Pro Gln Tyr Ile Asp Lys Met Ile Glu Trp Val Gly
485 490 495

Gln Asp Ser Leu Arg Ser Gln Leu Thr Tyr Phe Phe Asp His His Leu
500 505 510

Tyr Asn Gln Gly Asn Glu Pro Asp Ile His Val Pro Tyr Leu Phe Asn
515 520 525

Arg Leu Gly Ala Pro Glu Lys Thr Gln Gln Ile Val Arg Ser Leu Met
530 535 540

Thr Glu Pro Met Ile His Lys Tyr Gly Gly Asn Ser Glu Phe Lys Thr
545 550 555 560

Pro Tyr Leu Gly Lys Ala Phe Lys Asn Ala Pro Glu Gly Tyr Ser Pro
565 570 575

Glu Met Asp Glu Asp Asp Gly Thr Met Ser Ala Trp Tyr Val Phe Gly
580 585 590

Ala Met Gly Phe Tyr Pro Leu Leu Val Gly Asp Glu Tyr Tyr Asp Leu
595 600 605

Thr Ser Pro Leu Phe Asp Arg Val Leu Leu Arg Leu Thr Asn Gly Asn
610 615 620

Val Leu Thr Ile Gln Thr Glu Gly Arg Lys Lys Lys Asp Ala Pro Ile
625 630 635 640

<210> SEQ ID NO 40
<211> LENGTH: 624
<212> TYPE: PRT
<213> ORGANISM: Bacteroides cellulosilyticus

<400> SEQUENCE: 40

```
Met Val Gln Ala Gln Gln Thr Ser Phe Val Asn Pro Phe Ile Gly Thr
1               5                   10                  15

Ser Asp Asp His Gly Gln Thr Asp Pro Ser Ala Thr Ile Pro Phe Gly
            20                  25                  30

Met Ile Lys Pro Gly Pro Glu Thr Ile Pro Arg Gly Asn Gly Gly Tyr
        35                  40                  45

Asp Tyr Gln Ser Gln Gln Leu Lys Gly Phe Ser Gln Thr Arg Met Ser
    50                  55                  60

Gly Val Gly Cys Ile Gly Val Gly Gly Asn Leu Leu Ile Thr Pro Phe
65                  70                  75                  80

Val Gly Thr Ala Cys Lys Thr Leu Lys Met Asp Lys Ala Ser Glu Thr
                85                  90                  95

Ala Ile Pro Gly Tyr Tyr Ser Val Thr Leu Asp Asn Gln Leu Lys Val
            100                 105                 110

Glu Ile Thr Thr Gly Arg Thr Ala Ala Ile Tyr Arg Phe Thr Tyr Pro
        115                 120                 125

Ala Thr Glu Thr Ala Gly Ile Lys Ile Asn Phe Lys His Ser Tyr Gly
    130                 135                 140

Lys His Ile Ala Glu Glu His Ser Ile Ile Gly Asp Asn Ala Val Lys
145                 150                 155                 160

Gly Phe Val Arg Ser Ala Cys Thr Cys Asp Leu Gly Ser Tyr Lys Phe
                165                 170                 175

Tyr Tyr Tyr Ile Glu Lys Asp Lys Ser Thr Tyr Glu Pro Glu Asp Asn
            180                 185                 190

Asp Ser Glu Leu Leu Trp Lys Phe Gln Thr Glu Pro Asn Glu Gln Ile
        195                 200                 205

Ile Leu Lys Ile Gly Leu Ser Ser Val Ser Ala Glu Glu Ala Glu Ala
    210                 215                 220

Asn Leu Lys Lys Glu Cys Ser Asn Gln Ser Phe Glu Gln Ile Arg Thr
225                 230                 235                 240

Asn Ala Arg Ile Ala Trp Glu Asn Leu Leu Gly Gln Ile Gln Val Glu
                245                 250                 255

Thr Ser Asp Glu Asp Leu Lys Thr Ser Phe Tyr Thr Arg Leu Tyr His
            260                 265                 270

Ala Cys Gln Thr Pro Phe Thr Ile Asn Asp Tyr Ser Gly Ser Tyr Lys
        275                 280                 285

Gly Ser Asp Gly Lys Val Tyr Lys Ser Gln Gln Leu Pro Tyr Tyr His
    290                 295                 300

Gly Trp Ser Ile Trp Asp Thr Tyr Arg Thr Lys Tyr Pro Leu Leu Ser
305                 310                 315                 320

Ile Val Cys Pro Thr Glu Tyr Lys His Met Ile Ser Ser Leu Ala Glu
                325                 330                 335

Leu Tyr Lys Gln Gly Lys Pro Arg Ser Ala Thr Lys Thr Glu Pro Phe
            340                 345                 350

Leu Thr Thr Arg Thr Glu His Ser Ile Ile Thr Ile Leu Asp Ala Leu
        355                 360                 365

Gln Lys Gly Met Phe Asp Gly Ser Leu Asp Glu Leu Leu Pro Leu Met
    370                 375                 380
```

```
Leu Lys Glu Ala Glu Asp Ile Ser Asn Asp Ser Pro Asp Lys Ala Leu
385                 390                 395                 400

Glu Arg Gly Tyr Asp Phe Trp Gly Val Ser Glu Leu Ala Gly Lys Met
                405                 410                 415

Gly Asn Lys Glu Leu Lys Lys Glu Phe Ser Leu Arg Ser Lys Glu Tyr
            420                 425                 430

Arg Pro Ile Trp Leu Gln Lys Phe Lys Asp Ile Gly Pro Thr Ser Asp
        435                 440                 445

Ile Met His Gly Asp Gly Leu Tyr Glu Gly Thr Ile Trp Gln Tyr Arg
    450                 455                 460

Trp Phe Val Pro His Asp Phe Asp Trp Val Ile Ala Thr Leu Gly Ser
465                 470                 475                 480

Lys Lys Lys Val Leu Ser Glu Leu Asp Tyr Phe Phe Glu Asn Asn Leu
                485                 490                 495

Phe Asn Met Gly Asn Gln Pro Asp Ile His Val Pro Phe Leu Tyr Tyr
            500                 505                 510

Tyr Leu Gly Ala Pro Trp Lys Thr Gln Lys Leu Val His Gln Ile Leu
        515                 520                 525

Leu Glu Pro Thr Thr Asn Tyr Tyr Gly Thr His Glu Lys Trp Glu Lys
    530                 535                 540

Pro Tyr Ile Gly Lys Ile Phe Asn Thr Thr Pro Gln Gly Tyr Leu Lys
545                 550                 555                 560

Glu Met Asp Asp Asp Ala Gly Thr Met Ser Ser Trp Phe Val Leu Ser
                565                 570                 575

Ser Ile Gly Leu Phe Pro Val Cys Pro Gly Ile Pro Tyr Tyr Trp Ile
            580                 585                 590

Asn Ala Pro Val Phe Asp Thr Val Thr Leu His Pro Thr Ser Gln Gln
        595                 600                 605

Glu Phe Lys Ile Tyr Val Asn Arg Pro Asp Ala Glu Cys Ile Tyr Ile
    610                 615                 620


<210> SEQ ID NO 41
<211> LENGTH: 631
<212> TYPE: PRT
<213> ORGANISM: Leeuwenhoekiella blandensis

<400> SEQUENCE: 41

Met Lys Asn Tyr Ile Ala Val Leu Phe Thr Leu Val Leu Ala Phe Thr
1               5                   10                  15

Ser Val Ala Gln Glu Ser Leu Thr Asp Tyr Val Asn Val Phe Leu Gly
            20                  25                  30

Thr Ser Gly Asp His Gly Gln Met Ser Pro Ser Ala Thr Thr Pro Phe
        35                  40                  45

Asn Met Met Asn Leu Gly Pro Gln Thr Asn Pro His Gln His Thr Gly
    50                  55                  60

Tyr Glu Tyr Tyr Ala Lys Gln Phe Asp Gly Phe Thr His Thr Arg Met
65                  70                  75                  80

Glu Gly Val Gly Cys Thr Gly Ser Gly Gly Asn Ile Leu Ile Lys Pro
                85                  90                  95

Ile Leu Asn Ala Glu Val Ser Thr Lys Leu Ile Lys Lys Thr Gln Asp
            100                 105                 110

Ala Val Pro Gly Phe Tyr His Val Asn Phe Glu Asn Gly Ile Asp Ala
        115                 120                 125

Lys Leu Thr Val Ala Gln Asn Leu Gly Met His Gln Tyr Ser Phe Pro
    130                 135                 140
```

-continued

```
Asn Ala Asn Ser Gly Leu Tyr Ile Asp Leu Ser Phe Ala Leu Ser Asn
145                 150                 155                 160

Arg Phe Val Ala Glu Thr His Glu Ile Arg Arg Asn Leu Ile Ser Gly
                165                 170                 175

Tyr Met Asp Thr Lys Thr Thr Cys His Ala Gly Thr Tyr Arg Ile Tyr
            180                 185                 190

Tyr Ala Ile Lys Leu Pro Glu Glu Ala Gln Ile Gln Asn Val Gly Glu
        195                 200                 205

His Gln Leu Met Val Lys Gly Leu Gly Asp Ala Ala Glu Val Gln Val
    210                 215                 220

Gly Phe Ser Ser Val Asn Glu Gly Tyr Ala Lys Lys Arg Ile Thr Ser
225                 230                 235                 240

Asp Asp Phe Glu Thr Leu Lys Gly Lys Ala Ser Ala Ser Trp Asn Ala
                245                 250                 255

Tyr Leu Asn Thr Ile Glu Val Ser Gly Glu Lys Asp Arg Leu Gln Leu
            260                 265                 270

Phe Tyr Ser Leu Leu Tyr Arg Thr Ala Gln Ser Pro Phe Leu Val Ser
        275                 280                 285

Glu Glu Asp Gly Thr Phe Arg Ala Thr Asp Gly Ser Val Gln Asn Glu
    290                 295                 300

Asp Tyr Lys Val Tyr Asn Gly Trp Ala Ile Trp Asp Asn Tyr Arg Glu
305                 310                 315                 320

Gln Leu Pro Phe Leu Ser Leu Ala His Pro Glu Val Tyr Gln Asp Ile
                325                 330                 335

Thr Thr Ser Ile Ala Asn Leu Tyr Arg Phe Gly Lys Lys Asn Trp Ala
            340                 345                 350

Thr Glu His Glu Thr Ser Pro Thr Val Arg Thr Glu His Ala Met Val
        355                 360                 365

Val Leu Leu Asp Ala Tyr Lys Lys Gly Tyr Asp Val Asp Phe Glu Ala
    370                 375                 380

Ile Lys Asp Ser Leu Leu Tyr Glu Ala Asp His Leu Asp Phe Gly Ala
385                 390                 395                 400

Pro Asp Lys Ala Leu Glu Ser Ser Tyr Asp Leu Trp Ala Met Ser Glu
                405                 410                 415

Ile Leu Lys Ala Thr Gly Asp Gln Thr Ala Ser Lys Lys Tyr Leu Asp
            420                 425                 430

Lys Ala Leu Asp Tyr Lys Ala Tyr Trp Asp Lys Asp Phe Lys Asp Leu
        435                 440                 445

Ser Lys Ser Asp Val Asp Arg Met Gln Ala Arg Gly Leu Tyr Gln Gly
    450                 455                 460

Thr Ile Trp Gln Tyr Arg Trp Phe Val Pro Trp Asp Val Asn Gly Leu
465                 470                 475                 480

Gln Glu Leu Ala Gly Gly Ala Glu Thr Phe Glu Asn Gln Leu Asp Gln
                485                 490                 495

Phe Phe Glu Glu Phe Asn Tyr Asn His Ala Asn Gln Pro Asp Leu Gln
            500                 505                 510

Val Pro Gly Leu Tyr Asn Ala Thr Ser Gln Pro Trp Lys Ser Gln Lys
        515                 520                 525

Leu Phe Arg Glu Ile Leu Leu Asp Thr Val Val Gln Thr Tyr Phe Asn
    530                 535                 540

Asp Asn Ser Lys Gly Ile Asp Pro Tyr Val Gly Arg Ile Tyr Gln Asn
545                 550                 555                 560
```

```
Lys Pro Lys Ala Tyr Leu Arg Thr Met Asp Asp Asp Ala Gly Thr Met
                565                 570                 575

Ser Ser Trp Phe Val Leu His Ser Met Gly Leu Ser Val Ala Asn Val
            580                 585                 590

Gly Ser Pro Val Tyr Tyr Leu Thr Ala Pro Ile Phe Lys Glu Val Lys
        595                 600                 605

Leu Asn Leu Ala Pro Gly Lys Thr Phe Ser Ile Ser Val Lys Asn Tyr
    610                 615                 620

Asn Lys Glu His Phe Tyr Val
625                 630


<210> SEQ ID NO 42
<211> LENGTH: 646
<212> TYPE: PRT
<213> ORGANISM: Sphingobacterium spiritivorum

<400> SEQUENCE: 42

Met Gln Val Leu Thr Asp Leu Leu Leu Val Ser Met Lys Asn Phe Leu
1               5                   10                  15

Ser Gln Phe Ser Val Cys Val Leu Leu Ile Leu Ser Ser Gln Gln Phe
            20                  25                  30

Val Tyr Ala Gln Ser Arg Ser Ser Leu Thr Asn Val Phe Leu Gly Ser
        35                  40                  45

Ser Gly Asp Tyr Gly Gln Met Ser Pro Ala Ala Ser Ser Pro Phe His
    50                  55                  60

Gln Met Ser Ile Ala Pro Gln Thr Tyr Pro Thr Leu His Met Gly Tyr
65                  70                  75                  80

Glu Tyr Leu Ala Lys Glu Ile Leu Gly Phe Thr His Asn Arg Phe Glu
                85                  90                  95

Gly Val Gly Cys Lys Gly Ser Gly Gly Leu Ile Leu Val Lys Pro Phe
            100                 105                 110

Leu Gly Gly Gln Asp Asp Gln Gln Pro Leu Leu Lys Val Thr Glu Gln
        115                 120                 125

Ala Gly Pro Gly Phe Tyr Glu Ile Gly Leu Lys Asn Arg Ile Lys Ala
    130                 135                 140

Ala Phe Ala Val Asp Gln Asn Phe Gly Ile His Glu Tyr Ser Phe Pro
145                 150                 155                 160

Lys Gly Lys Lys Gly Phe Ser Ile Asp Leu Ala His Ala Phe Asn Gly
                165                 170                 175

Ala Phe Val Ser Asn Thr Tyr Asp Met Asp Ala Lys Gly Met Leu Lys
            180                 185                 190

Gly Ser Val Arg Ala Arg Thr Thr Cys Gly Val Gly Ile Tyr Thr Ile
        195                 200                 205

His Tyr Ala Ile Lys Val Ser Ser Ser His Val Trp Glu Gly Lys Gly
    210                 215                 220

Asn Gln Leu Thr Leu His Leu Glu Glu Asn Ser Glu Lys Val Thr Ile
225                 230                 235                 240

Gln Ile Ala Phe Ser Ala Val Ser Val Gln Lys Ala Val Glu Thr Leu
                245                 250                 255

Leu His Asn Ala Asp Arg Ser Tyr Ser Glu Val Arg Asn Ala Ser Gln
            260                 265                 270

Gln Gln Trp Asp Ile Cys Leu Ser His Ile Glu Val Lys Gly Asp Pro
        275                 280                 285

Glu Arg Glu Lys Leu Phe Tyr Ser Leu Phe Tyr Arg Thr Leu Gln Ser
    290                 295                 300
```

-continued

```
Pro Tyr Gln Thr Ser Glu Ala Asp Gly Gln Tyr Ala Gly Thr Asp Gly
305                 310                 315                 320

Lys Met His Ser Ala Lys Gly Lys Arg Tyr His Gly Trp Ala Ile Trp
                325                 330                 335

Asp Asn Tyr Lys Thr Gln Leu Pro Leu Leu Glu Leu Leu Tyr Pro Gln
            340                 345                 350

Leu Tyr Gln Asp Val Val Ser Ser Ile Ser Asp Leu Tyr Arg Tyr Gly
        355                 360                 365

Lys Tyr Asp Phe Ala Gly Pro Asn Glu Pro Ala Asn Ser Val Arg Thr
    370                 375                 380

Glu His Ala Ala Val Val Leu Leu Asp Ala Arg Asn Lys Gly Tyr Asp
385                 390                 395                 400

Ile His Phe Asp Ala Val Lys Asp Ser Leu Ile Arg Asp Thr Ala Arg
                405                 410                 415

Phe Asp Phe Ser Lys Pro Asp Lys Ala Leu Glu Ala Ala Tyr Asp Met
            420                 425                 430

Trp Ala Met Ala Gln Leu Phe Asp Lys Lys Gly Thr His Tyr Ala Gln
        435                 440                 445

Arg Ala Gly Ser Tyr Lys Thr Val Trp Gln Lys Glu Phe Lys Asp Leu
    450                 455                 460

Ser Arg Asn Asp Val Asp Arg Met Ser Ala Arg Asn Met Tyr Gln Gly
465                 470                 475                 480

Thr Ile Arg Gln Tyr Arg Trp Asn Val Pro Phe Asp Ile Gly Gly Leu
                485                 490                 495

Val Asp Leu Ala Gly Gly Lys Lys Ala Leu Thr Glu Gln Leu Asp Glu
            500                 505                 510

Phe Phe Asp Glu His Tyr Phe Asn Arg Ala Asn Glu Pro Asp Met Gln
        515                 520                 525

Ser Pro Thr Leu Tyr Tyr Ala Ser Asp Lys Pro Trp Lys Tyr Gln Ser
    530                 535                 540

Leu Val His Gln Leu Ala Val Asp Thr Val Ile Gln Tyr Tyr Phe Asn
545                 550                 555                 560

Asp Asn Ser Arg Gly Ile Asp Pro Phe Ile Asp Arg Ile Tyr Lys Asn
                565                 570                 575

Glu Ser Lys Ala Tyr Ile Arg Thr Met Asp Asp Asp Ala Gly Ala Met
            580                 585                 590

Ser Gly Trp Phe Val Leu Thr Ala Leu Gly Leu His Gln Pro Val Ile
        595                 600                 605

Gly His Pro Val Tyr Tyr Leu Ser Val Pro Leu Phe Pro Glu Ile Asn
    610                 615                 620

Leu Arg Arg Ala Asp Asn Thr Leu Gln Ile Arg Val His Asn Phe Gly
625                 630                 635                 640

Ser Gln Asn Lys Tyr Ile
                645
```

<210> SEQ ID NO 43
<211> LENGTH: 642
<212> TYPE: PRT
<213> ORGANISM: Pedobacter sp.

<400> SEQUENCE: 43

```
Met Phe Phe Met Leu Lys Met Asn Leu Arg Leu Leu Ala Phe Phe Leu
1               5                   10                  15

Leu Leu Leu Val Asn Lys Thr Ile Tyr Ala Gln Gln Thr Gly Lys Asp
```

-continued

```
            20                  25                  30

Lys Leu Val Asn Val Phe Leu Gly Ser Ser Gly Asp His Gly Gln Met
        35                  40                  45

Ser Pro Ala Ala Ser Tyr Pro Phe Ser Ala Leu Ser Ile Ala Pro Gln
    50                  55                  60

Thr Tyr Pro Met Thr His Thr Gly Tyr Glu His Leu Ala Lys Glu Val
65                  70                  75                  80

Phe Gly Phe Thr His Asn Arg Phe Glu Gly Val Gly Cys Gln Gly Ser
                85                  90                  95

Gly Gly Ile Ile Leu Val Lys Pro Phe Leu Gly Ala Glu Asn Asp Glu
            100                 105                 110

Leu Pro Leu Val Lys Ala Ser Glu Thr Ala Ala Pro Gly Tyr Tyr Asp
        115                 120                 125

Ile Ala Phe Thr Asn Gly Ile Lys Ala Gly Phe Val Val Asn Lys Gln
    130                 135                 140

Thr Ala Met His Asp Tyr Ile Met Pro Ala Gly Lys Lys Gly Phe Ser
145                 150                 155                 160

Ile Asp Leu Gly His Thr Phe Asn Asn Ala Leu Val Asp Glu Ser His
                165                 170                 175

Thr Ile Asp Gly Asn Val Ile Lys Gly Trp Val Ala Ala Lys Thr Thr
            180                 185                 190

Cys His Ala Gly Thr Tyr Arg Ile Tyr Tyr Gln Leu Ser Phe Asn Gln
        195                 200                 205

Ser Val Lys Trp Lys Asp Leu Gly Glu His Arg Leu Val Ala Val Pro
    210                 215                 220

Ala Asp Asp Ala Thr Ala Val Gln Leu Arg Val Asp Ile Ser Ala Val
225                 230                 235                 240

Ser Thr Glu Tyr Ala Val Lys Ala Ser Lys Lys Lys Leu Ser Phe Glu
                245                 250                 255

Glu Ala Lys Lys Asn Ser Ala Met Ala Trp Asp Glu Leu Leu Ser Ser
            260                 265                 270

Val Asp Val Lys Gly Asn Ala Glu Arg Glu Arg Leu Phe Tyr Ser Leu
        275                 280                 285

Leu Tyr Arg Thr Ile Gln Ser Pro Tyr Thr Ile Ser Glu Pro Asp Gly
    290                 295                 300

Thr Tyr Lys Ala Ile Asn Gly Ser Thr Gln Lys Ser Lys Glu Met Arg
305                 310                 315                 320

Tyr Asn Gly Trp Ala Ile Trp Asp Asn Tyr Lys Thr Gln Leu Pro Leu
                325                 330                 335

Leu Ser Val Leu Tyr Pro Lys Arg Tyr Gly Asp Ile Val Gly Ser Ile
            340                 345                 350

Ala Asn Leu Tyr Pro Tyr Gly Lys Lys Asp Tyr Ala Gly Pro Asn Glu
        355                 360                 365

Pro Ser Asn Thr Val Arg Thr Glu His Ala Met Val Val Leu Tyr Asp
    370                 375                 380

Ala Met Lys Lys Gly Tyr Lys Ile Asp Phe Pro Ala Ile Lys Asp Ser
385                 390                 395                 400

Val Leu Ala Glu Val Gln Arg Leu Asp Phe Ser Lys Pro Asp Lys Ser
                405                 410                 415

Leu Glu Ala Ser Tyr Asp Leu Trp Ala Val Ser Gly Met Phe Lys Leu
            420                 425                 430

Ser Gly Asp Ala Ala Met Ser Glu Lys Tyr Lys Thr Met Ala Met Asp
        435                 440                 445
```

Tyr Lys Lys Tyr Trp Asp Lys Asp Phe Lys Asp Leu Ser Lys Lys Asp
    450                 455                 460

Val Asp Arg Met Gly Ala Arg Ser Leu Tyr Gln Gly Thr Ile Arg Gln
465                 470                 475                 480

Tyr Arg Trp Ala Val Pro Phe Asp Val Lys Gly Leu Val Glu Leu Thr
                485                 490                 495

Gly Gly Ala Gln Ala Phe Thr Glu Gln Leu Asp Asp Phe Phe Asp Asn
            500                 505                 510

Asp Tyr Phe Asn Lys Ala Asn Glu Pro Asp Leu Gln Thr Gln Glu Leu
        515                 520                 525

Tyr Asn Gly Ser Ala Lys Pro Trp Lys Tyr Gln Ser Leu Val His Lys
    530                 535                 540

Leu Ala Leu Asp Thr Val Ile Gln His Tyr Phe Asn Asp Asn Ser Arg
545                 550                 555                 560

Gly Val Gly Ser Phe Ile Asp Arg Ile Tyr Lys Asn Glu Pro Lys Ala
                565                 570                 575

Phe Val Arg Thr Met Asp Asp Asp Ala Gly Ala Met Ser Gly Trp Phe
            580                 585                 590

Val Leu Thr Ala Met Gly Ile Gln Pro Ala Cys Val Gly Thr Pro Ile
        595                 600                 605

Tyr Tyr Leu Asn Val Pro Leu Phe Glu Ser Val Thr Ile Lys Ser Gly
    610                 615                 620

Ala Lys Pro Leu Gln Ile Lys Val Glu His Phe Ser Asp Gln Asn Val
625                 630                 635                 640

Tyr Ile

<210> SEQ ID NO 44
<211> LENGTH: 810
<212> TYPE: PRT
<213> ORGANISM: Magnaporthe grisea

<400> SEQUENCE: 44

Met Ala Leu Ile His Ile Phe Phe Leu Leu Ser Ser Leu Val Ser Leu
1               5                   10                  15

Ala Gln Gln Ala Glu Leu Ala Asp Tyr Val Phe Thr Asn Thr Gly Ser
            20                  25                  30

Glu Gly Gly Gly Asn Thr Phe Pro Gly Val Ser Glu Pro Phe Gly Met
        35                  40                  45

Val Lys Leu Gly Pro Asp Val Phe Gln Asp Arg Val Asp Ser Tyr Ser
    50                  55                  60

Gly Tyr Leu Pro Asn Gly Lys Ile Lys Ala Phe Ser Met Leu His Leu
65                  70                  75                  80

Ser Gly Thr Gly Gly Ala Pro Lys Tyr Gly Val Val Ala Gln Met Pro
                85                  90                  95

Val Val Gly Asn Ile Ala Asn Pro Leu Asp Asp Tyr Leu Ala Ala Arg
            100                 105                 110

Asp Ala Pro Asp Met Thr Glu Val Gly Tyr Tyr Lys Ser Arg Leu Ala
        115                 120                 125

Thr Gly Ile Thr Val Glu Leu Ala Ala Ser Ser Arg Ala Gly Met Leu
    130                 135                 140

Gln Tyr Thr Phe Pro Ser Gly Pro Thr Pro Arg Asn Val Ile Val Asp
145                 150                 155                 160

Val Ser His Val Leu Pro Ser Tyr Arg Gly Gln Gly Leu Gly Gln Arg
                165                 170                 175

-continued

```
Tyr Leu Gly Gly Ser Ile Ser Val Asp Arg Asp Asp Ser Gly Asn Val
            180                 185                 190

Gln Tyr Lys Gly Ser Gly Ser Tyr Asp Asn Gly Trp Asn Arg Ala Pro
        195                 200                 205

Lys Trp Thr Val Tyr Phe Cys Gly Ala Phe Asn Ser Ser Ala Thr Phe
    210                 215                 220

Lys Thr Phe Val Gly Thr Asn Ala Thr Ala Asn Thr Leu Ser Lys Phe
225                 230                 235                 240

Ser Asn Asp Asn Lys Val Glu Ser Leu Ser Arg Leu Gly Ala Val Phe
                245                 250                 255

Thr Phe Asp Ala Ala Asn Val Val Ser Arg Val Gly Val Ser Phe Ile
            260                 265                 270

Ser Glu Asp Gln Ala Cys Thr Asn Leu Asp Gln Gln Ile Pro Glu Ser
        275                 280                 285

Thr Ser Ile Ser Gln Leu Arg Gln Lys Thr Arg Asp Val Trp Asn Thr
    290                 295                 300

Asp Val Leu Ser Arg Val Ala Ser Asn Asp Lys Asn Thr Thr Lys Leu
305                 310                 315                 320

Gln His Leu Tyr Thr Ser Met Tyr Phe Met His Leu Met Pro Ile Asn
                325                 330                 335

Lys Thr Gly Glu Asn Pro Glu Trp Lys Ser Thr Glu Pro Tyr Tyr Asp
            340                 345                 350

Asp Ile Phe Thr Leu Trp Asp Leu Phe Arg Cys Thr Thr Ala Leu Leu
        355                 360                 365

His Val Phe Gln Pro Lys Val Tyr Glu Glu Phe Ile Arg Ser Leu Ile
    370                 375                 380

Asp Thr Trp Arg His Glu Gly Tyr Leu Pro Asp Ala Arg Ser Ser Phe
385                 390                 395                 400

Phe Asn Gly Ala Thr Gln Gly Gly Ser Asn Ala Asp Thr Val Leu Ala
                405                 410                 415

Asp Ala Tyr Val Lys Gly Val Arg Gly Gln Ile Asn Trp Glu Asp Gly
            420                 425                 430

Phe Ala Ala Met Val Lys Asp Ala Glu Val Val Pro Ala Leu Asn Asp
        435                 440                 445

Asp Pro Arg Asp Lys Thr Gly Ser Thr Lys Glu Gly Arg Gly Ala Leu
    450                 455                 460

Pro Asp Trp Lys Glu Arg Gly Phe Leu Ser Thr Lys Phe Glu Arg Ser
465                 470                 475                 480

Val Ser Arg Ala Val Glu Tyr Ser Gln Asn Asp Phe Gly Leu Ser Gln
                485                 490                 495

Val Ala Lys Gly Leu Gly Lys Thr Ala Glu Ala Glu Lys Tyr Met Lys
            500                 505                 510

Arg Ser Arg Gln Trp Arg Ser His Trp Asn Lys Asp Met Lys Ala Leu
        515                 520                 525

Gly Phe Ser Gly Phe Leu Gly Pro Lys Gly Glu Asp Gly Gln Phe Glu
    530                 535                 540

Glu Gln Asp Pro Leu Asn Cys Arg Gly Cys Tyr Trp Gly Asp Asn Tyr
545                 550                 555                 560

Tyr Glu Ala Leu Pro Trp Glu Tyr Thr Phe Gly Pro His His Asp Ile
                565                 570                 575

Ser Thr Leu Ile Asp Tyr Ser Gly Gly Pro Arg Arg Phe Ala Ser Arg
            580                 585                 590
```

```
Leu Gln Trp Thr Phe Glu Pro Asn Val Arg Pro Lys Gly His Glu Arg
        595                 600                 605

Phe Asn Arg Met Ile Phe Asp Pro Gly Asn Glu Pro Ser Phe Thr Thr
    610                 615                 620

Pro Tyr Leu Tyr Asn Phe Val Gly Arg Gln Asp Met Thr Val Asn Thr
625                 630                 635                 640

Thr Arg Tyr Leu Gly Lys Thr Tyr Tyr Gly Val Arg Pro Asn Gly Leu
                645                 650                 655

Pro Gly Asn Ser Asp Ala Gly Ala Met Glu Ser Trp Ile Leu Trp Val
            660                 665                 670

Met Leu Gly Leu Tyr Pro Met Thr Gly Gln Thr Thr Phe Leu Ile Gly
        675                 680                 685

Ser Pro Trp Leu Asp Asp Ile Thr Ile Ser Leu Gly Asp Gly Lys Ser
    690                 695                 700

Leu Gln Ile Thr Ser Thr Gly Gly Ser Glu Asp Ser Phe Tyr Val Pro
705                 710                 715                 720

Val Ala Val Thr Val Pro Ile Val Val Val Ala Ala Phe Ala Ile Cys
                725                 730                 735

Val Thr Phe Phe Phe Ile Arg Arg Arg Arg Ala Ala Ala Ala Gln Lys
            740                 745                 750

Ala Leu Ser Ser Gly Ser Gly Thr Pro Glu Ser Gly Ile Glu Thr Leu
        755                 760                 765

Thr Pro Thr Ser Gln Pro Val Asp Thr Ser Lys Thr Asn Val Gln Val
    770                 775                 780

Glu Ile Val Gly Ala Pro Pro Leu Asp Ser Thr Gln Gly Ala Asn Ile
785                 790                 795                 800

Ala Gln Leu Pro Pro Pro Val Ala Asn Arg
                805                 810


<210> SEQ ID NO 45
<211> LENGTH: 701
<212> TYPE: PRT
<213> ORGANISM: Bacteroides sp.

<400> SEQUENCE: 45

Met Lys Ile Leu His Phe Cys Ala Ala Ile Thr Met Ala Ala Met Leu
1               5                   10                  15

Ser Gly Cys Asn Gly Gly Gln Ser Gln Thr Ala Asn Arg Thr Pro Val
            20                  25                  30

Asp Tyr Val Asn Pro Tyr Ile Gly Asn Ile Ser His Leu Leu Val Pro
        35                  40                  45

Thr Phe Pro Thr Ile Gln Leu Pro Asn Ser Met Leu Arg Val Tyr Pro
    50                  55                  60

Glu Arg Ala Asp Tyr Thr Thr Glu Leu Leu Asn Gly Leu Pro Leu Ile
65                  70                  75                  80

Val Thr Asn His Arg Glu Arg Ser Ala Phe Asn Leu Ser Pro Tyr Gln
                85                  90                  95

Gly Lys Glu Leu Gln Pro Ile Ile Thr Tyr Asn Tyr Asp Asn Glu His
            100                 105                 110

Leu Thr Pro Tyr Ser Tyr Glu Val Asp Leu Asn Asp Asn Ser Met Lys
        115                 120                 125

Ala Glu Tyr Ala Leu Ser His Gln Ser Ala Leu Tyr Arg Ile Thr Phe
    130                 135                 140

Glu Ala Asp Lys Pro Ala Tyr Ile Ile Val Asn Ser Arg Asn Gly Ser
145                 150                 155                 160
```

Ile His Val Gly Glu Asn Phe Ile Ser Gly His Gln Gln Leu Ser Ala
165 170 175

Asn Thr Asn Val Tyr Val Tyr Ile Glu Pro Gln Glu Lys Pro Val Ser
180 185 190

Thr Gly Ile Leu Lys Asp Gly Val Ile Glu Ala Ser Lys Asp Asn Ala
195 200 205

Glu Gly Ile Asn Ala Cys Ala Ala Trp Arg Phe Ala Asp Gly Thr Thr
210 215 220

Thr Val Ser Leu Arg Tyr Gly Ile Ser Phe Ile Ser Glu Glu Gln Ala
225 230 235 240

Glu Lys Asn Met Arg Asn Glu Leu Lys Asp Tyr Asn Ile Lys Asn Leu
245 250 255

Ala Lys Thr Gly Arg Gln Ile Trp Asn Glu Ala Leu Gly Arg Ile Lys
260 265 270

Val Glu Gly Gly Thr Glu Asp Asp Lys Thr Val Leu Tyr Ser Ser Phe
275 280 285

Tyr Arg Thr Phe Glu Arg Pro Ile Cys Met Ser Glu Ala Gly Gly Arg
290 295 300

Tyr Phe Ser Ala Phe Asp Gly Glu Val His Asp Asp Asn Gly Thr Pro
305 310 315 320

Phe Tyr Asn Asp Asp Trp Ile Trp Asp Thr Tyr Arg Ala Ala His Pro
325 330 335

Leu Arg Thr Leu Ile Asp Gln Lys Lys Glu Glu Asp Ile Ile Ala Ser
340 345 350

Phe Leu Leu Met Ala Glu Gln Met Gly Thr Met Trp Met Pro Thr Phe
355 360 365

Pro Glu Val Thr Gly Asp Ser Arg Arg Met Asn Ser Asn His Ala Val
370 375 380

Ala Thr Ile Ala Asp Ala Leu Ala Lys Gly Leu Asn Val Asp Ala Ala
385 390 395 400

Lys Ala Tyr Glu Ala Cys Arg Lys Gly Ile Glu Glu Lys Thr Leu Ala
405 410 415

Pro Trp Ser Gly Ala Ala Ala Gly Trp Leu Asp Asn Phe Tyr Arg Glu
420 425 430

Asn Gly Tyr Ile Pro Ala Leu Arg Pro Asp Glu Lys Glu Thr Asp Pro
435 440 445

Asn Val His Pro Phe Glu Lys Arg Gln Pro Val Ala Val Thr Leu Gly
450 455 460

Thr Ser Tyr Asp Gln Trp Cys Leu Ser Arg Ile Ala Glu Ile Leu Gly
465 470 475 480

Lys Lys Asp Glu Ala Ala His Tyr Leu Gln Cys Ser Tyr Asn Tyr Arg
485 490 495

Asn Leu Phe Asn Lys Glu Thr Gly Phe Phe His Pro Lys Asp Lys Glu
500 505 510

Gly Asn Trp Ile Thr Pro Phe Asp Tyr Arg Tyr Ala Gly Gly Met Gly
515 520 525

Ala Arg Glu Tyr Tyr Gly Glu Asn Asn Gly Trp Val Tyr Arg Trp Asp
530 535 540

Val Pro His Asn Val Ala Asp Leu Ile Asn Leu Met Gly Gly Lys Glu
545 550 555 560

Gln Phe Ile Ala Asn Leu Asp Arg Thr Phe Ser Glu Pro Leu Gly Arg
565 570 575

```
Ser Lys Tyr Glu Phe Tyr Ala Gln Leu Pro Asp His Thr Gly Asn Val
            580                 585                 590

Gly Gln Phe Ser Met Ala Asn Glu Pro Ser Leu His Val Pro Tyr Leu
        595                 600                 605

Tyr Asn Tyr Ala Gly Gln Pro Trp Lys Thr Gln Lys Arg Ile Arg Gln
    610                 615                 620

Met Leu Lys Thr Trp Phe Arg Asn Asp Leu Met Gly Met Pro Gly Asp
625                 630                 635                 640

Glu Asp Gly Gly Gly Met Thr Ser Phe Val Val Phe Ser Ser Leu Gly
                645                 650                 655

Phe Tyr Pro Val Thr Pro Gly Ala Pro Val Tyr Asn Ile Gly Ser Pro
            660                 665                 670

Leu Phe Thr His Ala Glu Ile Thr Leu Ser Asn Gly Ser Val Phe Glu
        675                 680                 685

Ile Glu Ala Pro Asn Val Ser Glu Glu Asn Lys Tyr Ile
    690                 695                 700


<210> SEQ ID NO 46
<211> LENGTH: 701
<212> TYPE: PRT
<213> ORGANISM: Bacteroides sp.

<400> SEQUENCE: 46

Met Lys Ile Leu His Phe Cys Ala Ala Ile Thr Met Ala Ala Met Leu
1               5                   10                  15

Ser Gly Cys Asn Gly Gly Gln Ser Gln Thr Ala Asn Arg Ala Pro Val
            20                  25                  30

Asp Tyr Val Asn Pro Tyr Ile Gly Asn Ile Ser His Leu Leu Val Pro
        35                  40                  45

Thr Phe Pro Thr Ile Gln Leu Pro Asn Ser Met Leu Arg Val Tyr Pro
    50                  55                  60

Glu Arg Ala Asp Tyr Thr Thr Glu Leu Leu Asn Gly Leu Pro Leu Ile
65                  70                  75                  80

Val Thr Asn His Arg Glu Arg Ser Ala Phe Asn Leu Ser Pro Tyr Gln
                85                  90                  95

Gly Lys Glu Leu Arg Pro Ile Ile Thr Tyr Asn Tyr Asp Asn Glu His
            100                 105                 110

Leu Thr Pro Tyr Ser Tyr Glu Val Asp Leu Asn Asp Asn Ser Met Lys
        115                 120                 125

Ala Glu Tyr Ala Leu Ser His Gln Ser Ala Leu Tyr Arg Ile Thr Phe
    130                 135                 140

Glu Ala Asp Lys Pro Ala Tyr Ile Ile Val Asn Ser Arg Asn Gly Ser
145                 150                 155                 160

Ile His Val Gly Glu Asn Phe Ile Ser Gly His Gln Gln Leu Ser Ala
                165                 170                 175

Asn Thr Asn Val Tyr Val Tyr Ile Glu Pro Gln Glu Lys Pro Val Ser
            180                 185                 190

Thr Gly Ile Leu Lys Asp Gly Val Ile Glu Ala Ser Lys Asp Asn Ala
        195                 200                 205

Glu Gly Ile Asn Ala Cys Ala Ala Trp Arg Phe Ala Asp Gly Thr Thr
    210                 215                 220

Thr Val Ser Leu Arg Tyr Gly Ile Ser Phe Ile Ser Glu Glu Gln Ala
225                 230                 235                 240

Glu Lys Asn Met Arg Asn Glu Leu Lys Asp Tyr Asn Ile Lys Asn Leu
                245                 250                 255
```

```
Ala Lys Ala Gly Arg Gln Ile Trp Asn Glu Ala Leu Gly Arg Ile Lys
            260                 265                 270

Val Glu Gly Gly Thr Glu Asp Asp Lys Thr Val Leu Tyr Ser Ser Phe
        275                 280                 285

Tyr Arg Thr Phe Glu Arg Pro Ile Cys Met Ser Glu Ala Gly Gly Arg
    290                 295                 300

Tyr Phe Ser Ala Phe Asp Gly Glu Val His Asp Asp Asn Gly Thr Pro
305                 310                 315                 320

Phe Tyr Asn Asp Asp Trp Ile Trp Asp Thr Tyr Arg Ala Ala His Pro
                325                 330                 335

Leu Arg Thr Leu Ile Asp Gln Lys Lys Glu Glu Asp Ile Ile Ala Ser
            340                 345                 350

Phe Leu Leu Met Ala Glu Gln Met Gly Thr Met Trp Met Pro Thr Phe
        355                 360                 365

Pro Glu Val Thr Gly Asp Ser Arg Arg Met Asn Ser Asn His Ala Val
    370                 375                 380

Ala Thr Ile Ala Asp Ala Leu Ala Lys Gly Leu Asn Ile Asp Ala Ala
385                 390                 395                 400

Lys Ala Tyr Glu Ala Cys Arg Lys Gly Ile Glu Glu Lys Thr Leu Ala
                405                 410                 415

Pro Trp Ser Gly Ala Ala Ala Gly Trp Leu Asp Asn Phe Tyr Arg Glu
            420                 425                 430

Asn Gly Tyr Ile Pro Ala Leu Arg Pro Asp Glu Lys Glu Thr Asp Pro
        435                 440                 445

Asn Val His Pro Phe Glu Lys Arg Gln Pro Val Ala Val Thr Leu Gly
    450                 455                 460

Thr Ser Tyr Asp Gln Trp Cys Leu Ser Arg Ile Ala Glu Ile Leu Gly
465                 470                 475                 480

Lys Lys Asp Glu Ala Ala His Tyr Leu Gln Cys Ser Tyr Asn Tyr Arg
                485                 490                 495

Asn Leu Phe Asn Lys Glu Thr Gly Phe Phe His Pro Lys Asp Lys Glu
            500                 505                 510

Gly Asn Trp Ile Thr Pro Phe Asp Tyr Arg Tyr Ala Gly Gly Met Gly
        515                 520                 525

Ala Arg Glu Tyr Tyr Gly Glu Asn Asn Gly Trp Val Tyr Arg Trp Asp
    530                 535                 540

Val Pro His Asn Val Ala Asp Leu Ile Asn Leu Met Gly Gly Lys Glu
545                 550                 555                 560

Gln Phe Ile Ala Asn Leu Asp Arg Thr Phe Ser Glu Pro Leu Gly Arg
                565                 570                 575

Ser Lys Tyr Glu Phe Tyr Ala Gln Leu Pro Asp His Thr Gly Asn Val
            580                 585                 590

Gly Gln Phe Ser Met Ala Asn Glu Pro Ser Leu His Val Pro Tyr Leu
        595                 600                 605

Tyr Asn Tyr Ala Gly Gln Pro Trp Lys Thr Gln Lys Arg Ile Arg Gln
    610                 615                 620

Met Leu Lys Thr Trp Phe Arg Asn Asp Leu Met Gly Met Pro Gly Asp
625                 630                 635                 640

Glu Asp Gly Gly Gly Met Thr Ser Phe Val Val Phe Ser Ser Leu Gly
                645                 650                 655

Phe Tyr Pro Val Thr Pro Gly Ala Pro Val Tyr Asn Ile Gly Ser Pro
            660                 665                 670
```

-continued

Leu Phe Thr His Ala Glu Ile Thr Leu Ser Asn Gly Ser Val Phe Glu
675 680 685

Ile Glu Ala Pro Asn Val Ser Glu Glu Asn Lys Tyr Ile
690 695 700

<210> SEQ ID NO 47
<211> LENGTH: 706
<212> TYPE: PRT
<213> ORGANISM: Bacteroides sp.

<400> SEQUENCE: 47

Met Lys Thr Lys Leu Lys Thr Ser Met Ala Leu Leu Ala Ser Ala Phe
1 5 10 15

Leu Trp Val Ser Cys Ala Gly Gly Gly Gly Thr Pro Pro Ser Ala Met
20 25 30

Asp Pro Val Asp Tyr Val Asn Pro Tyr Met Gly Asn Ile Ser His Leu
35 40 45

Leu Val Pro Thr Phe Pro Thr Val His Leu Pro Asn Ser Met Leu Arg
50 55 60

Val Tyr Pro Glu Arg Ala Asp Phe Thr Gly Asp Arg Leu Gly Gly Leu
65 70 75 80

Pro Ile Ile Val Thr Asn His Arg Glu Arg Ser Ala Phe Asn Leu Cys
85 90 95

Pro Tyr Gln Gly Asp Glu Ser Gly Leu Arg Pro Val Ile Ala Tyr Ser
100 105 110

Tyr Asp Arg Glu Lys Ile Leu Pro Tyr Arg Tyr Gln Val Tyr Leu Asp
115 120 125

Asn Gly Glu Ile Asp Val Asp Phe Ala Pro Ser His Gln Ser Ala Val
130 135 140

Tyr Ser Leu Thr Phe Glu Lys Glu Gly Pro Ala Tyr Leu Val Phe Asn
145 150 155 160

Ser Arg Asn Gly Gln Leu Gln Val Asn Gly Asn Ala Val Ser Gly Tyr
165 170 175

Gln Tyr Ile Asp Lys Lys Thr Lys Val Phe Leu Tyr Ala Glu Thr Asn
180 185 190

Gln Lys Pro Val Lys Ala Gly Val Leu Ser Asn Gly Ser Val Lys Tyr
195 200 205

Asp Glu Thr Ser Val Glu Gly Thr Asn Ala Ala Ile Ala Leu Ser Phe
210 215 220

Gly Glu Asp Val Lys Lys Leu Gly Val Arg Tyr Gly Ile Ser Phe Ile
225 230 235 240

Ser Glu Glu Gln Ala Lys Lys Asn Leu Glu Arg Glu Ile Ala Ala Tyr
245 250 255

Asp Val Asp Val Val Ala Lys Ile Ala Arg Asn Asp Trp Asn Asp Ala
260 265 270

Leu Gly Lys Ile Gln Val Gln Gly Gly Thr Lys Asp Glu Lys Thr Val
275 280 285

Phe Tyr Thr Ser Leu Tyr Arg Cys Tyr Glu Arg Pro Ile Asn Leu Ser
290 295 300

Glu Asp Gly His Tyr Tyr Ser Ala Phe Asp Gly Lys Ile His Glu Asp
305 310 315 320

Gly Gly Arg Pro Phe Tyr Thr Asp Asp Trp Ile Trp Asp Thr Tyr Arg
325 330 335

Ala Thr His Pro Leu Arg Val Leu Ile Asp Asn Glu Arg Glu Asn Asp
340 345 350

Ile Ile Asn Ser Tyr Leu Leu Met Ala Glu Gln Met Gly Thr Asp Trp
355 360 365

Met Pro Thr Phe Pro Glu Val Thr Gly Asp Thr Arg Arg Met Asn Ser
370 375 380

Asn His Ala Val Ala Thr Val Ile Asp Ala Tyr Arg Lys Gly Leu Arg
385 390 395 400

Gly Phe Glu Leu Glu Lys Ala Tyr Ile Ala Cys Lys Lys Gly Ile Glu
405 410 415

Glu Lys Thr Leu Ile Pro Trp Ser Ala Ala Pro Ala Gly Trp Leu Asp
420 425 430

Asp Phe Tyr Lys Glu His Gly Tyr Ile Pro Ala Leu Arg Pro Gly Glu
435 440 445

Lys Glu Thr Val Pro Asn Val Ser Ile Trp Glu Lys Arg Gln Pro Ile
450 455 460

Ala Val Thr Leu Gly Thr Ser Tyr Asp Glu Trp Cys Leu Ser Gln Ile
465 470 475 480

Ala Gln Glu Leu Gly Lys Lys Asp Glu Ala Asp Tyr Tyr Leu Arg Arg
485 490 495

Ser Tyr Asn Tyr Arg Asn Val Phe Asn Pro Glu Thr Gly Phe Phe His
500 505 510

Pro Lys Asp Lys Asp Gly Lys Phe Ile Tyr Pro Leu Asp Tyr Arg Tyr
515 520 525

Asp Gly Gly Leu Gly Ala Arg Asp Tyr Tyr Asp Glu Asn Asn Gly Tyr
530 535 540

Ile Tyr Arg Trp Asp Val Gln His Asn Ile Gly Asp Leu Ile Ser Leu
545 550 555 560

Ile Gly Gly Asn Glu Ala Phe Thr Ser Ala Leu Asp Ser Met Phe Asn
565 570 575

Thr Pro Leu Gly Met Ser Lys Trp Gln Phe Tyr Ser Thr Leu Pro Asp
580 585 590

His Thr Gly Asn Val Gly Met Phe Ser Met Ala Asn Glu Pro Ser Leu
595 600 605

His Ile Pro Tyr Leu Tyr Asn Tyr Ala Gly Lys Pro Trp Met Thr Gln
610 615 620

Lys Arg Ile Arg Thr Leu Leu Asn Gln Trp Phe Arg Asn Asp Leu Met
625 630 635 640

Gly Val Pro Gly Asp Glu Asp Gly Gly Gly Met Ser Ala Phe Val Val
645 650 655

Phe Ser Gln Met Gly Phe Tyr Pro Val Thr Pro Gly Ser Pro Thr Tyr
660 665 670

Asn Ile Gly Ser Pro Met Phe Thr Asp Val Lys Val Asp Met Gly Asn
675 680 685

Gly Asn Thr Phe Glu Ile Arg Ala Asn Asn Ala Ser Asp Glu Asn Lys
690 695 700

Tyr Val
705

<210> SEQ ID NO 48
<211> LENGTH: 691
<212> TYPE: PRT
<213> ORGANISM: Bacteroides sp.

<400> SEQUENCE: 48

Met Ala Ser Ser Cys Val Tyr Ser Pro Pro Lys Glu Pro Val Asp Tyr

-continued

```
1               5                   10                  15

Val Asn Pro Asn Ile Gly Thr Ile Gly His Leu Leu Val Ala Thr Ala
            20                  25                  30

Ser Met Val Gln Leu Pro His Gly Met Val Gln Ile Gly Gln Asn Pro
        35                  40                  45

Tyr Pro Pro Leu Ala Asp Arg Tyr Leu Ala Asp Arg Ile Ser Gly Phe
    50                  55                  60

Ser Val Arg Ala Leu Pro Lys Tyr Thr Thr Lys Pro Phe Ser Trp Ile
65                  70                  75                  80

Met Ala Thr Thr Gly Ala Pro Arg Ile Asn Pro Asn Asp Tyr Ala Ser
                85                  90                  95

Gly Phe Asp His Asp Phe Glu Lys Val Thr Pro Tyr Tyr Ser Trp Ile
            100                 105                 110

Leu Leu Glu Asp Tyr Asp Ile Glu Ala Ala Met Thr Val Thr Gln His
        115                 120                 125

Ser Ser Phe Tyr Lys Phe Lys Tyr Pro Lys Ser Ser Glu Ser Asn Ile
    130                 135                 140

Leu Met Asn Asn Asn Gln Cys Val Arg Val Val Gly Asn Asn Cys Ile
145                 150                 155                 160

Glu Ser Val Glu Ala Val Asp Ser Thr Gln Thr Ala Tyr Tyr Tyr Ala
                165                 170                 175

Ile Phe Ser Lys Pro Phe Arg Ser Tyr Val Thr Trp Lys Asp Ser Leu
            180                 185                 190

Ile Ser Gln Asp Val Lys Gln Glu Gly Leu Asp Ile Gly Ala Leu Val
        195                 200                 205

Thr Phe Asp Thr Ser Gln Asp Glu Glu Ile Met Val Lys Ile Gly Val
    210                 215                 220

Ser Phe Ile Asp Met Glu Gln Ala Lys Arg Asn Leu Glu Met Glu Ile
225                 230                 235                 240

Pro Ala Trp Asp Phe Asp Lys Val Lys Asn Asp Gly Arg Glu Ile Trp
                245                 250                 255

Asn Asn Ala Leu Gly Lys Ile Lys Ile Glu Gly Gly Thr Asp Lys Gln
            260                 265                 270

Lys Thr Ile Phe Tyr Ser Ala Leu Tyr Arg Val Met Leu Gly Ser Gln
        275                 280                 285

Thr Leu Asp Arg Ser Glu Tyr Gly Arg Tyr Tyr Ser Arg Leu Asp Lys
    290                 295                 300

Gln Val His Asp Thr Glu Gly His Ala Phe Tyr Gln Val Gly Ser Asn
305                 310                 315                 320

Trp Gly Ser His His Ser Leu Phe Pro Leu Val Leu Leu Leu Glu Pro
                325                 330                 335

Glu Ile Gln Asn Asp Ile Met Arg Ser Tyr Ile Arg Met Gln Asp Glu
            340                 345                 350

Gly Asp Trp Leu Val Asn Ser Gly Gly Tyr Arg Asn Met Ile Gly Arg
        355                 360                 365

His Glu Val Ala Thr Ile Thr Asp Thr Tyr Met Lys Gly Phe Arg Asp
    370                 375                 380

Phe Asp Ile Glu Lys Ala Tyr Glu Ala Met Lys Arg Asn Ser Lys Glu
385                 390                 395                 400

Ala Thr Met Leu Ser Arg His Ile Gly Lys Asp Trp Arg Leu Asn Glu
                405                 410                 415

Leu Asp Lys Val Tyr Leu Glu Lys Gly Phe Tyr Pro Ala Lys Pro Ser
            420                 425                 430
```

Asp Gln Pro Glu Trp Val Lys Glu Val Gly Phe Gly Arg Gln Ser Val
435 440 445

Ala Leu Thr Leu Glu Asn Cys Tyr Asp Asp Trp Cys Met Ser Ile Leu
450 455 460

Ala Lys Glu Leu Gly Lys Glu Asp Asp Tyr Gln Tyr Tyr Leu Asn Arg
465 470 475 480

Ala Tyr Asn Tyr Arg Asn Val Phe Asp Ser Lys Ser Gly Phe Met Arg
485 490 495

Pro Lys Thr Ala Asp Gly Lys Trp Ile Glu Pro Phe Asp Pro Ile Trp
500 505 510

Ser Gly Gly Gln Gly Gly Arg Asp Phe Tyr Thr Glu Asn Asn Gly Trp
515 520 525

Asn Tyr Thr Trp Tyr Val Leu His Asp Pro Gln Gly Leu Ile Asn Leu
530 535 540

Met Gly Gly Gln Glu Pro Phe Val Ala Lys Leu Gln Gln Met Phe Glu
545 550 555 560

Thr Asn Val Pro Leu Tyr Lys Lys Tyr Asp Phe Leu Lys Gln Tyr Pro
565 570 575

Asp Met Thr Gly Trp Ile Gly Met Tyr Ser His Gly Asn Glu Ile Thr
580 585 590

Trp His Ile Pro Tyr Leu Tyr Asn Tyr Ala Gly Lys Pro Trp Met Thr
595 600 605

Gln Arg Arg Ile Arg Gln Ile Leu Asp Leu Trp Tyr Gly Asp Gly Pro
610 615 620

Leu Gly Phe Cys Gly Asp Glu Asp Tyr Gly Glu Met Ser Ser Trp Tyr
625 630 635 640

Ile Leu Ser Ala Met Gly Phe Tyr Thr Val Ala Pro Gly Arg Pro Val
645 650 655

Tyr Asp Ile Gly Ser Pro Leu Phe Glu Lys Ser Thr Ile Asp Ile Gly
660 665 670

Asp Gly Lys Lys Phe Thr Ile Glu Cys Arg Asn Ile Ser Thr Gln Asn
675 680 685

Lys Tyr Ile
690

<210> SEQ ID NO 49
<211> LENGTH: 706
<212> TYPE: PRT
<213> ORGANISM: Parabacteroides distasoni

<400> SEQUENCE: 49

Met Lys Thr Lys Leu Lys Thr Ser Met Ala Leu Leu Ala Ser Val Phe
1 5 10 15

Leu Trp Val Ser Cys Ala Gly Gly Gly Gly Thr Ser Pro Ser Ala Met
20 25 30

Asp Pro Val Asp Tyr Val Asn Pro Tyr Met Gly Asn Ile Ser His Leu
35 40 45

Leu Val Pro Thr Phe Pro Thr Val His Leu Pro Asn Ser Met Leu Arg
50 55 60

Val Tyr Pro Glu Arg Ala Asp Phe Thr Gly Asp Arg Leu Gly Gly Leu
65 70 75 80

Pro Ile Ile Val Thr Asn His Arg Glu Arg Ser Ala Phe Asn Leu Cys
85 90 95

Pro Tyr Gln Gly Asp Glu Ser Gly Leu Arg Pro Val Ile Ala Tyr Ser

-continued

```
            100                 105                 110

Tyr Asp Arg Glu Lys Ile Leu Pro Tyr Arg Tyr Gln Val Tyr Leu Asp
        115                 120                 125

Asn Glu Glu Ile Asp Val Asp Phe Ala Pro Ser His Gln Ser Ala Val
    130                 135                 140

Tyr Ser Leu Thr Phe Glu Lys Glu Gly Pro Ala Tyr Leu Val Phe Asn
145                 150                 155                 160

Ser Arg Asn Gly Gln Leu Gln Val Asn Gly Asn Ala Val Ser Gly Tyr
                165                 170                 175

Gln Tyr Ile Asp Lys Lys Thr Lys Val Phe Leu Tyr Ala Glu Thr Asn
            180                 185                 190

Gln Lys Pro Val Lys Ala Gly Val Leu Ser Asn Gly Ser Val Asn Tyr
        195                 200                 205

Asn Glu Thr Ser Val Glu Gly Ile Asn Ala Ala Ile Ala Leu Ser Phe
    210                 215                 220

Gly Glu Asp Val Lys Lys Leu Gly Val Arg Tyr Gly Ile Ser Phe Ile
225                 230                 235                 240

Ser Glu Glu Gln Ala Lys Lys Asn Leu Glu Arg Glu Ile Ala Ala Tyr
                245                 250                 255

Asp Val Asp Val Val Ala Lys Ile Ala Arg Asn Asp Trp Asn Asp Ala
            260                 265                 270

Leu Gly Lys Ile Gln Val Gln Gly Gly Thr Lys Asp Glu Lys Thr Val
        275                 280                 285

Phe Tyr Thr Ser Leu Tyr Arg Cys Tyr Glu Arg Pro Ile Asn Leu Ser
    290                 295                 300

Glu Asp Gly His Tyr Tyr Ser Ala Phe Asp Gly Lys Ile His Glu Asp
305                 310                 315                 320

Gly Gly Arg Ser Phe Tyr Thr Asp Asp Trp Ile Trp Asp Thr Tyr Arg
                325                 330                 335

Ala Thr His Pro Leu Arg Val Leu Ile Asp Asn Glu Arg Glu Asn Asp
            340                 345                 350

Ile Ile Asn Ser Tyr Leu Leu Met Ala Glu Gln Met Gly Thr Asp Trp
        355                 360                 365

Met Pro Thr Phe Pro Glu Val Thr Gly Asp Thr Arg Arg Met Asn Ser
    370                 375                 380

Asn His Ala Val Ala Thr Val Ile Asp Ala Tyr Arg Lys Gly Leu Arg
385                 390                 395                 400

Gly Phe Glu Leu Glu Lys Ala Tyr Ile Ala Cys Lys Lys Gly Ile Glu
                405                 410                 415

Glu Lys Thr Leu Ile Pro Trp Ser Ala Ala Pro Ala Gly Trp Leu Asp
            420                 425                 430

Asp Phe Tyr Lys Glu His Gly Tyr Ile Pro Ala Leu Arg Pro Gly Glu
        435                 440                 445

Lys Glu Thr Val Pro Asn Val Ser Ile Trp Glu Lys Arg Gln Pro Ile
    450                 455                 460

Ala Val Thr Leu Gly Thr Ser Tyr Asp Glu Trp Cys Leu Ser Gln Ile
465                 470                 475                 480

Ala Gln Glu Leu Gly Lys Lys Asp Glu Ala Asp Tyr Tyr Leu Arg Arg
                485                 490                 495

Ser Tyr Asn Phe Asn Thr Pro Leu Gly Met Ser Lys Trp Gln Phe Tyr
            500                 505                 510

Ser Thr Leu Pro Asp His Thr Gly Asn Val Gly Met Phe Ser Met Ala
        515                 520                 525
```

Asn Glu Pro Ser Leu His Ile Pro Tyr Leu Tyr Asn Tyr Ala Gly Lys
530 535 540

Pro Trp Met Thr Gln Lys Arg Ile Arg Thr Leu Leu Asn Gln Trp Phe
545 550 555 560

Arg Asn Asp Leu Met Gly Val Tyr Arg Asn Val Phe Asn Pro Glu Thr
565 570 575

Gly Phe Phe His Pro Lys Asp Lys Asp Gly Lys Phe Ile Tyr Pro Leu
580 585 590

Asp Tyr Arg Tyr Asp Gly Gly Leu Gly Ala Arg Asp Tyr Tyr Asp Glu
595 600 605

Asn Asn Gly Tyr Ile Tyr Arg Trp Asp Val Gln His Asn Ile Gly Asp
610 615 620

Leu Ile Ser Leu Ile Gly Gly Asn Glu Ala Phe Thr Ser Ala Leu Asp
625 630 635 640

Ser Met Pro Gly Asp Glu Asp Gly Gly Gly Met Ser Ala Phe Val Val
645 650 655

Phe Ser Gln Met Gly Phe Tyr Pro Val Thr Pro Gly Ser Pro Thr Tyr
660 665 670

Asn Ile Gly Ser Pro Met Phe Thr Asp Val Lys Val Asp Met Gly Asn
675 680 685

Gly Asn Thr Phe Glu Ile Arg Ala Asn Asn Ala Ser Asp Glu Asn Lys
690 695 700

Tyr Val
705

<210> SEQ ID NO 50
<211> LENGTH: 1650
<212> TYPE: PRT
<213> ORGANISM: Cellulosimicrobium cellulans

<400> SEQUENCE: 50

Ala Pro Glu Pro Pro Ser Ala Asp Tyr Ala Ser Leu Val Asp Val Phe
1 5 10 15

Val Gly Thr Glu Gly Asp Phe Gly Asn Asp Met Pro Ala Ala Gln Ala
20 25 30

Pro Asn Gly Leu Ala Lys Val Asn Pro Arg Thr Thr Pro Gly Arg Asn
35 40 45

Asn Thr Gly Tyr Asp Tyr Ala Gln Ser Lys Ile Ser Gly Phe Thr His
50 55 60

Thr Asn Leu Asp Gly Val Gly Gly Ser Gly Gly Gly Gly Asp Leu Leu
65 70 75 80

Val Val Pro Thr Ser Gly Ser Tyr Thr Ala Arg Pro Gly Thr Gly Thr
85 90 95

Tyr Ala His Pro Phe Ser His Asp Asp Glu Asp Ala Gly Pro Gly Phe
100 105 110

Tyr Ser Val Gly Leu Gly Asn Val Ala Gly Thr Asp Gly Ala Ile Thr
115 120 125

Gly Ala Pro Gly Thr Ile Glu Ala Glu Val Ala Ala Ala Thr Arg Ser
130 135 140

Gly Val His Arg Tyr Ala Phe Pro Ala Gly Ser Thr Pro Ser Leu Val
145 150 155 160

Val Asp Leu Glu Thr Asn Asn Thr Ser Arg Arg Ser Ser Ser Val Gln
165 170 175

Val Glu Thr Arg Ala Asp Gly Thr Val Glu Leu Ser Gly Gln Val Thr

-continued

```
            180                 185                 190

Gly Tyr Phe Tyr Asn Ala Ala Tyr Thr Leu Tyr Tyr Thr Ala Arg Thr
        195                 200                 205

Leu Gln Pro Ala Thr Val Gln Thr Trp Gly Asp Asp Asp Arg Leu Val
    210                 215                 220

Asp Ala Thr Ala Gln Asp Gly Val Asp Thr Gly Ala Ile Leu Thr Phe
225                 230                 235                 240

Asp Pro Ala Asp Ala Gly Glu Ile Gly Leu Gln Val Thr Leu Ser Pro
                245                 250                 255

Val Ser Val Glu Gln Ala Arg Ile Asp Gln Gln Val Glu Leu Gly Asp
            260                 265                 270

Leu Ser Phe Asp Ala Ile Arg Asp Arg Thr Arg Ala Glu Trp Asn Ala
        275                 280                 285

Thr Leu Gly Arg Val Ala Ile Asp Ala Ser Thr Ala Thr Asp Pro Thr
    290                 295                 300

Gly Glu Leu Gln Arg Leu Phe Tyr Thr His Leu Tyr Arg Met Phe Ala
305                 310                 315                 320

Met Pro Met Asn Ala Thr Ser Thr Ser Gly Thr Tyr Arg Gly Val Asp
                325                 330                 335

Gly Ala Val His Ala Ala Gln Gly Phe Thr Tyr Tyr Asp Ser Trp Ala
            340                 345                 350

Thr Trp Asp Asp Phe Arg Lys Phe Ser Val Ile Ala Tyr Ile Asp Pro
        355                 360                 365

Ala Leu Tyr Arg Asp Met Val Gln Ser Leu Val Tyr Leu Phe Ala Asp
    370                 375                 380

Ala Glu Ala Thr Gly Thr Gly Gly Gly Leu Gly Gly Phe Val His Ser
385                 390                 395                 400

Val Pro Thr Val Arg Trp Glu Arg Ser Ser Val Val Val Ala Asp Ala
                405                 410                 415

Ile Ala Lys Gly Phe Asp Gly Phe Asp Arg Leu Asp Glu Ala Tyr Pro
            420                 425                 430

Ala Leu Gln Arg Leu Val Gly Gln Tyr Ser Ala Asp Glu Leu Arg Arg
        435                 440                 445

Gly Tyr Val Ala Gly Asn Pro Gly Ala Ser Val Gln Arg Gly Tyr Asp
    450                 455                 460

Gln Tyr Gly Leu Ser Val Ile Ala Asp Glu Leu Gly Leu Thr Glu Glu
465                 470                 475                 480

Ala Glu Thr Leu Arg Glu Gln Ala Ser Trp Pro Ile Glu Lys Leu Thr
                485                 490                 495

Lys Pro Gly Ala Trp Thr Ala Ala Asp Gly Thr Gln Val Gly Leu Leu
            500                 505                 510

Thr Pro Arg Ala Ala Asp Gly Ser Trp Gln Ser Ala Asp His Ala Lys
        515                 520                 525

Phe Glu Ala Ala Gly Leu Tyr Gln Gly Thr Leu Trp Gln Tyr His Trp
    530                 535                 540

Tyr Asp Ala Tyr Asp Met Asp Ala Leu Val Glu Ala Met Gly Gly His
545                 550                 555                 560

Glu Ala Ala Arg Leu Gly Met Arg His Met Phe Gly Glu His Ala Pro
                565                 570                 575

Asp Asp Gly Lys Ala Met Leu His Ser Asn Ala Asn Glu Ile Asp Leu
            580                 585                 590

Gln Ala Pro Tyr Leu Phe Asn Tyr Thr Gly Glu Pro Ser Leu Thr Gln
        595                 600                 605
```

```
Lys Trp Ala Arg Ala Ile Tyr Thr Lys Glu Thr Trp Asn Arg Tyr Ile
    610                 615                 620

Ala Thr Gly Ser Ser Ser Ala Val Pro Ser Gly Gly Gly Glu Phe Thr
625                 630                 635                 640

Pro Pro Leu Lys Thr Lys Val Tyr Arg Leu Asp Pro Arg Gly Met Leu
                645                 650                 655

Pro Thr Met Asp Asn Asp Ala Gly Thr Met Ser Thr Met Phe Val Ala
            660                 665                 670

Ala Ala Val Gly Leu Phe Pro Val Thr Ala Gly Ser Ser Gln Phe Gln
        675                 680                 685

Val Gly Ser Pro Phe Phe Asp Ser Thr Thr Ile Thr Tyr Asp Asp Gly
    690                 695                 700

Ser Ala Phe Thr Val Thr Ala Asp Gly Val Ser Glu Asp Ala Phe Tyr
705                 710                 715                 720

Val Gln Ser Ala Thr Leu Asp Gly Ala Thr Phe Gly Asn Thr Trp Val
                725                 730                 735

Asp Tyr Ala Thr Val Val Gly Gly Ala Asp Leu Ala Phe Arg Met Gly
            740                 745                 750

Glu Gln Pro Ser Asp Trp Gly Thr Asp Thr Ala Pro Ala Phe Ser Met
        755                 760                 765

Ser Thr Ala Thr Asp Glu Pro Ala Glu Gly Pro Arg Val Ser Ala Glu
    770                 775                 780

Pro Thr Thr Val Gln Thr Gly Asp Gly Gly Ala Leu Asp Ala Thr Val
785                 790                 795                 800

Thr Leu Thr Leu Asp Gly Ala Arg Leu Ala Ala Pro Ala Gly Thr Asp
                805                 810                 815

Leu Val Thr Ser Gly Ala Ala Ser Val Val Gly Leu Pro Asp Gly Val
            820                 825                 830

Thr Ala Ala Val Thr Val Ala Ser Pro Thr Ala Leu Thr Val Ser Leu
        835                 840                 845

Thr Gly Thr Ala Ser Ala Asp Ala Arg Phe Phe Val His Leu Arg Asp
    850                 855                 860

Ala Ala Leu Ala Asp Gly Val Ala Ala Ala Ser Leu Gln Gly Gln Gly
865                 870                 875                 880

Val Ser Val Arg Ser Pro Leu Arg Leu Ser Val Ala Ser Ala Glu Arg
                885                 890                 895

Asp Ala Leu Ala Ala Leu Val Asp Asp Ala Val Leu Val Arg His Gly
            900                 905                 910

Asn Tyr Ser Ser Val Thr Phe Asp Arg Phe Ser Thr Ala Leu Thr Lys
        915                 920                 925

Ala Gln Glu Ala Leu Gly Asp Glu Ala Ala Thr Ser Ile Ala Leu Arg
    930                 935                 940

Phe Ala Ala Asp Arg Leu Gly Ala Ala Ala Asp Ala Leu Asp Leu Thr
945                 950                 955                 960

Gly Gly Gly Tyr Arg Thr Leu Glu Ala Glu Gln Ser Glu Ala Trp Ser
                965                 970                 975

Gly Gly Glu Leu Lys Asn Glu Ala Asn Ser Ser Ser Gly Asn Leu Gly
            980                 985                 990

Gly Val Arg Ser Gly Ser Trp Val Gln Tyr Arg Asp Met Thr Phe Glu
        995                 1000                1005

Thr Ala Ala Gly Asp Thr Pro Pro Arg Phe Leu Thr Val Arg Tyr Asp
    1010                1015                1020
```

-continued

```
Thr Ser Phe Ala Pro Thr Asp Thr Pro Ser Thr Val Arg Val His Ala
1025                1030                1035                1040

Gly Asp Val Ser Gly Pro Val Val Ala Thr Val Asp Leu Lys Gly Thr
                1045                1050                1055

Ser Gly Trp Gly Lys Tyr Thr Glu Val Thr Ala Glu Leu Gly Asp Val
            1060                1065                1070

Gln Ala Leu Val Asp Ala Gln Val Val Thr Phe Glu Leu Leu Ala Pro
        1075                1080                1085

Ser Gly Arg Ser Trp Val Gly Asn Phe Asp Trp Phe Arg Phe Ser Ala
    1090                1095                1100

Glu Asp Pro Ala Ala Pro Gly Gln Pro Gly Glu Ser Pro Thr Val Thr
1105                1110                1115                1120

Ile Glu Ala Glu Asp Trp Thr Ala Ser Ser Gly Arg Gly Leu Lys Lys
                1125                1130                1135

Glu Ser Ser Thr Trp Thr Ser Gly Pro Val Thr Asn Val Gly Gly Thr
            1140                1145                1150

Ala Asp Gly Asp Trp Ile Ala Tyr Gly Glu Val Asp Leu Gly Glu Leu
        1155                1160                1165

Pro Leu Gly Glu Leu Ser Val His Tyr Val His Asn Ser Asn Arg Ser
    1170                1175                1180

Gly Asn Asn Ser Ala Leu Ser Val Tyr Leu Asp Ala Phe Asp Pro Ala
1185                1190                1195                1200

Asn Pro Gly Glu Pro Phe Val Thr Val Pro Leu Pro Thr Thr Gly Ser
                1205                1210                1215

Ser Trp Thr Ala Asp Gly Thr Ala Thr Val Val Leu Pro Glu Thr Val
            1220                1225                1230

Gln Gly Thr His Glu Val Phe Val Arg Leu Ser Thr Glu Pro Tyr Ala
        1235                1240                1245

Asp His Pro Tyr Val Ala Asn Leu Asp Ser Leu Thr Phe Ala Pro Gly
    1250                1255                1260

Gly Pro Thr Ser Val Val Val Glu Ser Glu Ala Trp Thr Ser Asn Ser
1265                1270                1275                1280

Gly Arg Gly Leu Lys Asn Glu Ser Ser Thr Trp Thr Ser Gly Pro Val
                1285                1290                1295

Thr Asn Val Gly Gly Thr Ala Asp Gly Asp Trp Leu Ala Tyr Gly Glu
            1300                1305                1310

Ile Asp Leu Gly Ser Ala Ala Leu Asp Gln Leu Ser Val His Tyr Val
        1315                1320                1325

His Asn Ser Asn Arg Ser Gly Arg Asn Ser Ala Leu Ser Val Tyr Leu
    1330                1335                1340

Asp Ala Phe Asp Pro Ala Asn Pro Gly Glu Pro Phe Val Thr Val Pro
1345                1350                1355                1360

Leu Ala Asn Thr Gly Ser Ser Trp Thr Thr Asp Gly Thr Ala Val Val
                1365                1370                1375

Asp Leu Pro Ser Thr Val Arg Gly Lys His Gln Val Trp Val Arg Leu
            1380                1385                1390

Ser Thr Glu Ala Tyr Ala Asp His Pro Tyr Val Ala Asn Leu Asp Ser
        1395                1400                1405

Met Arg Phe Phe Thr Asp Ala Tyr Asp Val Glu Val Pro Pro Thr Asp
    1410                1415                1420

Thr Ala Ala Leu Ala Ala Val Val Asp Ala Ala Gly Thr Pro Glu Ala
1425                1430                1435                1440

Glu Ile Ala Arg Tyr Gly Arg Ile Asp Ala Arg Val Phe Thr Arg Glu
```

-continued

```
            1445                1450                1455

Leu Ala Ala Ala Arg Ser Val Leu Ala Asp Ala Gly Ala Thr Gln Ala
        1460                1465                1470

Gln Ala Asp Glu Arg Ala Arg Arg Leu Gly Leu Ala Thr Asp Gln Leu
    1475                1480                1485

Val Pro Ala Glu Arg Arg Arg Leu Glu Asn Leu Val Ala Ser Ala Glu
    1490                1495                1500

Ala Leu Thr Asp Glu Gly Tyr Ser Pro Glu Ser Trp Gln Ala Phe Arg
1505                1510                1515                1520

Thr Ala Leu Ala Ala Ala Thr Gly Thr Leu Asp Asp Ala Ala Ala Ser
            1525                1530                1535

Asp Glu Ala Leu His Asp Ala Arg Leu Ala Leu Gln Gly Ala Val Asp
        1540                1545                1550

Ala Leu Glu Glu Pro Ala Asp Val Val Leu Val Glu Val Glu Val Ser
    1555                1560                1565

Pro Arg Cys Leu Ala Gly Lys Pro Tyr Val Ala Val Arg Ala Val Asn
    1570                1575                1580

Val Ser Asp Ala Ala Val Asp Val Glu Leu Ala Ser Ser Leu Gly Thr
1585                1590                1595                1600

Arg Ser Phe Val Gly Val Ala Pro Gly Ala Ser Ala Tyr Gln Ser Phe
            1605                1610                1615

Ala Ala Arg Ser Ala Thr Gly Asp Leu Asp Val Thr Val Thr Ala Thr
        1620                1625                1630

Gly Ala Asp Gly Thr Gln Thr Val Glu Gln Val Val Thr Val Pro Ser
    1635                1640                1645

Cys Ser
    1650


<210> SEQ ID NO 51
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 4, 5, 7
<223> OTHER INFORMATION: Xaa = Gly, Ala, Ser, Thr, or Cys

<400> SEQUENCE: 51

Gly Val Gly Xaa Xaa Gly Xaa Gly Gly
1               5


<210> SEQ ID NO 52
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 3
<223> OTHER INFORMATION: Xaa = Any amino acid except Pro

<400> SEQUENCE: 52

Val Arg Xaa Glu
1


<210> SEQ ID NO 53
<211> LENGTH: 5
<212> TYPE: PRT
```

<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 5
<223> OTHER INFORMATION: Xaa = Leu, Ile, Val, Ala, Phe, Tyr, or Met

<400> SEQUENCE: 53

Xaa Tyr Gln Gly Xaa
1 5

<210> SEQ ID NO 54
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 3
<223> OTHER INFORMATION: Xaa = Any amino acid except Pro

<400> SEQUENCE: 54

Gly Asp Xaa Gly Asn
1 5

<210> SEQ ID NO 55
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 4, 5, 7
<223> OTHER INFORMATION: Xaa = Gly, Ser, Thr, Val, Ala, Cys, or Gln

<400> SEQUENCE: 55

Gly Val Gly Xaa Xaa Gly Xaa Gly Gly
1 5

<210> SEQ ID NO 56
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 56

His His His His His His
1 5

<210> SEQ ID NO 57
<211> LENGTH: 5
<212> TYPE: PRT
<213> ORGANISM: Artificial Sequence
<220> FEATURE:
<223> OTHER INFORMATION: Synthetic peptide

<400> SEQUENCE: 57

Leu Tyr Gln Gly Thr
1 5

<210> SEQ ID NO 58
<211> LENGTH: 4
<212> TYPE: PRT
<213> ORGANISM: Artificial Sequence
<220> FEATURE:

-continued

```
<223> OTHER INFORMATION: Synthetic peptide

<400> SEQUENCE: 58

Asp Glu Val Asp
1
```

UNITED STATES PATENT AND TRADEMARK OFFICE
CERTIFICATE OF CORRECTION

PATENT NO. : 10,392,609 B2
APPLICATION NO. : 15/350648
DATED : August 27, 2019
INVENTOR(S) : Callewaert et al.

It is certified that error appears in the above-identified patent and that said Letters Patent is hereby corrected as shown below:

In the Claims

Column 265, Line 54, Claim 8, delete "*Oogataea,*" and insert -- *Ogataea* --;

Column 265, Lines 64-65, Claim 10, delete "*Aspergillus penicilloides*" and insert -- *Aspergillus penicillioides* --.

Signed and Sealed this
Nineteenth Day of May, 2020

Andrei Iancu
*Director of the United States Patent and Trademark Office*